US 6,265,418 B1

(12) United States Patent
Kuroki et al.

(10) Patent No.: US 6,265,418 B1
(45) Date of Patent: Jul. 24, 2001

(54) N-ACYLAMINO ACID AMIDE COMPOUNDS AND INTERMEDIATES FOR PREPARATION THEREOF

(75) Inventors: Yoshiaki Kuroki; Hitoshi Ueno; Masayuki Tanaka; Katsunori Takata; Takahiro Motoyama; Kousuke Baba, all of Ube (JP)

(73) Assignee: Ube Industries, Ltd., Yamaguchi (JP)

( * ) Notice: Subject to any disclaimer, the term of this patent is extended or adjusted under 35 U.S.C. 154(b) by 0 days.

(21) Appl. No.: 09/463,753

(22) PCT Filed: Jul. 31, 1998

(86) PCT No.: PCT/JP98/03422
§ 371 Date: Jan. 31, 2000
§ 102(e) Date: Jan. 31, 2000

(87) PCT Pub. No.: WO99/06402
PCT Pub. Date: Nov. 2, 1999

(30) Foreign Application Priority Data

Jul. 31, 1997 (JP) ................................. 9-237588

(51) Int. Cl.$^7$ ............... A61K 31/435; C07D 471/04; C07D 495/04; C07D 487/18

(52) U.S. Cl. ............ 514/301; 514/302; 514/303; 514/300; 546/113; 546/114; 546/115; 546/82; 546/84

(58) Field of Search .................. 546/82, 113, 114, 546/115, 118, 120, 84; 514/293, 300, 301, 302, 303

(56) References Cited

FOREIGN PATENT DOCUMENTS 62-215523   9/1987   (JP) .
63-33382    2/1988   (JP) .

Primary Examiner—Bernard Dentz
(74) Attorney, Agent, or Firm—Birch, Stewart, Kolasch and Birch, LLP

(57) ABSTRACT

The present invention discloses the compound represented by the formula (I):

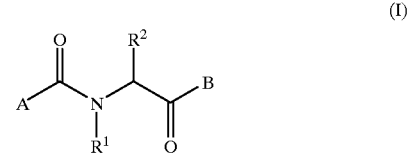

(I)

wherein A represents the following formula (a-1) or the following formula (a-2):

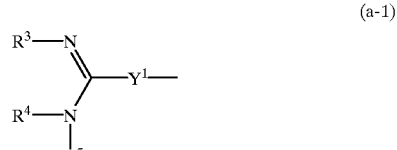

(a-1)

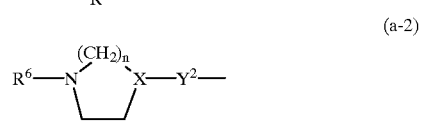

(a-2)

B represents the following formula (b):

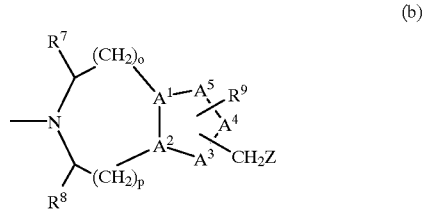

(b)

(wherein the symbols are each as defined in the specification) or a pharmaceutically acceptable salts thereof, and intermediates for the preparation thereof, which have excellent platelet aggregation inhibitory activity and other properties and useful as prophylactic or therapeutic agents for diseases associated with a fibrinogen receptor, thrombosis, infarction and the like.

29 Claims, No Drawings

N-ACYLAMINO ACID AMIDE COMPOUNDS AND INTERMEDIATES FOR PREPARATION THEREOF

This application is the national phase under 35 U.S.C. § 371 of PCT International Application No. PCT/JP98/03422 which has an International filing date of Jul. 31, 1998, which designated the United States of America.

1. Technical Field

The present invention relates to a novel N-acylamino acid amide compound having an excellent platelet aggregation inhibiting action, etc., and useful as a prophylactic agent or treating agent of diseases to which a fibrinogen receptor pertains, embolism and thrombosis, or a pharmaceutically acceptable salt thereof and a preparation intermediate of said compound.

2. Background Art

Recently, it has been attracted attention that a medicine (fibrinogen receptor antagonist) which directly inhibits the bonding between a platelet membrane glycoprotein GPIIb/IIIa complex (fibrinogen receptor) and fibrinogen is an anti-platelet medicine which inhibits aggregation of platelets due to stimulation by all the intrinsic platelet aggregation causing substances.

Until now, it has been reported that a peptide derivative such as Arg-Gly-Asp-Ser (hereinafter abbreviated to as RGDS.), etc. (see Thrombosys, Res., 56, 6, 687 (1989)) or a compound having a piperidino group or an amidino group (see EP 478 363 A2 publication, EP 529 858 A1 publication, WO 93 07867 publication, J. Med. Chem., 35, 4383 (1992), J. Med. Chem., 39, 3139 (1996)), etc. have an antagonistic action against a fibrinogen receptor and have a platelet aggregation inhibiting action, and suggested that they are hopeful as a treating or prophylactic medicine of various diseases to which formation of thrombus pertains.

However, the above-mentioned compounds are still not sufficient in their effects as a medical product in respect of oral absorptive property or stability in vivo, etc.

An object of the present invention is to provide a compound having excellent fibrinogen receptor antagonistic action and having excellent oral absorptive property and durability.

The present inventors have earnestly studied and as a result, they have found a novel N-acylamino acid amide compound and its preparation intermediate to accomplish the present invention.

DISCLOSURE OF THE INVENTION

That is, the present invention relates to an N-acylamino acid amide compound represented by the following formula (I):

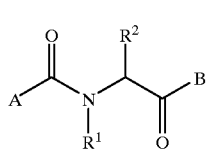

wherein $R^1$ represents a hydrogen atom or a $C_1$ to $C_4$ alkyl group;

$R^2$ represents a hydrogen atom, a $C_1$ to $C_4$ alkyl group, a benzyl group which may be substituted or a pyridylmethyl group which may be substituted (said substituent is a hydroxyl group, a nitro group, a cyano group, a trifluoromethyl group, a carboxyl group, an amino group, a benzoylamino group, a halogen atom, a $C_1$ to $C_4$ alkyl group, a $C_1$ to $C_4$ alkoxy group, a $C_7$ to $C_{10}$ aralkyloxy group, a ($C_1$ to $C_4$ alkoxy)carbonyl group, a $C_1$ to $C_6$ alkanoylamino group, a $C_1$ to $C_4$ alkylsulfonylamino group, a phenylsulfonylamino group which may be substituted (said substituent is a halogen atom, a methyl group or a methoxy group) or a $C_7$ to $C_{10}$ aralkylsulfonylamino group);

A represents the formula (a-1):

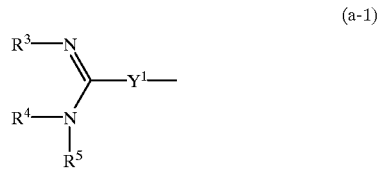

wherein $R^3$, $R^4$ and $R^5$ each independently represents a hydrogen atom, a hydroxyl group, a $C_1$ to $C_4$ alkyl group, a $C_7$ to $C_{10}$ aralkyl group, a $C_1$ to $C_6$ alkanoyl group, a ($C_2$ to $C_6$ alkanoyl)oxymethyl group, a ($C_1$ to $C_{10}$ alkoxy)carbonyl group, a ($C_3$ to $C_7$ cycloalkoxy)carbonyl group, a ($C_2$ to $C_6$ alkenyl)oxycarbonyl group, a ($C_7$ to $C_{10}$ aralkyl)oxycarbonyl group, a phenoxycarbonyl group which may be substituted (said substituent is a $C_1$ to $C_{10}$ alkyl group or a $C_1$ to $C_{10}$ alkoxy group), a ($C_1$ to $C_2$ alkoxy)carbonyl group substituted by a $C_1$ to $C_4$ alkoxy group, a ($C_2$ to $C_6$ alkanoyl)oxymethoxycarbonyl group, an aromatic acyloxymethoxycarbonyl group (the aromatic ring portion is a phenyl group or a pyridyl group) or an alkylene group formed by $R^4$ and $R^5$ in combination and may contain therein one hetero atom selected from the group consisting of O, N and S, $Y^1$ represents a phenylene group which may be substituted (said substituent is a halogen atom, a $C_1$ to $C_4$ alkyl group or a $C_1$ to $C_4$ alkoxy group) or a 5- or 6-membered divalent heteroaromatic ring group containing 1 or 2 hetero atoms selected from the group consisting of O, N and S, or represents the formula (a-2):

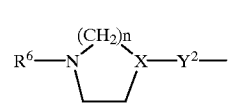

wherein $R^6$ represents a hydrogen atom, a $C_1$ to $C_4$ alkyl group, a $C_7$ to $C_{10}$ aralkyl group, a $C_1$ to $C_6$ alkanoyl group, a ($C_2$ to $C_6$ alkanoyl)oxymethyl group or a ($C_1$ to $C_4$ alkoxy)carbonyl group; X represents a nitrogen atom or >CH— group; $Y^2$ represents a —$(CH_2)_m$— group (where m=1, 2 or 3), a —CH=CH— group (cis or trans), a —C≡C— group, a —$CH_2$—CH=CH— group (cis or trans), a —CH=CH—$CH_2$— group (cis or trans), a —$CH_2$—C≡C— group, a —C≡C—$CH_2$— group, a —$OCH_2$— group, a —$SCH_2$— group, a —$OCH_2CH_2$— group, a —$CH_2OCH_2$— group, a —$SCH_2CH_2$— group or a —$CH_2SCH_2$— group; and n is 1, 2 or 3;

B represents the formula (b):

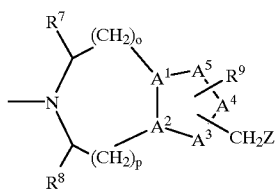

(b)

wherein $A^1$, $A^2$, $A^3$, $A^4$ and $A^5$ represent atoms selected from the group consisting of C, N, O and S, and the 5-membered ring formed by $A^1$ to $A^5$ represents a heteroaromatic ring containing 1 or 2 hetero atoms selected from the group consisting of N, O and S, said heteroaromatic ring has, as an essential component, a —$CH_2Z$ group, and as a desired component, it may be substituted by $R^9$ ($R^9$ represents a hydroxyl group, a trifluoromethyl group, a $C_1$ to $C_4$ alkyl group, a $C_1$ to $C_4$ alkoxy group or a ($C_7$ to $C_{10}$ aralkyl)oxycarbonyl group), $R^7$ and $R^8$ each represents a hydrogen atom, or a $C_2$ to $C_3$ alkylene group formed by $R^7$ and $R^8$ in combination thereof, Z represents a carboxyl group which may be protected, and o and p each represents 0 or 1, or a pharmaceutically acceptable salt thereof.

Moreover, the present invention relates to a compound represented by the general formula (II):

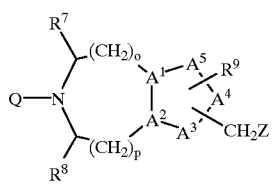

(II)

wherein $A^1$, $A^2$, $A^3$, $A^4$, $A^5$, $R^7$, $R^8$, $R^9$, Z, o and p have the same meanings as defined above, and Q represents a hydrogen atom, a ($C_1$–$C_4$ alkoxy)carbonyl group, a benzyloxycarbonyl group or a trityl group, which is useful as a preparation intermediate of the compound having the formula (I), or a salt thereof.

BEST MODE FOR CARRYING OUT THE INVENTION

As the $C_1$ to $C_4$ alkyl group shown by $R^1$ in the compound represented by the formula (I) (hereinafter also referred to as Compound (I)) of the present invention, there may be mentioned, for example, a straight or branched $C_1$ to $C_4$ alkyl group such as methyl, ethyl, propyl, isopropyl, butyl, isobutyl, s-butyl, t-butyl, etc.

$R^1$ is preferably a hydrogen atom, methyl, ethyl and propyl groups, more preferably a hydrogen atom or a methyl group, particularly preferably a hydrogen atom.

As the $C_1$ to $C_4$ alkyl group shown by $R^2$, the group having the same meaning as those defined in the above mentioned $R^1$, preferably a methyl, isopropyl, isobutyl and s-butyl groups, more preferably a methyl group.

As the pyridylmethyl group shown by $R^2$, there may be mentioned, for example, a 2-pyridylmethyl, 3-pyridylmethyl and 4-pyridylmethyl groups. It is preferably a 3-pyridylmethyl and 4-pyridylmethyl groups, more preferably a 4-pyridylmethyl group.

The benzyl group or the pyridylmethyl group shown by $R^2$ may have a substituent on the aromatic ring, and as the substituent, there may be mentioned, for example, a hydroxyl group; a nitro group; a cyano group; a trifluoromethyl group; a carboxyl group; a benzoylamino group; an amino group; a halogen atom such as a fluorine, chlorine, bromine and iodine atoms; the $C_1$ to $C_4$ alkyl group having the same meanings as defined in $R^1$; a $C_1$ to $C_4$ alkoxy group such as a methoxy, ethoxy, propoxy, isopropoxy, butoxy, isobutoxy, s-butoxy and t-butoxy groups; a $C_7$ to $C_{10}$ aralkyloxy group such as a benzyloxy, phenethyloxy, phenylpropoxy and phenylbutoxy groups; a ($C_1$ to $C_4$ alkoxy)carbonyl group the alkoxy portion of which has the same meaning as defined above such as a methoxycarbonyl, ethoxycarbonyl, propoxycarbonyl, isopropoxycarbonyl, butoxycarbonyl, isobutoxycarbonyl, s-butoxycarbonyl and t-butoxycarbonyl groups; a $C_1$ to $C_6$ alkanoylamino group such as a formylamino, acetylamino, propanoylamino, butanoylamino, pentanoylamino and hexanoylamino groups; a $C_1$ to $C_4$ alkylsulfonylamino group such as methylsulfonylamino, ethylsulfonylamino, propylsulfonylamino, butylsulfonylamino and isobutylsulfonylamino groups; a phenylsulfonylamino group which may be substituted by the above-mentioned halogen atom, a methyl group or a methoxy group such as a phenylsulfonylamino, (fluorophenyl)sulfonylamino (including respective isomers), (chlorophenyl)sulfonylamino (including respective isomers), (bromophenyl)sulfonylamino (including respective isomers), (iodophenyl)sulfonylamino (including respective isomers), (methylphenyl)sulfonylamino (including respective isomers) and (methoxyphenyl)sulfonylamino (including respective isomers); and a $C_7$ to $C_{10}$ aralkylsulfonylamino group such as a benzylsulfonylamino, phenethylsulfonylamino, phenylpropylsulfonylamino and phenylbutylsulfonylamino groups, and the like.

As the above-mentioned substituents, it is preferably a hydroxyl group, a nitro group, a cyano group, a trifluoromethyl group, an amino group, a benzoylamino group, a halogen atom, a benzyloxy group, a $C_1$ to $C_4$ alkylsulfonylamino group, a phenylsulfonylamino group which may be substituted by a halogen and a benzylsulfonylamino group, more preferably a nitro group, a cyano group, a fluorine atom, a chlorine atom, a benzyloxy group, a $C_1$ to $C_4$ alkylsulfonylamino group, a phenylsulfonylamino group which may be substituted by a fluorine atom or a chlorine atom and a benzylsulfonylamino group, particularly preferably a nitro group, a benzyloxy group, a methylsulfonylamino group, an ethylsulfonylamino group, a propylsulfonylamino group, a butylsulfonylamino group, an isobutylsulfonylaminQ group, a 4-fluorophenylsulfonylamino group and a benzylsulfonylamino group.

As the position of the above-mentioned substituents to be bound, it is not particularly limited but preferably the 4-position or 3-position of the benzyl group, the 4-position or 5-position of the 2-pyridylmethyl group, the 5-position or 6-position of the 3-pyridylmethyl group and the 2-position of the 4-pyridylmethyl group, more preferably the 4-position of the benzyl group, the 5-position of the 2-pyridylmethyl group and the 6-position of the 3-pyridylmethyl group. Also, the number of the substituent is not particularly limited, but preferably 1 or 2.

Preferred group of $R^2$ may specifically include a hydrogen atom, a methyl group, an isopropyl group, an isobutyl group, a s-butyl group, a 4-pyridylmethyl group, a 3-pyridylmethyl group, a benzyl group, a 4-hydroxybenzyl group, a 3-nitrobenzyl group, a 4-nitrobenzyl group, a 3-cyanobenzyl group, a 4-cyanobenzyl group, a 4-trifluoromethylbenzyl group, a 4-aminobenzyl group, a 4-(benzoylamino)benzyl group, a 3-fluorobenzyl group, a 4-fluorobenzyl group, a 3-chlorobenzyl group, a 4-chlorobenzyl group, a 3-bromobenzyl group, a 4-bromobenzyl group, a 4-iodobenzyl group, a 4-benzyloxybenzyl group, a 3-(methylsulfonylamino)benzyl group, a 4-(methylsulfonylamino)benzyl group, a 3-(ethylsulfonylamino)benzyl group, a 4-(ethylsulfonylamino)benzyl group, a 4-(propylsulfonylamino)benzyl group, a 4-(butylsulfonylamino)benzyl group, a 4-(isobutylsulfonylamino)benzyl group, a 4-(phenylsulfonylamino)benzyl group, a 4-[(4-fluorophenyl)sulfonylamino]benzyl group, a 4-[(4-chlorophenyl)sulfonylamino]benzyl group, a 4-(4-bromophenyl)sulfonylamino benzyl group, a 4-nitro-3-fluorobenzyl group, a 4-nitro-3-chlorobenzyl group, a 4-hydroxy-3-fluorobenzyl group, a 4-hydroxy-3-chlorobenzyl group, a 2-nitro-4-pyridylmethyl group, a 6-nitro-3-pyridylmethyl group, a 2-chloro-4-pyridymethyl group and a 4-(benzylsulfonylamino)benzyl group, more preferably a methyl group, a benzyl group, a 4-nitrobenzyl group, a 4-cyanobenzyl group, a 4-fluorobenzyl group, a 4-chlorobenzyl group, a 4-benzyloxybenzyl group, a 4-methylsulfonylaminobenzyl group, a 4-(ethylsulfonylamino)benzyl group, a 4-(propylsulfonylamino)benzyl group, a 4-(butylsulfonylamino)benzyl group, a 4-(isobutylsulfonylamino)benzyl group, a 4-(phenylsulfonylamino)benzyl group, a 4-[(4-fluorophenyl)sulfonylamino]benzyl group, a 4-[(4-chlorophenyl)sulfonylamino]benzyl group and a 4-(benzylsulfonylamino)benzyl group, particularly preferably a methyl group, a 4-benzyloxybenzyl group, a 4-nitrobenzyl group, a 4-(methylsulfonylamino)benzyl group, a 4-(ethylsulfonylamino)benzyl group, a 4-(propylsulfonylamino)benzyl group, a 4-(butylsulfonylamino)benzyl group, a 4-(isobutylsulfonylamino)benzyl group, a 4-(phenylsulfonylamino)benzyl group and a 4-(benzylsulfonylamino)benzyl group.

$R^3$, $R^4$ and $R^5$ shown in the formula (a-1) as A in the formula (I) may be mentioned, each independently, for example, a hydrogen atom; a hydroxyl group; a $C_1$ to $C_4$ alkyl group having the same meanings as defined above; a $C_7$ to $C_{10}$ aralkyl group such as a benzyl, phenethyl, phenylpropyl and phenylbutyl groups; a $C_1$ to $C_4$ alkoxy group having the same meanings as defined above; a $C_{10}$ to $C_6$ alkanoyl group such as a formyl, acetyl, propanoyl, butanoyl, isobutanoyl, pivaloyl, valeroyl and hexanoyl groups; a ($C_2$ to $C_6$ alkanoyl)oxymethyl group having a $C_2$ to $C_6$ alkanoyl group as the alkanoyl portion such as an acetoxymethyl, propanoyloxymethyl, butanoyloxymethyl, isobutanoyloxymethyl, pivaloyloxymethyl, valeroyloxymethyl and hexanoyloxymethyl groups; a ($C_1$ to $C_{10}$ alkoxy)carbonyl group such as the ($C_1$ to $C_4$ alkoxy)carbonyl group having the same meaning as defined above, a pentyloxycarbonyl, hexyloxycarbonyl, heptyloxycarbonyl, octyloxycarbonyl, nonyloxycarbonyl and decyloxycarbonyl groups; a ($C_3$ to $C_7$ cycloalkoxy)carbonyl group such as a cyclopropoxycarbonyl, cyclobutoxycarbonyl, cyclopentyloxycarbonyl, cyclohexyloxycarbonyl and cycloheptyloxycarbonyl groups; a ($C_2$ to $C_6$ alkenyl)oxycarbonyl group such as a vinyloxycarbonyl, 1-propenyloxycarbonyl, allyloxycarbonyl, isopropenyloxycarbonyl, 1-butenyloxycarbonyl, 2-butenyloxycarbonyl, 3-butenyloxycarbonyl, 1-methyl-1-propenyloxycarbonyl, 2-methyl-1-propenyloxycarbonyl, 2-methyl-2-propenyloxycarbonyl, 1-pentenyloxycarbonyl, 2-pentenyloxycarbonyl, 3-pentenyloxycarbonyl, 4-pentenyloxycarbonyl, 1-methyl-1-butenyloxycarbonyl, 2-methyl-2-butenyloxycarbonyl, 3-methyl-2-butenyloxycarbonyl, 1-hexenyloxycarbonyl and 2-hexenyloxycarbonyl groups; a ($C_7$ to $C_{10}$ aralkyl)oxycarbonyl group such as a benzyloxycarbonyl, phenethyloxycarbonyl, phenylpropoxycarbonyl and phenylbutoxycarbonyl groups; a phenoxycarbonyl group which may be substituted by a $C_1$ to $C_{10}$ alkyl group or a $C_1$ to $C_{10}$ alkoxy group such as a phenoxycarbonyl, 4-methylphenoxycarbonyl, 4-ethylphenoxycarbonyl, 4-propylphenoxycarbonyl, 4-butylphenoxycarbonyl, 4-pentylphenoxycarbonyl, 4-hexylphenoxycarbonyl, 4-heptylphenoxycarbonyl, 4-octylphenoxycarbonyl, 4-nonylphenoxycarbonyl, 4-decylphenoxycarbonyl, 4-methoxyphenoxycarbonyl, 4-ethoxyphenoxycarbonyl, 4-propoxyphenoxycarbonyl, 4-butoxyphenoxycarbonyl, 4-pentyloxyphenoxycarbonyl, 4-hexyloxyphenoxycarbonyl, 4-heptyloxyphenoxycarbonyl, 4-octyloxyphenoxycarbonyl, 4-nonyloxyphenoxycarbonyl and 4-decyloxyphenoxycarbonyl; a ($C_1$ to $C_2$ alkoxy)carbonyl group substituted by a $C_1$ to $C_4$ alkoxy group such as a methoxymethoxycarbonyl group, a 2-methoxyethoxycarbonyl group, an ethoxymethoxycarbonyl group, a 2-ethoxyethoxycarbonyl group, a propoxymethoxycarbonyl group, a 2-propoxyethoxycarbonyl group, an isopropoxymethoxycarbonyl group, a 2-isopropoxyethoxycarbonyl group, a butoxymethoxycarbonyl group, a 2-butoxyethoxycarbonyl group, an isobutoxymethoxycarbonyl group, a 2-isobutoxyethoxycarbonyl group, a t-butoxymethoxycarbonyl group and a 2-t-butoxyethoxycarbonyl group; a ($C_2$ to $C_6$ alkanoyl)oxymethoxycarbonyl group such as an acetoxymethoxycarbonyl, propanoyloxymethoxycarbonyl, butanoyloxymethoxycarbonyl, isobutanoyloxymethoxycarbonyl, valeroyloxymethoxycarbonyl, pivaloyloxymethoxycarbonyl and hexanoyloxymethoxycarbonyl groups; and an aromatic acyloxymethoxycarbonyl group in which the aromatic ring portion is a phenyl group or a pyridyl group such as a benzoyloxymethoxycarbonyl, nicotinoyloxymethoxycarbonyl, isonicotinoyloxymethoxycarbonyl and picolinoyloxymethoxycarbonyl groups.

It is preferably a hydrogen atom, a hydroxyl group, a $C_1$ to $C_3$ alkyl group, a $C_2$ to $C_5$ alkanoyl group, an acetoxymethyl group, a pivaloyloxymethyl group, a ($C_1$ to $C_6$ alkoxy)carbonyl group, a ($C_5$ to $C_6$ cycloalkoxy)carbonyl group, a ($C_2$ to $C_4$ alkenyl)oxycarbonyl group, a benzyloxycarbonyl group, a phenoxycarbonyl group which may be substituted by a $C_1$ to $C_4$ alkyl group or a $C_1$ to $C_{10}$ alkoxy group, an ethoxycarbonyl group the 2-positionof which is substituted-bya $C_1$ to $C_4$ alkoxygroup, a ($C_2$ to $C_6$ alkanoyl) oxymethoxycarbonyl group and an aromatic acyloxymethoxycarbonyl group, more preferably a hydrogen atom, a hydroxyl group, a methyl group, a ($C_1$ to $C_4$ alkoxy)carbonyl group, a ($C_2$ to $C_4$ alkenyl)oxycarbonyl group, a phenoxycarbonyl group which may be substituted by a $C_1$ to $C_2$ alkyl group or a $C_1$ to $C_4$ alkoxy group, an ethoxycarbonyl group the 2-position of which is substituted by a $C_2$ to $C_4$ alkoxy group, a ($C_2$ to $C_5$ alkanoyl) oxymethoxycarbonyl group, a benzoyloxymethoxycarbonyl group and a nicotinoyloxymethoxycarbonyl group, and particularly preferably a hydrogen atom, a hydroxyl group, a methoxycarbonyl group, an ethoxycarbonyl group, a propoxycarbonyl group, an isopropoxycarbonyl group, a butoxycarbonyl group, an isobutoxycarbonyl group, a t-butoxycarbonyl group, an isopropenyloxycarbonyl group, an acetoxymethoxycarbonyl group, a pivaloyloxymethoxycarbonyl group, a phenoxycarbonyl group, a 2-t-butoxyethoxycarbonyl group and a benzoyloxymethoxycarbonyl group As an alkylene group formed by $R^4$ and $R^5$ in combination thereof, in the formula (a-1), which may contain one hetero atom selected from the group consisting of O, N and S, there may be mentioned, for example, a tetramethylene group, a pentamethylene group, a —$CH_2CH_2OCH_2CH_2$— group, a —$CH_2CH_2SCH_2CH_2$— group and a —$CH_2CH_2NHCH_2CH_2$— group, preferably a pentamethylene group, a —$CH_2CH_2OCH_2CH_2$— group and a —$CH_2CH_2NHCH_2CH_2$— group, more preferably a —$CH_2CH_2OCH_2CH_2$— group.

As the preferred combination of the above-mentioned $R^3$, $R^4$ and $R^5$, the case where $R^3$ is a group selected from the group consisting of a hydrogen atom, a hydroxyl group, a $C_1$ to $C_3$ alkyl group, a $C_2$ to $C_5$ alkanoyl group, an acetoxymethyl group, a pivaloyloxymethyl group, a ($C_1$ to $C_6$ alkoxy) carbonyl group, a ($C_5$ to $C_6$ cycloalkoxy)carbonyl group, a ($C_2$ to $C_4$ alkenyl)oxycarbonyl group, a benzyloxycarbonyl group, a phenoxycarbonyl group which may be substituted by a $C_1$ to $C_4$ alkyl group or a $C_1$ to $C_{10}$ alkoxy group, an ethoxycarbonyl group the 2-position of which is substituted by a $C_1$ to $C_4$ alkoxy group, a ($C_2$ to $C_6$ alkanoyl) oxymethoxycarbonyl group and an aromatic 5-acyloxymethoxycarbonyl group, and $R^4$ and $R^5$ are each independently a hydrogen atom or a ($C_1$ to $C_4$ alkoxy) carbonyl group or $R^4$ and $R^5$ form, in combination thereof, a pentamethylene group, —$CH_2CH_2OCH_2CH_2$— group or a —$CH_2CH_2NHCH_2CH_2$— group, more preferably the case where $R^3$ is a group selected from the group consisting of a hydrogen atom, a hydroxyl group, a methyl group, a ($C_1$ to $C_4$ alkoxy) carbonyl group, a ($C_2$ to $C_4$ alkenyl)oxycarbonyl group, a phenoxycarbonyl group which may be substituted by a $C_1$ to $C_2$ alkyl group or a $C_1$ to $C_4$ alkoxy group, an ethoxycarbonyl group the 2-position of which is substituted by a $C_2$ to $C_4$ alkoxy group, a ($C_2$ to $C_5$ alkanoyl)oxymethoxycarbonyl group, a benzoyloxymethoxycarbonyl group and a nicotinoyloxymethoxycarbonyl group, and $R^4$ and $R^5$ are each independently a hydrogen atom or a ($C_1$ to $C_4$ alkoxy) carbonyl group or $R^4$ and $R^5$ form, in combination thereof, —$CH_2CH_2OCH_2CH_2$— group, particularly preferably the case where $R^3$ is a group selected from the group consisting of a hydrogen atom, a hydroxyl group, a methoxycarbonyl group, an ethoxycarbonyl group, a propoxycarbonyl group, an isopropoxycarbonyl group, a butoxycarbonyl group, an isobutoxycarbonyl group, a t-butoxycarbonyl group, an isopropenyloxycarbonyl group, an acetoxymethoxycarbonyl group, a pivaloyloxymethoxycarbonyl group, a phenoxycarbonyl group, a 2-t-butoxyethoxycarbonyl group and a benzoyloxymethoxycarbonyl group, and $R^4$ and $R^5$ are each a hydrogen atom Incidentally, in the formula (a-1), when $R^4$ (or $R^5$) is a hydrogen atom, there exist tautomerism shown by the following formula:

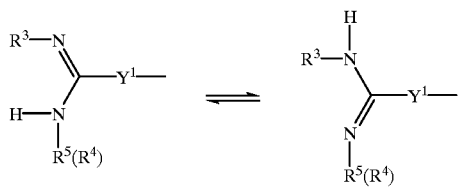

wherein $R^3$, $R^4$ and $R^5$ have the same meanings as defined above.

Thus, the substituent $R^3$ of the imino group and the substituent $R^5$ (or $R^4$) of the amino group can be mutually changed. Accordingly, the compounds mentioned below are nomenclatured without distinguishing both, but they include the above-mentioned two isomers.

As the substituent of the phenylene group of $Y^1$, there may be mentioned, for example, a halogen atom having the same meanings as defined above; a $C_1$ to $C_4$ alkyl group having the same meanings as defined above; or a $C_1$ to $C_4$ alkoxy group having the same meanings as defined above, preferably a halogen atom, a methyl group, an ethyl group, a methoxy group and an ethoxy group, more preferably a fluorine atom, a chlorine atom, a methyl group and a methoxy group, particularly preferably a fluorine atom and a chlorine atom.

As the 5- or 6-membered divalent heteroaromatic ring group containing 1 or 2 hetero atoms selected from the group consisting of O, N and S of $Y^1$, there may be mentioned, for example, a 5-membered heteroaromatic ring group such as a furandiyl group, a thiophendiyl group, a pyrroldiyl group, an oxazoldiyl group, an isoxazoldiyl group, a thiazoldiyl group, an isothiazoldiyl group, an imidazoldiyl group and a pyrazoldiyl group, etc., a 6-membered heteroaromatic ring group such as a pyridindiyl group, a pyridazindiyl group, a pyrimidindiyl group and a pyrazindiyl group, etc., preferably a 6-membered heteroaromatic ring group such as a pyridindiyl group, a pyridazindiyl group, a pyrimidindiyl group and a pyrazindiyl group, particularly preferably a pyridindiyl group.

As the phenylene group and a divalent heterocyclic group of $Y^1$, those having bonding arms at the positions of the second atom and the third atom on the ring are preferred. As $Y^1$, there may be specifically mentioned, for example, a 1,4-phenylene group; a 1,3-phenylene group; a 1,4-phenylene group substituted by a halogen atom, a $C_1$ to $C_4$ alkyl group or a $C_1$ to $C_4$ alkoxy group; a 2,4- or 2,5-furandiyl group; a 2,4- or 2,5-thiophendiyl group; a 2,4-pyrroldiyl group; a 2,4- or 2,5-oxazoldiyl group; a 3,5-isoxazoldiyl group, a 2,4- or 2,5-thiazoldiyl group, a 3,5-isothiazoldiyl group, a 2,4-imidazoldiyl group, a 3,5-pyrazoldiyl group; a 2,5-, 2,4- or 2,6-pyridindiyl group; a 3,5- or 3,6-pyridazindiyl group; a 2,4-, 2,5- or 4,6-pyrimidindiyl group; a 2,5- or 2,6-pyrazindiyl groups, preferably, a 1,4-phenylene group; a 1,4-phenylene group which is substituted by a fluorine atom, a chlorine atom, a methyl group or a methoxy group; a 2,5-pyridindiyl group; a 3,6-pyridazindiyl group; a 2,5-pyrimidindiyl group; and a 2,5-pyrazindiyl group, more preferably a 1,4-phenylene group; a 1,4-phenylene group which is substituted by a fluorine atom, a chlorine atom, a methyl group or a methoxy group; and a 2,5-pyridindiyl group, particularly preferably a 1,4-phenylene group; a 1,4-phenylene group which is substituted by a fluorine atom or a chlorine atom.

As the group represented by the formula (a-1), preferred groups are specifically mentioned, for example,
a 4-amidinophenyl group,
a 4-(N-hydroxyamidino)phenyl group,
a 4-(N-methylamidino)phenyl group,
a 4-(N-ethylamidino)phenyl group,
a 4-(N-propylamidino)phenyl group,
a 4-(N-acetylamidino)phenyl group,
a 4-(N-propanoylamidino)phenyl group,
a 4-(N-butanoylamidino)phenyl group,
a 4-(N-pivaloylamidino)phenyl group,
a 4-(N-acetoxymethylamidino)phenyl group,
a 4-(N-pivaloyloxymethylamidino)phenyl group,
a 4-(N-methoxycarbonylamidino)phenyl group,
a 4-(N-ethoxycarbonylamidino)phenyl group,
a 4-(N-propoxycarbonylamidino)phenyl group,
a 4-(N-isopropoxycarbonylamidino)phenyl group,
a 4-(N-butoxycarbonylamidino)phenyl group,
a 4-(N-isobutoxycarbonylamidino)phenyl group,
a 4-(N-t-butoxycarbonylamidino)phenyl group,
a 4-(N-pentyloxycarbonylamidino)phenyl group,
a 4-(N-hexyloxycarbonylamidino)phenyl group,
a 4-(N-cyclopentyloxy carbonylamidino)phenyl group,
a 4-(N-cyclohexyloxycarbonylamidino)phenyl group,
a 4-(N-vinyloxycarbonylamidino)phenyl group,
a 4-[N-(1-propenyloxy)carbonylamidino]phenyl group,
a 4-(N-allyloxycarbonylamidino)phenyl group,
a 4-(N-isopropenyloxycarbonylamidino)phenyl group,
a 4-[N-(1-methyl-1-propenyloxy)carbonylamidino]phenyl group,
a 4-(N-benzyloxycarbonylamidino)phenyl group,
a 4-(N-phenoxycarbonylamidino)phenyl group,
a 4-[N-(4-methylphenoxycarbonyl)amidino]phenyl group,
a 4-[N-(4-ethylphenoxycarbonyl)amidino]phenyl group,
a 4-[N-(4-propylphenoxycarbonyl)amidino]phenyl group,
a 4-[N-(4-isopropylphenoxycarbonyl)amidino]phenyl group,
a 4-[N-(4-butylphenoxycarbonyl)amidino]phenyl group,
a 4-[N-(4-isobutylphenoxycarbonyl)amidino]phenyl group,
a 4-[N-(4-methoxyphenoxycarbonyl)amidino]phenyl group,
a 4-[N-(4-ethoxylphenoxycarbonyl)amidino]phenyl group,
a 4-[N-(4-propoxyphenoxycarbonyl)amidino]phenyl group,
a 4-[N-(4-butoxyphenoxycarbonyl)amidino]phenyl group,
a 4-[N-(4-pentyloxyphenoxycarbonyl)amidino]phenyl group,
a 4-[N-(4-hexyloxyphenoxycarbonyl)amidino]phenyl group,
a 4-[N-(4-heptyloxyphenoxycarbonyl)amidino]phenyl group,
a 4-[N-(4-octyloxyphenoxycarbonyl)amidino]phenyl group,
a 4-[N-(2-methoxyethoxy)carbonylamidino]phenyl group,
a 4-[N-(2-ethoxyethoxy)carbonylamidino]phenyl group,
a 4-[N-(2-propoxyethoxy)carbonylamidino]phenyl group,
a 4-[N-(2-isopropoxyethoxy)carbonylamidino]phenyl group,
a 4-[N-(2-butoxyethoxy)carbonylamidino]phenyl group,
a 4-[N-(2-isobutoxyethoxy)carbonylamidino]phenyl group,
a 4-[N-(2-s-butoxyethoxy)carbonylamidino]phenyl group,
a 4-[N-(2-t-butoxyethoxy)carbonylamidino]phenyl group,
a 4-(N-acetoxymethoxycarbonylamidino)phenyl group,
a 4-(N-propanoyloxymethoxycarbonylamidino)phenyl group,
a 4-(N-butanoyloxymethoxycarbonylamidino)phenyl group,
a 4-(N-valeroyloxymethoxycarbonylamidino)phenyl group,
a 4-(N-pivaloyloxymethoxycarbonylamidino)phenyl group,
a 4-(N-hexanoyloxymethoxycarbonylamidino)phenyl group,
a 4-(N-benzoyloxymethoxycarbonylamidino)phenyl group,
a 4-(N-nicotinoyloxymethoxycarbonylamidino)phenyl group,
a 4-(N-isonicotinoyloxymethoxycarbonylamidino)phenyl group,
a 4-(N,N'-dimethoxycarbonylamidino)phenyl group,
a 4-(N,N'-diethoxycarbonylamidino)phenyl group,
a 4-(N,N'-dipropoxycarbonylamidino)phenyl group,
a 4-(N,N'-di-t-butoxycarbonylamidino)phenyl group,
a 4-(N,N,N'-trimethoxycarbonylamidino)phenyl group,
a 4-(N,N,N'-triethoxycarbonylamidino)phenyl group,
a 4-(N,N,N'-tripropoxycarbonylamidino)phenyl group,
a 4-(N,N,N'-tributoxycarbonylamidino)phenyl group,
a 4-(N,N,N'-tri-t-butoxycarbonylamidino)phenyl group,
a 4-amidino-2-fluorophenyl group,
a 4-amidino-2-chlorophenyl group,
a 4-amidino-2-methoxyphenyl group,
a 4-amidino-2-methylphenyl group,
a 4-amidino-3-fluorophenyl group,
a 4-amidino-3-chlorophenyl group,
a 4-amidino-3-methoxyphenyl group,
a 4-amidino-3-cethylphenyl group,
a 5-amidinopyridin-2-yl group,
a 2-amidinopyridin-5-yl group, 16
a 6-amidinopyridazin-3-yl group,
a 2-amidinopyrimidin-5-yl group,
a 5-amidinopyrimidin-2-yl group,
a 4-(N-hydroxyamidino)-2-fluorophenyl group,
a 4-(N-hydroxyamidino)-2-chlorophenyl group,
a 4-(N-hydroxyamidino)-2-methoxyphenyl group,
a 4-(N-hydroxyamidino)-2-methylphenyl group,
a 4-(N-hydroxyamidino)-3-fluorophenyl group,
a 4-(N-hydroxyamidino)-3-chlorophenyl group,
a 4-(N-methylamidino)-2-fluorophenyl group,
a 4-(N-methylamidino)-2-chlorophenyl group,
a 4-(N-methoxycarbonylamidino)-2-fluorophenyl group,
a 4-(N-methoxycarbonylamidino)-2-chlorophenyl group,
a 4-(N-ethoxycarbonylamidino)-2-fluorophenyl group,
a 4-(N-ethoxycarbonylamidino)-2-chlorophenyl group,
a 4-(N-ethoxycarbonylamidino)-2-methylphenyl group,
a 4-(N-ethoxycarbonylamidino)-2-methoxyphenyl group,
a 4-(N-ethoxycarbonylamidino)-3-fluorophenyl group,
a 4-(N-ethoxycarbonylamidino)-3-chlorophenyl group,
a 4-(N-propoxycarbonylamidino)-2-fluorophenyl group,
a 4-(N-butoxycarbonylamidino)-2-fluorophenyl group,
a 4-(N-isopropenyloxycarbonylamidino)-2-fluorophenyl group,
a 4-(N-phenoxycarbonylamidino)-2-fluorophenyl group,
a 4-(piperazinoimidoyl)phenyl group,
a 4-(morpholinoimidoyl)phenyl group,
a 4-(piperidinoimidoyl)phenyl group,
a 4-(N-benzylamidino)phenyl group,
a 4-[N-(2-pyridylcarbonyloxymethoxycarbonylamidino)] phenyl group,
a 4-(N,N-dimethylamidino)phenyl group,
a 4-(N,N'-dimethylamidino)phenyl group,
a 4-(N,N-diethylamidino)phenyl group,
a 4-(N,N'-dibutoxycarbonylamidino)phenyl group, a 4-(N-benzyl-N'-t-butoxycarbonylamidino)phenyl group,
a 4-(N-methyl-N'-t-butoxycarbonylamidino)phenyl group,
a 4-amidino-2-ethoxyphenyl group,
a 4-amidino-2-ethylphenyl group,
a 4-(N-methylamidino)-3-fluorophenyl group,
a 5-(N-ethoxycarbonylamidino)pyridin-2-yl group,
a 2-(N-ethoxycarbonylamidino)pyridin-5-yl group,
a 4-(pyrrolidinoimidoyl)phenyl group,
a 4-(N-t-butoxycarbonylmorpholinoimidoyl)phenyl group,
a 5-(N-hydroxyamidino)pyridin-2-yl group,
a 2-(N-hydroxyamidino)pyridin-5-yl group,
a 5-(N-propoxycarbonylamidino)pyridin-2-yl group,
a 2-(N-propoxycarbonylamidino)pyridin-5-yl group,
a 5-(N-butoxycarbonylamidino)pyridin-2-yl group,
a 2-(N-butoxycarbonylamidino)pyridin-5-yl group,
a 4-(N-phenoxycarbonylamidino)-2-methylphenyl group,
a 4-(N-phenoxycarbonylamidino)-2-methoxyphenyl group,
a 5-(N-phenoxycarbonylamidino)pyridin-2-yl group,
a 2-(N-phenoxycarbonylamidino)pyridin-5-yl group,
a 5-(N-benzoyloxymethoxycarbonylamidino)pyridin-2-yl group,
a 2-(N-benzoyloxymethoxycarbonylamidino)pyridin-5-yl group,
a 5-(N-isopropenyloxymethoxycarbonylamidino)pyridin-2-yl group,
a 2-(N-isopropenyloxymethoxycarbonylamidino)pyridin-5-yl group,
a 4-(N-isopropenyloxycarbonylamidino)-2-methylphenyl group,
a 4-(N-isopropenyloxycarbonylamidino)-2-methoxyphenyl group,
a 4-(N-benzoyloxymethoxycarbonylamidino)-2-methylphenyl group,
a 4-(N-benzoyloxymethoxycarbonylamidino)-2-methoxyphenyl group,
a 5-(N-benzyloxycarbonylamidino)pyridin-2-yl group,
a 2-(N-benzyloxycarbonylamidino)pyridin-5-yl group,
a 4-[N-(2-t-butoxyethoxy)carbonylamidino]-2-methylphenyl group,
a 4-[N-(2-t-butoxyethoxy)carbonylamidino]-2-methoxyphenyl group,
a 5-[N-(2-t-butoxyethoxy)carbonylamidino]pyridin-2-yl group,
a 2-[N-(2-t-butoxyethoxy)carbonylamidino]pyridin-5-yl group,
and the like,
more preferably
a 4-amidinophenyl group,
a 4-(N-hydroxyamidino)phenyl group,
a 4-(N-methylamidino)phenyl group,
a 4-(N-methoxycarbonylamidino)phenyl group,
a 4-(N-ethoxycarbonylamidino)phenyl group,
a 4-(N-propoxycarbonylamidino)phenyl group,
a 4-(N-isopropoxycarbonylamidino)phenyl group,
a 4-(N-butoxycarbonylamidino)phenyl group,
a 4-(N-isobutoxycarbonylamidino)phenyl group,
a 4-(N-t-butoxycarbonylamidino)phenyl group,
a 4-[N-(1-propenyloxy)carbonylamidino]phenyl group,
a 4-[N-(2-propenyloxy)carbonylamidino]phenyl group,
a 4-(N-isopropenyloxycarbonylamidino)phenyl group,
a 4-[N-(1-methyl-1-propenyloxy)carbonylamidino]phenyl group,
a 4-(N-phenoxycarbonylamidino)phenyl group,
a 4-[N-(4-methylphenoxycarbonyl)amidino]phenyl group,
a 4-[N-(4-ethylphenoxycarbonyl)amidino]phenyl group,
a 4-[N-(4-methoxyphenoxycarbonyl)amidino]phenyl group,
a 4-[N-(4-ethoxyphenoxycarbonyl)amidino]phenyl group,
a 4-[N-(4-propoxyphenoxycarbonyl)amidino]phenyl group,
a 4-[N-(4-butoxyphenoxycarbonyl)amidino]phenyl group,
a 4-[N-(2-ethoxyethoxy)carbonylamidino]phenyl group,
a 4-[N-(2-propoxyethoxy)carbonylamidino]phenyl group,
a 4-[N-(2-isopropoxyethoxy)carbonylamidino]phenyl group,
a 4-[N-(2-butoxyethoxy)carbonylamidino]phenyl group,
a 4-[N-(2-isobutoxyethoxy)carbonylamidino]phenyl group,
a 4-[N-(2-t-butoxyethoxy)carbonylamidino]phenyl group,
a 4-(N-acetoxymethoxycarbonylamidino)phenyl group,
a 4-(N-propanoyloxymethoxycarbonylamidino)phenyl group,
a 4-(N-butanoyloxymethoxycarbonylamidino)phenyl group,
a 4-(N-valeroyloxymethoxycarbonylamidino)phenyl group,
a 4-(N-pivaloyloxymethoxycarbonylamidino)phenyl group,
a 4-(N-benzoyloxymethoxycarbonylamidino)phenyl group,
a 4-(N-nicotinoyloxymethoxycarbonylamidino)phenyl group,
a 4-(N,N,N'-trimethoxycarbonylamidino)phenyl group,
a 4-(N,N,N'-triethoxycarbonylamidino)phenyl group,
a 4-(N,N,N'-tripropoxycarbonylamidino)phenyl group,
a 4-(N,N,N'-tributoxycarbonylamidino)phenyl group,
a 4-(N,N,N'-tri-t-butoxycarbonylamidino)phenyl group,
a 4-amidino-2-fluorophenyl group,
a 4-amidino-2-chlorophenyl group,
a 4-amidino-2-methoxyphenyl group,
a 4-amidino-2-methylphenyl group,
a 4-amidino-3-fluorophenyl group,
a 4-amidino-3-chlorophenyl group,
a 5-amidinopyridin-2-yl group,
a 2-amidinopyridin-5-yl group,
a 4-(N-hydroxyamidino)-2-fluorophenyl group,
a 4-(N-hydroxyamidino)-2-chorophenyl group,
a 4-(N-hydroxyamidino)-2-cethoxyphenyl group,
a 4-(N-hydroxyamidino)-2-methylphenyl group,
a 4-(N-hydroxyamidino)-3-fluorophenyl group,
a 4-(N-hydroxyamidino)-3-chlorophenyl group,
a 4-(N-methoxycarbonylamnidino)-2-fluorophenyl group,
a 4-(N-methoxycarbonylamidino)-2-chlorophenyl group,
a 4-(N-ethoxycarbonylamidino)-2-fluorophenyl group,
a 4-(N-ethoxycarbonylamidino)-2-chlorophenyl group,
a 4-(N-ethoxycarbonylamidino)-2-methyphenyl group,
a 4-(N-ethoxycarbonylamidino)-2-methoxyphenyl group,
a 4-(N-ethoxycarbonylamidino)-3-fluorophenyl group,
a 4-(N-ethoxycarbonylamidino)-3-chlorophenyl group,
a 4-(N-propoxycarbonylamidino)-2-fluorophenyl group,
a 4-(N-butoxycarbonylamidino)-2-fluorophenyl group,
a 4-(N-isopropenyloxy carbonylamidino)-2-fluorophenyl group,
a 4-(N-phenoxycarbonylamidino)-2-fluorophenyl group,
a 4-(morpholinoimidoyl)phenyl group,
and the like,
and further more preferably
a 4-amidinophenyl group,
a 4-(N-hydroxyamidino)phenyl group,
a 4-(N-methoxycarbonylamidino)phenyl group,
a 4-(N-ethoxycarbonylamidino)phenyl group,
a 4-(N-propoxycarbonylamidino)phenyl group,
a 4-(N-isopropoxycarbonylamidino)phenyl group,
a 4-(N-butoxycarbonylamidino)phenyl group,
a 4-(N-isobutoxycarbonylamidino)phenyl group,
a 4-(N-t-butoxycarbonylamidino)phenyl group,
a 4-(N-isopropenyloxycarbonylamidino)phenyl group,
a 4-(N-phenoxycarbonylamidino)phenyl group,
a 4-[N-(2-t-butoxyethoxy)carbonylamidino]phenyl group,
a 4-(N-acetoxymethoxycarbonylamidino)phenyl group,
a 4-(N-pivaloyloxymethoxycarbonylamidino)phenyl group, a 4-(N-benzoyloxymethoxycarbonylamidino)phenyl group,
a 4-(N,N,N'-tri-t-butoxycarbonylamidino)phenyl group,
a 4-amidino-2-fluorophenyl group,
a 4-amidino-2-chlorophenyl group,
a 4-amidino-2-methoxyphenyl group,
a 4-amidino-2-methylphenyl group,
a 5-amidinopyridin-2-yl group,
a 4-(N-hydroxyamidino)-2-fluorophenyl group,
a 4-(N-hydroxyamidino)-2-chlorophenyl group,
a 4-(N-hydroxyamidino)-2-methoxyphenyl group,
a 4-(N-hydroxyamidino)-2-methylphenyl group,
a 4-(N-methoxycarbonylamidino)-2-fluorophenyl group,
a 4-(N-methoxycarbonylamidino)-2-chlorophenyl group,
a 4-(N-ethoxycarbonylamidino)-2-fluorophenyl group,
a 4-(N-ethoxycarbonylamidino)-2-chlorophenyl group,
a 4-(N-ethoxycarbonylamidino)-2-methylphenyl group,
a 4-(N-ethoxycarbonylamidino)-2-methoxyphenyl group,
a 4-(N-isopropenyloxycarbonylamidino)-2-fluorophenyl group
and a 4-(N-phenoxycarbonylamidino)-2-fluorophenyl group.

Particularly preferred are
a 4-amidinophenyl group,
a 4-(N-hydroxyamidino)phenyl group,
a 4-(N-ethoxycarbonylamidino)phenyl group,
a 4-(N-propoxycarbonylamidino)phenyl group,
a 4-(N-isopropoxycarbonylamidino)phenyl group,
a 4-(N-butoxycarbonylamidino)phenyl group,
a 4-(N-isopropenyloxycarbonylamidino)phenyl group,
a 4-(N-phenoxycarbonylamidino)phenyl group,
a 4-[N-(2-t-butoxyethoxy)carbonylamidino]phenyl group,
a 4-(N-acetoxymethoxycarbonylamidino)phenyl group,
a 4-(N-pivaloyloxymethoxycarbonylamidino)phenyl group,
a 4-(N-benzoyloxymethoxycarbonylamidino)phenyl group,
a 4-amidino-2-fluorophenyl group,
a 4-amidino-2-chlorophenyl group,
a 4-amidino-2-methoxyphenyl group,
a 4-amidino-2-methylphenyl group,
a 4-(N-hydroxyamidino)-2-fluorophenyl group,
a 4-(N-hydroxyamidino)-2-chlorophenyl group,
a 4-(N-hydroxyamidino)-2-methoxyphenyl group,
a 4-(N-hydroxyamidino)-2-methylphenyl group and
a 4-(N-ethoxycarbonylamidino)-2-fluorophenyl group.

As $R^6$ shown in the formula (a-2) as A in the formula (I), there may be mentioned, for example, a hydrogen atom; a $C_1$ to $C_4$ alkyl group having the same meanings as defined above; a $C_7$ to $C_{10}$ aralkyl group having the same meanings as defined above; a $C_1$ to $C_6$ alkanoyl group having the same meanings as defined above; a ($C_2$ to $C_6$ alkanoyl)oxymethyl group having the same meanings as defined above; a ($C_1$ to $C_4$ alkoxy)carbonyl group; etc., preferably a hydrogen atom, a methyl group, an ethyl group, an acetyl group, a propanoyl group, a butanoyl group, an acetoxymethyl group, a propanoyloxymethyl group, a pivaloyloxymethyl group, a methoxycarbonyl group, an ethoxycarbonyl group, a propoxycarbonyl group, an isopropoxycarbonyl group, a butoxycarbonyl group, an isobutoxycarbonyl group, a s-butoxycarbonyl group, and a t-butoxycarbonyl group, more preferably a hydrogen atom, an acetoxymethyl group, a pivaloyloxymethyl group, a methoxycarbonyl group, an ethoxycarbonyl group, a propoxycarbonyl group, an isopropoxycarbonyl group, a butoxycarbonyl group, a t-butoxycarbonyl group, particularly preferably a hydrogen atom, an acetoxymethyl group and a pivaloyloxymethyl group.

As X shown in the formula (a-2) of A in the formula (I), there may be mentioned, for example, a nitrogen atom and a >CH— group,
preferably a >CH— group.

As n shown in the formula (a-2) of A in the formula (I), it is, for example, 1, 2 or 3, preferably 1 or 2, particulaly preferably 2.

As $Y^2$ shown in the formula (a-2) of A in the formula (I), there may be mentioned, for example, a —CH$_2$— group, a —CH$_2$CH$_2$— group, a —CH$_2$CH$_2$CH$_2$— group, a —CH=CH— group (cis or trans), a —C≡C— group, a —CH$_2$—CH=CH— group (cis or trans), a —CH=CH—CH$_2$— group (cis or trans), a —CH$_2$—C≡C— group, a —C≡C—CH$_2$— group, a —OCH$_2$— group, a —SCH$_2$— group, a —OCH$_2$CH$_2$— group, a —CH$_2$OCH$_2$— group, a —SCH$_2$CH$_2$— group or a —CH$_2$SCH$_2$— group (provided that when X is a nitrogen atom, it is not a —OCH$_2$— group, a —C≡C— group, a —C≡C—CH$_2$— group or a —OCH$_2$CH$_2$— group),
preferably a —CH$_2$CH$_2$— group, a —CH$_2$CH$_2$CH$_2$— group, a —CH=CH— group, a —OCH$_2$— group or a —CH$_2$OCH$_2$— group,
more preferably a —CH$_2$CH$_2$— group or a —OCH$_2$— group, and
particularly preferably a —OCH$_2$— group.

As a preferred group of the group shown by the formula (a-2), there may be specifically mentioned a 2-(4-piperidyl)ethyl group, a 3-(4-piperidyl)propyl group, a 2-(4-piperidyl)vinyl group, a (4-piperidyloxy)methyl group, a (4-piperidylmethoxy)methyl group, a 2-(3-pyrrolidinyl)ethyl group, a 3-(3-pyrrolidinyl)propyl group, a (3-pyrrolidinylmethoxy)methyl group, a 2-(1-piperazinyl)ethyl group, a 3-(1-piperazinyl)propyl group, a 2-(1-methyl-4-piperidyl)ethyl group, a (1-methyl-4-piperidyloxy)methyl group, a 2-(1-methyl-3-pyrrolidinyl)ethyl group, a (1-methyl-3-pyrrolidinyloxy)methyl group, a 2-(1-acetyl-4-piperidyl)ethyl group, a (1-acetyl-4-piperidyloxy)methyl group, a 2-(1-propanoyl-4-piperidyl)ethyl group, a 2-(1-acetoxymethyl-4-piperidyl)ethyl group, a 3-(1-acetoxymethyl-4-piperidyl)propyl group, a 2-(1-acetoxymethyl-4-piperidyl)vinyl group, a (1-acetoxymethyl-4-piperidyloxy)methyl group, a 2-(1-pivaloyloxymethyl-4-piperidyl)ethyl group, a 3-(1-pivaloyloxymethyl-4-piperidyl)propyl group, a (1-pivaloyloxymethyl-4-piperidyloxy)methyl group, a 2-(1-methoxycarbonyl-4-piperidyl)ethyl group, a (1-methoxycarbonyl-4-piperidyloxy)methyl group, a 2-(1-ethoxycarbonyl-4-piperidyl)ethyl group, a 3-(1-ethoxycarbonyl-4-piperidyl)propyl group, a (1-ethoxycarbonyl-4-piperidyloxy)methyl group, a 2-(1-propoxycarbonyl-4-piperidyl)ethyl group, a (1-propoxycarbonyl-4-piperidyloxy)methyl group, a 2-(1-isopropoxycarbonyl-4-piperidyl)ethyl group, a (1-isopropoxycarbonyl-4-piperidyloxy)methyl group, a 2-(1-butoxycarbonyl-4-piperidyl)ethyl group, a (1-butoxycarbonyl-4-piperidyloxy)methyl group, a 2-(1-t-butoxycarbonyl-4-piperidyl)ethyl group and a (1-t-butoxycarbonyl-4-piperidyloxy)methyl group,
more preferably a 2-(4-piperidyl)ethyl group, a (4-piperidyloxy)methyl group, a 2-(1-acetyl-4-piperidyl)ethyl group, a (1-acetyl-4-piperidyloxy)methyl group, a 2-(1-acetoxymethyl-4-piperidyl)ethyl group, a (1-acetoxymethyl-4-piperidyloxy)methyl group, a 2-(1-pivaloyloxymethyl-4-piperidyl)ethyl group, a (1-pivaloyloxymethyl-4-piperidyloxy)methyl group, a 2-(1-methoxycarbonyl-4-piperidyl)ethyl group, a (1-methoxycarbonyl-4-piperidyloxy)methyl group, a 2-(1-ethoxycarbonyl-4-piperidyl)ethyl group, a (1-ethoxycarbonyl-4-piperidyloxy)methyl group, a 2-(1-propoxycarbonyl-4-piperidyl)ethyl group, a (1-propoxycarbonyl-4-piperidyloxy)methyl group, a 2-(1-t-butoxycarbonyl-4-piperidyl)ethyl group and a (1-t-butoxycarbonyl-4-piperidyloxy)methyl group, particularly preferably a 2-(4-piperidyl)ethyl group, a (4-piperidyloxy)methyl group, a 2-(1-acetoxymethyl-4-piperidyl)ethyl group, a (1-acetoxymethyl-4-piperidyloxy)methyl group, a 2-(1-pivaloyloxymethyl-4-piperidyl)ethyl group and a (1-pivaloyloxymethyl-4-piperidyloxy)methyl group.

As a heteroaromatic ring containing one or two hetero atoms selected from N, O and S which is formed by $A^1$, $A^2$, $A^3$, $A^4$ and $A^5$ in the compound represented by the formula (b) and the general formula (II) (hereinafter also referred to as Compound (II)), there may be mentioned, for example,
(1) a furan ring where $A^1=A^2=A^4=A^5=C$ and $A^3=O$,
(2) a furan ring where $A^1=A^2=A^3=A^5=C$ and $A^4=O$,
(3) a thiophene ring where $A^1=A^2=A^4=A^5=C$ and $A^3=S$,
(4) a thiophene ring where $A^1=A^2=A^3=A^5=C$ and $A^4=S$,
(5) a pyrrole ring where $A^1=A^3=A^4=A^5=C$ and $A^2=N$,
(6) a pyrrole ring where $A^1=A^2=A^4=A^5=C$ and $A^3=N$,
(7) a pyrrole ring where $A^1=A^2=A^3=A^5=C$ and $A^4=N$,
(8) an oxazole ring where $A^1=A^2=A^4=C$, $A^3=O$ and $A^5=N$,
(9) a thiazole ring where $A^1=A^2=A^4=C$, $A^3=S$ and $A^5=N$,
(10) a pyrazole ring where $A^1=A^4=A^5=C$ and $A^2=A^3=N$,
(11) a pyrazole ring where $A^1=A^2=A^5=C$ and $A^3=A^4=N$,
(12) an imidazole ring where $A^1=A^3=A^5=C$ and $A^2=A^4=N$,
(13) an imidazole ring where $A^1=A^3=A^4=C$ and $A^2=A^5=N$, and
(14) an imidazole ring where $A^1=A^2=A^4=C$ and $A^3=A^5=N$, preferably the heteroaromatic ring shown by the above-mentioned (1), (3), (6), (7), (8), (9), (11) and (14), more preferably the heteroaromatic ring shown by (3), (6), (7), (9) and (11). Incidentally, in the case of the pyrazole ring of (11) and the imidazole ring of (14), there exist two isomers in which the position of the double bond is different from each other (that is, in the case of the pyrazole ring, a pyrazole ring in which the bonds of $A^1-A^2$ and $A^4-A^5$ are double bonds and a pyrazole ring in which the bonds of $A^2-A^3$ and $A^1-A^5$ are double bonds, and in the case of the imidazole ring, an imidazole ring in which the bonds of $A^1-A^2$ and $A^3-A^4$ are double bonds and an imidazole ring in which the bonds of $A^1-A^2$ and $A^4-A^5$ are double bonds), and these both of the isomers are included.

As the position of the —$CH_2Z$ group to be bound, it may be either of $A^3$, $A^4$ or $A^5$ so long as it is the position capable of binding, preferably the position of $A^3$ or $A^4$, more preferably the position of $A^4$.

The above-mentioned heteroaromatic ring may have a further substituent $R^9$, if possible, and $R^9$ may include, for example, a $C_1$ to $C_4$ alkyl group having the same meanings as defined above; a $C_1$ to $C_4$ alkoxy group having the same meanings as defined above, a hydroxyl group, a trifluoromethyl group or a ($C_7$ to $C_{10}$)aralkyloxycarbonyl group having the same meanings as defined above, preferably a methyl group, an ethyl group, a propyl group, a methoxy group, an ethoxy group, a benzyloxycarbonyl group, a hydroxyl group or a trifluoromethyl group, more preferably a methyl group, an ethyl group, a methoxy group or a trifluoromethyl group, and particularly preferably a methyl group.

As o and p, preferred is the case where o=1 and p=0 or o=0 and p=1, more preferably the case where o=0 and p=1.

As $R^7$ and $R^8$ in the formula (b) and the general formula (II), they are both hydrogen atoms or a $C_2$ to $C_3$ alkylene group formed by them in conbination, and as the $C_2$ to $C_3$ alkylene group, there may be mentioned, for example, an ethylene, trimethylene groups, preferably an ethylene group.

As $R^7$ and $R^8$, preferably they are both hydrogen atoms or an ethylene group in which they are in combination thereof.

Preferred groups of the formula (b) may specifically yinclude:

a 2-$CH_2Z$ group-substituted-4,5,6,7-tetrahydrofuro[3,2-c]pyridin-5-yl group, a 2-$CH_2Z$ group-substituted-4,5,6,7-tetrahydrofuro[2,3-c]pyridin-6-yl group, a 2-$CH_2Z$ group-substituted-4,5,6,7-tetrahydrothieno[3,2-c]pyridin-5-yl group, a 2-$CH_2Z$ group-substituted-4,5,6,7-tetrahydrothieno[2,3-c]pyridin-6-yl group, a (1- or 2-$CH_2Z$ group-substituted)-4,5,6,7-tetrahydropyrrolo[3,2-c]pyridin-5-yl group, a 2-$CH_2Z$ group-substituted-4,5,6,7-tetrahydropyrrolo[3,4-c]pyridin-5-yl group, a (1- or 2-$CH_2Z$ group-substituted)-4,5,6,7-tetrahydropyrrolo[2,3-c]pyridin-6-yl group, a 2-$CH_2Z$ group-substituted-4,5,6,7-tetrahydroxazolo[5,4-c]pyridin-6-yl group, a 2-$CH_2Z$ group-substituted-4,5,6,7-tetrahydroxazolo[4,5-c]pyridin-5-yl group, a 2-$CH_2Z$ group-substituted-4,5,6,7-tetrahydrothiazolo[5,4-c]pyridin-6-yl group, a 2-$CH_2Z$ group-substituted-4,5,6,7-tetrahydrothiazolo[4,5-c]pyridin-5-yl group, a 2-$CH_2Z$ group-substituted-4,5,6,7-tetrahydropyrazolo[4,3-c]pyridin-5-yl group, a 2-$CH_2Z$ group-substituted-4,5,6,7-tetrahydropyrazolo[3,4-c]pyridin-6-yl group, a 1-$CH_2Z$ group-substituted-4,5,6,7-tetrahydropyrazolo[4,5-c]pyridin-5-yl group, a 1-$CH_2Z$ group-substituted-4,5,6,7-tetrahydropyrazolo[5,4-c]pyridin-6-yl group, a (1- or 2-$CH_2Z$ group-substituted)-4,5,6,7-tetrahydroimidazo[4,5-c]pyridin-5-yl group, a 1-$CH_2Z$ group-substituted-4,5,6,7-tetrahydroimidazo[5,4-c]pyridin-6-yl group, a 2-$CH_2Z$ group-substituted-4,6-ethano-4,5,6,7-tetrahydrofuro[3,2-c]pyridin-5-yl group, a 2-$CH_2Z$ group-substituted-5,7-ethano-4,5,6,7-tetrahydrofuro[2,3-c]pyridin-6-yl group, a 2-$CH_2Z$ group-substituted-4,6-ethano-4,5,6,7-tetrahydrothieno[3,2-c]pyridin-5-yl group, a 2-$CH_2Z$ group-substituted-5,7-ethano-4,5,6,7-tetrahydrothieno[2,3-c]pyridin-6-yl group, a (1- or 2-$CH_2Z$ group-substituted)-4,6-ethano-4,5,6,7-tetrahydropyrrolo[3,2-c]pyridin-5-yl group, a 2-$CH_2Z$ group-substituted-4,6-ethano-4,5,6,7-tetrahydropyrrolo[3,4-c]pyridin-5-yl group, a (1- or 2-$CH_2Z$ group-substituted)-5,7-ethano-4,5,6,7-tetrahydropyrrolo[2,3-c]pyridin-6-yl group, a 2-$CH_2Z$ group-substituted-5,7-ethano-4,5,6,7-tetrahydroxazolo[5,4-c]pyridin-6-yl group, a 2-CH₂Z group-substituted-4,6-ethano-4,5,6,7-tetrahydroxazolo[4,5-c]pyridin-5-yl group, a 2-CH₂Z group-substituted-5,7-ethano-4,5,6,7-tetrahydrothiazolo[5,4-c]pyridin-6-yl group, a 2-CH₂Z group-substituted-4,6-ethano-4,5,6,7-tetrahydrothiazolo[4,5-c]pyridin-5-yl group, a 2-CH₂Z group-substituted-4,6-ethano-4,5,6,7-tetrahydropyrazolo[4,3-c]pyridin-5-yl group, a 2-CH₂Z group-substituted-5,7-ethano-4,5,6,7-tetrahydropyrazolo[3,4-c]pyridin-6-yl group, a 1-CH₂Z group-substituted-4,6-ethano-4,5,6,7-tetrahydropyrazolo[4,5-c]pyridin-5-yl group, a 1-CH₂Z group-substituted-5,7-ethano-4,5,6,7-tetrahydropyrazolo[5,4-c]pyridin-6-yl group, a (1- or 2-CH₂Z group-substituted)-4,6-ethano-4,5,6,7-tetrahydroimidazo[4,5-c]pyridin-5-yl group, a 1-CH₂Z group-substituted-5,7-ethano-4,5,6,7-tetrahydroimidazo[5,4-c]pyridin-6-yl group, a 2-CH₂Z group-substituted-3-methyl-4,5,6,7-tetrahydrothieno[3,2-c]pyridin-5-yl group, a 2-CH₂Z group-substituted-3-methyl-4,5,6,7-tetrahydrothieno[2,3-c]pyridin-6-yl group, a 2-CH₂Z group-substituted-1-methyl-4,5,6,7-tetrahydropyrrolo[3,2-c]pyridin-5-yl group, a 2-CH₂Z group-substituted-3-methyl-4,5,6,7-tetrahydropyrrolo[3,2-c]pyridin-5-yl group, a 2-CH₂Z group-substituted-1-methyl-4,5,6,7-tetrahydropyrrolo[3,4-c]pyridin-5-yl group, a 2-CH₂Z group-substituted-3-methyl-4,5,6,7-tetrahydropyrrolo[3,4-c]pyridin-5-yl group, a 2-CH₂Z group-substituted-1-methyl-4,5,6,7-tetrahydropyrrolo[2,3-c]pyridin-6-yl group, a 2-CH₂Z group-substituted-3-methyl-4,5,6,7-tetrahydropyrrolo[2,3-c]pyridin-6-yl group, a 2-CH₂Z group-substituted-3-methyl-4,5,6,7-tetrahydropyrazolo[4,3-c]pyridin-5-yl group, a 1-CH₂Z group-substituted-3-methyl-4,5,6,7-tetrahydropyrazolo[4,5-c]pyridin-5-yl group, a 2-CH₂Z group-substituted-3-methyl-4,5,6,7-tetrahydropyrazolo[3,4-c]pyridin-6-yl group, a 2-CH₂Z group-substituted-3-methyl-4,6-ethano-4,5,6,7-tetrahydrothieno[3,2-c]pyridin-5-yl group, a 2-CH₂Z group-substituted-1-methyl-4,6-ethano-4,5,6,7-tetrahydropyrrolo[3,2-c]pyridin-5-yl group, a 2-CH₂Z group-substituted-1-methyl-4,6-ethano-4,5,6,7-tetrahydropyrrolo[3,4-c]pyridin-5-yl group, a 2-CH₂Z group-substituted-3-methyl-4,6-ethano-4,5,6,7-tetrahydropyrrolo[3,4-c]pyridin-5-yl group, a 2-CH₂Z group-substituted-3-methyl-4,6-ethano-4,5,6,7-tetrahydropyrazolo[4,3-c]pyridin-5-yl group, a 2-CH₂Z group-substituted-3-methyl-5,7-ethano-4,5,6,7-tetrahydropyrazolo[3,4-c]pyridin-6-yl group, a 1-CH₂Z group-substituted-3-methyl-4,6-ethano-4,5,6,7-tetrahydropyrazolo[4,5-c]pyridin-5-yl group, a 2-CH₂Z group-substituted-3-ethyl-4,5,6,7-tetrahydrothieno[3,2-c]pyridin-5-yl group, a 2-CH₂Z group-substituted-3-ethyl-4,5,6,7-tetrahydrothieno[2,3-c]pyridin-6-yl group, a 2-CH₂Z group-substituted-1-ethyl-4,5,6,7-tetrahydropyrrolo[3,4-c]pyridin-5-yl group, a 2-CH₂Z group-substituted-3-ethyl-4,5,6,7-tetrahydropyrrolo[3,4-c]pyridin-5-yl group, a 2-CH₂Z group-substituted-3-ethyl-4,5,6,7-tetrahydropyrazolo[4,3-c]pyridin-5-yl group, a 1-CH₂Z group-substituted-3-ethyl-4,5,6,7-tetrahydropyrazolo[4,5-c]pyridin-5-yl group, a 2-CH₂Z group-substituted-3-ethyl-4,6-ethano-4,5,6,7-tetrahydrothieno[3,2-c]pyridin-5-yl group, a 2-CH₂Z group-substituted-1-ethyl-4,6-ethano-4,5,6,7-tetrahydropyrrolo[3,4-c]pyridin-5-yl group, a 2-CH₂Z group-substituted-3-ethyl-4,6-ethano-4,5,6,7-tetrahydropyrrolo[3,4-c]pyridin-5-yl group, a 2-CH₂Z group-substituted-3-ethyl-4,6-ethano- 4,5,6,7-tetrahydropyrazolo[4,3-c]pyridin-5-yl group, a 2-CH₂Z group-substituted-3-propyl-4,5,6,7-tetrahydrothieno[3,2-c]pyridin-5-yl group, a 2-CH₂Z group-substituted-3-propyl-4,5,6,7-tetrahydrothieno[2,3-c]pyridin-6-yl group, a 2-CH₂Z group-substituted-1-propyl-4,5,6,7-tetrahydropyrrolo[3,4-c]pyridin-5-yl group, a 2-CH₂Z group-substituted-3-propyl-4,5,6,7-tetrahydropyrrolo[3,4-c]pyridin-5-yl group,.

a 2-CH₂Z group-substituted-3-propyl-4,5,6,7-tetrahydropyrazolo[4,3-c]pyridin-5-yl group, a 1-CH₂Z group-substituted-3-propyl-4,5,6,7-tetrahydropyrazolo[4,5-c]pyridin-5-yl group, a 2-CH₂Z group-substituted-3-propyl-4,6-ethano-4,5,6,7-tetrahydrothieno[3,2-c]pyridin-5-yl group, a 2-CH₂Z group-substituted-1-propyl-4,6-ethano-4,5,6,7-tetrahydropyrrolo[3,4-c]pyridin-5-yl group, a 2-CH₂Z group-substituted-3-propyl-4,6-ethano-4,5,6,7-tetrahydropyrrolo[3,4-c]pyridin-5-yl group, a 2-CH₂Z group-substituted-3-propyl-4,6-ethano-4,5,6,7-tetrahydropyrazolo[4,3-c]pyridin-5-yl group, a 2-CH₂Z group-substituted-3-trifluoromethyl-4,5,6,7-tetrahydrothieno[3,2-c]pyridin-5-yl group, a 2-CH₂Z group-substituted-3-trifluoromethyl-4,5,6,7-tetrahydrothieno[2,3-c]pyridin-6-yl group, a 2-CH₂Z group-substituted-1-trifluoromethyl-4,5,6,7-tetrahydropyrrolo[3,4-c]pyridin-5-yl group, a 2-CH₂Z group-substituted-3-trifluoromethyl-4,5,6,7-tetrahydropyrrolo[3,4-c]pyridin-5-yl group, a 2-CH₂Z group-substituted-3-trifluoromethyl-4,5,6,7-tetrahydropyrazolo[4,3-c]pyridin-5-yl group, a 2-CH₂Z group-substituted-3-trifluoromethyl-4,6-ethano-4,5,6,7-tetrahydrothieno[3,2-c]pyridin-5-yl group, a 2-CH₂Z group-substituted-3-trifluoromethyl-4,6-ethano-4,5,6,7-tetrahydropyrazolo[4,3-c]pyridin-5-yl group, a 2-CH₂Z group-substituted-3-trifluoromethyl-5,7-ethano- 4,5,6,7-tetrahydropyrazolo[3,4-c]pyridin-6-yl group, a 2-CH₂Z group-substituted-3-hydroxy-4,5,6,7-tetrahydropyrazolo[4,3-c]pyridin-5-yl group, a 2-CH₂Z group-substituted-3-hydroxy-4,5,6,7-tetrahydropyrazolo[3,4-c]pyridin-6-yl group, a 2-CH₂Z group-substituted-3-methoxy-4,5,6,7-tetrahydropyrazolo[4,3-c]pyridin-5-yl group, a 2-CH₂Z group-substituted-3-methoxy-4,5,6,7-tetrahydropyrazolo[3,4-c]pyridin-6-yl group, a 2-CH₂Z group-substituted-3-hydroxy-4,6-ethano-4,5,6,7-tetrahydropyrazolo[4,3-c]pyridin-5-yl group, a 2-CH₂Z group-substituted-3-hydroxy-5,7-ethano-4,5,6,7-tetrahydropyrazolo[3,4-c]pyridin-6-yl group, a 2-CH$_2$Z group-substituted-3-methoxy-4,6-ethano-4,5,6,7-tetrahydropyrazolo[4,3-c]pyridin-5-yl group, a 2-CH$_2$Z group-substituted-3-methoxy-5,7-ethano-4,5,6,7-tetrahydropyrazolo[3,4-c]pyridin-6-yl group, more preferably a 2-CH$_2$Z group-substituted-4,5,6,7-tetrahydrothieno[3,2-c]pyridin-5-yl group, a 2-CH$_2$Z group-substituted-4,5,6,7-tetrahydrothieno[2,3-c]pyridin-6-yl group, a 2-CH$_2$Z group-substituted-4,5,6,7-tetrahydropyrrolo[3,2-c]pyridin-5-yl group, a 2-CH$_2$Z group-substituted-4,5,6,7-tetrahydropyrrolo[3,4-c]pyridin-5-yl group, a 2-CH$_2$Z group-substituted-4,5,6,7-tetrahydrothiazolo[5,4-c]pyridin-6-yl group, a 2-CH$_2$Z group-substituted-4,5,6,7-tetrahydrothiazolo[4,5-c]pyridin-5-yl group, a 2-CH$_2$Z group-substituted-4,5,6,7-tetrahydropyrazolo[4,3-c]pyridin-5-yl group, a 2-CH$_2$Z group-substituted-4,5,6,7-tetrahydropyrazolo[3,4-c]pyridin-6-yl group, a 1-CH$_2$Z group-substituted-4,5,6,7-tetrahydropyrazolo[4,5-c]pyridin-5-yl group, a 2-CH$_2$Z group-substituted-4,6-ethano-4,5,6,7-tetrahydrothieno[3,2-c]pyridin-5-yl group, a 2-CH$_2$Z group-substituted-5,7-ethano-4,5,6,7-tetrahydrothieno[2,3-c]pyridin-6-yl group, a 2-CH$_2$Z group-substituted-4,6-ethano-4,5,6,7-tetrahydropyrrolo[3,2-c]pyridin-5-yl group, a 2-CH$_2$Z group-substituted-4,6-ethano-4,5,6,7-tetrahydropyrrolo[3,4-c]pyridin-5-yl group, a 2-CH$_2$Z group-substituted-5,7-ethano-4,5,6,7-tetrahydrothiazolo[5,4-c]pyridin-6-yl group, a 2-CH$_2$Z group-substituted-4,6-ethano-4,5,6,7-tetrahydropyrazolo[4,3-c]pyridin-5-yl group, a 1-CH$_2$Z group-substituted-4,6-ethano-4,5,6,7-tetrahydropyrazolo[4,5-c]pyridin-5-yl group, a 2-CH$_2$Z group-substituted-3-methyl-4,5,6,7-tetrahydrothieno[3,2-c]pyridin-5-yl group, a 2-CH$_2$Z group-substituted-1-methyl-4,5,6,7-tetrahydropyrrolo[3,2-c]pyridin-5-yl group, a 2-CH$_2$Z group-substituted-1-methyl-4,5,6,7-tetrahydropyrrolo[3,4-c]pyridin-5-yl group, a 2-CH$_2$Z group-substituted-3-methyl-4,5,6,7-tetrahydropyrrolo[3,4-c]pyridin-5-yl group, a 2-CH$_2$Z group-substituted-3-methyl-4,5,6,7-tetrahydropyrazolo[4,3-c]pyridin-5-yl group, a 2-CH$_2$Z group-substituted-3-methyl-4,5,6,7-tetrahydropyrazolo[3,4-c]pyridin-6-yl group, a 1-CH$_2$Z group-substituted-3-methyl-4,5,6,7-tetrahydropyrazolo[4,5-c]pyridin-5-yl group, a 2-CH$_2$Z group-substituted-1-methyl-4,6-ethano-4,5,6,7-tetrahydropyrrolo[3,2-c]pyridin-5-yl group, a 2-CH$_2$Z group-substituted-1-methyl-4,6-ethano-4,5,6,7-tetrahydropyrrolo[3,4-c]pyridin-5-yl group, a 2-CH$_2$Z group-substituted-3-methyl-4,6-ethano-4,5,6,7-tetrahydropyrrolo[3,4-c]pyridin-5-yl group, a 2-CH$_2$Z group-substituted-3-methyl-4,6-ethano-4,5,6,7-tetrahydropyrazolo[4,3-c]pyridin-5-yl group, a 1-CH$_2$Z group-substituted-3-methyl-4,6-ethano-4,5,6,7-tetrahydropyrazolo[4,5-c]pyridin-5-yl group, a 2-CH$_2$Z group-substituted-3-methyl-4,6-ethano-4,5,6,7-tetrahydrothieno[3,2-c]pyridin-5-yl group, a 2-CH$_2$Z group-substituted-3-ethyl-4,5,6,7-tetrahydrothieno[3,2-c]pyridin-5-yl group, a 2-CH$_2$Z group-substituted-3-ethyl-4,5,6,7-tetrahydropyrazolo[4,3-c]pyridin-5-yl group, a 2-CH$_2$Z group-substituted-3-propyl-4,5,6,7-tetrahydrothieno[3,2-c]pyridin-5-yl group, a 2-CH$_2$Z group-substituted-3-propyl-4,5,6,7-tetrahydropyrazolo[4,3-c]pyridin-5-yl group, a 2-CH$_2$Z group-substituted-3-trifluoromethyl-4,5,6,7-tetrahydrothieno[3,2-c]pyridin-5-yl group, a 2-CH$_2$Z group-substituted-3-trifluoromethyl-4,5,6,7-tetrahydropyrazolo[4,3-c]pyridin-5-yl group, a 2-CH$_2$Z group-substituted-3-hydroxy-4,5,6,7-tetrahydropyrazolo[4,3-c]pyridin-5-yl group, a 2-CH$_2$Z group-substituted-3-hydroxy-4,5,6,7-tetrahydropyrazolo[3,4-c]pyridin-6-ylgroup, a 2-CH$_2$Z group-substituted-3-methoxy-4,5,6,7-tetrahydropyrazolo[4,3-c]pyridin-5-yl group, a 2-CH$_2$Z group-substituted-3-methoxy-4,5,6,7-tetrahydropyrazolo[3,4-c]pyridin-6-yl group, a 2-CH$_2$Z group-substituted-3-hydroxy-4,6-ethano-4,5,6,7-tetrahydropyrazolo[4,3-c]pyridin-5-yl group, a 2-CH$_2$Z group-substituted-3-hydroxy-5,7-ethano-4,5,6,7-tetrahydropyrazolo[3,4-c]pyridin-6-yl group, a 2-CH$_2$Z group-substituted-3-methoxy-4,6-ethano-4,5,6,7-tetrahydropyrazolo[4,3-c]pyridin-5-yl group, and a 2-CH$_2$Z group-substituted-3-methoxy-5,7-ethano-4,5,6,7-tetrahydropyrazolo[3,4-c]pyridin-6-yl group, further more preferably a 2-CH$_2$Z group-substituted-4,5,6,7-tetrahydrothieno[3,2-c]pyridin-5-yl group, a 2-CH$_2$Z group-substituted-4,5,6,7-tetrahydropyrrolo[3,2-c]pyridin-5-yl group, a 2-CH$_2$Z group-substituted-4,5,6,7-tetrahydropyrrolo[3,4-c]pyridin-5-yl group, a 2-CH$_2$Z group-substituted-4,5,6,7-tetrahydrothiazolo[5,4-c]pyridin-6-yl group, a 2-CH$_2$Z group-substituted-4,5,6,7-tetrahydropyrazolo[4,3-c]pyridin-5-yl group, a 1-CH$_2$Z group-substituted-4,5,6,7-tetrahydropyrazolo[4,5-c]pyridin-5-yl group, a 2-CH$_2$Z group-substituted-4,6-ethano-4,5,6,7-tetrahydrothieno[3,2-c]pyridin-5-yl group, a 2-CH$_2$Z group-substituted-4,6-ethano-4,5,6,7-tetrahydropyrrolo[3,2-c]pyridin-5-yl group, a 2-CH$_2$Z group-substituted-4,6-ethano-4,5,6,7-tetrahydropyrrolo[3,4-c]pyridin-5-yl group, a 2-CH$_2$Z group-substituted-5,7-ethano-4,5,6,7-tetrahydrothiazolo[5,4-c]pyridin-6-yl group, a 2-CH$_2$Z group-substituted-4,6-ethano-4,5,6,7-tetrahydropyrazolo[4,3-c]pyridin-5-yl group, a 1-CH$_2$Z group-substituted-4,6-ethano-4,5,6,7-tetrahydropyrazolo[4,5-c]pyridin-5-yl group, a 2-CH$_2$Z group-substituted-3-methyl-4,5,6,7-tetrahydrothieno[3,2-c]pyridin-5-yl group, a 2-CH$_2$Z group-substituted-1-methyl-4,5,6,7-tetrahydropyrrolo[3,2-c]pyridin-5-yl group, a 2-CH$_2$Z group-substituted-1-methyl-4,5,6,7-tetrahydropyrrolo[3,4-c]pyridin-5-yl group, a 2-CH$_2$Z group-substituted-3-methyl-4,5,6,7-tetrahydropyrrolo[3,4-c]pyridin-5-yl group, a 2-CH$_2$Z group-substituted-3-methyl-4,5,6,7-tetrahydropyrazolo[4,3-c]pyridin-5-yl group, a 1-CH$_2$Z group-substituted-3-methyl-4,5,6,7-tetrahydropyrazolo[4,5-c]pyridin-5-yl group, a 2-CH$_2$Z group-substituted-1-methyl-4,6-ethano-4,5,6,7-tetrahydropyrrolo[3,2-c]pyridin-5-yl group, a 2-CH$_2$Z group-substituted-1-methyl-4,6-ethano-4,5,6,7-tetrahydropyrrolo[3,4-c]pyridin-5-yl group, a 2-CH$_2$Z group-substituted-3-methyl-4,6-ethano-4,5,6,7-tetrahydropyrrolo[3,4-c]pyridin-5-yl group, a 2-CH$_2$Z group-substituted-3-methyl-4,6-ethano-4,5,6,7-tetrahydropyrazolo[4,3-c]pyridin-5-yl group, a 1-CH$_2$Z group-substituted-3-methyl-4,6-ethano-4,5,6,7-tetrahydropyrazolo[4,5-c]pyridin-5-yl group, a 2-CH$_2$Z group-substituted-3-methyl-4,6-ethano-4,5,6,7-tetrahydrothieno[3,2-c]pyridin-5-yl group, and a 2-CH$_2$Z group-substituted-3-ethyl-4,5,6,7-tetrahydrothieno[3,2-c]pyridin-5-yl group, particularly preferably a 2-CH$_2$Z group-substituted-4,5,6,7-tetrahydrothiazolo[5,4-c]pyridin-6-yl group, a 2-CH$_2$Z group-substituted-4,5,6,7-tetrahydropyrazolo[4,3-c]pyridin-5-yl group, a 2-CH$_2$Z group-substituted-5,7-ethano-4,5,6,7-tetrahydrothiazolo[5,4-c]pyridin-6-yl group, a 2-CH$_2$Z group-substituted-4,6-ethano-4,5,6,7-tetrahydropyrazolo[4,3-c]pyridin-5-yl group, a 2-CH$_2$Z group-substituted-3-methyl-4,5,6,7-tetrahydropyrazolo[4,3-c]pyridin-5-yl group, and a 2-CH$_2$Z group-substituted-3-methyl-4,6-ethano-4,5,6,7-tetrahydropyrazolo[4,3-c]pyridin-5-yl group.

As the protective group for the carboxyl group which may be protected shown by Z in the formula (b) and the general formula (II), there may be mentioned, for example, a $C_1$ to $C_4$ alkyl group having the same meanings as defined in $R^1$; an aralkyl group such as a benzyl, phenethyl groups; a $C_1$ to $C_4$ alkyl group substituted by a $C_2$ to $C_5$ alkanoyloxy group such as an acetoxymethyl, 1-acetoxyethyl, 1-acetoxypropyl, 1-acetoxybutyl, propanoyloxymethyl, 1-propanoyloxyethyl, butanoyloxymethyl, 1-butanoyloxyethyl, pivaloyloxymethyl, 1-pivaloyloxyethyl, 1-pivaloyloxypropyl and 1-pivaloyloxybutyl groups; a $C_1$ to $C_4$ alkyl group substituted by a ($C_1$ to $C_4$ alkoxy)carbonyloxy group such as a methoxycarbonyloxymethyl, 1-methoxycarbonyloxyethyl, ethoxycarbonyloxymethyl, 1-ethoxycarbonyloxyethyl, propoxycarbonyloxymethyl, 1-propoxycarbonyloxyethyl, isopropoxycarbonyloxymethyl, 1-isopropoxycarbonyloxyethyl, butoxycarbonyloxymethyl, 1-butoxycarbonyloxyethyl, t-butoxycarbonyloxymethyl and 1-t-butoxycarbonyloxyethyl groups; a N,N-dialkylaminocarbonylalkyl group such as a N,N-dimethylaminocarbonylmethyl and N,N-diethylaminocarbonylmethyl groups; a 2-(N,N-dialkylamino)ethyl group such as a 2-(N,N-dimethylamino)ethyl and 2-(N,N-diethylamino)ethyl groups; an alkyl group substituted by a 5-membered or 6-membered heterosaturated monocyclic group containing 1 or 2 hetero atoms selected from N, O and S such as a 2-morpholinoethyl, 2-piperidinoethyl and 2-(4-methylpiperidino) ethyl groups; or a group which can be converted into a carboxyl group by easily deprotecting in a living body such as a (5-methyl-2-oxo-1,3-dioxolen-1-yl)methyl group or a (5-phenyl-2-oxo-1,3-dioxolen-1-yl)methyl group, preferably a $C_1$ to $C_4$ alkyl group, a benzyl group, a $C_1$ to $C_2$ alkyl group substituted by a $C_2$ to $C_5$ alkanoyloxy group, a $C_1$ to $C_2$ alkyl group substituted by a ($C_1$ to $C_4$ alkoxy)carbonyloxy group, a (5-methyl-2-oxo-1,3-dioxolen-1-yl)methyl group or a (5-phenyl-2-oxo-1,3-dioxolen-1-yl)methyl group, more preferably a methyl group, an ethyl group, a propyl group, an isopropyl group, a butyl group, an isobutyl group, a t-butyl group, a benzyl group, an acetoxymethyl group, a 1-acetoxyethyl group, a pivaloyloxymethyl group, a 1-pivaloyloxyethyl group, an ethoxycarbonyloxymethyl group, a 1-ethoxycarbonyloxyethyl group or a (5-methyl-2-oxo-1,3-dioxolen-1-yl)methyl group, and particularly preferably a methyl group, an ethyl group, a propyl group, an isopropyl group, a butyl group, a t-butyl group, a benzyl group, an acetoxymethyl group, a pivaloyloxymethyl group or a 1-pivaloyloxyethyl group.

Also, as Q in the general formula (II), there may be mentioned a hydrogen atom, a ($C_1$ to $C_4$ alkoxy)carbonyl group having the same meanings as defined above, a benzyloxycarbonyl group or a trityl group, preferably a hydrogen atom, an ethoxycarbonyl group, a t-butoxycarbonyl group, a benzyloxycarbonyl group or a trityl group, particularly preferably a hydrogen atom.

In the compound (I) and the compound (II) of the present invention, an optical isomer based on the asymmetric carbon atom or a geometric isomer based on the double bond and the ring structure in the molecule exists in some cases, and these isomers are also included in the present invention. Incidentally, the compound (I) and the compound (II) of the present invention may be a hydrate, and in the following, they are referred to as the compound (I) and the compound (II) including the hydrates thereof. As the salt of the compound (I) and the compound (II), there may be mentioned a pharmaceutically acceptable salt including, for example, an inorganic salt such as a carbonate, a hydrochloride, a hydrobromide, a sulfate, a nitrate, a phosphate, etc.; an organic salt such as an acetate, a tartarate, a citrate, a fumarate, a maleate, a toluenesulfonate, a benzenesulfonate, a methanesulfonate, a trifluoroacetic acid, etc; a metal salt such as a sodium salt, a potassium salt, a calcium salt, an aluminum salt, etc; a salt with an organic base such as a triethylamine salt, a guanidine salt, an ammonium salt, a hydrazine salt, a quinine salt, a cinchonine salt, etc.

In the compound (I) of the present invention, suitably the following compounds can be mentioned.

1) A compound in which $R^1$ is a hydrogen atom or a methyl group.

2) A compound in which $R^2$ is a hydrogen atom, a $C_1$ to $C_4$ alkyl group, a benzyl group which may be substituted or a pyridylmethyl group which may be substituted (said substituent is a hydroxyl group, a nitro group, a cyano group, a trifluoromethyl group, an amino group, a benzoylamino group, a halogen atom, a benzyloxy group, a $C_1$ to $C_4$ alkylsulfonylamino group, a phenylsulfonylamino group which may be substituted by a halogen atom or a benzylsulfonylamino group).

3) A compound in which $R^2$ is a methyl group, an isopropyl group, an isobutyl group, a s-butyl group or a benzyl group which may be substituted (said substituent is a nitro group, a cyano group, a fluorine atom, a chlorine atom, a benzyloxy group, a $C_1$ to $C_4$ alkylsulfonylamino group, a phenylsulfonylamino group which may be substituted by a fluorine atom or a chlorine atom or a benzylsulfonylamino group).

4) A compound wherein $R^2$ is a methyl group or a benzyl group which may be substituted (said substituent is a nitro group, a benzyloxy group, a methylsulfonylamino group, an ethylsulfonylamino group, a propylsulfonylamino group, a butylsulfonylamino group, an isobutylsulfonylamino group, a phenylsulfonylamino group or a benzylsulfonylamino group).

5) A compound inwhichA is the group of the formula (a-1), $R^3$, $R^4$ and $R^5$ in the group of the formula (a-1) each independently represents a hydrogen atom, a hydroxyl group, a $C_1$ to $C_3$ alkyl group, a $C_2$ to $C_5$ alkanoyl group, an acetoxymethyl group, a pivaloyloxymethyl group, a ($C_1$ to $C_6$ alkoxy)carbonyl group, a ($C_5$ to $C_6$ cycloalkoxy)carbonyl group, a ($C_2$ to $C_4$ alkenyl)oxycarbonyl group, a benzyloxycarbonyl group, a phenoxycarbonyl group which may be substituted by a $C_1$ to $C_4$ alkyl group or a $C_1$ to $C_{10}$ alkoxy group, an ethoxycarbonyl group the 2-position of which is substituted by a $C_1$ to $C_4$ alkoxy group, a ($C_2$ to $C_6$ alkanoyl)oxymethoxycarbonyl group, an aromatic acyloxymethoxycarbonyl group or a group formed by $R^4$ and $R^5$ in combination and selected from the group consisting of a tetramethylene group, a pentamethylene group, a —$CH_2CH_2OCH_2CH_2$— group, a —$CH_2CH_2SCH_2CH_2$— group and a —$CH_2CH_2NHCH_2CH_2$— group, $Y^1$ is a 1,4-phenylene group which may be substituted (said substituent is a halogen atom, a $C_1$ to $C_4$ alkyl group or a $C_1$ to $C_4$ alkoxy group), a 2,5-pyridinediyl group, a 3,6-pyridazinediyl group, a 2,5-pyrimidinediyl group or a 2,5-pyrazinediyl group.

6) A compound in which A is the group of the formula (a-1), $R^3$, $R^4$ and $R^5$ in the group of the formula (a-1) each independently represents a hydrogen atom, a hydroxyl group, a methyl group, a ($C_1$ to $C_4$ alkoxy)carbonyl group, a ($C_2$ to $C_4$ alkenyl)oxycarbonyl group, a phenoxycarbonyl group which may be substituted by a $C_1$ to $C_2$ alkyl group or a $C_1$ to $C_4$ alkoxy group, an ethoxycarbonyl group the 2-position of which is substituted by a $C_2$ to $C_4$ alkoxy group, a ($C_2$ to $C_5$ alkanoyl)oxymethoxycarbonyl group, a benzoyloxymethoxycarbonyl group, a nicotinoyloxymethoxycarbonyl group, a group formed by $R^4$ and $R^5$ in combination and selected from the group consisting of a pentamethylene group, a —$CH_2CH_2OCH_2CH_2$— group and a —$CH_2CH_2NHCH_2CH_2$— group, $Y^1$ is a 1,4-phenylene group which may be substituted (said substituent is a halogen atom, a methyl group, an ethyl group, a methoxy group or an ethoxy group) or a 2,5-pyridinediyl group.

7) A compound in whichA is the group of the formula (a-1), $R^3$, $R^4$ and $R^5$ in the group of the formula (a-1) each independently represents a hydrogen atom, a hydroxyl group, a methoxycarbonyl group, an ethoxycarbonyl group, a propoxycarbonyl group, an isopropoxycarbonyl group, a butoxycarbonyl group, an isobutoxycarbonyl group, a t-butoxycarbonyl group, an isopropenyloxycarbonyl group, an acetoxymethoxycarbonyl group, a pivaloyloxymethoxycarbonyl group, a phenoxycarbonyl group, a 2-t-butoxyethoxycarbonyl group, a benzoyloxymethoxycarbonyl group, and a group formed by $R^4$ and $R^5$ in combination and selected from the group consisting of a —$CH_2CH_2OCH_2CH_2$— group, $Y^1$ is a 1,4-phenylene group which may be substituted (said substituent is a fluorine atom, a chlorine atom, a methyl group or a methoxy group) or a 2,5-pyridinediyl group.

8) A compound in which A is the group of the formula (a-2), $R^6$ in the group of the formula (a-2) is a hydrogen atom, a methyl group, an ethyl group, an acetyl group, a propanoyl group, a butanoyl group, an acetoxymethyl group, a propanoyloxymethyl group, a pivaloyloxymethyl group or a ($C_1$ to $C_4$ alkoxy)carbonyl group, X is a >CH— group, $Y^2$ is a —$CH_2CH_2$— group, a —$CH_2CH_2CH_2$— group, a —CH=CH— group, a —$OCH_2$— group or a —$CH_2OCH_2$— group, and n is 1 or 2.

9) A compound in which A is the group of the formula (a-2), $R^6$ in the group of the formula (a-2) is a hydrogen atom, an acetoxymethyl group, a pivaloyloxymethyl group, a methoxycarbonyl group, an ethoxycarbonyl group, a propoxycarbonyl group, an isopropoxycarbonyl group, a butoxycarbonyl group or a t-butoxycarbonyi group, X is a >CH— group, $Y^2$ is a —$CH_2CH_2$— group or a —$OCH_2$— group, and n is 2.

10) A compound in which A is the group of the formula (a-2), $R^6$ in the group of the formula (a-2) is a hydrogen atom, an acetoxymethyl group or a pivalgyloxymethyl group, X is a >CH— group, $Y^2$ is a —$OCH_2$— group, and n is 2.

11) A compound in which the heteroaromatic ring in the group of the formula (b) is a furan ring where $A^1=A^2=A^4=A^5=C$ and $A^3=O$; a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; an oxazole ring where $A^1=A^2=A^4=C$, $A^3=O$ and $A^5=N$; a thiazole ring where $A^1=A^2=A^4=C$, $A^3=S$ and $A^5=N$; a pyrazole ring where $A^1=A^2=A^5=C$ and $A^3=A^4=N$; or an imidazole ring where $A^1=A^2=A^4=C$ and $A^3=A^5=N$, o=0 and p=1 or o=1 and p=0.

12) A compound in which the heteroaromatic ring in the group of the formula (b) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, o=0 and p=1 or o=1 and p=0, $R^7$ and $R^8$ each represents a hydrogen atom or an ethylene group formed in combination thereof, and $R^9$ is a methyl group, an ethyl group, a methoxy group, an ethoxy group, a benzyloxycarbonyl group, a hydroxyl group or a trifluoromethyl group.

13) A compound in which the heteroaromatic ring in the group of the formula (b) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, the position of the —$CH_2Z$ group to be bound is the $A^3$ or $A^4$ position, o=0 and p=1 or o=1 and p=0, $R^7$ and $R^8$ each represents a hydrogen atom or an ethylene group formed in combination thereof, $R^9$ is a methyl group, an ethyl group, a methoxy group or a trifluoromethyl group, and the protective group for the carboxyl group which may be protected of Z is a $C_1$ to $C_4$ alkyl group, a benzyl group, a $C_1$ to $C_2$ alkyl group substituted by a $C_2$ to $C_5$ alkanoyloxy group, a $C_1$ to $C_2$ alkyl group substituted by a ($C_1$ to $C_4$ alkoxy)carbonyloxy group, a (5-methyl-2-oxo-1,3-dioxolen-1-yl)methyl group or a (5-phenyl-2-oxo-1,3-dioxolen-1-yl)methyl group.

14) A compound in which the heteroaromatic ring in the group of the formula (b) is a thiophene ring where $A^1=A^2=A^4=A^5=C$ and $A^3=S$; a thiazole ring where $A^1=A^2=A^4=C$, $A^3=S$ and $A^5=N$; or a pyrazole ring where $A^1=A^2=A^5=C$ and $A^3=A^4=N$, the position of the —$CH_2Z$ group to be bound is the $A^4$ position, o=0 and p=1, $R^7$ and $R^8$ each represents a hydrogen atom or an ethylene group formed in combination thereof, $R^9$ is a methyl group, and the protective group for the carboxyl group which may be protected of Z is a methyl group, an ethyl group, a propyl group, an isopropyl group, a butyl group, an isobutyl group, a benzyl group, an acetoxymethyl group, a 1-acetoxyethyl group, a pivaloyloxymethyl group, a 1-pivaloyloxyethyl group, an ethoxycarbonyloxymethyl group, a 1-ethoxycarbonyloxyethyl group, or a (5-methyl-2-oxo-1,3-dioxolen-1-yl)methyl group.

15) A compound in which $R^1$ is a hydrogen atom or a methyl group, $R^2$ is a hydrogen atom, a $C_1$ to $C_4$ alkyl group, a benzyl group which may be substituted or a pyridylmethyl group which may be substituted (said substituent is a hydroxyl group, a nitro group, a cyano group, a trifluoromethyl group, an amino group, a benzoylamino group, a halogen atom, a benzyloxy group, a $C_1$ to $C_4$ alkylsulfonylamino group, a phenylsulfonylamino group which may be substituted.by a halogen atom, or a benzylsulfonylamino group), A is the group of the formula (a-1), $R^3$ in the group of the formula (a-1) is a group selected from the group consisting of a hydrogen atom, a hydroxyl group, a $C_1$ to $C_3$ alkyl group, a $C_2$ to $C_5$ alkanoyl group, an acetoxymethyl group, a pivaloyloxymethyl group, a ($C_1$ to $C_6$ alkoxy)carbonyl group, a ($C_5$ to $C_6$ cycloalkoxy)carbonyl group, a ($C_2$ to $C_4$ alkenyl)oxycarbonyl group, a benzyloxycarbonyl group, a phenoxycarbonyl group which may be substituted by a $C_1$ to $C_4$ alkyl group or a $C_1$ to $C_{10}$ alkoxy group, an ethoxycarbonyl group the 2-position of which is substituted by a $C_1$ to $C_4$ alkoxy group, a ($C_2$ to $C_6$ alkanoyl)oxymethoxycarbonyl group and an aromatic acyloxymethoxycarbonyl group, $R^4$ and $R^5$ each independently represents a hydrogen atom or a ($C_1$ to $C_6$ alkoxy)carbonyl group, or a group formed by $R^4$ and $R^5$ in combination and selected from the group consisting of a tetramethylene group, a pentamethylene group, a —$CH_2CH_2OCH_2CH_2$— group, a —$CH_2CH_2SCH_2CH_2$— group and a —$CH_2CH_2NHCH_2CH_2$— group, $Y^1$ is a 1,4-phenylene group which may be substituted (said substituent is a halogen atom, a $C_1$ to $C_4$ alkyl group or a $C_1$ to $C_4$ alkoxy group), a 2,5-pyridinediyl group, a 3,6-pyridazinediyl group, a 2,5-pyrimidinediyl group or a 2,5-pyrazinediyl group, the heteroaromatic ring in the group of the formula (b) is a furan ring where $A^1=A^2=A^4=A^5=C$ and $A^3=O$; a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; an oxazole ring where $A^1=A^2=A^4=C$, $A^3=O$ and $A^5=N$; a thiazole ring where $A^1=A^2=A^4=C$, $A^3=S$ and $A^5=N$; a pyrazole ring where $A^1=A^2=A^5=C$ and $A^3=A^4=N$; or an imidazole ring where $A^1=A^2=A^4=C$ and $A^3=A^5=N$, o=0 and p=1 or o=1 and p=0.

16) A compound in which $R^1$ is a hydrogen atom or a methyl group, $R^2$ is a methyl group, an isopropyl group, an isobutyl group, a s-butyl group or a benzyl group which may be substituted (said substituent is a nitro group, a cyano group, a fluorine atom, a chlorine atom, a benzyloxy group, a $C_1$ to $C_4$ alkylsulfonylamino group, a phenylsulfonylamino group which may be substituted by a fluorine atom or a chlorine atom, or a benzylsulfonylamino group), A is the group of the formula (a-1), $R^3$ in the group of the formula (a-1) is a group selected from the group consisting of a hydrogen atom, a hydroxyl group, a methyl group, a ($C_1$ to $C_4$ alkoxy)carbonyl group, a ($C_2$ to $C_4$ alkenyl) oxycarbonyl group, a phenoxycarbonyl group which may be substituted by a $C_1$ to $C_2$ alkyl group or a $C_1$ to $C_4$ alkoxy group, an ethoxycarbonyl group the 2-position of which is substituted by a $C_2$ to $C_4$ alkoxy group, a ($C_2$ to $C_5$ alkanoyl) oxymethoxycarbonyl group, a benzoyloxymethoxycarbonyl group and a nicotinoyloxymethoxycarbonyl group, $R^4$ and $R^5$ each independently represents a hydrogen atom or a ($C_1$ to $C_4$ alkoxy)carbonyl group, or a group formed by $R^4$ and $R^5$ in combination and selected from the group consisting of a pentamethylene group, a —$CH_2CH_2OCH_2CH_2$— group and a —$CH_2CH_2NHCH_2CH_2$— group, $Y^1$ is a 1,4-phenylene group which may be substituted (said substituent is a halogen atom, a methyl group, an ethyl group, a methoxy group or an ethoxy group) or a 2,5-pyridinediyl group, the heteroaromatic ring in the group of the formula (b) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, o=0 and p=1 or o=1 and p=0, $R^7$ and $R^8$ each represents a hydrogen atom or an ethylene group formed in combination thereof, and $R^9$ is a methyl group, an ethyl group, a methoxy group, an ethoxy group, a benzyloxycarbonyl group, a hydroxyl group or a trifluoromethyl group.

17) A compound in which $R^1$ is a hydrogen atom or a methyl group, $R^2$ is a methyl group or a benzyl group which may be substituted (said substituent is a nitro group, a benzyloxy group, a methylsulfonylamino group, an ethylsulfonylamino group, a propylsulfonylamino group, a butylsulfonylamino group, an isobutylsulfonylamino group, a phenylsulfonylamino group, or a benzylsulfonylamino group), A is the group of the formula (a-1), $R^3$ in the group of the formula (a-1) is a group selected from the group consisting of a hydrogen atom, a hydroxyl group, a methoxycarbonyl group, an ethoxycarbonyl group, a propoxycarbonyl group, an isopropoxycarbonyl group, a butoxycarbonyl group, an isobutoxycarbonyl group, a t-butoxycarbonyl group, an isopropenyloxycarbonyl group, an acetoxymethoxycarbonyl group, a pivaloyloxymethoxycarbonyl group, a phenoxycarbonyl group, a 2-t-butoxyethoxycarbonyl group and a benzoyloxymethoxycarbonyl group, $R^4$ and $R^5$ each independently represents a hydrogen atom or a ($C_1$ to $C_4$ alkoxy)carbonyl group, or a —$CH_2CH_2OCH_2CH_2$— group formed by $R^4$ and $R^5$ in combination, $Y^1$ is a 1,4-phenylene group which may be substituted (said substituent is a fluorine atom, a chlorine atom, a methyl group or a methoxy group) or a 2,5-pyridinediyl group, the heteroaromatic ring in the group of the formula (b) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, the binding position of the -$CH_2Z$ group is the $A^3$ or $A^4$ position, o=0 and p=1 or o=1 and p=0, $R^7$ and $R^8$ each represents a hydrogen atom or an ethylene group formed in combination thereof, $R^9$ is a methyl group, an ethyl group, a methoxy group or a trifluoromethyl group, and the protective group for the protectedcarboxyl group of Z is a $C_1$ to $C_4$ alkyl group, a $C_1$ to $C_2$ alkyl group substituted by a $C_2$ to $C_5$ alkanoyloxy group, a benzyl group, a $C_1$ to $C_2$ alkyl group substituted by a ($C_1$ to $C_4$ alkoxy)carbonyloxy group, a (5-methyl-2-oxo-1,3-dioxolen-1-yl)methyl group or a (5-phenyl-2-oxo-1,3-dioxolen-1-yl)methyl group.

18) A compound in which $R^1$ is a hydrogen atom or a methyl group, $R^2$ is a methyl group or a benzyl group which may be substituted (said substituent is a nitro group, a benzyloxy group, a methylsulfonylamino group, an ethylsulfonylamino group, a propylsulfonylamino group, a butylsulfonylamino group, an isobutylsulfonylamino group, a phenylsulfonylamino group, or a benzylsulfonylamino group), A is the group of the formula (a-1), $R^3$ in the group of the formula (a-1) is a group selected from the group consisting of a hydrogen atom, a hydroxyl group, a methoxycarbonyl group, an ethoxycarbonyl group, a propoxycarbonyl group, an isopropoxycarbonyl group, a butoxycarbonyl group, an isobutoxycarbonyl group, a t-butoxycarbonyl group, an isopropenyloxycarbonyl group, an acetoxymethoxycarbonyl group, a pivaloyloxymethoxycarbonyl group, a phenoxycarbonyl group, a 2-t-butoxyethoxycarbonyl group and a benzoyloxymethoxycarbonyl group, $R^4$ and $R^5$ each represents a hydrogen atom, $Y^1$ is a 1,4-phenylene group which may be substituted (said substituent is a fluorine atom, a chlorine atom, a methyl group or a methoxy group) or a 2,5-pyridinediyl group, the heteroaromatic ring in the group of the formula (b) is a thiophene ring where $A^1=A^2=A^4=A^5=C$ and $A^3=S$; a thiazole ring where $A^1=A^2=A^4=C$, $A^3=S$ and $A^5=N$; or a pyrazole ring where $A^1=A^2=A^5=C$ and $A^3=A^4=N$, the position of the —$CH_2Z$ group is the $A^4$ position, o=0 and p=1, $R^7$ and $R^8$ each represents a hydrogen atom or an ethylene group formed in combination thereof, $R^9$ is a methyl group, and the protective group for the carboxyl group which may be protected of Z is a methyl group, an ethyl group, a propyl group, an isopropyl group, a butyl group, an isobutyl group, a benzyl group, an acetoxymethyl group, a 1-acetoxyethyl group, a pivaloyloxymethyl group, a 1-pivaloyloxyethyl group, an ethoxycarbonyloxymethyl group, a 1-ethoxycarbonyloxyethyl group, or a (5-methyl-2-oxo-1,3-dioxolen-1-yl)methyl group.

19) A compound in which $R^1$ is a hydrogen atom or a methyl group, $R^2$ is a hydrogen atom, a $C^1$ to $C_4$ alkyl group, a benzyl group which may be substituted or a pyridylmethyl group which may be substituted (said substituent is a hydroxyl group, a nitro group, a cyano group, a trifluoromethyl group, an amino group, a benzoylamino group, a halogen atom, a benzyloxy group, a $C_1$ to $C_4$ alkylsulfonylamino group, a phenylsulfonylamino group which may be substituted by a halogen atom, or a benzylsulfonylamino group), A is the group of the formula (a-2), $R^6$ in the group of the formula (a-2) is a hydrogen atom, a methyl group, an ethyl group, an acetyl group, a propanoyl group, a butanoyl group, an acetoxymethyl group, a propanoyloxymethyl group, a pivaloyloxymethyl group or a ($C_1$ to $C_4$ alkoxy)carbonyl group, X is a >CH— group, $Y^2$ is a —$CH_2CH_2$— group, a —$CH_2CH_2CH_2$— group, a —CH=CH— group, a —$OCH_2$— group or a —$CH_2OCH_2$— group, and n is 1 or 2, the heteroaromatic ring in the group of the formula (b) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, o=0 and p=1 or o=1 and p=0, $R^7$ and $R^8$ each represents a hydrogen atom or an ethylene group formed in combination thereof, and $R^9$ is a methyl group, an ethyl group, a methoxy group, an ethoxy group, a benzyloxycarbonyl group, a hydroxyl group or a trifluoromethyl group.

20) A compound in which $R^1$ is a hydrogen atom or a methyl group, $R^2$ is a methyl group, an isopropyl group, an isobutyl group, a s-butyl group or a benzyl group which may be substituted (said substituent is a nitro group, a cyano group, a fluorine atom, a chlorine atom, a benzyloxy group, a $C_1$ to $C_4$ alkylsulfonylamino group, a phenylsulfonylamino group which may be substituted by a fluorine atom or a chlorine atom or a benzylsulfonylamino group), A is the group of the formula (a-2), $R^6$ in the group of the formula (a-2) is a hydrogen atom, an acetoxymethyl group, a pivaloyloxymethyl group, a methoxycarbonyl group, an ethoxycarbonyl group, a propoxycarbonyl group, an isopropoxycarbonyl group, a butoxycarbonyl group or a t-butoxycarbonyl group, X is a >CH— group, $Y^2$ is a —$CH_2CH_2$— group or a —$OCH_2$— group, n is 2, the heteroaromatic ring in the group of the formula (b) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, the binding position of the —$CH_2Z$ group is the $A^3$ or $A^4$ position, o=0 and p=1 or o=0 and p=0, $R^7$ and $R^8$ each represents a hydrogen atom or an ethylene group formed in combination thereof, $R^9$ is a methyl group, an ethyl group, a methoxy group or a trifluoromethyl group, and the protective group for the carboxyl group which may be protected of Z is a $C_1$ to $C_4$ alkyl group, a benzyl group, a $C_1$ to $C_2$ alkyl group substituted by a $C_2$ to $C_5$ alkanoyloxy group, a $C_1$ to $C_2$ alkyl group substituted by a ($C_1$ to $C_4$ alkoxy)carbonyloxy group, a (5-methyl-2-oxo-1,3-dioxolen-1-yl)methyl group or a (5-phenyl-2-oxo-1,3-dioxolen-1-yl)methyl group.

21) A compound in which $R^1$ is a hydrogen atom or a methyl group, $R^2$ is a methyl group or a benzyl group which may be substituted (said substituent is a nitro group, a benzyloxy group, a methylsulfonylamino group, an ethylsulfonylamino group, a propylsulfonylamino group, a butylsulfonylamino group, an isobutylsulfonylamino group, a phenylsulfonylamino group, or a benzylsulfonylamino group), A is the group of the formula (a-2), $R^6$ in the group of the formula (a-2) is a hydrogen atom, an acetoxymethyl group or a pivaloyloxymethyl group, X is a >CH— group, $Y^2$ is a —$OCH_2$— group, and n is 2, the heteroaromatic ring in the group of the formula (b) is a thiophene ring where $A^1=A^2=A^4=A^5=C$ and $A^3=S$; a thiazole ring where $A^1=A^2=A^4=C$, $A^3=S$ and $A^5$=N; or a pyrazole ring where $A^1$=$A^2$=$A^5$=C and $A^3$=$A^4$=N, the binding position of the —CH$_2$Z group is the $A^4$ position, o=0 and p=1, $R^7$ and $R^8$ each represents a hydrogen atom or an ethylene group formed in combination thereof, $R^9$ is a methyl group, and the protective group for the carboxyl group which may be protected of Z is a methyl group, an ethyl group, a propyl group, an isopropyl group, a butyl group, an isobutyl group, a benzyl group, an acetoxymethyl group, a 1-acetoxyethyl group, a pivaloyloxymethyl group, a 1-pivaloyloxyethyl group, an ethoxycarbonyloxymethyl group, a 1-ethoxycarbonyloxyethyl group, or a (5-methyl-2-oxo-1,3-dioxolen-1-yl)methyl group.

As the preferred compounds in the compound (I), the compounds shown in the following Table 1 to Table 12 can be specifically exemplified.

TABLE 1

| No | A | $R^1$ | $R^2$ | $R^7,R^8$ | o,p | $R^{9'}$ |
|---|---|---|---|---|---|---|
| 1-1 | 4-Amd-Ph | H | Bn | H,H | 0,1 | H |
| 1-2 | 4-Amd-Ph | H | 4-OH-Bn | H,H | 0,1 | H |
| 1-3 | 4-Amd-Ph | H | 4-NO$_2$-Bn | H,H | 0,1 | H |
| 1-4 | 4-Amd-Ph | H | 4-CN-Bn | H,H | 0,1 | H |
| 1-5 | 4-Amd-Ph | H | 4-CF$_3$-Bn | H,H | 0,1 | H |
| 1-6 | 4-Amd-Ph | H | 4-F-Bn | H,H | 0,1 | H |
| 1-7 | 4-Amd-Ph | H | 4-BnO-Bn | H,H | 0,1 | H |
| 1-8 | 4-Amd-Ph | H | 4-MeSO$_2$NH-Bn | H,H | 0,1 | H |
| 1-9 | 4-Amd-Ph | H | 4-BuSO$_2$NH-Bn | H,H | 0,1 | H |
| 1-10 | 4-Amd-Ph | H | 4-BnSO$_2$NH-Bn | H,H | 0,1 | H |
| 1-11 | 4-Amd-Ph | H | 4-PhSO$_2$NH-Bn | H,H | 0,1 | H |
| 1-12 | 4-Amd-Ph | H | 4-(4-F-PhSO$_2$NH)-Bn | H,H | 0,1 | H |
| 1-13 | 4-Amd-Ph | H | 4-MeOCO-Bn | H,H | 0,1 | H |
| 1-14 | 4-Amd-Ph | H | 4-PyCH$_2$ | H,H | 0,1 | H |
| 1-15 | 4-Amd-Ph | H | 3-NO$_2$-Bn | H,H | 0,1 | H |
| 1-16 | 4-Amd-Ph | H | 4-NO$_2$-2-Cl-Bn- | H,H | 0,1 | H |
| 1-17 | 4-Amd-Ph | H | 4-COOH-Bn | H,H | 0,1 | H |
| 1-18 | 4-Amd-Ph | H | 4-NO$_2$-Bn | H,H | 0,1 | Me |
| 1-19 | 4-Amd-Ph | H | 4-NO$_2$-Bn | H,H | 0,1 | Et |
| 1-20 | 4-Amd-Ph | H | 4-NO$_2$-Bn | H,H | 0,1 | Pr |
| 1-21 | 4-Amd-Ph | H | 4-NO$_2$-Bn | H,H | 0,1 | CF$_3$ |
| 1-22 | 4-Amd-Ph | H | 4-NO$_2$-Bn | —CH$_2$CH$_2$— | 0,1 | H |
| 1-23 | 4-Amd-Ph | H | 4-MeSO$_2$NH-Bn | —CH$_2$CH$_2$— | 0,1 | H |
| 1-24 | 4-Amd-Ph | H | 4-BuSO$_2$NH-Bn | —CH$_2$CH$_2$— | 0,1 | H |
| 1-25 | 4-Amd-Ph | H | 4-NO$_2$-Bn | H,H | 1,0 | H |
| 1-26 | 4-Amd-Ph | H | 4-BnSO$_2$NH-Bn | H,H | 1,0 | H |
| 1-27 | 4-Amd-Ph | H | 4-PhSO$_2$NH-Bn | H,H | 1,0 | H |
| 1-28 | 4-Amd-Ph | H | 4-NO$_2$-Bn | —CH$_2$CH$_2$— | 1,0 | H |
| 1-29 | 4-Amd-Ph | H | 4-BuSO$_2$NH-Bn | —CH$_2$CH$_2$— | 1,0 | H |
| 1-30 | 4-Amd-Ph | H | 4-NO$_2$-Bn | H,H | 1,0 | Me |
| 1-31 | 4-Amd-Ph | Me | 4-NO$_2$-Bn | H,H | 0,1 | H |
| 1-32 | 4-(Me-Amd)-Ph | H | 4-NO$_2$-Bn | H,H | 0,1 | H |
| 1-33 | 4-(Et-Amd)-Ph | H | 4-NO$_2$-Bn | H,H | 0,1 | H |
| 1-34 | 4-(Pr-Amd)-Ph | H | 4-NO$_2$-Bn | H,H | 0,1 | H |
| 1-35 | 4-(N,N-Me$_2$-Amd)-Ph | H | 4-NO$_2$-Bn | H,H | 0,1 | H |
| 1-36 | 4-(N,N-Et$_2$-Amd)-Ph | H | 4-NO$_2$-Bn | H,H | 0,1 | H |
| 1-37 | 4-(N,N'-Me$_2$-Amd)-Ph | H | 4-NO$_2$-Bn | H,H | 0,1 | H |
| 1-38 | 4-(N-AcOCH$_2$-Amd)-Ph | H | 4-NO$_2$-Bn | H,H | 0,1 | H |
| 1-39 | 4-(PivaOCH$_2$-Amd)-Ph | H | 4-NO$_2$-Bn | H,H | 0,1 | H |
| 1-40 | 4-(HO-Amd)-Ph | H | 4-NO$_2$-Bn | H,H | 0,1 | H |
| 1-41 | 4-(HO-Amd)-Ph | H | 4-BuSO$_2$NH-Bn | H,H | 0,1 | H |
| 1-42 | 4-(HO-Amd)-Ph | H | 4-BnSO$_2$NH-Bn | H,H | 0,1 | H |
| 1-43 | 4-(HO-Amd)-Ph | H | 4-PhSO$_2$NH-Bn | H,H | 0,1 | H |
| 1-44 | 4-(HO-Amd)-Ph | H | 4-NO$_2$-Bn | H,H | 0,1 | Me |
| 1-45 | 4-(HO-Amd)-Ph | H | 4-MeSO$_2$NH-Bn | H,H | 0,1 | Me |
| 1-46 | 4-(HO-Amd)-Ph | H | 4-BuSO$_2$NH-Bn | H,H | 0,1 | Me |
| 1-47 | 4-(HO-Amd)-Ph | H | 4-NO$_2$-Bn | —CH$_2$CH$_2$— | 0,1 | H |
| 1-48 | 4-(HO-Amd)-Ph | H | 4-BuSO$_2$NH-Bn | —CH$_2$CH$_2$— | 0,1 | Et |
| 1-49 | 4-(HO-Amd)-Ph | H | 4-BuSO$_2$NH-Bn | H,H | 1,0 | H |
| 1-50 | 4-(HO-Amd)-Ph | H | 4-NO$_2$-Bn | —CH$_2$CH$_2$— | 1,0 | H |
| 1-51 | 4-(HO-Amd)-Ph | H | 4-NO$_2$-Bn | H,H | 1,0 | Me |
| 1-52 | 4-(HO-Amd)-Ph | H | 4-NO$_2$-Bn | —CH$_2$CH$_2$— | 1,0 | Et |
| 1-53 | 4-(HO-Amd)-Ph | H | 4-BuSO$_2$NH-Bn | —CH$_2$CH$_2$— | 1,0 | Me |
| 1-54 | 4-(Ac-Amd)-Ph | H | 4-NO$_2$-Bn | H,H | 0,1 | H |
| 1-55 | 4-(Butyr-Amd)-Ph | H | 4-NO$_2$-Bn | H,H | 0,1 | H |

TABLE 1-continued $$\text{A}-\overset{\text{O}}{\underset{}{\text{C}}}-\underset{\text{R}^1}{\text{N}}-\underset{\text{R}^2}{\overset{}{\text{C}}}-\overset{\text{O}}{\underset{}{\text{C}}}-\underset{\text{R}^8}{\text{N}}\underbrace{\begin{array}{c}\text{R}^7\\(\text{CH}_2)_o\\(\text{CH}_2)_p\end{array}}_{}\underbrace{\begin{array}{c}\text{R}^{9'}\\\\\text{S}\end{array}}_{}\text{COOH}$$

| No | A | $R^1$ | $R^2$ | $R^7,R^8$ | o,p | $R^{9'}$ |
|---|---|---|---|---|---|---|
| 1-56 | 4-(MeOCO-Amd)-Ph | H | 4-$NO_2$-Bn | H,H | 0,1 | H |
| 1-57 | 4-(MeOCO-Amd)-Ph | H | 4-$BuSO_2NH$-Bn | H,H | 0,1 | H |
| 1-58 | 4-(MeOCO-Amd)-Ph | H | 4-$NO_2$-Bn | H,H | 0,1 | Me |
| 1-59 | 4-(MeOCO-Amd)-Ph | H | 4-$NO_2$-Bn | —$CH_2CH_2$— | 0,1 | $CF_3$ |
| 1-60 | 4-((t-BuOCO)$_3$-Amd)-Ph | H | Bn | H,H | 0,1 | H |
| 1-61 | 4-(MeOCO-Amd)-Ph | H | 4-$NO_2$-Bn | H,H | 1,0 | $CF_3$ |
| 1-62 | 4-(MeOCO-Amd)-Ph | H | 4-$PhSO_2NH$-Bn | H,H | 1,0 | H |
| 1-63 | 4-(MeOCO-Amd)-Ph | H | 4-$NO_2$-Bn | —$CH_2CH_2$— | 1,0 | H |
| 1-64 | 4-(MeOCO-Amd)-Ph | H | 4-$BnSO_2NH$-Bn | —$CH_2CH_2$— | 1,0 | H |
| 1-65 | 4-(MeOCO-Amd)-Ph | H | 4-$NO_2$-Bn | H,H | 1,0 | Pr |
| 1-66 | 4-(MeOCO-Amd)-Ph | H | 4-$NO_2$-Bn | —$CH_2CH_2$— | 1,0 | Me |
| 1-67 | 4-(EtOCO-Amd)-Ph | H | 4-$NO_2$-Bn | H,H | 0,1 | H |
| 1-68 | 4-(EtOCO-Amd)-Ph | H | 4-$MeSO_2NH$-Bn | H,H | 0,1 | H |
| 1-69 | 4-((t-BuOCO)$_3$-Amd)-Ph | H | 4-F-Bn | H,H | 0,1 | H |
| 1-70 | 4-((t-BuOCO)$_3$-Amd)-Ph | H | 4-CN-Bn | H,H | 0,1 | H |
| 1-71 | 4-(EtOCO-Amd)-Ph | H | 4-$BuSO_2NH$-Bn | H,H | 0,1 | H |
| 1-72 | 4-((t-BuOCO)$_3$-Amd)-Ph | H | 4-$CF_3$-Bn | H,H | 0,1 | H |
| 1-73 | 4-((t-BuOCO)$_3$-Amd)-Ph | H | 4-PhCONH-Bn | H,H | 0,1 | H |
| 1-74 | 4-(EtOCO-Amd)-Ph | H | 4-$NO_2$-Bn | H,H | 0,1 | Me |
| 1-75 | 4-Amd-Ph | H | 4-PhCONH-Bn | H,H | 0,1 | H |
| 1-76 | 4-(EtOCO-Amd)-Ph | H | 4-$BuSO_2NH$-Bn | H,H | 0,1 | Me |
| 1-77 | 4-((t-BuOCO)$_3$-Amd)-Ph | H | 3-$NO_2$-Bn | H,H | 0,1 | H |
| 1-78 | 4-(N-t-BuOCO-Pipe)-$CH_2CH_2$ | H | 4-$NO_2$-Bn | H,H | 0,1 | H |
| 1-79 | 4-(EtOCO-Amd)-Ph | H | 4-$NO_2$-Bn | —$CH_2CH_2$— | 0,1 | H |
| 1-80 | 4-(EtOCO-Amd)-Ph | H | 4-$BuSO_2NH$-Bn | —$CH_2CH_2$— | 0,1 | H |
| 1-81 | 4-(EtOCO-Amd)-Ph | H | 4-$NO_2$-Bn | H,H | 1,0 | H |
| 1-82 | 4-(EtOCO-Amd)-Ph | H | 4-$NO_2$-Bn | —$CH_2CH_2$— | 1,0 | H |
| 1-83 | 4-(EtOCO-Amd)-Ph | H | 4-$NO_2$-Bn | H,H | 1,0 | Me |
| 1-84 | 4-((BuOCO)$_3$-Amd)-Ph | H | 2-Cl-4-$NO_2$-Bn | H,H | 0,1 | H |
| 1-85 | 4-(BuOCO-Amd)-Ph | H | 4-$BuSO_2NH$-Bn | H,H | 0,1 | H |
| 1-86 | 4-(BuOCO-Amd)-Ph | H | 4-$NO_2$-Bn | H,H | 0,1 | Me |
| 1-87 | 4-(BuOCO-Amd)-Ph | H | 4-$MeSO_2NH$-Bn | H,H | 0,1 | Me |
| 1-88 | 4-(BuOCO-Amd)-Ph | H | 4-$BuSO_2NH$-Bn | H,H | 0,1 | Me |
| 1-89 | 4-(BuOCO-Amd)-Ph | H | 4-$NO_2$-Bn | —$CH_2CH_2$— | 0,1 | H |
| 1-90 | 4-(BuOCO-Amd)-Ph | H | 4-$NO_2$-Bn | H,H | 1,0 | H |
| 1-91 | 4-((BuOCO)$_3$-Amd)-Ph | H | 4-$PyCH_2$ | H,H | 0,1 | H |
| 1-92 | 4-(BuOCO-Amd)-Ph | H | 4-$NO_2$-Bn | —$CH_2CH_2$— | 1,0 | H |
| 1-93 | 4-(N-t-BuOCO)Pipe-CH=CH | H | 4-$NO_2$-Bn | H,H | 0,1 | H |
| 1-94 | 4-(BuOCO-Amd)-Ph | H | 4-$BuSO_2NH$-Bn | —$CH_2CH_2$— | 1,0 | H |
| 1-95 | 4-(BuOCO-Amd)-Ph | H | 4-$BnSO_2NH$-Bn | —$CH_2CH_2$— | 1,0 | H |
| 1-96 | N-t-BuOCO-4-Pipe$OCH_2$ | H | 4-$NO_2$-Bn | H,H | 0,1 | H |
| 1-97 | 4-(BuOCO-Amd)-Ph | H | 4-$NO_2$-Bn | H,H | 1,0 | Me |
| 1-98 | 4-(BuOCO-Amd)-Ph | H | 4-$MeSO_2NH$-Bn | H,H | 1,0 | Me |
| 1-99 | 4-(BuOCO-Amd)-Ph | H | 4-$BnSO_2NH$-Bn | —$CH_2CH_2$— | 1,0 | Me |
| 1-100 | 4-(BuOCO-Amd)-Ph | H | 4-$PhSO_2NH$-Bn | —$CH_2CH_2$— | 1,0 | Me |
| 1-101 | 4-(t-BuOCO-Amd)-Ph | H | 4-$NO_2$-Bn | H,H | 0,1 | H |
| 1-102 | 4-(t-BuOCO-Amd)-Ph | H | 4-$MeSO_2NH$-Bn | H,H | 0,1 | H |
| 1-103 | 4-(t-BuOCO-Amd)-Ph | H | 4-$EtSO_2NH$-Bn | H,H | 0,1 | H |
| 1-104 | 4-(t-BuOCO-Amd)-Ph | H | 4-$PrSO_2NH$-Bn | H,H | 0,1 | H |
| 1-105 | 4-(t-BuOCO-Amd)-Ph | H | 4-$BuSO_2NH$-Bn | H,H | 0,1 | H |
| 1-106 | 4-(t-BuOCO-Amd)-Ph | H | 4-$BnSO_2NH$-Bn | H,H | 0,1 | H |
| 1-107 | 4-(t-BuOCO-Amd)-Ph | H | 4-$PhSO_2NH$-Bn | H,H | 0,1 | H |
| 1-108 | 4-(t-BuOCO-Amd)-Ph | H | 4-$NO_2$-Bn | H,H | 0,1 | Me |
| 1-109 | 4-(t-BuOCO-Amd)-Ph | H | 4-$MeSO_2NH$-Bn | —$CH_2CH_2$— | 0,1 | H |
| 1-110 | 4-(t-BuOCO-Amd)-Ph | H | 4-$BuSO_2NH$-Bn | —$CH_2CH_2$— | 0,1 | H |
| 1-111 | 4-(t-BuOCO-Amd)-Ph | H | 4-$PhSO_2NH$-Bn | —$CH_2CH_2$— | 0,1 | H |
| 1-112 | 4-(t-BuOCO-Amd)-Ph | H | 4-$NO_2$-Bn | H,H | 1,0 | H |
| 1-113 | 4-(t-BuOCO-Amd)-Ph | H | 4-$MeSO_2NH$-Bn | —$CH_2CH_2$— | 1,0 | Me |
| 1-114 | 4-(N,N-(EtOCO)$_2$)-Amd-Ph | H | 4-$NO_2$-Bn | H,H | 0,1 | H |
| 1-115 | 4-(N,N'-(EtOCO)$_2$)-Amd-Ph | H | 4-$NO_2$-Bn | H,H | 0,1 | H |
| 1-116 | 4-((t-BuOCO)$_3$-Amd)-Ph | H | 4-$NO_2$-Bn | H,H | 0,1 | H |
| 1-117 | 4-((t-BuOCO)$_3$-Amd)-Ph | H | 4-$MeSO_2NH$-Bn | H,H | 0,1 | H |
| 1-118 | 4-((t-BuOCO)$_3$-Amd)-Ph | H | 4-$BuSO_2NH$-Bn | H,H | 0,1 | H |
| 1-119 | 4-((t-BuOCO)$_3$-Amd)-Ph | H | 4-$BnSO_2NH$-Bn | H,H | 0,1 | H |
| 1-120 | 4-((t-BuOCO)$_3$-Amd)-Ph | H | 4-$PhSO_2NH$-Bn | H,H | 0,1 | H |
| 1-121 | 4-((t-BuOCO)$_3$-Amd)-Ph | H | 4-$NO_2$-Bn | H,H | 0,1 | Me |
| 1-122 | 4-((t-BuOCO)$_3$-Amd)-Ph | H | 4-(4-F-Ph-$SO_2NH$)-Bn | H,H | 0,1 | H |

TABLE 1-continued

[Structure: A-N(R¹)-C(=O)-CH(R²)-N-... with (CH₂)ₒ and (CH₂)ₚ bridging, R⁷, R⁸ on the ring carbons, thiophene ring with R⁹' and CH₂COOH substituent]

| No | A | R¹ | R² | R⁷,R⁸ | o,p | R⁹' |
|---|---|---|---|---|---|---|
| 1-123 | 4-((t-BuOCO)₃-Amd)-Ph | H | 4-NO₂-Bn | —CH₂CH₂— | 0,1 | H |
| 1-124 | 4-((t-BuOCO)₃-Amd)-Ph | H | 4-MeSO₂NH-Bn | —CH₂CH₂— | 0,1 | H |
| 1-125 | 4-((t-BuOCO)₃-Amd)-Ph | Me | 4-NO₂-Bn | H,H | 0,1 | H |
| 1-126 | 4-((t-BuOCO)₃-Amd)-Ph | H | 4-MeSO₂NH-Bn | H,H | 1,0 | H |
| 1-127 | 4-((t-BuOCO)₃-Amd)-Ph | H | 4-PhSO₂NH-Bn | —CH₂CH₂— | 1,0 | H |
| 1-128 | 4-((t-BuOCO)₃-Amd)-Ph | H | 4-NO₂-Bn | H,H | 1,0 | Me |
| 1-129 | 4-((t-BuOCO)₃-Amd)-Ph | H | 4-NO₂-Bn | —CH₂CH₂— | 1,0 | Me |
| 1-130 | 4-Amd-2-F-Ph | H | 4-NO₂-Bn | H,H | 0,1 | H |
| 1-131 | 4-Amd-2-Cl-Ph | H | 4-NO₂-Bn | H,H | 0,1 | H |
| 1-132 | 4-Amd-2-Me-Ph | H | 4-NO₂-Bn | H,H | 0,1 | H |
| 1-133 | 4-Amd-2-Et-Ph | H | 4-NO₂-Bn | H,H | 0,1 | H |
| 1-134 | 4-Amd-2-MeO-Ph | H | 4-NO₂-Bn | H,H | 0,1 | H |
| 1-135 | 4-Amd-2-EtO-Ph | H | 4-NO₂-Bn | H,H | 0,1 | H |
| 1-136 | 4-PipeOCH₂ | H | 4-OH-Bn | H,H | 0,1 | H |
| 1-137 | 4-PipeOCH₂ | H | 4-NO₂-Bn | H,H | 0,1 | H |
| 1-138 | 4-PipeOCH₂ | H | 4-BuSO₂NH-Bn | H,H | 0,1 | H |
| 1-139 | 4-PipeOCH₂ | H | 4-NO₂-Bn | —CH₂CH₂— | 0,1 | H |
| 1-140 | 4-PipeOCH₂ | H | 4-NO₂-Bn | H,H | 1,0 | H |
| 1-141 | 4-PipeOCH₂ | H | 4-NO₂-Bn | —CH₂CH₂— | 1,0 | H |
| 1-142 | 4-PipeOCH₂ | H | 4-NO₂-Bn | H,H | 1,0 | Me |
| 1-143 | 4-PipeCH=CH | H | 4-NO₂-Bn | H,H | 0,1 | H |
| 1-144 | 4-PipeCH₂CH₂CH₂ | H | 4-NO₂-Bn | H,H | 0,1 | H |
| 1-145 | 4-PipeCH₂CH₂ | H | 4-NO₂-Bn | H,H | 0,1 | H |
| 1-146 | N-Ac-4-PipeOCH₂ | H | 4-NO₂-Bn | H,H | 0,1 | H |
| 1-147 | N-Ac-4-PipeOCH₂ | H | 4-BuSO₂NH-Bn | H,H | 0,1 | H |
| 1-148 | N-PivaOCH₂-4-PipeOCH₂ | H | 4-NO₂-Bn | H,H | 0,1 | H |
| 1-149 | N-PivaOCH₂-4-PipeOCH₂ | H | 4-BuSO₂NH-Bn | H,H | 0,1 | H |
| 1-150 | N-EtOCO-4-PipeOCH₂ | H | 4-NO₂-Bn | H,H | 0,1 | H |
| 1-151 | N-EtOCO-4-PipeOCH₂ | H | 4-BuSO₂NH-Bn | H,H | 0,1 | H |
| 1-152 | 4-(N'-t-BuOCO-N-Bn-Amd)-Ph | H | 4-NO₂-Bn | H,H | 0,1 | H |
| 1-153 | 4-(N-Bn-Amd)-Ph | H | 4-NO₂-Bn | H,H | 0,1 | H |
| 1-154 | 4-(N'-t-BuOCO-N-Me-Amd)-Ph | H | 4-NO₂-Bn | H,H | 0,1 | H |
| 1-155 | 4-((t-BuOCO)₃-Amd)-Ph | H | 4-NO₂-Bn | H,H | 0,1 | CF₃ |
| 1-156 | 4-((t-BuOCO)₃-Amd)-Ph | H | 4-BnO-Bn | H,H | 0,1 | H |
| 1-157 | 4-Amd-Ph | H | 4-NH₂-Bn | H,H | 0,1 | H |
| 1-158 | 4-((t-BuOCO)₃-Amd)-Ph | H | 4-PyCH₂ | H,H | 0,1 | CF₃ |
| 1-159 | 4-((t-BuOCO)₃-Amd)-Ph | H | 4-NO₂-Bn | H,H | 0,1 | Pr |
| 1-160 | 4-(AcOCH₂OCO-Amd)-Ph | H | 4-NO₂-Bn | H,H | 0,1 | H |
| 1-161 | 4-(PivaOCH₂OCO-Amd)-Ph | H | 4-NO₂-Bn | H,H | 0,1 | H |
| 1-162 | 4-(PhCOOCH₂OCO-Amd)-Ph | H | 4-NO₂-Bn | H,H | 0,1 | H |
| 1-163 | 4-(2-PyCOOCH₂OCO-Amd)-Ph | H | 4-NO₂-Bn | H,H | 0,1 | H |
| 1-164 | 4-(3-PyCOOCH₂OCO-Amd)-Ph | H | 4-NO₂-Bn | H,H | 0,1 | H |
| 1-165 | 4-(4-PyCOOCH₂OCO-Amd)-Ph | H | 4-NO₂-Bn | H,H | 0,1 | H |
| 1-166 | 4-(t-BuOCH₂CH₂OCO-Amd)-Ph | H | 4-NO₂-Bn | H,H | 0,1 | H |
| 1-167 | 4-(PhOCO-Amd)-Ph | H | 4-NO₂-Bn | H,H | 0,1 | H |
| 1-168 | 4-(CH₂=C(CH₃)OCO-Amd)-Ph | H | 4-NO₂-Bn | H,H | 0,1 | H |
| 1-169 | 4-(CH₂=CHCH₂OCO-Amd)-Ph | H | 4-NO₂-Bn | H,H | 0,1 | H |
| 1-170 | 4-(BnOCO-Amd)-Ph | H | 4-NO₂-Bn | H,H | 0,1 | H |
| 1-171 | 4-(AcOCH₂OCO-Amd)-Ph | H | 4-MeSO₂NH-Bn | H,H | 0,1 | H |
| 1-172 | 4-(PivaOCH₂OCO-Amd)-Ph | H | 4-MeSO₂NH-Bn | H,H | 0,1 | H |
| 1-173 | 4-(PhCOOCH₂OCO-Amd)-Ph | H | 4-MeSO₂NH-Bn | H,H | 0,1 | H |
| 1-174 | 4-(2-PyCOOCH₂OCO-Amd)-Ph | H | 4-MeSO₂NH-Bn | H,H | 0,1 | H |
| 1-175 | 4-(3-PyCOOCH₂CCO-Amd)-Ph | H | 4-MeSO₂NH-Bn | H,H | 0,1 | H |
| 1-176 | 4-(4-PyCOOCH₂OCO-Amd)-Ph | H | 4-MeSO₂NH-Bn | H,H | 0,1 | H |
| 1-177 | 4-(t-BuOCH₂CH₂OCO-Amd)-Ph | H | 4-MeSO₂NH-Bn | H,H | 0,1 | H |
| 1-178 | 4-(PhOCO-Amd)-Ph | H | 4-MeSO₂NH-Bn | H,H | 0,1 | H |
| 1-179 | 4-(CH₂=C(CH₃)OCO-Amd)-Ph | H | 4-MeSO₂NH-Bn | H,H | 0,1 | H |
| 1-180 | 4-(CH₂=CHCH₂OCO-Amd)-Ph | H | 4-MeSO₂NH-Bn | H,H | 0,1 | H |
| 1-181 | 4-(BnOCO-Amd)-Ph | H | 4-MeSO₂NH-Bn | H,H | 0,1 | H |
| 1-182 | 4-(AcOCH₂OCO-Amd)-Ph | H | 4-BuSO₂NH-Bn | H,H | 0,1 | H |
| 1-183 | 4-(PivaOCH₂OCO-Amd)-Ph | H | 4-BuSO₂NH-Bn | H,H | 0,1 | H |
| 1-184 | 4-(PhCOOCH₂OCO-Amd)-Ph | H | 4-BuSO₂NH-Bn | H,H | 0,1 | H |
| 1-185 | 4-(2-PyCOOCH₂OCO-Amd)-Ph | H | 4-BuSO₂NH-Bn | H,H | 0,1 | H |
| 1-186 | 4-(3-PyCOOCH₂OCO-Amd)-Ph | H | 4-BuSO₂NH-Bn | H,H | 0,1 | H |
| 1-187 | 4-(4-PyCOOCH₂OCO-Amd)-Ph | H | 4-BuSO₂NH-Bn | H,H | 0,1 | H |
| 1-188 | 4-(t-BuOCH₂CH₂OCO-Amd)-Ph | H | 4-BuSO₂NH-Bn | H,H | 0,1 | H |
| 1-189 | 4-(PhOCO-Amd)-Ph | H | 4-BuSO₂NH-Bn | H,H | 0,1 | H |

TABLE 1-continued

| No | A | R¹ | R² | R⁷,R⁸ | o,p | R⁹' |
|---|---|---|---|---|---|---|
| 1-190 | 4-(CH$_2$=C(CH$_3$)OCO-Amd)-Ph | H | 4-BuSO$_2$NH-Bn | H,H | 0,1 | H |
| 1-191 | 4-(CH$_2$=CHCH$_2$OCO-Amd)-Ph | H | 4-BuSO$_2$NH-Bn | H,H | 0,1 | H |
| 1-192 | 4-(BnOCO-Amd)-Ph | H | 4-BuSO$_2$NH-Bn | H,H | 0,1 | H |
| 1-193 | 4-(AcOCH$_2$OCO-Amd)-Ph | H | 4-PyCH$_2$ | H,H | 0,1 | H |
| 1-194 | 4-(PivaOCH$_2$OCO-Amd)-Ph | H | 4-PyCH$_2$ | H,H | 0,1 | H |
| 1-195 | 4-(PhCOOCH$_2$OCO-Amd)-Ph | H | 4-PyCH$_2$ | H,H | 0,1 | H |
| 1-196 | 4-(2-PyCOOCH$_2$OCO-Amd)-Ph | H | 4-PyCH$_2$ | H,H | 0,1 | H |
| 1-197 | 4-(3-PyCOOCH$_2$OCO-Amd)-Ph | H | 4-PyCH$_2$ | H,H | 0,1 | H |
| 1-198 | 4-(4-PyCOOCH$_2$OCO-Amd)-Ph | H | 4-PyCH$_2$ | H,H | 0,1 | H |
| 1-199 | 4-(t-BuOCH$_2$CH$_2$OCO-Amd)-Ph | H | 4-PyCH$_2$ | H,H | 0,1 | H |
| 1-200 | 4-(PhOCO-Amd)-Ph | H | 4-PyCH$_2$ | H,H | 0,1 | H |
| 1-201 | 4-(CH$_2$=C(CH$_3$)OCO-Amd)-Ph | H | 4-PyCH$_2$ | H,H | 0,1 | H |
| 1-202 | 4-(CH$_2$=CHCH$_2$OCO-Amd)-Ph | H | 4-PyCH$_2$ | H,H | 0,1 | H |
| 1-203 | 4-(BnOCO-Amd)-Ph | H | 4-PyCH$_2$ | H,H | 0,1 | H |
| 1-204 | 4-(AcOCH$_2$OCO-Amd)-Ph | H | 4-NO$_2$-Bn | —CH$_2$CH$_2$— | 0,1 | H |
| 1-205 | 4-(PivaOCH$_2$OCO-Amd)-Ph | H | 4-NO$_2$-Bn | —CH$_2$CH$_2$— | 0,1 | H |
| 1-206 | 4-(PhCOOCH$_2$OCO-Amd)-Ph | H | 4-NO$_2$-Bn | —CH$_2$CH$_2$— | 0,1 | H |
| 1-207 | 4-(2-PyCOOCH$_2$OCO-Amd)-Ph | H | 4-NO$_2$-Bn | —CH$_2$CH$_2$— | 0,1 | H |
| 1-208 | 4-(3-PyCOOCH$_2$OCO-Amd)-Ph | H | 4-NO$_2$-Bn | —CH$_2$CH$_2$— | 0,1 | H |
| 1-209 | 4-(4-PyCOOCH$_2$OCO-Amd)-Ph | H | 4-NO$_2$-Bn | —CH$_2$CH$_2$— | 0,1 | H |
| 1-210 | 4-(t-BuOCH$_2$CH$_2$OCO-Amd)-Ph | H | 4-NO$_2$-Bn | —CH$_2$CH$_2$— | 0,1 | H |
| 1-211 | 4-(PhOCO-Amd)-Ph | H | 4-NO$_2$-Bn | —CH$_2$CH$_2$— | 0,1 | H |
| 1-212 | 4-(CH$_2$=C(CH$_3$)OCO-Amd)-Ph | H | 4-NO$_2$-Bn | —CH$_2$CH$_2$— | 0,1 | H |
| 1-213 | 4-(CH$_2$=CHCH$_2$OCO-Amd)-Ph | H | 4-NO$_2$-Bn | —CH$_2$CH$_2$— | 0,1 | H |
| 1-214 | 4-(BnOCO-Amd)-Ph | H | 4-NO$_2$-Bn | —CH$_2$CH$_2$— | 0,1 | H |

TABLE 2

| No | A | R¹ | R² | R⁷,R⁸ | o, p | R$_2$ |
|---|---|---|---|---|---|---|
| 2-1 | 4-Amd-Ph | H | Bn | H,H | 0, 1 | H |
| 2-2 | 4-Amd-Ph | H | 4-OH-Bn | H,H | 0, 1 | H |
| 2-3 | 4-Amd-Ph | H | 4-NO$_2$-Bn | H,H | 0, 1 | H |
| 2-4 | 4-Amd-Ph | H | 4-CN-Bn | H,H | 0, 1 | H |
| 2-5 | 4-Amd-Ph | H | 4-CF$_3$-Bn | H,H | 0, 1 | H |
| 2-6 | 4-Amd-Ph | H | 4-F-Bn | H,H | 0, 1 | H |
| 2-7 | 4-Amd-Ph | H | 4-BnO-Bn | H,H | 0, 1 | H |
| 2-8 | 4-Amd-Ph | H | 4-MeSO$_2$NH-Bn | H,H | 0, 1 | H |
| 2-9 | 4-Amd-Ph | H | 4-BuSO$_2$NH-Bn | H,H | 0, 1 | H |
| 2-10 | 4-Amd-Ph | H | 4-BnSO$_2$NH-Bn | H,H | 0, 1 | H |
| 2-11 | 4-Amd-Ph | H | 4-PhSO$_2$NH-Bn | H,H | 0, 1 | H |
| 2-12 | 4-Amd-Ph | H | 4-(4-F-PhSO$_2$NH)-Bn | H,H | 0, 1 | H |
| 2-13 | 4-Amd-Ph | H | 4-MeOCO-Bn | H,H | 0, 1 | H |
| 2-14 | 4-Amd-Ph | H | 4-PyCH$_2$ | H,H | 0, 1 | H |
| 2-15 | 4-Amd-Ph | H | 3-PyCH$_2$ | H,H | 0, 1 | H |
| 2-16 | 4-Amd-Ph | H | 3-NO$_2$-Bn | H,H | 0, 1 | H |
| 2-17 | 4-Amd-Ph | H | 3-CN-Bn | H,H | 0, 1 | H |
| 2-18 | 4-Amd-Ph | H | 3-F-Bn | H,H | 0, 1 | H |
| 2-19 | 4-Amd-Ph | H | 4-OH-2-F-Bn | H,H | 0, 1 | H |
| 2-20 | 4-Amd-Ph | H | 4-OH-3-Cl-Bn | H,H | 0, 1 | H |
| 2-21 | 4-Amd-Ph | H | 4-NO$_2$-2-Cl-Bn | H,H | 0, 1 | H |
| 2-22 | 4-Amd-Ph | H | 4-NO$_2$-3-F-Bn | H,H | 0, 1 | H |
| 2-23 | 4-Amd-Ph | H | 4-NO$_2$-Bn | H,H | 0, 1 | HO |
| 2-24 | 4-Amd-Ph | H | 4-NO$_2$-Bn | H,H | 0, 1 | MeO |
| 2-25 | 4-Amd-Ph | H | 4-BuSO$_2$NH-Bn | H,H | 0, 1 | Me |

TABLE 2-continued

| No | A | R¹ | R² | R⁷,R⁸ | o, p | R₂ |
|---|---|---|---|---|---|---|
| 2-26 | 4-Amd-Ph | H | 4-NO₂-Bn | H,H | 0, 1 | Et |
| 2-27 | 4-Amd-Ph | H | 4-NO₂-Bn | H,H | 0, 1 | Pr |
| 2-28 | 4-Amd-Ph | H | 4-NO₂-Bn | H,H | 0, 1 | CF₃ |
| 2-29 | 4-Amd-Ph | H | 4-NO₂-Bn | —CH₂CH₂— | 0, 1 | H |
| 2-30 | 4-Amd-Ph | H | 4-MeSO₂NH-Bn | —CH₂CH₂— | 0, 1 | Et |
| 2-31 | 4-Amd-Ph | H | 4-BuSO₂NH-O₂n | —CH₂CH₂— | 0, 1 | Pr |
| 2-32 | 4-Amd-Ph | H | 4-NO₂-Bn | —CH₂CH₂— | 0, 1 | CF₃ |
| 2-33 | 4-Amd-Ph | H | 4-NO₂-Bn | H,H | 1, 0 | H |
| 2-34 | 4-Amd-Ph | H | 4-BnSO₂NH-Bn | H,H | 1, 0 | H |
| 2-35 | 4-Amd-Ph | H | 4-PhSO₂NH-Bn | H,H | 1, 0 | H |
| 2-36 | 4-Amd-Ph | H | 4-NO₂-Bn | —CH₂CH₂— | 1, 0 | H |
| 2-37 | 4-Amd-Ph | H | 4-BuSO₂NH-Bn | —CH₂CH₂— | 1, 0 | H |
| 2-38 | 4-Amd-Ph | H | 4-NO₂-Bn | H,H | 1, 0 | Me |
| 2-39 | 4-Amd-Ph | H | 4-BuSO₂NH-Bn | H,H | 1, 0 | Me |
| 2-40 | 4-Amd-Ph | H | 4-NO₂-Bn | —CH₂CH₂— | 1, 0 | Me |
| 2-41 | 4-Amd-Ph | H | 4-MeSOiNH-Bn | —CH₂CH₂— | 1, 0 | Me |
| 2-42 | 4-Amd-Ph | H | 4-BuSO₂NH-Bn | —CH₂CH₂— | 1, 0 | Me |
| 2-43 | 4-Amd-Ph | Me | 4-NO₂-Bn | H,H | 0, 1 | H |
| 2-44 | 4-Amd-Ph | Me | 4-MeSO₂NH-Bn | H,H | 0, 1 | H |
| 2-45 | 4-Amd-Ph | Me | 4-EtSO₂NH-Bn | H,H | 0, 1 | H |
| 2-46 | 4-Amd-Ph | Me | 4-PrSO₂NH-Bn | H,H | 0, 1 | H |
| 2-47 | 4-Amd-Ph | Me | 4-BuSO₂NH-Bn | H,H | 0, 1 | H |
| 2-48 | 4-Amd-Ph | Me | 4-BnSO₂NH-Bn | H,H | 0, 1 | H |
| 2-49 | 4-Amd-Ph | Me | 4-PhSO₂NH-Bn | H,H | 0, 1 | H |
| 2-50 | 4-Amd-Ph | Me | 4-NO₂-Bn | —CH₂CH₂— | 0, 1 | H |
| 2-51 | 4-Amd-Ph | Me | 4-BuSO₂NH-Bn | —CH₂CH₂— | 0, 1 | H |
| 2-52 | 4-Amd-Ph | Me | 4-BnSO₂NH-Bn | —CH₂CH₂— | 0, 1 | HO |
| 2-53 | 4-Amd-Ph | Me | 4-PhSO₂NH-Bn | —CH₂CH₂— | 0, 1 | MeO |
| 2-54 | 4-Amd-Ph | Me | 4-NO₂-Bn | H,H | 1, 0 | H |
| 2-55 | 4-Amd-Ph | Me | 4-BuSO₂NH-Bn | H,H | 1, 0 | H |
| 2-56 | 4-Amd-Ph | Me | 4-NO₂-Bn | —CH₂CH₂— | 1, 0 | H |
| 2-57 | 4-Amd-Ph | Me | 4-MeSO₂NH-Bn | —CH₂CH₂— | 1, 0 | HO |
| 2-58 | 4-Amd-Ph | Me | 4-BuSOO₂NH-Bn | —CH₂CH₂— | 1, 0 | MeO |
| 2-59 | 4-Amd-Ph | Me | 4-NO₂-Bn | H,H | 1, 0 | Me |
| 2-60 | 4-Amd-Ph | Me | 4-MeSO₂NH-Bn | H,H | 1, 0 | Me |
| 2-61 | 4-Amd-Ph | Me | 4-BuSO₂NH-Bn | H,H | 1, 0 | Me |
| 2-62 | 4-Amd-Ph | H | 4-I-Bn | H,H | 0, 1 | H |
| 2-63 | 4-Amd-Ph | H | 4-F-Bn | H,H | 0, 1 | H |
| 2-64 | 4-Amd-Ph | H | 4-BnO-Bn | H,H | 0, 1 | H |
| 2-65 | 4-Amd-2-F-Ph | H | 4-NO₂-Bn | H,H | 0, 1 | H |
| 2-66 | 4-Amd-2-Cl-Ph | H | 4-NO₂-Bn | H,H | 0, 1 | H |
| 2-67 | 4-Amd-2-MeO-Ph | H | 4-NO₂-Bn | H,H | 0, 1 | H |
| 2-68 | 4-Amd-2-Me-Ph | H | 4-NO₂-Bn | H,H | 0, 1 | H |
| 2-69 | 4-Amd-3-F-Ph | H | 4-NO₂-Bn | H,H | 0, 1 | H |
| 2-70 | 4-Amd-3-Cl-Ph | H | 4-NO₂-Bn | H,H | 0, 1 | H |
| 2-71 | 4-Amd-3-MeO-Ph | H | 4-NO₂-Bn | H,H | 0, 1 | H |
| 2-72 | 4-(Me-Amd)-Ph | H | 4-NO₂-Bn | H,H | 0, 1 | H |
| 2-73 | 4-(Et-Amd)-Ph | H | 4-NO₂-Bn | H,H | 0, 1 | H |
| 2-74 | 4-(Pr-Amd)-Ph | H | 4-NO₂-Bn | H,H | 0, 1 | H |
| 2-75 | 4-(AcOCHO₂-Amd)-Ph | H | 4-NO₂-Bn | H,H | 0, 1 | H |
| 2-76 | 4-(PivaOCHO₂-Amd)-Ph | H | 4-NO₂-Bn | H,H | 0, 1 | H |
| 2-77 | 4-(N,N-Me₂-Amd)-Ph | H | 4-NO₂-Bn | H,H | 0, 1 | H |
| 2-78 | 4-(N,N-Et₂-Amd)-Ph | H | 4-NO₂-Bn | H,H | 0, 1 | H |
| 2-79 | 4-(N,N'-Me₂-Amd)-Ph | H | 4-NO₂-Bn | H,H | 0, 1 | H |
| 2-80 | 4-(Me-Amd)-3-F-Ph | H | 4-NO₂-Bn | H,H | 0, 1 | H |
| 2-81 | 4-(HO-Amd)-Ph | H | 4-NO₂-Bn | H,H | 0, 1 | H |
| 2-82 | 4-(HO-Amd)-Ph | H | 4-BuSO₂NH-Bn | H,H | 0, 1 | H |
| 2-83 | 4-(HO-Amd)-Ph | H | 4-BnSO₂NH-Bn | H,H | 0, 1 | H |
| 2-84 | 4-(HO-Amd)-Ph | H | 4-PhSO₂NH-Bn | H,H | 0, 1 | H |
| 2-85 | 4-(HO-Amd)-Ph | H | 4-NO₂-Bn | H,H | 0, 1 | Me |
| 2-86 | 4-(HO-Amd)-Ph | H | 4-MeSO₂NH-Bn | H,H | 0, 1 | Me |
| 2-87 | 4-(HO-Amd)-Ph | H | 4-EtSO₂NH-Bn | H,H | 0, 1 | Me |
| 2-88 | 4-(HO-Amd)-Ph | H | 4-PrSO₂NH-Bn | H,H | 0, 1 | Me |
| 2-89 | 4-(HO-Amd)-Ph | H | 4-BuSO₂NH-Bn | H,H | 0, 1 | Me |
| 2-90 | 4-(HO-Amd)-Ph | H | 4-BnSO₂NH-Bn | H,H | 0, 1 | Me |
| 2-91 | 4-(HO-Amd)-Ph | H | 4-PhSO₂NH-Bn | H,H | 0, 1 | Me |
| 2-92 | 4-(HO-Amd)-Ph | H | 4-NO₂-Bn | —CH₂CH₂— | 0, 1 | H |

TABLE 2-continued $$\text{Structure with } R^1, R^2, R^7, R^8, R^{9'}, A, (CH_2)_o, (CH_2)_p, \text{COOH}$$

| No | A | R$^1$ | R$^2$ | R$^7$,R$^8$ | o, p | R$_2$ |
|---|---|---|---|---|---|---|
| 2-93 | 4-(HO-Amd)-Ph | H | 4-BuSO$_2$NH-Bn | —CH$_2$CH$_2$— | 0, 1 | Me |
| 2-94 | 4-(HO-Amd)-Ph | H | 4-NO$_2$-Bn | H,H | 1, 0 | H |
| 2-95 | 4-(HO-Amd)-Ph | H | 4-MeSO$_2$NH-Bn | H,H | 1, 0 | H |
| 2-96 | 4-(HO-Amd)-Ph | H | 4-BuSO$_2$NH-Bn | H,H | 1, 0 | H |
| 2-97 | 4-(HO-Amd)-Ph | H | 4-NO$_2$-Bn | —CH$_2$CH$_2$— | 1, 0 | H |
| 2-98 | 4-(HO-Amd)-Ph | H | 4-NO$_2$-Bn | H,H | 1, 0 | Me |
| 2-99 | 4-(HO-Amd)-Ph | H | 4-NO$_2$-Bn | —CH$_2$CH$_2$— | 1, 0 | Me |
| 2-100 | 4-(HO-Amd)-Ph | H | 4-BuSO$_2$NH-Bn | —CH$_2$CH$_2$— | 1, 0 | Me |
| 2-101 | 4-(HO-Amd)-2-F-Ph | H | 4-NO$_2$-Bn | H,H | 0, 1 | H |
| 2-102 | 4-(HO-Amd)-3-F-Ph | H | 4-NO$_2$-Bn | H,H | 0, 1 | H |
| 2-103 | 4-(HO-Amd)-2-Cl-Ph | H | 4-NO$_2$-Bn | H,H | 0, 1 | H |
| 2-104 | 4-(HO-Amd)-3-Cl-Ph | H | 4-NO$_2$-Bn | H,H | 0, 1 | H |
| 2-105 | 4-(HO-Amd)-2-Cl-Ph | H | 4-NO$_2$-Bn | H,H | 1, 0 | H |
| 2-106 | 4-(Ac-Amd)-Ph | H | 4-NO$_2$-Bn | H,H | 0, 1 | H |
| 2-107 | 4-(Prop-Amd)-Ph | H | 4-NO$_2$-Bn | H,H | 0, 1 | H |
| 2-108 | 4-(Butyr-Amd)-Ph | H | 4-NO$_2$-Bn | H,H | 0, 1 | H |
| 2-109 | 4-(Piva-Amd)-Ph | H | 4-NO$_2$-Bn | H,H | 0, 1 | H |
| 2-110 | 4-(MeOCO-Amd)-Ph | H | 4-NO$_2$-Bn | H,H | 0, 1 | H |
| 2-111 | 4-(MeOCO-Amd)-Ph | H | 4-BuSO$_2$NH-Bn | H,H | 0, 1 | H |
| 2-112 | 4-(MeOCO-Amd)-Ph | H | 4-BnSO$_2$NH-Bn | H,H | 0, 1 | H |
| 2-113 | 4-(MeOCO-Amd)-Ph | H | 4-PhSO$_2$NH-Bn | H,H | 0, 1 | H |
| 2-114 | 4-(MeOCO-Amd)-Ph | 2 | 4-NO$_2$-Bn | H,H | 0, 1 | Me |
| 2-115 | 4-(MeOCO-Amd)-Ph | H | 4-NO$_2$-Bn | —CH$_2$CH$_2$— | 0, 1 | H |
| 2-116 | 4-(MeOCO-Amd)-Ph | H | 4-MeSO$_2$NH-Bn | —CH$_2$CH$_2$— | 0, 1 | H |
| 2-117 | 4-(MeOCO-Amd)-Ph | H | 4-NO$_2$-Bn | H,H | 1, 0 | H |
| 2-118 | 4-(MeOCO-Amd)-Ph | H | 4-PhSO$_2$NH-Bn | H,H | 1, 0 | H |
| 2-119 | 4-(MeOCO-Amd)-Ph | H | 4-NO$_2$-Bn | —CH$_2$CH$_2$— | 1, 0 | H |
| 2-120 | 4-(MeOCO-Amd)-Ph | H | 4-BnSO$_2$NH-Bn | —CH$_2$CH$_2$— | 1, 0 | H |
| 2-121 | 4-(MeOCO-Amd)-Ph | H | 4-NO$_2$-Bn | H,H | 1, 0 | Me |
| 2-122 | 4-(MeOCO-Amd)-Ph | H | 4-NO$_2$-Bn | —CH$_2$CH$_2$— | 1, 0 | Me |
| 2-123 | 4-(EtOCO-Amd)-Ph | H | 4-OH-Bn | H,H | 0, 1 | H |
| 2-124 | 4-(EtOCO-Amd)-Ph | H | 4-NO$_2$-Bn | H,H | 0, 1 | H |
| 2-125 | 4-(EtOCO-Amd)-Ph | H | 4-MeSO$_2$NH-Bn | H,H | 0, 1 | H |
| 2-126 | 4-(EtOCO-Amd)-Ph | H | 4-EtSO$_2$NH-Bn | H,H | 0, 1 | H |
| 2-127 | 4-(EtOCO-Amd)-Ph | H | 4-PrSO$_2$NH-Bn | H,H | 0, 1 | H |
| 2-128 | 4-(EtOCO-Amd)-Ph | H | 4-BuSO$_2$NH-Bn | H,H | 0, 1 | H |
| 2-129 | 4-(EtOCO-Amd)-Ph | H | 4-BnSO$_2$NH-Bn | H,H | 0, 1 | H |
| 2-130 | 4-(EtOCO-Amd)-Ph | H | 4-PhSO$_2$NH-Bn | H,H | 0, 1 | H |
| 2-131 | 4-(EtOCO-Amd)-Ph | H | 4-NO$_2$-Bn | H,H | 0, 1 | Me |
| 2-132 | 4-(EtOCO-Amd)-Ph | H | 4-MeSO$_2$NH-Bn | H,H | 0, 1 | Me |
| 2-133 | 4-(EtOCO-Amd)-Ph | H | 4-BuSO$_2$NH-Bn | H,H | 0, 1 | Me |
| 2-134 | 4-(EtOCO-Amd)-Ph | H | 4-BnSO$_2$NH-Bn | H,H | 0, 1 | Me |
| 2-135 | 4-(EtOCO-Amd)-Ph | H | 4-PhSO$_2$NH-Bn | H,H | 0, 1 | Me |
| 2-136 | 4-(EtOCO-Amd)-Ph | H | 4-NO$_2$-Bn | —CH$_2$CH$_2$— | 0, 1 | H |
| 2-137 | 4-(EtOCO-Amd)-Ph | H | 4-MeSO$_2$NH-Bn | —CH$_2$CH$_2$— | 0, 1 | H |
| 2-138 | 4-(EtOCO-Amd)-Ph | H | 4-EtSO$_2$NH-Bn | —CH$_2$CH$_2$— | 0, 1 | H |
| 2-139 | 4-(EtOCO-Amd)-Ph | H | 4-PrSO$_2$NH-Bn | —CH$_2$CH$_2$— | 0, 1 | H |
| 2-140 | 4-(EtOCO-Amd)-Ph | H | 4-BuSO$_2$NH-Bn | —CH$_2$CH$_2$— | 0, 1 | H |
| 2-141 | 4-(EtOCO-Amd)-Ph | H | 4-BnSO$_2$NH-Bn | —CH$_2$CH$_2$— | 0, 1 | H |
| 2-142 | 4-(EtOCO-Amd)-Ph | H | 4-PhSO$_2$NH-Bn | —CH$_2$CH$_2$— | 0, 1 | H |
| 2-143 | 4-(EtOCO-Amd)-Ph | H | 4-NO$_2$-Bn | H,H | 1, 0 | H |
| 2-144 | 4-(EtOCO-Amd)-Ph | H | 4-NO$_2$-Bn | —CH$_2$CH$_2$— | 1, 0 | H |
| 2-145 | 4-(EtOCO-Amd)-Ph | H | 4-NO$_2$-Bn | H,H | 1, 0 | Me |
| 2-146 | 4-(EtOCO-Amd)-Ph | H | 4-NO$_2$-Bn | —CH$_2$CH$_2$— | 1, 0 | Me |
| 2-147 | 4-(ProCO-Amd)-Ph | H | 4-NO$_2$-Bn | H,H | 0, 1 | H |
| 2-148 | 4-(isoPrOCO-Amd)-Ph | H | 4-NO$_2$-Bn | H,H | 0, 1 | H |
| 2-149 | 4-(BuOCO-Amd)-Ph | H | 4-MeSO$_2$NH-Bn | H,H | 0, 1 | H |
| 2-150 | 4-(BuOCO-Amd)-Ph | H | 4-EtSO$_2$NH-Bn | H,H | 0, 1 | H |
| 2-151 | 4-(BuOCO-Amd)-Ph | H | 4-PrSO$_2$NH-Bn | H,H | 0, 1 | H |
| 2-152 | 4-(BuOCO-Amd)-Ph | H | 4-BuSO$_2$NH-Bn | H,H | 0, 1 | H |
| 2-153 | 4-(BuOCO-Amd)-Ph | H | 4-BnSO$_2$NH-Bn | H,H | 0, 1 | H |
| 2-154 | 4-(BuOCO-Amd)-Ph | H | 4-PhSO$_2$NH-Bn | H,H | 0, 1 | H |
| 2-155 | 4-(BuOCO-Amd)-Ph | H | 4-NO$_2$-Bn | H,H | 0, 1 | Me |
| 2-156 | 4-(BuOCO-Amd)-Ph | H | 4-MeSO$_2$NH-Bn | H,H | 0, 1 | Me |
| 2-157 | 4-(BuOCO-Amd)-Ph | H | 4-EtSO$_2$NH-Bn | H,H | 0, 1 | Me |
| 2-158 | 4-(BuOCO-Amd)-Ph | H | 4-PrSO$_2$NH-Bn | H,H | 0, 1 | Me |
| 2-159 | 4-(BuOCO-Amd)-Ph | H | 4-BuSO$_2$NH-Bn | H,H | 0, 1 | Me |

TABLE 2-continued

| No | A | R¹ | R² | R⁷,R⁸ | o, p | R₂ |
|---|---|---|---|---|---|---|
| 2-160 | 4-(BuOCO-Amd)-Ph | H | 4-BnSO₂NH-Bn | H,H | 0, 1 | Me |
| 2-161 | 4-(BuOCO-Amd)-Ph | H | 4-PhSO₂NH-Bn | H,H | 0, 1 | Me |
| 2-162 | 4-(BuOCO-Amd)-Ph | H | 4-NO₂-Bn | —CH₂CH₂— | 0, 1 | H |
| 2-163 | 4-(BuOCO-Amd)-Ph | H | 4-PhSO₂NH-Bn | —CH₂CH₂— | 0, 1 | H |
| 2-164 | 4-(BuOCO-Amd)-Ph | H | 4-NO₂-Bn | H,H | 1, 0 | H |
| 2-165 | 4-(BuOCO-Amd)-Ph | H | 4-MeSO₂NH-Bn | H,H | 1, 0 | HO |
| 2-166 | 4-(BuOCO-Amd)-Ph | H | 4-NO₂-Bn | —CH₂CH₂— | 1, 0 | MeO |
| 2-167 | 4-(BuOCO-Amd)-Ph | H | 4-MeSO₂NH-Bn | —CH₂CH₂— | 1, 0 | H |
| 2-168 | 4-(BuOCO-Amd)-Ph | H | 4-BuSO₂NH-Bn | —CH₂CH₂— | 1, 0 | H |
| 2-169 | 4-(BuOCO-Amd)-Ph | H | 4-BnSO₂NH-Bn | —CH₂CH₂— | 1, 0 | H |
| 2-170 | 4-(BuOCO-Amd)-Ph | H | 4-PhSO₂NH-Bn | —CH₂CH₂— | 1, 0 | H |
| 2-171 | 4-(BuOCO-Amd)-Ph | H | 4-NO₂-Bn | H,H | 1, 0 | Me |
| 2-172 | 4-(BuOCO-Amd)-Ph | H | 4-MeSO₂NH-Bn | H,H | 1, 0 | Me |
| 2-173 | 4-(BuOCO-Amd)-Ph | H | 4-BnSO₂NH-Bn | —CH₂CH₂— | 1, 0 | Me |
| 2-174 | 4-(BuOCO-Amd)-Ph | H | 4-PhSO₂NH-Bn | —CH₂CH₂— | 1, 0 | Me |
| 2-175 | 4-(t-BuOCO-Amd)-Ph | H | 4-NO₂-Bn | H,H | 0, 1 | H |
| 2-176 | 4-(t-BuOCO-Amd)-Ph | H | 4-MeSO₂NH-Bn | H,H | 0, 1 | H |
| 2-177 | 4-(t-BuOCO-Amd)-Ph | H | 4-EtSO₂NH-Bn | H,H | 0, 1 | H |
| 2-178 | 4-(t-BuOCO-Amd)-Ph | H | 4-PrSO₂NH-Bn | H,H | 0, 1 | H |
| 2-179 | 4-(t-BuOCO-Amd)-Ph | H | 4-BuSO₂NH-Bn | H,H | 0, 1 | H |
| 2-180 | 4-(HexOCO-Amd)-Ph | H | 4-NO₂-Bn | H,H | 0, 1 | H |
| 2-181 | 4-(cycloHexOCO-Amd)-Ph | H | 4-NO₂-Bn | H,H | 0, 1 | H |
| 2-182 | 4-(t-BuOCO-Amd)-Ph | H | 4-NO₂-Bn | H,H | 0, 1 | Me |
| 2-183 | 4-(t-BuOCO-Amd)-Ph | H | 4-MeSO₂NH-Bn | —CH₂CH₂— | 0, 1 | H |
| 2-184 | 4-(t-BuOCO-Amd)-Ph | H | 4-BuSO₂NH-Bn | —CH₂CH₂— | 0, 1 | H |
| 2-185 | 4-(t-BuOCO-Amd)-Ph | H | 4-PhSO₂NH-Bn | —CH₂CH₂— | 0, 1 | H |
| 2-186 | 4-(t-BuOCO-Amd)-Ph | H | 4-NO₂-Bn | H,H | 1, 0 | H |
| 2-187 | 4-(t-BuOCO-Amd)-Ph | H | 4-MeSO₂NH-Bn | H,H | 1, 0 | H |
| 2-188 | 4-(t-BuOCO-Amd)-Ph | H | 4-BuSO₂NH-Bn | H,H | 1, 0 | H |
| 2-189 | 4-(t-BuOCO-Amd)-Ph | H | 4-BnSO₂NH-Bn | H,H | 1, 0 | H |
| 2-190 | 4-(t-BuOCO-Amd)-Ph | H | 4-PhSO₂NH-Bn | H,H | 1 ,0 | H |
| 2-191 | 4-(t-BuOCO-Amd)-Ph | H | 4-NO₂-Bn | —CH₂CH₂— | 1, 0 | H |
| 2-192 | 4-(t-BuOCO-Amd)-Ph | H | 4-BuSO₂NH-Bn | —CH₂CH₂— | 1, 0 | H |
| 2-193 | 4-(t-BuOCO-Amd)-Ph | H | 4-NO₂-Bn | H,H | 1, 0 | Me |
| 2-194 | 4-(t-BuOCO-Amd)-Ph | H | 4-MeSO₂NH-Bn | H,H | 1, 0 | Me |
| 2-195 | 4-(t-BuOCO-Amd)-Ph | H | 4-MeSO₂NH-Bn | —CH₂CH₂— | 1, 0 | Me |
| 2-196 | 4-(N,N'-(MeOCO)₂-Amd)-Ph | H | 4-NO₂-Bn | H,H | 0, 1 | H |
| 2-197 | 4-(N,N'-(EtOCO)₂-Amd)-Ph | H | 4-NO₂-Bn | H,H | 0, 1 | H |
| 2-198 | 4-(N,N'-(ProCO)₂-Amd)-Ph | H | 4-NO₂-Bn | H,H | 0, 1 | H |
| 2-199 | 4-(N,N'-(BuOCO)₂-Amd)-Ph | H | 4-NO₂-Bn | H,H | 0, 1 | H |
| 2-200 | 4-(N,N'-(t-BuOCO)₂-Amd)-Ph | H | 4-NO₂-Bn | H,H | 0, 1 | H |
| 2-201 | 4-((t-BuOCO)₃-Amd)-Ph | H | 4-NO₂-Bn | H,H | 0, 1 | H |
| 2-202 | 4-((t-BuOCO)₃-Amd)-Ph | H | 4-NO₂-Bn | H,H | 0, 1 | HO |
| 2-203 | 4-((t-BuOCO)₃-Amd)-Ph | H | 4-BuSO₂NH-Bn | H,H | 0, 1 | H |
| 2-204 | 4-((t-BuOCO)₃-Amd)-Ph | H | 4-BnSO₂NH-Bn | H,H | 0, 1 | H |
| 2-205 | 4-((t-BuOCO)₃-Amd)-Ph | H | 4-NO₂-Bn | H,H | 0, 1 | MeO |
| 2-206 | 4-((t-BuOCO)₃-Amd)-Ph | H | 4-NO₂-Bn | H,H | 0, 1 | Me |
| 2-207 | 4-((t-BuOCO)₃-Amd)-Ph | H | 4-MeSO₂NH-Bn | H,H | 0, 1 | Me |
| 2-208 | 4-((t-BuOCO)₃-Amd)-Ph | H | 4-NO₂-Bn | —CH₂CH₂— | 0, 1 | H |
| 2-209 | 4-((t-BuOCO)₃-Amd)-Ph | H | 4-MeSO₂NH-Bn | —CH₂CH₂— | 0, 1 | H |
| 2-210 | 4-((t-BuOCO)₃-Amd)-Ph | H | 4-NO₂-Bn | H,H | 1, 0 | H |
| 2-211 | 4-((t-BuOCO)₃-Amd)-Ph | H | 4-MeSO₂NH-Bn | H,H | 1, 0 | H |
| 2-212 | 4-((t-BuOCO)₃-Amd)-Ph | H | 4-PhSO₂NH-Bn | —CH₂CH₂— | 1,O | H |
| 2-213 | 4-((t-BuOCO)₃-Amd)-Ph | H | 4-NO₂-Bn | H,H | 1, 0 | Me |
| 2-214 | 4-((t-BuOCO)₃-Amd)-Ph | H | 4-NO₂-Bn | —CH₂CH₂— | 1, 0 | Me |
| 2-215 | 4-(MeOCO-Amd)-2-F-Ph | H | 4-NO₂-Bn | H,H | 0, 1 | H |
| 2-216 | 4-(EtOCO-Amd)-2-F-Ph | H | 4-NO₂-Bn | H,H | 0, 1 | H |
| 2-217 | 4-(EtOCO-Amd)-3-F-Ph | H | 4-NO₂-Bn | H,H | 0, 1 | H |
| 2-218 | 4-(EtOCO-Amd)-2-Cl-Ph | H | 4-NO₂-Bn | H,H | 0, 1 | H |
| 2-219 | 4-(EtOCO-Amd)-2-MeO-Ph | H | 4-NO₂-Bn | H,H | 0, 1 | H |
| 2-220 | 5-Amd-2-Py | H | 4-NO₂-Bn | H,H | 0, 1 | H |
| 2-221 | 6-Amd-3-Py | H | 4-NO₂-Bn | H,H | 0, 1 | H |
| 2-222 | 5-(EtOCO-Amd)-2-Py | H | 4-NO₂-Bn | H,H | 0, 1 | H |
| 2-223 | 6-(EtOCO-Amd)-3-Py | H | 4-NO₂-Bn | H,H | 0, 1 | H |
| 2-224 | 4-(Pipera-Imd)-Ph | H | 4-NO₂-Bn | H,H | 0, 1 | H |
| 2-225 | 4-(Pyrr-Imd)-Ph | H | 4-NO₂-Bn | H,H | 0, 1 | H |
| 2-226 | 4-(Mor-Imd)-Ph | H | 4-NO₂-Bn | H,H | 0, 1 | H |

TABLE 2-continued

| No | A | R¹ | R² | R⁷,R⁸ | o, p | R₂ |
|---|---|---|---|---|---|---|
| 2-227 | 4-(Piper-Imd)-Ph | H | 4-NO₂-Bn | H,H | 0, 1 | H |
| 2-228 | 4-PipeOCH₂ | H | 4-OH-Bn | H,H | 0, 1 | MeO |
| 2-229 | 4-PipeOCH₂ | H | 4-NO₂-Bn | H,H | 0, 1 | H |
| 2-230 | N-t-BuOCO-4-PipeOCH₂ | H | 4-NO₂-Bn | H,H | 0, 1 | H |
| 2-231 | 4-PipeOCH₂ | H | 4-NO₂-Bn | —CH₂CH₂— | 0, 1 | H |
| 2-232 | 4-PipeOCH₂ | H | 4-NO₂-Bn | H,H | 1, 0 | H |
| 2-233 | 4-PipeOCH₂ | H | 4-NO₂-Bn | —CH₂CH₂— | 1, 0 | H |
| 2-234 | 4-PipeOCH₂ | H | 4-NO₂-Bn | H,H | 1, 0 | Me |
| 2-235 | 4-PipeCH=CH | H | 4-NO₂-Bn | H,H | 0, 1 | H |
| 2-236 | 4-PipeCO₂CH₂ | H | 4-NO₂-Bn | H,H | 0, 1 | H |
| 2-237 | 4-PipeCHO₂CH₂ | H | 4-NO₂-Bn | H,H | 0, 1 | H |
| 2-238 | N-Ac-4-PipeOCH₂ | H | 4O₂NO₂-Bn | H,H | 0, 1 | H |
| 2-239 | N-Ac-4-PipeOCH₂ | H | 4-BuSO₂NH-Bn | H,H | 0, 1 | H |
| 2-240 | N-PivaOCHO₂4-PipeOCH₂ | H | 4-NO₂-Bn | H,H | 0, 1 | H |
| 2-241 | N-PivaOCHO₂4-PipeOCH₂ | H | 4-BuSO₂NH-Bn | H,H | 0, 1 | H |
| 2-242 | N-EtOCO4-PipeOCH₂ | H | 4-NO₂-Bn | H,H | 0, 1 | H |
| 2-243 | N-EtOCO4-PipeOCH₂ | H | 4-BuSO₂NH-Bn | H,H | 0, 1 | H |
| 2-244 | 4-(t-BuOCO-Mor-Imd)-Ph | H | 4-NO₂-Bn | H,H | 0, 1 | H |
| 2-245 | 4-(AcOCH₂OCO-Amd)-Ph | H | 4-NO₂-Bn | H,H | 0, 1 | H |
| 2-246 | 4-(PivaOCH₂OCO-Amd)-Ph | H | 4-NO₂-Bn | H,H | 0, 1 | H |
| 2-247 | 4-(PhCOOCH₂OCO-Amd)-Ph | H | 4-NO₂-Bn | H,H | 0, 1 | H |
| 2-248 | 4-(2-PyCOOCH₂OCO-Amd)-Ph | H | 4-NO₂-Bn | H,H | 0, 1 | H |
| 2-249 | 4-(3-PyCOOCH₂OCO-Amd)-Ph | H | 4-NO₂-Bn | H,H | 0, 1 | H |
| 2-250 | 4-(4-PyCOOCH₂OCO-Amd)-Ph | H | 4-NO₂-Bn | H,H | 0, 1 | H |
| 2-251 | 4-(t-BuOCH₂CH₂OCO-Amd)-Ph | H | 4-NO₂-Bn | H,H | 0, 1 | H |
| 2-252 | 4-(PhOCO-Amd)-Ph | H | 4-NO₂-Bn | H,H | 0, 1 | H |
| 2-253 | 4-(CH₂=C(CH₃)OCO-Amd)-Ph | H | 4-NO₂-Bn | H,H | 0, 1 | H |
| 2-254 | 4-(CH₂=CHCH₂OCO-Amd)-Ph | H | 4-NO₂-Bn | H,H | 0, 1 | H |
| 2-255 | 4-(BnOCO-Amd)-Ph | H | 4-NO₂-Bn | H,H | 0, 1 | H |
| 2-256 | 4-(4-OctOPhOCO-Amd)-Ph | H | 4-NO₂-Bn | H,H | 0, 1 | H |
| 2-257 | 4-(PivaOCH₂OCO-Amd)-Ph | H | 4-NO₂-Bn | —CH₂CH₂— | 0, 1 | H |
| 2-258 | 4-(PhCOOCH₂OCO-Amd)-Ph | H | 4-NO₂-Bn | —CH₂CH₂— | 0, 1 | H |
| 2-259 | 4-((t-BuOCO)₃-Amd)-Ph | H | 4-NO₂-Bn | —CH₂CH₂— | 1, 0 | Me |
| 2-260 | 4-(MeOCO-Amd)-2-F-Ph | H | 4-NO₂-Bn | —CH₂CH₂— | 0, 1 | H |
| 2-261 | 4-(EtOCO-Amd)-2-F-Ph | H | 4-NO₂-Bn | —CH₂CH₂— | 0, 1 | H |
| 2-262 | 4-O₂tOCO-Aind)-3-F-Ph | H | 4-NO₂-Bn | —CH₂CH₂— | 0, 1 | H |
| 2-263 | 4-(HO-Amd)-2-Me-Ph | H | 4-NO₂-Bn | H,H | 0, 1 | H |
| 2-264 | 4-(HO-Amd)-2-MeO-Ph | H | 4-NO₂-Bn | H,H | 0, 1 | H |
| 2-265 | 5-Amd-2-Py | H | 4-NO₂-Bn | —CH₂CH₂— | 0, 1 | H |
| 2-266 | 6-Amd-3-Py | H | 4-NO₂-Bn | —CH₂CH₂— | 0, 1 | H |
| 2-267 | 5-(MeOCO-Amd)-2-Py | H | 4-NO₂-Bn | H,H | 0, 1 | H |
| 2-268 | 6-(MeOCO-Amd)-3-Py | H | 4-NO₂-Bn | H,H | 0, 1 | H |
| 2-269 | 5-(HO-Amd)-2-Py | H | 4-NO₂-Bn | H,H | 0, 1 | H |
| 2-270 | 6-(HO-Amd)-3-Py | H | 4-NO₂-Bn | H,H | 0, 1 | H |
| 2-271 | 5-(ProCO-Mnd)-2-Py | H | 4-NO₂-Bn | H,H | 0, 1 | H |
| 2-272 | 6-(ProCO-Mnd)-3-Py | H | 4-NO₂-Bn | H,H | 0, 1 | H |
| 2-273 | 5-(BuOCO-Amd)-2-Py | H | 4-NO₂-Bn | H,H | 0, 1 | H |
| 2-274 | 6-(BuOCO-Amd)-3-Py | H | 4-NO₂-Bn | H,H | 0, 1 | H |
| 2-275 | 4-(PhOCO-Amd)-2-Me-Ph | H | 4-NO₂-Bn | H,H | 0, 1 | H |
| 2-276 | 4-(PhOCO-Amd)-2-MeO-Ph | H | 4-NO₂-Bn | H,H | 0, 1 | H |
| 2-277 | 5-(PhOCO-Amd)-2-Py | H | 4-NO₂-Bn | H,H | 0, 1 | H |
| 2-278 | 6-(PhOCO-Amd)-3-Py | H | 4-NO₂-Bn | H,H | 0, 1 | H |
| 2-279 | 5-(PhCOOCO₂OCO-Amd)-2-Py | H | 4-NO₂-Bn | H,H | 0, 1 | H |
| 2-280 | 6-(PhCOOCHO₂OCO-Amd)-3-Py | H | 4-NO₂-Bn | H,H | 0, 1 | H |
| 2-281 | 5-(CHO₂O₂(CO₂)OCO-Amd)-2-Py | H | 4-NO₂-Bn | H,H | 0, 1 | H |
| 2-282 | 6-(CHO₂=C(CH₃)OCO-Amd)-3-Py | H | 4-NO₂-Bn | H,H | 0, 1 | H |
| 2-283 | 4-(CHO₂=C(CH₃)OCO-Amd)-2-Me-Ph | H | 4-NO₂-Bn | H,H | 0, 1 | H |
| 2-284 | 4-(CH₂=C(CH₃)OCO-Amd)-2-MeO-Ph | H | 4-NO₂-Bn | H,H | 0, 1 | H |
| 2-285 | 4-(PhCOOCHO₂OCO-Mnd)-2-Me-Ph | H | 4-NO₂-Bn | H,H | 0, 1 | H |
| 2-286 | 4-(PhCOOCO₂OCO-Amd)-2-MeO-Ph | H | 4-NO₂-Bn | H,H | 0, 1 | H |
| 2-287 | 5-(BnOCO-Amd)-2-Py | H | 4-NO₂-Bn | H,H | 0, 1 | H |
| 2-288 | 6-(BnOCO-Amd)-3-Py | H | 4-NO₂-Bn | H,H | 0, 1 | H |
| 2-289 | 4-(t-BuOCHO₂CHO₂OCO-Amd)-2-Me-Ph | H | 4-NO₂-Bn | H,H | 0, 1 | H |
| 2-290 | 4-(t-BuOCHO₂CHO₂OCO-Amd)-2-MeO-Ph | H | 4-NO₂-Bn | H,H | 0, 1 | H |
| 2-291 | 5-(t-BuOCH₂CH₂OCO-Amd)-2-Py | H | 4-NO₂-Bn | H,H | 0, 1 | H |
| 2-292 | 6-(t-BuOCH₂CH₂OCO-Amd)-3-Py | H | 4-NO₂-Bn | H,H | 0, 1 | H |
| 2-293 | 4-((t-BuOCO)₃-Amd)-Ph | H | Me | H,H | 0, 1 | H |

TABLE 2-continued

| No | A | R¹ | R² | R⁷,R⁸ | o, p | R₂ |
|---|---|---|---|---|---|---|
| 2-294 | 4-((t-BuOCO)₃-Amd)-Ph | H | isoPr | H,H | 0, 1 | H |
| 2-295 | 4-((t-BuOCO)₃-Amd)-Ph | H | isoBu | H,H | 0, 1 | H |
| 2-296 | 4-((t-BuOCO)₃-Amd)-Ph | H | s-Bu | H,H | 0, 1 | H |
| 2-297 | 4-((t-BuOCO)₃-Amd)-Ph | H | Bn | H,H | 0, 1 | H |
| 2-298 | 4-((t-BuOCO)₃-Amd)-Ph | H | 4-F-Bn | H,H | 0, 1 | H |
| 2-299 | 4-((t-BuOCO)₃-Amd)-Ph | H | 4-I-Bn | H,H | 0, 1 | H |
| 2-300 | 4-((t-BuOCO)₃-Amd)-Ph | H | 4-OH-Bn | H,H | 0, 1 | H |
| 2-301 | 4-((t-BuOCO)₃-Amd)-Ph | H | 4-BnO-Bn | H,H | 0, 1 | H |
| 2-302 | 4-((t-BuOCO)₃-Amd)-Ph | H | 4-CN-Bn | H,H | 0, 1 | H |
| 2-303 | 4-((t-BuOCO)₃-Amd)-Ph | Me | 4-NO₂-Bn | H,H | 0, 1 | H |
| 2-304 | 4-(2-PyCOOCHO₂OCO-Amd)-Ph | H | 4-NO₂-Bn | —CH₂CH₂— | 0, 1 | H |
| 2-305 | 4-(3-PyCOOCHO₂OCO-Amd)-Ph | H | 4-NO₂-Bn | —CH₂CH₂— | 0, 1 | H |
| 2-306 | 4-(4-PyCOOCHO₂OCO-Amd)-Ph | H | 4-NO₂-Bn | —CH₂CH₂— | 0, 1 | H |
| 2-307 | 4-(t-BuOCH₂CH₂OCO-Amd)-Ph | H | 4-NO₂-Bn | —CH₂CH₂— | 0, 1 | H |
| 2-308 | 4-(PhOCO-Amd)-Ph | H | 4-NO₂-Bn | —CH₂CH₂— | 0, 1 | H |
| 2-309 | 4-(CH₂=C(CH₃)OCO-Amd)-Ph | H | 4-NO₂-Bn | —CH₂CH₂— | 0, 1 | H |
| 2-310 | 4-(CH₂=CHCH₂OCO-Amd)-Ph | H | 4-NO₂-Bn | —CH₂CH₂— | 0, 1 | H |
| 2-311 | 4-(BnOCO-Amd)-Ph | H | 4-NO₂-Bn | —CH₂CH₂— | 0, 1 | H |
| 2-312 | 4-(AcOCH₂OCO-Amd)-Ph | H | 4-OH-Bn | H,H | 0, 1 | H |
| 2-313 | 4-(PiVaOCH₂OCO-Amd)-Ph | H | 4-OH-Bn | H,H | 0, 1 | H |
| 2-314 | 4-(PhCOOCH₂OCO-Amd)-Ph | H | 4-OH-Bn | H,H | 0, 1 | H |
| 2-315 | 4-(2-PyCOOCH₂OCO-Amd)-Ph | H | 4-OH-Bn | H,H | 0, 1 | H |
| 2-316 | 4-(3-PyCOOCH₂OCO-Amd)-Ph | H | 4-OH-Bn | H,H | 0, 1 | H |
| 2-317 | 4-(4-PyCOOCH₂OCO-Amd)-Ph | H | 4-OH-Bn | H,H | 0, 1 | H |
| 2-318 | 4-(t-BuOCH₂CH₂OCO-Amd)-Ph | H | 4-OH-Bn | H,H | 0, 1 | H |
| 2-319 | 4-(PhOCO-Amd)-Ph | H | 4-OH-Bn | H,H | 0, 1 | H |
| 2-320 | 4-(CHO₂=C(CH₃)OCO-Amd)-Ph | H | 4-OH-Bn | H,H | 0, 1 | H |
| 2-321 | 4-(CH₂=CHCH₂OCO-Amd)-Ph | H | 4-OH-Bn | H,H | 0, 1 | H |
| 2-322 | 4-(BnOCO-Amd)-Ph | H | 4-OH-Bn | H,H | 0, 1 | H |
| 2-323 | 4-(AcOCHO₂OCO-Amd)-Ph | H | 4-MeSO₂NH-Bn | H,H | 0, 1 | H |
| 2-324 | 4-(PivaOCO₂OCO-Amd)-Ph | H | 4-MeSO₂NH-Bn | H,H | 0, 1 | H |
| 2-325 | 4-(PhCOOCH₂OCO-Amd)-Ph | H | 4-MeSO₂NH-Bn | H,H | 0, 1 | H |
| 2-326 | 4-(2-PyCOOCH₂OCO-Amd)-Ph | H | 4-MeSO₂NH-Bn | H,H | 0, 1 | H |
| 2-327 | 4-(3-PyCOOCH₂OCO-Amd)-Ph | H | 4-MeSO₂NH-Bn | H,H | 0, 1 | H |
| 2-328 | 4-(4-PyCOOCH₂OCO-Amd)-Ph | H | 4-MeSO₂NH-Bn | H,H | 0, 1 | H |
| 2-329 | 4-(t-BuOCH₂CH₂OCO-Amd)-Ph | H | 4-MeSO₂NH-Bn | H,H | 0, 1 | H |
| 2-330 | 4-(PhOCO-Amd)-Ph | H | 4-MeSO₂NH-Bn | H,H | 0, 1 | H |
| 2-331 | 4-(CHO₂=C(CH₃)OCO-Amd)-Ph | H | 4-MeSO₂NH-Bn | H,H | 0, 1 | H |
| 2-332 | 4-(CHO₂=CH₂OCO-Amd)-Ph | H | 4-MeSO₂NH-Bn | H,H | 0, 1 | H |
| 2-333 | 4-(BnOCO-Amd)-Ph | H | 4-MeSO₂NH-Bn | H,H | 0, 1 | H |
| 2-334 | 4-(AcOCH₂OCO-Amd)-Ph | H | 4-BuSO₂NH-Bn | H,H | 0, 1 | H |
| 2-335 | 4-(PiVaOCH₂OCO-Amd)-Ph | H | 4-BuSO₂NH-Bn | H,H | 0, 1 | H |
| 2-336 | 4-(PhCOOCHO₂OCO-Amd)-Ph | H | 4-BuSO₂NH-Bn | H,H | 0, 1 | H |
| 2-337 | 4-(2-PyCOOCHO₂OCO-Amd)-Ph | H | 4-BuSO₂NH-Bn | H,H | 0, 1 | H |
| 2-338 | 4-(3-PyCOOCO₂OCO-Amd)-Ph | H | 4-BuSO₂NH-Bn | H,H | 0, 1 | H |
| 2-339 | 4-(4-PyCOOCH₂OCO-Amd)-Ph | H | 4-BuSO₂NH-Bn | H,H | 0, 1 | H |
| 2-340 | 4-(t-BuOCHO₂CHO₂OCO-Amd)-Ph | H | 4-BuSO₂NH-Bn | H,H | 0, 1 | H |
| 2-341 | 4-PhOCO-Amd)-Ph | H | 4-BuSO₂NH-Bn | H,H | 0, 1 | H |
| 2-342 | 4-(CHO₂=C(CH₃)OCO-Amd)-Ph | H | 4-BuSO₂NH-Bn | H,H | 0, 1 | H |
| 2-343 | 4-(CHO₂=CHCH₂OCO-Amd)-Ph | H | 4-BuSO₂NH-Bn | H,H | 0, 1 | H |
| 2-344 | 4-(BnOCO-Amd)-Ph | H | 4-BuSO₂NH-Bn | H,H | 0, 1 | H |
| 2-345 | 4-(AcOCH₂OCO-Amd)-Ph | H | 4-PhSO₂NH-Bn | H,H | 0, 1 | H |
| 2-346 | 4-(PivaOCH₂OCO-Amd)-Ph | H | 4-PhSO₂NH-Bn | H,H | 0, 1 | H |
| 2-347 | 4-(PhCOOCH₂OCO-Amd)-Ph | H | 4-PhSO₂NH-Bn | H,H | 0, 1 | H |
| 2-348 | 4-(2-PyCOOCH₂OCO-Amd)-Ph | H | 4-PhSO₂NH-Bn | H,H | 0, 1 | H |
| 2-349 | 4-(3-PyCOOCH₂OCO-Amd)-Ph | H | 4-PhSO₂NH-Bn | H,H | 0, 1 | H |
| 2-350 | 4-(4-PyCOOCH₂OCO-Amd)-Ph | H | 4-PhSO₂NH-Bn | H,H | 0, 1 | H |
| 2-351 | 4-(t-BuOCH₂CH₂OCO-Amd)-Ph | H | 4-PhSO₂NH-Bn | H,H | 0, 1 | H |
| 2-352 | 4-(PhOCO-Amd)-Ph | H | 4-PhSO₂NH-Bn | H,H | 0, 1 | H |
| 2-353 | 4-(CHO₂=C(CH₃)OCO-Amd)-Ph | H | 4-PhSO₂NH-Bn | H,H | 0, 1 | H |
| 2-354 | 4-(CH₂=CHCH₂OCO-Amd)-Ph | H | 4-PhSO₂NH-Bn | H,H | 0, 1 | H |
| 2-355 | 4-(BnOCO-Amd)-Ph | H | 4-PhSO₂NH-Bn | H,H | 0, 1 | H |
| 2-356 | 4-(AcOCH₂OCO-Amd)-Ph | H | 4-PyCH₂ | H,H | 0, 1 | H |
| 2-357 | 4-(PiVaOCH₂OCO-Amd)-Ph | H | 4-PyCH₂ | H,H | 0, 1 | H |
| 2-358 | 4-(PhCOOCH₂OCO-Amd)-Ph | H | 4-PyCH₂ | H,H | 0, 1 | H |
| 2-359 | 4-(2-PyCOOCH₂OCO-Amd)-Ph | H | 4-PyCH₂ | H,H | 0, 1 | H |
| 2-360 | 4-(3-PyCOOCH₂OCO-Amd)-Ph | H | 4-PyCH₂ | H,H | 0, 1 | H |

TABLE 2-continued

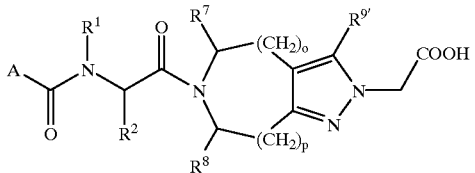

| No | A | $R^1$ | $R^2$ | $R^7,R^8$ | o, p | $R_2$ |
|---|---|---|---|---|---|---|
| 2-361 | 4-(4-PyCOOCH$_2$OCO-Amd)-Ph | H | 4-PyCH$_2$ | H,H | 0, 1 | H |
| 2-362 | 4-(t-BuOCH$_2$CHO$_2$OCO-Amd)-Ph | H | 4-PyCH$_2$ | H,H | 0, 1 | H |
| 2-363 | 4-(PhOCO-Amd)-Ph | H | 4-PyCH$_2$ | H,H | 0, 1 | H |
| 2-364 | 4-(CH$_2$=C(CH$_3$)OCO-Amd)-Ph | H | 4-PyCH$_2$ | H,H | 0, 1 | H |
| 2-365 | 4-(CHO$_2$=CHCH$_2$OCO-Amd)-Ph | H | 4-PyCH$_2$ | H,H | 0, 1 | H |
| 2-366 | 4-(BnOCO-Amd)-Ph | H | 4-PyCH$_2$ | H,H | 0, 1 | H |
| 2-367 | 4-(AcOCH$_2$OCO-Amd)-Ph | H | 4-OH-Bn | H,H | 0, 1 | H |
| 2-368 | 4-(PivaOCH$_2$OCO-Amd)-Ph | H | 4-OH-Bn | H,H | 0, 1 | H |
| 2-369 | 4-(PhCOOCH$_2$OCO-Amd)-Ph | H | 4-OH-Bn | H,H | 0, 1 | H |
| 2-370 | 4-(2-PyCOOCH$_2$OCO-Amd)-Ph | H | 4-OH-Bn | H,H | 0, 1 | H |
| 2-371 | 4-(3-PyCOOCH$_2$OCO-Amd)-Ph | H | 4-OH-Bn | H,H | 0, 1 | H |
| 2-372 | 4-(4-PyCOOCH$_2$OCO-Amd)-Ph | H | 4-OH-Bn | H,H | 0, 1 | H |
| 2-373 | 4-(t-BuOCH$_2$CO$_2$OCO-Amd)-Ph | H | 4-OH-Bn | H,H | 0, 1 | H |
| 2-374 | 4-(PhOCO-Amd)-Ph | H | 4-OH-Bn | H,H | 0, 1 | H |
| 2-375 | 4-(CHO$_2$=C(CH$_3$)OCO-Amd)-Ph | H | 4-OH-Bn | H,H | 0, 1 | H |
| 2-376 | 4-(CHO$_2$=CHCH$_2$OCO-Amd)-Ph | H | 4-OH-Bn | H,H | 0, 1 | H |
| 2-377 | 4-(BnOCO-Amd)-Ph | H | 4-OH-Bn | H,H | 0, 1 | H |
| 2-378 | 4-(AcOCH$_2$OCO-Amd)-Ph | H | Bn | H,H | 0, 1 | H |
| 2-379 | 4-(PiVaOCH$_2$OCO-Amd)-Ph | H | Bn | H,H | 0, 1 | H |
| 2-380 | 4-(PhCOOCH$_2$OCO-Amd)-Ph | H | Bn | H,H | 0, 1 | H |
| 2-381 | 4-(2-PyCOOCH$_2$OCO-Amd)-Ph | H | Bn | H,H | 0, 1 | H |
| 2-382 | 4-(3-PyCOOCH$_2$OCO-Amd)-Ph | H | Bn | H,H | 0, 1 | H |
| 2-383 | 4-(4-PyCOOCH$_2$OCO-Amd)-Ph | H | Bn | H,H | 0, 1 | H |
| 2-384 | 4-(t-BuOCH$_2$CHO$_2$OCO-Amd)-Ph | H | Bn | H,H | 0, 1 | H |
| 2-385 | 4-(PhOCO-Amd)-Ph | H | Bn | H,H | 0, 1 | H |
| 2-386 | 4-(CH$_2$=C(CH$_3$)OCO-Amd)-Ph | H | Bn | H,H | 0, 1 | H |
| 2-387 | 4-(CH$_2$=CHCH$_2$OCO-Amd)-Ph | H | Bn | H,H | 0, 1 | H |
| 2-388 | 4-(BnOCO-Amd)-Ph | H | Bn | H,H | 0, 1 | H |
| 2-389 | 4-Amd-Ph | H | H | H,H | 0, 1 | H |
| 2-390 | 4-(HO-Amd)-Ph | H | H | H,H | 0, 1 | H |
| 2-391 | 4-(MeOCO-Amd)-Ph | H | H | H,H | 0, 1 | H |
| 2-392 | 4-(EtOCO-Amd)-Ph | H | H | H,H | 0, 1 | H |
| 2-393 | 4-(BuOCO-Amd)-Ph | H | H | H,H | 0, 1 | H |
| 2-394 | 4-Amd-Ph | H | Me | H,H | 0, 1 | H |
| 2-395 | 4-(HO-Amd)-Ph | H | Me | H,H | 0, 1 | H |
| 2-396 | 4-(MeOCO-Amd)-Ph | H | Me | H,H | 0, 1 | H |
| 2-397 | 4-(EtOCO-Amd)-Ph | H | Me | H,H | 0, 1 | H |
| 2-398 | 4-(AcOCH$_2$OCO-Amd)-Ph | H | Me | H,H | 0, 1 | H |
| 2-399 | 4-(PivaOCH$_2$OCO-Aind)-Ph | H | Me | H,H | 0, 1 | H |
| 2-400 | 4-(PhCOOCH$_2$OCO-Amd)-Ph | H | Me | H,H | 0, 1 | H |
| 2-401 | 4-(2-PyCOOCH$_2$OCO-Amd)-Ph | H | Me | H,H | 0, 1 | H |
| 2-402 | 4-(3-PyCOOCH$_2$OCO-Amd)-Ph | H | Me | H,H | 0, 1 | H |
| 2-403 | 4-(4-PyCOOCH$_2$OCO-Amd)-Ph | H | Me | H,H | 0, 1 | H |
| 2-404 | 4-(t-BuOCH$_2$CH$_2$OCO-Amd)-Ph | H | Me | H,H | 0, 1 | H |
| 2-405 | 4-(PhOCO-Amd)-Ph | H | Me | H,H | 0, 1 | H |
| 2-406 | 4-(CH$_2$=C(CH$_3$)OCO-AiYid)-Ph | H | Me | H,H | 0, 1 | H |
| 2-407 | 4-(CH$_2$=CHCH$_2$OCO-Amd)-Ph | H | Me | H,H | 0, 1 | H |
| 2-408 | 4-(BnOCO-Amd)-Ph | H | Me | H,H | 0, 1 | H |
| 2-409 | 4-Amd-Ph | H | isoPr | H,H | 0, 1 | H |
| 2-410 | 4-(HO-Amd)-Ph | H | isoPr | H,H | 0, 1 | H |
| 2-411 | 4-(MeOCO-Amd)-Ph | H | isoPr | H,H | 0, 1 | H |
| 2-412 | 4-(EtOCO-Amd)-Ph | H | isoPr | H,H | 0, 1 | H |
| 2-413 | 4-(AcOCH$_2$OCO-Amd)-Ph | H | isoPr | H,H | 0, 1 | H |
| 2-414 | 4-(PhCOOCH$_2$OCO-Amd)-Ph | H | isoPr | H,H | 0, 1 | H |
| 2-415 | 4-(3-PyCOOCH$_2$OCO-Amd)-Ph | H | isoPr | H,H | 0, 1 | H |
| 2-416 | 4-(4-PyCOOCH$_2$OCO-Amd)-Ph | H | isoPr | H,H | 0, 1 | H |
| 2-417 | 4-(t-BuOCH$_2$CH$_2$OCO-Amd)-Ph | H | isoPr | H,H | 0, 1 | H |
| 2-418 | 4-(PhOCO-Amd)-Ph | H | isoPr | H,H | 0, 1 | H |
| 2-419 | 4-(CH$_2$=C(CH$_3$)OCO-Amd)-Ph | H | isoPr | H,H | 0, 1 | H |
| 2-420 | 4-Amd-Ph | H | isoBu | H,H | 0, 1 | H |
| 2-421 | 4-(HO-Amd)-Ph | H | isoBu | H,H | 0, 1 | H |
| 2-422 | 4-(MeOCO-Amd)-Ph | H | isoBu | H,H | 0, 1 | H |
| 2-423 | 4-(EtOCO-Amd)-Ph | H | isoBu | H,H | 0, 1 | H |
| 2-424 | 4-(AcOCH$_2$OCO-Amd)-Ph | H | isoBu | H,H | 0, 1 | H |
| 2-425 | 4-(PhCOOCH$_2$OCO-Amd)-Ph | H | isoBu | H,H | 0, 1 | H |
| 2-426 | 4-(3-PyCOOCH$_2$OCO-Amd)-Ph | H | isoBu | H,H | 0, 1 | H |
| 2-427 | 4-(4-PyCOOCH$_2$OCO-Amd)-Ph | H | isoBu | H,H | 0, 1 | H |

TABLE 2-continued

Structure: A-C(O)-N(R¹)-CH(R²)-C(O)-N[(CH₂)ₒ-CH(R⁷)...][(CH₂)ₚ-CH(R⁸)...]-pyrazole(R⁹')-CH₂COOH

| No | A | R¹ | R² | R⁷,R⁸ | o, p | R₂ |
|---|---|---|---|---|---|---|
| 2-428 | 4-(t-BuOCH₂CH₂OCO-Amd)-Ph | H | isoBu | H,H | 0, 1 | H |
| 2-429 | 4-(PhOCO-Amd)-Ph | H | isoBu | H,H | 0, 1 | H |
| 2-430 | 4-(CH₂=C(CH₃)OCO-Amd)-Ph | H | isoBu | H,H | 0, 1 | H |
| 2-431 | 4-Amd-Ph | H | s-Bu | H,H | 0, 1 | H |
| 2-432 | 4-(HO-Amd)-Ph | H | s-Bu | H,H | 0, 1 | H |
| 2-433 | 4-(EtOCO-Amd)-Ph | H | s-Bu | H,H | 0, 1 | H |
| 2-434 | 4-(PhCOOCH₂OCO-Amd)-Ph | H | s-Bu | H,H | 0, 1 | H |
| 2-435 | 4-(3-PyCOOCH₂OCO-Amd)-Ph | H | s-Bu | H,H | 0, 1 | H |
| 2-436 | 4-(4-PyCOOCH₂OCO-Amd)-Ph | H | s-Bu | H,H | 0, 1 | H |
| 2-437 | 4-(PhOCO-Amd)-Ph | H | s-Bu | H,H | 0, 1 | H |
| 2-438 | 4-(CH₂=C(CH₃)OCO-Amd)-Ph | H | s-Bu | H,H | 0, 1 | H |
| 2-439 | 4-Amd-Ph | H | H | —CH₂CH₂— | 0, 1 | H |
| 2-440 | 4-(HO-Amd)-Ph | H | H | —CH₂CH₂— | 0, 1 | H |
| 2-441 | 4-(MeOCO-Amd)-Ph | H | H | —CH₂CH₂— | 0, 1 | H |
| 2-442 | 4-(EtOCO-Amd)-Ph | H | H | —CH₂CH₂— | 0, 1 | H |
| 2-443 | 4-(PhCOOCHO₂OCO-Amd)-Ph | H | H | —CH₂CH₂— | 0, 1 | H |
| 2-444 | 4-(CH₂=CHCH₂OCO-Amd)-Ph | H | H | —CH₂CH₂— | 0, 1 | H |
| 2-445 | 4-Amd-Ph | H | Me | —CH₂CH₂— | 0, 1 | H |
| 2-446 | 4-(HO-Amd)-Ph | H | Me | —CH₂CH₂— | 0, 1 | H |
| 2-447 | 4-(MeOCO-Amd)-Ph | H | Me | —CH₂CH₂— | 0, 1 | H |
| 2-448 | 4-(EtOCO-Amd)-Ph | H | Me | —CH₂CH₂— | 0, 1 | H |
| 2-449 | 4-(PhCOOCH₂OCO-Amd)-Ph | H | Me | —CH₂CH₂— | 0, 1 | H |
| 2-450 | 4-(3-PyCOOCH₂OCO-Amd)-Ph | H | Me | —CH₂CH₂— | 0, 1 | H |
| 2-451 | 4-(4-PyCOOCH₂OCO-Amd)-Ph | H | Me | —CH₂CH₂— | 0, 1 | H |
| 2-452 | 4-(t-BuOCH₂CH₂OCO-Amd)-Ph | H | Me | —CH₂CH₂— | 0, 1 | H |
| 2-453 | 4-(PhOCO-Amd)-Ph | H | Me | —CH₂CH₂— | 0, 1 | H |
| 2-454 | 4-(CH₂=(CH₃)OCO-Amd)-Ph | H | Me | —CH₂CH₂— | 0, 1 | H |
| 2-455 | 4-(CH₂=CHCHO₂OCO-Amd)-Ph | H | Me | —CH₂CH₂— | 0, 1 | H |
| 2-456 | 4-Amd-Ph | H | isoPr | —CH₂CH₂— | 0, 1 | H |
| 2-457 | 4-(HO-Amd)-Ph | H | isoPr | —CH₂CH₂— | 0, 1 | H |
| 2-458 | 4-(MeOCO-Amd)-Ph | H | isoPr | —CH₂CH₂— | 0, 1 | H |
| 2-459 | 4-(EtOCO-Amd)-Ph | H | isoPr | —CH₂CH₂— | 0, 1 | H |
| 2-460 | 4-(PhCOOCH₂OCO-Amd)-Ph | H | isoPr | —CH₂CH₂— | 0, 1 | H |
| 2-461 | 4-(3-PyCOOCH₂OCO-Amd)-Ph | H | isoPr | —CH₂CH₂— | 0, 1 | H |
| 2-462 | 4-(4-PyCOOCH₂OCO-Amd)-Ph | H | isoPr | —CH₂CH₂— | 0, 1 | H |
| 2-463 | 4-(t-BuOCH₂CH₂OCO-Amd)-Ph | H | isopr | —CH₂CH₂— | 0, 1 | H |
| 2-464 | 4-(PhOCO-Amd)-Ph | H | isoPr | —CH₂CH₂— | 0, 1 | H |
| 2-465 | 4-(CH₂=C(CH₃)OCO-Amd)-Ph | H | isoPr | —CH₂CH₂— | 0, 1 | H |
| 2-466 | 4-Am-Ph | H | isoBu | —CH₂CH₂— | 0, 1 | H |
| 2-467 | 4-(HO-Amd)-Ph | H | isoBu | —CH₂CH₂— | 0, 1 | H |
| 2-468 | 4-(MeOCO-Amd)-Ph | H | isoBu | —CH₂CH₂— | 0, 1 | H |
| 2-469 | 4-(EtOCO-Amd)-Ph | H | isoBu | —CH₂CH₂— | 0, 1 | H |
| 2-470 | 4-(PhCOOCH₂OCO-Amd)-Ph | H | isoBu | —CH₂CH₂— | 0, 1 | H |
| 2-471 | 4-(3-PyCOOCH₂OCO-Amd)-Ph | H | isoBu | —CH₂CH₂— | 0, 1 | H |
| 2-472 | 4-(4-PyCOOCH₂OCO-Amd)-Ph | H | isoBu | —CH₂CH₂— | 0, 1 | H |
| 2-473 | 4-(t-BuOCH₂CHO₂OCO-Amd)-Ph | H | isoBu | —CH₂CH₂— | 0, 1 | H |
| 2-474 | 4-(PhOCO-Amd)-Ph | H | isoBu | —CH₂CH₂— | 0, 1 | H |
| 2-475 | 4-(CH₂=C(CH₃)OCO-Amd)-Ph | H | isoBu | —CH₂CH₂— | 0, 1 | H |
| 2-476 | 4-Amd-Ph | H | s-Bu | —CH₂CH₂— | 0, 1 | H |
| 2-477 | 4-(HO-Amd)-Ph | H | s-Bu | —CH₂CH₂— | 0, 1 | H |
| 2-478 | 4-(EtOCO-Amd)-Ph | H | s-Bu | —CH₂CH₂— | 0, 1 | H |
| 2-479 | 4-(PhCOOCO₂OCO-Amd)-Ph | H | s-Bu | —CH₂CH₂— | 0, 1 | H |
| 2-480 | 4-(3-PyCOOCHO₂OCO-Amd)-Ph | H | s-Bu | —CH₂CH₂— | 0, 1 | H |
| 2-481 | 4-(4-PyCOOCHOCO-Amd)-Ph | H | s-Bu | —CH₂CH₂— | 0, 1 | H |
| 2-482 | 4-(PhOCO-Amd)-Ph | H | s-Bu | —CH₂CH₂— | 0, 1 | H |
| 2-483 | 4-(CH₂=C(CH₃)OCO-Amd)-Ph | H | s-Bu | —CH₂CH₂— | 0, 1 | H |

TABLE 3

Structure: A-C(=O)-N(R¹)-CH(R²)-C(=O)-N-[ring with R⁷, R⁸, (CH₂)ₒ, (CH₂)ₚ, R⁹']-N-CH₂-COOH (pyrazole/diazepine system)

| No | A | R¹ | R² | R⁷,R⁸ | o,p | R⁹' |
|---|---|---|---|---|---|---|
| 3-1 | 4-Amd-Ph | H | Bn | H,H | 0,1 | H |
| 3-2 | 4-Amd-Ph | H | 4-OH-Bn | H,H | 0,1 | H |
| 3-3 | 4-Amd-Ph | H | 4-NO₂-Bn | H,H | 0,1 | H |
| 3-4 | 4-Amd-Ph | H | 4-CN-Bn | H,H | 0,1 | H |
| 3-5 | 4-Amd-Ph | H | 4-CF₃-Bn | H,H | 0,1 | H |
| 3-6 | 4-Amd-Ph | H | 4-F-Bn | H,H | 0,1 | H |
| 3-7 | 4-Amd-Ph | H | 4-BnO-Bn | H,H | 0,1 | H |
| 3-8 | 4-Amd-Ph | H | 4-MeSO₂NH-Bn | H,H | 0,1 | H |
| 3-9 | 4-Amd-Ph | H | 4-BuSO₂NH-Bn | H,H | 0,1 | H |
| 3-10 | 4-Amd-Ph | H | 4-BnSO₂NH-Bn | H,H | 0,1 | H |
| 3-11 | 4-Amd-Ph | H | 4-PhSO₂NH-Bn | H,H | 0,1 | H |
| 3-12 | 4-Amd-Ph | H | 4-(4-F-PhSO₂NH)-Bn | H,H | 0,1 | H |
| 3-13 | 4-Amd-Ph | H | 4-MeOCO-Bn | H,H | 0,1 | H |
| 3-14 | 4-Amd-Ph | H | 4-PyCH₂ | H,H | 0,1 | H |
| 3-15 | 4-Amd-Ph | H | 3-NO₂-Bn | H,H | 0,1 | H |
| 3-16 | 4-Amd-Ph | H | 4-NO₂-2-Cl-Bn | H,H | 0,1 | H |
| 3-17 | 4-Amd-Ph | H | 4-COOH-Bn | H,H | 0,1 | H |
| 3-18 | 4-Amd-Ph | H | 4-NO₂-Bn | H,H | 0,1 | Me |
| 3-19 | 4-Amd-Ph | H | 4-NO₂-Bn | H,H | 0,1 | Et |
| 3-20 | 4-Amd-Ph | H | 4-NO₂-Bn | H,H | 0,1 | Pr |
| 3-21 | 4-Amd-Ph | H | 4-BuSO₂NH-Bn | H,H | 0,1 | Me |
| 3-22 | 4-Amd-Ph | H | 4-NO₂-Bn | —CH₂CH₂— | 0,1 | H |
| 3-23 | 4-Amd-Ph | H | 4-MESO₂NH-Bn | —CH₂CH₂— | 0,1 | H |
| 3-24 | 4-Amd-Ph | H | 4-BuSO₂NH-Bn | —CH₂CH₂— | 0,1 | H |
| 3-25 | 4-Amd-Ph | H | 4-NO₂-Bn | H,H | 1,0 | H |
| 3-26 | 4-Amd-Ph | H | 4-BnSO₂NH-Bn | H,H | 1,0 | H |
| 3-27 | 4-Amd-Ph | H | 4-PhSO₂NH-Bn | H,H | 1,0 | H |
| 3-28 | 4-Amd-Ph | H | 4-NO₂-Bn | —CH₂CH₂— | 1,0 | H |
| 3-29 | 4-Amd-Ph | H | 4-BuSO₂NH-Bn | —CH₂CH₂— | 1,0 | H |
| 3-30 | 4-Amd-Ph | H | 4-NO₂-Bn | H,H | 1,0 | Me |
| 3-31 | 4-(Me-Amd)-Ph | H | 4-NO₂-Bn | H,H | 0,1 | H |
| 3-32 | 4-(Et-Amd)-Ph | H | 4-NO₂-Bn | H,H | 0,1 | H |
| 3-33 | 4-(Pr-Amd)-Ph | H | 4-NO₂-Bn | H,H | 0,1 | H |
| 3-34 | 4-(N,N-Me₂-Amd)-Ph | H | 4-NO₂-Bn | H,H | 0,1 | H |
| 3-35 | 4-(N,N-Et₂-Amd)-Ph | H | 4-NO₂-Bn | H,H | 0,1 | H |
| 3-36 | 4-(N,N'-Me₂-Amd)-Ph | H | 4-NO₂-Bn | H,H | 0,1 | H |
| 3-37 | 4-(N-AcOCH₂-Amd)-Ph | H | 4-NO₂-Bn | H,H | 0,1 | H |
| 3-38 | 4-(PivaOCH₂-Amd)-Ph | H | 4-NO₂-Bn | H,H | 0,1 | H |
| 3-39 | 4-(HO-Amd)-Ph | H | 4-NO₂-Bn | H,H | 0,1 | H |
| 3-40 | 4-(HO-Amd)-Ph | H | 4-BuSO₂NH-Bn | H,H | 0,1 | H |
| 3-41 | 4-(HO-Amd)-Ph | H | 4-BnSO₂NH-Bn | H,H | 0,1 | H |
| 3-42 | 4-(HO-Amd)-Ph | H | 4-PhSO₂NH-Bn | H,H | 0,1 | H |
| 3-43 | 4-(HO-Amd)-Ph | H | 4-NO₂-Bn | H,H | 0,1 | Me |
| 3-44 | 4-(HO-Amd)-Ph | H | 4-MeSO₂NH-Bn | H,H | 0,1 | Me |
| 3-45 | 4-(HO-Amd)-Ph | H | 4-BuSO₂NH-Bn | H,H | 0,1 | Me |
| 3-46 | 4-(HO-Amd)-Ph | H | 4-NO₂-Bn | —CH₂CH₂— | 0,1 | H |
| 3-47 | 4-(HO-Amd)-Ph | H | 4-BuSO₂NH-Bn | —CH₂CH₂— | 0,1 | H |
| 3-48 | 4-(HO-Amd)-Ph | H | 4-BuSO₂NH-Bn | H,H | 1,0 | H |
| 3-49 | 4-(HO-Amd)-Ph | H | 4-NO₂-Bn | —CH₂CH₂— | 1,0 | H |
| 3-50 | 4-(HO-Amd)-Ph | H | 4-NO₂-Bn | H,H | 1,0 | Me |
| 3-51 | 4-(HO-Amd)-Ph | H | 4-NO₂-Bn | —CH₂CH₂— | 1,0 | Me |
| 3-52 | 4-(HO-Amd)-Ph | H | 4-BuSO₂NH-Bn | —CH₂CH₂— | 1,0 | Me |
| 3-53 | 4-(Ac-Amd)-Ph | H | 4-NO₂-Bn | H,H | 0,1 | H |
| 3-54 | 4-(Butyr-Amd)-Ph | H | 4-NO₂-Bn | H,H | 0,1 | H |
| 3-55 | 4-(MeOCO-Amd)-Ph | H | 4-NO₂-Bn | H,H | 0,1 | H |
| 3-56 | 4-(MeOCO-Amd)-Ph | H | 4-BuSO₂NH-Bn | H,H | 0,1 | H |
| 3-57 | 4-(MeOCO-Amd)-Ph | H | 4-NO₂-Bn | H,H | 0,1 | Me |
| 3-58 | 4-(MeOCO-Amd)-Ph | H | 4-NO₂-Bn | —CH₂CH₂— | 0,1 | H |
| 3-59 | 4-(MeOCO-Amd)-Ph | H | 4-MeSO₂NH-Bn | —CH₂CH₂— | 0,1 | H |
| 3-60 | 4-(MeOCO-Amd)-Ph | H | 4-NO₂-Bn | H,H | 1,0 | H |
| 3-61 | 4-(MeOCO-Amd)-Ph | H | 4-PhSO₂NH-Bn | H,H | 1,0 | H |
| 3-62 | 4-(MeOCO-Amd)-Ph | H | 4-NO₂-Bn | —CH₂CH₂— | 1,0 | H |
| 3-63 | 4-(MeOCO-Amd)-Ph | H | 4-BnSO₂NH-Bn | —CH₂CH₂— | 1,0 | H |
| 3-64 | 4-(MeOCO-Amd)-Ph | H | 4-NO₂-Bn | H,H | 1,0 | Me |
| 3-65 | 4-(MeOCO-Amd)-Ph | H | 4-NO₂-Bn | —CH₂CH₂— | 1,0 | Me |
| 3-66 | 4-(EtOCO-Amd)-Ph | H | 4-NO₂-Bn | H,H | 0,1 | H |
| 3-67 | 4-(EtOCO-Amd)-Ph | H | 4-MeSO₂NH-Bn | H,H | 0,1 | H |

TABLE 3-continued

| No | A | R¹ | R² | R⁷,R⁸ | o,p | R⁹' |
|---|---|---|---|---|---|---|
| 3-68 | 4-(EtOCO-Amd)-Ph | H | 4-EtSO$_2$NH-Bn | H,H | 0,1 | H |
| 3-69 | 4-(EtOCO-Amd)-Ph | H | 4-PrSO$_2$NH-Bn | H,H | 0,1 | H |
| 3-70 | 4-(EtOCO-Amd)-Ph | H | 4-BuSO$_2$NH-Bn | H,H | 0,1 | H |
| 3-71 | 4-(EtOCO-Amd)-Ph | H | 4-BnSO$_2$NH-Bn | H,H | 0,1 | H |
| 3-72 | 4-(EtOCO-Amd)-Ph | H | 4-PhSO$_2$NH-Bn | H,H | 0,1 | H |
| 3-73 | 4-(EtOCO-Amd)-Ph | H | 4-NO$_2$-Bn | H,H | 0,1 | Me |
| 3-74 | 4-(EtOCO-Amd)-Ph | H | 4-MeSO$_2$NH-Bn | H,H | 0,1 | Me |
| 3-75 | 4-(EtOCO-Amd)-Ph | H | 4-BuSO$_2$NH-Bn | H,H | 0,1 | Me |
| 3-76 | 4-(EtOCO-Amd)-Ph | H | 4-BnSO$_2$NH-Bn | H,H | 0,1 | Me |
| 3-77 | 4-(EtOCO-Amd)-Ph | H | 4-PhSO$_2$NH-Bn | H,H | 0,1 | Me |
| 3-78 | 4-(EtOCO-Amd)-Ph | H | 4-NO$_2$-Bn | —CH$_2$CH$_2$— | 0,1 | H |
| 3-79 | 4-(EtOCO-Amd)-Ph | H | 4-BuSO$_2$NH-Bn | —CH$_2$CH$_2$— | 0,1 | Me |
| 3-80 | 4-(EtOCO-Amd)-Ph | H | 4-NO$_2$-Bn | H,H | 1,0 | H |
| 3-81 | 4-(EtOCO-Amd)-Ph | H | 4-NO$_2$-Bn | —CH$_2$CH$_2$— | 1,0 | H |
| 3-82 | 4-(EtOCO-Amd)-Ph | H | 4-NO$_2$-Bn | H,H | 1,0 | Me |
| 3-83 | 4-(BuOCO-Amd)-Ph | H | 4-MeSO$_2$NH-Bn | H,H | 0,1 | H |
| 3-84 | 4-(BuOCO-Amd)-Ph | H | 4-BuSO$_2$NH-Bn | H,H | 0,1 | H |
| 3-85 | 4-(BuOCO-Amd)-Ph | H | 4-NO$_2$-Bn | H,H | 0,1 | Me |
| 3-86 | 4-(BuOCO-Amd)-Ph | H | 4-MeSO$_2$NH-Bn | H,H | 0,1 | Me |
| 3-87 | 4-(BuOCO-Amd)-Ph | H | 4-BuSO$_2$NH-Bn | H,H | 0,1 | Me |
| 3-88 | 4-(BuOCO-Amd)-Ph | H | 4-NO$_2$-Bn | —CH$_2$CH$_2$— | 0,1 | H |
| 3-89 | 4-(BuOCO-Amd)-Ph | H | 4-NO$_2$-Bn | H,H | 1,0 | H |
| 3-90 | 4-(BuOCO-Amd)-Ph | H | 4-MeSO$_2$NH-Bn | H,H | 1,0 | H |
| 3-91 | 4-(BuOCO-Amd)-Ph | H | 4-NO$_2$-Bn | —CH$_2$CH$_2$— | 1,0 | H |
| 3-92 | 4-(BuOCO-Amd)-Ph | H | 4-MeSO$_2$NH-Bn | —CH$_2$CH$_2$— | 1,0 | H |
| 3-93 | 4-(BuOCO-Amd)-Ph | H | 4-BuSO$_2$NH-Bn | —CH$_2$CH$_2$— | 1,0 | H |
| 3-94 | 4-(BuOCO-Amd)-Ph | H | 4-BnSO$_2$NH-Bn | —CH$_2$CH$_2$— | 1,0 | H |
| 3-95 | 4-(BuOCO-Amd)-Ph | H | 4-PhSO$_2$NH-Bn | —CH$_2$CH$_2$— | 1,0 | H |
| 3-96 | 4-(BuOCO-Amd)-Ph | H | 4-NO$_2$-Bn | H,H | 1,0 | Me |
| 3-97 | 4-(BuOCO-Amd)-Ph | H | 4-MeSO$_2$NH-Bn | H,H | 1,0 | Me |
| 3-98 | 4-(BuOCO-Amd)-Ph | H | 4-BnSO$_2$NH-Bn | —CH$_2$CH$_2$— | 1,0 | Me |
| 3-99 | 4-(BuOCO-Amd)-Ph | H | 4-PhSO$_2$NH-Bn | —CH$_2$CH$_2$— | 1,0 | Me |
| 3-100 | 4-(t-BuOCO-Amd)-Ph | H | 4-NO$_2$-Bn | H,H | 0,1 | H |
| 3-101 | 4-(t-BuOCO-Amd)-Ph | H | 4-MeSO$_2$NH-Bn | H,H | 0,1 | H |
| 3-102 | 4-(t-BuOCO-Amd)-Ph | H | 4-EtSO$_2$NH-Bn | H,H | 0,1 | H |
| 3-103 | 4-(t-BuOCO-Amd)-Ph | H | 4-PrSO$_2$NH-Bn | H,H | 0,1 | H |
| 3-104 | 4-(t-BuOCO-Amd)-Ph | H | 4-BuSO$_2$NH-Bn | H,H | 0,1 | H |
| 3-105 | 4-(t-BuOCO-Amd)-Ph | H | 4-BnSO$_2$NH-Bn | H,H | 0,1 | H |
| 3-106 | 4-(t-BuOCO-Amd)-Ph | H | 4-PhSO$_2$NH-Bn | H,H | 0,1 | H |
| 3-107 | 4-(t-BuOCO-Amd)-Ph | H | 4-NO$_2$-Bn | H,H | 0,1 | Me |
| 3-108 | 4-(t-BuOCO-Amd)-Ph | H | 4-MeSO$_2$NH-Bn | —CH$_2$CH$_2$— | 0,1 | H |
| 3-109 | 4-(t-BuOCO-Amd)-Ph | H | 4-BuSO$_2$NH-Bn | —CH$_2$CH$_2$— | 0,1 | H |
| 3-110 | 4-(t-BuOCO-Amd)-Ph | H | 4-PhSO$_2$NH-Bn | —CH$_2$CH$_2$— | 0,1 | H |
| 3-111 | 4-(t-BuOCO-Amd)-Ph | H | 4-NO$_2$-Bn | H,H | 1,0 | H |
| 3-112 | 4-(t-BuOCO-Amd)-Ph | H | 4-MeSO$_2$NH-Bn | —CH$_2$CH$_2$— | 1,0 | Me |
| 3-113 | 4-(N,N-(EtOCO)$_2$)-Amd-Ph | H | 4-NO$_2$-Bn | H,H | 0,1 | H |
| 3-114 | 4-(N,N'-(EtOCO)$_2$)-Amd-Ph | H | 4-NO$_2$-Bn | H,H | 0,1 | H |
| 3-115 | 4-((t-BuOCO)$_3$-Amd)-Ph | H | 4-NO$_2$-Bn | H,H | 0,1 | H |
| 3-116 | 4-((t-BuOCO)$_3$-Amd)-Ph | H | 4-MeSO$_2$NH-Bn | H,H | 0,1 | H |
| 3-117 | 4-((t-BuOCO)$_3$-Amd)-Ph | H | 4-BuSO$_2$NH-Bn | H,H | 0,1 | H |
| 3-118 | 4-((t-BuOCO)$_3$-Amd)-Ph | H | 4-BnSO$_2$NH-Bn | H,H | 0,1 | H |
| 3-119 | 4-((t-BuOCO)$_3$-Amd)-Ph | H | 4-PhSO$_2$NH-Bn | H,H | 0,1 | H |
| 3-120 | 4-((t-BuOCO)$_3$-Amd)-Ph | H | 4-NO$_2$-Bn | H,H | 0,1 | Me |
| 3-121 | 4-((t-BuOCO)$_3$-Amd)-Ph | H | 4-MeSO$_2$NH-Bn | H,H | 0,1 | Me |
| 3-122 | 4-((t-BuOCO)$_3$-Amd)-Ph | H | 4-NO$_2$-Bn | —CH$_2$CH$_2$— | 0,1 | H |
| 3-123 | 4-((t-BuOCO)$_3$-Amd)-Ph | H | 4-MeSO$_2$NH-Bn | —CH$_2$CH$_2$— | 0,1 | H |
| 3-124 | 4-((t-BuOCO)$_3$-Amd)-Ph | H | 4-NO$_2$-Bn | H,H | 1,0 | H |
| 3-125 | 4-((t-BuOCO)$_3$-Amd)-Ph | H | 4-MeSO$_2$NH-Bn | H,H | 1,0 | H |
| 3-126 | 4-((t-BuOCO)$_3$-Amd)-Ph | H | 4-PhSO$_2$NH-Bn | —CH$_2$CH$_2$— | 1,0 | H |
| 3-127 | 4-((t-BuOCO)$_3$-Amd)-Ph | H | 4-NO$_2$-Bn | H,H | 1,0 | Me |
| 3-128 | 4-((t-BuOCO)$_3$-Amd)-Ph | H | 4-NO$_2$-Bn | —CH$_2$CH$_2$— | 1,0 | Me |
| 3-129 | 4-Amd-2-F-Ph | H | 4-NO$_2$-Bn | H,H | 0,1 | H |
| 3-130 | 4-Amd-2-Cl-Ph | H | 4-NO$_2$-Bn | H,H | 0,1 | H |
| 3-131 | 4-Amd-2-Me-Ph | H | 4-NO$_2$-Bn | H,H | 0,1 | H |
| 3-132 | 4-Amd-2-Et-Ph | H | 4-NO$_2$-Bn | H,H | 0,1 | H |
| 3-133 | 4-Amd-2-MeO-Ph | H | 4-NO$_2$-Bn | H,H | 0,1 | H |
| 3-134 | 4-Amd-2-EtO-Ph | H | 4-NO$_2$-Bn | H,H | 0,1 | H |

TABLE 3-continued

| No | A | R¹ | R² | R⁷,R⁸ | o,p | R⁹' |
|---|---|---|---|---|---|---|
| 3-135 | 4-PipeOCH₂ | H | 4-OH-Bn | H,H | 0,1 | H |
| 3-136 | 4-PipeOCH₂ | H | 4-NO₂-Bn | H,H | 0,1 | H |
| 3-137 | 4-PipeOCH₂ | H | 4-BuSO₂NH-Bn | H,H | 0,1 | H |
| 3-138 | 4-PipeOCH₂ | H | 4-NO₂-Bn | —CH₂CH₂— | 0,1 | H |
| 3-139 | 4-PipeOCH₂ | H | 4-NO₂-Bn | H,H | 1,0 | H |
| 3-140 | 4-PipeOCH₂ | H | 4-NO₂-Bn | —CH₂CH₂— | 1,0 | H |
| 3-141 | 4-PipeOCH₂ | H | 4-NO₂-Bn | H,H | 1,0 | Me |
| 3-142 | 4-PipeCH=CH | H | 4-NO₂-Bn | H,H | 0,1 | H |
| 3-143 | 4-PipeCH₂CH₂CH₂ | H | 4-NO₂-Bn | H,H | 0,1 | H |
| 3-144 | 4-PipeCH₂CH₂ | H | 4-NO₂-Bn | H,H | 0,1 | H |
| 3-145 | N-Ac-4-PipeOCH₂ | H | 4-NO₂-Bn | H,H | 0,1 | H |
| 3-146 | N-Ac-4-PipeOCH₂ | H | 4-BuSO₂NH-Bn | H,H | 0,1 | H |
| 3-147 | N-PivaOCH₂-4-PipeOCH₂ | H | 4-NO₂-Bn | H,H | 0,1 | H |
| 3-148 | N-PivaOCH₂-4-PipeOCH₂ | H | 4-BuSO₂NH-Bn | H,H | 0,1 | H |
| 3-149 | N-EtOCO-4-PipeOCH₂ | H | 4-NO₂-Bn | H,H | 0,1 | H |
| 3-150 | N-EtOCO-4-PipeOCH₂ | H | 4-BuSO₂NH-Bn | H,H | 0,1 | H |
| 3-151 | 4-(AcOCH₂OCO-Amd)-Ph | H | 4-NO₂-Bn | H,H | 0,1 | H |
| 3-152 | 4-(PivaOCH₂OCO-Amd)-Ph | H | 4-NO₂-Bn | H,H | 0,1 | H |
| 3-153 | 4-(PhCOOCH₂OCO-Amd)4-Ph | H | 4-NO₂-Bn | H,H | 0,1 | H |
| 3-154 | 4-(2-PyCOOCH₂OCO-Amd)-Ph | H | 4-NO₂-Bn | H,H | 0,1 | H |
| 3-155 | 4-(3-PyCOOCH₂OCO-Amd)-Ph | H | 4-NO₂-Bn | H,H | 0,1 | H |
| 3-156 | 4-(4-PyCOOCH₂OCO-Amd)-Ph | H | 4-NO₂-Bn | H,H | 0,1 | H |
| 3-157 | 4-(t-BuOCH₂CH₂OCO-Amd)-Ph | H | 4-NO₂-Bn | H,H | 0,1 | H |
| 3-158 | 4-(PhOCO-Amd)-Ph | H | 4-NO₂-Bn | H,H | 0,1 | H |
| 3-159 | 4-(CH₂=C(CH₃)OCO-Amd)-Ph | H | 4-NO₂-Bn | H,H | 0,1 | H |
| 3-160 | 4-(CH₂=CHCH₂OCO-Amd)-Ph | H | 4-NO₂-Bn | H,H | 0,1 | H |
| 3-161 | 4-(BnOCO-Amd)-Ph | H | 4-NO₂-Bn | H,H | 0,1 | H |
| 3-162 | 4-Amd-Ph | H | H | H,H | 0,1 | H |
| 3-163 | 4-(HO-Amd)-Ph | H | H | H,H | 0,1 | H |
| 3-164 | 4-(MeOCO-Amd)-Ph | H | H | H,H | 0,1 | H |
| 3-165 | 4-(EtOCO-Amd)-Ph | H | H | H,H | 0,1 | H |
| 3-166 | 4-Amd-Ph | H | Me | H,H | 0,1 | H |
| 3-167 | 4-(HO-Amd)-Ph | H | Me | H,H | 0,1 | H |
| 3-168 | 4-(MeOCO-Amd)-Ph | H | Me | H,H | 0,1 | H |
| 3-169 | 4-(EtOCO-Amd)-Ph | H | Me | H,H | 0,1 | H |
| 3-170 | 4-(AcOCH₂OCO-Amd)-Ph | H | Me | H,H | 0,1 | H |
| 3-171 | 4-(PivaOCH₂OCO-Amd)-Ph | H | Me | H,H | 0,1 | H |
| 3-172 | 4-(PhCOOCH₂OCO-Amd)-Ph | H | Me | H,H | 0,1 | H |
| 3-173 | 4-(2-PyCOOCH₂OCO-Amd)-Ph | H | Me | H,H | 0,1 | H |
| 3-174 | 4-(3-PyCOOCH₂OCO-Amd)-Ph | H | Me | H,H | 0,1 | H |
| 3-175 | 4-(4-PyCOOCH₂OCO-Amd)-Ph | H | Me | H,H | 0,1 | H |
| 3-176 | 4-(t-BuOCH₂CH₂OCO-Amd)-Ph | H | Me | H,H | 0,1 | H |
| 3-177 | 4-(PhOCO-Amd)-Ph | H | Me | H,H | 0,1 | H |
| 3-178 | 4-(CH₂=C(CH₃)OCO-Amd)-Ph | H | Me | H,H | 0,1 | H |
| 3-179 | 4-(CH₂=CHCH₂OCO-Amd)-Ph | H | Me | H,H | 0,1 | H |
| 3-180 | 4-(BnOCO-Amd)-Ph | H | Me | H,H | 0,1 | H |
| 3-181 | 4-Amd-Ph | H | isoPr | H,H | 0,1 | H |
| 3-182 | 4-(HO-Amd)-Ph | H | isoPr | H,H | 0,1 | H |
| 3-183 | 4-(MeOCO-Amd)-Ph | H | isoPr | H,H | 0,1 | H |
| 3-184 | 4-(EtOCO-Amd)-Ph | H | isoPr | H,H | 0,1 | H |
| 3-185 | 4-(AcOCH₂OCO-Amd)-Ph | H | isoPr | H,H | 0,1 | H |
| 3-186 | 4-(PhCOOCH₂OCO-Amd)-Ph | H | isoPr | H,H | 0,1 | H |
| 3-187 | 4-(3-PyCOOCH₂OCO-Amd)-Ph | H | isoPr | H,H | 0,1 | H |
| 3-188 | 4-(4-PyCOOCH₂OCO-Amd)-Ph | H | isoPr | H,H | 0,1 | H |
| 3-189 | 4-(t-BuOCH₂CH₂OCO-Amd)-Ph | H | isoPr | H,H | 0,1 | H |
| 3-190 | 4-(PhOCO-Amd)-Ph | H | isoPr | H,H | 0,1 | H |
| 3-191 | 4-(CH₂=C(CH₃)OCO-Amd)-Ph | H | isoPr | H,H | 0,1 | H |
| 3-192 | 4-Amd-Ph | H | isoBu | H,H | 0,1 | H |
| 3-193 | 4-(HO-Amd)-Ph | H | isoBu | H,H | 0,1 | H |
| 3-194 | 4-(MeOCO-Amd)-Ph | H | isoBu | H,H | 0,1 | H |
| 3-195 | 4-(EtOCO-Amd)-Ph | H | isoBu | H,H | 0,1 | H |
| 3-196 | 4-(AcOCH₂OCO-Amd)-Ph | H | isoBu | H,H | 0,1 | H |
| 3-197 | 4-(PhCOOCH₂OCO-Amd)-Ph | H | isoBu | H,H | 0,1 | H |
| 3-198 | 4-(3-PyCOOCH₂OCO-Amd)-Ph | H | isoBu | H,H | 0,1 | H |
| 3-199 | 4-(4-PyCOOCH₂OCO-Amd)-Ph | H | isoBu | H,H | 0,1 | H |
| 3-200 | 4-(t-BuOCH₂CH₂OCO-Amd)-Ph | H | isoBu | H,H | 0,1 | H |
| 3-201 | 4-(PhOCO-Amd)-Ph | H | isoBu | H,H | 0,1 | H |

TABLE 3-continued

| No | A | R¹ | R² | R⁷,R⁸ | o,p | R⁹' |
|---|---|---|---|---|---|---|
| 3-202 | 4-(CH$_2$=C(CH$_3$)OCO-Amd)-Ph | H | isoBu | H,H | 0,1 | H |
| 3-203 | 4-Amd-Ph | H | s-Bu | H,H | 0,1 | H |
| 3-204 | 4-(HO-Amd)-Ph | H | s-Bu | H,H | 0,1 | H |
| 3-205 | 4-(EtOCO-Amd)-Ph | H | s-Bu | H,H | 0,1 | H |
| 3-206 | 4-(PhCOOCH$_2$OCO-Amd)-Ph | H | s-Bu | H,H | 0,1 | H |
| 3-207 | 4-(3-PyCOOCH$_2$OCO-Amd)-Ph | H | s-Bu | H,H | 0,1 | H |
| 3-208 | 4-(4-PyCOOCH$_2$OCO-Amd)-Ph | H | s-Bu | H,H | 0,1 | H |
| 3-209 | 4-(PhOCO-Amd)-Ph | H | s-Bu | H,H | 0,1 | H |
| 3-210 | 4-(CH$_2$=C(CH$_3$)OCO-Amd)-Ph | H | s-Bu | H,H | 0,1 | H |
| 3-211 | 4-Amd-Ph | H | H | —CH$_2$CH$_2$— | 0,1 | H |
| 3-212 | 4-(HO-Amd)-Ph | H | H | —CH$_2$CH$_2$— | 0,1 | H |
| 3-213 | 4-(MeOCO-Amd)-Ph | H | H | —CH$_2$CH$_2$— | 0,1 | H |
| 3-214 | 4-(EtOCO-Amd)-Ph | H | H | —CH$_2$CH$_2$— | 0,1 | H |
| 3-215 | 4-(PhCOOCH$_2$OCO-Amd)-Ph | H | H | —CH$_2$CH$_2$— | 0,1 | H |
| 3-216 | 4-(CH$_2$=CHCH$_2$OCO-Amd)-Ph | H | H | —CH$_2$CH$_2$— | 0,1 | H |
| 3-217 | 4-Amd-Ph | H | Me | —CH$_2$CH$_2$— | 0,1 | H |
| 3-218 | 4-(HO-Amd)-Ph | H | Me | —CH$_2$CH$_2$— | 0,1 | H |
| 3-219 | 4-(MeOCO-Amd)-Ph | H | Me | —CH$_2$CH$_2$— | 0,1 | H |
| 3-220 | 4-(EtOCO-Amd)-Ph | H | Me | —CH$_2$CH$_2$— | 0,1 | H |
| 3-221 | 4-(PhCOOCH$_2$OCO-Amd)-Ph | H | Me | —CH$_2$CH$_2$— | 0,1 | H |
| 3-222 | 4-(3-PyCOOCH$_2$OCO-Amd)-Ph | H | Me | —CH$_2$CH$_2$— | 0,1 | H |
| 3-223 | 4-(4-PyCOOCH$_2$OCO-Amd)-Ph | H | Me | —CH$_2$CH$_2$— | 0,1 | H |
| 3-224 | 4-(t-BuOCH$_2$CH$_2$OCO-Amd)-Ph | H | Me | —CH$_2$CH$_2$— | 0,1 | H |
| 3-225 | 4-(PhOCO-Amd)-Ph | H | Me | —CH$_2$CH$_2$— | 0,1 | H |
| 3-226 | 4-(CH$_2$=C(CH$_3$)OCO-Amd)-Ph | H | Me | —CH$_2$CH$_2$— | 0,1 | H |
| 3-227 | 4-(CH$_2$=CHCH$_2$OCO-Amd)-Ph | H | Me | —CH$_2$CH$_2$— | 0,1 | H |
| 3-228 | 4-Amd-Ph | H | isoPr | —CH$_2$CH$_2$— | 0,1 | H |
| 3-229 | 4-(HO-Amd)-Ph | H | isoPr | —CH$_2$CH$_2$— | 0,1 | H |
| 3-230 | 4-(MeOCO-Amd)-Ph | H | isoPr | —CH$_2$CH$_2$— | 0,1 | H |
| 3-231 | 4-(EtOCO-Amd)-Ph | H | isoPr | —CH$_2$CH$_2$— | 0,1 | H |
| 3-232 | 4-(PhCOOCH$_2$OCO-Amd)-Ph | H | isoPr | —CH$_2$CH$_2$— | 0,1 | H |
| 3-233 | 4-(3-PyCOOCH$_2$OCO-Amd)-Ph | H | isoPr | —CH$_2$CH$_2$— | 0,1 | H |
| 3-234 | 4-(4-PyCOOCH$_2$OCO-Amd)-Ph | H | isoPr | —CH$_2$CH$_2$— | 0,1 | H |
| 3-235 | 4-(t-BuOCH$_2$CH$_2$OCO-Amd)-Ph | H | isoPr | —CH$_2$CH$_2$— | 0,1 | H |
| 3-236 | 4-(PhOCO-Amd)-Ph | H | isoPr | —CH$_2$CH$_2$— | 0,1 | H |
| 3-237 | 4-(CH$_2$=C(CH$_3$)OCO-Amd)-Ph | H | isoPr | —CH$_2$CH$_2$— | 0,1 | H |
| 3-238 | 4-Am-Ph | H | isoBu | —CH$_2$CH$_2$— | 0,1 | H |
| 3-239 | 4-(HO-Amd)-Ph | H | isoBu | —CH$_2$CH$_2$— | 0,1 | H |
| 3-240 | 4-(MeOCO-Amd)-Ph | H | isoBu | —CH$_2$CH$_2$— | 0,1 | H |
| 3-241 | 4-(EtOCO-Amd)-Ph | H | isoBu | —CH$_2$CH$_2$— | 0,1 | H |
| 3-242 | 4-(PhCOOCH$_2$OCO-Amd)-Ph | H | isoBu | —CH$_2$CH$_2$— | 0,1 | H |
| 3-243 | 4-(3-PyCOOCH$_2$OCO-Amd)-Ph | H | isoBu | —CH$_2$CH$_2$— | 0,1 | H |
| 3-244 | 4-(4-PyCOOCH$_2$OCO-Amd)-Ph | H | isoBu | —CH$_2$CH$_2$— | 0,1 | H |
| 3-245 | 4-(t-BuOCH$_2$CH$_2$OCO-Amd)-Ph | H | isoBu | —CH$_2$CH$_2$— | 0,1 | H |
| 3-246 | 4-(PhOCO-Amd)-Ph | H | isoBu | —CH$_2$CH$_2$— | 0,1 | H |
| 3-247 | 4-(CH$_2$=C(CH$_3$)OCO-Amd)-Ph | H | isoBu | —CH$_2$CH$_2$— | 0,1 | H |
| 3-248 | 4-Amd-Ph | H | s-Bu | —CH$_2$CH$_2$— | 0,1 | H |
| 3-249 | 4-(HO-Amd)-Ph | H | s-Bu | —CH$_2$CH$_2$— | 0,1 | H |
| 3-250 | 4-(EtOCO-Amd)-Ph | H | s-Bu | —CH$_2$CH$_2$— | 0,1 | H |
| 3-251 | 4-(PhCOOCH$_2$OCO-Amd)-Ph | H | s-Bu | —CH$_2$CH$_2$— | 0,1 | H |
| 3-252 | 4-(3-PyCOOCH$_2$OCO-Amd)-Ph | H | s-Bu | —CH$_2$CH$_2$— | 0,1 | H |
| 3-253 | 4-(4-PyCOOCH$_2$OCO-Amd)-Ph | H | s-Bu | —CH$_2$CH$_2$— | 0,1 | H |
| 3-254 | 4-(PhOCO-Amd)-Ph | H | s-Bu | —CH$_2$CH$_2$— | 0,1 | H |
| 3-255 | 4-(CH$_2$=C(CH$_3$)OCO-Amd)-Ph | H | s-Bu | —CH$_2$CH$_2$— | 0,1 | H |

TABLE 4

| No | A | R¹ | R² | R⁷, R⁸ | o,p |
|---|---|---|---|---|---|
| 4-1 | 4-Amd-Ph | H | Bn | H,H | 0, 1 |
| 4-2 | 4-Amd-Ph | H | 4-OH-Bn | H,H | 0, 1 |
| 4-3 | 4-Amd-Ph | H | 4-NO$_2$-Bn | H,H | 0, 1 |
| 4-4 | 4-Amd-Ph | H | 4-CN-Bn | H,H | 0, 1 |
| 4-5 | 4-Amd-Ph | H | 4-CF$_3$-Bn | H,H | 0, 1 |
| 4-6 | 4-Amd-Ph | H | 4-F-Bn | H,H | 0, 1 |
| 4-7 | 4-Amd-Ph | H | 4-BnO-Bn | H,H | 0, 1 |
| 4-8 | 4-Amd-Ph | H | 4-MeSO$_2$NH-Bn | H,H | 0, 1 |
| 4-9 | 4-Amd-Ph | H | 4-BuSO$_2$NH-Bn | H,H | 0, 1 |
| 4-10 | 4-Amd-Ph | H | 4-BnSO$_2$NH-Bn | H,H | 0, 1 |
| 4-11 | 4-Amd-Ph | H | 4-PhSO$_2$NH-Bn | H,H | 0, 1 |
| 4-12 | 4-Amd-Ph | H | 4-(4-F-PhSO$_2$NH)-Bn | H,H | 0, 1 |
| 4-13 | 4-Amd-Ph | H | 4-MeOCO-Bn | H,H | 0, 1 |
| 4-14 | 4-Amd-Ph | H | 4-PyCH$_2$ | H,H | 0, 1 |
| 4-15 | 4-Amd-Ph | H | 3-NO$_2$-Bn | H,H | 0, 1 |
| 4-16 | 4-Amd-Ph | H | 4-NO$_2$-2-Cl-Bn | H,H | 0, 1 |
| 4-17 | 4-Amd-Ph | H | 4-COOH-Bn | H,H | 0, 1 |
| 4-18 | 4-Amd-Ph | H | 4-NO$_2$-Bn | —CH$_2$CH$_2$— | 0, 1 |
| 4-19 | 4-Amd-Ph | H | 4-MeSO$_2$NH-Bn | —CH$_2$CH$_2$— | 0, 1 |
| 4-20 | 4-Amd-Ph | H | 4-BuSO$_2$NH-Bn | —CH$_2$CH$_2$— | 0, 1 |
| 4-21 | 4-Amd-Ph | H | 4-NO$_2$-Bn | H,H | 1, 0 |
| 4-22 | 4-Amd-Ph | H | 4-BnSO$_2$NH-Bn | H,H | 1, 0 |
| 4-23 | 4-Amd-Ph | H | 4-PhSO$_2$NH-Bn | H,H | 1, 0 |
| 4-24 | 4-Amd-Ph | H | 4-NO$_2$-Bn | —CH$_2$CH$_2$— | 1, 0 |
| 4-25 | 4-Amd-Ph | H | 4-BuSO$_2$NH-Bn | —CH$_2$CH$_2$— | 1, 0 |
| 4-26 | 4-Amd-2-F-Ph | H | 4-NO$_2$-Bn | H,H | 0, 1 |
| 4-27 | 4-Amd-2-Cl-Ph | H | 4-NO$_2$-Bn | H,H | 0, 1 |
| 4-28 | 4-Amd-2-Me-Ph | H | 4-NO$_2$-Bn | H,H | 0, 1 |
| 4-29 | 4-Amd-2-Et-Ph | H | 4-NO$_2$-Bn | H,H | 0, 1 |
| 4-30 | 4-Amd-2-MeO-Ph | H | 4-NO$_2$-Bn | H,H | 0, 1 |
| 4-31 | 4-Amd-2-EtO-Ph | H | 4-NO$_2$-Bn | H,H | 0, 1 |
| 4-32 | 4-(Me-Amd)-Ph | H | 4-NO$_2$-2-Bn | H,H | 0, 1 |
| 4-33 | 4-(Et-Amd)-Ph | H | 4-NO$_2$-Bn | H,H | 0, 1 |
| 4-34 | 4-(Pr-Amd)-Ph | H | 4-NO$_2$-Bn | H,H | 0, 1 |
| 4-35 | 4-(N,N-Me$_2$-Amd)-Ph | H | 4-NO$_2$-Bn | H,H | 0, 1 |
| 4-36 | 4-(N,N-Et$_2$-Amd)-Ph | H | 4-NO$_2$-Bn | H,H | 0, 1 |
| 4-37 | 4-(N,N'-Me$_2$-Amd)-Ph | H | 4-NO$_2$-Bn | H,H | 0, 1 |
| 4-38 | 4-(AcOCH$_2$-Amd)-Ph | H | 4-NO$_2$-Bn | H,H | 0, 1 |
| 4-39 | 4-(PivaOCH$_2$-Amd)-Ph | H | 4-NO$_2$-Bn | H,H | 0, 1 |
| 4-40 | 4-(HO-Amd)-Ph | H | 4-NO$_2$-Bn | H,H | 0, 1 |
| 4-41 | 4-(HO-Amd)-Ph | H | 4-BuSO$_2$NH-Bn | H,H | 0, 1 |
| 4-42 | 4-(HO-Amd)-Ph | H | 4-BnSO$_2$NH-Bn | H,H | 0, 1 |
| 4-43 | 4-(HO-Amd)-Ph | H | 4-PhSO$_2$NH-Bn | H,H | 0, 1 |
| 4-44 | 4-(HO-Amd)-Ph | H | 4-NO$_2$-Bn | —CH$_2$CH$_2$— | 0, 1 |
| 4-45 | 4-(HO-Amd)-Ph | H | 4-BuSO$_2$NH-Bn | —CH$_2$CH$_2$— | 0, 1 |
| 4-46 | 4-(HO-Amd)-Ph | H | 4-BuSO$_2$NH-Bn | H,H | 1,O |
| 4-47 | 4-(HO-Amd)-Ph | H | 4-NO$_2$-Bn | —CH$_2$CH$_2$— | 1, 0 |
| 4-48 | 4-(Ac-Amd)-Ph | H | 4-NO$_2$-Bn | H,H | 0, 1 |
| 4-49 | 4-(Butyr-Amd)-Ph | H | 4-NO$_2$-Bn | H,H | 0, 1 |
| 4-50 | 4-(MeOCO-Amd)-Ph | H | 4-NO$_2$-Bn | H,H | 0, 1 |
| 4-51 | 4-(MeOCO-Amd)-Ph | H | 4-BuSO$_2$NH-Bn | H,H | 0, 1 |
| 4-52 | 4-(MeOCO-Amd)-Ph | H | 4-NO$_2$-Bn | —CH$_2$CH$_2$— | 0, 1 |
| 4-53 | 4-(MeOCO-Amd)-Ph | H | 4-MeSO$_2$NH-Bn | —CH$_2$CH$_2$— | 0, 1 |
| 4-54 | 4-(MeOCO-Amd)-Ph | H | 4-NO$_2$-Bn | H,H | 1, 0 |
| 4-55 | 4-(MeOCO-Amd)-Ph | H | 4-PhSO$_2$NH-Bn | H,H | 1, 0 |
| 4-56 | 4-(MeOCO-Amd)-Ph | H | 4-NO$_2$-Bn | —CH$_2$CH$_2$— | 1, 0 |
| 4-57 | 4-(MeOCO-Amd)-Ph | H | 4-BnSO$_2$NH-Bn | —CH$_2$CH$_2$— | 1, 0 |
| 4-58 | 4-(EtOCO-Amd)-Ph | H | 4-NO$_2$-Bn | H,H | 0, 1 |
| 4-59 | 4-(EtOCO-Amd)-Ph | H | 4-MeSO$_2$NH-Bn | H,H | 0, 1 |
| 4-60 | 4-(EtOCO-Amd)-Ph | H | 4-EtSO$_2$NH-Bn | H,H | 0, 1 |
| 4-61 | 4-(EtOCO-Amd)-Ph | H | 4-PrSO$_2$NH-Bn | H,H | 0, 1 |
| 4-62 | 4-(EtOCO-Amd)-Ph | H | 4-BuSO$_2$NH-Bn | H,H | 0, 1 |
| 4-63 | 4-(EtOCO-Amd)-Ph | H | 4-BnSO$_2$NH-Bn | H,H | 0, 1 |
| 4-64 | 4-(EtOCO-Amd)-Ph | H | 4-PhSO$_2$NH-Bn | H,H | 0, 1 |
| 4-65 | 4-(EtOCO-Amd)-Ph | H | 4-NO$_2$-Bn | —CH$_2$CH$_2$— | 0, 1 |
| 4-66 | 4-(EtOCO-Amd)-Ph | H | 4-BuSO$_2$NH-Bn | —CH$_2$CH$_2$— | 0, 1 |
| 4-67 | 4-(EtOCO-Amd)-Ph | H | 4-NO$_2$-Bn | H,H | 1, 0 |

TABLE 4-continued

| No | A | $R^1$ | $R^2$ | $R^7$, $R^8$ | o,p |
|---|---|---|---|---|---|
| 4-68 | 4-(EtOCO-Amd)-Ph | H | 4-NO$_2$-Bn | —CH$_2$CH$_2$— | 1, 0 |
| 4-69 | 4-(BuOCO-Amd)-Ph | H | 4-MeSO$_2$NH-Bn | H,H | 0, 1 |
| 4-70 | 4-(BuOCO-Amd)-Ph | H | 4-BuSO$_2$NH-Bn | H,H | 0, 1 |
| 4-71 | 4-(BuOCO-Amd)-Ph | H | 4-NO$_2$-Bn | —CH$_2$CH$_2$— | 0, 1 |
| 4-72 | 4-(BuOCO-Amd)-Ph | H | 4-NO$_2$-Bn | H,H | 1, 0 |
| 4-73 | 4-(BuOCO-Amd)-Ph | H | 4-MeSO$_2$NH-Bn | H,H | 1, 0 |
| 4-74 | 4-(BuOCO-Amd)-Ph | H | 4-NO$_2$-Bn | —CH$_2$CH$_2$— | 1, 0 |
| 4-75 | 4-(BuOCO-Amd)-Ph | H | 4-MeSO$_2$NH-Bn | —CH$_2$CH$_2$— | 1, 0 |
| 4-76 | 4-(BuOCO-Amd)-Ph | H | 4-BuSO$_2$NH-Bn | —CH$_2$CH$_2$— | 1, 0 |
| 4-77 | 4-(BuOCO-Amd)-Ph | H | 4-BnSO$_2$NH-Bn | —CH$_2$CH$_2$— | 1, 0 |
| 4-78 | 4-(BuOCO-Amd)-Ph | H | 4-PhSO$_2$NH-Bn | —CH$_2$CH$_2$— | 1, 0 |
| 4-79 | 4-(t-BuOCO-Amd)-Ph | H | 4-NO$_2$-Bn | H,H | 0, 1 |
| 4-80 | 4-(t-BuOCO-Amd)-Ph | H | 4-MeSO$_2$NH-Bn | H,H | 0, 1 |
| 4-81 | 4-(t-BuOCO-Amd)-Ph | H | 4-EtSO$_2$NH-Bn | H,H | 0, 1 |
| 4-82 | 4-(t-BuOCO-Amd)-Ph | H | 4-PrSO$_2$NH-Bn | H,H | 0, 1 |
| 4-83 | 4-(t-BuOCO-Amd)-Ph | H | 4-BuSO$_2$NH-Bn | H,H | 0, 1 |
| 4-84 | 4-(t-BuOCO-Amd)-Ph | H | 4-BnSO$_2$NH-Bn | H,H | 0, 1 |
| 4-85 | 4-(t-BuOCO-Amd)-Ph | H | 4-PhSO$_2$NH-Bn | H,H | 0, 1 |
| 4-86 | 4-(t-BuOCO-Amd)-Ph | H | 4-MeSO$_2$NH-Bn | —CH$_2$CH$_2$— | 0, 1 |
| 4-87 | 4-(t-BuOCO-Amd)-Ph | H | 4-BuSO$_2$NH-Bn | —CH$_2$CH$_2$— | 0, 1 |
| 4-88 | 4-(t-BuOCO-Amd)-Ph | H | 4-PhSO$_2$NH-Bn | —CH$_2$CH$_2$— | 0, 1 |
| 4-89 | 4-(t-BuOCO-Amd)-Ph | H | 4-NO$_2$-Bn | H,H | 1, 0 |
| 4-90 | 4-(N,N-(EtOCO)$_2$)-Amd-Ph | H | 4-NO$_2$-Bn | H,H | 0, 1 |
| 4-91 | 4-(N,N'-(EtOCO)$_2$)-Amd-Ph | H | 4-NO$_2$-Bn | H,H | 0, 1 |
| 4-92 | 4-((t-BuOCO)$_3$-Amd)-Ph | H | 4-NO$_2$-Bn | H,H | 0, 1 |
| 4-93 | 4-((t-BuOCO)$_3$-Amd)-Ph | H | 4-MeSO$_2$NH-Bn | H,H | 0, 1 |
| 4-94 | 4-((t-BuOCO)$_3$-Amd)-Ph | H | 4-BuSO$_2$NH-Bn | H,H | 0, 1 |
| 4-95 | 4-((t-BuOCO)$_3$-Amd)-Ph | H | 4-BnSO$_2$NH-Bn | H,H | 0, 1 |
| 4-96 | 4-((t-BuOCO)$_3$-Amd)-Ph | H | 4-PhSO$_2$NH-Bn | H,H | 0, 1 |
| 4-97 | 4-((t-BuOCO)$_3$-Amd)-Ph | H | 4-NO$_2$-Bn | —CH$_2$CH$_2$— | 0, 1 |
| 4-98 | 4-((t-BuOCO)$_3$-Amd)-Ph | H | 4-MeSO$_2$NH-Bn | —CH$_2$CH$_2$— | 0, 1 |
| 4-99 | 4-((t-BuOCO)$_3$-Amd)-Ph | H | 4-NO$_2$-Bn | H,H | 1, 0 |
| 4-100 | 4-((t-BuOCO)$_3$-Amd)-Ph | H | 4-MeSO$_2$NH-Bn | H,H | 1, 0 |
| 4-101 | 4-((t-BuOCO)$_3$-Amd)-Ph | H | 4-PhSO$_2$NH-Bn | —CH$_2$CH$_2$— | 1, 0 |
| 4-102 | 4-PipeOCH$_2$ | H | 4-OH-Bn | H,H | 0, 1 |
| 4-103 | 4-PipeOCH$_2$ | H | 4-NOO$_2$-Bn | H,H | 0, 1 |
| 4-104 | 4-PipeOCH$_2$ | H | 4-BuSO$_2$NH-Bn | H,H | 0, 1 |
| 4-105 | 4-PipeOCH$_2$ | H | 4-NO$_2$-Bn | —CH$_2$CH$_2$— | 0, 1 |
| 4-106 | 4-PipeOCH$_2$ | H | 4-NO$_2$-Bn | H,H | 1, 0 |
| 4-107 | 4-PipeOCH$_2$ | H | 4-NO$_2$-Bn | —CH$_2$CH$_2$— | 1, 0 |
| 4-108 | 4-PipeCH═CH | H | 4-NO$_2$-Bn | H,H | 0, 1 |
| 4-109 | 4-PipeCH$_2$CH$_2$CH$_2$ | H | 4-NO$_2$-Bn | H,H | 0, 1 |
| 4-110 | 4-PipeCH$_2$CH$_2$ | H | 4-NO$_2$-Bn | H,H | 0, 1 |
| 4-111 | N-Ac-4-PipeOCH$_2$ | H | 4-NO$_2$-Bn | H,H | 0, 1 |
| 4-112 | N-Ac-4-PipeOCH$_2$ | H | 4-BuSO$_2$NH-Bn | H,H | 0, 1 |
| 4-113 | N-PivaOCH$_2$-4-PipeOCH$_2$ | H | 4-NO$_2$-Bn | H,H | 0, 1 |
| 4-114 | N-PivaOCH$_2$-4-PipeOCH$_2$ | H | 4-BuSO$_2$NH-Bn | H,H | 0, 1 |
| 4-115 | N-EtOCO-4-PipeOCH$_2$ | H | 4-NO$_2$-Bn | H,H | 0, 1 |
| 4-116 | N-EtOCO-4-PipeOCH$_2$ | H | 4-BuSO$_2$NH-Bn | H,H | 0, 1 |
| 4-117 | 4-(PhCOOCH$_2$OCO-Amd)-Ph | H | 4-NO$_2$-Bn | H,H | 0, 1 |
| 4-118 | 4-(2-PyCOOCH$_2$OCO-Amd)-Ph | H | 4-NO$_2$-Bn | H,H | 0, 1 |
| 4-119 | 4-(3-PyCOOCH$_2$OCO-Amd)-Ph | H | 4-NO$_2$-Bn | H,H | 0, 1 |
| 4-120 | 4-(4-PyCOOCH$_2$OCO-Amd)-Ph | H | 4-NO$_2$-Bn | H,H | 0, 1 |
| 4-121 | 4-(t-BuOCH$_2$CH$_2$OCO-Amd)-Ph | H | 4-NO$_2$-Bn | H,H | 0, 1 |
| 4-122 | 4-(PhOCO-Amd)-Ph | H | 4-NO$_2$-Bn | H,H | 0, 1 |
| 4-123 | 4-(CH$_2$═C(CH$_3$)OCO-Amd)-Ph | H | 4-NO$_2$-Bn | H,H | 0, 1 |
| 4-124 | 4-Amd-Ph | H | Me | H,H | 0, 1 |
| 4-125 | 4-(HO-Amd)-Ph | H | Me | H,H | 0, 1 |
| 4-126 | 4-(MeOCO-Amd)-Ph | H | Me | H,H | 0, 1 |
| 4-127 | 4-(EtOCO-Amd)-Ph | H | Me | H,H | 0, 1 |
| 4-128 | 4-(AcOCH$_2$OCO-Amd)-Ph | H | Me | H,H | 0, 1 |
| 4-129 | 4-(PivaOCH$_2$OCO-Amd)-Ph | H | Me | H,H | 0, 1 |
| 4-130 | 4-(PhCOOCH$_2$OCO-Amd)-Ph | H | Me | H,H | 0, 1 |
| 4-131 | 4-(2-PyCOOCH$_2$OCO-Amd)-Ph | H | Me | H,H | 0, 1 |
| 4-132 | 4-(3-PyCOOCH$_2$OCO-Amd)-Ph | H | Me | H,H | 0, 1 |
| 4-133 | 4-(4-PyCOOCH$_2$OCO-Amd)-Ph | H | Me | H,H | 0, 1 |
| 4-134 | 4-(t-BuOCH$_2$CH$_2$OCO-Amd)-Ph | H | Me | H,H | 0, 1 |

TABLE 4-continued

| No | A | R¹ | R² | R⁷, R⁸ | o,p |
|---|---|---|---|---|---|
| 4-135 | 4-(PhOCO-Amd)-Ph | H | Me | H,H | 0, 1 |
| 4-136 | 4-(CH₂=C(CH₃)OCO-Amd)-Ph | H | Me | H,H | 0, 1 |
| 4-137 | 4-(CH₂=CHCH₂OCO-Amd)-Ph | H | Me | H,H | 0, 1 |
| 4-138 | 4-(BnOCO-Amd)-Ph | H | Me | H,H | 0, 1 |
| 4-139 | 4-Amd-Ph | H | isoPr | H,H | 0, 1 |
| 4-140 | 4-(HO-Amd)-Ph | H | isoPr | H,H | 0, 1 |
| 4-141 | 4-(MeOCO-Amd)-Ph | H | isoPr | H,H | 0, 1 |
| 4-142 | 4-O₂tOCO-Amd)-Ph | H | isoPr | H,H | 0, 1 |
| 4-143 | 4-(AcOCH₂OCO-Amd)-Ph | H. | isoPr | H,H | 0, 1 |
| 4-144 | 4-(PhCOOCH₂OCO-Amd)-Ph | H | isoPr | H,H | 0, 1 |
| 4-145 | 4-(3-PyCOOCH₂OCO-Amd)-Ph | H | isoPr | H,H | 0, 1 |
| 4-146 | 4-(4-PyCOOCH₂OCO-Amd)-Ph | H | isoPr | H,H | 0, 1 |
| 4-147 | 4-(t-BuOCH₂CH₂OCO-Amd)-Ph | H | isopr | H,H | 0, 1 |
| 4-148 | 4-(PhOCO-Amd)-Ph | H | isoPr | H,H | 0, 1 |
| 4-149 | 4-(CH₂=C(CH₃)OCO-Amd)-Ph | H | isoPr | H,H | 0, 1 |
| 4-150 | 4-Amd-Ph | H | isoBu | H,H | 0, 1 |
| 4-151 | 4-(HO-Amd)-Ph | H | isoBu | H,H | 0, 1 |
| 4-152 | 4-(MeOCO-Amd)-Ph | H | isoBu | H,H | 0, 1 |
| 4-153 | 4-O₂tOCO-Amd)-Ph | H | isoBu | H,H | 0, 1 |
| 4-154 | 4-(AcOCH₂OCO-Amd)-Ph | H | isoBu | H,H | 0, 1 |
| 4-155 | 4-(PhCOOCH₂OCO-Aind)-Ph | H | isoBu | H,H | 0, 1 |
| 4-156 | 4-(3-PyCOOCH₂OCO-Amd)-Ph | H | isoBu | H,H | 0, 1 |
| 4-157 | 4-(4-PyCOOCH₂OCO-Amd)-Ph | H | isoBu | H,H | 0, 1 |
| 4-158 | 4-(t-BuOCH₂CH₂OCO-Amd)-Ph | H | isoBu | H,H | 0, 1 |
| 4-159 | 4-(PhOCO-Amd)-Ph | H | isoBu | H,H | 0, 1 |
| 4-160 | 4-(CH₂=C(CH₃)OCO-Amd)-Ph | H | isoBu | H,H | 0, 1 |
| 4-161 | 4-Amd-Ph | H | s-Bu | H,H | 0, 1 |
| 4-162 | 4-(HO-Amd)-Ph | H | s-Bu | H,H | 0, 1 |
| 4-163 | 4-(EtOCO-Amd)-Ph | H | s-Bu | H,H | 0, 1 |
| 4-164 | 4-(PhCOOCH₂OCO-Amd)-Ph | H | s-Bu | H,H | 0, 1 |
| 4-165 | 4-(3-PyCOOCH₂OCO-Amd)-Ph | H | s-Bu | H,H | 0, 1 |
| 4-166 | 4-(4-PyCOOCH₂OCO-Amd)-Ph | H | s-Bu | H,H | |
| 4-167 | 4-(PhOCO-Amd)-Ph | H | s-Bu | H,H | 0, 1 |
| 4-168 | 4-(CH₂=C(CH₃)OCO-Amd)-Ph | H | s-Bu | H,H | 0, 1 |
| 4-169 | 4-Amd-Ph | H | H | —CH₂CH₂— | 0, 1 |
| 4-170 | 4-(HO-Amd)-Ph | H | H | —CH₂CH₂— | 0, 1 |
| 4-171 | 4-(MeOCO-Amd)-Ph | H | H | —CH₂CH₂— | 0, 1 |
| 4-172 | 4-O₂tOCO-Amd)-Ph | H | H | —CH₂CH₂— | 0, 1 |
| 4-173 | 4-(PhCOOCHO₂OCO-Amd)-Ph | H | H | —CH₂CH₂— | 0, 1 |
| 4-174 | 4-(CHO₂=CHCH₂OCO-Amd)-Ph | H | H | —CH₂CH₂— | 0, 1 |
| 4-175 | 4-Amd-Ph | H | Me | —CH₂CH₂— | 0, 1 |
| 4-176 | 4-(HO-Amd)-Ph | H | Me | —CH₂CH₂— | 0, 1 |
| 4-177 | 4-(MeOCO-Amd)-Ph | H | Me | —CH₂CH₂— | 0, 1 |
| 4-178 | 4-O₂OCO-Amd)-Ph | H | Me | —CH₂CH₂— | 0, 1 |
| 4-179 | 4-(PhCOOCH₂OCO-Amd)-Ph | H | Me | —CH₂CH₂— | 0, 1 |
| 4-180 | 4-(3-PyCOOCHO₂OCO-Amd)-Ph | H | Me | —CH₂CH₂— | 0, 1 |
| 4-181 | 4-(4-PyCOOCH₂OCO-Amd)-Ph | H | Me | —CH₂CH₂— | 0, 1 |
| 4-182 | 4-(t-BuOCHO₂CH₂OCO-Amd)-Ph | H | Me | —CH₂CH₂— | 0, 1 |
| 4-183 | 4-(PhOCO-Amd)-Ph | H | Me | —CH₂CH₂— | 0, 1 |
| 4-184 | 4-(CH₂=C(CH₃)OCO-Amd)-Ph | H | Me | —CH₂CH₂— | 0, 1 |
| 4-185 | 4-(CH₂=CHCH₂OCO-Amd)-Ph | H | Me | —CH₂CH₂— | 0, 1 |
| 4-186 | 4-Amd-Ph | H | isoPr | —CH₂CH₂— | 0, 1 |
| 4-187 | 4-(HO-Amd)-Ph | H | isoPr | —CH₂CH₂— | 0, 1 |
| 4-188 | 4-(MeOCO-Amd)-Ph | H | isoPr | —CH₂CH₂— | 0, 1 |
| 4-189 | 4-(EtOCO-Amd)-Ph | H | isoPr | —CH₂CH₂— | 0, 1 |
| 4-190 | 4-(PhCOOCH₂OCO-Amd)-Ph | H | isoPr | —CH₂CH₂— | 0, 1 |
| 4-191 | 4-(3-PyCOOCHO₂OCO-Amd)-Ph | H | isoPr | —CH₂CH₂— | 0, 1 |
| 4-192 | 4-(4-PyCOOCH₂OCO-Amd)-Ph | H | isoPr | —CH₂CH₂— | 0, 1 |
| 4-193 | 4-(t-BuOCHO₂CHO₂OCO-Amd)-Ph | H | isoPr | —CH₂CH₂— | 0, 1 |
| 4-194 | 4-(PhOCO-Amd)-Ph | H | isoPr | —CH₂CH₂— | 0, 1 |
| 4-195 | 4-(CHO₂=C(CH₃)OCO-Amd)-Ph | H | isPr | —CH₂CH₂— | 0, 1 |
| 4-196 | 4-Am-Ph | H | isoBu | —CH₂CH₂— | 0, 1 |
| 4-197 | 4-(HO-Amd)-Ph | H | isoBu | —CH₂CH₂— | 0, 1 |
| 4-198 | 4-(MeOCO-Amd)-Ph | H | isoBu | —CH₂CH₂— | 0, 1 |
| 4-199 | 4-(EtOCO-Amd)-Ph | H | isoBu | —CH₂CH₂— | 0, 1 |
| 4-200 | 4-(PhCOOCH₂OCO-Amd)-Ph | H | isoBu | —CH₂CH₂— | 0, 1 |
| 4-201 | 4-(3-PyCOOCH₂OCO-Amd)-Ph | H | isoBu | —CH₂CH₂— | 0, 1 |

TABLE 4-continued

| No | A | R¹ | R² | R⁷, R⁸ | o,p |
|---|---|---|---|---|---|
| 4-202 | 4-(4-PyCOOCHO₂OCO-Amd)-Ph | H | isoBu | —CH₂CH₂— | 0, 1 |
| 4-203 | 4-(t-BuOCH₂CH₂OCO-Amd)-Ph | H | isoBu | —CH₂CH₂— | 0, 1 |
| 4-204 | 4-(PhOCO-Amd)-Ph | H | isoBu | —CH₂CH₂— | 0, 1 |
| 4-205 | 4-(CO₂=C(CH₃)OCO-Amd)-Ph | H | isoBu | —CH₂CH₂— | 0, 1 |
| 4-206 | 4-Amd-Ph | H | s-Bu | —CH₂CH₂— | 0, 1 |
| 4-207 | 4-(HO-Amd)-Ph | H | s-Bu | —CH₂CH₂— | 0, 1 |
| 4-208 | 4-(EtOCO-Amd)-Ph | H | s-Bu | —CH₂CH₂— | 0, 1 |
| 4-209 | 4-(PhCOOCH₂OCO-Amd)-Ph | H | s-Bu | —CH₂CH₂— | 0, 1 |
| 4-210 | 4-(3-PyCOOCH₂OCO-Amd)-Ph | H | s-Bu | —CH₂CH₂— | 0, 1 |
| 4-211 | 4-(4-PyCOOCH₂OCO-Amd)-Ph | H | s-Bu | —CH₂CH₂— | 0, 1 |
| 4-212 | 4-(PhOCO-Amd)-Ph | H | s-Bu | —CH₂CH₂— | 0, 1 |
| 4-213 | 4-(CHO₂=C(CH₃)OCO-Amd)-Ph | H | s-Bu | —CH₂CH₂— | 0, 1 |

TABLE 5

| No | A | R¹ | R² | R⁷, R⁸ | o,p | R⁹ |
|---|---|---|---|---|---|---|
| 5-1 | 4-Amd-Ph | H | Bn | H,H | 0, 1 | H |
| 5-2 | 4-Amd-Ph | H | 4-OH-Bn | H,H | 0, 1 | H |
| 5-3 | 4-Amd-Ph | H | 4-NO₂-Bn | H,H | 0, 1 | H |
| 5-4 | 4-Amd-Ph | H | 4-CN-Bn | H,H | 0, 1 | H |
| 5-5 | 4-Amd-Ph | H | 4-CF₃-Bn | H,H | 0, 1 | H |
| 5-6 | 4-Amd-Ph | H | 4-F-Bn | H,H | 0, 1 | H |
| 5-7 | 4-Amd-Ph | H | 4-BnO-Bn | H,H | 0, 1 | H |
| 5-8 | 4-Amd-Ph | H | 4-MeSO₂NH-Bn | H,H | 0, 1 | H |
| 5-9 | 4-Amd-Ph | H | 4-BuSO₂NH-Bn | H,H | 0, 1 | H |
| 5-10 | 4-Amd-Ph | H | 4-BnSO₂NH-Bn | H,H | 0, 1 | H |
| 5-11 | 4-Amd-Ph | H | 4-PhSO₂NH-Bn | H,H | 0, 1 | H |
| 5-12 | 4-Amd-Ph | H | 4-(4-F-PhSO₂NH)-Bn | H,H | 0, 1 | H |
| 5-13 | 4-Amd-Ph | H | 4-MeOCO-Bn | H,H | 0, 1 | H |
| 5-14 | 4-Amd-Ph | H | 4-PyCH₂ | H,H | 0, 1 | H |
| 5-15 | 4-Amd-Ph | H | 3-NO₂-Bn | H,H | 0, 1 | H |
| 5-16 | 4-Amd-Ph | H | 4-NO₂-2-Cl-Bn | H,H | 0, 1 | H |
| 5-17 | 4-Amd-Ph | H | 4-COOH-Bn | H,H | 0, 1 | H |
| 5-18 | 4-Amd-Ph | H | 4-NO₂-Bn | H,H | 0, 1 | Me |
| 5-19 | 4-Amd-Ph | H | 4-NO₂-Bn | H,H | 0, 1 | Et |
| 5-20 | 4-Amd-Ph | H | 4-NO₂-Bn | H,H | 0, 1 | Pr |
| 5-21 | 4-Amd-Ph | H | 4-BuSO₂NH-Bn | H,H | 0, 1 | Me |
| 5-22 | 4-Amd-Ph | H | 4-NO₂-Bn | —CH₂CH₂— | 0, 1 | H |
| 5-23 | 4-Amd-Ph | H | 4-MeSO₂NH-Bn | —CH₂CH₂— | 0, 1 | H |
| 5-24 | 4-Amd-Ph | H | 4-BuSO₂NH-Bn | —CH₂CH₂— | 0, 1 | H |
| 5-25 | 4-Amd-Ph | H | 4-NO₂-Bn | H,H | 1, 0 | H |
| 5-26 | 4-Amd-Ph | H | 4-BnSO₂NH-Bn | H,H | 1, 0 | H |
| 5-27 | 4-Amd-Ph | H | 4-PhSO₂NH-Bn | H,H | 1, 0 | H |
| 5-28 | 4-Amd-Ph | H | 4-NO₂-Bn | —CH₂CH₂— | 1, 0 | H |
| 5-29 | 4-Amd-Ph | H | 4-BuSO₂NH-Bn | —CH₂CH₂— | 1, 0 | H |
| 5-30 | 4-Amd-Ph | H | 4-NO₂-Bn | H,H | 1, 0 | Me |
| 5-31 | 4-Amd-Ph | Me | 4-NO₂-Bn | H,H | 0, 1 | H |
| 5-32 | 4-(Me-Amd)-Ph | H | 4-NO₂-Bn | H,H | 0, 1 | H |
| 5-33 | 4-(Et-Amd)-Ph | H | 4-NO₂-Bn | H,H | 0, 1 | H |
| 5-34 | 4-(Pr-Amd)-Ph | H | 4-NO₂-Bn | H,H | 0, 1 | H |
| 5-35 | 4-(N,N-Me₂-Amd)-Ph | H | 4-NO₂-Bn | H,H | 0, 1 | H |
| 5-36 | 4-(N,N-Et₂-Amd)-Ph | H | 4-NO₂-Bn | H,H | 0, 1 | H |
| 5-37 | 4-(N,N'-Me₂-Amd)-Ph | H | 4-NO₂-Bn | H,H | 0, 1 | H |
| 5-38 | 4-(N-AcOCHO₂-Amd)-Ph | H | 4-NO₂-Bn | H,H | 0, 1 | H |

TABLE 5-continued

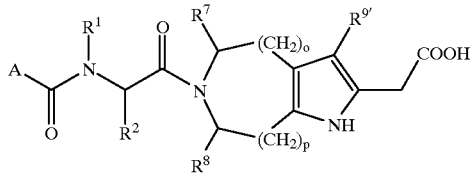

| No | A | R¹ | R² | R⁷, R⁸ | o,p | R⁹ |
|---|---|---|---|---|---|---|
| 5-39 | 4-(PivaOCHO₂-Amd)-Ph | H | 4-NO₂-Bn | H,H | 0, 1 | H |
| 5-40 | 4-(HO-Amd)-Ph | H | 4-NO₂-Bn | H,H | 0, 1 | H |
| 5-41 | 4-(HO-Amd)-Ph | H | 4-BuSO₂NH-Bn | H,H | 0, 1 | H |
| 5-42 | 4-(HO-Amd)-Ph | H | 4-BnSO₂NH-Bn | H,H | 0, 1 | H |
| 5-43 | 4-(HO-Amd)-Ph | H | 4-PhSO₂NH-Bn | H,H | 0, 1 | H |
| 5-44 | 4-(HO-Amd)-Ph | H | 4-NO₂-Bn | H,H | 0, 1 | Me |
| 5-45 | 4-(HO-Amd)-Ph | H | 4-MeSO₂NH-Bn | H,H | 0, 1 | Me |
| 5-46 | 4-(HO-Amd)-Ph | H | 4-BuSO₂NH-Bn | H,H | 0, 1 | Me |
| 5-47 | 4-(HO-Amd)-Ph | H | 4-NO₂-Bn | —CH₂CH₂— | 0, 1 | H |
| 5-48 | 4-(HO-Amd)-Ph | H | 4-BuSO₂NH-Bn | —CH₂CH₂— | 0, 1 | H |
| 5-49 | 4-(HO-Amd)-Ph | H | 4-BuSO₂NH-Bn | H,H | 1, 0 | H |
| 5-50 | 4-(HO-Amd)-Ph | H | 4-NO₂-Bn | —CH₂CH₂— | 1, 0 | H |
| 5-51 | 4-(HO-Amd)-Ph | H | 4-NO₂-Bn | H,H | 1, 0 | Me |
| 5-52 | 4-(HO-Amd)-Ph | H | 4-NO₂-Bn | —CH₂CH₂— | 1, 0 | Me |
| 5-53 | 4-(HO-Amd)-Ph | H | 4-BuSO₂NH-Bn | —CH₂CH₂— | 1, 0 | Me |
| 5-54 | 4-(Ac-Amd)-Ph | H | 4-NO₂-Bn | H,H | 0, 1 | H |
| 5-55 | 4-(Butyr-Amd)-Ph | H | 4-NO₂-Bn | H,H | 0, 1 | H |
| 5-56 | 4-(MeOCO-Amd)-Ph | H | 4-NO₂-Bn | H,H | 0, 1 | H |
| 5-57 | 4-(MeOCO-Amd)-Ph | H | 4-BuSO₂NH-Bn | H,H | 0, 1 | H |
| 5-58 | 4-(MeOCO-Amd)-Ph | H | 4-NO₂-Bn | H,H | 0, 1 | Me |
| 5-59 | 4-(MeOCO-Amd)-Ph | H | 4-NO₂-Bn | —CH₂CH₂— | 0, 1 | H |
| 5-60 | 4-(MeOCO-Amd)-Ph | H | 4-MeSO₂NH-Bn | —CH₂CH₂— | 0, 1 | H |
| 5-61 | 4-(MeOCO-Amd)-Ph | H | 4-NO₂-Bn | H,H | 1, 0 | H |
| 5-62 | 4-(MeOCO-Amd)-Ph | H | 4-PhSO₂NH-Bn | H,H | 1, 0 | H |
| 5-63 | 4-(MeOCO-Amd)-Ph | H | 4-NO₂-Bn | —CH₂CH₂— | 1, 0 | H |
| 5-64 | 4-(MeOCO-Amd)-Ph | H | 4-BnSO₂NH-Bn | —CH₂CH₂— | 1, 0 | H |
| 5-65 | 4-(MeOCO-Amd)-Ph | H | 4-NO₂-Bn | H,H | 1, 0 | Me |
| 5-66 | 4-(MeOCO-Amd)-Ph | H | 4-NO₂-Bn | —CH₂CH₂— | 1, 0 | Me |
| 5-67 | 4-(EtOCO-Amd)-Ph | H | 4-NO₂-Bn | H,H | 0, 1 | H |
| 5-68 | 4-(EtOCO-Amd)-Ph | H | 4-MeSO₂NH-Bn | H,H | 0, 1 | H |
| 5-69 | 4-(EtOCO-Amd)-Ph | H | 4-EtSO₂NH-Bn | H,H | 0, 1 | H |
| 5-70 | 4-(EtOCO-Amd)-Ph | H | 4-PrSO₂NH-Bn | H,H | 0, 1 | H |
| 5-71 | 4-(EtOCO-Amd)-Ph | H | 4-BuSO₂NH-Bn | H,H | 0, 1 | H |
| 5-72 | 4-(EtOCO-Amd)-Ph | H | 4-BnSO₂NH-Bn | H,H | 0, 1 | H |
| 5-73 | 4-(EtOCO-Amd)-Ph | H | 4-PhSO₂NH-Bn | H,H | 0, 1 | H |
| 5-74 | 4-(EtOCO-Amd)-Ph | H | 4-NO₂-Bn | H,H | 0, 1 | Me |
| 5-75 | 4-(EtOCO-Amd)-Ph | H | 4-MeSO₂NH-Bn | H,H | 0, 1 | Me |
| 5-76 | 4-(EtOCO-Amd)-Ph | H | 4-BuSO₂NH-Bn | H,H | 0, 1 | Me |
| 5-77 | 4-(EtOCO-Amd)-Ph | H | 4-BnSO₂NH-Bn | H,H | 0, 1 | Me |
| 5-78 | 4-(EtOCO-Amd)-Ph | H | 4-PhSO₂NH-Bn | H,H | 0, 1 | Me |
| 5-79 | 4-(EtOCO-Amd)-Ph | H | 4-NO₂-Bn | —CH₂CH₂— | 0, 1 | H |
| 5-80 | 4-(EtOCO-Amd)-Ph | H | 4-BuSO₂NH-Bn | —CH₂CH₂— | 0, 1 | H |
| 5-81 | 4-(EtOCO-Amd)-Ph | H | 4-NO₂-Bn | H,H | 1, 0 | H |
| 5-82 | 4-(EtOCO-Amd)-Ph | H | 4-NO₂-Bn | —CH₂CH₂— | 1, 0 | H |
| 5-83 | 4-(EtOCO-Amd)-Ph | H | 4-NO₂-Bn | H,H | 1, 0 | Me |
| 5-84 | 4-(BuOCO-Amd)-Ph | H | 4-MeSO₂NH-Bn | H,H | 0, 1 | H |
| 5-85 | 4-(BuOCO-Amd)-Ph | H | 4-BuSO₂NH-Bn | H,H | 0, 1 | H |
| 5-86 | 4-(BuOCO-Amd)-Ph | H | 4-NO₂-Bn | H,H | 0, 1 | Me |
| 5-87 | 4-(BuOCO-Amd)-Ph | H | 4-MeSOO₂NH-Bn | H,H | 0, 1 | Me |
| 5-88 | 4-(BuOCO-Amd)-Ph | H | 4-BuSO₂NH-Bn | H,H | 0, 1 | Me |
| 5-89 | 4-(BuOCO-Amd)-Ph | H | 4-NO₂-Bn | —CH₂CH₂— | 0, 1 | H |
| 5-90 | 4-(BuOCO-Amd)-Ph | H | 4-NO₂-Bn | H,H | 1, 0 | H |
| 5-91 | 4-(BuOCO-Amd)-Ph | H | 4-MeSO₂NH-Bn | H,H | 1, 0 | H |
| 5-92 | 4-(BuOCO-Amd)-Ph | H | 4-NO₂-Bn | —CH₂CH₂— | 1, 0 | H |
| 5-93 | 4-(BuOCO-Amd)-Ph | H | 4-MeSO₂NH-Bn | —CH₂CH₂— | 1, 0 | H |
| 5-94 | 4-(BuOCO-Amd)-Ph | H | 4-BuSO₂NH-Bn | —CH₂CH₂— | 1, 0 | H |
| 5-95 | 4-(BuOCO-Amd)-Ph | H | 4-BnSO₂NH-Bn | —CH₂CH₂— | 1, 0 | H |
| 5-96 | 4-(BuOCO-Amd)-Ph | H | 4-PhSO₂NH-Bn | —CH₂CH₂— | 1, 0 | H |
| 5-97 | 4-(BuOCO-Amd)-Ph | H | 4-NO₂-Bn | H,H | 1, 0 | Me |
| 5-98 | 4-(BuOCO-Amd)-Ph | H | 4-MeSO₂NH-Bn | H,H | 1, 0 | Me |
| 5-99 | 4-(BuOCO-Amd)-Ph | H | 4-BnSO₂NH-Bn | —CH₂CH₂— | 1, 0 | Me |
| 5-100 | 4-(BuOCO-Amd)-Ph | H | 4-PhSO₂NH-Bn | —CH₂CH₂— | 1, 0 | Me |
| 5-101 | 4-(t-BuOCO-Amd)-Ph | H | 4-NO₂-Bn | H,H | 0, 1 | H |
| 5-102 | 4-(t-BuOCO-Amd)-Ph | H | 4-MeSO₂NH-Bn | H,H | 0, 1 | H |
| 5-103 | 4-(t-BuOCO-Amd)-Ph | H | 4-EtSO₂NH-Bn | H,H | 0, 1 | H |
| 5-104 | 4-(t-BuOCO-Amd)-Ph | H | 4-PrSO₂NH-Bn | H,H | 0, 1 | H |
| 5-105 | 4-(t-BuOCO-Amd)-Ph | H | 4-BuSO₂NH-Bn | H,H | 0, 1 | H |

TABLE 5-continued

| No | A | R¹ | R² | R⁷, R⁸ | o,p | R⁹ |
|---|---|---|---|---|---|---|
| 5-106 | 4-(t-BuOCO-Amd)-Ph | H | 4-BnSO₂NH-Bn | H,H | 0, 1 | H |
| 5-107 | 4-(t-BuOCO-Amd)-Ph | H | 4-PhSO₂NH-Bh | H,H | 0, 1 | H |
| 5-108 | 4-(t-BuOCO-Amd)-Ph | H | 4-NO₂-Bn | H,H | 0, 1 | Me |
| 5-109 | 4-(t-BuOCO-Amd)-Ph | H | 4-MeSO₂NH-Bn | —CH₂CH₂— | 0, 1 | H |
| 5-110 | 4-(t-BuOCO-Amd)-Ph | H | 4-BuSO₂NH-Bn | —CH₂CH₂— | 0, 1 | H |
| 5-111 | 4-(t-BuOCO-Amd)-Ph | H | 4-PhSO₂NH-Bn | —CH₂CH₂— | 0, 1 | H |
| 5-112 | 4-(t-BuOCO-Amd)-Ph | H | 4-NO₂-Bn | H,H | 1, 0 | H |
| 5-113 | 4-(t-BuOCO-Amd)-Ph | H | 4-MeSO₂NH-Bn | —CH₂CH₂— | 1, 0 | Me |
| 5-114 | 4-(N,N-EtOCO)₂)-Amd-Ph | H | 4-NO₂-Bn | H,H | 0, 1 | H |
| 5-115 | 4-(N,N'-EtOCO)₂)-Amd-Ph | H | 4-NO₂-Bn | H,H | 0, 1 | H |
| 5-116 | 4-((t-BuOCO)₃-Amd)-Ph | H | 4-NO₂-Bn | H,H | 0, 1 | H |
| 5-117 | 4-((t-BuOCO)₃-Amd)-Ph | H | 4-MeSO₂NH-Bn | H,H | 0, 1 | H |
| 5-118 | 4-((t-BuOCO)₃-Amd)-Ph | H | 4-BuSO₂NH-Bn | H,H | 0, 1 | H |
| 5-119 | 4-((t-BuOCO)₃-Amd)-Ph | H | 4-BnSO₂NH-Bn | H,H | 0, 1 | H |
| 5-120 | 4-((t-BuOCO)₃-Amd)-Ph | H | 4-PhSO₂NH-Bn | H,H | 0, 1 | H |
| 5-121 | 4-((t-BuOCO)₃-Amd)-Ph | H | 4-NO₂-Bn | H,H | 0, 1 | Me |
| 5-122 | 4-((t-BuOCO)₃-Amd)-Ph | H | 4-MeSO₂NH-Bn | H,H | 0, 1 | Me |
| 5-123 | 4-((t-BuOCO)₃-Amd)-Ph | H | 4-NO₂-Bn | —CH₂CH₂— | 0, 1 | H |
| 5-124 | 4-((t-BuOCO)₃-Amd)-Ph | H | 4-MeSO₂NH-Bn | —CH₂CH₂— | 0, 1 | H |
| 5-125 | 4-((t-BuOCO)₃-Amd)-Ph | H | 4-NO₂-Bn | H,H | 1, 0 | H |
| 5-126 | 4-((t-BuOCO)₃-Amd)-Ph | H | 4-MeSO₂NH-Bn | H,H | 1, 0 | H |
| 5-127 | 4-((t-BuOCO)₃-Amd)-Ph | H | 4-PhSO₂NH-Bn | —CH₂CH₂— | 1, 0 | H |
| 5-128 | 4-((t-BuOCO)₃-Amd)-Ph | H | 4-NO₂-Bn | H,H | 1, 0 | Me |
| 5-129 | 4-((t-BuOCO)₃-Amd)-Ph | H | 4-NO₂-Bn | —CH₂CH₂— | 1, 0 | Me |
| 5-130 | 4-Amd-2-F-Ph | H | 4-NO₂-Bn | H,H | 0, 1 | H |
| 5-131 | 4-Amd-2-Cl-Ph | H | 4-NO₂-Bn | H,H | 0, 1 | H |
| 5-132 | 4-Amd-2-Me-Ph | H | 4-NO₂-Bn | H,H | 0, 1 | H |
| 5-133 | 4-Amd-2-Et-Ph | H | 4-NO₂-Bn | H,H | 0, 1 | H |
| 5-134 | 4-Amd-2-MeO-Ph | H | 4-NO₂-Bn | H,H | 0, 1 | H |
| 5-135 | 4-Amd-2-EtO-Ph | H | 4-NO₂-Bn | H,H | 0, 1 | H |
| 5-136 | 4-PipeOCH₂ | H | 4-OH-Bn | H,H | 0, 1 | H |
| 5-137 | 4-PipeOCH₂ | H | 4-NO₂-Bn | H,H | 0, 1 | H |
| 5-138 | 4-PipeOCH₂ | H | 4-BuSO₂NH-Bn | H,H | 0, 1 | H |
| 5-139 | 4-PipeOCH₂ | H | 4-NO₂-Bn | —CH₂CH₂— | 0, 1 | H |
| 5-140 | 4-PipeOCH₂ | H | 4-NO₂-Bn | H,H | 1, 0 | H |
| 5-141 | 4-PipeOCH₂ | H | 4-NO₂-Bn | —CH₂CH₂— | 1, 0 | H |
| 5-142 | 4-PipeOCH₂ | H | 4-NO₂-Bn | H,H | 1, 0 | Me |
| 5-143 | 4-PipeCH=CH | H | 4-NO₂-Bn | H,H | 0, 1 | H |
| 5-144 | 4-PipeCHO₂CHO₂CH₂ | H | 4-NO₂-Bn | H,H | 0, 1 | H |
| 5-145 | 4-PipeCHO₂CH₂ | H | 4-NO₂-Bn | H,H | 0, 1 | H |
| 5-147 | N-AC-4-PipeOCH₂ | H | 4-BuSO₂NH-Bn | H,H | 0, 1 | H |
| 5-148 | N-PivaOCHO₂4-PipeOCH₂ | H | 4-NO₂-Bn | H,H | 0, 1 | H |
| 5-149 | N-PivaOCHO₂-4-PipeOCH₂ | H | 4-BuSO₂NH-Bn | H,H | 0, 1 | H |
| 5-150 | N-EtOCO-4-PipeOCH₂ | H | 4-NO₂-Bn | H,H | 0, 1 | H |
| 5-151 | N-EtOCO-4-PipeOCH₂ | H | 4-BuSO₂NH-Bn | H,H | 0, 1 | H |
| 5-152 | 4-(AcOCH₂OCO-Amd)-Ph | H | 4-NO₂-Bn | H,H | 0, 1 | H |
| 5-153 | 4-(PivaOCH₂OCO-Amd)-Ph | H | 4-NO₂-Bn | H,H | 0, 1 | H |
| 5-154 | 4-(PhCOOCH₂OCO-Amd)-Ph | H | 4-NO₂-Bn | H,H | 0, 1 | H |
| 5-155 | 4-(2-PyCOOCH₂OCO-Amd)-Ph | H | 4-NO₂-Bn | H,H | 0, 1 | H |
| 5-156 | 4-(3-PyCOOCH₂OCO-Amd)-Ph | H | 4-NO₂-Bn | H,H | 0, 1 | H |
| 5-157 | 4-(4-PyCOOCH₂OCO-Amd)-Ph | H | 4-NO₂-Bn | H,H | 0, 1 | H |
| 5-158 | 4-(t-BuOCH₂CH₂OCO-Amd)-Ph | H | 4-NO₂-Bn | H,H | 0, 1 | H |
| 5-159 | 4-(PhOCO-Amd)-Ph | H | 4-NO₂-Bn | H,H | 0, 1 | H |
| 5-160 | 4-(CH₂=C(CH₃)OCO-Amd)-Ph | H | 4-NO₂-Bn | H,H | 0, 1 | H |
| 5-161 | 4-(CH₂=CHCH₂OCO-Amd)-Ph | H | 4-NO₂-Bn | H,H | 0, 1 | H |
| 5-162 | 4-(BnOCO-Amd)-Ph | H | 4-NO₂-Bn | H,H | 0, 1 | H |
| 5-163 | 4-(AcOCH₂OCO-Amd)-Ph | H | 4-BuSO₂NH-Bn | H,H | 0, 1 | H |
| 5-164 | 4-(PivaOCH₂OCO-Amd)-Ph | H | 4-BuSO₂NH-Bn | H,H | 0, 1 | H |
| 5-165 | 4-(PhCOOCH₂OCO-Amd)-Ph | H | 4-BuSO₂NH-Bn | H,H | 0, 1 | H |
| 5-166 | 4-(3-PyCOOCH₂OCO-Amd)-Ph | H | 4-BuSO₂NH-Bn | H,H | 0, 1 | H |
| 5-167 | 4-(t-BuOCH₂CH₂OCO-Amd)-Ph | H | 4-BuSO₂NH-Bn | H,H | 0, 1 | H |
| 5-168 | 4-(PhOCO-Amd)-Ph | H | 4-BuSO₂NH-Bn | H,H | 0, 1 | H |
| 5-169 | 4-(CH₂=C(CH₃)OCO-Amd)-Ph | H | 4-BuSO₂NH-Bn | H,H | 0, 1 | H |

TABLE 6

Structure: A-C(O)-N(R¹)-CH(R²)-C(O)-N-[ring with (CH₂)ₒ, (CH₂)ₚ, R⁷, R⁸, R⁹']-pyrrole-N-CH₂-COOH

| No | A | R¹ | R² | R⁷, R⁸ | o,p | R⁹ |
|---|---|---|---|---|---|---|
| 6-1 | 4-Amd-Ph | H | Bn | H,H | 0, 1 | H |
| 6-2 | 4-Amd-Ph | H | 4-OH-Bn | H,H | 0, 1 | H |
| 6-3 | 4-Amd-Ph | H | 4-NO₂-Bn | H,H | 0, 1 | H |
| 6-4 | 4-Amd-Ph | H | 4-CN-Bn | H,H | 0, 1 | H |
| 6-5 | 4-Amd-Ph | H | 4-CF3-Bn | H,H | 0, 1 | H |
| 6-6 | 4-Amd-Ph | H | 4-F-Bn | H,H | 0, 1 | H |
| 6-7 | 4-Amd-Ph | H | 4-BnO-Bn | H,H | 0, 1 | H |
| 6-8 | 4-Amd-Ph | H | 4-MeSO₂NH-Bn | H,H | 0, 1 | H |
| 6-9 | 4-Amd-Ph | H | 4-BuSO₂NH-Bn | H,H | 0, 1 | H |
| 6-10 | 4-Amd-Ph | H | 4-BnSO₂NH-Bn | H,H | 0, 1 | H |
| 6-11 | 4-Amd-Ph | H | 4-PhSO₂NH-Bn | H,H | 0, 1 | H |
| 6-12 | 4-Amd-Ph | H | 4-(4-F-PhSO₂NH)-Bn | H,H | 0, 1 | H |
| 6-13 | 4-Amd-Ph | H | 4-MeOCO-Bn | H,H | 0, 1 | H |
| 6-14 | 4-Amd-Ph | H | 4-PYCH₂ | H,H | 0, 1 | H |
| 6-15 | 4-Amd-Ph | H | 3-NO₂-Bn | H,H | 0, 1 | H |
| 6-16 | 4-Amd-Ph | H | 4-NO₂-2-Cl-Bn | H,H | 1, 0 | isoPr |
| 6-17 | 4-Amd-Ph | H | 4-NO₂-Bn | H,H | 0, 1 | isoPr |
| 6-18 | 4-Amd-Ph | H | 4-NO₂-Bn | H,H | 0, 1 | Me |
| 6-19 | 4-Amd-Ph | H | 4-BuSO₂NH-Bn | H,H | 0, 1 | Me |
| 6-20 | 4-Amd-Ph | H | 4-NO₂-Bn | H,H | 0, 1 | Et |
| 6-21 | 4-Amd-Ph | H | 4-NO₂-Bn | H,H | 0, 1 | Pr |
| 6-22 | 4-Amd-Ph | H | 4-NO₂-Bn | —CH₂CH₂— | 0, 1 | H |
| 6-23 | 4-Amd-Ph | H | 4-MeSO₂NH-Bn | —CH₂CH₂— | 0, 1 | H |
| 6-24 | 4-Amd-Ph | H | 4-BuSO₂NH-Bn | —CH₂CH₂— | 0, 1 | H |
| 6-25 | 4-Amd-Ph | H | 4-NO₂-Bn | H,H | 1, 0 | Me |
| 6-26 | 4-(Me-Amd)-Ph | H | 4-NO₂-Bn | H,H | 1, 0 | Et |
| 6-27 | 4-(Et-Amd)-Ph | H | 4-NO₂-Bn | H,H | 1, 0 | Pr |
| 6-28 | 4-(Pr-Amd)-Ph | H | 4-NO₂-Bn | H,H | 0, 1 | H |
| 6-29 | 4-(N,N-Me₂-Amd)-Ph | H | 4-NO₂-Bn | H,H | 0, 1 | H |
| 6-30 | 4-(N,N-Et₂-Amd)-Ph | H | 4-NO₂-Bn | H,H | 0, 1 | H |
| 6-31 | 4-(N,N'-Me₂-Amd)-Ph | H | 4-NO₂-Bn | H,H | 0, 1 | H |
| 6-32 | 4-(N-ACOCH₂-Amd)-Ph | H | 4-NO₂-Bn | H,H | 0, 1 | H |
| 6-33 | 4-(PivaOCHO₂-Amd)-Ph | H | 4-NO₂-Bn | H,H | 0, 1 | H |
| 6-34 | 4-(HO-Amd)-Ph | H | 4-NO₂-Bn | H,H | 0, 1 | H |
| 6-35 | 4-(HO-Amd)-Ph | H | 4-BuSO₂NH-Bn | H,H | 0, 1 | H |
| 6-36 | 4-(HO-Amd)-Ph | H | 4-BnSO₂NH-Bn | H,H | 0, 1 | H |
| 6-37 | 4-(HO-Amd)-Ph | H | 4-PhSO₂NH-Bn | H,H | 0, 1 | H |
| 6-38 | 4-(HO-Amd)-Ph | H | 4-NO₂-Bn | H,H | 0, 1 | Me |
| 6-39 | 4-(HO-Amd)-Ph | H | 4-MeSO₂NH-Bn | H,H | 0, 1 | Me |
| 6-40 | 4-(HO-Amd)-Ph | H | 4-BuSO₂NH-Bn | H,H | 0, 1 | Me |
| 6-41 | 4-(HO-Amd)-Ph | H | 4-NO₂-Bn | —CH₂CH₂— | 0, 1 | H |
| 6-42 | 4-(HO-Amd)-Ph | H | 4-BuSO₂NH-Bn | —CH₂CH₂— | 0, 1 | H |
| 6-43 | 4-(HO-Amd)-Ph | H | 4-NO₂-Bn | H,H | 1, 0 | Me |
| 6-44 | 4-(HO-Amd)-Ph | H | 4-NO₂-Bn | —CH₂CH₂— | 1, 0 | Me |
| 6-45 | 4-(HO-Amd)-Ph | H | 4-BuSO₂NH-Bn | —CH₂CH₂— | 1, 0 | Me |
| 6-46 | 4-(Ac-Amd)-Ph | H | 4-NO₂-Bn | H,H | 0, 1 | H |
| 6-47 | 4-(Butyr-Amd)-Ph | H | 4-NO₂-Bn | H,H | 0, 1 | H |
| 6-48 | 4-(MeOCO-Amd)-Ph | H | 4-NO₂-Bn | H,H | 0, 1 | H |
| 6-49 | 4-(MeOCO-Amd)-Ph | H | 4-BuSO₂NH-Bn | H,H | 0, 1 | H |
| 6-50 | 4-(MeOCO-Amd)-Ph | H | 4-NO₂-Bn | H,H | 0, 1 | Me |
| 6-51 | 4-(MeOCO-Amd)-Ph | H | 4-NO₂-Bn | —CH₂CH₂— | 0, 1 | H |
| 6-52 | 4-(MeOCO-Amd)-Ph | H | 4-MeSO₂NH-Bn | —CH₂CH₂— | 0, 1 | H |
| 6-53 | 4-(MeOCO-Amd)-Ph | H | 4-NO₂-Bn | —CH₂CH₂— | 0, 1 | Me |
| 6-54 | 4-(MeOCO-Amd)-Ph | H | 4-NO₂-Bn | —CH₂CH₂— | 1, 0 | Me |
| 6-55 | 4-(EtOCO-Amd)-Ph | H | 4-NO₂-Bn | H,H | 0, 1 | H |
| 6-56 | 4-(EtOCO-Amd)-Ph | H | 4-MeSO₂NH-Bn | H,H | 0, 1 | H |
| 6-57 | 4-(EtOCO-Amd)-Ph | H | 4-EtSO₂NH-Bn | H,H | 0, 1 | H |
| 6-58 | 4-(EtOCO-Amd)-Ph | H | 4-PtSO₂NH-Bn | H,H | 0, 1 | H |
| 6-59 | 4-(EtOCO-Amd)-Ph | H | 4-BuSO₂NH-Bn | H,H | 0, 1 | H |
| 6-60 | 4-(EtOCO-Amd)-Ph | H | 4-BnSO₂NH-Bn | H,H | 0, 1 | H |
| 6-61 | 4-(EtOCO-Amd)-Ph | H | 4-PhSO₂NH-Bn | H,H | 0, 1 | H |
| 6-62 | 4-(EtOCO-Amd)-Ph | H | 4-NO₂-Bn | H,H | 0, 1 | Me |
| 6-63 | 4-(EtOCO-Amd)-Ph | H | 4-NO₂-Bn | H,H | 0, 1 | Et |
| 6-64 | 4-(EtOCO-Amd)-Ph | H | 4-NO₂-Bn | H,H | 0, 1 | Pr |
| 6-65 | 4-(EtOCO-Amd)-Ph | H | 4-NO₂-Bn | H,H | 0, 1 | Et |
| 6-66 | 4-(EtOCO-Amd)-Ph | H | 4-NO₂-Bn | H,H | 0, 1 | Pr |
| 6-67 | 4-(EtOCO-Amd)-Ph | H | 4-NO₂-Bn | —CH₂CH₂— | 0, 1 | H |

TABLE 6-continued

| No | A | R$^1$ | R$^2$ | R$^7$, R$^8$ | o,p | R$^9$ |
|---|---|---|---|---|---|---|
| 6-68 | 4-(EtOCO-Amd)-Ph | H | 4-BuSO$_2$NH-Bn | —CH$_2$CH$_2$— | 0, 1 | H |
| 6-69 | 4-(EtOCO-Amd)-Ph | H | 4-NO$_2$-Bn | H,H | 1, 0 | Me |
| 6-70 | 4-(BuOCO-Amd)-Ph | H | 4-MeSO$_2$NH-Bn | H,H | 0, 1 | H |
| 6-71 | 4-(BuOCO-Amd)-Ph | H | 4-BuSO$_2$NH-Bn | H,H | 0, 1 | H |
| 6-72 | 4-(BuOCO-Amd)-Ph | H | 4-NO$_2$-Bn | H,H | 0, 1 | Me |
| 6-73 | 4-(BuOCO-Amd)-Ph | H | 4-MeSO$_2$NH-Bn | H,H | 0, 1 | Me |
| 6-74 | 4-(BuOCO-Amd)-Ph | H | 4-BuSO$_2$NH-Bn | H,H | 0, 1 | Me |
| 6-75 | 4-(BuOCO-Amd)-Ph | H | 4-NO$_2$-Bn | —CH$_2$CH$_2$— | 0, 1 | H |
| 6-76 | 4-(BuOCO-Amd)-Ph | H | 4-NO$_2$-Bn | H,H | 1, 0 | Me |
| 6-77 | 4-(BuOCO-Amd)-Ph | H | 4-MeSO$_2$NH-Bn | H,H | 1, 0 | H |
| 6-78 | 4-(BuOCO-Amd)-Ph | H | 4-BnSO$_2$NH-Bn | —CH$_2$CH$_2$— | 1, 0 | Me |
| 6-79 | 4-(BuOCO-Amd)-Ph | H | 4-PhSO$_2$NH-Bn | —CH$_2$CH$_2$— | 1, 0 | Me |
| 6-80 | 4-(t-BuOCO-Amd)-Ph | H | 4-NO$_2$-Bn | H,H | 0, 1 | H |
| 6-81 | 4-(t-BuOCO-Amd)-Ph | H | 4-MeSO$_2$NH-Bn | H,H | 0, 1 | H |
| 6-82 | 4-(t-BuOCO-Amd)-Ph | H | 4-EtSO$_2$NH-Bn | H,H | 0, 1 | H |
| 6-83 | 4-(t-BuOCO-Amd)-Ph | H | 4-PrSO$_2$NH-Bn | H,H | 0, 1 | H |
| 6-84 | 4-(t-BuOCO-Amd)-Ph | H | 4-BuSO$_2$NH-Bn | H,H | 0, 1 | H |
| 6-85 | 4-(t-BuOCO-Amd)-Ph | H | 4-BnSO$_2$NH-Bn | H,H | 0, 1 | H |
| 6-86 | 4-(t-BuOCO-Amd)-Ph | H | 4-PhSO$_2$NH-Bn | H,H | 0, 1 | H |
| 6-87 | 4-(t-BuOCO-Amd)-Ph | H | 4-NO$_2$-Bn | H,H | 0, 1 | Me |
| 6-88 | 4-(t-BuOCO-Amd)-Ph | H | 4-MeSO$_2$NH-Bn | —CH$_2$CH$_2$— | 0, 1 | H |
| 6-89 | 4-(t-BuOCO-Amd)-Ph | H | 4-BuSO$_2$NH-Bn | —CH$_2$CH$_2$— | 0, 1 | H |
| 6-90 | 4-(t-BuOCO-Amd)-Ph | H | 4-PhSO$_2$NH-Bn | —CH$_2$CH$_2$— | 0, 1 | H |
| 6-91 | 4-(t-BuOCO-Amd)-Ph | H | 4-MeSO$_2$NH-Bn | —CH$_2$CH$_2$— | 1, 0 | Me |
| 6-92 | 4-(N,N-(EtOCO)$_2$)-Amd-Ph | H | 4-NO$_2$-Bn | H,H | 0, 1 | H |
| 6-93 | 4-(N,N'-(EtOCO)$_2$)-Amd-Ph | H | 4-NO$_2$-Bn | H,H | 0, 1 | H |
| 6-94 | 4-((t-BuOCO)$_3$-Amd)-Ph | H | 4-NO$_2$-Bn | H,H | 0, 1 | H |
| 6-95 | 4-((t-BuOCO)$_3$-Amd)-Ph | H | 4-MeSO$_2$NH-Bn | H,H | 0, 1 | H |
| 6-96 | 4-((t-BuOCO)$_3$-Amd)-Ph | H | 4-BuSO$_2$NH-Bn | H,H | 0, 1 | H |
| 6-97 | 4-((t-BuOCO)$_3$-Amd)-Ph | H | 4-BnSO$_2$NH-Bn | H,H | 0, 1 | H |
| 6-98 | 4-((t-BuOCO)$_3$-Amd)-Ph | H | 4-PhSO$_2$NH-Bn | H,H | 0, 1 | H |
| 6-99 | 4-((t-BuOCO)$_3$-Amd)-Ph | H | 4-NO$_2$-Bn | H,H | 0, 1 | Me |
| 6-100 | 4-((t-BuOCO)$_3$-Amd)-Ph | H | 4-MeSO$_2$NH-Bn | H,H | 0, 1 | Me |
| 6-101 | 4-((t-BuOCO)$_3$-Amd)-Ph | H | 4-NO$_2$-Bn | —CH$_2$CH$_2$— | 0, 1 | H |
| 6-102 | 4-((t-BuOCO)$_3$-Amd)-Ph | H | 4-MeSO$_2$NH-Bn | —CH$_2$CH$_2$— | 0, 1 | H |
| 6-103 | 4-((t-BuOCO)$_3$-Amd)-Ph | H | 4-NO$_2$Bn | H,H | 1, 0 | Me |
| 6-104 | 4-((t-BuOCO)$_3$-Amd)-Ph | H | 4-NO$_2$-Bn | —CH$_2$CH$_2$— | 1, 0 | Me |
| 6-105 | 4-Amd-2-F-Ph | H | 4-NO$_2$-Bn | H,H | 0, 1 | H |
| 6-106 | 4-Amd-2-Cl-Ph | H | 4-NO$_2$-Bn | H,H | 0, 1 | H |
| 6-107 | 4-Amd-O$_2$Me-Ph | H | 4-NO$_2$-Bn | H,H | 0, 1 | H |
| 6-108 | 4-Amd-2-Et-Ph | H | 4-NO$_2$-Bn | H,H | 0, 1 | H |
| 6-109 | 4-Amd-2-MeO-Ph | H | 4-NO$_2$-Bn | H,H | 0, 1 | H |
| 6-110 | 4-Amd-2-EtO-Ph | H | 4-NO$_2$-Bn | H,H | 0, 1 | H |
| 6-111 | 4-PipeOCH$_2$ | H | 4-OH-Bn | H,H | 0, 1 | H |
| 6-112 | 4-PipeOCH$_2$ | H | 4-NO$_2$-Bn | H,H | 0, 1 | H |
| 6-113 | 4-PipeOC$_2$ | H | 4-BuSO$_2$NH-Bn | H,H | 0, 1 | H |
| 6-114 | 4-PipeOCH$_2$ | H | 4-NO$_2$-Bn | —CH$_2$CH$_2$— | 0, 1 | H |
| 6-115 | 4-PipeOC$_2$ | H | 4-NO$_2$-Bn | H,H | 1, 0 | Me |
| 6-116 | 4-PipeCH=CH | H | 4-NO$_2$-Bn | H,H | 0, 1 | H |
| 6-117 | 4-PipeCH$_2$CH$_2$CH$_2$ | H | 4-NO$_2$-Bn | H,H | 0, 1 | H |
| 6-118 | 4-PipeCHO$_2$CH$_2$ | H | 4-NO$_2$-Bn | H,H | 0, 1 | H |
| 6-119 | N-Ac4-PipeOCH$_2$ | H | 4-NO$_2$-Bn | H,H | 0, 1 | H |
| 6-120 | N-Ac4-PipeOCH$_2$ | H | 4-BuSO$_2$NH-Bn | H,H | 0, 1 | H |
| 6-121 | N-PivaOCHO$_2$4-PipeOCH$_2$ | H | 4-NO$_2$-Bn | H,H | 0, 1 | H |
| 6-122 | N-PivaOCHO$_2$4-PipeOCH$_2$ | H | 4-BuSO$_2$NH-Bn | H,H | 0, 1 | H |
| 6-123 | N-EtOCO-4-PipeOCH$_2$ | H | 4-NO$_2$-Bn | H,H | 0, 1 | H |
| 6-124 | N-EtOCO-4-PipeOC$_2$ | H | 4-BuSO$_2$NH-Bn | H,H | 0, 1 | H |
| 6-125 | 4-(AcOCH$_2$OCO-Amd)-Ph | H | 4-NO$_2$-Bn | H,H | 0, 1 | H |
| 6-126 | 4-(PivaOCH$_2$OCO-Amd)-Ph | H | 4-NO$_2$-Bn | H,H | 0, 1 | H |
| 6-127 | 4-(PhCOOCH$_2$OCO-Amd)-Ph | H | 4-NO$_2$-Bn | H,H | 0, 1 | H |
| 6-128 | 4-(2-PyCOOCH$_2$OCO-Amd)-Ph | H | 4-NO$_2$-Bn | H,H | 0, 1 | H |
| 6-129 | 4-(3-PyCOOCH$_2$OCO-Amd)-Ph | H | 4-NO$_2$-Bn | H,H | 0, 1 | H |
| 6-130 | 4-(4-PyCOOCH$_2$OCO-Amd)-Ph | H | 4-NO$_2$-Bn | H,H | 0, 1 | H |
| 6-131 | 4-(t-BuOCH$_2$CH$_2$OCO-Amd)-Ph | H | 4-NO$_2$-Bn | H,H | 0, 1 | H |
| 6-132 | 4-(PhOCO-Amd)-Ph | H | 4-NO$_2$-Bn | H,H | 0, 1 | H |
| 6-133 | 4-(CH$_2$=C(CH$_3$)OCO-Amd)-Ph | H | 4-NO$_2$-Bn | H,H | 0, 1 | H |
| 6-134 | 4-(AcOCH$_2$OCO-Amd)-Ph | H | 4-OH-Bn | H,H | 0, 1 | H |

TABLE 6-continued

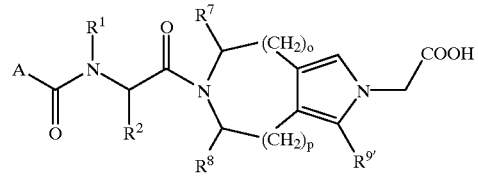

| No | A | R$^1$ | R$^2$ | R$^7$, R$^8$ | o,p | R$^{9'}$ |
|---|---|---|---|---|---|---|
| 6-135 | 4-(PivaOCH$_2$OCO-Amd)-Ph | H | 4-OH-Bn | H,H | 0, 1 | H |
| 6-136 | 4-(PhCOOCH$_2$OCO-Amd)-Ph | H | 4-OH-Bn | H,H | 0, 1 | H |
| 6-137 | 4-(2-PyCOOCH$_2$OCO-Amd)-Ph | H | 4-OH-Bn | H,H | 0, 1 | H |
| 6-138 | 4-(3-PyCOOCH$_2$OCO-Amd)-Ph | H | 4-OH-Bn | H,H | 0, 1 | H |
| 6-139 | 4-(4-PyCOOCH$_2$OCO-Amd)-Ph | H | 4-OH-Bn | H,H | 0, 1 | H |
| 6-140 | 4-(t-BuOCH$_2$CH$_2$OCO-Amd)-Ph | H | 4-OH-Bn | H,H | 0, 1 | H |
| 6-141 | 4-(PhOCO-Amd)-Ph | H | 4-OH-Bn | H,H | 0, 1 | H |
| 6-142 | 4-(CH$_2$=C(CH$_3$)OCO-Amd)-Ph | H | 4-OH-Bn | H,H | 0, 1 | H |
| 6-143 | 4-(AcOCH$_2$OCO-Amd)-Ph | H | Bn | H,H | 0, 1 | H |
| 6-144 | 4-(PivaOCH$_2$OCO-Amd)-Ph | H | Bn | H,H | 0, 1 | H |
| 6-145 | 4-(PhCOOCH$_2$OCO-Amd)-Ph | H | Bn | H,H | 0, 1 | H |
| 6-146 | 4-(2-PyCOOCH$_2$OCO-Amd)-Ph | H | Bn | H,H | 0, 1 | H |
| 6-147 | 4-(3-PyCOOCH$_2$OCO-Amd)-Ph | H | Bn | H,H | 0, 1 | H |
| 6-148 | 4-(4-PyCOOCH$_2$OCO-Amd)-Ph | H | Bn | H,H | 0, 1 | H |
| 6-149 | 4-(t-BuOCH$_2$CH$_2$OCO-Amd)-Ph | H | Bn | H,H | 0, 1 | H |
| 6-150 | 4-(PhOCO-Amd)-Ph | H | Bn | H,H | 0, 1 | H |
| 6-151 | 4-(CH$_2$=C(CH$_3$)OCO-Amd)-Ph | H | Bn | H,H | 0, 1 | H |
| 6-152 | 4-(AcOCH$_2$OCO-Amd)-Ph | H | 4-MeSO$_2$NH-Bn | H,H | 0, 1 | H |
| 6-153 | 4-(PivaOCH$_2$OCO-Amd)-Ph | H | 4-MeSO$_2$NH-Bn | H,H | 0, 1 | H |
| 6-154 | 4-(PhCOOCH$_2$OCO-Amd)-Ph | H | 4-MeSO$_2$NH-Bn | H,H | 0, 1 | H |
| 6-155 | 4-(2-PyCOOCH$_2$OCO-Amd)-Ph | H | 4-MeSO$_2$NH-Bn | H,H | 0, 1 | H |
| 6-156 | 4-(3-PyCOOCH$_2$OCO-Amd)-Ph | H | 4-MeSO$_2$NH-Bn | H,H | 0, 1 | H |
| 6-157 | 4-(4-PyCOOCH$_2$OCO-Amd)-Ph | H | 4-MeSO$_2$NH-Bn | H,H | 0, 1 | H |
| 6-158 | 4-(t-BuOCH$_2$CH$_2$OCO-Amd)-Ph | H | 4-MeSO$_2$NH-Bn | H,H | 0, 1 | H |
| 6-159 | 4-(PhOCO-Amd)-Ph | H | 4-MeSO$_2$NH-Bn | H,H | 0, 1 | H |
| 6-160 | 4-(CH$_2$=C(CH$_3$)OCO-Amd)-Ph | H | 4-MeSO$_2$NH-Bn | H,H | 0, 1 | H |
| 6-161 | 4-(AcOCH$_2$OCO-Amd)-Ph | H | 4-BuSO$_2$NH-Bn | H,H | 0, 1 | H |
| 6-162 | 4-(PivaOCH$_2$OCO-Amd)-Ph | H | 4-BuSO$_2$NH-Bn | H,H | 0, 1 | H |
| 6-163 | 4-(PhCOOCH$_2$OCO-Amd)-Ph | H | 4-BuSO$_2$NH-Bn | H,H | 0, 1 | H |
| 6-164 | 4-(2-PyCOOCH$_2$OCO-Amd)-Ph | H | 4-BuSO$_2$NH-Bn | H,H | 0, 1 | H |
| 6-165 | 4-(3-PyCOOCH$_2$OCO-Amd)-Ph | H | 4-BuSO$_2$NH-Bn | H,H | 0, 1 | H |
| 6-166 | 4-(4-PyCOOCH$_2$OCO-Amd)-Ph | H | 4-BuSO$_2$NH-Bn | H,H | 0, 1 | H |
| 6-167 | 4-(t-BuOCH$_2$CH$_2$OCO-Amd)-Ph | H | 4-BuSO$_2$NH-Bn | H,H | 0, 1 | H |
| 6-168 | 4-(PhOCO-Amd)-Ph | H | 4-BuSO$_2$NH-Bn | H,H | 0, 1 | H |
| 6-169 | 4-(CH$_2$=C(CH$_3$)OCO-Amd)-Ph | H | 4-BuSO$_2$NH-Bn | H,H | 0, 1 | H |

TABLE 7

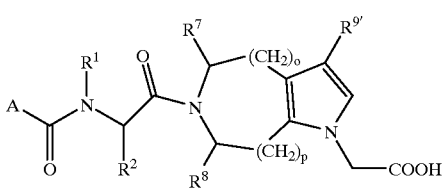

| No | A | R$^1$ | R$^2$ | R$^7$,R$^8$ | o,p | R$^{9'}$ |
|---|---|---|---|---|---|---|
| 7-1 | 4-Amd—Ph | H | 4-MeSO$_2$NH—Bn | H,H | 0,1 | H |
| 7-2 | 4-Amd—Ph | H | 4-BuSO$_2$NH—Bn | H,H | 0,1 | H |
| 7-3 | 4-Amd—Ph | H | 4-BnSO$_2$NH—Bn | H,H | 0,1 | H |
| 7-4 | 4-Amd—Ph | H | 4-PhSO$_2$NH—Bn | H,H | 0,1 | H |
| 7-5 | 4-Amd—Ph | H | 4-NO$_2$—Bn | H,H | 0,1 | Me |
| 7-6 | 4-Amd—Ph | H | 4-BuSO$_2$NH—Bn | H,H | 0,1 | Me |
| 7-7 | 4-Amd—Ph | H | 4-PhSO$_2$NH—Bn | H,H | 0,1 | Me |
| 7-8 | 4-Amd—Ph | H | 4-NO$_2$—Bn | —CH$_2$CH$_2$— | 0,1 | H |
| 7-9 | 4-Amd—Ph | H | 4-MeSO$_2$NH—Bn | —CH$_2$CH$_2$— | 0,1 | H |
| 7-10 | 4-Amd—Ph | H | 4-BuSO$_2$NH—Bn | —CH$_2$CH$_2$— | 0,1 | H |
| 7-11 | 4-Amd—Ph | H | 4-NO$_2$—Bn | H,H | 1,0 | H |
| 7-12 | 4-Amd—Ph | H | 4-BnSO$_2$NH—Bn | H,H | 1,0 | H |
| 7-13 | 4-Amd—Ph | H | 4-PhSO$_2$NH—Bn | H,H | 1,0 | H |
| 7-14 | 4-Amd—Ph | H | 4-NO$_2$—Bn | —CH$_2$CH$_2$— | 1,0 | H |
| 7-15 | 4-Amd—Ph | H | 4-BuSO$_2$NH—Bn | —CH$_2$CH$_2$— | 1,0 | H |

TABLE 7-continued

| No | A | R¹ | R² | R⁷,R⁸ | o,p | R⁹' |
|---|---|---|---|---|---|---|
| 7-16 | 4-Amd—Ph | H | 4-NO₂—Bn | H,H | 1,0 | Me |
| 7-17 | 4-(HO—Amd)—Ph | H | 4-NO₂—Bn | H,H | 0,1 | H |
| 7-18 | 4-(MeOCO—Amd)—Ph | H | 4-NO₂—Bn | H,H | 0,1 | H |
| 7-19 | 4-(MeOCO—Amd)—Ph | H | 4-BuSO₂NH—Bn | H,H | 0,1 | H |
| 7-20 | 4-(MeOCO—Amd)—Ph | H | 4-NO₂—Bn | H,H | 0,1 | Me |
| 7-21 | 4-(MeOCO—Amd)—Ph | H | 4-NO₂—Bn | —CH₂CH₂— | 0,1 | H |
| 7-22 | 4-(MeOCO—Amd)—Ph | H | 4-MeSO₂NH—Bn | —CH₂CH₂— | 0,1 | H |
| 7-23 | 4-(MeOCO—Amd)—Ph | H | 4-NO₂—Bn | H,H | 1,0 | H |
| 7-24 | 4-(MeOCO—Amd)—Ph | H | 4-PhSO₂NH—Bn | H,H | 1,0 | H |
| 7-25 | 4-(MeOCO—Amd)—Ph | H | 4-NO₂—Bn | —CH₂CH₂— | 1,0 | H |
| 7-26 | 4-(MeOCO—Amd)—Ph | H | 4-BnSO₂NH—Bn | —CH₂CH₂— | 1,0 | H |
| 7-27 | 4-(MeOCO—Amd)—Ph | H | 4-NO₂—Bn | H,H | 1,0 | Me |
| 7-28 | 4-(MeOCO—Amd)—Ph | H | 4-NO₂—Bn | —CH₂CH₂— | 1,0 | Me |
| 7-29 | 4-(EtOCO—Amd)—Ph | H | 4-NO₂—Bn | H,H | 0,1 | H |
| 7-30 | 4-(EtOCO—Amd)—Ph | H | 4-MeSO₂NH—Bn | H,H | 0,1 | H |
| 7-31 | 4-(EtOCO—Amd)—Ph | H | 4-EtSO₂NH—Bn | H,H | 0,1 | H |
| 7-32 | 4-(EtOCO—Amd)—Ph | H | 4-PrSO₂NH—Bn | H,H | 0,1 | H |
| 7-33 | 4-(EtOCO—Amd)—Ph | H | 4-BuSO₂NH—Bn | H,H | 0,1 | H |
| 7-34 | 4-(EtOCO—Amd)—Ph | H | 4-BnSO₂NH—Bn | H,H | 0,1 | H |
| 7-35 | 4-(EtOCO—Amd)—Ph | H | 4-PhSO₂NH—Bn | H,H | 0,1 | H |
| 7-36 | 4-(EtOCO—Amd)—Ph | H | 4-NO₂—Bn | H,H | 0,1 | Me |
| 7-37 | 4-(EtOCO—Amd)—Ph | H | 4-MeSO₂NH—Bn | H,H | 0,1 | Me |
| 7-38 | 4-(EtOCO—Amd)—Ph | H | 4-BuSO₂NH—Bn | H,H | 0,1 | Me |
| 7-39 | 4-(EtOCO—Amd)—Ph | H | 4-BnSO₂NH—Bn | H,H | 0,1 | Me |
| 7-40 | 4-(EtOCO—Amd)—Ph | H | 4-PhSO₂NH—Bn | H,H | 0,1 | Me |
| 7-41 | 4-(EtOCO—Amd)—Ph | H | 4-NO₂—Bn | —CH₂CH₂— | 0,1 | H |
| 7-42 | 4-(EtOCO—Amd)—Ph | H | 4-BuSO₂NH—Bn | —CH₂CH₂— | 0,1 | H |
| 7-43 | 4-(EtOCO—Amd)—Ph | H | 4-NO₂—Bn | H,H | 1,0 | H |
| 7-44 | 4-(EtOCO—Amd)—Ph | H | 4-NO₂—Bn | —CH₂CH₂— | 1,0 | H |
| 7-45 | 4-(EtOCO—Amd)—Ph | H | 4-NO₂—Bn | H,H | 1,0 | Me |
| 7-46 | 4-(AcOCH₂OCO—Amd)—Ph | H | 4-NO₂—Bn | H,H | 0,1 | H |
| 7-47 | 4-(PivaOCH₂OCO—Amd)—Ph | H | 4-NO₂—Bn | H,H | 0,1 | H |
| 7-48 | 4-(PhCOOCH₂OCO—Amd)—Ph | H | 4-NO₂—Bn | H,H | 0,1 | H |
| 7-49 | 4-(2-PyCOOCH₂OCO—Amd)—Ph | H | 4-NO₂—Bn | H,H | 0,1 | H |
| 7-50 | 4-(3-PyCOOCH₂OCO—Amd)—Ph | H | 4-NO₂—Bn | H,H | 0,1 | H |
| 7-51 | 4-(4-PyCOOCH₂OCO—Amd)—Ph | H | 4-NO₂—Bn | H,H | 0,1 | H |
| 7-52 | 4-(t-BuOCH₂CH₂OCO—Amd)—Ph | H | 4-NO₂—Bn | H,H | 0,1 | H |
| 7-53 | 4-(PhOCO—Amd)—Ph | H | 4-NO₂—Bn | H,H | 0,1 | H |
| 7-54 | 4-(CH₂=C(CH₃)OCO—Amd)—Ph | H | 4-NO₂—Bn | H,H | 0,1 | H |
| 7-55 | 4-(AcOCH₂OCO—Amd)—Ph | H | 4-OH—Bn | H,H | 0,1 | H |
| 7-56 | 4-(PivaOCH₂OCO—Amd)—Ph | H | 4-OH—Bn | H,H | 0,1 | H |
| 7-57 | 4-(PhCOOCH₂OCO—Amd)—Ph | H | 4-OH—Bn | H,H | 0,1 | H |
| 7-58 | 4-(2-PyCOOCH₂OCO—Amd)—Ph | H | 4-OH—Bn | H,H | 0,1 | H |
| 7-59 | 4-(3-PyCOOCH₂OCO—Amd)—Ph | H | 4-OH—Bn | H,H | 0,1 | H |
| 7-60 | 4-(4-PyCOOCH₂OCO—Amd)—Ph | H | 4-OH—Bn | H,H | 0,1 | H |
| 7-61 | 4-(t-BuOCH₂CH₂OCO—Amd)—Ph | H | 4-OH—Bn | H,H | 0,1 | H |
| 7-62 | 4-(PhOCO—Amd)—Ph | H | 4-OH—Bn | H,H | 0,1 | H |
| 7-63 | 4-(CH₂=C(CH₃)OCO—Amd)—Ph | H | 4-OH—Bn | H,H | 0,1 | H |
| 7-64 | 4-(AcOCH₂OCO—Amd)—Ph | H | Bn | H,H | 0,1 | H |
| 7-65 | 4-(PivaOCH₂OCO—Amd) | H | Bn | H,H | 0,1 | H |
| 7-66 | 4-(PhCOOCH₂OCO—Amd)—Ph | H | Bn | H,H | 0,1 | H |
| 7-67 | 4-(2-PyCOOCH₂OCO—Amd)—Ph | H | Bn | H,H | 0,1 | H |
| 7-68 | 4-(3-PyCOOCH₂OCO—Amd)—Ph | H | Bn | H,H | 0,1 | H |
| 7-69 | 4-(4-PyCOOCH₂OCO—Amd)—Ph | H | Bn | H,H | 0,1 | H |
| 7-70 | 4-(t-BuOCH₂CH₂OCO—Amd)—Ph | H | Bn | H,H | 0,1 | H |
| 7-71 | 4-(PhOCO—Amd)—Ph | H | Bn | H,H | 0,1 | H |
| 7-72 | 4-(CH₂=C(CH₃)OCO—Amd)—Ph | H | Bn | H,H | 0,1 | H |
| 7-73 | 4-(3-PyCOOCH₂OCO—Amd)—Ph | H | 4-BuSO₂NH—Bn | H,H | 0,1 | H |
| 7-74 | 4-(4-PyCOOCH₂OCO—Amd)—Ph | H | 4-BuSO₂NH—Bn | H,H | 0,1 | H |
| 7-75 | 4-(t-BuOCH₂CH₂OCO—Amd)—Ph | H | 4-BuSO₂NH—Bn | H,H | 0,1 | H |
| 7-76 | 4-(PhOCO—Amd)—Ph | H | 4-BuSO₂NH—Bn | H,H | 0,1 | H |
| 7-77 | 4-(CH₂=C(CH₃)OCO—Amd)—Ph | H | 4-BuSO₂NH—Bn | H,H | 0,1 | H |

TABLE 8

| No | A | R¹ | R² | R⁷,R⁸ | o,p | R⁹' |
|---|---|---|---|---|---|---|
| 8-1 | 4-Amd—Ph | H | 4-BuSO₂NH—Bn | H,H | 0,1 | Me |
| 8-2 | 4-Amd—Ph | H | 4-NO₂—Bn | H,H | 0,1 | Me |
| 8-3 | 4-Amd—Ph | H | 4-BuSO₂NH—Bn | H,H | 0,1 | Et |
| 8-4 | 4-Amd—Ph | H | 4-NO₂—Bn | H,H | 0,1 | Et |
| 8-5 | 4-Amd—Ph | H | 4-NO₂—Bn | —CH₂CH₂— | 0,1 | Me |
| 8-6 | 4-Amd—Ph | H | 4-MeSO₂NH—Bn | —CH₂CH₂— | 0,1 | Me |
| 8-7 | 4-Amd—Ph | H | 4-BuSO₂NH—Bn | —CH₂CH₂— | 0,1 | Me |
| 8-8 | 4-Amd—Ph | H | 4-NO₂—Bn | H,H | 1,0 | Et |
| 8-9 | 4-Amd—Ph | H | 4-NO₂—Bn | —CH₂CH₂— | 1,0 | Me |
| 8-10 | 4-Amd—Ph | H | 4-BuSO₂NH—Bn | —CH₂CH₂— | 1,0 | Et |
| 8-11 | 4-Amd—Ph | Me | 4-NO₂—Bn | H,H | 1,0 | Me |
| 8-12 | 4-(EtOCO—Amd)—Ph | H | 4-NO₂—Bn | H,H | 0,1 | Me |
| 8-13 | 4-(EtOCO—Amd)—Ph | H | 4-BuSO₂NH—Bn | H,H | 0,1 | Et |
| 8-14 | 4-(EtOCO—Amd)—Ph | H | 4-NO₂—Bn | H,H | 0,1 | Et |
| 8-15 | 4-(EtOCO—Amd)—Ph | H | 4-MeSO₂NH—Bn | H,H | 0,1 | Me |
| 8-16 | 4-(EtOCO—Amd)—Ph | H | 4-BuSO₂NH—Bn | H,H | 0,1 | Me |
| 8-17 | 4-(EtOCO—Amd)—Ph | H | 4-NO₂—Bn | —CH₂CH₂— | 0,1 | Et |
| 8-18 | 4-(EtOCO—Amd)—Ph | H | 4-BuSO₂NH—Bn | —CH₂CH₂— | 0,1 | Et |
| 8-19 | 4-(EtOCO—Amd)—Ph | H | 4-NO₂—Bn | H,H | 1,0 | Et |
| 8-20 | 4-(EtOCO—Amd)—Ph | H | 4-NO₂—Bn | —CH₂CH₂— | 1,0 | Et |
| 8-21 | 4-((t-BuOCO)₃—Amd—Ph | H | 4-NO₂—Bn | H,H | 0,1 | Me |
| 8-22 | 4-Amd—Ph | H | 4-NO₂—Bn | H,H | 0,1 | Me |
| 8-23 | 4-((t-BuOCO)₃—Amd—Ph | H | 4-NO₂—Bn | H,H | 0,1 | BnOCO |
| 8-24 | 4-Amd—Ph | H | 4-NO₂—Bn | H,H | 0,1 | BnOCO |
| 8-25 | 4-(HO—Amd)—Ph | H | 4-NO₂—Bn | H,H | 0,1 | Me |
| 8-26 | 4-(HO—Amd)—Ph | H | 4-MeSO₂NH—Bn | H,H | 0,1 | BnOCO |
| 8-27 | 4-(HO—Amd)—Ph | H | 4-BuSO₂NH—Bn | H,H | 0,1 | BnOCO |
| 8-28 | 4-(HO—Amd)—Ph | H | 4-NO₂—Bn | H,H | 0,1 | Me |
| 8-29 | 4-(HO—Amd)—Ph | H | 4-NO₂—Bn | —CH₂CH₂— | 0,1 | Me |
| 8-30 | 4-(PhCOOCH₂OCO—Amd)—Ph | H | 4-NO₂—Bn | H,H | 0,1 | Me |
| 8-31 | 4-(3-PyCOOCH₂OCO—Amd)—Ph | H | 4-NO₂—Bn | H,H | 0,1 | Me |
| 8-32 | 4-(4-PyCOOCH₂OCO—Amd)—Ph | H | 4-NO₂—Bn | H,H | 0,1 | Me |
| 8-33 | 4-(PhOCO—Amd)—Ph | H | 4-NO₂—Bn | H,H | 0,1 | Me |
| 8-34 | 4-(CH₂=C(CH₃)OCO—Amd)—Ph | H | 4-NO₂—Bn | H,H | 0,1 | Me |
| 8-35 | 4-(PhCOOCH₂OCO—Amd)—Ph | H | 4-MeSO₂NH—Bn | H,H | 0,1 | Me |
| 8-36 | 4-(3-PyCOOCH₂OCO—Amd)—Ph | H | 4-MeSO₂NH—Bn | H,H | 0,1 | BnOCO |
| 8-37 | 4-(4-PyCOOCH₂OCO—Amd)—Ph | H | 4-MeSO₂NH—Bn | H,H | 0,1 | BnOCO |
| 8-38 | 4-(t-BuOCH₂CH₂OCO—Amd)—Ph | H | 4-MeSO₂NH—Bn | H,H | 0,1 | BnOCO |
| 8-39 | 4-(PhOCO—Amd)—Ph | H | 4-MeSO₂NH—Bn | H,H | 0,1 | BnOCO |
| 8-40 | 4-(CH₂=C(CH₃)OCO—Amd)—Ph | H | 4-MeSO₂NH—Bn | H,H | 0,1 | BnOCO |
| 8-41 | 4-(3-PyCOOCH₂OCO—Amd)—Ph | H | 4-BuSO₂NH—Bn | H,H | 0,1 | BnOCO |
| 8-42 | 4-(4-PyCOOCH₂OCO—Amd)—Ph | H | 4-BuSO₂NH—Bn | H,H | 0,1 | BnOCO |
| 8-43 | 4-(t-BuOCH₂CH₂OCO—Amd)—Ph | H | 4-BuSO₂NH—Bn | H,H | 0,1 | BnOCO |
| 8-44 | 4-(PhOCO—Amd)—Ph | H | 4-BuSO₂NH—Bn | H,H | 0,1 | BnOCO |
| 8-45 | 4-(CH₂=C(CH₃)OCO—Amd)—Ph | H | 4-BuSO₂NH—Bn | H,H | 0,1 | BnOCO |

TABLE 9

| No | A | R¹ | R² | R⁷,R⁸ | o,p |
|---|---|---|---|---|---|
| 9-1 | 4-Amd—Ph | H | 4-MeSO₂NH—Bn | H,H | 0,1 |
| 9-2 | 4-Amd—Ph | H | 4-BuSO₂NH—Bn | H,H | 0,1 |
| 9-3 | 4-Amd—Ph | H | 4-NO₂—Bn | —CH₂CH₂— | 0,1 |
| 9-4 | 4-Amd—Ph | H | 4-MeSO₂NH—Bn | —CH₂CH₂— | 0,1 |
| 9-5 | 4-Amd—Ph | H | 4-BuSO₂NH—Bn | —CH₂CH₂— | 0,1 |

TABLE 9-continued

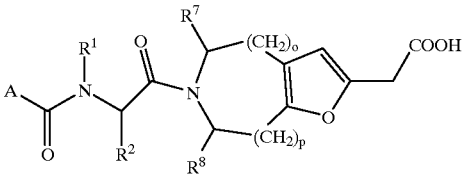

| No | A | R¹ | R² | R⁷,R⁸ | o,p |
|---|---|---|---|---|---|
| 9-6 | 4-Amd—Ph | H | 4-NO₂—Bn | H,H | 1,0 |
| 9-7 | 4-Amd—Ph | H | 4-BnSO₂NH—Bn | H,H | 1,0 |
| 9-8 | 4-Amd—Ph | H | 4-NO₂—Bn | —CH₂CH₂— | 1,0 |
| 9-9 | 4-Amd—Ph | H | 4-BuSO₂NH—Bn | —CH₂CH₂— | 1,0 |
| 9-10 | 4-(EtOCO—Amd)—Ph | H | 4-NO₂—Bn | H,H | 0,1 |
| 9-11 | 4-(EtOCO—Amd)—Ph | H | 4-BuSO₂NH—Bn | H,H | 0,1 |
| 9-12 | 4-(EtOCO—Amd)—Ph | H | 4-NO₂—Bn | —CH₂CH₂— | 0,1 |
| 9-13 | 4-(EtOCO—Amd)—Ph | H | 4-BuSO₂NH—Bn | —CH₂CH₂— | 0,1 |
| 9-14 | 4-(EtOCO—Amd)—Ph | H | 4-NO₂—Bn | H,H | 1,0 |
| 9-15 | 4-(EtOCO—Amd)—Ph | H | 4-NO₂—Bn | —CH₂CH₂— | 1,0 |
| 9-16 | 4-(HO—Amd)—Ph | H | 4-MeSO₂NH—Bn | H,H | 0,1 |
| 9-17 | 4-(HO—Amd)—Ph | H | 4-BuSO₂NH—Bn | H,H | 0,1 |
| 9-18 | 4-(HO—Amd)—Ph | H | 4-NO₂—Bn | H,H | 0,1 |
| 9-19 | 4-(AcOCH₂OCO—Amd)—Ph | H | 4-NO₂—Bn | H,H | 0,1 |
| 9-20 | 4-(PivaOCH₂OCO—Amd)—Ph | H | 4-NO₂—Bn | H,H | 0,1 |
| 9-21 | 4-(PhCOOCH₂OCO—Amd)—Ph | H | 4-NO₂—Bn | H,H | 0,1 |
| 9-22 | 4-(3-PyCOOCH₂OCO—Amd)—Ph | H | 4-NO₂—Bn | H,H | 0,1 |
| 9-23 | 4-(4-PyCOOCH₂OCO—Amd)—Ph | H | 4-NO₂—Bn | H,H | 0,1 |
| 9-24 | 4-(PhOCO—Amd)—Ph | H | 4-NO₂—Bn | H,H | 0,1 |
| 9-25 | 4-(CH₂=C(CH₃)OCO—Amd)—Ph | H | 4-NO₂—Bn | H,H | 0,1 |
| 9-26 | 4-(PhCOOCH₂OCO—Amd)—Ph | H | 4-MeSO₂NH—Bn | H,H | 0,1 |
| 9-27 | 4-(2-PyCOOCH₂OCO—Amd)—Ph | H | 4-MeSO₂NH—Bn | H,H | 0,1 |
| 9-28 | 4-(3-PyCOOCH₂OCO—Amd)—Ph | H | 4-MeSO₂NH—Bn | H,H | 0,1 |
| 9-29 | 4-(4-PyCOOCH₂OCO—Amd)—Ph | H | 4-MeSO₂NH—Bn | H,H | 0,1 |
| 9-30 | 4-(t-BuOCH₂CH₂OCO—Amd)—Ph | H | 4-MeSO₂NH—Bn | H,H | 0,1 |
| 9-31 | 4-(PhOCO—Amd)—Ph | H | 4-MeSO₂NH—Bn | H,H | 0,1 |
| 9-32 | 4-(CH₂=C(CH₃)OCO—Amd)—Ph | H | 4-MeSO₂NH—Bn | H,H | 0,1 |
| 9-33 | 4-(AcOCH₂OCO—Amd)—Ph | H | 4-BuSO₂NH—Bn | H,H | 0,1 |
| 9-34 | 4-(PivaOCH₂OCO—Amd)—Ph | H | 4-BuSO₂NH—Bn | H,H | 0,1 |
| 9-35 | 4-(2-PyCOOCH₂OCO—Amd)—Ph | H | 4-BuSO₂NH—Bn | H,H | 0,1 |
| 9-36 | 4-(3-PyCOOCH₂OCO—Amd)—Ph | H | 4-BuSO₂NH—Bn | H,H | 0,1 |
| 9-37 | 4-(4-PyCOOCH₂OCO—Amd)—Ph | H | 4-BuSO₂NH—Bn | H,H | 0,1 |
| 9-38 | 4-(t-BuOCH₂CH₂OCO—Amd)—Ph | H | 4-BuSO₂NH—Bn | H,H | 0,1 |
| 9-39 | 4-(PhOCO—Amd)—Ph | H | 4-BuSO₂NH—Bn | H,H | 0,1 |
| 9-40 | 4-(CH₂=C(CH₃)OCO—Amd)—Ph | H | 4-BuSO₂NH—Bn | H,H | 0,1 |

TABLE 10

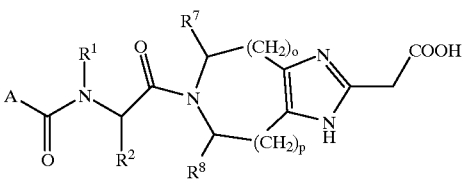

| No | A | R¹ | R² | R⁷,R⁸ | o,p |
|---|---|---|---|---|---|
| 10-1 | 4-Amd—Ph | H | 4-MeSO₂NH—Bn | H,H | 0,1 |
| 10-2 | 4-Amd—Ph | H | 4-BuSO₂NH—Bn | H,H | 0,1 |
| 10-3 | 4-Amd—Ph | H | 4-BnSO₂NH—Bn | H,H | 0,1 |
| 10-4 | 4-Amd—Ph | H | 4-NO₂—Bn | —CH₂CH₂— | 0,1 |
| 10-5 | 4-Amd—Ph | H | 4-MeSO₂NH—Bn | —CH₂CH₂— | 0,1 |
| 10-6 | 4-Amd—Ph | H | 4-BuSO₂NH—Bn | —CH₂CH₂— | 0,1 |
| 10-7 | 4-(MeOCO—Amd)—Ph | H | 4-NO₂—Bn | H,H | 0,1 |
| 10-8 | 4-(MeOCO—Amd)—Ph | H | 4-BuSO₂NH—Bn | H,H | 0,1 |
| 10-9 | 4-(MeOCO—Amd)—Ph | H | 4-NO₂—Bn | —CH₂CH₂— | 0,1 |
| 10-10 | 4-(MeOCO—Amd)—Ph | H | 4-MeSO₂NH—Bn | —CH₂CH₂— | 0,1 |
| 10-11 | 4-(EtOCO—Amd)—Ph | H | 4-NO₂—Bn | H,H | 0,1 |
| 10-12 | 4-(EtOCO—Amd)—Ph | H | 4-MeSO₂NH—Bn | H,H | 0,1 |
| 10-13 | 4-(EtOCO—Amd)—Ph | H | 4-BuSO₂NH—Bn | H,H | 0,1 |
| 10-14 | 4-(EtOCO—Amd)—Ph | H | 4-BnSO₂NH—Bn | H,H | 0,1 |
| 10-15 | 4-(EtOCO—Amd)—Ph | H | 4-NO₂—Bn | —CH₂CH₂— | 0,1 |

TABLE 10-continued

| No | A | R¹ | R² | R⁷,R⁸ | o,p |
|---|---|---|---|---|---|
| 10-16 | 4-(EtOCO—Amd)—Ph | H | 4-BuSO₂NH—Bn | —CH₂CH₂— | 0,1 |
| 10-17 | 4-(HO—Amd)—Ph | H | 4-NO₂—Bn | H,H | 0,1 |
| 10-18 | 4-(HO—Amd)—Ph | H | 4-BuSO₂NH—Bn | H,H | 0,1 |
| 10-19 | 4-(AcOCH₂OCO—Amd)—Ph | H | 4-NO₂—Bn | H,H | 0,1 |
| 10-20 | 4-(PivaOCH₂OCO—Amd)—Ph | H | 4-NO₂—Bn | H,H | 0,1 |
| 10-21 | 4-(PhCOOCH₂OCO—Amd)—Ph | H | 4-NO₂—Bn | H,H | 0,1 |
| 10-22 | 4-(3-PyCOOCH₂OCO—Amd)—Ph | H | 4-NO₂—Bn | H,H | 0,1 |
| 10-23 | 4-(4-PyCOOCH₂OCO—Amd)—Ph | H | 4-NO₂—Bn | H,H | 0,1 |
| 10-24 | 4-(PhOCO—Amd)—Ph | H | 4-NO₂—Bn | H,H | 0,1 |
| 10-25 | 4-(CH₂=C(CH₃)OCO—Amd)—Ph | H | 4-NO₂—Bn | H,H | 0,1 |
| 10-26 | 4-(PhCOOCH₂OCO—Amd)—Ph | H | 4-MeSO₂NH—Bn | H,H | 0,1 |
| 10-27 | 4-(2-PyCOOCH₂OCO—Amd)—Ph | H | 4-MeSO₂NH—Bn | H,H | 0,1 |
| 10-28 | 4-(3-PyCOOCH₂OCO—Amd)—Ph | H | 4-MeSO₂NH—Bn | H,H | 0,1 |
| 10-29 | 4-(4-PyCOOCH₂OCO—Amd)—Ph | H | 4-MeSO₂NH—Bn | H,H | 0,1 |
| 10-30 | 4-(t-BuOCH₂OCO—Amd)—Ph | H | 4-MeSO₂NH—Bn | H,H | 0,1 |
| 10-31 | 4-(PhOCO—Amd)—Ph | H | 4-MeSO₂NH—Bn | H,H | 0,1 |
| 10-32 | 4-(CH₂=C(CH₃)OCO—Amd)—Ph | H | 4-MeSO₂NH—Bn | H,H | 0,1 |
| 10-33 | 4-(AcOCH₂OCO—Amd)—Ph | H | 4-BuSO₂NH—Bn | H,H | 0,1 |
| 10-34 | 4-(PivaOCH₂OCO—Amd)—Ph | H | 4-BuSO₂NH—Bn | H,H | 0,1 |
| 10-35 | 4-(2-PyCOOCH₂OCO—Amd)—Ph | H | 4-BuSO₂NH—Bn | H,H | 0,1 |
| 10-36 | 4-(3-PyCOOCH₂OCO—Amd)—Ph | H | 4-BuSO₂NH—Bn | H,H | 0,1 |
| 10-37 | 4-(4-PyCOOCH₂OCO—Amd)—Ph | H | 4-BuSO₂NH—Bn | H,H | 0,1 |
| 10-38 | 4-(t-BuOCH₂CH₂OCO—Amd)—Ph | H | 4-BuSO₂NH—Bn | H,H | 0,1 |
| 10-39 | 4-(PhOCO—Amd)—Ph | H | 4-BuSO₂NH—Bn | H,H | 0,1 |
| 10-40 | 4-(CH₂=C(CH₃)OCO—Amd)—Ph | H | 4-BuSO₂NH—Bn | H,H | 0,1 |

TABLE 11

| No | A | R¹ | R² | R⁷,R⁸ | o,p |
|---|---|---|---|---|---|
| 11-1 | 4-Amd—Ph | H | 4-BuSO₂NH—Bn | H,H | 0,1 |
| 11-2 | 4-Amd—Ph | H | 4-BuSO₂NH—Bn | H,H | 1,0 |
| 11-3 | 4-Amd—Ph | H | 4-BnSO₂NH—Bn | H,H | 0,1 |
| 11-4 | 4-Amd—Ph | H | 4-NO₂—Bn | —CH₂CH₂— | 0,1 |
| 11-5 | 4-Amd—Ph | H | 4-NO₂—Bn | —CH₂CH₂— | 1,0 |
| 11-6 | 4-Amd—Ph | H | 4-BuSO₂NH—Bn | —CH₂CH₂— | 0,1 |
| 11-7 | 4-(MeOCO—Amd)—Ph | H | 4-NO₂—Bn | H,H | 0,1 |
| 11-8 | 4-(MeOCO—Amd)—Ph | H | 4-BuSO₂NH—Bn | H,H | 0,1 |
| 11-9 | 4-(MeOCO—Amd)—Ph | H | 4-NO₂—Bn | —CH₂CH₂— | 0,1 |
| 11-10 | 4-(MeOCO—Amd)—Ph | H | 4-MeSO₂NH—Bn | —CH₂CH₂— | 0,1 |
| 11-11 | 4-(EtOCO—Amd)—Ph | H | 4-NO₂—Bn | H,H | 0,1 |
| 11-12 | 4-(EtOCO—Amd)—Ph | H | 4-MeSO₂NH—Bn | H,H | 0,1 |
| 11-13 | 4-(EtOCO—Amd)—Ph | H | 4-BuSO₂NH—Bn | H,H | 0,1 |
| 11-14 | 4-(EtOCO—Amd)—Ph | H | 4-BnSO₂NH—Bn | H,H | 0,1 |
| 11-15 | 4-(EtOCO—Amd)—Ph | H | 4-NO₂—Bn | —CH₂CH₂— | 0,1 |
| 11-16 | 4-(EtOCO—Amd)—Ph | H | 4-BuSO₂NH—Bn | —CH₂CH₂— | 0,1 |
| 11-17 | 4-(HO—Amd)—Ph | H | 4-NO₂—Bn | H,H | 0,1 |
| 11-18 | 4-(HO—Amd)—Ph | H | 4-BuSO₂NH—Bn | H,H | 0,1 |
| 11-19 | 4-(AcOCH₂OCO—Amd)—Ph | H | A-NO₂—Bn | H,H | 0,1 |
| 11-20 | 4-(PivaOCH₂OCO—Amd)—Ph | H | 4-NO₂—Bn | H,H | 0,1 |
| 11-21 | 4-(PhCOOCH₂OCO—Amd)—Ph | H | 4-NO₂—Bn | H,H | 0,1 |
| 11-22 | 4-(3-PyCOOCH₂OCO—Amd)—Ph | H | 4-NO₂—Bn | H,H | 0,1 |
| 11-23 | 4-(4-PyCOOCH₂OCO—Amd)—Ph | H | 4-NO₂—Bn | H,H | 0,1 |
| 11-24 | 4-(PhOCO—Amd)—Ph | H | 4-NO₂—Bn | H,H | 0,1 |
| 11-25 | 4-(CH₂=C(CH₃)OCO—Amd)—Ph | H | 4-NO₂—Bn | H,H | 0,1 |

TABLE 11-continued

| No | A | R¹ | R² | R⁷,R⁸ | o,p |
|---|---|---|---|---|---|
| 11-26 | 4-(PhCOOCH₂OCO—Amd)—Ph | H | 4-MeSO₂NH—Bn | H,H | 0,1 |
| 11-27 | 4-(2-PyCOOCH₂OCO—Amd)—Ph | H | 4-MeSO₂NH—Bn | H,H | 0,1 |
| 11-28 | 4-(3-PyCOOCH₂OCO—Amd)—Ph | H | 4-MeSO₂NH—Bn | H,H | 0,1 |
| 11-29 | 4-(4-PyCOOCH₂OCO—Amd)—Ph | H | 4-MeSO₂NH—Bn | H,H | 0,1 |
| 11-30 | 4-(t-BuOCH₂CH₂OCO—Amd)—Ph | H | 4-MeSO₂NH—Bn | H,H | 0,1 |
| 11-31 | 4-(PhOCO—Amd)—Ph | H | 4-MeSO₂NH—Bn | H,H | 0,1 |
| 11-32 | 4-(CH₂=C(CH₃)OCO—Amd)—Ph | H | 4-MeSO₂NH—Bn | H,H | 0,1 |
| 11-33 | 4-(AcOCH₂OCO—Amd)—Ph | H | 4-BuSO₂NH—Bn | H,H | 0,1 |
| 11-34 | 4-(PivaOCH₂OCO—Amd)—Ph | H | 4-BuSO₂NH—Bn | H,H | 0,1 |
| 11-35 | 4-(2-PyCOOCH₂OCO—Amd)—Ph | H | 4-BuSO₂NH—Bn | H,H | 0,1 |
| 11-36 | 4-(3-PyCOOCH₂OCO—Amd)—Ph | R | 4-BuSO₂NH—Bn | H,H | 0,1 |
| 11-37 | 4-(4-PyCOOCH₂OCO—Amd)—Ph | H | 4-BuSO₂NH—Bn | H,H | 0,1 |
| 11-38 | 4-(t-BuOCH₂CH₂OCO—Amd)—Ph | H | 4-BuSO₂NH—Bn | H,H | 0,1 |
| 11-39 | 4-(PhOCO—Amd)—Ph | H | 4-BuSO₂NH—Bn | H,H | 0,1 |
| 11-40 | 4-(CH₂=C(CH₃)OCO—Amd)—Ph | H | 4-BuSO₂NH—Bn | H,H | 0,1 |

TABLE 12

| No | A | R¹ | R² | R⁷,R⁸ | o,p |
|---|---|---|---|---|---|
| 12-1 | 4-Amd—Ph | H | 4-NO₂—Bn | H,H | 0,1 |
| 12-2 | 4-Amd—Ph | H | 4-BuSO₂NH—Bn | H,H | 0,1 |
| 12-3 | 4-Amd—Ph | H | 4-BnSO₂NH—Bn | H,H | 1,0 |
| 12-4 | 4-Amd—Ph | H | 4-NO₂—Bn | —CH₂CH₂— | 0,1 |
| 12-5 | 4-Amd—Ph | H | 4-NO₂—Bn | —CH₂CH₂— | 1,0 |
| 12-6 | 4-Amd—Ph | H | 4-BuSO₂NH—Bn | —CH₂CH₂— | 0,1 |
| 12-7 | 4-(MeOCO—Amd)—Ph | H | 4-NO₂—Bn | H,H | 0,1 |
| 12-8 | 4-(MeOCO—Amd)—Ph | H | 4-BuSO₂NH—Bn | H,H | 0,1 |
| 12-9 | 4-(MeOCO—Amd)—Ph | H | 4-NO₂—Bn | —CH₂CH₂— | 0,1 |
| 12-10 | 4-(MeOCO—Amd)—Ph | H | 4-MeSO₂NH—Bn | —CH₂CH₂— | 1,0 |
| 12-11 | 4-(EtOCO—Amd)—Ph | H | 4-NO₂—Bn | H,H | 0,1 |
| 12-12 | 4-(EtOCO—Amd)—Ph | H | 4-MeSO₂NH—Bn | H,H | 1,0 |
| 12-13 | 4-(EtOCO—Amd)—Ph | H | 4-BuSO₂NH—Bn | H,H | 0,1 |
| 12-14 | 4-(EtOCO—Amd)—Ph | H | 4-BnSO₂NH—Bn | H,H | 0,1 |
| 12-15 | 4-(EtOCO—Amd)—Ph | H | 4-NO₂—Bn | —CH₂CH₂— | 1,0 |
| 12-16 | 4-(EtOCO—Amd)—Ph | H | 4-BuSO₂NH—Bn | —CH₂CH₂— | 0,1 |
| 12-17 | 4-(HO—Amd)—Ph | H | 4-NO₂—Bn | H,H | 0,1 |
| 12-18 | 4-(HO—Amd)—Ph | H | 4-BuSO₂NH—Bn | H,H | 0,1 |
| 12-19 | 4-(AcOCH₂OCO—Amd)—Ph | H | 4-NO₂—Bn | H,H | 0,1 |
| 12-20 | 4-(PivaOCH₂OCO—Amd)—Ph | H | 4-NO₂—Bn | H,H | 0,1 |
| 12-21 | 4-(PhCOOCH₂OCO—Amd)—Ph | H | 4-NO₂—Bn | H,H | 0,1 |
| 12-22 | 4-(3-PyCOOCH₂OCO—Amd)—Ph | H | 4-NO₂—Bn | H,H | 0,1 |
| 12-23 | 4-(4-PyCOOCH₂OCO—Amd)—Ph | H | 4-NO₂—Bn | H,H | 0,1 |
| 12-24 | 4-(PhOCO—Amd)—Ph | H | 4-NO₂—Bn | H,H | 0,1 |
| 12-25 | 4-(CH₂=C(CH₃)OCO—Amd)—Ph | H | 4-NO₂—Bn | H,H | 0,1 |
| 12-26 | 4-(PhCOOCH₂OCO—Amd)—Ph | H | 4-MeSO₂NH—Bn | H,H | 0,1 |
| 12-27 | 4-(2-PyCOOCH₂OCO—Amd)—Ph | H | 4-MeSO₂NH—Bn | H,H | 0,1 |
| 12-28 | 4-(3-PyCOOCH₂OCO—Amd)—Ph | H | 4-MeSO₂NH—Bn | H,H | 0,1 |
| 12-29 | 4-(4-PyCOOCH₂OCO—Amd)—Ph | H | 4-MeSO₂NH—Bn | H,H | 0,1 |
| 12-30 | 4-(t-BuOCH₂CH₂OCO—Amd)—Ph | H | 4-MeSO₂NH—Bn | H,H | 0,1 |
| 12-31 | 4-(PhOCO—Amd)—Ph | H | 4-MeSO₂NH—Bn | H,H | 0,1 |
| 12-32 | 4-(CH₂=C(CH₃)OCO—Amd)—Ph | H | 4-MeSO₂NH—Bn | H,H | 0,1 |
| 12-33 | 4-(AcOCH₂OCO—Amd)—Ph | H | 4-BuSO₂NH—Bn | H,H | 0,1 |
| 12-34 | 4-(PivaOCH₂OCO—Amd)—Ph | H | 4-BuSO₂NH—Bn | H,H | 0,1 |
| 12-35 | 4-(2-PyCOOCH₂OCO—Amd)—Ph | H | 4-BuSO₂NH—Bn | H,H | 0,1 |

TABLE 12-continued

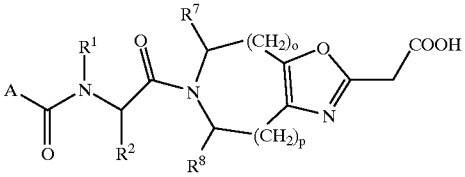

| No | A | R¹ | R² | R⁷,R⁸ | o,p |
|---|---|---|---|---|---|
| 12-36 | 4-(3-PyCOOCH₂OCO—Amd)—Ph | H | 4-BuSO₂NH—Bn | H,H | 0,1 |
| 12-37 | 4-(4-PyCOOCH₂OCO—Amd)—Ph | H | 4-BuSO₂NH—Bn | H,H | 0,1 |
| 12-38 | 4-(t-BuOCH₂CH₂OCO—Amd)—Ph | H | 4-BuSO₂NH—Bn | H,H | 0,1 |
| 12-39 | 4-(PhOCO—Amd)—Ph | H | 4-BuSO₂NH—Bn | H,H | 0,1 |
| 12-40 | 4-(CH₂=C(CH₃)OCO—Amd)—Ph | H | 4-BuSO₂NH—Bn | H,H | 0,1 |

Incidentally, in the above-mentioned respective Tables, the abbreviated symbols show the following groups.

Ac: an acetyl group; Amd: an amidino group; Bn: a benzyl group; Bu: a butyl group; Butyr: a butanoyl group; Et: an ethyl group; Imd: an imidoyl group; Me: a methyl group; Mor: a morpholino group; Ph: a phenyl group; Pipe: a piperidyl group; Pipera: a piperazino group; Piperi: a piperidino group; Pyrr: a pyrrolidino group; Piva: a pivaloyl group; Pr: a propyl group; Prop: a propanoyl group; Py: a pyridyl group; Oct: an octyl group; Hex: a hexyl group; t-Bu: a tertiary butyl group.

Also, $R^9$ represents the group having the same meanings as defined in the above-mentioned $R^9$ and a hydrogen atom.

Incidentally, a compound in which the carboxyl group of the above-mentioned respective Tables is protected by the above-mentioned protective group can be mentioned as a preferred compound.

More preferred compounds may include Compounds No.s 1-1, 1-2, 1-3, 1-4, 1-5, 1-6, 1-7, 1-8, 1-9, 1-10, 1-11, 1-12, 1-14, 1-15, 1-16, 1-18, 1-20, 1-21, 1-22, 1-31, 1-32, 1-40, 1-60, 1-67, 1-69, 1-70, 1-72, 1-73, 1-74, 1-75, 1-77, 1-78, 1-84, 1-91, 1-93, 1-96, 1-116, 1-117, 1-118, 1-119, 1-120, 1-121, 1-123, 1-125, 1-130, 1-131, 1-132, 1-134, 1-137, 1-143, 1-145, 1-152, 1-153, 1-154, 1-156, 1-157, 1-159, 1-167, 1-168, 1-206, 1-212, 2-1, 2-2, 2-3, 2-4, 2-5, 2-6, 2-7, 2-8, 2-9, 2-10, 2-11, 2-14, 2-23, 2-24, 2-29, 2-33, 2-43, 2-44, 2-47, 2-50, 2-51, 2-62, 2-63, 2-64, 2-65, 2-66, 2-67, 2-68, 2-71, 2-81, 2-82, 2-85, 2-89, 2-92, 2-94, 2-96, 2-109, 2-110, 2-111, 2-114, 2-117, 2-119, 2-123, 2-124, 2-128, 2-131, 2-133, 2-136, 2-140, 2-143, 2-144, 2-148, 2-175, 2-180, 2-181, 2-201, 2-202, 2-205, 2-208, 2-220, 2-222, 2-226, 2-229, 2-230, 2-231, 2-232, 2-244, 2-245, 2-246, 2-247, 2-249, 2-251, 2-252, 2-253, 2-254, 2-255, 2-256, 2-258, 2-263, 2-264, 2-269, 2-270, 2-275, 2-276, 2-293, 2-294, 2-297, 2-298, 2-299, 2-301, 2-302, 2-303, 2-305, 2-307, 2-308, 2-309, 2-336, 2-338, 2-340, 2-341, 2-342, 2-347, 2-385, 2-386, 2-394, 2-395, 2-409, 2-410, 2-445, 2-446, 3-3, 3-9, 3-21, 3-22, 3-39, 3-40, 3-55, 3-56, 3-57, 3-58, 3-66, 3-78, 3-79, 3-82, 3-115, 3-133, 3-153, 3-155, 3-156, 3-157, 3-158, 3-159, 3-166, 3-167, 3-217, 3-218, 4-3, 4-9, 4-18, 4-20, 4-28, 4-30, 4-40, 4-41, 4-44, 4-50, 4-52, 4-58, 4-65, 4-92, 4-117, 4-119, 4-121, 4-122, 4-123, 5-3, 5-18, 5-21, 5-22, 5-40, 5-44, 5-47, 5-67, 5-71, 5-74, 5-76, 5-79, 5-116, 5-132, 5-134, 5-154, 5-156, 5-159, 5-160, 6-3, 6-9, 6-18, 6-34, 6-38, 6-55, 6-59, 6-67, 6-68, 6-94, 6-109, 6-127, 6-129, 6-131, 6-132, 6-133, 8-2, 8-5, 8-7, 8-12, 8-23, 8-24, 8-28, 8-29, 8-33, 8-34 and compounds in which the carboxyl groups thereof are protected (said protective group is a $C_1$ to $C_4$ alkyl group, a benzyl group, a $C_1$ to $C_2$ alkyl group substituted by a $C_2$ to $C_5$ alkanoyloxy group, a $C_1$ to $C_2$ alkyl group substituted by a ($C_1$ to $C_4$ alkoxy)carbonyloxy group, a (5-methyl-2-oxo-1,3-dioxolen-1-yl)methyl group or a (5-phenyl-2-oxo-1,3-dioxolen-1-yl)methyl group.), more preferably Compounds No.s 1-1, 1-2, 1-3, 1-4, 1-5, 1-6, 1-7, 1-8, 1-9, 1-10, 1-11, 1-12, 1-14, 1-16, 1-18, 1-20, 1-21, 1-22, 1-31, 1-32, 1-40, 1-67, 1-74, 1-75, 1-130, 1-131, 1-132, 1-134, 1-137, 1-143, 1-145, 1-153, 1-157, 1-167, 1-168, 1-206, 1-212, 2-1, 2-2, 2-3, 2-4, 2-5, 2-6, 2-7, 2-8, 2-9, 2-10, 2-11, 2-14, 2-24, 2-29, 2-43, 2-47, 2-50, 2-62, 2-63, 2-64, 2-65, 2-66, 2-67, 2-68, 2-81, 2-82, 2-85, 2-92, 2-109, 2-110, 2-111, 2-124, 2-128, 2-136, 2-140, 2-148, 2-180, 2-181, 2-220, 2-222, 2-226, 2-229, 2-231, 2-232, 2-245, 2-246, 2-247, 2-249, 2-251, 2-252, 2-253, 2-254, 2-255, 2-256, 2-258, 2-263, 2-264, 2-307, 2-308, 2-309, 2-336, 2-341, 2-342, 2-394, 2-395, 2-409, 2-410, 3-3, 3-22, 3-39, 4-3, 4-18, 4-30, 4-40, 4-44, 4-58, 4-65, 4-117, 4-122, 4-123, 5-3, 5-18, 5-22, 5-40, 5-44, 5-47, 5-67, 5-134, 5-154, 5-159, 5-160, 6-3, 6-34, 6-38, 6-55, 6-127, 6-132, 6-133, 8-24, 8-28, 8-29 and compounds in which the carboxyl groups thereof are protected (said protective group is a methyl group, an ethyl group, a propyl group, an isopropyl group, a butyl group, an isobutyl group, a benzyl group, an acetoxymethyl group, a 1-acetoxyethyl group, a pivaloyloxymethyl group, a 1-pivaloyloxyethyl group, an ethoxycarbonyloxymethyl group, a 1-ethoxycarbonyloxyethyl group, or a (5-methyl-2-oxo- 1,3-dioxolen-1-yl)methyl group.), further more preferably Compounds No.s 1-2, 1-3, 1-4, 1-5, 1-6, 1-7, 1-8, 1-9, 1-10, 1-11, 1-12, 1-14, 1-16, 1-18, 1-22, 1-40, 1-67, 1-130, 1-131, 1-132, 1-134, 1-137, 1-143, 1-145, 1-157, 1-167, 1-168, 1-206, 1-212, 2-1, 2-2, 2-3, 2-7, 2-29, 2-43, 2-65, 2-66, 2-67, 2-68, 2-81, 2-92, 2-110, 2-124, 2-128, 2-136, 2-148, 2-180, 2-181, 2-220, 2-226, 2-229, 2-245, 2-246, 2-247, 2-249, 2-251, 2-252, 2-253, 2-254, 2-258, 2-308, 2-309, 2-394, 2-409, 3-3, 3-39, 4-3, 4-40, 4-58, 4-117, 4-122, 4-123, 5-3, 5-22, 5-40, 5-67, 5-154, 5-159, 5-160, 6-3, 6-34, 6-55, 6-127, 6-132, 6-133, and compounds in which the carboxyl groups thereof are protected (said protective group is an ethyl group, a propyl group, an isopropyl group, a butyl group, a benzyl group, an acetoxymethyl group, a pivaloyloxymethyl group or a 1-pivaloyloxyethyl group.), particularly preferably Compound No. 1-3; 5-[N-(4-amidinobenzoyl)-L-4-nitrophenylalanyl]-4,5,6,7-tetrahydrothieno[3,2-c]pyridin-2-acetic acid, Ethyl ester of Compound No. 1-3; ethyl 5-[N-(4-amidinobenzoyl)-L-4-nitrophenylalanyl]-4,5,6,7-tetrahydrothieno[3,2-c]pyridin-2-acetate, Ethyl ester of Compound No. 1-9; ethyl 5-[N-(4-amidinobenzoyl)-L-4-(butylsulfonylamino) phenylalanyl]-4,5,6,7-tetrahydrothieno[3,2-c]pyridin-2-acetate, Ethyl ester of Compound No. 1-11; ethyl 5-[N-(4-amidinobenzoyl)-L-4-(phenylsulfonylamino) phenylalanyl]-4,5,6,7-tetrahydrothieno[3,2-c]pyridin-2-acetate, Ethyl ester of Compound No. 1-18; ethyl 5-[N-(4-amidinobenzoyl)-L-4-nitrophenylalanyl]-3-methyl-4,5,6,7-tetrahydrothieno[3,2-c]pyridin-2-acetate, Ethyl ester of Compound No. 1-22; ethyl 5-[N-(4-amidinobenzoyl)-L-4-nitrophenylalanyl]-4,6-ethano-4,5,6,7-tetrahydrothieno[3,2-c]pyridin-2-acetate, Ethyl ester of Compound No. 1-40; ethyl 5-[N-[4-(N-hydroxyamidino)benzoyl]-L-4-nitrophenylalanyl]-4,5,6,7-tetrahydrothieno[3,2-c]pyridin-2-acetate, Ethyl ester of Compound No. 1-67; ethyl 5-[N-[4-(N-ethoxycarbonylamidino)benzoyl]-L-4-nitrophenylalanyl]-4,5,6,7-tetrahydrothieno[3,2-c]pyridin-2-acetate, Compound No. 2-1; 5-[N-(4-amidinobenzoyl)-L-phenylalanyl]-4,5,6,7-tetrahydropyrazolo[4,3-c]pyridin-2-acetic acid, Compound No. 2-3; 5-[N-(4-amidinobenzoyl)-L-4-nitrophenylalanyl]-4,5,6,7-tetrahydropyrazolo[4,3-c]pyridin-2-acetic acid, Ethyl ester of Compound No. 2-3; ethyl 5-[N-(4-amidinobenzoyl)-L-4-nitrophenylalanyl]-4,5,6,7-tetrahydropyrazolo[4,3-c]pyridin-2-acetate, Isopropyl ester of Compound No. 2-3; isopropyl 5-[N-(4-amidinobenzoyl)-L-4-nitrophenylalanyl]-4,5,6,7-tetrahydropyrazolo[4,3-c]pyridin-2-acetate, Pivaloyloxymethyl ester of Compound No. 2-3; pivaloyloxymethyl 5-[N-(4-amidinobenzoyl)-L-4-nitrophenylalanyl]-4,5,6,7-tetrahydropyrazolo[4,3-c]pyridin-2-acetate, Compound No. 2-7; 5-[N-(4-amidinobenzoyl)-L-O-benzyltyrosyl]-4,5,6,7-tetrahydropyrazolo[4,3-c]pyridin-2-acetic acid, Compound No. 2-29; 5-[N-(4-amidinobenzoyl)-L-4-nitrophenylalanyl]-4,6-ethano-4,5,6,7-tetrahydropyrazolo[4,3-c]pyridin-2-acetic acid, Ethyl ester of Compound No. 2-29; ethyl 5-[N-(4-amidinobenzoyl)-L-4-nitrophenylalanyl]-4,6-ethano-4,5,6,7-tetrahydropyrazolo[4,3-c]pyridin-2-acetate, Compound No. 2-43; 5-[N-(4-amidinobenzoyl)-N-methyl-L-4-nitrophenylalanyl]-4,5,6,7-tetrahydropyrazolo[4,3-c]pyridin-2-acetic acid, Ethyl ester of Compound No. 2-65; ethyl 5-[N-(4-amidino-2-fluorobenzoyl)-L-4-nitrophenylalanyl]-4,5,6,7-tetrahydropyrazolo[4,3-c]pyridin-2-acetate, Ethyl ester of Compound No. 2-66; ethyl 5-[N-(4-amidino-2-chlorobenzoyl)-L-4-nitrophenylalanyl]-4,5,6,7-tetrahydropyrazolo[4,3-c]pyridin-2-acetate, Ethyl ester of Compound No. 2-67; ethyl 5-[N-(4-amidino-2-methoxybenzoyl)-L-4-nitrophenylalanyl]-4,5,6,7-tetrahydropyrazolo[4,3-c]pyridin-2-acetate, Ethyl ester of Compound No. 2-68; ethyl 5-[N-(4-amidino-2-methylbenzoyl)-L-4-nitrophenylalanyl]-4,5,6,7-tetrahydropyrazolo[4,3-c]pyridin-2-acetate, Compound No. 2-81; 5-[N-[4-(N-hydroxyamidino)benzoyl]-L-4-nitrophenylalanyl]-4,5,6,7-tetrahydropyrazolo[4,3-c]pyridin-2-acetic acid, Ethyl ester of Compound No. 2-81; ethyl 5-[N-[4-(N-hydroxyamidino)benzoyl]-L-4-nitrophenylalanyl]-4,5,6,7-tetrahydropyrazolo[4,3-c]pyridin-2-acetate, Ethyl ester of Compound No. 2-92; ethyl 5-[N-[4-(N-hydroxyamidino)benzoyl]-L-4-nitrophenylalanyl]-4,6-ethano-4,5,6,7-tetrahydropyrazolo[4,3-c]pyridin-2-acetate, Ethyl ester of Compound No. 2-124; ethyl 5-[N-[4-(N-ethoxycarbonylamidino)benzoyl]-L-4-nitrophenylalanyl]-4,5,6,7-tetrahydropyrazolo[4,3-c]pyridin-2-acetate, Pivaloyloxymethyl ester of Compound No. 2-124; pivaloyloxymethyl 5-[N-[4-(N-ethoxycarbonylamidino)benzoyl]-L-4-nitrophenylalanyl]-4,5,6,7-tetrahydropyrazolo[4,3-c]pyridin-2-acetate, Ethyl ester of Compound No. 2-136; ethyl 5-[N-[4-(N-ethoxycarbonylamidino)benzoyl]-L-4-nitrophenylalanyl]-4,6-ethano-4,5,6,7-tetrahydropyrazolo[4,3-c]pyridin-2-acetate, Ethyl ester of Compound No. 2-220; ethyl 5-[N-(5-amidino-2-pyridylcarbonyl)-L-4-nitrophenylalanyl]-4,5,6,7-tetrahydropyrazolo[4,3-c]pyridin-2-acetate, Ethyl ester of Compound No. 2-226; ethyl 5-[N-[4-(morpholinoimidoyl)benzoyl]-L-4-nitrophenylalanyl]-4,5,6,7-tetrahydropyrazolo[4,3-c]pyridin-2-acetate, Ethyl ester of Compound No. 2-229; ethyl 5-[N-(piperidin-4-yloxyacetyl)-L-4-nitrophenylalanyl]-4,5,6,7-tetrahydropyrazolo[4,3-c]pyridin-2-acetate, Ethyl ester of Compound No. 2-247; ethyl 5-[N-[4-(N-benzoyloxymethoxycarbonylamidino)benzoyl]-L-4-nitrophenylalanyl]-4,5,6,7-tetrahydropyrazolo[4,3-c]pyridin-2-acetate, Ethyl ester of Compound No. 2-251; ethyl 5-[N-[4-[N-(2-t-butoxyethoxy)carbonylamidino]benzoyl]-L-4-nitrophenylalanyl]-4,5,6,7-tetrahydropyrazolo[4,3-c]pyridin-2-acetate, Ethyl ester of Compound No. 2-252; ethyl 5-[N-[4-(N-phenoxycarbonylamidino)benzoyl]-L-4-nitrophenylalanyl]-4,5,6,7-tetrahydropyrazolo[4,3-c]pyridin-2-acetate, Ethyl ester of Compound No. 2-253; ethyl 5-[N-[4-(N-isopropenyloxycarbonylamidino)benzoyl]-L-4-nitrophenylalanyl]-4,5,6,7-tetrahydropyrazolo[4,3-c]pyridin-2-acetate, Compound No. 2-394; 5-[N-(4-amidinobenzoyl)-L-alanyl]-4,5,6,7-tetrahydropyrazolo[4,3-c]pyridin-2-acetate, Ethyl ester of Compound No. 3-3; ethyl 5-[N-(4-amidinobenzoyl)-L-4-nitrophenylalanyl]-4,5,6,7-tetrahydropyrazolo[4,5-c]pyridin-1-acetate, Compound No. 4-3; 5-[N-(4-amidinobenzoyl)-L-4-nitrophenylalanyl]-4,5,6,7-tetrahydrothiazolo[5,4-c]pyridin-2-acetic acid, Ethyl ester of Compound No. 4-3; ethyl 5-[N-(4-amidinobenzoyl)-L-4-nitrophenylalanyl]-4,5,6,7-tetrahydrothiazolo[5,4-c]pyridin-2-acetate, Ethyl ester of Compound No. 4-40; ethyl 5-[N-[4-(N-hydroxyamidino)benzoyl]-L-4-nitrophenylalanyl]-4,5,6,7-tetrahydrothiazolo[5,4-c]pyridin-2-acetate, Benzyl ester of Compound No. 5-3; benzyl 5-[N-(4-amidinobenzoyl)-L-4-nitrophenylalanyl]-4,5,6,7-tetrahydropyrrolo[3,2-c]pyridin-2-acetate, or Ethyl ester of Compound No. 6-3; ethyl 5-[N-(4-amidinobenzoyl)-L-4-nitrophenylalanyl]-4,5,6,7-tetrahydropyrrolo[3,4-c]pyridin-2-acetate.

Also, inthe compound (II) of thepresent invention, there may be suitably mentioned 1) a compound in which the heteroaromatic ring in the formula (II) is a furan ring where $A^1=A^2=A^4=A^5=C$ and $A^3=O$; a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; an oxazole ring where $A^1=A^2=A^4=C$, $A^3=O$ and $A^5=N$; a thiazole ring where $A^1=A^2=A^4=C$, $A^3=S$ and $A^5=N$; a pyrazole ring where $A^1=A^2=A^5=C$ and $A^3=A^4=N$; or an imidazole ring where $A^1=A^2=A^4=C$ and $A^3=A^5=N$, Z is a $C_1$-$C_4$ alkyl group or a benzyl group; o=0 and p=1 or o=1 and p=0, 2) a compound in which the heteroaromatic ring in the formula (II) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, $R^7$ and $R^8$ each represents a hydrogen atom or an ethylene group formed in combination thereof, $R^9$ is a methyl group, an ethyl group, a methoxy group, an ethoxy group, a trifluoromethyl group or a benzyloxycarbonyl group, Z is a methyl group, an ethyl group, a propyl group, an isopropyl group, a butyl group, a t-butyl group or a benzyl group, Q is a hydrogen atom, an ethoxycarbonyl group, a t-butoxycarbonyl group, a benzyloxycarbonyl group or a trityl group, and o=0 and p=1 or o=1 and p=0, 3) A compound in which the heteroaromatic ring in the formula (II) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, $R^7$ and $R^8$ each represents a hydrogen atom or an ethylene group formed in combination thereof, $R^9$ is a methyl group, an ethyl group, a methoxy group, an ethoxy group, a trifluoromethyl group or a benzyloxycarbonyl group, Z is a methyl group, an ethyl group, a propyl group, a t-butyl group or a benzyl group, Q is a hydrogen atom, an ethoxycarbonyl group, a t-butoxycarbonyl group, a benzyloxycarbonyl group or a trityl group, and o=0 and p=1.

The compound (I) and the compound (II) of the present invention can be produced by Preparation methods 1 to 3 and Preparation methods 4 to 9 shown below.

(Preparation method 1)

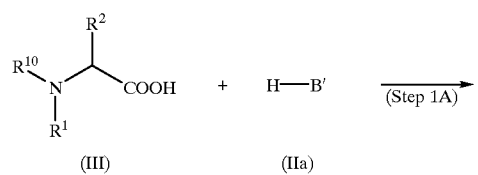

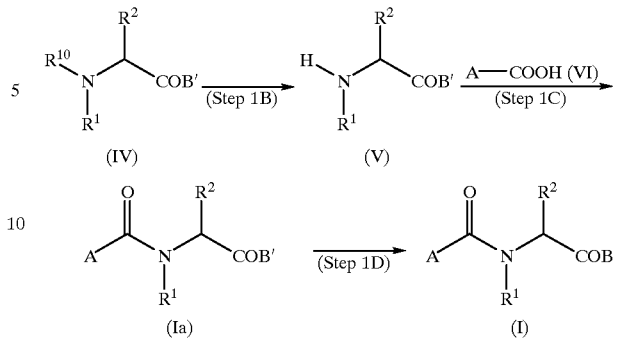

wherein $R^1$, $R^2$, A and B have the same meanings as defined above, B represents a group of the formula (b) wherein Z is a protected carboxyl group, and $R^{10}$ represents a t-butoxycarbonyl group or a benzyloxycarbonyl group.

Preparation method 1 comprises a step (Step 1A) of obtaining Compound (IV) by subjecting to condensation reaction (amidation reaction) of Compound (IIa) (i.e., in the compound represented by the formula (II), Z is a protected carboxyl group and Q is a hydrogen atom) with Compound (III), then, astep (Step 1B) of obtaining Compound (V) by deprotecting the protective group for the amino group, and a step (Step 1C) of obtaining Compound (Ia) wherein Z is a protected carboxyl group in the formula (I) by subjecting to condensation reaction (amidation reaction) of Compound (V) with Compound (VI), and if necessary, a step (Step 1D) of obtaining a desired compound (I) by converting the substituent(s) contained in A and/or B.

Step 1A: The condensation reaction of Compound (IIa) with Compound (III) in Step 1A can be carried out by the conventionally known method as a usual amide bond forming reaction in the peptide chemistry, for example, by optionally selecting Method ① a method of using a condensing agent, Method ② a method of leading the carboxyl group of Compound (III) to an active ester derivative and then reacting it with Compound (IIa), Method ③ a method of leading the carboxyl group of Compound (III) to a mixed acid anhydride derivative and then reacting it with Compound (IIa), or Method ④ a method of leading the carboxyl group of Compound (III) to an acid halide compound and then reacting it with Compound (IIa), and the like.

In Step 1A, the method of using a condensing agent of Method ① can be carried out by reacting Compound (IIa) with Compound (III) in the presence of a condensing agent, in the presence or absence (preferably in the presence) of a base in an organic solvent.

As the condensing agent to be used in said reaction, there may be mentioned, for example, N,N'-dicyclohexylcarboxydiimide (DCC), 1-ethyl-3-(3-dimethylaminopropyl)carbodiimide hydrochloride (EDC), N,N'-carbonyldiimidazole (CDI), diphenylphosphoryl azide, diethyl cyanophosphate, benzotriazol-1-yl-oxy-tris-(dimethylamino)phosphonium hexafluorophosphate (BOP), benzotriazol-1-yl-oxy-tris-pyrrolidinophosphonium hexafluorophosphate (PyBOP), 6-chloro-2,4-dimethoxy-1,3,5-triazole (CDT), 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), bromo-tris-pyrrolidino-phosphonium hexafluorophosphate (PyBroP), 2-(5-norbornene-2,3-dicarboximido)-1,1,3,3-tetramethyluronium tetrafluoroborate (TNTU), O-(N-succinimidyl)-1,1,3,3-tetramethyluronium tetrafluoroborate (TSTU) and the like, preferably DCC, EDC, BOP, PyBOP, HBTU, CDT and TBTU.

An amount of the condensing agent to be used is usually 1- to 5-fold mole, preferably 1- to 3-fold mole based on Compound (III).

As the base, there may be used, for example, an organic base such as triethylamine, diisopropylethylamine, N-methylpiperidine, N-methylmorpholine and 4-dimethylaminopyridine.

As the reaction solvent, there may be preferably mentioned an ether such as dioxane, tetrahydrofuran, diethyl ether, dimethoxyethane and diethoxyethane, a nitrile such as acetonitrile, an organic base such as pyridine and picoline, an amide such as N,N-dimethylformamide and N-methylpyrrolidone, a sulfoxide such as dimethylsulfoxide, a halogenated hydrocarbon such as chloroform, methylene chloride and 1,2-dichloroethane, and these solvents may be used singly or as a mixed solvent.

The reaction is carried out usually in the range of −20 to 100° C. (preferably 0 to 50° C.) for 0.5 to 24 hours.

In step 1A, the method which is carried out via an active ester derivative of Method ② can be carried out firstly by reacting Compound (III) with a hydroxy compound in the presence of a condensing agent in the presence or absence (preferably in the presence) of a base in an organic solvent to convert Compound (III) toanactiveesterderivative, andthen, reacting it with Compound (IIa).

As the hydroxy compound to be used in the reaction, there may be mentioned, for example, a phenol such as 2,4,5-trichlorophenol, pentachlorophenol, 2-nitrophenol and 4-nitrophenol, or a N-hydroxy compound such as N-hydroxysuccinimide, N-hydroxy-5-norbornene-endo-2,3-dicarboximide (HONB), 1-hydroxybenzotriazole (HOBt) and N-hydroxypiperidine.

As the reaction conditions such as a condensing agent, base, organic solvent and the like in the synthesis of the active ester derivative, the same ones as in the above-mentoined Method ① can be used and the similar conditions as the reaction conditions can be used.

The amidation reaction can be carried out by adding Compound (IIa) in an amount of 1- to 5-fold mole (preferably 1- to 2-fold mole) to the reaction mixture containing the active ester derivative of Compound (III) obtained as mentioned above without isolation. The reaction can be carried out usually in the range of 0 to 50° C. for 0.5 to 24 hours.

In Step 1A, the method which is carried out via a mixed acid anhydride derivative of Method ③ can be carried out by reacting Compound (III) with a chloroformic acid ester such as ethyl chloroformate or a phosphonic acid halide such as diethylphosphonic chloride in the presence of a base in an organic solvent to convert Compound (III) to a corresponding mixed acid anhydride, and then, reacting it with Compound (IIa).

In Step 1A, the method which is carried out via an acid halide compound of Method ④ can be carried out according to, for example, the method described in "New Experimental Chemistry Lecture" edited by the Chemical Society of Japan, vol. 14 (II), pp. 1104 and 1194, for example, by reacting Compound (III) with a halogenating agent such as thionyl chloride, phosphorus trichloride, phosphorus tribromide, phosphorus oxychloride and phosphorus pentachloride to obtain an acid halide compound, and then, reacting it with Compound (IIa).

Step 1B: Compound (IV) obtained in Step 1A is then led to Compound (V) by subjecting to deprotecting reaction of the protective group for the amino group. Deprotection of the protective group for the amino group can be carried out by optionally selecting the method described in Literature I ("Protective Groups in Organic Synthesis, 2nd. Ed.", written by T. W. Greene and P. G. H. Wuts, John Wiley & Sons, p. 309), for example, the method of using an acid (preferably trifluoroacetic acid), the method of hydrogenolysis, and the like.

Step 1C: The condensation reaction of Compound (V) with Compound (VI) in Step 1C can be carried out similarly by optionally selecting the method described in the above-mentioned Step 1A.

Step 1D: Step 1D is a step which is carried out, if desired, and includes (1) a reaction of deprotecting the protective group for the carboxyl group contained in the group B' to convert it to a carboxyl group (Reaction 1Da), (2) a reaction of converting the substituent(s) $R^3$ and/or $R^4$ and/or $R^5$ on the nitrogen atom of the group A, or an optional substituent contained in $R^6$ to a hydrogen atom (Reaction 1Db), (3) a reaction of introducing a protective group into the carboxyl group contained in the group B (Reaction 1Dc), (4) a reaction of acylating or alkoxycarbonylating the hydrogen atom on the nitrogen atom contained in the substituent(s) $R^3$ and/or $R^4$ and/or $R^5$ of the group A, or in $R^6$ (Reaction 1Dd), and a desired compound can be obtained by optionally selecting these reactions or carrying out the same in combination thereof in a desired order.

The reaction of deprotecting the protective group for the carboxyl group to convert it into a carboxyl group of Reaction 1Da can be carried out according to the method described in the above-mentioned literature I, for example, by optionally selecting the method of using an acid or an alkali or the method according to hydrogenolysis an the like.

Reaction 1Db is a reaction of converting a t-butoxycarbonyl group, a benzyloxycarbonyl group or a benzyl group into a hydrogen atom in the case of a compound having, for example, a t-butoxycarbonyl group, a benzyloxycarbonyl group or a benzyl group as the substituent(s) $R^3$ and/or $R^4$ and/or $R^5$ on the nitrogen atom of the group A. Said reaction can be easily carried out in the same manner as in the deprotecting reaction of the protective group for the amino group mentioned in the above Step 1B, for example, a method of using an acid such as trifluoroacetic acid, p-toluenesulfonic acid, hydrochloric acid, sulfuric acid and the like, a method of using hydrogenolysis and the like.

Incidentally, by suitably selecting the reaction conditions, the above-mentioned Reaction 1Da and Reaction 1Db may be carried out simultaneously.

Reaction 1Dc is a reaction to introduce a desired protective group into the compound wherein Z is a carboxyl group obtained by the above-mentioned Reaction 1Da, and, for example, it may be carried out by optionally selecting the conventionally known methods (see "Experimental Chemistry Lecture 22" edited by the Chemical Society of Japan, The fourth edition) such as a method of esterifying under acidic conditions, a method of using a condensing agent or a method of using a halogenated compound.

Reaction 1Dd is a reaction to lead Compound (Ia) having a hydrogen atom as the substituent(s) $R^3$ and/or $R^4$ and/or $R^5$, or $R^6$ on the nitrogen atom of the group A or the compound obtained by the above Reaction 1Db to a desired compound by subjecting said compound to acylation or alkoxycarbonylation (including phenoxycarbonylation).

The acylation reaction can be easily carried out according to the method described in "Experimental Chemistry Lecture 22" edited by the Chemical Society of Japan, The fourth edition, p. 230 or a method similar thereto by using an acylating agent such as an acid halide, an acid anhydride or an (active) ester compound in the presence or absence (preferably in the presence) of a base.

In particular, in the case of the acylation reaction on the amidino group where the group A is represented by the formula (a-1), it is preferably carried out by using a chloromethyl ester of a carboxylic acid having a $C_1$ to $C_6$ alkanoyl group such as chloromethyl acetate, chloromethyl propionate, chloromethyl butanoate, chloromethyl isobutanoate, chloromethyl pentanoate, chloromethyl hexanoate and chloromethyl pivalate in the presence of a base in a solvent. An amount of the chloromethyl ester of the carboxylic acid as an acylating agent is generally 1- to 20-fold mole, preferably 2- to 15-fold mole based on the reaction substrate.

The reaction solvent is not particularly limited so long as it is inactive to the present reaction, and there may be mentioned, for example, an ether such as dioxane, tetrahydrofuran, diethyl ether, dimethoxyethane and diethoxyethane; a nitrile such as acetonitrile; an amide such as N,N-dimethylformamide, N,N-dimethylacetamide and N-methylpyrrolidone; a sulfoxide such as dimethylsulfoxide; and an aromatic amine such as pyridine and picoline, preferably an ether and an amide. As the base, there may be mentioned, for example, a tertiary amine such as triethylamine, tributylamine, diisopropylethylamine, 1,8-diazabicyclo[5.4.0]undecene (DBU), 1,5-diazabicyclo [4.3.0]-7-nonen and the like; a metal alkoxide such as sodium methoxide, sodium ethoxide and potassium t-butoxide; a metal amide such as lithium bis(trimethylsilyl) amide and lithium diisopropylamide; and an alkali metal carbonate such as sodium carbonate and potassium carbonate, preferably a tertiary amine, a metal amide and an alkali metal carbonate. An amount thereof is 1- to 20-fold mole, preferably 2- to 15-fold mole based on the reaction substrate. The reaction temperature is −78 to 25° C., preferably −78 to 0° C. The reaction time is 30 minutes to 5 hours, preferably 1 to 3 hours.

The alkoxycarbonylation reaction or the phenoxycarbonylation reaction can be carried out, for example, according to the method disclosed in J. Med. Chem., 31, 318 (1988); Synthesis, 12, 1159 (1990); EP 567 966 A1 publication, Bioorg. & Med. Chem. Lett., 6, 2425 (1996) and the like or a method similar thereto, by using, as an alkoxycarbonylating agent or a phenoxycarbonylating agent, a chloroformic acid ester having a ($C_1$–$C_{10}$ alkoxy)carbonyl group, a ($C_3$–$C_7$ cycloalkoxy)carbonyl group, a ($C_2$–$C_6$ alkenyl) oxycarbonyl group, a ($C_7$–$C_{10}$ aralkyl)oxycarbonyl group or a phenoxycarbonyl group which may be substituted, such as methyl chloroformate, ethyl chloroformate, propyl chloroformate, isopropyl chloroformate, butyl chloroformate, pentyl chloroformate, hexyl chloroformate, cyclopentyl chloroformate, cyclohexyl chloroformate, benzyl chloroformate, phenyl chloroformate, isopropenyl chloroformate and allyl chloroformate; a dicarbonic acid diester having a ($C_1$–$C_{10}$ alkoxy)carbonyl group, a ($C_3$–$C_7$ cycloalkoxy)carbonyl group, or a ($C_2$–$C_6$ alkenyl) oxycarbonyl group portion such as diethyl dicarbonate, dipropyl dicarbonate, dibutyl dicarbonate, di-t-butyl dicarbonate, dicyclopentyl dicarbonate, dicyclohexyl dicarbonate and diallyl dicarbonate; or a (4-nitrophenyl) carbonate carbonate having a ($C_1$–$C_{10}$ alkoxy)carbonyl group, a ($C_3$–$C_7$ cycloalkoxy)carbonyl group, a ($C_2$–$C_6$ alkanoyl)oxymethoxycarbonyl group, a ($C_1$–$C_2$ alkoxy) carbonyl group substituted by a $C_1$–$C_4$ alkoxy group or a phenoxycarbonyl group which may be substituted, such as methyl (4-nitrophenyl)carbonate, ethyl (4-nitrophenyl) carbonate, propyl (4-nitrophenyl)carbonate, pentyl (4-nitrophenyl)carbonate, hexyl (4-nitrophenyl)carbonate, cyclopentyl (4-nitrophenyl)carbonate, cyclohexyl (4-nitrophenyl)carbonate, acetoxymethyl (4-nitrophenyl) carbonate, propanoyloxymethyl (4-nitrophenyl)carbonate, butanoyloxymethyl (4-nitrophenyl)carbonate, pivaloyloxymethyl (4-nitrophenyl)carbonate, benzoyloxymethyl (4-nitrophenyl)carbonate, nicotinoyloxymethyl (4-nitrophenyl)carbonate, isonicotinoyloxymethyl (4-nitrophenyl)carbonate, 2-t-butoxyethyl (4-nitrophenyl) carbonate, phenyl (4-nitrophenyl)carbonate and 4-octyloxyphenyl (4-nitrophenyl)carbonate. Also, alkoxycarbonylation reaction can be carried out in the same manner as in the acylation reaction using the above-mentioned chloromethyl carboxylate by using, as an alkoxycarbonylating agent, for example, a (chloromethyl)carbonate having a ($C_2$–$C_6$ alkanoyl)oxymethoxycarbonyl group, or a ($C_1$–$C_2$ alkoxy)carbonyl group substituted by a $C_1$–$C_4$ alkoxy group, such as acetoxymethyl (chloromethyl)carbonate, pivaloyloxymethyl (chloromethyl)carbonate, benzoyloxymethyl (chloromethyl)carbonate, nicotinoyloxymethyl (chloromethyl)carbonate, isonicotinoyloxymethyl (chloromethyl)carbonate and 2-t-butoxyethyl (chloromethyl)carbonate.

Moreover, it is possible to convert the substituent on the benzyl group of $R^2$ in the optional stage of Preparation method 1. For example, in Compound (IV), Compound (V) or Compound (Ia), the respective compounds having a nitro group as a substituent on the benzyl group, $R^2$, can be converted into an amino group by reducing the nitro group or converted into a sulfonylamino group or an acylamino group by further subjecting the formed amino group to sulfonylation or acylation. Also, the benzyloxy group as a substituent on the benzyl group, $R^2$, can be converted into a hydroxyl group by de-benzylation reaction. These conversion reactions can be carried out by optionally selecting the method described in, for example, ("Experimental Chemistry Lecture 20" edited by the Chemical Society of Japan, 4th Ed., p. 279, EP 478 363 A2 publication, the above-mentioned Literature I, p. 156).

(Preparation method 2)

wherein $R^1$, $R^2$, A and B' have the same meanings as defined above, and $R^{11}$ represents a methyl group, an ethyl group, a

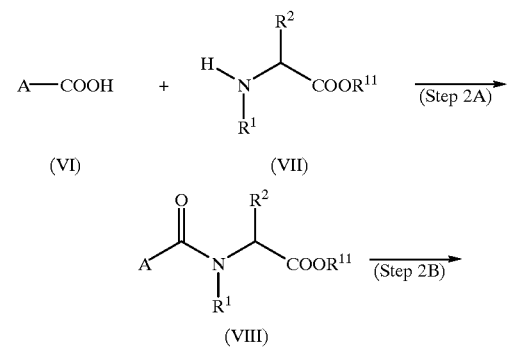

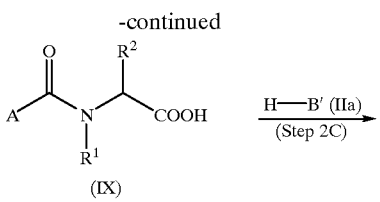

t-butyl group or a benzyl group.

Preparation method 2 is another method for producing Compound (Ia), and comprises a step (Step 2A) of obtaining Compound (VIII) by effecting condensation reaction of Compound (VI) and Compound (VII), then, a step (Step 2B) of obtaining Compound (IX) by the deprotecting reaction, and further a step (Step 2C) of obtaining Compound (Ia) by effecting condensation reaction with Compound (IIa).

Two condensation reactions of Step 2A and Step 2C in Preparation method 2 are carried out in the same manner as in Step 1A in the above-mentioned Preparation method 1, and the deprotective reaction of the protective group for the carboxyl group in Step 2B can be carried out in the same manner as in Step 1Da in Step 1D of the above-mentioned Preparation method 1.

(Preparation method 3)

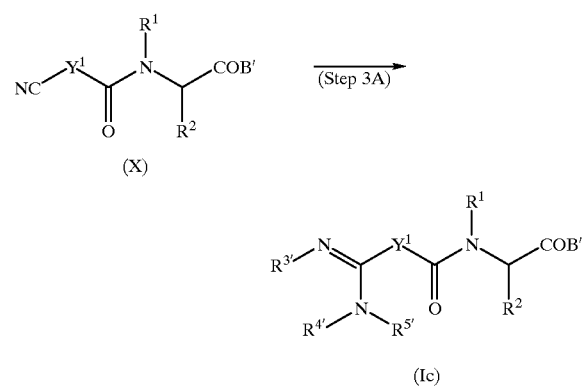

wherein $R^1$, $R^2$, B' and $Y^1$ have the same meanings as defined above, $R^{3'}$ represents a hydrogen atom or a hydroxyl group, $R^{4'}$ and $R^{5'}$ each independently represent a hydrogen atom, a $C_1$–$C_4$ alkyl group, a $C_7$–$C_{10}$ aralkyl group or an alkylene group formed by $R^{4'}$ and $R^{5'}$ in combination which may contain one hetero atom selected from the group consisting of O, N and S.

Preparation method 3 is another method for producing Compound (Ic), and is a method for producing the same by converting the cyano group of Compound (X) (said compound can be produced in the same manner by using a cyano compound represented by NC-$Y^1$—COOH (wherein $Y^1$ has the same meaning as defined above) in place of Compound (VI) in the above-mentioned (Preparation method 1) or (Preparation method 2)) into a desired amidino group, or an N-substituted amidino group.

Conversion of the cyano group to the amidino group in Step 3A can be carried out by optionally selecting the conventionally known various methods (for example, S. Patai Ed. "The Chemistry of amidine and imidate" John Wiley & Sons (1975) p. 283). For example, a thioamide derivative is firstly obtained by reacting Compound (X) and 1- to 5-fold mole (preferably 2- to 3-fold mole) of sodium hydrosulfide in a solvent (preferably acetone, dimethylformamide, etc.) in the presence of 0.1- to 1-fold mole (preferably 0.5- to 1-fold mole) of magnesium chloride at room temperature for 0.5 to 8 hours (preferably 1 to 3 hours). Then, the resulting thioamide derivative and methyl iodide were reacted in a solvent (preferably acetone, dimethylformamide, etc.) at room temperature to 100° C. (preferably room temperature to 60° C.) for 1 to 8 hours (preferably 1 to 3 hours) to obtain a methylthioimidoyl derivative. Moreover, the resulting methylthioimidoyl compound and an amine compound ($R^{4'}R^{5'}$NH (wherein $R^{4'}$ and $R^{5'}$ have the same meanings as defined above)) or a salt thereof (for example, acetate, hydrochloride, carbonate, etc.) are reacted in an alcohol (preferably methanol, ethanol) solvent at 25 to 100° C. (preferably 50 to 80° C.) for 1 to 12 hours (preferably 2 to 6 hours) to easily obtain a corresponding amidine compound (Ic) (for example, see WO 95 34543 publication). Also, it is also carried out by the method (Pinner reaction) in which Compound (X) is reacted with hydrogen chloride in the presence of an alcohol (preferably ethanol) to lead the cyano group to an imidoyl ester group, and the compound is reacted with the above-mentioned amine compound.

On the other hand, conversion of the cyano group to an N-hydroxyamidino group can be easily carried out by reacting Compound (X) and 1- to 10-fold mole (preferably 1.5- to 5-fold mole) of hydroxyl amine (prepared by hydroxylamine hydrochloride or hydroxylamine sulfate and a metal alkoxide (for example, sodium methoxide, sodium ethoxide, sodium butoxide, or potassium t-butoxide, preferably sodium ethoxide)) in a solvent (preferably an alcohol such as methanol, ethanol, propanol, isopropanol, butanol, etc.). Said reaction can be carried out at 0 to 80° C., preferably 10 to 50° C. and the reaction time varies depending on the reaction temperature but usually for 1 to 24 hours (for example, see J. Chem. Soc. (c), 861 (1969), J. Med. Chem., 39, 3139 (1996)).

In the respective reactions as mentioned above, the formed objective compound can be isolated from the reaction mixture according to the conventional manner, and can be purified by using a usual purifying means such as the recrystallization method, column chromatography method, etc., if necessary.

Also, Compound (I) can be converted into a desired salt acording to the conventional manner, if necessary, but can be isolated as a salt directly from the reaction mixture.

Also, in Compound (I), there is a case in which an optical isomer or a geometric isomer exists. In such a case, by using a starting material in which the optical isomer or the geometric isomer has been isolated, an optical isomer or a geometric isomer of the desired compound can be obtained.

Also, a mixture of the optical isomer or the geometric isomer is treated according to the conventional optical resolution method or the separating method, respective isomers can be obtained.

Incidentally, in Preparation method 1 and Preparation method 2, Compound (III), Compound (VI) and Compound (VII) to be used as the starting materials are each conventionally known or can be easily obtained according to the conventionally known method.

On the other hand, the present compounds (II) which include Compound (IIa) to be used in Preparation method 1 and Preparation method 2 and compounds available for producing Compound (IIa) are novel compounds, and can be produced by the methods of Preparation method 4, Preparation method 5, Preparation method 6, Preparation method 7, Preparation method 8 or Preparation method 9 mentioned below.

(Preparation method 4)

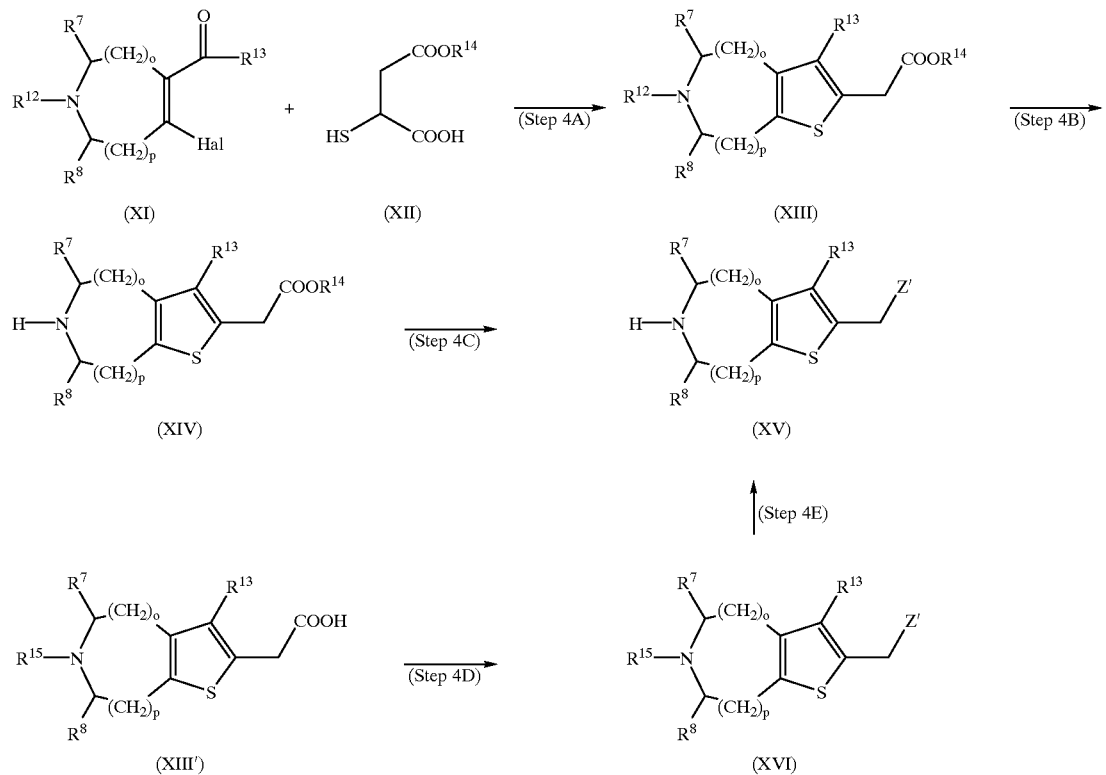

wherein $R^7$, $R^8$, o and p have the same meanings as defined above, $R^{12}$ represents a ($C_1$–$C_4$ alkoxy) carbonyl group such as a methoxycarbonyl group, an ethoxycarbonyl group, a propoxycarbonyl group, a butoxycarbonyl group and a t-butoxycarbonyl group, a benzyloxycarbonyl group or a trityl group, $R^{13}$ represents a hydrogen atom, a $C_1$–$C_4$ alkyl group or a trifluoromethyl group, $R^{14}$ represents a hydrogen atom, a $C_1$–$C_4$ alkyl group or a $C_7$–$C_{10}$ aralkyl group, $R^{15}$ represents a t-butoxycarbonyl group or a trityl group, Hal represents a halogen atom (preferably a chlorine atom or a bromine atom), and Z' represents a protected carboxyl group.

Preparation method 4 is a method for producing a compound in which the heteroaromatic ring in the formula (II) is a thiophene ring wherein $A^1=A^2=A^4=A^5=C$ and $A^3=S$, and comprises a step (Step 4A) of obtaining Compound (XIII) by reacting Compound (XI) and Compound (XII), then, a step (Step 4B) of obtaining Compound (XIV) by deprotecting reaction of the protective group for an amino group, and, if necessary, a step (Step 4C) of producing Compound (XV) by introducing a desired protective group into the carboxyl group, and as another step of obtaining Compound (XV), a step (Step 4D) of obtaining Compound (XVI) by introducing a protective group into the carboxyl group of Compound (XIII'), and a step (Step 4E) of producing Compound (XV) by deprotective reaction of the protective group for the amino group.

Step 4A: The reaction of Compound (XI) and Compound (XII) is carried out in the presence of a base in a solvent.

An amount of Compound (XII) is 1- to 5-fold mole, preferably 1- to 2-fold mole based on Compound (XI).

As the reaction solvent, it is not particularly limited so long as it is inactive to the present reaction, and there may be mentioned, for example, an ether such as dioxane, tetrahydrofuran, diethyl ether, dimethoxyethane and diethoxyethane; a nitrile such as acetonitrile; an amide such as N,N-dimethylformamide, N,N-dimethylacetamide and N-methylpyrrolidone; a sulfoxide such as dimethylsulfoxide; and a heteroaromatic amine such as pyridine and picoline, preferably pyridine and dimethylsulfoxide.

As the base, there may be mentioned, for example, a tertiary amine such as triethylamine, tributylamine, diisopropylethylamine, 1,8-diazabicyclo[5.4.0]-7-undecene (DBU), 1,5-diazabicyclo[4.3.0]-7-nonene (DBN) and the like; a metal alkoxide such as sodium methoxide, sodium ethoxide and potassium t-butoxide; or an alkali metal carbonate such as sodium carbonate and potassium carbonate, preferably a tertiary amine such as triethylamine, tributylamine and diisopropylethylamine.

An amount of the base is usually 2- to 5-fold mole, but in the case of a tertiary amine, it may be used in a markedly excess amount also as a solvent. The reaction temperature is preferably 0 to 150° C., more preferably 10 to 100° C.

The reaction time is usually 0.5 to 18 hours, preferably 0.5 to 12 hours.

Also, the reaction may be carried out by adding a secondary amine such as piperidine and morpholine to accelerate the reaction.

Step 4B: The deprotective reaction of the protective group for the amino group of Compound (XIII) can be carried out by optionally selecting the conventionally known method (for example, the method disclosed in Literature I) depending on the nature of the protective group. For example, deprotection can be easily carried out by the method of using an alkali or an acid when the protective group is a methoxycarbonyl group, an ethoxycarbonyl group or a benzyloxycarbonyl group, and by the method of using an acid when the protective group is a t-butoxycarbonyl group or a trityl group. Also, in the case of a benzyloxycarbonyl group or a trityl group, deprotection can be also carried out by the method of effecting hydrogenolysis.

In Compound (XIII) or Compound (XIV) obtained by the respective steps as mentioned above, the carboxyl group thereof can be converted into carboxy (XV) having a desired protective group according to the step as mentioned below.

Step 4C: Step 4C is a step of producing Compound (XV) by introducing a protective group for the carboxyl group of Compound (XIV) wherein $R^{14}$ is a hydrogen atom (said compound can be produced by using Compound (XII) wherein $R^{14}$ is a hydrogen atom as a starting material, or can be produced by deprotecting the protective groups for $R^{12}$ and $R^{14}$ simultaneously in Step 4B), and can be easily carried out by reacting (esterification) with a desired alcohol under acidic conditions.

Step 4D: Step 4D is a step of introducing a protective group into the carboxyl group of Compound (XIII') wherein $R^{12}$ is a t-butoxycarbonyl group or a trityl group and $R^{14}$ is a hydrogen atom in Compound (XIII) (said compound can be produced by using Compound (XI) wherein $R^{12}$ is a t-butoxycarbonyl group or a trityl group and Compound (XII) wherein $R^{14}$ is a hydrogen atom as starting materials, or by reacting Compound (XIV) wherein $R^{14}$ is a hydrogen atom and di-t-butyl dicarbonate or trityl chloride), and can be carried out by optionally selecting the introducing method of the protective group for the carboxyl group mentioned in the above Preparation method 1.

Step 4E: Step 4E is a step of obtaining Compound (XV) by deprotecting the protective group for the amino group of Compound (XVI), and can be carried out by optionally selecting the method as disclosed in the above-mentioned Literature I, and preferably carried out by the method of using an acid (more preferably trifluoroacetic acid or p-toluenesulfonic acid).

Incidentally, it is also possible to carry out protection (esterification) of the carboxyl group and deprotection of the protective group for the amino group simultaneously by reacting Compound (XIII') in a desired alcohol solvent (preferably a $C_1$–$C_4$ alcohol such as methanol, ethanol, propanol, isopropanol, butanol, isobutanol, and the like; a $C_7$–$C_{10}$ aralkyl alcohol such as benzyl alcohol, phenethyl alcohol and the like) in the presence of an acid (preferably hydrogen chloride, and as a simple and easy method, a substance which generates hydrogen chloride by reacting with an alcohol such as thionyl chloride, oxalyl chloride or acetyl chloride may be used in place of hydrogen chloride).

(Preparation method 5)

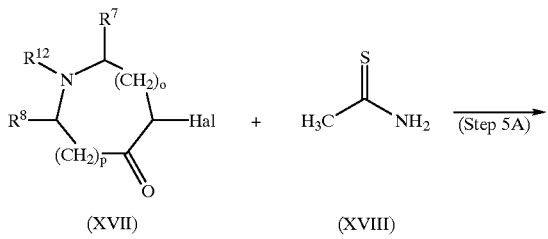

(XVII)     (XVIII)

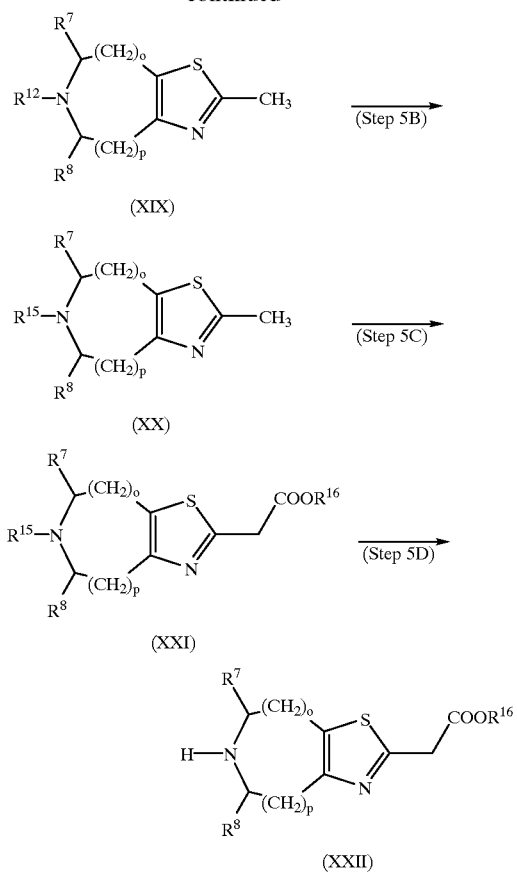

wherein $R^7$, $R^8$, $R^{12}$, $R^{15}$, Hal, o and p have the same meanings as defined above, and $R^{16}$ represents a $C_1$–$C_4$ alkyl group or a $C_7$–$C_{10}$ aralkyl group.

Preparation method 5 is a method for producing a compound in which the heteroaromatic ring in the formula (II) is a thiazole ring wherein $A^1$=$A^2$=$A^4$=C, $A^3$=S and $A^5$=N, and comprises a step (Step 5A) of obtaining Compound (XIX) by reacting Compound (XVII) and thioacetamide (XVIII), and, if necessary, a step (Step 5B) of replacing the protective group for the amino group, a step (Step 5C) of obtaining Compound (XXI) by alkoxycarbonylating Compound (XX), and a step (Step 5D) of producing Compound (XXII) by deprotecting Compound (XXI).

Step 5A: The reaction of Compound (XVII) and thioacetamide (XVIII) can be carried out by heating in a solvent. An amount of thioacetamide is usually 1- to 10-fold mole, preferably 1- to 3-fold mole based on Compound (XVII).

As the reaction solvent, it is not particularly limited so long as it is inactive to the present reaction, and there may be mentioned, for example, an alcohol such as methanol, ethanol, propanol, isopropanol and butanol; an ether such as dioxane, tetrahydrofuran, diethyl ether, dimethoxyethane and diethoxyethane; a nitrile such as acetonitrile; an amide such as N,N-dimethylformamide, N,N-dimethylacetamide and N-methylpyrrolidone; and a sulfoxide such as dimethylsulfoxide, preferably an amide such as N,N-dimethylformamide, N,N-diacetamide and N-methylpyrrolidone or a sulfoxide such as dimethylsulfoxide.

The reaction temperature is 20 to 200° C., preferably 50 to 150° C. The reaction time is usually 30 minutes to 12 hours.

Step 5B: Step 5B is a step necessary for the case only when Compound (XVII) wherein $R^{12}$ has a protective group such as a methoxycarbonyl group or an ethoxycarbonyl group is used as a starting material, and can be carried out by firstly deprotecting the above-mentioned protective group, then introducing a desired protective group (preferably a t-butoxycarbonyl group or a trityl group). Deprotection and introduction of these protective groups can be carried out according to the method described in the above-mentioned Step 4B or Literature 1.

Step 5C: The reaction of obtaining Compound (XXI) from Compound (XX) can be carried out in an innert gas atmosphere such as nitrogen, helium, argon, etc. and treated with a strong base, then reacting with an alkoxycarbonylating agent.

The reaction solvent is preferably an ether such as dioxane, tetrahydrofuran, diethyl ether, dimethoxyethane, diethoxyethane, and the like, and the strong base is preferably a base such as n-butyl lithium, t-butyl lithium, lithium diisopropylamide, lithium bis(trimethylsilyl)amide, etc.

The alkoxycarbonylating agent may include a carbonic acid diester in which the alkyl group portion is a $C_1$–$C_4$ alkyl group or a $C_7$–$C_{10}$ aralkyl group such as dimethyl carbonate, diethyl carbonate, dipropyl carbonate, dibutyl carbonate, dibenzyl carbonate, diphenethyl carbonate and the like, and a chlorocarbonic acid ester in which the alkyl group portion is a $C_1$–$C_4$ alkyl group or a $C_7$–$C_{10}$ aralkyl group such as methyl chlorocarbonate, ethyl chlorocarbonate, propyl chlorocarbonate, butyl chlorocarbonate, benzyl chlorocarbonate, phenethyl chlorocarbonate and the like.

The reaction temperature is –70 to 10° C., preferably –60 to 0° C.

The reaction time is not specifically limited but 1 to 6 hours.

Step 5D: Deprotective reaction of the protective group for the amino group of Compound (XXI) can be carried out by optionally selecting from the methods already mentioned, preferably the deprotective reaction under acidic conditions can be employed.

Also, in Compound (XXI) or Compound (XXII) obtained above, it is possible to convert the protective group $R^{16}$ for the carboxyl group or the protective group $R^{15}$ for the amino group into a desired protective group. Conversion of these protective groups can be carried out by optionally selecting the methods as mentioned in Step 1D in the above Preparation method 1 or Step 4C, Step 4D and Step 4E in the above Preparation method 4.

(Preparation method 6)

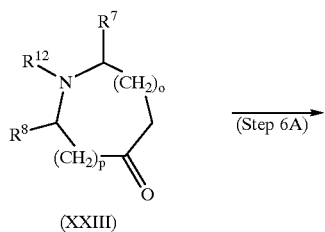

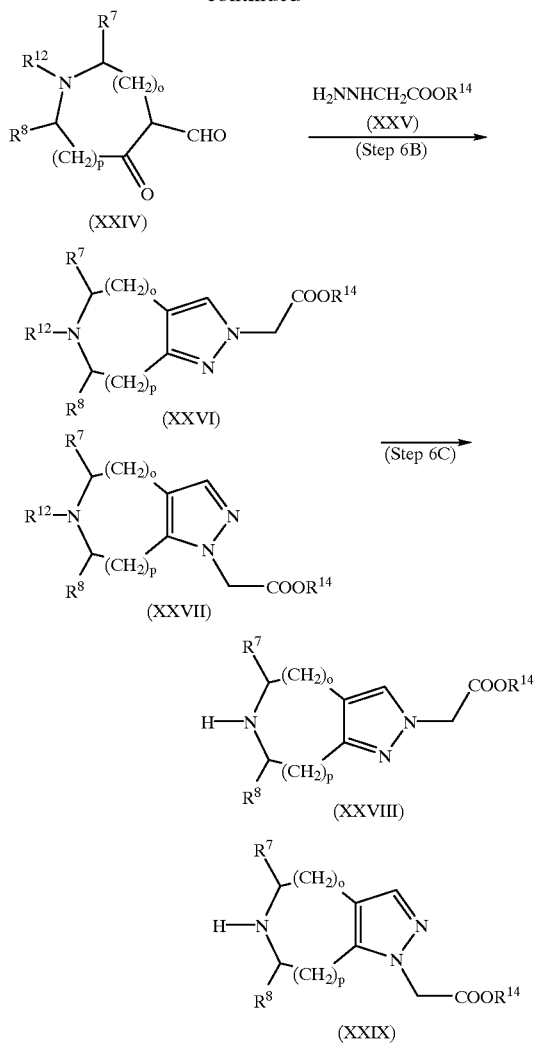

wherein $R^7$, $R^8$, $R^{12}$, $R^{14}$, o and p have the same meanings as defined above.

Preparation method 6 is a method for producing a compound in which the heteroaromatic ring in the formula (II) is a pyrazole ring wherein $A^1=A^2=A^5=C$ and $A^3=A^4=N$, and comprises a step (Step 6A) of obtaining Compound (XXIV) by formylating Compound (XXIII), a step (Step 6B) of obtaining Compound (XXVI) and Compound (XXVII) by the reaction of Compound (XXIV) and a hydrazine derivative (XXV), and a step (Step 6C) of producing Compound (XXVIII) or Compound (XXIX) by deprotecting Compound (XXVI) or Compound (XXVII).

Step 6A: The formylation reaction of Compound (XXIII) can be carried out by reacting Compound (XXIII) and a formic acid ester in the presence of a base.

As the formic acid ester, there may be used, for example, methyl formate, ethyl formate, propyl formate, and the like, and an amount thereof is usually 1- to 5-fold mole, preferably 1- to 3-fold mole based on Compound (XXIII).

As the reaction solvent, it is not particularly limited so long as it is inactive to the present reaction, and there may be mentioned, for example, an alcohol such as methanol, ethanol, propanol, isopropanol and butanol; an ether such as dioxane, tetrahydrofuran, diethyl ether, dimethoxyethane and diethoxyethane; an aromatic hydrocarbon such as benzene, 116 toluene and xylene; a nitrile such as acetonitrile; an amide such as N,N-dimethylformamide, N,N-dimethylacetamide and N-methylpyrrolidone; a sulfoxide such as dimethylsulfoxide, and a mixed solvent of the above, preferably an alcohol, an ether, an aromatic hydrocarbon, an amide or a mixed solvent thereof.

As the base, there may be mentioned, for example, an alkali metal alkoxide such as sodium methoxide, sodium ethoxide and potassium t-butoxide; an organic metal such as n-butyl lithium, t-butyl lithium, lithium diisopropylamide and lithium bis(trimethylsilyl)amide; and an alkali metal hydride such as sodium hydride and potassium hydride, preferably an alkali metal alkoxide.

An amount of the base is usually 1- to 5-fold mole, preferably 1- to 2-fold mole based on Compound (XXIII).

The reaction temperature is preferably −50 to 50° C., more preferably −20 to 30° C. The reaction time is usually 0.5 to 18 hours.

Compound (XXIV) formed by the above-mentioned formylation reaction can be isolated as a lithium salt, a sodium salt or a potassium salt, but usually used in the next step as a reaction mixture without isolation, or used in the next step after concentration. Or else, when an excessive base is used, it is used in the next step by adding an acid such as acetic acid, etc. to the resulting reaction mixture and after adjusting basic property.

Step 6B: The reaction of Compound (XXIV) and Compound (XXV) can be carried out usually by adding Compound (XXV) to the reaction mixture obtained in the above-mentioned Step 6A.

An amount of Compound (XXV) is usually 1- to 5-fold mole, preferably 1- to 3-fold mole based on Compound (XXIII) used in Step 6A.

The reaction is usually carried out at the temperature range of −78 to 50° C. (preferably −78 to 30° C.) for 0.5 to 24 hours.

In the reaction of Step 6B, Compound (XXVI) and Compound (XXVII) are usually formed and the formation ratio of these compounds can be controlled by the conditions such as a kind and an amount of the used solvent or base, the reaction temperature and the like.

Compound (XXVI) and Compound (XXVII) can be separated by using a usual separating method such as crystallization, the column chromatography method and the like, but there is a case where separation is difficult depending on the kind of the compounds. In such a case, a mixture of Compound (XXVI) and Compound (XXVII) is used in the next step and separation is carried out in Step 6C mentioned below, or separation can be carried out by replacing the protective group $R^{14}$ for the carboxyl group to convert it into an ester derivative (for example, t-butyl ester, etc.) which is capable of effecting separation.

Step 6C: Step 6C is a step of obtaining Compound (XXVIII) or Compound (XXIX) or a mixture thereof by deprotecting Compound (XXVI) or Compound (XXVII) or a mixture of both, and the reaction can be carried out in the same manner as in Step 4B of Preparation method 4.

A mixture of Compound (XXVIII) and Compound (XXIX) is separated by using the usual separating method such as crystallization or the column chromatography method, or separated after converting the mixture to amide derivatives (for example, compounds in which the protective group of N is an α-methoxyphenylacetyl group) which are capable of effecting separation, and then, separately hydrolyzed to obtain Compound (XXVIII) or Compound (XXIX).

(Preparation method 7)

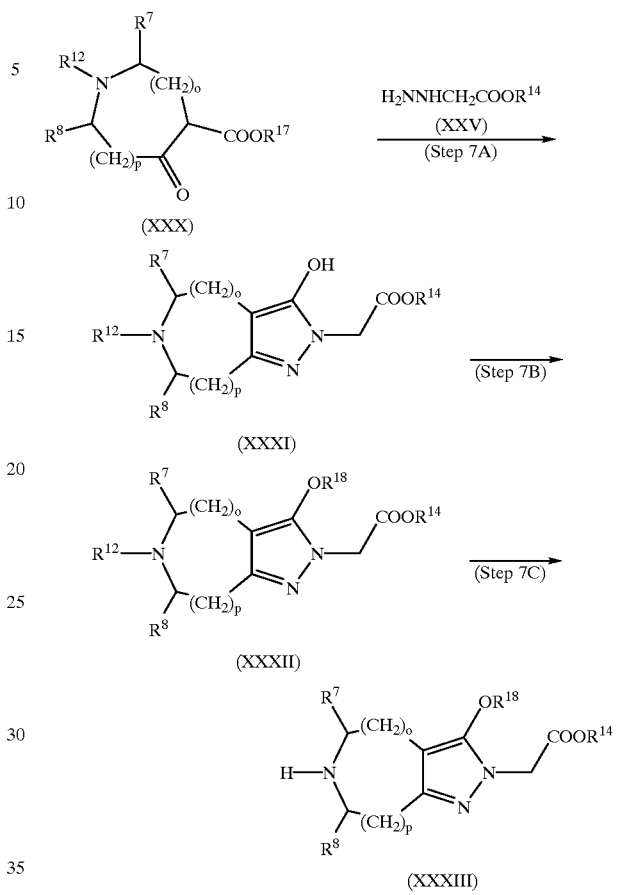

wherein $R^7$, $R^8$, $R^{12}$, $R^{14}$, o and p have the same meanings as defined above, $R^{17}$ represents a methyl group or an ethyl group, and $R^{18}$ represents a $C_1$–$C_4$ alkyl group.

Preparation method 7 is a method for producing a compound in which the heteroaromatic ring in the formula (II) is a pyrazole ring wherein $A^1$=$A2$=$A^5$=$C$ and $A^3$=$A^4$=$N$ and $R^9$ is a hydroxyl group or a $C_1$–$C_4$ alkoxy group, and comprises a step (Step 7A) of obtaining Compound (XXXI) by reacting Compound (XXX) and Compound (XXV), a step (Step 7B) of obtaining Compound (XXXII) by alkylating Compound (XXXI), and a step (Step 7C) of producing Compound (XXXIII) by deprotecting Compound (XXXII).

Step 7A: The reactionof Compound (XXX) andCompound (XXV) can be carried out by using Compound (XXV) usually in the range of 1- to 5-fold mole, preferably 1- to 3-fold mole based on Compound (XXX) in a solvent.

As the reaction solvent, it is not particularly limited so long as it is inactive to the present reaction, and there may be mentioned, for example, an alcohol such as methanol, ethanol, propanol, isopropanol and butanol; an ether such as dioxane, tetrahydrofuran, diethyl ether, dimethoxyethane and diethoxyethane; an aromatic hydrocarbon such as benzene, toluene and xylene; a halogenated hydrocarbon such as methylene chloride, 1,2-dichloroethane, chloroform and carbon tetrachloride; a nitrile such as acetonitrile; an amide such as N,N-dimethylformamide, N,N-dimethylacetamide and N-methylpyrrolidone; a sulfoxide such as dimethylsulfoxide, and a mixed solvent of the above, preferably an alcohol, an amide, a sulfoxide or a mixed solvent thereof.

The reaction temperature is preferably −50 to 50° C., more preferably −20 to 30° C. The reaction time is usually 0.5 to 12 hours.

Step 7B: Alkylation reaction of Compound (XXXI) is carried out by reacting Compound (XXXI) and an alkylating agent in the presence of a base in a solvent.

As the alkylating agent, there may be used, for example, a $C_1$–$C_4$ alkylsulfate such as dimethyl sulfate and diethyl sulfate; a halogenated $C_1$–$C_4$ alkyl such as methyl iodide, ethyl iodide, propyl iodide and butyl iodide, and an amount thereof is in the range of 1- to 5-fold mole, preferably 1- to 2-fold mole based on Compound (XXXI).

As the reaction solvent, it is not particularly limited so long as it is inactive to the present reaction, and there may be mentioned, for example, water; an alcohol such as methanol, ethanol, propanol, isopropanol and butanol; an ether such as dioxane, tetrahydrofuran, diethyl ether, dimethoxyethane and diethoxyethane; an aromatic hydrocarbon such as benzene, toluene and xylene; a nitrile such as acetonitrile; an amide such as N, N-dimethylformamide, N, N-dimethylacetamide and N-methylpyrrolidone; a sulfoxide such as dimethylsulfoxide, and a mixed solvent of the above, preferably an alcohol, an amide, a sulfoxide or a mixed solvent thereof.

As the base, there may be mentioned, for example, an alkali metal hydroxide such as sodium hydroxide, potassium hydroxide and lithium hydroxide; an alkali metal carbonate such as sodium carbonate, potassium carbonate, sodium hyrogen carbonate and potassium hydrogen carbonate; an alkali metal alkoxide such as sodium methoxide, sodium ethoxide and potassium t-butoxide; and a tertiary amine such as triethylamine, tributylamine, pyridine, picoline, lutidine, collidine, 1,8-diazabicyclo[5.4.0]-7-undecene, 1,5-diazabicyclo[4.3.0]-7-nonen and the like, and an amount thereof is in the range of 1- to 5-fold mole, preferably 1- to 2-fold mole based on Compound (XXX).

The reaction temperature is −10 to 100° C., preferably 0 to 50° C.

Step 7C: The reaction of producing Compound (XXXIII) by deprotecting Compound (XXXII) can be carried out in the same manner as in Step 4B of the above-mentioned Preparation method 4.

(Preparation method 8)

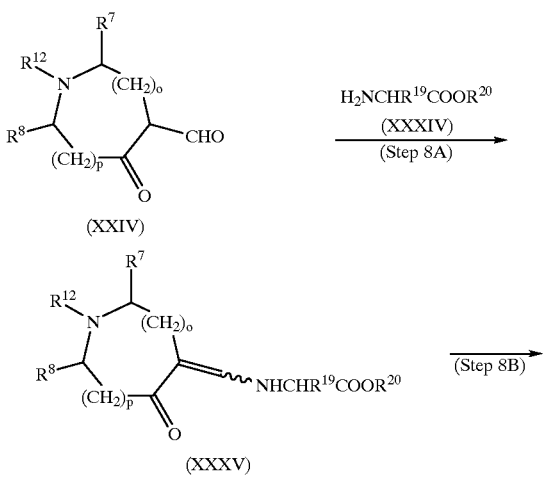

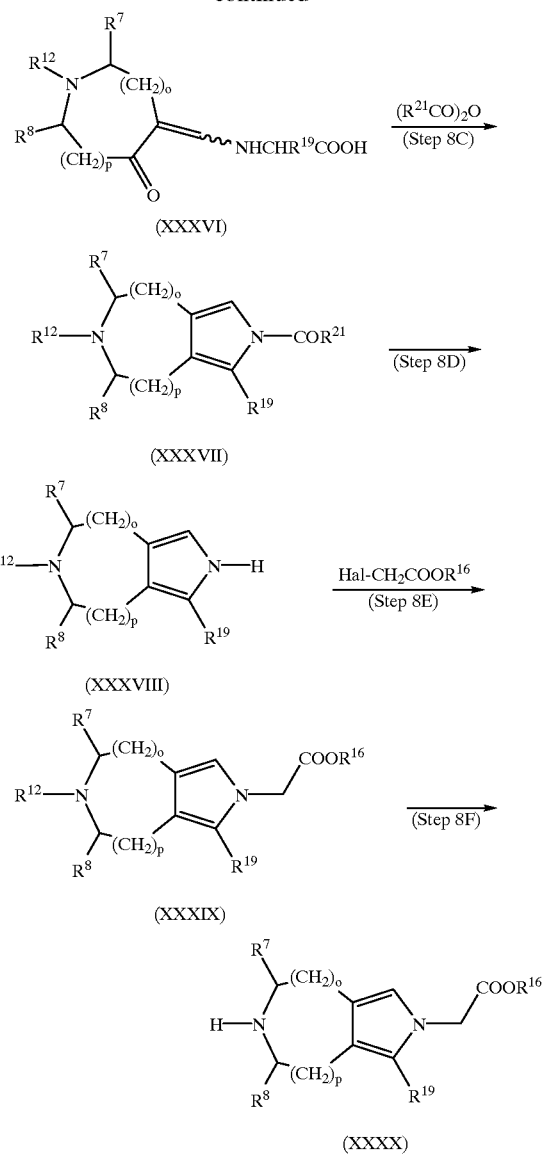

wherein $R^7$, $R^8$, $R^{12}$, $R^{16}$, Hal, o and p have the same meanings as defined above, $R^{19}$ represents a hydrogen atom or a $C_1$–$C_4$ alkyl group, $R^{20}$ represents a hydrogen atom, a methyl group or an ethyl group, and $R^{21}$ represents a methyl group, an ethyl group, a propyl group, a butyl group, a trifluoromethyl group or a phenyl group.

Preparation method 8 is a method for producing a compound in which the heteroaromatic ring in the formula (II) is a pyrrole ring wherein $A^1$=$A^2$=$A^3$=$A^5$=C and $A^4$=N, and comprises a step (Step 8A) of obtaining Compound (XXXV) by reacting Compound (XXIV) and Compound (XXXIV), a step (Step 8B) of obtaining Compound (XXXVI) by hydrolyzing Compound (XXXV), a step (Step 8C) of obtaining Compound (XXXVII) by cyclizing Compound (XXXVI), a step (Step 8D) of obtaining Compound (XXXVIII) by deacylating Compound (XXXVII), a step (Step 8E) of obtaining Compound (XXXIX) by alkoxycarbonylmethylating Compound (XXXVIII), and a step (Step 8F) of producing Compound (XXXX) by deprotecting Compound (XXXIX).

Step 8A: Step 8A is carried out by adding Compound (XXXIV) to the reaction mixture of Compound (XXIV) obtained by the method described in Step 6A of the above-mentioned Preparation method 6 and reacting them.

An amount of Compound (XXXIV) is usually in the range of 1- to 3-fold mole, preferably 1- to 1.5-fold mole based on Compound (XXIII).

The reaction temperature is preferably −50 to 50° C., more preferably −20 to 30° C.

The reaction time is 1 to 24 hours, preferably 2 to 12 hours.

Step 8B: Step 8B is a step of obtaining Compound (XXXVI) by hydrolyzing an ester when Compound (XXXV) is an ester derivative [i.e., Compound (XXXV) wherein $R^{20}$ is a methyl group or an ethyl group]. Accordingly, when Compound (XXXIV) wherein $R^{20}$ is a hydrogen atom is used as a starting material in Step 8A, Compound (XXXVI) can be directly obtained as a product so that this step can be omitted.

Hydrolysis of the ester in Step 8B can be easily carried out by the conventionally known method, for example, in an alcohol solvent such as methanol, ethanol, propanol, etc. (preferably methanol), usually in the range of 1- to 3-fold mole, preferably 1- to 1.5-fold mole based on the ester derivative of Compound (XXXV) by using an alkali metal hydroxide such as lithium hydroxide, sodium hydroxide, potassium hydroxide, etc.

Step 8C: Step 8C can be carried out by reacting Compound (XXXVI) and acid anhydride in a solvent or without solvent under heating.

As the acid anhydride, acetic anhydride, propionic anhydride, butanoic anhydride, trifluoroacetic anhydride, benzoic anhydride, etc. can be used. An amount of the acid anhydride is preferably in the range of 2- to 5-fold mole based on Compound (XXXVI), but may be used in a largely excessive amount also as a solvent.

As the reaction solvent, there may be mentioned, for example, an aromatic hydrocarbon such as benzene, toluene and xylene; a nitrile such as acetonitrile; an amide such as N,N-dimethylformamide, N, N-dimethylacetamide and N-methylpyrrolidone; dimethylsulfoxide, and the like.

The reaction temperature is usually 50 to 150° C., preferably 50 to 100° C.

The reaction time is 10 minutes to 2 hours, preferably 30 minutes to 1 hour.

Step 8D: Conversion from Compound (XXXVII) to Compound (XXXVIII) can be carried out in an alcohol solvent by, using a base.

As the alcohol solvent, it is preferably methanol, ethanol and isopropanol, more preferably methanol.

As the base, there may be used, for example, an alkali metal hydroxide such as lithium hydroxide, sodium hydroxide and potassium hydroxide; an alkali metal alkoxide such as sodium methoxide, sodium ethoxide and potassium t-butoxide; and a primary or secondary amine such as ammonia, monomethylamine, dimethylamine, ethylamine, diethylamine, pyrrolidine, morpholine, preferably a primary or secondary amine.

An amount the base to be used is in the range of 1- to 20-fold mole, preferably 5- to 15-fold mole based on Compound (XXXVII).

The reaction temperature is usually 0 to 50° C., preferably 20 to 40° C.

The reaction time is usually 1 to 6 hours, preferably 1 to 2 hours.

Step 8E: Alkoxycarbonylmethylating reaction of Compound (XXVIII) can be carried out by treating Compound (XXXVIII) with a strong base in an inert gas atmosphere such as nitrogen, helium or argon, and then, reacting with an alkoxycarbonylmethylating agent.

As the reaction solvent, for example, it is preferably an ether such as dioxane, tetrahydrofuran, diethyl ether, dimethoxyethane and diethoxyethane, and as the strong base, there may be mentioned a base such as sodium hydride, potassium hydride, sodium bis(trimethylsilyl)amide, potassium bis(trimethylsilyl)amide, lithium bis(trimethylsilyl)amide, n-butyl lithium, t-butyl lithium and lithium diisopropylamide, preferably sodium hydride, potassium hydride, sodium bis(trimethylsilyl)amide and potassium bis(trimethylsilyl)amide.

An amount the base to be used is usually in the range of 1- to 3-fold mole, preferably 1- to 1.5-fold mole based on Compound (XXXVIII).

As the alkoxycarbonylmethylating agent, there may be mentioned, for example, a halogeno acetic acid ester having a $C_1$–$C_4$ alkyl group or a $C_7$–$C_{10}$ aralkyl group at the alkoxy portion such as ethyl bromoacetate, methyl bromoacetate, propyl bromoacetate, ethyl iodoacetate, methyl iodoacetate, propyl iodoacetate, isopropyl iodoacetate, butyl iodoacetate, benzyl iodoacetate and phenethyl iodoacetate.

An amount of the alkoxycarbonylmethylating agent to be used is usually in the range of 1- to 3-fold mole, preferably 1- to 1.5-fold mole based on Compound (XXXVII).

The reaction temperature is usually −70 to 10° C., preferably −60 to 0° C.

The reaction time is usually 1 to 10 hours, preferably 2 to 5 hours.

Step 8F: The step of obtaining Compound (XXXX) by deprotecting Compound (XXXIX) can be carried out in the same manner as in Step 4B in the above-mentioned Preparation method 4.

(Preparation method 9)

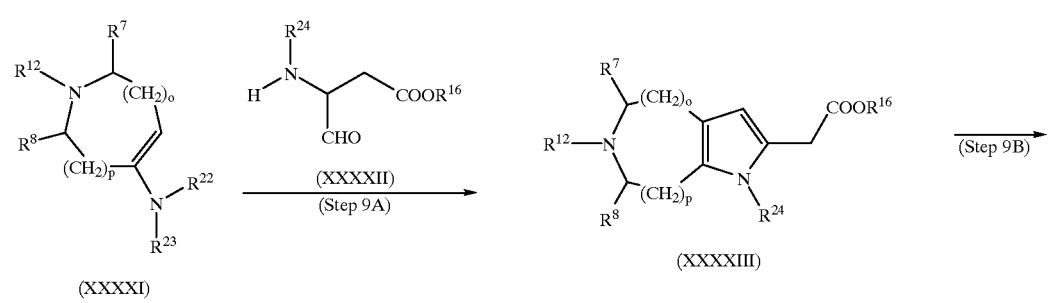

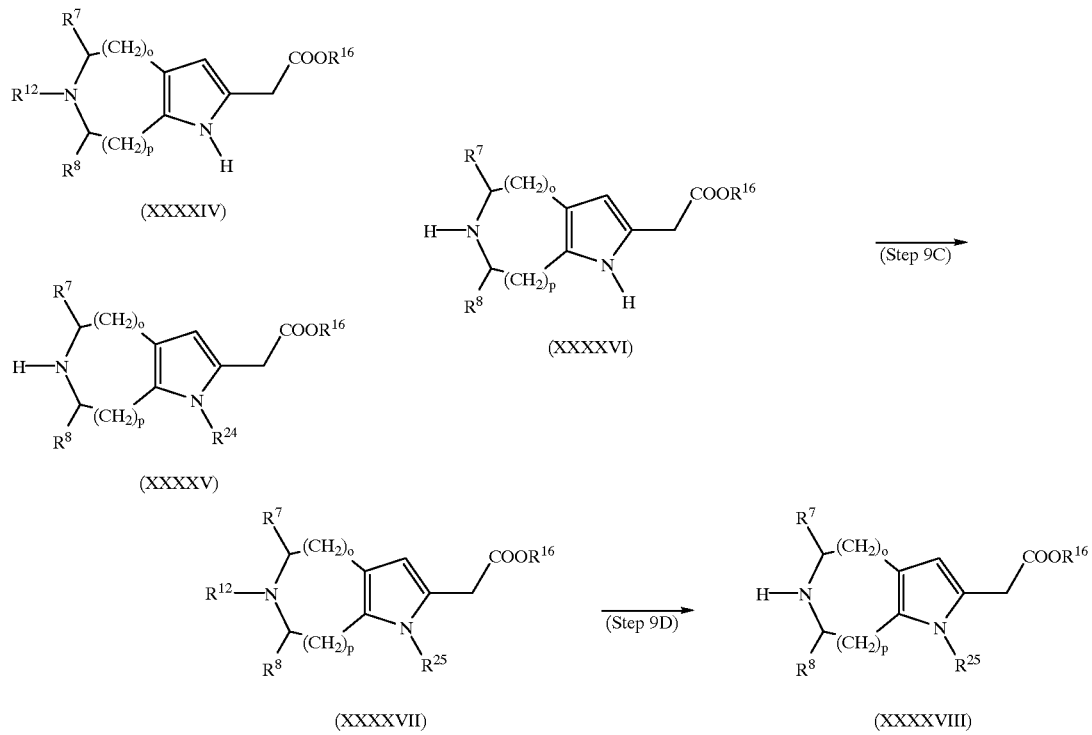

wherein $R^7$, $R^8$, $R^9$, $R^{12}$, $R^{16}$, o and p have the same meanings as defined above, a $R^{22}R^{23}N$ group represents a dimethylamino group, a diethylamino group, a pyrrolidino group, a piperazino group, or a morpholino group (preferably a morpholino group), $R^{24}$ represents a t-butoxycarbonyl group or a benzyloxycarbonyl group, and $R^{25}$ represents a $C_1$–$C_4$ alkyl group.

Preparation method 9 is a method for producing a compound in which the heteroaromatic ring in the formula (II) is a pyrrole ring wherein $A^1$=$A^2$=$A^4$=$A^5$=C and $A^3$=N, and comprises a step (Step 9A) of obtaining Compound (XXXXIII) by reacting Compound (XXXXI) and Compound (XXXXII), a step (Step 9B) of obtaining Compound (XXXXIV), Compound (XXXXV) or Compound (XXXXVI) by deprotecting Compound (XXXXIII), a step (Step 9C) of obtaining Compound (XXXXVII) by alkylating Compound (XXXXIV), and a step (Step 9D) of producing Compound (XXXXVIII) by deprotecting Compound (XXXXVII).

Step 9A: Step 9A can be carried out by reacting Compound (XXXXI) and Compound (XXXXII) in the presence of a Lewis acid in a solvent.

The reaction solvent is not particularly limited so long as it is inactive to the reaction, and may be mentioned, for example, a halogenated hydrocarbon such as methylene chloride, 1,2-dichloroethane and chloroform; an aromatic hydrocarbon such as benzene, toluene and xylene; and a mixed solvent thereof, preferably a halogenated hydrocarbon.

As the Lewis acid, there may be mentioned, for example, boron trifluoride ethyl etherate, aluminum trichloride, tin tetrachloride, zinc chloride, titanium tetrachloride, tetraethoxytitanium, tetraisopropoxytitanium and the like, preferably boron trifluoride ethyl etherate.

An amount of the Lewis acid to be used is in the range of 1- to 3-fold mole, preferably 1- to 1.5-fold mole based on Compound (XXXXI).

The reaction temperature is usually −78 to 50° C., preferably −60 to 30° C.

The reaction time is usually 1 to 6 hours, preferably 1 to 3 hours.

Step 9B: Step 9B is a step of deprotecting the protective groups $R^{12}$ and $R^{24}$ on the nitrogen atoms of Compound (XXXIII), and, if desired, the protective group $R^{24}$ or $R^{12}$ alone may be selectively deprotected to obtain Compound (XXXXIV) or Compound (XXXXV), or both of the protective groups $R^{12}$ and $R^{24}$ may be simultaneously deprotected to obtain Compound (XXXXVI). The above-mentioned respective reactions can be carried out by suitably selecting the protective groups $R^{12}$ and $R^{24}$ and the deprotection conditions. For example, when $R^{12}$ is a t-butoxycarbonyl group and $R^{24}$ is a benzyloxycarbonyl group, the method of hydrogenolysis is used as the deprotecting method, Compound (XXXXIV) in which only the benzyloxycarbonyl group, $R^{24}$ is deprotected can be obtained, while the method of using an acid (preferably trifluoroacetic acid) is used, Compound (XXXXV) in which the t-butoxycarbonyl group, $R^{12}$ is deprotected can be obtained. Also, when the protective groups $R^{12}$ and $R^{24}$ are both t-butoxycarbonyl groups or benzyloxycarbonyl groups, according to the method of using an acid (preferably trifluoroacetic acid) or hydrogenolysis, Compound (XXXXVI) in which both of the protective groups are simultaneously deprotected can be obtained. The reaction conditions, etc. can be employed by optionally selecting the conditions of the descriptions in the above-mentioned Literature I.

Step 9C: Alkylation of Compound (XXXXIV) can be carried out by treating Compound (XXXXIV) with a strong base in an innert gas atmosphere such as nitrogen, helium and argon, and then, reacting with an alkylating agent.

As the alkylating agent, a $C_1$–$C_4$ alkylsulfate or a halogenated $C_1$–$C_4$ alkyl which are the same as in the above-mentioned Step 7B can be used, and the reaction conditions such as a reaction solvent, a base, etc. can be employed as in the above-mentioned Step 8E.

Step 9D: The step of obtaining Compound (XXXXVIII) by deprotecting Compound (XXXXVII) can be carried out in the same manner as in Step 4B in the above-mentioned Preparation method 4.

In the respective steps as mentioned above, the desired compound of the respective reactions can be collected from the reaction mixture according to the conventional method. For example, when an insoluble material is present, the material is optionally filtered off, when the reaction mixture is an acidic or an alkaline, it is optionally neutralized and the solvent is removed under reduced pressure, or after removing the solvent under reduced pressure, water is added to the residue, the mixture is extracted with a water-immiscible organic solvent such as ethyl acetate and dried over anhydrous mangesium sulfate or the like, and the solvent is removed to obtain the desired compound. If necessary, the compound can be further purified by the conventional manner, for example, recrystallization, column chromatography method and the like.

Also, in Compound (II) obtained in the above-mentioned Preparation method 4 to Preparation method 9, there is a case where an optical isomer exists. In such a case, by optionally employing the conventionally known optical resolution method (for example, fractional crystallization method, optical resolution column chromatography method, diastereomer method and the like), the mixture can be divided into the respective optical isomers.

For example, when the diastereomer method is employed, Compound (II) wherein Q is a hydrogen atom and an optically active carboxylic acid derivative (for example, R- or L-α-methoxyphenyl acetic acid, etc.) are subjected to condensation reaction to obtain a diastereomer mixture of amide derivatives, and after separating the respective diastereomers by the usual separating means (for example, column chromatography method), the amide bond is hydrolyzed to obtain an optically active compound (II).

Similarly, in the case of Compound (II) wherein Z is a carboxyl group, by utilizing the carboxyl group, the compound is reacted with an optically active amine or an optically active alcohol to lead amide derivatives or ester derivatives, respectively, and after separating the respective diastereomers, the separated diastereomer is hydrolyzed to obtain an optical isomer.

Compound (I) of the present invention and a salt thereof inhibit fibrinogen-binding to an fibrinogen receptor (GPIIb/IIIa), and interfere platelet thrombosis, so that the compounds can be used for treatment or prophylaxis of peripheral aneurysm, acute cardiac infarction, deep venous thrombosis, pulmonary imperforation, dissecting aneurysm, transient ischemic attack, cerebral apoplexy and other imperforation-related disorder, unstable angina pectoris, disseminated intravascular coagulation, septicemia, surgical or infectious shock, postoperative and postpartum injury, angioplasty of various arteries, cardiopulmonary and coronary bypass surgical operations, incompatible blood transfusion, amotio placentae, thrombotic thrombocytopenic purpura, asthma, acute or chronic nephritic diseases, inflammation, arterial sclerosis, hemolytic-uremic syndrome, symmetric peripheral necrosis, bed sore, rejection of transplanted organs of mammals including human beings.

Moreover, Compound (I) of the present invention can be used for strengthening efficacy of a thrombus dissolving agent, preventing re-imperforation after PTCA, preventing thrombocytopenia by dialysis, heparin-induced thrombocytopenia, and preventing thrombosis due to artificial vessels and organs. Moreover, Compound (I) of the present invention can be used with an antiplatelet agent or anticoagulation agent such as heparin, aspirin and warfarin in combination.

When Compound (I) of the present invention is to be used as a medicine, a preparation auxiliary such as an excipient, a carrier and a diluent which have generally been used for preparation may be optionally mixed. The medicine can be administered orally or parenterally in the form of a tablet, capsule, powder, syrup, granule, pill, suspension, emulsion, powder preparation, suppository, ointment or injection according to the conventional manner. Also, an administration method, an administration dose and a number of administration can be optionally selected depending on age, body weight and symptom of the patient. Usually, for an adult person, the compound can be administered orally or parenterally 0.01–1000 mg (preferably 0.1–500 mg) per day once or divided into several times.

Also, Compound (I) did not show any toxicity by oral administration to rats with several times of the dose as mentioned above (calculated based on the body weight).
Utilizability in industry Compound (I) of the present invention has a fibrinogen receptor antagonistic activity, and not only shows oral activity but also excellent sustained action whereby it is useful as a prophylactic or therapeutic agent of thrombosis and infarction.

EXAMPLES

In the following, the present invention is described in detail by referring to Test examples and Examples, but the present invention is not limited by these.

Test Example 1

ADP (adenosine diphosphate) induced-platelet aggregation inhibiting activity
(1) Preparation Method of Platelet-rich Plasma By using 0.1 volume of 3.8% sodium citrate as an anticoagulant, citrate-added blood collected from an elbow vein of a healthy male volunteer was centrifuged at 500×g (=1600 rpm) for 3 minutes and the supernatant was fractionated as platelet-rich plasma (PRP). The under layer was further centrifuged at 1800×g (3200 rpm) for 15 minutes and the supernatant was fractionated as platelet-poor blood plasma (PPP) and used for ADP aggregation (coagulation) measurement.
(2) Measurement Method of ADP-induced Platelet Aggregation PRP obtained as mentioned above was diluted by the platelet-poor plasma (PPP) to adjust the number of platelet to 30 to 40×10$^4$/µL, and platelet aggregation induced by ADP was measured by using an aggrigometer (available from NBS Co., Hematracer Va.). First, 185 µL of PRP was placed in a glass cuvette for exclusive use, 5 µL of a test compound solution or a solvent (control) for preparing test compound was added thereto, and the mixture was pre-incubated while stirring (1000 ppm) at 37° C. for 5 minutes. Thereafter, 10 µL (final concentration 10 µM) of an ADP solution was added thereto to induce platelet aggregation. Change in transmittance caused by platelet aggregation was recorded for 3 minutes after addition of ADP.

Transmittances of PRP and PPP were made 0 and 100%, respectively, and the maximum transmittance after adding ADP was made the maximum aggregation ratio. The maximum aggregation ratio when the test compound was added divided by that ratio when the solvent for preparation was added was shown in terms of a percentage, and a 50% inhibiting concentration (IC$_{50}$) was calculated.

Incidentally, when the test compound has a protected carboxyl group, the sample was applied to the test after carrying out the following deprotection treatment. First, the test compound was dissolved in ethanol, and hydrolyzed (at room temperature for 2 hours) by adding an equal volume of a 0.1 N aqueous sodium hydroxide solution. Then, the solution was neutralized by adding a 0.1 N aqueous hydrochloric acid solution, and the resulting solution was diluted by using a preparation solvent (composition: ethanol/0.1 N aqueous sodium hydroxide solution/0.1 N aqueous hydrochloric acid solution=1/1/1) to a predetermined concentration to make a test compound solution. The results are shown in Table 13.

TABLE 13 in vitro Platelet aggregation inhibition activity

| Compound of Example I | IC$_{50}$ ($\mu$M) |
|---|---|
| 5 | 0.03 |
| 14' | 0.04 |
| 22' | 0.03 |
| 38' | 0.03 |
| 40' | 0.06 |
| 79 | 0.02 |
| 91' | 0.05 |
| 93' | 0.04 |
| 95' | 0.05 |
| 97' | 0.03 |
| 100' | 0.09 |
| 108' | 0.04 |
| 109' | 0.04 |
| 110' | 0.04 |
| 111' | 0.05 |
| 112' | 0.04 |
| 114' | 0.04 |
| 126 | 0.08 |
| 128 | 0.05 |
| 136 | 0.06 |
| 138 | 0.06 |
| 142' | 0.05 |
| RGDS | 4.0 |

(Note) The compound to which prime (') was added was converted into a carboxylic acid compound, and then, an activity thereof was measured.

Test Example 2
Ex Vivo ADP Induced-platelet Aggregation Inhibiting Activity

As a test animal, 2 to 3 monkeys (cynomolgus monkeys) born in China were used as one group.

Test compounds were suspended in a dimethylsulfoxide: 0.5% aqueous sodium carboxymethylcellulose solution (=1:99) and orally administered. To the animals for control group, a dimethylsulfoxide: 0.5% aqueous sodium carboxymethylcellulose solution (=1:99) containing no test compound was orally administered.

With regard to the respective groups, 5 ml of blood was each collected from femoral vein at the predetermined times before and after administration of the test compound by using a syringe to which 3.8% of sodium citrate was added. The resulting citrate-added blood was centrifuged at 80×g (=700 rpm) for 10 minutes, and then, the supernatant was fractionated as platelet rich plasma (PRP). The under layer was further centrifuged at 2000×g (3200 rpm) for 10 minutes and the supernatant was fractionated as platelet-poor plasma (PPP) and used for ADP aggregation (coagulation) measurement.

PRP was diluted by PPP to adjust the number of platelet to 30 to 40×10$^4$/$\mu$L, and platelet aggregation induced by ADP was measured by using a nephelometric platelet aggregation meter (available from NBS Co., Hematracer 801). First, 190 $\mu$L of PRP was placed in a glass cuvette for exclusive use and pre-incubated while stirring (1000 ppm) at 37° C. for 5 minutes. Thereafter, 10 $\mu$L (final concentration 20 $\mu$M) of an ADP solution was added thereto to induce platelet aggregation. Change in transmittance caused by platelet aggregation was recorded for 3 minutes after addition of ADP.

Transmittances of PRP and PPP were made 0 and 100%, respectively, and the maximum transmittance after adding ADP was made the maximum aggregation ratio.

The platelet aggregation inhibiting ratio was shown in terms of a percentage of the maximum aggregation ratio when the test compound was added divided by the maximum aggregation ratio when the solvent for preparation was added.

As a result, the compounds of Examples I-76, 77, 93 and 95 showed excellent platelet aggregation inhibiting activities even in oral administration, and showed excellent sustained activity.

Test Example 3
Ex Vivo ADP Induced-platelet Aggregation Inhibiting Activity

As a test animal, 2 to 3 beagle dogs were used as one group.

Test compounds were suspended in a dimethylsulfoxide: 0.5% aqueous sodium carboxymethylcellulose solution (=1:99) and orally administered. To the animals for control group, a dimethylsulfoxide: 0.5% aqueous sodium carboxymethylcellulose solution (=1:99) containing no test compound was orally administered.

With regard to the respective groups, 5 ml of blood was each collected from cervical vein at the predetermined times before and after administration of the test compound by using a syringe to which 3.8% of sodium citrate was added. The resulting citrate-added blood was centrifuged at 80×g (=700 rpm) for 10 minutes, and then, the supernatant was fractionated as platelet-rich plasma (PRP). The under layer was further centrifuged at 2000×g (3200 rpm) for 10 minutes and the supernatant was fractionated as platelet-poor plasma (PPP) and used for ADP aggregation (coagulation) measurement.

PRP was diluted by PPP to adjust the number of platelet to 30 to 40×10$^4$/$\mu$L, and platelet aggregation induced by ADP was measured by using an aggrigometer (available from NBS Co., Hematracer 801). First, 190 $\mu$L of PRP was placed in a glass cuvette for exclusive use and pre-incubated while stirring (1000 ppm) at 37° C. for 5 minutes. Thereafter, 10 $\mu$L of an ADP solution (final concentration 10 $\mu$M) and an epinephrine solution (final concentration 1 $\mu$M) was added thereto to induce platelet aggregation. Change in transmittance caused by platelet aggregation was recorded for 3 minutes after addition of ADP.

Transmittances of PRP and PPP were made 0 and 100%, respectively, and the maximum transmittance after adding ADP was made the maximum aggregation ratio.

The platelet aggregation inhibiting ratio was shown in terms of a percentage of the maximum aggregation ratio when the test compound was added divided by the maximum aggregation ratio when the solvent for preparation was added. The results are shown in Table 14.

TABLE 14 ex vivo Platelet aggregation inhibiting activity

| Compound | Administered dose | Platelet aggregation inhibiting ratio (%) | | |
| --- | --- | --- | --- | --- |
| Example I | (mg/kg p.o.) | 1 | 4 | 8 (hr) |
| 77 | 1 | 60 | 85 | 63 |
| 85 | 0.3 | 61 | 94 | 41 |
| 115 | 0.3 | 35 | 43 | 22 |

In the following examples, $^1$H-NMR was measured at 270 Hz otherwise specifically mentioned.

Also, in Examples, abbreviations of chemical names as mentioned below are used.

THF: tetrahydrofuran,
DMSO: dimethylsulfoxide,
DMF: N,N-dimethylformamide,
BOP: benzotriazol-1-yl-oxy-tris-(dimethylamino)phosphonium hexafluorophosphate,
DABCO: 1,4-diazabicyclo[2.2.2]octane,
DCC: N,N'-dicyclohexylcarbodiimide,
DCHA: dicyclohexylamine,
EDC: 1-ethyl-3-(3-dimethylaminopropyl)carbodiimide hydrochloride,
HBTU: 2-(1H-benzotriazol-1-yl)-1,1,3,3-tetramethyluronium hexafluorophosphate,
HOBt: N-hydroxybenzotriazole,
PyBOP: benzotriazol-1-yl-oxy-tris-pyrrolidinophosphonium hexafluorophosphate,
TBTU: 2-(1H-benzotriazol-1-yl)-1,1,3,3-tetrametyluronium tetrafluoroborate,
TsOH: p-toluenesulfonic acid.

Example I-1

Ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate (Ethyl ester of Exemplary compound No. 1-116)

(1-A) In 0.35 g (1.3 mmol) of ethyl 4,5,6,7-tetrahydrothieno[3,2-c]pyridin-2-acetate HCl salt were dissolved by adding 10 ml of methylene chloride and 0.14 g (1.4 mmol) of triethylamine, then, to the solution were added 0.42 g (1.4 immol) of N-t-butoxycarbonyl-L-4-nitrophenylalanine, 16 mg (0.13 mmol) of 4-dimethylaminopyridine and 0.66 g (1.5 mmol) of BOP, and the mixture was stirred at room temperature for 3 hours.

The resulting reaction mixture was concentrated under reduced pressure, a 5% aqueous potassium hydrogen sulfate solution was added to the residue and the mixture was extracted with ethyl acetate. The organic layer was successively washed with a saturated aqueous sodium bicarbonate solution and a saturated saline solution, and dried over anhydrous sodium sulfate. The organic layer was concentrated under reduced pressure, the residue was purified by the silica gel column chromatography method (eluent: chloroform/ethyl acetate=20/1) to obtain 0.54 g (1.0 mmol) of ethyl 5-(N-t-butoxycarbonyl-L-4-nitrophenylalanyl)-4,5,6,7-tetrahydrothieno[3,2-c]pyridin-2-acetate.

$^1$H-NMR (CDCl$_3$) δ; 8.14–7.94 (m, 2H), 7.40–7.29 (m, 2H), 6.61, 6.32 (each s, total 1H), 5.56–5.35 (m, 1H), 5.01–4.88 (m, 1H), 4.70–4.29 (m, 2H), 4.26–4.03 (m, 1H), 4.18 (q, J=7.3 Hz, 2H), 3.73, 3.67 (eachs, total2H), 3.63–3.24 (m, 1H), 3.23–3.00 (m, 2H), 2.89–2.48 (m, 2H), 1.43, 1.40 (each s, total 9H), 1.32–1.25 (m, 3H).

CI-MS (m/z); 518

(1-B) To 10 ml of methylene chloride solution containing 0.54 g (1.0 mmol) of ethyl 5-(N-t-butoxycarbonyl-L-4-nitrophenylalanyl)-4,5,6,7-tetrahydrothieno[3,2-c]pyridin-2-acetate was added 1.7 ml of CF$_3$CO$_2$H under ice-cooling, and the mixture was stirred at room temperature for 2 hours.

The resulting reaction mixture was concentrated under reduced pressure to obtain ethyl 5-(L-4-nitrophenylalanyl)-4,5,6,7-tetrahydrothieno[3,2-c]pyridin-2-acetate CF$_3$CO$_2$H salt and the resulting compound was used in the next reaction without purification.

To ethyl 5-(L-4-nitrophenylalanyl)-4,5,6,7-tetrahydrothieno[3,2-c]pyridin-2-acetate CF$_3$CO$_2$H salt obtained above were added 20 ml of methylene chloride and 0.18 g (1.8 mmol) of triethylamine to dissolve the salt, and then, 0.48 g (1.0 mmol) of 4-(N,N,N'-tri-t-butoxycarbonylamidino)benzoic acid, 24 mg (0.20 mmol) of 4-dimethylaminopyridine and 0.68 g (1.5 mmol) of BOP were added to the solution, and the mixture was stirred at room temperature for 4 hours.

The resulting reaction mixture was concentrated under reduced pressure, a 5% aqueous potassium hydrogen sulfate solution was added to the residue and the mixture was extracted with ethyl acetate. The organic layer was successively washed with a saturated aqueous sodium bicarbonate solution and a saturated saline solution, and dried over anhydrous sodium sulfate. The organic layer was concentrated under reduced pressure, the residue was purified by the silica gel column chromatography method (eluent: chloroform/ethyl acetate=50/1) to obtain 0.75 g (0.87 mmol) of the title compound as a white solid.

$^1$H-NMR (CDCl$_3$) δ; 8.14–7.79 (m, 6H), 7.40–7.13 (m, 2H), 6.64, 6.34 (each s, total 1H), 5.56–5.39 (m, 1H), 4.74–4.30 (m, 2H), 4.25–4.14 (m, 2H), 4.11–3.56 (m, 1H), 3.74, 3.69 (each s, total 2H), 3.45–3.14 (m, 3H), 2.92–2.49 (m, 2H), 1.55 (s, 9H), 1.36 (s, 18H), 1.33–1.27 (m, 3H).

Example I-2

Ethyl 5-[N-(4-amidinobenzoyl)-L-4-nitrophenylalanyl]-4,5,6,7-tetrahydrothieno(3,2-c]pyridin-2-acetate.trifluoroacetate (Ethyl ester of Exemplary compound No. 1-3)

In 5 ml of methylene chloride was dissolved 0.75 g (0.87 mmol) of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, andunder ice-cooling, 3 ml of CF$_3$CO$_2$H was added to the solution and the mixture was stirred at room temperature for one hour.

The resulting reaction mixture was concentrated under reduced pressure, diethyl ether was added to the residue and the formed solid was collected by filtration. The solid collected by filtration was washed with diethyl ether and dried to obtain 0.45 g (0.66 mmol) of the title compound as pale yellowish powder.

Melting point; 167–172° C.

$^1$H-NMR (400 MHz, DMSO-d$_6$) δ; 8.10–8.00 (m, 2H), 7.98–7.94 (m, 2H), 7.85–7.83 (m, 2H), 7.63–7.53 (m, 2H), 6.71, 6.58 (each s, total 1H), 5.32–5.28 (m, 1H), 4.67–4.32 (m, 2H), 4.11–4.06 (m, 2H), 3.96–3.86 (m, 1H), 3.79–3.52 (m, 3H), 3.27–3.15 (m, 2H), 2.73–2.59 (m, 2H), 1.21–1.16 (m, 3H).

FAB-MS (m/z); 564

Example I-3

Ethyl 5-[N-(4-amidinobenzoyl)-L-4-nitrophenylalanyl]-4,5,6,7-tetrahydrothieno[3,2-c]pyridin-2-acetate hydrochloride (Ethyl ester of Exemplary compound No. 1-3)

In 0.5 ml of acetic acid was dissolved 0.20 g (0.29 mmol) of 5-[N-(4-amidinobenzoyl)-L-4-nitrophenylalanyl]-4,5,6,7-tetrahydrothieno[3,2-c]pyridin-2-acetate $CF_3CO_2H$, and 1 ml of diethyl ether saturated by hydrogen chloride was added to the solution and the mixture was stirred at room temperature for 10 minutes.

The resulting reaction mixture was concentrated under reduced pressure, the residue was dissolved in 0.5 ml of ethanol, diethyl ether was added to the solution and the precipitated solid material was collected by filtration. The precipitated solid material was purified by the silica gel column chromatography method (eluent: chloroform/methanol/acetic acid=19/1/1) to obtain 0.18 g (0.29 mmol) of the title compound as white powder.

Melting point; 138–143° C.
$^1$H-NMR (400 MHz, DMSO-$d_6$) δ; 8.10–8.00 (m, 2H), 7.98–7.94 (m, 2H), 7.85–7.83 (m, 2H), 7.63–7.53 (m, 2H), 6.71, 6.58 (each s, total 1H), 5.32–5.28 (m, 1H), 4.67–4.32 (m, 2H), 4.11–4.06 (m, 2H), 3.96–3.86 (m, 1H), 3.79–3.52 (m, 3H), 3.27–3.15 (m, 2H), 2.73–2.59 (m, 2H), 1.21–1.16 (m, 3H).

FAB-MS (m/z); 564
$[α]_D^{20}$; −38° (MeOH, c=0.568)

Example I-4

5-[N-[4-(N,N,N'-tri-t-butoxycarbonylamidino)benzoyl]-L-4-nitrophenylalanyl]-4,5,6,7-tetrahydrothieno[3,2-c]pyridin-2-acetic acid (Exemplary compound No. 1-116)

40 ml of ethanol and 18 ml of water were added to 2.78 g (3.22 mmol) of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate and dissolved. Then, 0.41 g (9.8 mmol) of lithium hydroxide $H_2O$ was added to the solution and the mixture was stirred at room temperature for 45 minutes.

To the resulting reaction mixture was added a 5% aqueous potassium hydrogen sulfate solution to make a pH 2, and the mixture was concentrated under reduced pressure and extracted with ethyl acetate. The organic layer was washed with a saturated saline solution, and dried over anhydrous sodium sulfate. The organic layer was concentrated under reduced pressure, the residue was purified by the silica gel column chromatography method (eluent: chloroform/ethyl acetate/acetic acid=20/1/0.25) to obtain 2.07 g (2.48 mmol) of the title compound as white solid.

Example I-5

5-[N-(4-amidinobenzoyl)-L-4-nitrophenylalanyl]-4,5,6,7-tetrahydrothieno[3,2-c]pyridin-2-acetic acid.trifluoroacetate (Exemplary compound No. 1-3)

In the same manner as in Example I-2 except for using 0.39 g (0.47 mmol) of 5-[N-[4-(N,N,N'-tri-t-butoxycarbonylamidino)benzoyl]-L- 4-nitrophenylalanyl]-4,5,6,7-tetrahydrothieno[3,2-c]pyridin-2-acetic acid in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.14 g (0.26 mmol) of the title compound as pale yellowish powder.

Melting point; 184–188° C.
$^1$H-NMR (400 MHz, DMSO-$d_6$) δ; 8.10–7.81 (m, 6H), 7.63–7.55 (m, 2H), 6.68, 6.51 (each s, total 1H), 5.31–5.29 (m, 1H), 4.68–4.30 (m, 2H), 3.90–3.81 (m, 1H), 3.75–3.57 (m, 3H), 3.25–3.12 (m, 2H), 2.73–2.61 (m, 2H).

FAB-MS (m/z); 536
$[α]_D^{20}$; −39° (MeOH, c=0.28)

Example I-6

Isopropyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate (Isopropyl ester of Exemplary compound No. 1-116)

To 0.50 g (0.59 mmol) of 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetic acid were added 15 ml of methylene chloride, 0.15 g (0.73 mmol) of DCC, 0.11 g (1.8 mmol) of isopropyl alcohol and 0.50 g (0.59 mmol) of 4-dimethylaminopyridine, and the mixture was stirred at room temperature for 4 hours.

The resulting reaction mixture was concentrated under reduced pressure, and the residue was purified by the silica gel column chromatography method (eluent: n-hexane/ethyl acetate=2/1) to obtain 0.25 g (0.28 mmol) of the title compound as pale yellowish foamy product.

$^1$H-NMR (CDCl$_3$) δ; 8.14–7.73 (m, 4H), 7.41–7.12 (m, 4H), 6.62, 6.34 (each s, total 1H), 5.58–5.39 (m, 1H), 5.11–5.00 (m, 1H), 4.76–4.07 (m, 3H), 3.78–3.57 (m, 2H), 3.54–3.14 (m, 4H), 2.83–2.71 (m, 1H), 1.56 (s, 9H), 1.39 (s, 18H), 1.29–1.21 (m, 6H).

FAB-MS (m/z); 878

Example I-7

Isopropyl 5-[N-(4-amidinobenzoyl)-L-4-nitrophenylalanyl]-4,5,6,7-tetrahydrothieno[3,2-c]pyridin-2-acetate trifluoroacetate (Isopropyl ester of Compound No. 1-3)

In the same manner as in Example I-2 except for using 0.25 g (0.28 mmol) of isopropyl 5-[N-(4-(N,N,N'-tri-t-butoxycarbonylamidinobenzoyl)-L-4-nitrophenylalanyl)-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 90 mg (0.16 mmol) of the title compound as pale yellowish powder.

Melting point; 164–168° C.
$^1$H-NMR (400 MHz, DMSO-$d_6$) δ; 8.10–7.95 (m, 4H), 7.85–7.83 (m, 2H), 7.63–7.55 (m, 2H), 6.71, 6.58 (each s, total 1H), 5.30–5.28 (m, 1H), 4.91–4.85 (m, 1H), 4.66–4.32 (m, 2H), 3.92–3.87 (m, 1H), 3.78–3.69 (m, 2H), 3.59–3.51 (m, 1H), 3.30–3.14 (m, 2H), 2.74–2.59 (m, 2H), 1.20–1.18 (m, 6H).

FAB-MS (m/z); 578

Example I-8

Ethyl 5-[N-[4-(N-ethoxycarbonylamidino)benzoyl]-L-4-nitrophenylalanyl]-4,5,6,7-tetrahydrothieno[3,2-c]pyridin-2-acetate (Ethyl ester of Exemplary compound No. 1-67)

In 3 ml of acetonitrile was dissolved 0.10 g (0.15 mmol) of ethyl 5-[N-(4-amidinobenzoyl)-L-4-nitrophenylalanyl]-4,5,6,7-tetrahydrothieno[3,2-c]pyridin-2-acetate.$CF_3CO_2H$, then, 0.020 g (0.20 mmol) of DABCO, 0.024 g (0.20 mmol) of 4-dimethylaminopyridine and 0.060 g (0.30 mmol) of diethyl dicarbonate were added to the solution and the mixture was stirred at room temperature for one hour.

The resulting reaction mixture was concentrated under reduced pressure, a 5% aqueous potassium hydrogen sulfate solution was added to the residue, and the mixture was extracted with ethyl acetate. The organic layer was washed successively with a saturated sodium bicarbonate solution and a saturated saline solution, and dried over anhydrous sodium sulfate. The organic layer was concentrated under reduced pressure, the residue was purified by the silica gel column chromatography method (eluent: chloroform/methanol=100/1 to 50/1) to obtain 0.10 g (0.14 mmol) of the title compound as white powder.

Melting point; 98–101° C.
$^1$H-NMR (400 MHz, CDCl$_3$) δ; 8.11–7.72 (m, 6H), 7.44–7.30 (m, 2H), 6.99–6.34 (m, 1H), 5.45–5.34 (m, 1H), 4.92–4.43 (m, 2H), 4.40–4.30 (m, 2H), 4.21–4.12 (m, 2H), 3.95–3.63 (m, 2H), 3.87–3.68 (m, 2H), 3.40–3.17 (m, 2H), 3.08–2.56 (m, 2H), 1.63 (brs, 2H), 1.40–1.34 (m, 3H), 1.30–1.21 (m, 3H).

FAB-MS (m/z); 636

$[\alpha]_D^{20}$; −47° (MeOH, c=0.180)

Example I-9

Ethyl 5-[N-[4-(N'-t-butoxycarbonyl-N-benzylamidino)benzoyl]-L-4-nitrophenylalanyl]-4,5,6,7-tetrahydrothieno[3,2-c]pyridin-2-acetate (Ethyl ester of Exemplary compound No. 1-152)

In the same manner as in Example I-1 except for using 0.47 g (1.33 mmol) of 4-(N'-t-butoxycarbonyl-N-benzylamidino)benzoic acid in place of 4-(N,N,N'-tri-t-butoxycarbonylamidino)benzoic acid, and using 1.0 g (2.0 mmol) of PyBOP in place of BOP, the reaction was carried out to obtain 0.19 g (0.24 mmol) of the title compound as brownish foamy product.

$^1$H-NMR (CDCl$_3$) δ; 8.14–7.15 (m, 13H), 6.63, 6.34 (each s, total 1H), 5.53–5.39 (m, 1H), 4.73–4.09 (m, 6H), 3.79–3.60 (m, 3H), 3.46–3.13 (m, 3H), 2.92–2.53 (m, 2H), 1.60–1.39 (m, 9H), 1.34–1.25 (m, 3H).

Example I-10

Ethyl 5-[N-[4-(N-benzylamidino)benzoyl]-L-4-nitrophenylalanyl]-4,5,6,7-tetrahydrothieno[3,2-c]pyridin-2-acetate.trifluoroacetate (Ethyl ester of Exemplary compound No. 1-153)

In the same manner as in Example I-2 except for using 0.18 g (0.24 mmol) of ethyl 5-[N-[4-(N'-t-butoxycarbonyl-N-benzylamidino)benzoyl]-L-4-nitrophenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.06 g (0.08 mmol) of the title compound as pale yellowish powder.

Melting point; 99–102° C.

$^1$H-NMR (400 MHz, DMSO-d$_6$) δ; 9.62–9.12 (m, 3H), 8.11–7.33 (m, 13H), 6.71, 6.59 (each s, total 1H), 5.35–5.26 (m, 1H), 4.69–4.31 (m, 4H), 4.11–4.04 (m, 2H), 3.98–3.52 (m, 4H), 3.22–3.12 (m, 2H), 2.74–2.57 (m, 2H), 1.22–1.15 (m, 3H).

FAB-MS (m/z); 654

Example I-11

Ethyl 5-[N-[4-(N'-t-butoxycarbonyl-N-methylamidino)benzoyl]-L-4-nitrophenylalanyl]-4,5,6,7-tetrahydrothieno[3,2-c]pyridin-2-acetate (Ethyl ester of Exemplary compound No. 1-154)

In the same manner as in Example I-1 except for using 0.17 g (0.61 mmol) of 4-(N'-t-butoxycarbonyl-N-methylamidino)benzoic acid in place of 4-(N,N,N'-tri-t-butoxycarbonylamidino)benzoic acid, and using 0.48 g (0.92 mmol) of PyBOP in place of BOP, the reaction was carried out to obtain 0.25 g (0.37 mmol) of the title compound as pale yellowish foamy product.

$^1$H-NMR (CDCl$_3$) δ; 8.14–7.28 (m, 8H), 6.64, 6.37 (each s, total 1H), 5.52–5.31 (m, 1H), 4.79–4.11 (m, 5H), 3.84–3.60 (m, 3H), 3.49–2.58 (m, 7H), 1.66–1.35 (m, 9H), 1.30–1.24 (m, 3H).

Example I-12

Ethyl 5-[N-[4-(N-methylamidino)benzoyl]-L-4-nitrophenylalanyl]-4,5,6,7-tetrahydrothieno[3,2-c]pyridin-2-acetate.trifluoroacetate (Ethyl ester of Exemplary compound No. 1-32)

In the same manner as in Example I-2 except for using 0.25 g (0.37 mmol) of ethyl 5-[N-[4-(N'-t-butoxycarbonyl-N-methylamidino)benzoyl]-L-4-nitrophenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin- 2-acetate, the reaction was carried out to obtain 0.03 g (0.04 mmol) of the title compound as pale yellowish powder.

Melting point; 112–114° C.

$^1$H-NMR (400 MHz, DMSO-d$_6$) δ; 9.86–8.95 (m, 3H), 8.12–7.45 (m, 8H), 6.71,6.59 (each s, total 1H), 5.37–5.26 (m, 1H), 4.69–4.32 (m, 2H), 4.14–4.05 (m, 2H), 3.99–3.69 (m, 3H), 3.61–3.14 (m, 4H), 3.04–2.98 (m, 2H), 2.80–2.59 (m, 2H), 1.23–1.18 (m, 3H).

FAB-MS (m/z); 578

Example I-13

Ethyl 5-[N-(4-N,N,N'-tri-t-butoxycarbonylamidinobenzoyl)-L-4-nitrophenylalanyl]-3-methyl-4,5,6,7-tetrahydrothieno[3,2-c]pyridin-2-acetate (Ethyl ester of Exemplary compound No. 1-121)

(13-A) In the same manner as in Example I-(1-A) except for using 0.66 g (2.7 mmol) of ethyl 3-methyl-4,5,6,7-tetrahydrothieno[3,2-c]pyridin-2-acetate.HCl salt in place of ethyl 4,5,6,7-tetrahydrothieno[3,2-c]pyridin-2-acetate.HCl salt, and purification was carried out by changing the eluent composition in the silica gel column chromatography method to (n-hexane/ethyl acetate/acetonitrile=7/2/1), the reaction was carried out to obtain 1.04 g (1.96 mmol) of ethyl 5-(N-t-butoxycarbonyl-L-4-nitrophenylalanyl)-3-methyl-4,5,6,7-tetrahydrothieno[3,2-c]pyridin-2-acetate as pale yellowish foamy product.

$^1$H-NMR (CDCl$_3$) δ; 8.12, 7.92 (each d, J=8.1 Hz, total 2H), 7.35,7.28 (each d, J=8.1 Hz, total 2H), 5.54,5.36 (each d, J=8.8 Hz, total 2H), 5.00–4.90 (m, 1H), 4.62–3.49 (m, 8H), 3.28–2.45 (m, 4H), 2.03, 1.80 (each s, total 3H), 1.44, 1.40 (each s, total 9H), 1.27 (t, J=7 Hz, 3H).

CI-MS (m/z); 432

(13-B) In the same manner as in Example I-(1-B) except for using 0.54 g (1.0 mmol) of ethyl 5-(N-t-butoxycarbonyl-L-4-nitrophenylalanyl)-3-methyl-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate and using 0.79 g (1.5 mmol) of PYBOP in place of BOP, and purification was carried out by changing the eluent composition in the silica gel column chromatography method to (chloroform/ethyl acetate=20/1), the reaction was carried out to obtain 0.83 g (0.95 mmol) of the title compound as pale yellowish foamy product.

$^1$H-NMR (CDCl$_3$) δ; 8.19–7.79 (m, 6H), 7.42–7.12 (m, 2H), 5.58–5.41 (m, 1H), 4.67–4.10 (m, 2H), 4.19–4.14 (m, 2H), 4.08–3.49 (m, 4H), 3.39–3.11 (m, 2H), 2.86–2.51 (m, 2H), 2.06, 1.84 (each s, total 3H), 1.60–1.55 (m, 9H), 1.41–1.36 (m, 18H), 1.32–1.28 (m, 3H).

FAB-MS (m/z); 878

Example I-14

Ethyl 5-[N-(4-amidinobenzoyl)-L-4-nitrophenylalanyl]-3-methyl-4,5,6,7-tetrahydrothieno[3,2-c]pyridin-2-acetate.trifluoroacetate (Ethyl ester of Exemplary compound No. 1-18)

In the same manner as in Example I-2 except for using 0.83 g (0.95 mmol) of ethyl 5-[N-(4-N,N,N'-tri-t-butoxycarbonylamidinobenzoyl)-L-4-nitrophenylalanyl]-3-methyl-4,5,6,7-tetrahydrothieno[3,2-c]pyridin-2-acetate in place of ethyl 5-[N-[4-(N,N,N'-tri-t- butoxycarbonylamidino)benzoyl]-L-4-nitrophenylalanyl]-4,5,6,7-tetrahydrothieno[3,2-c]pyridin-2-acetate, the reaction was carried out to obtain 0.54 g (0.93 mmol) of the title compound as pale yellowish powder.

Melting point; 123–126° C.

$^1$H-NMR (400 MHz, DMSO-d$_6$) δ; 8.11–7.95 (m, 4H), 7.86–7.83 (m, 2H), 7.64–7.51 (m, 2H), 5.40–5.28 (m, 1H), 4.61–4.20 (m, 2H), 4.06 (q, J=6.8 Hz, 2H), 3.96–3.38 (m, 4H), 3.25–3.15 (m, 2H), 2.73–2.54 (m, 2H), 1.96, 1.87 (each s, total 3H), 1.20–1.15 (m, 3H).

FAB-MS (m/z); 578

Example I-15

Ethyl 5-[N-(4-N,N,N'-tri-t-butoxycarbonylamidinobenzoyl)-L-4-nitrophenylalanyl]-3-propyl-4,5,6,7-tetrahydrothieno[3,2-c]pyridin-2-acetate (Ethyl ester of Exemplary compound No. 1-159)

(15-A) In the same manner as in Example I-(1-A) except for using 0.28 g (0.92 mmol) of ethyl 3-propyl-4,5,6,7-tetrahydrothieno[3,2-c]pyridin-2-acetate.HCl salt in place of ethyl 4,5,6,7-tetrahydrothieno[3,2-c]pyridin-2-acetate.HCl salt, the reaction was carried out to obtain 0.24 g (0.42 mmol) of ethyl 5-(N-t-butoxycarbonyl-L-4-nitrophenylalanyl)-3-propyl-4,5,6,7-tetrahydrothieno[3,2-c]pyridin-2-acetate as pale yellowish foamy product.

CI-MS (m/z); 504

(15-B) In the same manner as in Example I-(1-B) except for using 0.24 g (0.42 mmol) of ethyl 5-(N-t-butoxycarbonyl-L-4-nitrophenylalanyl)-3-propyl-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate and using 0.33 g (0.63 mmol) of PyBOP in place of BOP, the reaction was carried out to obtain 0.83 g (0.95 mmol) of the title compound as white foamy product.

$^1$H-NMR (CDCl$_3$) δ; 8.14–8.11 (m, 1H), 7.97–7.83 (m, 3H), 7.39–7.19 (m, 4H), 5.54–5.38 (m, 1H), 4.70–3.91 (m, 4H), 3.88–3.45 (m, 4H), 3.42–3.10 (m, 2H), 2.91–2.03 (m, 5H), 1.55, 1.54 (each s, total 9H), 1.38, 1.36 (each s, total 18H), 1.30–1.24 (m, 3H), 0.98–0.90 (m, 3H).

FAB-MS (m/z); 806

Example I-16

Ethyl 5-[N-(4-amidinobenzoyl)-L-4-nitrophenylalanyl]-3-propyl-4,5,6,7-tetrahydrothieno[3,2-c]pyridin-2-acetate.trifluoroacetate (Ethyl ester of Exemplary compound No. 1-20)

In the same manner as in Example I-2 except for using 0.33 g (0.36 mmol) of ethyl 5-[N-(4-N,N,N'-tri-t-butoxycarbonylamidinobenzoyl)-L-4-nitrophenylalanyl]-3-propyl-4,5,6,7-tetrahydrothieno[3,2-cipyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.20 g (0.27 mmol) of the title compound as white powder.

$^1$H-NMR (400 MHz, CD$_3$OD) δ; 8.09–8.07 (m, 1H), 8.01–7.94 (m, 3H), 7.88–7.85 (m, 2H), 7.54–7.45 (m, 2H), 5.47–5.43 (m, 1H), 4.70–4.10 (m, 5H), 3.90–3.81 (m, 1H), 3.70–3.51 (m, 2H), 3.51–3.22 (m, 4H), 2.80–2.22 (m, 2H), 1.53–1.38 (m, 2H), 1.28–1.22 (m, 3H), 0.97–0.89 (m, 3H).

FAB-MS (m/z); 606

Example I-17

Ethyl 5-[N-(4-N,N,N'-tri-t-butoxycarbonylamidinobenzoyl)-L-4-nitrophenylalanyl]-3-trifluoromethyl-4,5,6,7-tetrahydrothieno[3,2-c]pyridin-2-acetate (Ethyl ester of Exemplary compound No. 1-155)

(17-A) In the same manner as in Example I-(1-A) except for using 0.20 g (0.61 mol) of ethyl 3-trifluoromethyl-4,5,6,7-tetrahydrothieno[3,2-c]pyridin-2-acetate.HCl salt in place of ethyl 4,5,6,7-tetrahydrothieno[3,2-c]pyridin-2-acetate.HCl salt, the reaction was carried out to obtain 0.24 g (0.42 mmol) of ethyl 5-(N-t-butoxycarbonyl-L-4-nitrophenylalanyl)-3-trifluoromethyl-4,5,6,7-tetrahydrothieno[3,2-c]pyridin-2-acetate as pale yellowish foamy product.

CI-MS (m/z); 530

(17-B) In the same manner as in Example I-(1-B) except for using 0.050 g (0.085 mmol) of ethyl 5-(N-t-butoxycarbonyl-L-4-nitrophenylalanyl)-3-trifluoromethyl-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate and using 0.66 g (0.13 mmol) of PyBOP in place of BOP, the reaction was carried out to obtain 0.020 g (0.021 mmol) of the title compound as pale yellowish foamy product.

Example I-18

Ethyl 5-[N-(4-amidinobenzoyl)-L-4-nitrophenylalanyl]-3-trifluoromethyl-4,5,6,7-tetrahydrothieno[3,2-c]pyridin-2-acetate.trifluoroacetate (Ethyl ester of Exemplary compound No. 1-21)

In the same manner as in Example I-2 except for using 0.020 g (0.021 mmol) of ethyl 5-[N-(4-N,N,N'-tri-t-butoxycarbonylamidinobenzoyl)-L-4-nitrophenylalanyl]-3-trifluoromethyl- 4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.014 g (0.022 mmol) of the title compound as pale yellowish powder.

FAB-MS (m/z); 632

Example I-19

Ethyl 5-[N-[4-(N,N,N'-tri-t-butoxycarbonylamidino)benzoyl]-L-4-nitrophenylalanyl]-4,6-ethano-4,5,6,7-tetrahydrothieno[3,2-c]pyridin-2-acetate (Ethyl ester of Exemplary compound No. 1-123)

(19-A) In the same manner as in Example I-(1-A) except for using 1.76 g (5.00 mmol) of ethyl 4,6-ethano-4,5,6,7-tetrahydrothieno[3,2-c]pyridin-2-acetate.HCl salt in place of ethyl 4,5,6,7-tetrahydrothieno[3,2-c]pyridin-2-acetate.HCl salt, and purification was carried out by changing the eluent composition in the silica gel column chromatography method to (n-hexane/ethyl acetate/acetonitrile=7/2/1), the reaction was carried out to obtain 2.54 g (4.68 mmol) of ethyl 5-(N-t-butoxycarbonyl-L-4-nitrophenylalanyl)-4,6-ethano-4,5,6,7-tetrahydrothieno[3,2-c]pyridin-2-acetate as pale brownish foamy product.

$^1$H-NMR (CDCl$_3$) δ; 8.17–7.05 (m, 4H), 6.61,6.55, 6.45 (each s, total 1H), 5.42–4.63 (m, 4H), 4.27–4.12 (m, 2H), 3.73, 3.70 (each s, total 2H), 3.42–2.40 (m, 2H), 2.28–1.82 (m, 3H), 1.74–1.61 (m, 2H), 1.45–1.25 (m, 12H).

CI-MS (m/z); 544

(19-B) In the same manner as in Example I-(1-B) except for using 1.09 g (2.00 mmol) of ethyl 5-(N-t-butoxycarbonyl-L-4-nitrophenylalanyl)-4,6-ethano-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate and using 1.56 g (3.00 mmol) of PyBOP in place of BOP, the reaction was carried out to obtain 1.12 g (1.26 mmol) of the title compound as white foamy product.

$^1$H-NMR (CDCl$_3$) δ; 8.25–7.01 (m, 8H), 6.69–6.51 (m, 1H), 5.50–4.71 (m, 3H), 4.29–4.08 (m, 2H), 3.79–3.60 (m,

2H), 3.47–2.96 (m, 3H), 2.65–2.44 (m, 1H), 2.33–1.84 (m, 4H), 1.58–1.35 (m, 27H), 1.34–1.26 (m, 3H).

FAB-MS (m/z); 890

Example I-20

Ethyl 5-[N-(4-amidinobenzoyl)-L-4-nitrophenylalanyl]-4,6-ethano-4,5,6,7-tetrahydrothieno[3,2-c]pyridin-2-acetate.trifluoroacetate (Ethyl ester of Exemplary compound No. 1-22)

In the same manner as in Example I-2 except for using 1.12 g (1.26 mmol) of ethyl 5-[N-[4-(N,N,N'-tri-t-butoxycarbonylamidino)benzoyl]-L-4-nitrophenylalanyl]-4,6-ethano-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.72 g (1.22 mmol) of the title compound as white powder.

Melting point; 128–131° C.

$^1$H-NMR (400 MHz, DMSO-$d_6$) δ; 9.42–8.82 (m, 4H), 8.15–7.37 (m, 8H), 7.22–6.29 (m, 1H), 5.39–4.61 (m, 3H), 4.14–3.98 (m, 2H), 3.86–3.69 (m, 2H), 3.25–2.56 (m, 4H), 2.17–1.48 (m, 4H), 1.23–1.13 (m, 3H).

FAB-MS (m/z); 590

Example I-21

Ethyl 5-[N-[4-(N,N,N'-tri-t-butoxycarbonylamidino)benzoyl]-L-4-nitrophenylalanyl]-(+)-4,6-ethano-4,5,6,7-tetrahydrothieno[3,2-c]pyridin-2-acetate (Ethyl ester of Exemplary compound No. 1-123)

(21-A) In the same manner as in Example I-(1-A) except for using 0.45 g (1.6 mmol) of ethyl (+)-4,6-ethano-4,5,6,7-tetrahydrothieno[3,2-c]pyridin-2-acetate.HCl salt in place of ethyl 4,5,6,7-tetrahydrothieno[3,2-c]pyridin-2-acetate.HCl salt and using 1.25 g (2.40 mmol) of PyBOP in place of BOP, and purification was carried out by changing the eluent composition in the silica gel column chromatography method to (chloroform/ethyl acetate=20/1), the reaction was carried out to obtain 0.77 g (1.4 mmol) of ethyl 5-(N-t-butoxycarbonyl-L-4-nitrophenylalanyl)-(+)-4,6-ethano-4,5,6,7-tetrahydrothieno[3,2-c]pyridin-2-acetate as white foamy product.

$^1$H-NMR (CDCl$_3$) δ; 8.17, 7.89 (each d, J=8.8 Hz, total 2H), 7.42, 7.06 (each d, J=8.8 Hz, total 2H), 6.61, 6.45 (each s, total 1H), 5.47–4.70 (m, 4H), 4.24–4.14 (m, 2H), 3.70 (s, 2H), 3.29–2.44 (m, 4H), 2.21–1.35 (m, 13H), 1.27 (t, J=7.3 Hz, 3H).

CI-MS (m/z); 544

(21-B) In the same manner as in Example I-(1-B) except for using 0.77 g (1.4 mmol) of ethyl 5-(N-t-butoxycarbonyl-L-4-nitrophenylalanyl)-(+)-4,6-ethano-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate and using 1.09 g (2.10 mmol) of PyBOP in place of BOP, the reaction was carried out to obtain 0.91 g (1.0 mmol) of the title compound as pale yellowish foamy product.

$^1$H-NMR (CDCl$_3$) δ; 8.24–7.03 (m, 8H), 6.62, 6.52 (each s, total 1H), 5.38–4.09 (m, 5H), 3.72, 3.68 (each s, total 2H), 3.34–2.99 (m, 3H), 2.66–2.51 (m, 1H), 2.21–1.59 (m, 4H), 1.65–1.34 (m, 27H), 1.31–1.22 (m, 3H).

FAB-MS (m/z); 890

Example I-22

Ethyl 5-[N-(4-amidinobenzoyl)-L-4-nitrophenylalanyl]-(+)-4,6-ethano-4,5,6,7-tetrahydrothieno[3,2-c]pyridin-2-acetate.trifluoroacetate (Ethyl ester of Exemplary compound No. 1-22)

In the same manner as in Example I-2 except for using 0.91 g (1.0 mmol) of ethyl 5-[N-[4-(N,N,N'-tri-t-butoxycarbonylamidino)benzoyl]-L-4-nitrophenylalanyl3-(+)-4,6-ethano-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.61 g (0.87 mmol) of the title compound as pale yellowish powder.

Melting point; 132–135° C.

$^1$H-NMR (400 MHz, DMSO-$d_6$) δ; 9.41–9.10 (m, 4H), 8.19–7.39 (m, 8H), 6.71, 6.67 (each s, total 1H), 5.39–4.62 (m, 3H), 4.14–4.03 (m, 2H), 3.85–3.70 (m, 2H), 3.36–2.59 (m, 4H), 2.10–1.46 (m, 4H), 1.21–1.14 (m, 3H).

FAB-MS (m/z); 589

Example I-23

Ethyl 5-[N-[4-(N,N,N'-tri-t-butoxycarbonylamidino)benzoyl)-L-4-nitrophenylalanyl]-(−)-4,6-ethano-4,5,6,7-tetrahydrothieno[3,2-c]pyridin-2-acetate (Ethyl ester of Exemplary compound No. 1-123)

(23-A) In the same manner as in Example I-(1-A) except for using 0.20 g (0.70 mmol) of ethyl (−)-4,6-ethano-4,5,6,7-tetrahydrothieno[3,2-c]pyridin-2-acetate.HCl salt in place of ethyl 4,5,6,7-tetrahydrothieno[3,2-c]pyridin-2-acetate.HCl salt and using 0.55 g (1.0 mmol) of PyBOP in place of BOP, and purification was carried out by changing the eluent composition in the silica gel column chromatography method to (chloroform/ethyl acetate=20/1), the reaction was carried out to obtain 0.34 g (0.63 mmol) of ethyl 5-(N-t-butoxycarbonyl-L-4-nitrophenylalanyl)-(−)-4,6-ethano-4,5,6,7-tetrahydrothieno[3,2-c]pyridin-2-acetate as white foamy product.

$^1$H-NMR (CDCl$_3$) δ; 8.16, 7.90 (each d, J=8.8 Hz, total 2H), 7.37, 7.23 (each d, J=8.8 Hz, total 2H), 6.62, 6.55 (each s, total 1H), 5.44–4.59 (m, 4H), 4.26–4.13 (m, 2H), 3.74, 3.69 (each s, total 2H), 3.45–2.92 (m, 3H), 2.60–1.65 (m, 5H), 1.61–1.34 (m, 9H), 1.32–1.26 (m, 3H).

EI-MS (m/z); 443

(23-B) In the same manner as in Example I-(1-B) except for using 0.34 g (0.63 mmol) of ethyl 5-(N-t-butoxycarbonyl-L-4-nitrophenylalanyl)-(−)-4,6-ethano-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate and using 0.49 g (0.94 mmol) of PyBOP in place of BOP, the reaction was carried out to obtain 0.49 g (0.55 mmol) of the title compound as white foamy product.

$^1$H-NMR (CDCl$_3$) δ; 8.20–6.99 (m, 8H), 6.65, 6.54 (each s, total 1H), 5.49–4.69 (m, 3H), 4.30–4.11 (m, 2H), 3.75, 3.61 (each s, total 2H), 3.46–3.05 (m, 3H), 2.62–1.66 (m, 5H), 1.59–1.32 (m, 27H), 1.31–1.22 (m, 3H).

FAB-MS (m/z); 890

Example I-24

Ethyl 5-[N-(4-amidinobenzoyl)-L-4-nitrophenylalanyl]-(−)-4,6-ethano-4,5,6,7-tetrahydrothieno[3,2-c]pyridin-2-acetate.trifluoroacetate (Ethyl ester of Exemplary compound No. 1-22)

In the same manner as in Example I-2 except for using 0.49 g (0.55 mmol) of ethyl 5-[N-[4-(N,N,N'-tri-t-butoxycarbonylamidino)benzoyl)-L-4-nitrophenylalanyl]-(−)-4,6-ethano-4,5,6,7-tetrahydrothieno[3,2-c]pyridin-2-acetate in place of ethyl 5-[N-[4-(N,N,N'-tri-t-butoxycarbonylamidino)-benzoyl]-L-4-nitrophenylalanyl]-4,5,6,7-tetrahydrothieno[3,2-c]pyridin-2-acetate, the reaction was carried out to obtain 0.31 g (0.53 mmol) of the title compound as white powder.

Melting point; 130–132° C.

$^1$H-NMR (400 MHz, DMSO-$d_6$) δ; 9.41–8.85 (m, 4H), 8.09–7.48 (m, 8H), 6.72, 6.23 (each s, total 1H), 5.32–4.79 (m, 3H), 4.15–3.98 (m, 2H), 3.73, 3.41 (each s, total 2H), 3.24–2.57 (m, 4H), 2.19–1.59 (m, 4H), 1.25–1.11 (m, 3H).

FAB-MS (m/z); 589

Example I-25

Methyl 5-[N-[4-(N,N,N'-tri-t-butoxycarbonylamidino) benzoyl]-L-O-benzyltyrosyl]-4,5,6,7-tetrahydrothieno[3,2-c]pyridin-2-acetate (Methyl ester of Exemplary compound No. 1-156)

(25-A) In the same manner as in Example I-(1-A) except for using 0.74 g (2.0 mmol) of N-t-butoxycarbonyl-L-O-benzyltyrosine in place of N-t-butoxycarbonyl-L-4-nitrophenylalanine and using 0.52 g (2.00 mmol) of methyl 4,5,6,7-tetrahydrothieno[3,2-c]pyridin-2-acetate.HCl salt in place of ethyl 4,5,6,7-tetrahydrothieno[3,2-c]pyridin-2-acetate.HCl salt, and purification was carried out by changing the eluent composition in the silica gel column chromatography method to (chloroform/ethyl acetate=50/1), the reaction was carried out to obtain 1.12 g (1.98 mmol) of methyl 5-(N-t-butoxycarbonyl-L-O-benzyltyrosyl)-4,5,6,7-tetrahydrothieno[3,2-c]pyridin-2-acetate as white foamy product.

$^1$H-NMR (CDCl$_3$) δ; 7.45–7.29 (m, 5H), 7.11–7.02 (m, 2H), 6.86–6.75 (m, 2H), 6.60, 6.39 (each s, total 1H), 5.51–5.39 (m, 1H), 5.01, 4.95 (each s, total 2H), 4.90–4.79 (m, 1H), 4.69–4.26 (m, 2H), 3.88–3.80 (m, 1H), 3.76, 3.74 (each s, total 2H), 3.72, 3.69 (each s, total 3H), 3.60–3.15 (m, 2H), 3.00–2.81 (m, 2H), 2.76–2.16 (m, 2H), 1.42 (s, 9H).

CI-MS (m/z); 509

(25-B) In the same manner as in Example I-(1-B) except for using 1.12 g (1.99 mmol) of methyl 5-(N-t-butoxycarbonyl-L-O-benzyltyrosyl)-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate, the reaction was carried out to obtain 1.21 g (1.49 mmol) of the title compound as white foamy product.

$^1$H-NMR (CDCl$_3$) δ; 7.90–7.82 (m, 2H), 7.42–7.15 (m, 5H), 7.12–7.07 (m, 2H), 6.87–6.78 (m, 2H), 6.61, 6.44 (each s, total 1H), 5.39–5.32 (m, 1H), 5.03, 4.97 (each s, total 2H), 4.70–4.33 (m, 2H), 3.90–3.80 (m, 1H), 3.73, 3.68 (each s, total 2H), 3.72, 3.70 (each s, total 3H), 3.26–3.01 (m, 2H), 2.78–2.28 (m, 2H), 1.59–1.36 (m, 27H).

FAB-MS (m/z); 712

Example I-26

5-[N-[4-(N,N,N'-tri-t-butoxycarbonylamidino)benzoyl]-L-O-benzyltyrosyl]-4,5,6,7-tetrahydrothieno[3,2-c]pyridin-2-acetic acid (Exemplary compound No. 1-156)

In the same manner as in Example I-4 except for using 0.75 g (0.90 mmol) of methyl 5-[N-[4-(N,N,N'-tri-t-butoxycarbonylamidino)benzoyl]-L-O-benzyltyrosyl]-4,5,6,7-tetrahydrothieno[3,2-c]pyridin-2-acetate in place of ethyl 5-[N-[4-(N,N,N'-tri-t-butoxycarbonylamidino) benzoyl]-L- 4-nitrophenylalanyl]-4,5,6,7-tetrahydrothieno [3,2-c]pyridin-2-acetate, and purification was carried out by changing the eluent composition in the silica gel column chromatography method to (chloroform/methanol=20/1), the reaction was carried out to obtain 0.58 g (0.72 mmol) of the title compound as colorless foamy powder.

FAB-MS (m/z); 698

Example I-27

5-[N-(4-amidinobenzoyl)-L-tyrosyl]-4,5,6,7-tetrahydrothieno[3,2-c]pyridin-2-acetic acid.trifluoroacetate (Ethyl ester of Exemplary compound No. 1-2)

To 0.58 g (0.73 mmol) of 5-[N-[4-(N,N,N'-tri-t-butoxycarbonylamidino)benzoyl]-L-O-benzyltyrosyl]-4,5,6,7-tetrahydrothieno[3,2-c]pyridin-2-acetic acid were added 3 ml of thioanisole and 10 ml of CF$_3$CO$_2$H and the mixture was stirred at room temperature for 4 hours.

To the resulting reaction mixture was added 80 ml of diethyl ether and the precipitated solid was collected by filtration. The solid was washed with ether, dried to obtain 0.32 g (0.50 mmol) of the title compound as white powder.

Melting point; 179–181° C.

FAB-MS (m/z); 507

$[\alpha]_D^{20}$; +10° (MeOH, c=0.110)

Example I-28

Ethyl 5-[N-[4-(N,N,N'-tri-t-butoxycarbonylamidino) benzoyl]-L-O-benzyltyrosyl]-4,5,6,7-tetrahydrothieno[3,2-c]pyridin-2-acetate (Ethyl ester of Exemplary compound No. 1-156)

(28-A) In the same manner as in Example I-(1-A) except for using 0.40 g (0.92 mmol) of N-t-butoxycarbonyl-L-O-benzyltyrosine in place of N-t-butoxycarbonyl-L-4-nitrophenylalanine, and purification was carried out by changing the eluent composition in the silica gel column chromatography method to (chloroform/ethyl acetate=40/1–15/1), the reaction was carried out to obtain 0.47 g (0.73 mmol) of ethyl 5-(N-t-butoxycarbonyl-L-O-benzyltyrosyl)-4,5,6,7-tetrahydrothieno[3,2-c]pyridin-2-acetate as colorless foamy product.

$^1$H-NMR (CDCl$_3$) δ; 7.36–7.23 (m, 5H), 7.10–7.03 (m, 2H), 6.94–6.85 (m, 2H), 6.68–6.20 (m, 1H), 5.55–5.33 (m, 1H), 4.89–4.80 (m, 1H), 4.72–4.32 (m, 2H), 4.27, 4.20 (each s, total 2H), 4.14–4.05 (m, 2H), 3.79–3.48 (m, 3H), 3.10–2.57 (m, 4H), 1.45, 1.43 (each s, total 9H), 1.30–1.22 (m, 3H).

CI-MS (m/z); 542

(28-B) In the same manner as in Example I-(1-B) except for using 0.85 g (1.5 mmol) of ethyl 5-(N-t-butoxycarbonyl-L-O-benzyltyrosyl)-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate, the reaction was carried out to obtain 0.98 g (1.1 mmol) of the title compound as white foamy product.

$^1$H-NMR (CDCl$_3$) δ; 7.90–7.82 (m, 2H), 7.42–7.15 (m, 5H), 7.12–7.07 (m, 2H), 6.87–6.78 (m, 2H), 6.61, 6.44 (each s, total 1H), 5.39–5.32 (m, 1H), 5.03, 4.97 (each s, total 2H), 4.70–4.33 (m, 2H), 4.20–4.13 (m, 2H), 3.90–3.55 (m, 2H), 3.73, 3.68 (each s, total 2H), 3.26–3.01 (m, 2H), 2.78–2.28 (m, 2H), 1.59–1.36 (m, 27H), 1.29–1.25 (m, 3H).

Example I-29

Ethyl 5-(N-(4-amidinobenzoyl)-L-tyrosyl]-4,5,6,7-tetrahydrothieno[3,2-c]pyridin-2-acetate.trifluoroacetate (Ethyl ester of Exemplary compound No. 1-2)

In the same manner as in Example I-27 except for using 0.98 g (1.06 mmol) of ethyl 5-(N-[4-(N,N,N'-tri-t-butoxycarbonylamidino)benzoyl]-L-O-benzyltyrosyl]-4,5,6,7-tetrahydrothieno[3,2-c]pyridin-2-acetate in place of 5-[N-[4-(N,N,N'-tri-t-butoxycarbonylamidino)benzoyl]-L-O-benzyltyrosyl]-4,5,6,7-tetrahydrothieno[3,2-c]pyridin-2-acetic acid to obtain 0.51 g (0.78 mmol) of the title compound as white solid.

Melting point; 184–186° C.

$^1$H-NMR (400 MHz, CD$_3$OD) δ; 8.06–7.96 (m, 2H), 7.87–7.84 (m, 2H), 7.08–7.01 (m, 2H), 6.67–6.58 (m, 2H), 6.57, 6.50 (each s, total 1H), 5.31–5.23 (m, 1H), 4.63–4.20 (m, 2H), 4.17–4.12 (m, 2H), 3.97–3.58 (m, 2H), 3.75 (s, 2H), 3.15–3.01 (m, 2H), 2.78–2.33 (m, 2H), 1.98–1.27 (m, 3H).

FAB-MS (m/z); 535

Example I-30
Ethyl 5-(N-(4-amidinobenzoyl)-L-O-benzyltyrosyl]-4,5,6,7-tetrahydrothieno[3,2-c]pyridin-2-acetate.trifluoroacetate (Ethyl ester of Exemplary compound No. 1-7)

In the same manner as in Example I-2 except for using 0.22 g (0.24 mmol) of ethyl 5-[N-[4-(N,N,N'-tri-t-butoxycarbonylamidino)benzoyl]-L-O-benzyltyrosyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.15 g (0.20 mmol) of the title compound as white powder.

Melting point; 174–177° C.

$^1$H-NMR (400 MHz, DMSO-$d_6$) δ; 8.02–7.97 (m, 2H), 7.86–7.84 (m, 2H), 7.41–7.26 (m, 5H), 7.22 (m, 2H), 6.87–6.81 (m, 2H), 6.71, 6.67 (each s, total 1H), 5.14–5.12 (m, 1H), 5.01, 4.99 (each s, total 2H), 4.66–4.28 (m, 2H), 4.07 (q, J=7.2 Hz, 2H), 3.86–3.61 (m, 2H), 3.80, 3.79 (each s, total 2H), 3.02–2.94 (m, 2H), 2.72–2.48 (m, 2H), 1.17 (t, J=7.2 Hz, 3H).

FAB-MS (m/z); 625

Example I-31
Butyl 5-[N-[4-(N,N,N'-tri-t-butoxycarbonylamidino)benzoyl]-L-O-benzyltyrosyl]-4,5,6,7-tetrahydrothieno[3,2-c]pyridin-2-acetate (Butyl ester of Exemplary compound No. 1-156)

In the same manner as in Example I-6 except for using 0.25 g (0.31 mmol) of 5-[N-[4-(N,N,N'-tri-t-butoxycarbonylamidino)benzoyl]-L-O-benzyltyrosyl]-4,5,6,7-tetrahydrothieno[3,2-c]pyridin-2-acetic acid in place of 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetic acid and 0.07 g (0.9 mmol) of n-butanol in place of isopropyl alcohol, the reaction was carried out to obtain 0.26 g (0.30 mmol) of the title compound as white foamy product.

$^1$H-NMR (CDCl$_3$) δ; 7.90–7.81 (m, 4H), 7.41–7.15 (m, 5H), 7.12–7.07 (m, 2H), 6.87–6.78 (m, 2H), 6.15, 6.44 (each s, total 1H), 5.40–5.34 (m, 1H), 5.03, 4.97 (each s, total 2H), 4.70–4.33 (m, 2H), 4.13–4.08 (m, 2H), 3.90–3.54 (m, 2H), 3.73, 3.68 (each s, total 2H), 3.29–3.02 (m, 2H), 2.81–2.28 (m, 2H), 1.66–1.53 (m, 4H), 1.54–1.38 (m, 2.7H), 0.94–0.91 (t, J=7.3 Hz, 3H).

FAB-MS (m/z); 853

Example I-32
Butyl 5-[N-(4-amidinobenzoyl)-L-tyrosyl]-4,5,6,7-tetrahydrothieno[3,2-c]pyridin-2-acetate.trifluoroacetate (Butyl ester of Exemplary compound No. 1-2)

In the same manner as in Example 1–27 except for using 0.26 g (0.30 mmol) of butyl 5-(N-[4-(N,N,N'-tri-t-butoxycarbonylamidino)benzoyl]-L-O-benzyltyrosyl]-4,5,6,7-tetrahydrothieno[3,2-c]pyridin-2-acetate in place of 5-[N-[4-(N,N,N'-tri-t-butoxycarbonylamidino)benzoyl]-L-O-benzyltyrosyl]-4,5,6,7-tetrahydrothieno[3,2-c]pyridin-2-acetic acid, the reaction was carried out to obtain 0.10 g (0.14 mmol) of the title compound as white powder.

Melting point; 176–178° C.

$^1$H-NMR (400 MHz, CD$_3$OD) δ; 8.01–7.96 (m, 2H), 7.87–7.84 (m, 2H), 7.08–7.01 (m, 2H), 6.67–6.59 (m, 2H), 6.57, 6.50 (each s, total 1H), 5.30–5.23 (m, 1H), 4.63–4.20 (m, 2H), 4.12–4.08 (m, 2H), 3.97–3.59 (m, 2H), 3.75 (s, 2H), 3.14–3.01 (m, 2H), 2.80–2.36 (m, 2H), 1.65–1.56 (m, 2H), 1.42–1.35 (m, 2H), 0.94–0.91 (m, 3H).

FAB-MS (m/z); 563

Example I-33
Ethyl 5-[N-[4-(N,N,N'-tri-t-butoxycarbonylamidino)benzoyl]-D-O-benzyltyrosyl]-4,5,6,7-tetrahydrothieno[3,2-c]pyridin-2-acetate (Ethyl ester of Exemplary compound No. 1-156)

(33-A) In the same manner as in Example I-(1-A) except for using 0.75 g (2.00 mmol) of N-t-butoxycarbonyl-D-O-benzyltyrosine in place of N-t-butoxycarbonyl-L-4-nitrophenylalanine, and purification was carried out by changing the eluent composition in the silica gel column chromatography method to (chloroform/ethyl acetate=100/1), the reaction was carried out to obtain 1.10 g (1.90 mmol) of ethyl 5-(N-t-butoxycarbonyl-D-O-benzyltyrosyl)-4,5,6,7-tetrahydrothieno[3,2-c]pyridin-2-acetate as colorless foamy product.

$^1$H-NMR (CDCl$_3$) δ; 7.45–7.29 (m, 5H), 7.11–7.02 (m, 2H), 6.86–6.75 (m, 2H), 6.60, 6.39 (each s, total 1H), 5.51–5.39 (m, 1H), 5.01, 4.95 (each s, total 2H), 4.90–4.79 (m, 1H), 4.69–4.26 (m, 2H), 4.21–4.10 (m, 2H), 3.88–3.15 (m, 2H), 3.75–3.65 (m, 2H), 3.00–2.81 (m, 2H), 2.76–2.16 (m, 2H), 1.42 (s, 9H), 1.31–1.23 (m, 3H).

CI-MS (m/z); 579

(33-B) In the same manner as in Example I-(1-B) except for using 1.06 g (1.83 mmol) of ethyl 5-(N-t-butoxycarbonyl-D-O-benzyltyrosyl)-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate, the reaction was carried out to obtain 1.62 g (1.75 mmol) of the title compound as white foamy product.

$^1$H-NMR (CDCl$_3$) δ; 7.91–7.82 (m, 4H), 7.43–7.07 (m, 7H), 6.87–6.78 (m, 2H), 6.62, 6.44 (each s, total 1H), 5.41–5.30 (m, 1H), 5.03, 4.97 (each s, total 2H), 4.72–4.32 (m, 2H), 4.21–4.12 (m, 2H), 3.90–3.52 (m, 2H), 3.73, 3.68 (each s, total 2H), 3.29–2.98 (m, 2H), 2.80–2.27 (m, 2H), 1.59–1.36 (m, 27H), 1.31–1.24 (m, 3H).

FAB-MS (m/z); 825

Example I-34
Ethyl 5-[N-(4-amidinobenzoyl)-D-O-benzyltyrosyl]-4,5,6,7-tetrahydrothieno[3,2-c]pyridin-2-acetate.trifluoroacetate (Ethyl ester of Exemplary compound No. 1-7)

In the same manner as in Example I-2 except for using 0.40 g (0.43 mmol) of ethyl 5-[N-[4-(N,N,N'-tri-t-butoxycarbonylamidino)benzoyl]-D-O-benzyltyrosyl]-4,5,6,7-tetrahydrothieno[3,2-c]pyridin-2-acetate in place of ethyl 5-[N-[4-(N,N,N'-tri-t-butoxycarbonylamidino)benzoyl]-L- 4-nitrophenylalanyl]-4,5,6,7-tetrahydrothieno[3,2-c]pyridin-2-acetate, the reaction was carried out to obtain 0.22 g (0.29 mmol) of the title compound as white foamy product.

Melting point; 107–109° C.

$^1$H-NMR (400 MHz, CD$_3$OD) δ; 8.01–7.98 (m, 2H), 7.87–7.85 (m, 2H), 7.40–7.20 (m, 5H), 7.15–7.11 (m, 2H), 6.85–6.77 (m, 2H), 6.63, 6.49 (each s, total 1H), 5.28–5.23 (m, 1H), 5.02, 4.96 (each s, total 2H), 4.56–4.14 (m, 2H), 4.15–4.08 (m, 2H), 3.92–3.42 (m, 2H), 3.75–3.67 (m, 2H), 3.16–3.04 (m, 2H), 2.72–2.14 (m, 2H), 1.25–1.20 (m, 3H).

FAB-MS (m/z); 625

Example I-35
Ethyl 5-[N-(4-amidinobenzoyl)-D-tyrosyl]-4,5,6,7-tetrahydrothieno[3,2-c]pyridin-2-acetate.trifluoroacetate (Ethyl ester of Exemplary compound No. 1-2)

In the same manner as in Example I-27 except for using 1.22 g (1.32 mmol) of ethyl 5-[N-[4-(N,N,N'-tri-t- butoxycarbonylamidino)benzoyl]-D-O-benzyltyrosyl]-4,5,6,7-tetrahydrothieno[3,2-c]pyridin-2-acetate in place of 5-(N-(4-(N,N,N'-tri-t-butoxycarbonylamidino)benzoyl)-L-O-benzyltyrosyl]-4,5,6,7-tetrahydrothieno[3,2-c]pyridin-2-acetic acid, the reaction was carried out to obtain 0.67 g (1.0 mmol) of the title compound as white powder.

Melting point; 188–190° C.

$^1$H-NMR (400 MHz, CD$_3$OD) δ; 8.01–7.96 (m, 2H), 7.87–7.84 (m, 2H), 7.08–7.02 (m, 2H), 6.67–6.57 (m, 2H), 6.59, 6.50 (each s, total 1H), 5.30–5.23 (m, 1H), 4.63–4.17 (m, 2H), 4.16–4.12 (m, 2H), 3.96–3.59 (m, 2H), 3.74 (s, 2H), 3.15–3.01 (m, 2H), 2.82–2.29 (m, 2H), 1.27–1.23 (m, 3H).

FAB-MS (m/z); 535

$[\alpha]_D^{20}$; −11° (MeOH, c=0.524)

Example I-36

Ethyl 5-[N-(4-amidinobenzoyl)-L-4-aminophenylalanyl]-4,5,6,7-tetrahydrothieno[3,2-c]pyridin-2-acetate.di-trifluoroacetate (Ethyl ester of Exemplary compound No. 1-157)

(36-A) In 10 ml of ethyl alcohol was dissolved 0.50 g (0.97 mmol) of ethyl 5-(N-t-butoxycarbonyl-L-4-nitrophenylalanyl)-4,5,6,7-tetrahydrothieno[3,2-c]pyridin-2-acetate, and 0.50 g of 10% palladium carbon was added to the solution and the mixture was stirred under hydrogen atmosphere at 50° C. for 2 hours.

The catalyst was removed from the resulting reaction mixture by using Celite, and the filtrate was concentrated under reduced pressure. The residue was purified by the silica gel column chromatography method (eluent: chloroform/ethyl acetate=20/1) to obtain 0.30 g (0.62 mmol) of ethyl 5-(N-t-butoxycarbonyl-L-4-aminophenylalanyl)-4,5,6,7-tetrahydrothieno[3,2-c]pyridin-2-acetate as white solid.

$^1$H-NMR (CDCl$_3$) δ; 6.98–6.90 (m, 2H), 6.59–6.56 (m, 2H), 6.53, 6.34 (each s, total 1H), 5.52–5.37 (m, 1H), 4.89–4.76 (m, 1H), 4.61–3.89 (m, 2H), 4.24–4.15 (m, 2H), 3.74–3.71 (m, 2H), 3.60–3.29 (m, 2H), 3.00–2.54 (m, 4H), 1.43 (s, 9H), 1.35–1.23 (m, 3H).

CI-MS (m/z); 488

(36-B) To 0.30 g (0.62 mmol) of ethyl 5-(N-t-butoxycarbonyl-L-4-aminophenylalanyl)-4,5,6,7-tetrahydrothieno[3,2-c]pyridin-2-acetate were added 3 ml of methylene chloride and 3 ml of an aqueous sodium bicarbonate solution (prepared from 0.2 g of sodium hydrogen carbonate and 3 ml of water) and the mixture was ice-cooled, and 0.16 g (0.94 mmol) of benzyl chloroformate was added to the mixture, and the mixture was stirred at room temperature for 5 hours.

The methylene chloride layer was removed from the resulting reaction mixture, washed with a saturated aqueous saline solution and dried over anhydrous sodium sulfate. The organic layer was concentrated under reduced pressure and the residue was purified by the silica gel column chromatography method (eluent: n-hexane/ethyl acetate=2/1) to obtain 0.31 g (0.50 mmol) of ethyl 5-(N-t-butoxycarbonyl-L-4-(N-benzyloxycarbonylamino)phenylalanyl)-4,5,6,7-tetrahydrothieno[3,2-c]pyridin-2-acetate as white foamy product.

$^1$H-NMR (CDCl$_3$) δ; 7.42–7.34 (m, 4H), 7.22–6.95 (m, 5H), 6.59, 6.28 (each s, total 1H), 5.54–5.34 (m, 1H), 5.23–5.12 (m, 2H), 4.90–4.34 (m, 2H), 4.21–3.94 (m, 3H), 3.74–3.60 (m, 2H), 3.59–3.45 (m, 1H), 3.20–2.54 (m, 4H), 1.57–1.40 (m, 9H), 1.30–1.21 (m, 3H).

(36-C) In the same manner as in Example I-(1-B) except for using 0.31 g.(0.50 mmol) of ethyl 5-[N-t-butoxycarbonyl-L-4-(N-benzyloxycarbonylamino)phenylalanyl]-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate and 0.39 g (0.75 mmol) of PyBOP in place of BOP, the reaction was carried out to obtain 0.40 g (0.41 mmol) of ethyl 5-[N-(4-(N,N,N'-tri-t-butoxycarbonylamidino)benzoyl)-L-4-(N-benzyloxycarbonylamino)phenylalanyl]-4,5,6,7-tetrahydrothieno[3,2-c]pyridin-2-acetate as white foamy product.

$^1$H-NMR (CDCl$_3$) δ; 7.94–7.82 (m, 4H), 7.43–7.32 (m, 4H), 7.25–7.06 (m, 5H), 6.58, 6.29 (each s, total 1H), 5.41–5.30 (m, 1H), 5.25–5.13 (m, 2H), 4.66–4.35 (m, 2H), 4.25–4.12 (m, 2H), 4.11–3.47 (m, 4H), 3.29–3.10 (m, 2H), 3.03–2.59 (m, 2H), 1.54 (s, 9H), 1.36 (s, 18H), 1.28–1.23 (m, 3H).

FAB-MS (m/z); 869

(36-D) In the same manner as in Example I-27 except for using 0.40 g (0.41 mmol) of ethyl 5-[N-(4-(N,N,N'-tri-t-butoxycarbonylamidino)benzoyl)-L-4-(N-benzyloxycarbonylamino)phenylalanyl]-4,5,6,7-tetrahydrothieno[3,2-c]pyridin-2-acetate in place of 5-[N-[4-(N,N,N'-tri-t-butoxycarbonylamidino)benzoyl]-L-O-benzyltyrosyl]-4,5,6,7-tetrahydrothieno[3,2-c]pyridin-2-acetic acid to obtain 0.05 g (0.09 mmol) of the title compound as white powder.

Melting point; 123–126° C.

$^1$H-NMR (400 MHz, DMSO-d$_6$) δ; 8.02–7.95 (m, 2H), 7.86–7.83 (m, 2H), 7.19–7.15 (m, 2H), 6.81–6.72 (m, 2H), 6.71, 6.68 (each s, total 1H), 5.19–5.09 (m, 1H), 4.72–4.27 (m, 2H), 4.12–4.00 (m, 2H), 3.91–3.57 (m, 2H), 3.80 (s, 2H), 3.05–2.90 (m, 2H), 2.79–2.62 (m, 2H), 1.20–1.16 (m, 3H).

FAB-MS (m/z); 534

Example I-37

Ethyl 5-[N-[4-(N,N,N'-tri-t-butoxycarbonylamidino)benzoyl]-L-4-(butylsulfonylamino)phenylalanyl)-4,5,6,7-tetrahydrothieno[3,2-c]pyridin-2-acetate (Ethyl ester of Exemplary compound No. 1-118)

(37-A) In 4 ml of methylene chloride was dissolved 0.36 g (0.74 mmol) of 5-(N-t-butoxycarbonyl-L-4-aminophenylalanyl)-4,5,6,7-tetrahydrothieno[3,2-c]pyridin-2-acetate, and 0.4 ml of pyridine was added to the solution. Under ice-cooling, 0.23 g (1.5 mmol) of butane sulfonyl chloride was added to the mixture, and the mixture was stirred at room temperature for 2 hours. The reaction mixture was concentrated under reduced pressure, 5% of an aqueous potassium hydrogen sulfate solution was added to the residue and extracted with ethyl acetate. The organic layer was successively washed with a saturated aqueous sodium bicarbonate solution and a saturated aqueous saline solution, and dried over anhydrous sodium sulfate. The organic layer was concentrated under reduced pressure and the residue was purified by the silica gel column chromatography method (chloroform/ethyl acetate=25/1–18/1) to obtain 0.42 g (0.69 mmol) of ethyl 5-[N-t-butoxycarbonyl-L-4-(butylsulfonylamino)phenylalanyl]-4,5,6,7-tetrahydrothieno[3,2-c]pyridin-2-acetate as white foamy product.

$^1$H-NMR (CDCl$_3$) δ; 7.09–7.04 (m, 2H), 6.98–6.90 (m, 2H), 6.55, 6.21 (each s, total 1H), 5.56–5.33 (m, 1H), 4.89–4.57 (m, 2H), 4.31–4.20 (m, 2H), 4.18–4.00 (m, 1H), 3.85–3.74 (m, 2H), 3.72–3.45 (m, 1H), 3.10–2.79 (m, 6H), 2.65–2.52 (m, 2H), 1.82–1.70 (m, 2H), 1.45, 1.43 (each s, total 9H), 1.38–1.28 (m, 3H), 0.88 (t, J=7.3 Hz, 3H).

CI-MS (m/z); 608

(37-B) In the same manner as in Example I-(1-B) except for using 0.40 g (0.66 mmol) of ethyl 5-[N-t- butoxycarbonyl-L-4-(butylsulfonylamino)phenylalanyl]-4,5,6,7-tetrahydrothieno[3,2-c]pyridin-2-acetate in place of ethyl 5-[N-t-butoxycarbonyl-L-4-nitrophenylalanyl]- 4,5,6,7-tetrahydrothieno[3,2-c]pyridin-2-acetate, the reaction was carried out to obtain 0.70 g (0.73 mmol) of the title compound as white foamy product.

$^1$H-NMR (CDCl$_3$) δ; 7.95–7.84 (m, 3H), 7.36–7.28 (m, 1H), 7.14–6.93 (m, 4H), 6.58, 6.24 (each s, total 1H), 5.40–5.33 (m, 1H), 4.80–4.61 (m, 1H), 4.40–4.03 (m, 4H), 3.87–3.48 (m, 3H), 3.29–2.92 (m, 4H), 2.73–2.60 (m, 2H), 1.85–1.72 (m, 2H), 1.65–1.37 (m, 27H), 1.32–1.28 (m, 3H), 0.91–0.85 (m, 3H).

FAB-MS (m/z); 954

Example I-38

Ethyl 5-[N-(4-amidinobenzoyl)-L-4-(butylsulfonylamino)phenylalanyl]-4,5,6,7-tetrahydrothieno[3,2-c]pyridin-2-acetate.trifluoroacetate (Ethyl ester of Exemplary compound No. 1-9)

In the same manner as in Example I-2 except for using 0.70 g (0.73 mmol) of ethyl 5-[N-[4-(N,N,N'-tri-t-butoxycarbonylamidino)benzoyl]-L-4-(butylsulfonylamino)phenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.46 g (0.60 mmol) of the title compoundas white solid.

Melting point; 135–138° C.

$^1$H-NMR (400 MHz, CD$_3$OD) δ; 8.00–7.94 (m, 2H), 7.87–7.84 (m, 2H), 7.25–7.19 (m, 2H), 7.13–7.06 (m, 2H), 6.64, 6.52 (each s, total 1H), 5.36–5.28 (m, 1H), 4.64–4.18 (m, 2H), 4.18–4.11 (m, 2H), 3.89–3.61 (m, 2H), 3.75 (s, 2H), 3.19–3.06 (m, 2H), 3.00–2.93 (m, 2H), 2.83–2.35 (m, 2H), 1.73–1.63 (m, 2H), 1.34–1.26 (m, 2H), 1.24–1.22 (m, 3H), 0.86–0.82 (m, 3H).

FAB-MS (m/z); 654

Example I-39

Ethyl 5-[N-[4-(N,N,N'-tri-t-butoxycarbonylamidino)benzoyl]-L-4-(phenylsulfonylamino)phenylalanyl]-4,5,6,7-tetrahydrothieno[3,2-c]pyridin-2-acetate (Ethyl ester of Exemplary compound No. 1-120)

(39-A) In the same manner as in Example I-(1-A) except for using 0.32 g (0.75 mmol) of N-t-butoxycarbonyl-L-4-(phenylsulfonylamino)phenylalanine in place of N-t-butoxycarbonyl-L-4-nitrophenylalanine, and purification was carried out by changing the eluent composition in the silica gel column chromatography method to (chloroform/ethyl acetate=20/1–15/1), the reaction was carried out to obtain 0.47 g (0.75 mmol) of ethyl 5-[N-t-butoxycarbonyl-L-4-(phenylsulfonylamino)phenylalanyl]-4,5,6,7-tetrahydrothieno[3,2-c]pyridin-2-acetate as colorless foamy product.

$^1$H-NMR (CDCl$_3$) δ; 7.75–7.67 (m, 2H), 7.51–7.33 (m, 3H), 6.99–6.93 (m, 2H), 6.84–6.71 (m, 2H), 6.51, 6.25 (each s, total 1H), 5.53–5.33 (m, 1H), 4.85–4.44 (m, 2H), 4.37–4.29 (m, 2H), 4.28–3.85 (m, 2H), 3.80–3.70 (m, 2H), 3.05–2.88 (m, 2H), 2.80–2.44 (m, 2H), 1.45, 1.40 (each s, total 9H), 1.39–1.25 (m, 3H).

CI-MS (m/z); 528

(39-B) In the same manner as in Example I-(1-B) except for using 0.47 g (0.75 mmol) of ethyl 5-[N-t-butoxycarbonyl-L-4-(phenylsulfonylamino)phenylalanyl]-4,5,6,7-tetrahydrothieno[3,2-c]pyridin-2-acetate in place of ethyl 5-[N-t-butoxycarbonyl-L-4-nitrophenylalanyl]-4,5,6,7-tetrahydrothieno[3,2-c]pyridin-2-acetate, the reaction was carried out to obtain 0.43 g (0.44 mmol) of the title compound as white foamy product.

$^1$H-NMR (CDCl$_3$) δ; 7.95–7.84 (m, 4H), 7.10–7.68 (m, 2H), 7.53–7.40 (m, 2H), 7.36–7.23 (m, 1H), 7.10–6.77 (m, 4H), 6.55, 6.20 (each s, total 1H), 5.40–5.33 (m, 1H), 4.80–4.61 (m, 1H), 4.40–4.03 (m, 4H), 3.87–3.48 (m, 3H), 3.29–2.92 (m, 4H), 2.73–2.60 (m, 2H), 1.85–1.72 (m, 2H), 1.65–1.37 (m, 27H), 1.32–1.28 (m, 3H).

FAB-MS (m/z); 874

Example I-40

Ethyl 5-[N-(4-amidinobenzoyl)-L-4-(phenylsulfonylamino)phenylalanyl]-4,5,6,7-tetrahydrothieno[3,2-c]pyridin-2-acetate.trifluoroacetate (Ethyl ester of Exemplary compound No. 1-11)

In the same manner as in Example I-2 except for using 0.43 g (0.44 mmol) of ethyl 5-[N-[4-(N,N,N'-tri-t-butoxycarbonylamidino)benzoyl]-L-4-(phenylsulfonylamino)phenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.28 g (0.36 mmol) of the title compound as white powder.

Melting point; 138–140° C.

$^1$H-NMR (400 MHz, DMSO-d$_6$) δ; 8.00–7.94 (m, 2H), 7.86–7.83 (m, 2H), 7.71–7.66 (m, 2H), 7.39–7.27 (m, 3H), 7.13–7.09 (m, 2H), 7.03–6.94 (m, 2H), 6.63, 6.51 (each s, total 1H), 5.25–5.19 (m, 1H), 4.75–4.53 (m, 1H), 4.19–4.13 (m, 2H), 3.95–3.64 (m, 3H), 3.79 (s, 3H), 3.08–3.01 (m, 2H), 2.79–2.64 (m, 2H), 1.28–1.23 (m, 3H).

FAB-MS (m/z); 674

Example I-41

Ethyl 5-[N-[4-(N,N,N'-tri-t-butoxycarbonylamidino)benzoyl]-DL-4-(methylsulfonylamino)phenylalanyl]-4,5,6,7-tetrahydrothieno[3,2-c]pyridin-2-acetate (Ethyl ester of Exemplary compound No. 1-117)

(41-A) In the same manner as in Example I-(1-A) except for using 0.30 g (0.84 mmol) of N-t-butoxycarbonyl-DL-4-(methylsulfonylamino)phenylalanine in place of N-t-butoxycarbonyl-L-4-nitrophenylalanine, and purification was carried out by changing the eluent composition in the silica gel column chromatography method to (chloroform/ethyl acetate=10/1–5/1), the reaction was carried out to obtain, as a colorless foamy product, 0.44 g (0.78 mmol) of ethyl 5-[N-t-butoxycarbonyl-DL-4-(methylsulfonylamino)phenylalanyl]-4,5,6,7-tetrahydrothieno[3,2-c]pyridin-2-acetate as white foamy product.

$^1$H-NMR (CDCl$_3$) δ; 7.11–7.05 (m, 2H), 6.98–6.90 (m, 2H), 6.56, 6.21 (each s, total 1H), 5.57–5.35 (m, 1H), 4.90–4.54 (m, 2H), 4.32–4.21 (m, 2H), 4.11–4.05 (m, 1H), 3.85–3.72 (m, 2H), 3.71–3.46 (m, 1H), 3.10–2.90 (m, 2H), 2.94, 2.88 (each s, total 3H), 2.77–2.54 (m, 2H), 1.44, 1.42 (each s, total 9H), 1.38–1.25 (m, 3H).

CI-MS (m/z); 510

(41-B) In the same manner as in Example I-(1-B) except for using 0.44 g (0.78 mmol) of ethyl 5-[N-t-butoxycarbonyl-DL-4-(methylsulfonylamino)phenylalanyl]-4,5,6,7-tetrahydrothieno[3,2-c]pyridin-2-acetate in place of ethyl 5-[N-t-butoxycarbonyl-L-4-nitrophenylalanyl]-4,5,6,7-tetrahydrothieno[3,2-c]pyridin-2-acetate, the reaction was carried out to obtain 0.70 g (0.77 mmol) of the title compound as white foamy product.

$^1$H-NMR (CDCl$_3$) δ; 7.94–7.84 (m, 4H), 7.17–7.12 (m, 2H), 7.02–6.95 (m, 2H), 6.57, 6.25 (each s, total 1H), 5.40–5.30 (m, 1H), 4.82–4.62 (m, 1H), 4.37–4.06 (m, 4H), 3.88–3.68 (m, 3H), 3.65–3.47 (m, 1H), 3.28–2.88 (m, 2H), 2.95, 2.90 (each s, total 3H), 2.70–2.58 (m, 2H), 1.62–1.36 (m, 27H), 1.34–1.28 (m, 3H).

FAB-MS (m/z); 812

Example I-42
Ethyl 5-[N-(4-amidinobenzoyl)-DL-4-(methylsulfonylamino)phenylalanyl]-4,5,6,7-tetrahydrothieno[3,2-c]pyridin-2-acetate.trifluoroacetate (Ethyl ester of Exemplary compound No. 1-8)

In the same manner as in Example I-2 except for using 0.70 g (0.77 mmol) of ethyl 5-(N-[4-(N,N,N'-tri-t-butoxycarbonylamidino)benzoyl]-DL-4-(methylsulfonylamino)phenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.40 g (0.55 mmol) of the title compound as white powder.

Melting point; 179–181° C.

$^1$H-NMR (400 MHz, CD$_3$OD) δ; 8.00–7.95 (m, 2H), 7.87–7.85 (m, 2H), 7.26–7.20 (m, 2H), 7.13–7.05 (m, 2H), 6.52, 6.34 (each s, total 1H), 5.37–5.28 (m, 1H), 4.59–4.26 (m, 2H), 4.18–4.12 (m, 2H), 4.04–3.61 (m, 2H), 3.76 (s, 2H), 2.86, 2.82 (each s, total 3H), 2.84–2.32 (m, 2H), 1.27–1.17 (m, 3H).

FAB-MS (m/z); 612

Example I-43
Ethyl 5-[N-[4-(N,N,N'-tri-t-butoxycarbonylamidino)benzoyl]-DL-4-(benzylsulfonylamino)phenylalanyl]-4,5,6,7-tetrahydrothieno[3,2-c]pyridin-2-acetate (Ethyl ester of Exemplary compound No. 1-119)

(43-A) In the same manner as in Example I-(1-A) except for using 0.40 g (0.92 mmol) of N-t-butoxycarbonyl-DL-4-(benzylsulfonylamino)phenylalanine in place of N-t-butoxycarbonyl-L-4-nitrophenylalanine, and purification was carried out by changing the eluent composition in the silica gel column chromatography method to (chloroform/ethyl acetate=40/1-15/1), the reaction was carried out to obtain 0.47 g (0.73 mmol) of ethyl 5-[N-t-butoxycarbonyl-DL-4-(benzylsulfonylamino)phenylalanyl]-4,5,6,7-tetrahydrothieno[3,2-c]pyridin-2-acetate as colorless foamy product.

$^1$H-NMR (CDCl$_3$) δ; 7.36–7.23 (m, 5H), 7.10–7.03 (m, 2H), 6.94–6.85 (m, 2H), 6.68–6.20 (m, 1H), 5.55–5.33 (m, 1H), 4.89–4.80 (m, 1H), 4.72–4.32 (m, 2H), 4.27, 4.20 (each s, total 2H), 4.14–4.05 (m, 2H), 3.79–3.48 (m, 3H), 3.10–2.57 (m, 4H), 1.45, 1.43 (each s, total 9H), 1.30–1.22 (m, 3H).

CI-MS (m/z); 542

(43-B) In the same manner as in Example I-(1-B) except for using 0.47 g (0.73 mmol) of ethyl 5-[N-t-butoxycarbonyl-DL-4-(benzylsulfonylamino)phenylalanyl]-4,5,6,7-tetrahydrothieno[3,2-c]pyridin-2-acetate in place of ethyl 5-[N-t-butoxycarbonyl-L-4-nitrophenylalanyl]-4,5,6,7-tetrahydrothieno[3,2-c]pyridin-2-acetate, the reaction was carried out to obtain 0.77 g (0.78 mmol) of the title compound as white foamy product.

$^1$H-NMR (CDCl$_3$) δ; 7.94–7.81 (m, 4H), 7.36–7.18 (m, 5H), 7.14–7.06 (m, 2H), 6.95–6.87 (m, 2H), 6.70, 6.57, 6.22 (each s, total 1H), 5.40–5.29 (m, 1H), 4.73–4.20 (m, 2H), 4.27, 4.23 (each s, total 2H), 4.18–4.04 (m, 2H), 3.78–3.62 (m, 2H), 3.27–2.93 (m, 4H), 2.71–2.12 (m, 2H), 1.62–1.36 (m, 27H), 1.30–1.23 (m, 3H).

FAB-MS (m/z); 789

Example I-44
Ethyl 5-[N-(4-amidinobenzoyl)-DL-4-(benzylsulfonylamino)phenylalanyl]-4,5,6,7-tetrahydrothieno[3,2-c]pyridin-2-acetate.trifluoroacetate (Ethyl ester of Exemplary compound No. 1-10)

In the same manner as in Example I-2 except for using 0.77 g (0.78 mmol) of ethyl 5-[N-[4-(N,N,N'-tri-t-butoxycarbonylamidino)benzoyl]-DL-4-(benzylsulfonylamino)phenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.48 g (0.60 mmol) of the title compound as white powder.

Melting point; 230–232° C.

$^1$H-NMR (400 MHz, CD$_3$OD) δ; 8.01–7.96 (m, 2H), 7.87–7.84 (m, 2H), 7.32–7.17 (m, 7H), 7.08–7.02 (m, 2H), 6.63, 6.52 (each s, total 1H), 5.37, 5.31 (each dd, J=7.8 Hz, 7.2 Hz, total 1H), 4.63–4.27 (m, 2H), 4.32–4.24 (m, 2H), 4.14–4.08 (m, 2H), 3.97–3.68 (m, 2H), 3.69, 3.68 (each s, total 2H), 3.22–3.07 (m, 2H), 2.83–2.45 (m, 2H), 1.24–1.21 (m, 3H).

FAB-MS (m/z); 688

Example I-45
Ethyl 5-[N-[4-(N,N,N'-tri-t-butoxycarbonylamidino)benzoyl]-DL-4-[(4-fluorophenyl)sulfonylamino]phenylalanyl]-4,5,6,7-tetrahydrothieno[3,2-c]pyridin-2-acetate (Ethyl ester of Exemplary compound No. 1-122)

(45-A) In the same manner as in Example I-(1-A) except for using 0.33,g (0.75 mmol) of N-t-butoxycarbonyl-DL-4-[(4-fluorophenyl)sulfonylamino]phenylalanine in place of N-t-butoxycarbonyl-L-4-nitrophenylalanine, and purification was carried out by changing the eluent composition in the silica gel column chromatography method to (chloroform/ethyl acetate=40/1-20/1), the reaction was carried out to obtain 0.44 g (0.68 mmol) of ethyl 5-[N-t-butoxycarbonyl-DL-4-[(4-fluorophenyl)sulfonylamino]phenylalanyl]-4,5,6,7-tetrahydrothieno[3,2-c]pyridin-2-acetate as colorless foamy product.

$^1$H-NMR (CDCl$_3$) δ; 7.76–7.66 (m, 2H), 7.07–6.95 (m, 4H), 6.79–6.69 (m, 2H), 6.51, 6.16 (each s, total 1H), 5.53–5.31 (m, 1H), 4.84–4.52 (m, 2H), 4.36–4.19 (m, 2H), 4.08–3.90 (m, 1H), 3.85–3.38 (m, 3H), 3.06–2.75 (m, 3H), 2.64–2.56 (m, 1H), 1.43, 1.41 (each s, total 9H), 1.39–1.24 (m, 3H).

CI-MS (m/z); 590

(45-B) In the same manner as in Example I-(1-B) except for using 0.44 g (0.68 mmol) of ethyl 5-[N-t-butoxycarbonyl-DL-4-[(4-fluorophenyl)sulfonylamino]phenylalanyl]-4,5,6,7-tetrahydrothieno[3,2-c]pyridin-2-acetate in place of ethyl 5-[N-t-butoxycarbonyl-L-4-nitrophenylalanyl]-4,5,6,7-tetrahydrothieno[3,2-c]pyridin-2-acetate, the reaction was carried out to obtain 0.51 g (0.52 mmol) of the title compound as pale yellowish foamy product.

FAB-MS (m/z); 892

Example I-46
Ethyl 5-[N-(4-amidinobenzoyl)-DL-4-[(4-fluorophenyl)sulfonylamino]phenylalanyl]-4,5,6,7-tetrahydrothieno[3,2-c]pyridin-2-acetate.trifluoroacetate (Ethyl ester of Exemplary compound No. 1-12)

In the same manner as in Example I-2 except for using 0.51 g (0.52 mmol) of ethyl 5-[N-[4-(N,N,N'-tri-t-butoxycarbonylamidino)benzoyl]-DL-4-[(4-fluorophenyl)sulfonylamino]phenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.30 g (0.37 mmol) of the title compound as white powder.

Melting point; 138–140° C.

¹H-NMR (400 MHz, CD₃OD) δ; 7.99–7.93 (m, 2H), 7.87–7.84 (m, 2H), 7.73–7.67 (m, 2H), 7.16–6.93 (m, 6H), 6.52, 6.38 (each s, total 1H), 5.29–5.22 (m, 1H), 4.69–4.55 (m, 1H), 4.22–3.90 (m, 1H), 4.17–4.12 (m, 2H), 3.78, 3.77 (each s, total 2H), 3.85–3.25 (m, 2H), 3.12–3.02 (m, 2H), 2.80–2.32 (m, 2H), 1.27–1.23 (m, 3H).

FAB-MS (m/z); 692

Example I-47

Ethyl 5-(N-[4-(N,N,N'-tri-t-butoxycarbonylamidino) benzoyl]-DL-4-(phenylsulfonylamino)phenylalanyl)-4,5,6,7-tetrahydrothieno[3,2-c]pyridin-2-acetate (Ethyl ester of Exemplary compound No. 1-120)

(47-A) In the same manner as in Example I-(1-A) except for using 0.31 g (0.74 mmol) of N-t-butoxycarbonyl-DL-4-(phenylsulfonylamino)phenylalanine in place of N-t-butoxycarbonyl-L-4-nitrophenylalanine, and purification was carried out by changing the eluent composition in the silica gel column chromatography method to (chloroform/ethyl acetate=50/1–20/1), the reaction was carriedout to obtain 0.45 g (0.71mmol) of ethyl 5-[N-t-butoxycarbonyl-DL-4-(phenylsulfonylamino)phenylalanyl]-4,5,6,7-tetrahydrothieno[3,2-c]pyridin-2-acetate as white foamy product.

¹H-NMR (CDCl₃) δ; 7.75–7.67 (m, 2H), 7.51–7.33 (m, 3H), 6.99–6.93 (m, 2H), 6.84–6.71 (m, 2H), 6.51, 6.25 (each s, total 1H), 5.53–5.33 (m, 1H), 4.85–4.44 (m, 2H), 4.37–4.29 (m, 2H), 4.28–3.85 (m, 2H), 3.80–3.70 (m, 2H), 3.05–2.88 (m, 2H), 2.80–2.44 (m, 2H), 1.45, 1.40 (each s, total 9H), 1.39–1.25 (m, 3H).

CI-MS (m/z); 528

(47-B) In the same manner as in Example I-(1-B) except for using 0.45 g (0.74 mmol) of ethyl 5-[N-t-butoxycarbonyl-DL-4-(phenylsulfonylamino) phenylalanyl]-4,5,6,7-tetrahydrothieno[3,2-c]pyridin-2-acetate in place of ethyl 5-[N-t-butoxycarbonyl-L-4-nitrophenylalanyl]-4,5,6,7-tetrahydrothieno[3,2-c]pyridin-2-acetate, the reaction was carried out to obtain 0.45 g (0.46 mmol) of the title compound as white solid.

¹H-NMR (CDCl₃) δ; 7.92–7.81 (m, 2H), 7.75–7.69 (m, 2H), 7.53–7.32 (m, 4H), 7.25–7.23 (m, 1H), 7.09–7.01 (m, 2H), 6.88–6.77 (m, 2H), 6.55, 6.20 (each s, total 1H), 5.33–5.25 (m, 1H), 4.55–4.50 (m, 1H), 4.42–3.90 (m, 4H), 3.82, 3.76 (each s, total 2H), 3.86–3.70 (m, 1H), 3.49–3.17 (m, 1H), 3.09–2.87 (m, 2H), 2.68–2.00 (m, 2H), 1.59–1.39 (m, 27H), 1.37–1.32 (m, 3H).

FAB-MS (m/z); 974

Example I-48

Ethyl 5-[N-(4-amidinobenzoyl)-DL-4-(phenylsulfonylamino)phenylalanyl]-4,5,6,7-tetrahydrothieno[3,2-c]pyridin-2-acetate.trifluoroacetate (Ethyl ester of Exemplary compound No. 1-11)

In the same manner as in Example I-2 except for using 0.51 g (0.52 mmol) of ethyl 5-[N-[4-(N,N,N'-tri-t-butoxycarbonylamidino)benzoyl]-DL-4-(phenylsulfonylamino)phenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.30 g (0.37 mmol) of the title compound as white powder.

Melting point; 140–142° C.

¹H-NMR (400 MHz, CD₃OD) δ; 8.00–7.94 (m, 2H), 7.86–7.83 (m, 2H), 7.71–7.66 (m, 2H), 7.39–7.27 (m, 3H), 7.13–7.09 (m, 2H), 7.03–6.94 (m, 2H), 6.63, 6.51 (each s, total 1H), 5.25–5.19 (m, 1H), 4.75–4.53 (m, 1H), 4.19–4.13 (m, 2H), 3.95–3.64 (m, 3H), 3.79 (s, 3H), 3.08–3.01 (m, 2H), 2.79–2.64 (m, 2H), 1.28–1.23 (m, 3H).

FAB-MS (m/z); 674

Example I-49

Methyl 5-[N-[4-(N,N,N'-tri-t-butoxycarbonylamidino) benzoyl]-L-phenylalanyl]-4,5,6,7-tetrahydrothieno[3,2-c]pyridin-2-acetate (Methyl ester of Exemplary compound No. 1-60)

(49-A) In 6 ml of methylene chloride was dissolved 0.27 g (1.0 mmol) of N-t-butoxycarbonyl-L-phenylalanine, and 0.20 g (1.5 mmol) of HOBt and 0.25 g (1.2 mmol) of DCC were added to the solution and the mixture was stirred at room temperature for one hour. Then, 0.25 g (1.0 mmol) of methyl 4,5,6,7-tetrahydrothieno[3,2-c]pyridin-2-acetate.hydrochloride and 0.5 ml of triethylamine were added to the mixture, and the resulting mixture was stirred at room temperature for one hour.

The resulting reaction mixture was concentrated under reduced pressure and the residue was purified by the silica gel column chromatography method (eluent: chloroform/ethyl acetate=20/1) to obtain 0.45 g (1.0 mmol) of methyl 5-(N-t-butoxycarbonyl-L-phenylalanyl)-4,5,6,7-tetrahydrothieno[3,2-c]pyridin-2-acetate as colorless oily product.

CI-MS (m/z); 403

(49-B) In the same manner as in Example I-(1-B) except for using 0.45 g (1.00 mmol) of methyl 5-(N-t-butoxycarbonyl-L-phenylalanyl)-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate, the reaction was carried out to obtain 0.64 g (0.90 mmol) of the title compound as white foamy product.

Example I-50

5-[N-[4-(N,N,N'-tri-t-butoxycarbonylamidino)benzoyl]-L-phenylalanyl]-4,5,6,7-tetrahydrothieno[3,2-c]pyridin-2-acetic acid (Exemplary compound No. 1-60)

In the same manner as in Example I-4 except for using 0.64 g (0.90 mmol) of methyl 5-[N-[4-(N,N,N'-tri-t-butoxycarbonylamidino)benzoyl]-L-phenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.55 g (0.79 mmol) of the title compound as white foamy product.

Example I-51

Ethyl 5-[N-[4-(N,N,N'-tri-t-butoxycarbonylamidino) benzoyl]-L-phenylalanyl]-4,5,6,7-tetrahydrothieno[3,2-c]pyridin-2-acetate (Ethyl ester of Exemplary compound No. 1-60)

In the same manner as in Example I-6 except for using 0.55 g (0.79 mmol) of 5-[N-[4-(N,N,N'-tri-t-butoxycarbonylamidino)benzoyl]-L-phenylalanyl]-4,5,6,7-tetrahydrothieno[3,2-c]pyridin-2-acetic acid in place of 5-[N-[4-(N,N,N'-tri-t-butoxycarbonylamidino)benzoyl]-L-4-nitrophenylalanyl]- 4,5,6,7-tetrahydrothieno[3,2-c]pyridin-2-acetic acid and 0.11 g (2.4 mmol) of ethanol in place of isopropyl alcohol, the reaction was carried out to obtain 0.50 g (0.69 mmol) of the title compound as white foamy product.

¹H-NMR (CDCl₃) δ; 7.93–7.84 (m, 2H), 7.29–7.13 (m, 2H), 6.64, 6.44 (each s, total 1H), 5.48–5.36 (m, 1H), 4.72–4.35 (m, 2H), 4.25–4.18 (m, 2H), 3.91–3.55 (m, 2H), 3.75, 3.74 (each s, total 2H), 3.35–3.11 (m, 2H), 2.80–2.32 (m, 2H), 1.58–1.39 (m, 27H), 1.34–1.29 (m, 3H).

FAB-MS (m/z); 819

Example I-52
Ethyl 5-[N-(4-amidinobenzoyl)-L-phenylalanyl]-4,5,6,7-tetrahydrothieno[3,2-c]pyridin-2-acetate.trifluoroacetate (Ethyl ester of Exemplary compound No. 1-1)

In the same manner as in Example I-2 except for using 0.50 g (0.69 mmol) of ethyl 5-[N-[4-(N,N,N'-tri-t-butoxycarbonylamidino)benzoyl]-L-phenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.25 g (0.39 mmol) of the title compound as white powder.

Melting point; 173–175° C.

$^1$H-NMR (400 MHz, CD$_3$OD) δ; 8.00–7.95 (m, 2H), 7.87–7.84 (m, 2H), 7.28–7.04 (m, 5H), 6.63, 6.50 (each s, total 1H), 5.37–5.30 (m, 1H), 4.62–4.21 (m, 2H), 4.18–4.12 (m, 2H), 3.97–3.61 (m, 2H), 3.75, 3.72 (each s, total 2H), 3.25–3.11 (m, 2H), 2.71–2.31 (m, 2H), 1.28–1.23 (m, 3H).

FAB-MS (m/z); 519

$[\alpha]_D^{20}$; +14° (MeOH, c=0.27)

Example I-53
Ethyl 5-[N-[4-(N,N,N'-tri-t-butoxycarbonylamidino)benzoyl]-L-4-fluorophenylalanyl]-4,5,6,7-tetrahydrothieno[3,2-c]pyridin-2-acetate (Ethyl ester of Exemplary compound No. 1-69)

(53-A) In the same manner as in Example I-(1-A) except for using 0.28 g (1.0 mmol) of N-t-butoxycarbonyl-L-4-fluorophenylalanine in place of N-t-butoxycarbonyl-L-4-nitrophenylalanine, and purification was carried out by changing the eluent composition in the silica gel column chromatography method to (chloroform/ethyl acetate=40/1–20/1), the reaction was carried out to obtain 0.47 g (0.96mmol) of ethyl 5-[N-t-butoxycarbonyl-L-4-fluorophenylalanyl]-4,5,6,7-tetrahydrothieno[3,2-c]pyridin-2-acetate as colorless oily product.

$^1$H-NMR (CDCl$_3$) δ; 7.17–7.05 (m, 2H), 6.96–6.77 (m, 2H), 6.60, 6.36 (each s, total 1H), 5.50–5.37 (m, 1H), 4.91–4.80 (m, 1H), 4.67–4.26 (m, 1H), 4.25–4.15 (m, 2H), 4.12–3.91 (m, 1H), 3.72, 3.71 (each s, total 2H), 3.70–3.48 (m, 1H), 3.08–2.88 (m, 2H), 2.80–2.32 (m, 2H), 1.42, 1.41 (each s, total 9H), 1.31–1.23 (m, 3H).

CI-MS (m/z); 491

(53-B) In the same manner as in Example I-(1-B) except for using 0.47 g (0.94 mmol) of ethyl 5-(N-t-butoxycarbonyl-L-4-fluorophenylalanyl)-4,5,6,7-tetrahydrothieno[3,2-c]pyridin-2-acetate in place of ethyl 5-[N-t-butoxycarbonyl-L-4-nitrophenylalanyl]-4,5,6,7-tetrahydrothieno[3,2-c]pyridin-2-acetate, the reaction was carried out to obtain 0.75 g (0.90 mmol) of the title compound as yellowish foamy product.

$^1$H-NMR (CDCl$_3$) δ; 7.92–7.80 (m, 4H), 7.25–7.09 (m, 2H), 6.98–6.80 (m, 2H), 6.63, 6.40 (each s, total 1H), 5.42–5.30 (m, 1H), 4.66–4.20 (m, 2H), 4.22–4.14 (m, 2H), 4.13–3.96 (m, 1H), 3.73 (s, 2H), 3.68–3.35 (m, 1H), 3.18–3.00 (m, 2H), 2.83–2.37 (m, 2H), 1.60–1.36 (m, 27H), 1.32–1.26 (m, 3H).

FAB-MS (m/z); 837

Example I-54
Ethyl 5-[N-(4-amidinobenzoyl)-L-4-fluorophenylalanyl]-4,5,6,7-tetrahydrothieno[3,2-c]pyridin-2-acetate.trifluoroacetate (Ethyl ester of Exemplary compound No. 1-6)

In the same manner as in Example I-2 except for using 0.75 g (0.90 mmol) of ethyl 5-[N-[4-(N,N,N'-tri-t-butoxycarbonylamidino)benzoyl]-L-4-fluorophenylalanyl]-4,5,6,7-tertrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.44 g (0.68 mmol) of the title compound as white powder.

Melting point; 183–185° C.

$^1$H-NMR (400 MHz, CD$_3$OD) δ; 7.99–7.95 (m, 2H), 7.87–7.85 (m, 2H), 7.30–7.21 (m, 2H), 6.97–6.84 (m, 2H), 6.64, 6.50 (each s, total 1H), 5.37–5.30 (m, 1H), 4.64–4.32 (m, 2H), 4.18–4.12 (m, 2H), 4.09–3.57 (m, 2H), 3.75, 3.73 (each s, total 2H), 3.24–3.09 (m, 2H), 2.84–2.38 (m, 2H), 1.27–1.23 (m, 3H).

FAB-MS (m/z); 537

Example I-55
Ethyl 5-[N-[4-(N,N,N'-tri-t-butoxycarbonylamidino)benzoyl]-DL-4-cyanophenylalanyl]-4,5,6,7-tetrahydrothieno[3,2-c]pyridin-2-acetate (Ethyl ester of Exemplary compound No. 1-70)

(55-A) In the same manner as in Example I-(1-A) except for using 1.00 g (3.45 mmol) of N-t-butoxycarbonyl-DL-4-cyanophenylalanine in place of N-t-butoxycarbonyl-L-4-nitrophenylalanine, and purification was carried out by changing the eluent composition in the silica gel column chromatographymethod to (chloroform/ethyl acetate=19/1), the reaction was carried out to obtain 1.23 g (2.47 mmol) of ethyl 5-[N-t-butoxycarbonyl-DL-4-cyanophenylalanyl]-4,5,6,7-tetrahydrothieno[3,2-c]pyridin-2-acetate as colorless oily product.

$^1$H-NMR (CDCl$_3$) δ; 7.55–7.22 (m, 4H), 6.61, 6.35 (each s, total 1H), 5.47, 5.34 (each d, J=8 Hz, total 1H), 4.98–4.83 (m, 1H), 4.65–4.01 (m, 2H), 4.20 (q, J=7 Hz, 2H), 3.78, 3.74 (each s, total 2H), 3.72–3.32 (m, 2H), 3.20–2.91 (m, 2H), 2.85–2.40 (m, 2H), 1.42, 1.40 (each s, total 9H), 1.29 (t, J=7 Hz, 3H).

CI-MS (m/z); 498

(55-B) In the same manner as in Example I-(1-B) except for using 1.23 g (2.47 mmol) of ethyl 5-(N-t-butoxycarbonyl-DL-4-cyanophenylalanyl)-4,5,6,7-tetrahydrothieno[3,2-c]pyridin-2-acetate in place of ethyl 5-[N-t-butoxycarbonyl-L-4-nitrophenylalanyl]-4,5,6,7-tetrahydrothieno[3,2-c]pyridin-2-acetate, the reaction was carried out to obtain 1.69 g (2.00 mmol) of the title compound as yellowish foamy product.

$^1$H-NMR (CDCl$_3$) δ; 7.92–7.12 (m, 9H), 6.63, 6.37 (each s, total 1H), 5.53–5.37 (m, 1H), 4.71–3.97 (m, 4H), 3.80, 3.75 (each s, total 2H), 3.70–2.43 (m, 6H), 1.55 (s, 9H), 1.37 (s, 18H), 1.32–1.26 (m, 3H).

Example I-56
Ethyl 5-[N-(4-amidinobenzoyl)-DL-4-cyanophenylalanyl]-4,5,6,7-tetrahydrothieno[3,2-c]pyridin-2-acetate.trifluoroacetate (Ethyl ester of Exemplary compound No. 1-4)

In the same manner as in Example I-2 except for using 1.69 g (2.00 mmol) of ethyl 5-(N-(4-(N,N,N'-tri-t-butoxycarbonylamidinobenzoyl)-DL-4-cyanophenylalanyl)-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 1.04 g (1.58 mmol) of the title compound as white powder.

Melting point; 192–210° C. (decomposed)

$^1$H-NMR (400 MHz, DMSO-d$_6$) δ; 9.37 (s, 2H), 9.19 (s, 2H), 9.18, 9.10 (each d, J=8.4 Hz, total 1H), 7.97–7.93 (m, 2H), 7.84 (d, J=8.4 Hz, 2H), 7.69, 7.61 (each d, J=8.4 Hz, total 2H), 7.54, 7.49 (each d, J=8.4 Hz, total 2H), 6.71, 6.61 (each s, total 1H), 5.32–5.23 (m, 1H), 4.66–4.32 (m, 2H), 4.11–4.07 (m, 2H), 3.91–3.58 (m, 2H), 3.80 (s, 2H), 3.23–3.12 (m, 2H), 2.78–2.58 (m, 2H), 1.21–1.16 (m, 3H).
FAB-MS (m/z); 544

Example I-57

Ethyl 5-(N-[4-(N,N,N'-tri-t-butoxycarbonylamidino) benzoyl]-DL-4-trifluoromethylphenylalanyl)-4,5,6,7-tetrahydrothieno[3,2-c]pyridin-2-acetate (Ethyl ester of Exemplary compound No. 1-72)

(57-A) In the same manner as in Example I-(1-A) except for using 0.32 g (1.0 mmol) of N-t-butoxycarbonyl-DL-4-trifluoromethylphenylalanine in place of N-t-butoxycarbonyl-L-4-nitrophenylalanine and 0.78 g (1.5 mmol) of PyBOP in place of BOP, and purification was carried out by changing the eluent composition in the silica gel column chromatography method to (hexane/ethyl acetate=5/1–3/1), the reaction was carried out to obtain 0.31 g (0.82 mmol) of ethyl 5-[N-t-butoxycarbonyl-DL-4-trifluoromethylphenylalanyl]-4,5,6,7-tetrahydrothieno[3,2-c]pyridin-2-acetate as colorless oily product.

$^1$H-NMR (CDCl$_3$) δ; 7.52–7.40 (m, 2H), 7.31–7.24 (m, 2H), 6.61, 6.38 (each s, total 1H), 5.50–5.34 (m, 1H), 5.00–4.86 (m, 1H), 4.66–4.32 (m, 2H), 4.22–4.01 (m, 3H), 3.73, 3.70 (each s, total 2H), 3.68–3.46 (m, 1H), 3.18–2.99 (m, 2H), 2.80–2.37 (m, 2H), 1.41, 1.39 (each s, total 9H), 1.25 (t, J=8.0 Hz, 3H).
CI-MS (m/z); 485

(57-B) In the same manner as in Example I-(1-B) except for using 0.31 g (0.57 mmol) of ethyl 5-(N-t-butoxycarbonyl-DL-4-trifluoromethylphenylalanyl)-4,5,6,7-tetrahydrothieno[3,2-c]pyridin-2-acetate in place of ethyl 5-[N-t-butoxycarbonyl-L-4-nitrophenylalanyl]-4,5,6,7-tetrahydrothieno[3,2-c]pyridin-2-acetate, the reaction was carried out to obtain 0.49 g (0.55 mmol) of the title compound as white foamy product.

$^1$H-NMR (CDCl$_3$) δ; 7.89–7.79 (m, 4H), 7.53–7.15 (m, 4H), 6.63, 6.40 (each s, total 1H), 5.52–5.37 (m, 1H), 4.71–4.35 (m, 1H), 4.22–4.14 (m, 2H), 4.20–4.02 (m, 1H), 3.73, 3.71 (each s, total 2H), 3.70–3.47 (m, 2H), 3.55–3.20 (m, 2H), 2.80–2.34 (m, 2H), 1.59–1.36 (m, 27H), 1.31–1.25 (m, 3H).
FAB-MS (m/z); 787

Example I-58

Ethyl 5-[N-(4-amidinobenzoyl)-DL-4-trifluoromethylphenylalanyl]-4,5,6,7-tetrahydrothieno[3,2-c]pyridin-2-acetate.trifluoroacetate (Ethyl ester of Exemplary compound No. 1-5)

In the same manner as in Example I-2 except for using 0.49 g (0.55 mmol) of ethyl 5-[N-[4-(N,N,N'-tri-t-butoxycarbonylamidino)benzoyl]-DL-4-trifluoromethylphenylalanyl]- 4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.32 g (0.45 mmol) of the title compound as white powder.

Melting point; 192–198° C.
$^1$H-NMR (400 MHz, CD$_3$OD) δ; 7.98–7.91 (m, 2H), 7.87–7.84 (m, 2H), 7.55–7.42 (m, 4H), 6.65, 6.53 (each s, total 1H), 5.45–5.39 (m, 1H), 4.65–4.39 (m, 2H), 4.17–4.11 (m, 2H), 4.04–3.65 (m, 2H), 3.75, 3.70 (each s, total 2H), 3.35–3.17 (m, 2H), 2.84–2.35 (m, 2H), 1.26–1.23 (m, 3H).
FAB-MS (m/z); 587

Example I-59

Ethyl 5-[N-[4-(N,N,N'-tri-t-butoxycarbonylamidino) benzoyl]-DL-4-(N-benzoylamino)phenylalanyl]-4,5,6,7-tetrahydrothieno[3,2-c]pyridin-2-acetate (Ethyl ester of Exemplary compound No. 1-73)

(59-A) In the same manner as in Example I-(1-A) except for using 0.10 g (0.26 mmol) of N-t-butoxycarbonyl-DL-4-(N-benzoylamino)phenylalanine in place of N-t-butoxycarbonyl-L-4-nitrophenylalanine, and purification was carried out by changing the eluent composition in the silica gel column chromatography method to (chloroform/ethyl acetate=100/1–50/1), the reaction was carried out to obtain 0.06 g (0.1 mmol) of ethyl 5-(N-t-butoxycarbonyl-DL-4-(N-benzoylamino)phenylalanyl)-4,5,6,7-tetrahydrothieno[3,2-c]pyridin-2-acetate as pale yellowish foamy product.

$^1$H-NMR (CDCl$_3$) δ; 8.14–7.94 (m, 2H), 7.40–7.29 (m, 2H), 6.61, 6.32 (each s, total 1H), 5.56–5.35 (m, 1H), 5.01–4.88 (m, 1H), 4.70–4.29 (m, 2H), 4.26–4.03 (m, 1H), 4.18 (q, J=7.3 Hz, 2H), 3.73, 3.67 (each s, total 2H), 3.63–3.24 (m, 1H), 3.23–3.00 (m, 2H), 2.89–2.48 (m, 2H), 1.43, 1.40 (each s, total 9H), 1.32–1.25 (m, 3H).
CI-MS (m/z); 592

(59-B) In the same manner as in Example I-(1-B) except for using 0.06 g (0.10 mmol) of ethyl 5-[N-t-butoxycarbonyl-DL- 4-(N-benzoylamino)phenylalanyl]-4,5,6,7-tetrahydrothieno[3,2-c]pyridin-2-acetate in place of ethyl 5-[N-t-butoxycarbonyl-L-4-nitrophenylalanyl]-4,5,6,7-tetrahydrothieno[3,2-c]pyridin-2-acetate, the reaction was carried out to obtain 0.09 g (0.10 mmol) of the title compound as white foamy product.
FAB-MS (m/z); 638

Example I-60

Ethyl 5-[N-(4-amidinobenzoyl)-DL-4-(N-benzoylamino) phenylalanyl]-4,5,6,7-tetrahydrothieno[3,2-c]pyridin-2-acetate.trifluoroacetate (Ethyl ester of Exemplary compound No. 1-75)

In the same manner as in Example I-2 except for using 0.09 g (0.10 mmol) of ethyl 5-[N-[4-(N,N,N'-tri-t-butoxycarbonylamidino)benzoyl]-DL-4-(N-benzoylamino) phenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.05 g (0.07 mmol) of the title compound as white powder.

Melting point; 144–147° C.
$^1$H-NMR (400 MHz, CD$_3$OD) δ; 8.02–7.99 (m, 2H), 7.91–7.86 (m, 4H), 7.59–7.48 (m, 5H), 7.27–7.21 (m, 2H), 6.63, 6.51 (each s, total 1H), 5.38–5.32 (m, 1H), 4.55–4.38 (m, 2H), 4.17–4.06 (m, 2H), 3.79–3.45 (m, 2H), 3.74, 3.67 (each s, total 2H), 3.29–3.11 (m, 2H), 2.80–2.34 (m, 2H), 1.24–1.19 (m, 3H).
FAB-MS (m/z); 637

Example I-61

Ethyl 5-[N-[4-(N,N,N'-tri-t-butoxycarbonylamidino) benzoyl]-DL-3-nitrophenylalanyl]-4,5,6,7-tetrahydrothieno [3,2-c]pyridin-2-acetate (Ethyl ester of Exemplary compound No. 1-77)

(61-A) In the same manner as in Example I-(1-A) except for using 0.31 g (1.0 mmol) of N-t-butoxycarbonyl-DL-3-nitrophenylalanine in place of N-t-butoxycarbonyl-L-4-nitrophenylalanine and 0.78 g (1.5 mmol) of PyBOP in place of BOP, and purification was carried out by changing the eluent composition in the silica gel column chromatography method to (chloroform/ethyl acetate=100/1–50/1), the reaction was carried out to obtain 0.41 g (1.0 mmol) of ethyl 5-(N-t-butoxycarbonyl-DL-3-nitrophenylalanyl)-4,5,6,7-tetrahydrothieno[3,2-c]pyridin-2-acetate as colorless foamy product.

¹H-NMR (CDCl₃) δ; 8.09–7.87 (m, 2H), 7.53–7.28 (m, 2H), 6.61, 6.31 (each s, total 1H), 5.56–5.40 (m, 1H), 4.99–4.88 (m, 1H), 4.68–4.45 (m, 1H), 4.37–4.10 (m, 4H), 3.73, 3.70 (each s, total 2H), 3.70–3.56 (m, 1H), 3.37–2.99 (m, 2H), 2.88–2.46 (m, 2H), 1.43, 1.39 (each s, total 9H), 1.33–1.23 (m, 3H).

CI-MS (m/z); 518

(61-B) In the same manner as in Example I-(1-B) except for using 0.42 g (1.0 mmol) of ethyl 5-(N-t-butoxycarbonyl-DL-3-nitrophenylalanyl)-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate and using 0.78 g (1.5 mmol) of PyBOP In place of BOP, and purification was carried out by changing the eluent composition in the silica gel column chromatography method to (chloroform/ethyl acetate=70/1–20/1), the reaction was carried out to obtain 0.83 g (1.1 mmol) of the title compound as white foamy product.

¹H-NMR (CDCl₃) δ; 8.12–7.80 (m, 6H), 7.55–7.41 (m, 1H), 7.38–7.18 (m, 1H), 6.63, 6.34 (each s, total 1H), 5.54–5.40 (m, 1H), 4.73–4.20 (m, 2H), 4.26–4.17 (m, 2H), 3.74, 3.72 (each s, total 2H), 3.70–3.60 (m, 1H), 3.41–3.16 (m, 3H), 2.90–2.50 (m, 2H), 1.68–1.37 (m, 27H), 1.31–1.23 (m, 3H).

FAB-MS (m/z); 764

Example I-62

Ethyl 5-[N-(4-amidinobenzoyl)-DL-3-nitrophenylalanyl]-4,5,6,7-tetrahydrothieno[3,2-c]pyridin-2-acetate.trifluoroacetate (Ethyl ester of Exemplary compound No. 1-15)

In the same manner as in Example I-2 except for using 0.83 g (1.1 mmol) of ethyl 5-[N-[4-(N,N,N'-tri-t-butoxycarbonylamidino)benzoyl]-DL-3-nitrophenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.51 g (0.74 mmol) of the title compound as white powder.

Melting point; 206–208° C.

¹H-NMR (400 MHz, CD₃OD) δ; 8.18, 8.11 (each s, total 1H), 8.07–7.85 (m, 5H), 7.73–7.64 (m, 1H), 7.52–7.37 (m, 1H), 6.63, 6.39 (each s, total 1H), 5.44–5.41 (m, 1H), 4.63–4.42 (m, 2H), 4.32–4.27 (m, 1H), 4.19–4.13 (m, 2H), 3.88–3.86 (m, 1H), 3.75, 3.71 (each s, total 2H), 3.41–3.22 (mi 2H), 2.80–2.41 (m, 2H), 1.30–1.24 (m, 3H).

FAB-MS (m/z); 564

Example I-63

Ethyl 5-[N-[4-(N,N,N'-tri-t-butoxycarbonylamidino)benzoyl]-DL-2-chloro-4-nitrophenylalanyl]-4,5,6,7-tetrahydrothieno[3,2-c]pyridin-2-acetate (Ethyl ester of Exemplary compound No. 1-84)

(63-A) In the same manner as in Example I-(1-A) except for using 0.34 g (1.00 mmol) of N-t-butoxycarbonyl-DL-2-chloro-4-nitrophenylalanine in place of N-t-butoxycarbonyl-L-4-nitrophenylalanine and 0.80 g (1.5 mmol) of PyBOP in place of BOP, and purification was carried out by changing the eluent composition in the silica gel column chromatography method to (chloroform/ethyl acetate=50/1–20/1), the reaction was carried out to obtain 0.45 g (0.82 mmol) of ethyl 5-(N-t-butoxycarbonyl-DL-2-chloro-4-nitrophenylalanyl)-4,5,6,7-tetrahydrothieno[3,2-c]pyridin-2-acetate as colorless foamy product.

¹H-NM (CDCl₃) δ; 8.25, 8.02 (each d, J=2.2 Hz, total 1H), 8.01–7.86 (m, 1H), 7.40, 7.34 (each d, J=8.8 Hz, total 1H), 6.63, 6.44 (each s, total 1H), 5.57–5.44 (m, 1H), 5.16–5.05 (m, 1H), 4.66–4.50 (m, 1H), 4.45–4.28 (m, 2H), 4.26–4.14 (m, 2H), 3.84–3.75 (m, 1H), 3.74, 3.70 (each s, total 2H), 3.31–3.02 (m, 2H), 2.99–2.60 (m, 2H), 1.39, 1.32 (each s, total 9H), 1.31–1.26 (m, 3H).

CI-MS (m/z); 496

(63-B) In the same manner as in Example I-(1-B) except for using 0.45 g (0.82 mmol) of ethyl 5-(N-t-butoxycarbonyl-DL-2-chloro-4-nitrophenylalanyl)-4,5,6,7-tetrahydrothieno[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate and 0.64 g (1.2 mmol) of PyBOP in place of BOP, the reaction was carried out to obtain 0.69 g (0.76 mmol) of the title compound as pale yellowish foamy product.

¹H-NMR (CDCl₃) δ; 8.27–8.03 (m, 1H), 7.98–7.76 (m, 4H), 7.42–7.37 (m, 1H), 7.27–7.19 (m, 1H), 6.64, 6.45 (each s, total 1H), 5.70–5.61 (m, 1H), 4.65–4.35 (m, 2H), 4.25–4.15 (m, 2H), 3.89–3.72 (m, 1H), 3.74–3.69 (m, 2H), 3.49–3.18 (m, 3H), 2.98–2.65 (m, 2H), 1.60–1.39 (m, 27H), 1.33–1.21 (m, 3H).

FAB-MS (m/z); 798

Example I-64

Ethyl 5-[N-(4-amidinobenzoyl)-DL-2-chloro-4-nitrophenylalanyl]-4,5,6,7-tetrahydrothieno[3,2-c]pyridin-2-acetate.trifluoroacetate (Ethyl ester of Exemplary compound No. 1-16)

In the same manner as in Example I-2 except for using 0.69 g (0.76 mmol) of ethyl 5-[N-[4-(N,N,N'-tri-t-butoxycarbonylamidino)benzoyl]-DL-2-chloro-4-nitrophenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.48 g (0.67 mmol) of the title compound as white powder.

Melting point; 242–245° C.

¹H-NMR (400 MHz, CD₃OD) δ; 8.28, 8.06 (each s, total 1H), 8.03–7.85 (m, 5H), 7.58–7.49 (m, 1H), 6.66, 6.50 (each s, total 1H), 5.61–5.57 (m, 1H), 4.91–4.36 (m, 3H), 4.20–4.12 (m, 2H), 3.90–3.88 (m, 1H), 3.75–3.63 (m, 2H), 3.50–3.19 (m, 2H), 2.87–2.54 (m, 2H), 1.29–1.23 (m, 3H).

FAB-MS (m/z); 598

Example I-65

Ethyl 5-[N-[4-(N,N,N'-tri-t-butoxycarbonylamidino)benzoyl]-DL-3-(4-pyridyl)-alanyl]-4,5,6,7-tetrahydrothieno[3,2-c]pyridin-2-acetate (Ethyl ester of Exemplary compound No. 1-91)

(65-A) To 0.26 g (1.0 mmol) of ethyl 4,5,6,7-tetrahydrothieno[3,2-c]pyridin-2-acetate.HCl salt were added 4 ml of DMF and 0.5 ml of triethylamine to dissolve the salt, and then, 0.26 g (1.0 mmol) of N-t-butoxycarbonyl-DL-3-(4-pyridyl)-alanine and 0.40 g (1.0 mmol) of HBTU were added to the solution and the mixture was stirred at room temperature for 2 hours.

A saturated aqueous sodium bicarbonate solution was added to the resulting reaction mixture and the mixture was extracted with ethyl acetate. The organic layer was successively washed with water and a saturated aqueous saline solution, and dried over anhydrous sodium sulfate. The organic layer was concentrated under reduced pressure and the residue was purified by the silica gel column chromatography method (eluent: chloroform/methanol=150/1–75/1) to obtain 0.50 g (1.0 mmol) of ethyl 5-[N-t-butoxycarbonyl-DL-3-(4-pyridyl)alanyl]-4,5,6,7-tetrahydrothieno[3,2-c]pyridin-2-acetate as yellowish oily product.

¹H-NMR (CDCl₃) δ; 8.51–8.43 (m, 2H), 7.23–7.16 (m, 2H), 6.62, 6.48 (each s, total 1H), 5.57–5.35 (m, 1H), 5.02–4.90 (m, 1H), 4.70–4.42 (m, 1H), 4.23–4.14 (m, 2H), 4.14–3.95 (m, 1H), 3.74, 3.73 (each s, total 2H), 3.72–3.52 (m, 2H), 3.17–2.98 (m, 2H), 2.96–2.55 (m, 2H), 1.41, 1.40 (each s, total 9H), 1.31–1.25 (m, 3H).

CI-MS (m/z); 474

(65-B) In 4 ml of methylene chloride was dissolved 0.50 g (1.06 mmol) of ethyl 5-[N-t-butoxycarbonyl-DL-3-(4-pyridyl)-alanyl]-4,5,6,7-tetrahydrothieno[3,2-c]pyridin-2-acetate, and under ice-cooling, 1 ml of CF₃CO₂H was added to the solution and the mixture was stirred at room temperature for 2 hours.

The reaction mixture was concentrated under reduced pressure to obtain ethyl5-[DL-3-(4-pyridyl)-alanyl]-4,5,6,7-tetrahydrothieno[3,2-c]pyridin-2-acetate.CF₃CO₂H. This compound was dissolved in 5 ml of DMF, and 0.45 g (1.00 mmol) of 4-(N,N,N'-tri-t-butoxycarbonylamidino)benzoic acid, 1 ml of triethylamine and 0.40 g (1.10 mmol) of HBTU were added to the solution and the mixture was stirred at room temperature for 2 hours. A saturated aqueous sodium bicarbonate solution was added to the mixture and the mixture was extracted with ethyl acetate. The extract was washed with a saturated aqueous saline solution, and dried over anhydrous sodium sulfate. The organic layer was concentrated under reduced pressure and the residue was purified by the silica gel column chromatography method (eluent: chloroform/methanol=200/1–100/1) to obtain 0.35 g (0.43 mmol) of the title compound as yellowish oily product.

¹H-NMR (400 MHz, CD₃OD) δ; 8.56–8.48 (m, 2H), 8.17–7.81 (m, 4H), 7.34–7.20 (m, 2H), 6.64, 6.50 (each s, total 1H), 5.60–5.47 (m, 1H), 4.73–4.45 (m, 1H), 4.28–4.06 (m, 4H), 3.77, 3.74 (each s, total 2H), 3.75–3.61 (m, 2H), 3.40–3.16 (m, 2H), 2.85–2.60 (m, 2H), 1.54 (s, 9H), 1.36 (s, 18H), 1.31–1.25 (m, 3H).

FAB-MS (m/z); 820

Example I-66

Ethyl 5-[N-(4-amidinobenzoyl)-DL-3-(4-pyridyl)-alanyl]-4,5,6,7-tetrahydrothieno[3,2-c]pyridin-2-acetate.di-trifluoroacetate (Ethyl ester of Exemplary compound No. 1-14)

In the same manner as in Example I-2 except for using 0.27 g (0.33 mmol) of ethyl 5-(N-[4-(N,N,N'-tri-t-butoxycarbonylamidino)benzoyl]-DL-3-(4-pyridyl)-alanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothienof3,2-c]pyridin-2-acetate, the reaction was carried out to obtain 0.21 g (0.29 mmol) of the title compound as pale yellowish powder.

Melting point; 128–130° C.

¹H-NMR (400 MHz, CD₃OD) δ; 8.62–8.55 (m, 2H), 8.00–7.84 (m, 6H), 6.66, 6.52 (each s, total 1H), 5.61–5.54 (m, 1H), 4.71–4.42 (m, 2H), 4.20–4.12 (m, 2H), 4.24–3.74 (m, 2H), 3.76 (s, 2H), 3.61–3.31 (m, 2H), 2.84–2.61 (m, 2H), 1.29–1.22 (m, 3H).

FAB-MS (m/z); 520

Example I-67

Ethyl 5-[N-[3-(N-t-butoxycarbonyl-4-piperidyl)propenoyl]-L-4-nitrophenylalanyl]-4,5,6,7-tetrahydrothieno[3,2-c]pyridin-2-acetate (Ethyl ester of Exemplary compound No. 1-93)

In the same manner as in Example I-1 except for using 0.20 g (0.77 mmol) of 3-(N-t-butoxycarbonyl-4-piperidyl) propenoic acid in place of 4-(N,N,N'-tri-t-butoxycarbonylamidino)benzoic acid and 0.60 g (1.2 mmol) of PyBOP in place of BOP, and purification was carried out by changing the eluent composition in the silica gel column chromatography method to (chloroform/ethyl acetate=40/1–10/1), the reaction was carried out to obtain 0.46 g (0.70 mmol) of the title compound as white solid.

¹H-NMR (CDCl₃) δ; 8.10, 7.96 (each d, J=8.8 Hz, total 2H), 7.31, 7.27 (each d, J=8.8 Hz, total 2H), 6.86–6.75 (m, 1H), 6.61, 6.39 (each s, total 1H), 6.53–6.39 (m, 1H), 5.82–5.73 (m, 1H), 5.41–5.29 (m, 1H), 4.59–4.23 (m, 2H), 4.22–4.02 (m, 5H), 3.73, 3.67 (each s, total 2H), 3.65–3.03 (m, 3H), 2.88–2.60 (m, 3H), 2.60–2.19 (m, 2H), 1.78–1.65 (m, 2H), 1.63, 1.46 (each s, total 9H), 1.45–1.35 (m, 2H), 1.28 (t, J=7.3 Hz, 3H).

FAB-MS (m/z); 655

Example I-68

Ethyl 5-[N-[3-(4-piperidyl)propenoyl]-L-4-nitrophenylalanyl]-4,5,6,7-tetrahydrothieno[3,2-c]pyridin-2-acetate.trifluoroacetate (Ethyl ester of Exemplary compound No. 1-143)

In the same manner as in Example I-2 except for using 0.46 g (0.70 mmol) of ethyl 5-[N-[3-(N-t-butoxycarbonyl-4-piperidyl)propenoyl]-L-4-nitrophenylalanyl]- 4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.34 g (0.61 mmol) of the title compound as pale yellowish powder.

Melting point; 102–104° C.

¹H-NMR (400 MHz, CD₃OD) δ; 8.08–7.94 (m, 2H), 7.48–7.39 (m, 2H), 6.73–6.64 (m, 1H), 6.63, 6.42 (each s, total 1H), 6.07–5.98 (m, 1H), 5.30–5.24 (m, 1H), 4.58–4.44 (m, 1H), 4.34, 3.74 (each s, total 2H), 4.33–3.85 (m, 2H), 4.18–4.12 (m, 2H), 3.73–3.62 (m, 1H), 3.42–3.38 (m, 2H), 3.29–3.23 (m, 1H), 3.12–3.02 (m, 3H), 2.79–2.43 (m, 3H), 2.01–1.97 (m, 2H), 1.61–1.54 (m, 2H), 1.27–1.23 (m, 3H).

FAB-MS (m/z); 555

Example I-69

Ethyl 5-[N-[3-(N-t-butoxycarbonyl-4-piperidyl)propanoyl]-L-4-nitrophenylalanyl]-4,5,6,7-tetrahydrothieno[3,2-c]pyridin-2-acetate (Ethyl ester of Exemplary compound No. 1-78)

In the same manner as in Example I-1 except for using 0.20 g (0.77 mmol) of 3-(N-t-butoxycarbonyl-4-piperidyl) propionic acid in place of 4-(N,N,N'-tri-t-butoxycarbonylamidino)benzoic acid and 0.60 g (1.2 mmol) of PyBOP in place of BOP, the reaction was carried out to obtain 0.48 g (0.73 mmol) of the title compound as white solid.

¹H-NMR (CDCl₃) δ; 8.10, 7.96 (each d, J=8.8 Hz, total 2H), 7.32, 7.27 (each d, J=8.8 Hz, total 2H), 6.62, 6.31 (each s, total 1H), 6.52–6.40 (m, 1H), 5.37–5.19 (m, 1H), 4.68–4.27 (m, 2H), 4.24–4.12 (m, 2H), 4.11–4.04 (m, 2H), 3.73, 3.67 (each s, total 2H), 3.65–3.02 (m, 4H), 2.85–2.48 (m, 4H), 2.28–2.17 (m, 2H), 1.71–1.50 (m, 5H), 1.45 (s, 9H), 1.31–1.23 (m, 3H), 1.20–1.14 (m, 2H).

FAB-MS (m/z); 657

Example I-70

Ethyl 5-[N-[3-(4-piperidyl)propanoyl]-L-4-nitrophenylalanyl]-4,5,6,7-tetrahydrothieno[3,2-c]pyridin-2-acetate.p-toluenesulfonate (Ethyl ester of Exemplary compound No. 1-145)

In 5 ml of methylene chloride was dissolved 0.48 g (0.70 mmol) of ethyl 5-[N-[3-(N-t-butoxycarbonyl-4-piperidyl)

propanoyl]-L-4-nitrophenylalanyl]-4,5,6,7-tetrahydrothieno[3,2-c]pyridin-2-acetate, and then, 1 ml of $CF_3CO_2H$ was added to the solution and the mixture was stirred at room temperature for one hour.

The reaction mixture was concentrated under reduced pressure to obtain a residue. The resulting residue was dissolved in ethanol, 0.13 g (0.70 mmol) of $TsOH.H_2O$ was added to the solution and the liquid was made uniform. To the mixture was added diethyl ether and formed precipitates were collected by filtration. Theprecipitateswere washed-withdiethylether and dried to obtain 0.32 g (0.44 mmol) of the title compound as highly hygroscopic pale yellowish powder.

$^1$H-NMR (400 MHz, $CD_3OD$) δ; 8.10, 7.97 (each d, J=8.8 Hz, total 2H), 7.49, 7.41 (each d, J=8.8 Hz, total 2H), 6.64, 6.44 (each s, total 1H), 5.26–5.18 (m, 1H), 4.63–4.36 (m, 2H), 4.23–4.13 (m, 3H), 3.87–3.63 (m, 3H), 3.40–3.30 (m, 2H), 3.10–3.04 (m, 2H), 2.95–2.45 (m, 4H), 2.26–2.18 (m, 2H), 1.98–1.82 (m, 2H), 1.60–1.45 (m, 3H), 1.38–1.25 (m, 2H), 1.27–1.22 (m, 3H).

FAB-MS (m/z); 557

$[α]_D^{20}$; −16° (MeOH, c=0.308)

Example I-71
Ethyl 5-[(N-t-butoxycarbonyl-4-piperidyloxyacetyl)-L-4-nitrophenylalanyl]-4,5,6,7-tetrahydrothieno[3,2-c]pyridin-2-acetate (Ethyl ester of Exemplary compound No. 1-96)

In the same manner as in Example I-1 except for using 0.31 g (1.2 mmol) of N-t-butoxycarbonyl-4-piperidyloxyacetic acid in place of 4-(N,N,N'-tri-t-butoxycarbonylamidino)benzoic acid and 0.94 g (1.8 mmol) of PyBOP in place of BOP, the reaction was carried out to obtain 0.40 g (0.73 mmol) of the title compound. as colorless oily product.

$^1$H-NMR (400 MHz, $CD_3OD$) δ; 8.11, 7.97 (each d, J=8.8 Hz, total 2H), 7.35, 7.30 (each d, J=8.8 Hz, total 2H), 6.61, 6.33 (each s, total 1H), 5.37–5.22 (m, 1H), 4.68–4.44 (m, 1H), 4.33–4.04 (m, 2H), 4.18 (q, J=7.3 Hz, 2H), 3.99–3.96 (m, 2H), 3.91–3.66 (m, 3H), 3.73, 3.61 (each s, total 2H), 3.57–3.46 (m, NH), 3.41–3.22 (m, iH), 3.18–2.96 (m, 4H), 2.84–2.43 (m, 2H), 1.91–1.78 (m, 2H), 1.65–1.50 (m, 2H), 1.46 (s, 9H), 1.29 (t, J=7.3 Hz, 3H).

FAB-MS (m/z); 659

Example I-72
Ethyl 5-[N-(4-piperidyloxyacetyl)-L-4-nitrophenylalanyl]-4,5,6,7-tetrahydrothieno[3,2-c]pyridin-2-acetate.hydrochloride (Ethyl ester of Exemplary compound No. 1-137)

In the same manner as in Example I-70 except for using 0.40 g (0.73 mmol) of ethyl 5-[(N-t-butoxycarbonyl-4-piperidyloxyacetyl)-L-4-nitrophenylalanyl]-4,5,6,7-tetrahydrothieno[3,2-c]pyridin-2-acetate in place of 5-[N-[3-(N-t-butoxycarbonyl-4-piperidyl)propanoyl]-L-4-nitrophenylalanyl]-4,5,6,7-tetrahydrothieno[3,2-c]pyridin-2-acetate and an ether solution saturated by hydrogen chloride in place of $TsOH.H_2O$, the reaction was carried out to obtain 0.19 g (0.31 mmol) of the title compound as brownish powder.

$^1$H-NMR (400 MHz, $CDCl_3$) δ; 8.13–7.97 (m, 2H), 7.42–7.29 (m, 2H), 6.62, 6.31 (each s, total 1H), 5.30–5.21 (m, 1H), 4.68–4.23 (m, 2H), 4.21–4.15 (m, 2H), 4.06–3.90 (m, 3H), 3.73–3.62 (m, 4H), 3.53–3.07 (m, 6H), 2.80–2.48 (m, 2H), 2.25–2.14 (m, 2H), 2.09–2.01 (m, 2H), 1.32–1.25 (m, 3H).

FAB-MS (m/z); 559

Example I-73
Ethyl 5-[N-(4-N,N,N'-tri-t-butoxycarbonylamidinobenzoyl)-N-methyl-DL-4-nitrophenylalanyl]-4,5,6,7-tetrahydrothieno[3,2-c]pyridin-2-acetate (Ethyl ester of Exemplary compound No. 1-125)

(73-A) In 10 ml of methylene chloride was suspended 0.27 g (0.90 mmol) of N-methyl-DL-4-nitrophenylalanine ethyl ester.HCl, 0.092 g (0.91 mmol) of triethylamine, 0.47 g (1.0 mmol) of 4-(N,N,N'-tri-t-butoxycarbonylamidino)benzoic acid, 0.010 g (0.10 mmol) of 4-dimethylaminopyridine and 0.57 g (1.3 mmol) of BOP were added to the suspension, and the mixture was stirred at room temperature for 3 hours.

The reaction mixture was concentrated under reduced pressure, ethyl acetate was added to the residue, and the mixture was washed successively with a 5% aqueous potassium hydrogen sulfate solution, a saturated aqueous sodium bicarbonate solution and a saturated aqueous saline solution, and dried over anhydrous sodium sulfate. The organic layer was concentrated under reduced pressure and the residue was purified by the silica gel column chromatography method (eluent: n-hexane/ethyl acetate=7/3) to obtain 0.43 g (0.62 mmol) of N-[4-(N,N,N'-tri-t-butoxycarbonylamidino)benzoyl]-N-methyl-DL-4-nitrophenylalanine ethyl ester as pale yellowish foamy product.

$^1$H-NMR ($CDCl_3$) δ; 8.22, 8.12 (each d, J=8.1 Hz, total 2H), 7.84, 7.78 (each d, J=8.1 Hz, total 2H), 7.50, 7.12 (each d, J=8.1 Hz, total 2H), 7.25, 7.05 (each d, J=8.1 Hz, total 2H), 5.42–5.32, 4.65–4.45 (each m, total 1H), 4.38–4.22 (m, 2H), 3.65–3.55 (m, 1H), 3.40–3.25 (m, 1H), 3.09, 2.80 (each s, total 3H), 1.54 (s, 9H), 1.36 (s, 18H), 1.33–1.23 (m, 3H).

(73-B) In 10 ml of methanol was dissolved 0.43 g (0.62 mol) of N-[4-(N,N,N'-tri-t-butoxycarbonylamidino)benzoyl]-N-methyl-DL-4-nitrophenylalanine ethyl ester, a solution of 5 ml of water conaining 0.078 g (1.9 mmol) of lithiumhydroxide.$H_2O$ and the mixture was stirred at room temperature for 15 minutes.

To the resulting reaction mixture was added 1.5 ml of a 1N aqueous hydrogen chloride solution, and the mixture was concentrated under reduced pressure. To the residue was added ethyl acetate an the mixture was washed successively with a 5% aqueous potassium hydrogen sulfate solution, a.saturated aqueous sodium bicarbonate solution and a saturated aqueous saline solution, and dried over anhydrous sodium sulfate. The organic layer was concentratedunderreducedpressure toobtain 0.40 g (0.60 mmol) of N-[4-(N,N,N'-tri-t-butoxycarbonylamidino)benzoyl]-N-methyl-DL-4-nitrophenylalanine as pale yellowish foamy product.

(73-C) In 10 ml of methylene chloride was suspended 0.16 g (0.60 mmol) of ethyl 4,5,6,7-tetrahydrothieno[3,2-c]pyridin-2-acetate.HCl, and 0.062 g (0.61 mmol) of triethylamine, 0.40 g (0.60 mmol) of N-[4-(N,N,N'-tri-t-butoxycarbonylamidino)benzoyl]-N-methyl-DL-4-nitrophenylalanine, 0.33 g (0.73 mmol) of BOP and 0.012 g (0.10 mmol) of 4-dimethylaminopyridine were added to the suspension, and the mixture was stirred at room temperature for 3 hours.

The resulting reaction mixture was concentrated under reduced pressure, ethyl acetate was added to the residue and the mixture was washed successively with a 5% aqueous potassium hydrogen sulfate solution, a saturated aqueous sodium bicarbonate solution and a saturated aqueous saline solution, and dried over anhydrous sodium sulfate. The organic layer was concentrated under reduced pressure and the residue was purified by the silica gel column chromatography method (eluent: chloroform/ethyl acetate=20/1) to obtain 0.45 g (0.51 mmol) of the title compound as white foamy product.

$^1$H-NMR ($CDCl_3$) δ; 8.18, 8.14 (each d, J=8 Hz, total 2H), 7.86, 7.82 (each d, J=8 Hz, total 2H), 7.53, 7.50 (each d, J=8

Hz, total 2H), 7.25, 7.10 (each d, J=8 Hz, total 2H), 6.64, 6.55 (each s, total 1H), 6.03–5.88 (m, 1H), 4.78–4.40 (m, 2H), 4.25–4.10 (m, 2H), 4.05–3.90 (m, 1H), 3.88–3.75 (m, 1H), 3.74, 3.70 (each s, total 2H) 3.58–3.42 (m, 1H), 3.22–3.05 (m, 1H), 2.91, 2.83 (each s, total 3H), 2.80–2.70 (m, 2H), 1.53 (s, 9H), 1.37 (s, 18H), 1.31–1.23 (m, 3H).

FAB-MS (m/z); 878

Example I-74

Ethyl 5-[N-(4-amidinobenzoyl)-N-methyl-DL-4-nitrophenylalanyl]-4,5,6,7-tetrahydrothieno[3,2-c]pyridin-2-acetate.trifluoroacetate (Ethyl ester of Exemplary compound No. 1-31)

In the same manner as in Example I-2 except for using 0.45 g (0.51 mmol) of 5-[N-(4-N,N,N'-tri-t-butoxycarbonylamidinobenzoyl)-N-methyl-DL-4-nitrophenylalanyl]-4,5,6,7-tetrahydrothieno[3,2-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.28 g (0.40 mmol) of the title compound as pale yellowish powder.

Melting point; 145–150° C.

$^1$H-NMR (400 MHz, DMSO-$d_6$) δ; 9.34, 9.32 (each s, total 1H), 9.23 (s, 2H), 8.17, 8.14 (each d, J=8.8 Hz, total 2H), 7.80, 7.75 (each d, J=8.3 Hz, total 2H), 7.67, 7.63 (each d, J=8.8 Hz, total 2H), 7.30, 7.09 (each d, J=8.3 Hz, total 2H), 6.74, 6.61 (each s, total 1H), 5.94–5.84 (m, 1H), 4.65–4.42 (m, 2H), 4.11–4.05 (m, 2H), 3.93–3.83 (m, 1H), 3.82, 3.81 (each s, total 2H), 3.72–3.62 (m, 1H), 3.39–3.34 (m, 2H), 3.29–3.22 (m, 2H), 2.92–2.85 (m, 1H), 2.76 (s, 3H), 2.72–2.60 (m, 1H), 1.20–1.16 (m, 3H).

FAB-MS (m/z); 578

Example I-75

Ethyl 5-[N-(4-N,N,N'-tri-t-butoxycarbonylamidinobenzoyl)-L-4-nitrophenylalanyl]-4,5,6,7-tetrahydropyrazolo[4,3-c]pyridin-2-acetate (Ethyl ester of Exemplary compound No. 2-201)

(75-A) In the same manner as in Example I-(1-A) except for using 0.30 g (0.79 mnol) of ethyl 4,5,6,7-tetrahydropyrazolo[4,3-c]pyridin-2-acetate.TsOH in place of ethyl 4,5,6,7-tetrahydrothieno[3,2-c]pyridin-2-acetate.HCl, the reaction was carried out to obtain 0.38 g (0.76 mmol) of ethyl 5-(N-t-butoxycarbonyl-L-4-nitrophenylalanyl)-4,5,6,7-tetrahydropyrazolo[4,3-c]pyridin-2-acetate as white solid.

$^1$H-NMR (CDCl$_3$) δ; 8.11–7.97 (m, 2H), 7.36–7.02 (m, 3H), 5.55–5.35 (m, 1H), 5.02–4.19 (m, 8H), 3.78–2.42 (m, 5H), 1.42–1.39 (m, 9H), 1.29 (t, J=7.33 Hz, 3H).

CI-MS (m/z); 502

(75-B) In the same manner as in Example I-(1-B) except for using 0.25 g (0.50 mmol) of ethyl 5-(N-t-butoxycarbonyl-L-4-nitrophenylalanyl)-4,5,6,7-tetrahydropyrazolo[4,3-c]pyridin-2-acetate in place of ethyl 5-(N-t-butoxycarbonyl-L-4-nitrophenylalanyl)-4,5,6,7-tetrahydrothieno[3,2-c]-pyridin-2-acetate, the reacton was carried out to obtain 0.42 g (0.50 mmol) of the title compound as white foamy product.

$^1$H-NMR (CDCl$_3$) δ; 8.11–7.80 (m, 6H), 7.36–7.32 (m, 2H), 7.16–6.98 (m, 1H), 5.51–5.41 (m, 1H), 4.83–4.22 (m, 5H), 4.12 (q, J=7.3, 2H), 3.76–2.56 (m, 6H), 1.55 (s, 9H), 1.37 (s, 18H), 1.33–1.26 (m, 3H).

FAB-MS (m/z); 848

Example I-76

Ethyl 5-[N-(4-amidinobenzoyl)-L-4-nitrophenylalanyl]-4,5,6,7-tetrahydropyrazolo[4,3-c]pyridin-2-acetate.trifluoroacetate (Ethyl ester of Exemplary compound No. 2-3)

In the same manner as in Example I-2 except for using 0.27 g (0.28 mmol) of ethyl 5-[N-(4-N,N,N'-tri-t-butoxycarbonylamidinobenozyl)-L-4-nitrophenylalanyl]-4,5,6,7-tetrahydropyrazolo[4,3-c]pyridin-2-acetate in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 0.15 g (0.22 mmol) of the title compound as white powder.

Melting point; 133–136° C.

$^1$H-NMR (400MHz, DMSO-$d_6$) δ; 9.53 (s, 2H), 9.23, 9.09 (each d, J=8.8 Hz, total 1H), 9.10 (s, 2H), 8.09–7.56 (m, 8H), 7.52, 7.45 (each s, total 1H), 5.35–5.25 (m, 1H), 4.95–4.30 (m, 4H), 4.12 (q, J=7.3 Hz, 2H), 3.95–3.80 (m, 1H), 3.70–3.60 (m, 2H), 3.28–3.10 (m, 2H), 2.58–2.52 (m, 1H), 1.19 (t, J=7.3 Hz, 3H).

FAB-MS (m/z); 548

Example I-77

Ethyl 5-[N-[4-(N-ethoxycarbonylamidino)benzoyl]-L-4-nitrophenylalanyl]-4,5,6,7-tetrahydropyrazolo[4,3-c]pyridin-2-acetate (Ethyl ester of Exemplary compound No. 2-124)

In the same manner as in Example I-8 except for using 0.41 g (0.61 mmol) of ethyl 5-(N-(4-amidinobenzoyl)-L-4-nitrophenylalanyl)-4,5,6,7-tetrahydropyrazolo[4,3-c]pyridin- 2-acetate.CF$_3$CO$_2$H in place of ethyl 5-[N-(4-amidinobenozyl)-L-4-nitrophenylalanyl]-4,5,6,7-tetrahydrothieno[3,2-c]pyridin-2-acetate.CF$_3$CO$_2$H, the reaction was carried out to obtain 0.27 g (0.44 mmol) of the title compound as pale yellowish powder.

Melting point; 104–107° C.

$^1$H-NMR (400 MHz, DMSO-$d_6$) δ; 9.12–8.98 (m, 3H), 8.11–7.55 (m, 8H), 7.51, 7.44 (each s, total 1H), 5.36–5.24 (m, 1H), 4.98–4.31 (m, 4H), 4.18–4.03 (m, 4H), 3.91–3.82 (m, 1H), 3.75–3.59 (m, 1H), 3.29–3.13 (m, 2H), 2.65–2.52 (m, 2H), 1.29–1.09 (m, 6H).

FAB-MS (m/z); 620

Example I-78

5-[N-[4-(N,N,N'-tri-t-butoxycarbonylamidino)benzoyl]-L-4-nitrophenylalanyl]-4,5,6,7-tetrahydropyrazolo[4,3-c]pyridin-2-acetic acid (Exemplary compound No. 2-201)

In the same manner as in Example I-4 except for using 3.05 g (3.60 mol) of ethyl 5-[N-[4-(N,N,N'-tri-t-butoxycarbonylamidino)benzoyl]-L-4-nitrophenylalanyl]-4,5,6,7-tetrahydropyrazolo[4,3-c]pyridin-2-acetate in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 2.81 g (3.43 mmol) of the title compound as yellowish foamy product.

$^1$H-NMR (CDCl$_3$) S; 8.13–7.09 (m, 9H), 5.58–5.41 (m, 1H), 4.95–4.19 (m, 5H), 3.78–2.40 (m, 5H), 1.54 (s, 9H), 1.38–1.36 (m, 27H).

FAB-MS (m/z); 820

Example I-79

5-[N-(4-amidinobenzoyl)-L-4-nitrophenylalanyl]-4,5,6,7-tetrahydropyrazolo[4,3-c]pyridin-2-acetic acid.trifluoroacetate (Exemplary compound No. 2-3)

In the same manner as in Example 1–2 except for using 0.15 g (0.18 mmol) of 5-[N-[4-(N,N,N'-tri-t-butoxycarbonylamidino)benzyl]-L-4-nitrophenylalanyl)-4,5,6,7-tetrahydropyrazolo[4,3-c]pyridin-2-acetic acid in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 0.080 g (0.13 mmol) of the title compound as pale yellowish powder.

Melting point; 216° C.- (decomposed)

$^1$H-NMR (400 MHz, DMSO-$d_6$) δ; 9.78–9.06 (m, 5H), 8.11–8.01 (m, 2H), 7.99–7.89 (m, 2H), 7.85–7.78 (m, 2H), 7.63–7.10 (m, 3H), 5.39–5.27 (m, 1H), 4.83–4.23 (m, 4H), 3.99–3.59 (m, 2H), 3.20–3.11 (m, 2H), 2.60–2.50 (m, 2H).

FAB-MS (m/z); 520

Example I-80

Isopropyl 5-[N-[4-(N,N,N'-tri-t-butoxycarbonylamidino)benzoyl)-L-4-nitrophenylalanyl)-4,5,6,7-tetrahydropyrazolo[4,3-c]pyridin-2-acetate (Isopropyl ester of Exemplary compound No. 2-201)

In the same manner as in Example I-6 except for using 0.51 g (0.62 mmol) of 5-[N-[4-(N,N,N'-tri-t-butoxycarbonylamidino)benozyl]-L-4-nitrophenylalanyl]-4,5,6,7-tetrahydropyrazolo[4,3-c]pyridin-2-acetic acid in place of 5-[N-[4-(N,N,N'-tri-t-butoxycarbonylamidino)benozyl]-L-4-nitrophenylalanyl]-4,5,6,7-tetrahydrothieno[3,2-c]pyridin-2-acetic acid, the reaction was carried out to obtain 0.33 g (0.38 mmol) of the title compound as yellowish foamy product.

$^1$H-NMR (CDCl$_3$) δ; 8.13–7.80 (m, 6H), 7.40–7.01 (m, 3H), 5.56–5.40 (m, 1H), 5.15–5.04 (m, 1H), 4.84–4.10 (m, 4H), 3.77–3.15 (m, 4H), 2.89–2.55 (m, 2H), 1.55 (s, 9H), 1.37 (s, 18H), 1.28 (d, J=6.6 Hz, 6H).

FAB-MS (m/z); 862

Example I-81

Isopropyl 5-(N-(4-amidinobenzoyl)-L-4-nitrophenylalanyl)-4,5,6,7-tetrahydropyrazolo[4,3-c]pyridin-2-acetate.trifluoroacetate (Isopropyl ester of Exemplary compound No. 2-3)

In the same manner as in Example I-2 except for using 0.21 g (0.24 mmol) of isopropyl 5-[N-[4-(N,N,N'-tri-t-butoxycarbonylamidino)benozyl]-L-4-nitrophenylalanyl]-4,5,6,7-tetrahydropyrazolo[4,3-c]pyridin-2-acetate in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 0.13 g (0.19 mmol) of the title compound as white powder.

Melting point; 132–135° C.

$^1$H-NMR (400 MHz, DMSO-$d_6$) δ; 9.40–9.04 (m, 5H), 8.12–7.55 (m, 8H), 7.51, 7.44 (each s, total 1H), 5.38–5.25 (m, 1H), 4.98–4.29 (m, 5H), 3.94–3.81 (m, 1H), 3.70–3.60 (m, 1H), 3.21–3.11 (m, 2H), 2.59–2.51 (m, 2H), 1.20 (d, J=6.3 Hz, 6H).

FAB-MS (m/z); 562

Example I-82

Pivaloyloxymethyl 5-[N-[4-(N,N,N'-tri-t-butoxycarbonylamidino)benzoyl]-L-4-nitrophenylalanyl]-4,5,6,7-tetrahydropyrazolo[4,3-c]pyridin-2-acetate (Pivaloyloxymethyl ester of Exemplary compound No. 2-201)

In 50 ml of DMF was dissolved 2.00 g (2.44 mmol) of 5-[N-[4-(N,N,N'-tri-t-butoxycarbonylamidino)benozyl]-L-4-nitrophenylalanyl]-4,5,6,7-tetrahydropyrazolo[4,3-c]pyridin-2-acetic acid, and then, 0.65 g (4.3 mmol) of chloromethyl pivalate and 1. 08 g (10.7 mmol) of triethylamine were added to the solution, and the mixture was stirred at 55° C. for 3 hours.

The resulting reaction mixture was poured into water, and extracted with ethyl acetate. The organic layer was washed with a saturated aqueous saline solution and dried over anhydrous sodium sulfate. The organic layer was concentrated under reduced pressure and the residue was purified by the silica gel column chromatography method (eluent: ethyl acetate:n-hexane=1:2) to obtain 1.85 g (1.98 mmol) of the title compound as white foamy product.

Example I-83

Pivaloyloxymethyl 5-(N-(4-amidinobenzoyl)-L-4-nitrophenylalanyl]-4,5,6,7-tetrahydropyrazolo[4,3-c]pyridin-2-acetate.trifluoroacetate (Pivaloyloxymethyl ester of Exemplary compound No. 2-3)

In the same manner as in Example I-2 except for using 1.85 g (1.98 mmol) of pivaloyloxymethyl 5-[N-[4-(N,N,N'-tri-t-butoxycarbonylamidino)benozyl]-L-4-nitrophenylalanyl]-4,5,6,7-tetrahydropyrazolo[4,3-c]pyridin-2-acetate in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 1.55 g (1.80 mmol) of the title compound as white powder.

$^1$H-NMR (400 MHz, DMSO-$d_6$) δ; 9.40–9.03 (m, 5H), 8.10–7.56 (m, 8H), 7.53, 7.46 (each s, total 1H), 5.74 (s, 2H), 5.30–5.20 (m, 1H), 5.09–4.29 (m, 4H), 3.92–3.82 (m, 1H), 3.66–3.63 (m, 1H), 3.28–3.20 (m, 2H), 2.65–2.54 (m, 2H), 1.22–1.19 (m, 3H), 1.13–1.26 (m, 9H).

FAB-MS (m/z); 634

Example I-84

Pivaloyloxymethyl 5-[N-[4-(N-ethoxycarbonylamidino)benzoyl]-L-4-nitrophenylalanyl]-4,5,6,7-tetrahydropyrazolo[4,3-c]pyridin-2-acetate (Pivaloyloxymethyl ester of Exemplary compound No. 2-124)

In the same manner as in Example I-8 except for using 1.55 g (1.80 mmol) of pivaloyloxymethyl 5-[N-(4-amidinobenozyl)-L-4-nitrophenylalanyl]-4,5,6,7-tetrahydropyrazolo[4,3-c]pyridin-2-acetate.2CF$_3$CO$_2$H in place of ethyl 5-[N-(4-amidinobenozyl)-L-4-nitrophenylalanyl]-4,5,6,7-tetrahydrthieno[3,2-c]pyridin-2-acetate.CF$_3$CO$_2$H, the reaction was carried out to obtain 0.84 g (1.20 mmol) of the title compound as white solid.

Melting point; 103–106° C.

$^1$H-NMR (400 MHz, DMSO-$d_6$) δ; 9.12–8.98 (m, 3H), 8.09–7.55 (m, 8H), 7.52, 7.45 (each s, total 1H), 5.74 (s, 2H), 5.31–5.29 (m, 1H), 5.05–4.33 (m, 4H), 4.06 (q, J=7.32H, 2H), 3.90–3.80 (m, 1H), 3.70–3.65 (m, 1H), 3.28–3.16 (m, 2H), 2.66–2.57 (m, 2H), 1.21 (t, J=7.33 Hz, 3H), 1.13–1.06 (m, 9H).

FAB-MS (m/z); 706

Example I-85

Ethyl 5-[N-[4-(N-hydroxyamidino)benzoyl]-L-4-nitrophenylalanyl]-4,5,6,7-tetrahydropyrazolo[4,3-c]pyridin-2-acetate (Ethyl ester of Exemplary compound No. 2-81)

(85-A) In the same manner as in Example I-(1-B) except for using 1.08 g (2.00 mmol) of ethyl 5-(N-t-butoxycarbonyl-L-4-nitrophenylalanyl)-4,5,6,7-tetrahydropyrazolo[4,3-c]pyridin-2-acetate in place of ethyl 5-(N-t-butoxycarbonyl-L-4-nitrophenylalanyl)-4,5,6,7-tetrahydrothieno[3,2-c]pyridin-2-acetate, using 0.29 g (2.0 mmol) of cyanobenzoic acid in place of 4-(N,N,N'-tri-t-butoxycarbonylamidino)benzoic acid, using 0.35 g (2.0 mmol) of 6-chloro-2,4-dimethoxy-1,3,5-triazole in place of BOP and using 0.20 g (2.0 mmol) of N-methylmorpholine in place of triethyalmine, and purification was carried out by changing the eluent composition in the silica gel column chromatography method to (n-hexane/ethyl acetate=1/2–1/4), the reaction was carried out to obtain 0.88 g (1.7 mmol) of ethyl 5-[N-(4-cyanobenzoyl)-L-4-nitrophenylalanyl]-4,5,6,7-tetrahydropyrazolo[4,3-c]pyridin-2-acetate as white powder.

$^1$H-NMR (CDCl$_3$) δ; 8.12–7.98 (m, 2H), 7.90–7.72 (m, 4H), 7.34–7.04 (m, 3H), 5.53–5.37 (m, 1H), 4.85–4.10 (m, 6H), 3.80–3.15 (m, 4H), 2.89–2.55 (m, 2H), 1.33–1.26 (m, 3H).

FAB-MS (m/z); 531

(85-B) To 0.88 g (1.7 mmol) of of ethyl 5-[N-(4-cyanobenzoyl)-L-4-nitrophenylalanyl]-4,5,6,7-tetrahydropyrazolo[4,3-c]pyridin-2-acetate was added 10 ml of an ethanol solution containing 0.35 g (5.1 mmol) of hydroxylamine.HCl and 0.28 g (5.1 mmol) of sodium methoxide, and the mixture was stirred at room temperature for one hour and then allowed to stand overnight.

The resulting reaction mixture was concentrated under reduced pressure, a 5% aqueous potassium hydrogen sulfate solution was added to the residue and the mixture was extracted with ethyl acetate. The organic layer was washed successively with a saturated aqueous sodium bicarbonate solution and a saturated aqueous saline solution, and dried over anhydrous sodium sulfate. The organic layer was concentrated under reduced pressure and the residue was purified by the silica gel column chromatography method (eluent: chloroform/methanol=30/1) to obtain 0.21 g (0.37 mmol) of the title compound as white powder.

Melting point; 218–224° C.

$^1$H-NMR (400 MHz, DMSO-d$_6$) δ; 9.78 (s, 1H), 8.99–8.84 (m, 1H), 8.10–8.02 (m, 2H), 7.80–7.55 (m, 6H), 7.51–7.18 (m, 1H), 5.86 (brs, 2H), 5.31–5.20 (m, 1H), 4.93–4.81 (m, 2H), 4.70–4.32 (m, 2H), 4.15–4.01 (m, 2H), 3.93–3.55 (m, 2H), 3.46–3.13 (m, 2H), 2.64–2.45 (m, 2H), 1.22–1.15 (m, 3H).

FAB-MS (m/z); 564

Example I-86

Ethyl 5-(N-[4-(N,N,N'-tri-t-butoxycarbonylamidino)benzoyl]-L-4-nitrophenylalanyl]-3-hydroxy-4,5,6,7-tetrahydropyrazolo[4,3-c]pyridin-2-acetate (Ethyl ester of Exemplary compound No. 2-202)

(86-A) In the same manner as in Example I-(1-A) except for using 0.54 g (1.6 mmol) of ethyl 3-hydroxy-4,5,6,7-tetrahydropyrazolo[4,3-c]pyridin-2-acetate.CF$_3$CO$_2$H in place of ethyl 4,5,6,7-tetrahydrothieno[3,2-c]pyridin-2-acetate.HCl, the reaction was carried out to obtain 0.64 g (1.2 mmol) of ethyl 5-(N-t-butoxycarbonyl-L-4-nitrophenylalanyl)-3-hydroxy-4,5,6,7-tetrahydropyrazolo[4,3-c]pyridin-2-acetate as pale yellowish foamy product.

$^1$H-NMR (CDCl$_3$) δ; 8.22–8.10 (m, 2H), 7.46–7.33 (m, 2H), 5.62–5.15 (m, 1H), 5.02–4.08 (m, 8H), 3.82–2.50 (m, 6H), 1.41–1.38 (m, 9H), 1.33–1.23 (m, 3H).

(86-B) In the same manner as in Example I-(1-B) except for using 0.64 g (1.20 mmol) of ethyl 5-(N-t-butoxycarbonyl-L-4-nitrophenylalanyl)-3-hydroxy-4,5,6,7-tetrahydropyrazolo[4,3-c]pyridin-2-acetate in place of ethyl 5-(N-t-butoxycarbonyl-L-4-nitrophenylalanyl)-4,5,6,7-tetrahydrothieno[3,2-c]pyridin-2-acetate, the reaction was carried out to obtain 0.52 g (0.60 mmol) of the title compound as orange foamy product.

$^1$H-NMR (DMSO-d$_6$) δ; 10.85 (brs, 1H), 9.17, 9.10 (each d, J=7.3 Hz, total 1H), 8.10–7.53 (m, 8H), 5.29–5.22 (m, 1H), 4.61–3.40 (m, 8H), 3.28–3.17 (m, 2H), 2.45–2.38 (m, 2H), 1.45 (s, 9H), 1.28 (s, 18H), 1.20–1.15 (m, 3H).

FAB-MS (m/z); 864

Example I-87

Ethyl 5-(N-(4-amidinobenzoyl)-L-4-nitrophenylalanyl]-3-hydroxy-4,5,6,7-tetrahydropyrazolo[4,3-c]pyridin-2-acetate.trifluoroacetate (Ethyl ester of Exemplary compound No. 2-23)

In the same manner as in Example I-2 except for using 0.52 g (0.60 mmol) of ethyl 5-[N-[4-(N,N,N'-tri-t-butoxycarbonylamidino)benozyl]-L-4-nitrophenylalanyl)-3-hydroxy-4,5,6,7-tetrahydropyrazolo[4,3-c]pyridin-2-acetate in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 0.37 g (0.51 mmol) of the title compound as yellowish powder.

Melting point; 178–180° C.

$^1$H-NMR (400 MHz, DMSO-d$_6$) δ; 9.38, 9.36 (each s, total 2H), 9.21, 9.13 (each d, J=8.3 Hz, total 1H), 9.09 (s, 2H), 8.09, 8.05 (each d, J=8.8 Hz, total 2H), 7.99–7.95 (m, 2H), 7.86–7.82 (m, 2H), 7.61, 7.55 (each d, J=8.8 Hz, total 2H), 5.31–5.24 (m, 1H), 4.56–4.08 (m, 6H), 3.86–3.83 (m, 1H), 3.64–3.59 (m, 1H), 3.25–3.14 (m, 2H), 2.45–2.43 (m, 2H), 1.20–1.17 (m, 3H).

FAB-MS (m/z); 564

Example I-88

Ethyl 5-[N-[4-(N,N,N'-tri-t-butoxycarbonylamidino)benzoyl]-L-4-nitrophenylalanyl]-3-methoxy-4,5,6,7-tetrahydropyrazolo[4,3-c]pyridin-2-acetate (Ethyl ester of Exemplary compound No. 2-205)

(88-A) In the same manner as in Example I-(1-A) except for using 0.23 g (0.65 mmol) of ethyl 3-methoxy-4,5,6,7-tetrahydropyrazolo[4,3-c]pyridin-2-acetate.CF$_3$CO$_2$H in place of ethyl 4,5,6,7-tetrahydrothieno[3,2-c]pyridin-2-acetate.HCl, the reaction was carried out to obtain 0.34 g (0.64 mmol) of ethyl 5-(N-t-butoxycarbonyl-L-4-nitrophenylalanyl)-3-methoxy-4,5,6,7-tetrahydropyrazolo[4,3-c]pyridin-2-acetate as brownish oily product.

$^1$H-NMR (CDCl$_3$) δ; 8.12, 8.02 (each d, J=8.8 Hz, total 2H), 7.36, 7.33 (each d, J=8.8 Hz, total 2H), 5.52, 5.32 (each d, J=8.8 Hz, total 2H), 5.12–4.92 (m, 1H), 4.90–4.42 (m, 3H), 4.30–4.28 (m, 3H), 4.01, 3.84 (each s, total 3H), 3.82–3.00 (m, 4H), 2.82–2.46 (m, 2H), 1.41, 1.39 (each s, total 9H), 1.29, 1.26 (each t, J=7.3 Hz, total 3H).

(88-B) In the same manner as in Example I-(1-B) except for using 0.34 g (0.64 mmol) of ethyl 5-(N-t-butoxycarbonyl-L-4-nitrophenylalanyl)-3-methoxy-4,5,6,7-tetrahydropyrazolo[4,3-c]pyridin-2-acetate in place of ethyl 5-(N-t-butoxycarbonyl-L-4-nitrophenylalanyl)-4,5,6,7-tetrahydrothieno[3,2-c]pyridin-2-acetate, the reaction was carried out to obtain 0.40 g (0.46 mmol) of the title compound as pale brownish foamy product.

$^1$H-NMR (CDCl$_3$) δ; 8.15–7.79 (m, 6H), 7.40–7.10 (m, 3H), 5.50–5.38 (m, 1H), 4.89–4.60 (m, 3H), 4.42–4.20 (m, 3H), 4.00, 3.81 (each s, total 3H), 3.80–3.18 (m, 4H), 2.85–2.35 (m, 2H), 1.54 (s, 9H), 1.37 (s, 9H), 1.36 (s, 9H), 1.31–1.23 (m, 3H).

FAB-MS (m/z); 878

Example I-89

Ethyl 5-[N-(4-amidinobenzoyl)-L-4-nitrophenylalanyl]-3-methoxy-4,5,6,7-tetrahydropyrazolo[4,3-c]pyridin-2-acetate.trifluoroacetate (Ethyl ester of Exemplary compound No. 2-24)

In the same manner as in Example I-2 except for using 0.40 g (0.46 mmol) of ethyl 5-[N-[4-(N,N,N'-tri-t-butoxycarbonylamidino)benozyl]-L-4-nitrophenylalanyl]-3-methoxy-4,5,6,7-tetrahydropyrazolo[4,3-c]pyridin-2-acetate in place of ethyl 5-[N-[4-(N,N,N'-tri-t- butoxycarbonylamidino)benozyl]-L-4-nitrophenylalanyl]-4,5,6,7-tetrahydrothieno[3,2-c]pyridin-2-acetate, the reaction was carried out to obtain 0.24 g (0.34 mmol) of the title compound as pale yellowish powder.

Melting point; 128–133° C.

$^1$H-NMR (400 MHz, DMSO-$d_6$) δ; 9.36 (s, 2H), 9.25 (d, J=8.3 Hz, 1H), 9.14 (s, 2H), 8.09, 8.02 (each d, J=8.8 Hz, total 2H), 7.97, 7.89 (each d, J=8.8 Hz, total 2H), 7.85–7.83 (m, 2H), 7.62, 7.56 (each d, J=8.8 Hz, total 2H), 5.37–5.30 (m, 1H), 4.91–4.37 (m, 5H); 4.14–4.07 (m, 2H), 3.90, 3.87 (each s, total 3H), 3.84–3.78 (m, 1H), 3.62–3.52 (m, 1H), 3.30–3.12 (m, 3H), 2.46–2.38 (m, 1H), 1.20–1.15 (m, 3H).

FAB-MS (m/z); 578

Example I-90

Ethyl 5-[N-[4-(N,N,N'-tri-t-butoxycarbonylamidino) benzoyl]-L-4-nitrophenylalanyl]-4,6-ethano-4,5,6,7-tetrahydropyrazolo[4,3-c]pyridin-2-acetate (Ethyl ester of Exemplary compound No. 2-208)

(90-A) In the same manner as in Example I-(1-A) except for using 0.13 g (0.47 mmol) of ethyl 4,6-ethano-4,5,6,7-tetrahydropyrazolo[4,3-c]pyridin-2-acetate.HCl in place of ethyl 4,5,6,7-tetrahydrothieno[3,2-c]pyridin-2-acetate.HCl and using 0.37 g (0.71 mmol) of PyBOP in place of BOP, the reaction was carried out to obtain 0.20 g (0.37 mmol) of ethyl 5-(N-t-butoxycarbonyl-L-4-nitrophenylalanyl)-4,6-ethano-4,5,6,7-tetrahydropyrazolo[4,3-c]pyridin-2-acetate as white foamy product.

$^1$H-NMR (CDCl$_3$) δ; 8.17–7.08 (m, 5H), 5.58–4.50 (m, 6H), 4.24–4.16 (m, 2H), 3.40–1.55 (m, 7H), 1.45–1.23 (m, 12H).

CI-MS (m/z); 528

(90-B) In the same manner as in Example I-(1-B) except for using 0.19 g (0.37 mmol) of ethyl 5-(N-t-butoxycarbonyl-L-4-nitrophenylalanyl)-4,6-ethano-4,5,6,7-tetrahydropyrazolo[4,3-c]pyridin-2-acetate in place of ethyl 5-(N-t-butoxycarbonyl-L-4-nitrophenylalanyl)-4,5,6,7-tetrahydrothieno[3,2-c]pyridin-2-acetate and using 0.30 g (0.56 mmol) of PyBOP in place of BOP, the reaction was carried out to obtain 0.27 g (0.31 mmol) of the title compound as pale yellowish foamy product.

Example I-91

Ethyl 5-[N-(4-amidinobenzoyl)-L-4-nitrophenylalanyl]-4,6-ethano-4,5,6,7-tetrahydropyrazolo[4,3-c]pyridin-2-acetate.trifluoroacetate (Ethyl ester of Exemplary compound No. 2-29)

In the same manner as in Example I-2 except for using 0.27 g (0.31 mmol) of ethyl 5-[N-[4-(N,N,N'-tri-t-butoxycarbonylamidino)benozyl]-L-4-nitrophenylalanyl]-4,6-ethano-4,5,6,7-tetrahydropyrazolo[4,3-c]pyridin-2-acetate in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 0.16 g (0.23 mmol) of the title compound as white powder.

Melting point; 147–153° C.

$^1$H-NMR (400 MHz, DMSO-$d_6$) δ; 9.39–8.88 (m, 5H), 8.15–6.90 (m, 9H), 5.35–4.68 (m, 6H), 4.14–4.05 (m, 2H), 3.21–1.45(m, 7H), 1.23–1.13 (m, 3H).

FAB-MS (m/z); 574

Example I-92

Ethyl 5-[N-(N-t-butoxycarbonyl-4-piperidyloxyacetyl)-L-4-nitrophenylalanyl]-4,5,6,7-tetrahydropyrazolo[4,3-c]pyridin-2-acetate (Ethyl ester of Exemplary compound No. 2-230)

In the same manner as in Example I-(1-B) except for using 0.37 g (0.74 mmol) of ethyl 5-(N-t-butoxycarbonyl-L-4-nitrophenylalanyl)-4,5,6,7-tetrahydropyrazolo[4,3-c]pyridin-2-acetate in place of ethyl 5-(N-t-butoxycarbonyl-L-4-nitrophenylalanyl)-4,5,6,7-tetrahydrothieno[3,2-c]pyridin-2-acetate and using 0.31 g (1.2 mmol) of N-t-butoxycarbonyl-4-piperidyloxyacetic acid in place of 4-(N,N,N'-tri-t-butoxycarbonylamidino)benzoic acid, the reaction was carried out to obtain 0.27 g (0.42 mmol) of the title compound as pale yellowish foamy product.

$^1$H-NMR (CDCl$_3$) δ; 8.11–7.97 (m, 2H), 7.46–7.02 (m, 4H), 5.35–5.22 (m, 1H), 4.85–2.40 (m, 19H), 1.90–1.75 (m, 2H), 1.65, 1.46 (each s, total 9H), 1.60–1.40 (m, 2H), 1.32–1.23 (m, 3H).

FAB-MS (m/z); 643

Example I-93

Ethyl 5-[N-(4-piperidyloxyacetyl)-L-4-nitrophenylalanyl]-4,5,6,7-tetrahydropyrazolo[4,3-c]pyridin-2-acetate.trifluoroacetate (Ethyl ester of Exemplary compound No. 2-229)

In the same manner as in Example I-2 except for using 0.55 g (0.86 mmol) of ethyl 5-[N-(N-t-butoxycarbonyl-4-piperidyloxyacetyl)-L-4-nitrophenylalanyl]-4,5,6,7-tetrahydropyrazolo[4,3-c]pyridin-2-acetate in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 0.45 g (0.65 mmol) of the title compound as pale yellowish powder (hygroscopic).

$^1$H-NMR (400 MHz, DMSO-$d_6$) δ; 8.40–8.20 (m, 2H), 8.17–7.98 (m, 3H), 7.52–7.21 (m, 3H), 5.18–5.10 (m, 1H), 4.98–4.86 (n, 2H), 4.67–4.34 (m, 2H), 4.16–4.10 (m, 2H), 3.85 (s, 2H), 3.84–3.60 (m, 2H), 3.52–3.42 (m, 1H), 3.28–2.88 (m, 6H), 2.66–2.50 (m, 2H), 1.88–1.78 (m, 2H), 1.72–1.58 (m, 2H), 1.22–1.18 (m, 3H).

FAB-MS (m/z); 543

Example I-94

Ethyl 6-[N-[4-(N,N,N'-tri-t-butoxycarbonylamidino) benzoyl]-L-4-nitrophenylalanyl]-4,5,6,7-tetrahydrothiazolo[5,4-c]pyridin-2-acetate (Ethyl ester of Exemplary compound No. 4-92)

(94-A) In the same manner as in Example I-(1-A) except for using 1.70 g (5.00 mmol) of ethyl 4,5,6,7-tetrahydrothiazolo[5,4-c]pyridin-2-acetate.CF$_3$CO$_2$H in place of ethyl 4,5,6,7-tetrahydrothieno[3,4-c]pyridin-2-acetate.HCl, the reaction was carried out to obtain 2.59 g (5.00 mmol) of ethyl 6-(N-t-butoxycarbonyl-L-4-nitrophenylalanyl)-4,5,6,7-tetrahydrothiazolo[5,4-c]pyridin-2-acetate as pale yellowish foamy product.

$^1$H-NMR (CDCl$_3$) δ; 8.10, 7.97 (each d, J=8.8 Hz, total 2H), 7.36, 7.30 (each d, J=8.8 Hz, total 2H), 5.44, 5.31 (each d, J=8.8 Hz, total 1H), 4.87–4.91 (m, 5H), 4.00, 3.96 (each s, total 2H), 3.82–3.60 (m, 1H), 3.45–2.52 (m, 5H), 1.42, 1.39 (each s, total 9H), 1.33–1.23 (m, 3H).

CI-MS (m/z); 519

(94-B) In the same manner as in Example I-(1-B) except for using 1.65 g (3.20 mmol) of ethyl 6-(N-t-butoxycarbonyl-L-4-nitrophenylalanyl)-4,5,6,7-tetrahydrothiazolo[5,4-c]pyridin-2-acetate in place of ethyl 5-(N-t-butoxycarbonyl-L-4-nitrophenylalanyl)-4,5,6,7-tetrahydrothieno[3,2-c]pyridin-2-acetate, the reaction was carried out to obtain 2.34 g (2.71 mmol) of the title compound as pale yellowish foamy product.

$^1$H-NMR (CDCl$_3$) δ; 8.12–7.07 (m, 8H), 5.58–5.38 (m, 1H), 4.90–4.19 (m, 5H), 4.01, 3.98 (each s, total 2H), 3.80–3.60 (m, 1H), 3.45–2.55 (m, 5H), 1.54 (s, 9H), 1.37 (s, 18H), 1.33–1.23 (m, 3H).

FAB-MS (m/z); 865

Example I-95
Ethyl 6-[N-(4-amidinobenzoyl)-L-4-nitrophenylalanyl]-4,5,6,7-tetrahydrothiazolo[5,4-c]pyridin-2-acetate.ditrifluoroacetate (Ethyl ester of Exemplary compound No. 4-3)

In the same manner as in Example I-2 except for using 1.00 g (1.16 mmol) of ethyl 6-[N-[4-(N,N,N'-tri-t-butoxycarbonylamidino)benozyl]-L-4-nitrophenylalanyl]-4,5,6,7-tetrahydrothiazolo[5,4-c]pyridin-2-acetate in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 0.75 g (0.95 mmol) of the title compound as white powder.

Melting point; 120–126° C.
$^1$H-NMR (400 MHz, DMSO-d$_6$) δ; 9.37 (s, 2H), 9.25, 9.14 (each d, J=8.8 Hz, total 1H), 9.17 (s, 2H), 8.13–7.56 (m, 8H), 5.48–5.28 (m, 1H), 4.93–4.51 (m, 2H), 4.14–4.10 (m, 2H), 4.05, 4.00 (each s, total 2H), 3.98–3.88 (m, 1H), 3.80–3.70 (m, 1H), 3.29–3.18 (m, 3H), 2.70–2.55 (m, 1H), 1.22–1.17 (m, 3H).
FAB-MS (m/z); 565
$[α]_D^{20}$; −25° (MeOH, c=0.320)

Example I-96
Ethyl 5-(N-(4-N,N,N'-tri-t-butoxycarbonylamidinobenzoyl)-L-4-nitrophenylalanyl]-4,5,6,7-tetrahydropyrrolo[3,4-c]pyridin-2-acetate (Ethyl ester of Exemplary compound No. 6-94)

(96-A) In the same manner as in Example I-(1-A) except for using 0.12 g (0.36 mmol) of ethyl 4,5,6,7-tetrahydropyrrolo[3,4-c]pyridin-2-acetate.CF$_3$CO$_2$H in place of ethyl 4,5,6,7-tetrahydrothieno[3,2-c]pyridin-2-acetate.HCl, the reaction was carried out to obtain 0.18 g (0.36 mmol) of ethyl 5-(N-t-butoxycarbonyl-L-4-nitrophenylalanyl)-4,5,6,7-tetrahydropyrrolo[3,4-c]pyridin-2-acetate as pale yellowish foamy product.

$^1$H-NMR (CDCl$_3$) δ; 8.20–7.80 (m, 2H), 7.60–7.20 (m, 2H), 6.40, 6.25 (each s, total 1H), 6.32, 6.15 (each s, total 1H), 5.60, 5.45 (each d, J=8.8 Hz, total 1H), 5.00–4.85 (m, 1H), 4.61, 4.53 (each s, total 2H), 4.45 (s, 1H), 4.30–4.14 (m, 3H), 3.60–3.50 (m, 1H), 3.30–2.75 (m, 4H), 2.70–2.40 (m, 1H), 1.43, 1.42, 1.40 (each s, total 9H), 1.32–1.23 (m, 3H).
CI-MS (m/z); 501

(96-B) In the same manner as in Example I-(1-B) except for using 0.18 g (0.36 mmol) of ethyl 5-(N-t-butoxycarbonyl-L-4-nitrophenylalanyl)-4,5,6,7-tetrahydropyrrolo[3,4-c]pyridin-2-acetate in place of ethyl 5-(N-t-butoxycarbonyl-L-4-nitrophenylalanyl)-4,5,6,7-tetrahydrothieno[3,2-c]pyridin-2-acetate, the reaction was carried out to obtain 0.25 g (0.29 mmol) of the title compound as yellowish foamy product.

$^1$H-NMR (CDCl$_3$) δ; 8.10–7.82 (m, 6H), 7.36–7.20 (m, 2H), 6.43, 6.29 (each s, total 1H), 6.35, 6.19 (each s, total 1H), 5.52–5.38 (m, 1H), 4.66, 4.55 (each s, total 2H), 4.47 (s, 1H), 4.45–4.08 (m, 5H), 3.70–3.55 (m, 1H), 3.45–3.10 (m, 2H), 2.75–2.45 (m, 2H), 1.73–1.35 (m, 27H), 1.32–1.23 (m, 3H).
FAB-MS (m/z); 847

Example I-97
Ethyl 5-[N-(4-amidinobenzoyl)-L-4-nitrophenylalanyl]-4,5,6,7-tetrahydropyrrolo[3,4-c]pyridin-2-acetate.trifluoroacetate (Ethyl ester of Exemplary compound No. 6-3)

In the same manner as in Example I-2 except for using 0.24 g (0.28 mmol) of ethyl 5-[N-[4-(N,N,N'-tri-t-butoxycarbonylamidino)benozyl]-L-4-nitrophenylalanyl]-4,5,6,7-tetrahydropyrrolo[3,4-c]pyridin-2-acetate in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 0.15 g (0.23 mmol) of the title compound as pale brownish powder.

Melting point; 120–125° C.
$^1$H-NMR (400 MHz, DMSO-d$_6$) δ; 9.18, 9.06 (brs, 5H), 8.10–7.56 (m, 8H), 6.50, 6.42 (each s, total 1H), 6.45, 6.41 (each s, total 1H), 5.38–5.25 (m, 1H), 4.72–4.66 (m, 2H), 4.56 (s, 1H), 4.33–3.98 (m, 3H), 3.85–3.78 (m, 1H), 3.60–3.48 (m, 1H), 3.40–3.08 (m, 2H), 2.49–2.35 (m, 2H), 1.21–1.08 (m, 3H).
FAB-MS (m/z); 547

Example I-98
Ethyl 5-[N-(4-amidinobenzoyl)-L-4-nitrophenylalanyl]-4,5,6,7-tetrahydropyrazolo[4,3-c]pyridin-2-acetate.hydrochloride (Ethyl ester of Exemplary compound No. 2-3)

To a mixed solution of 4 ml of 1,4-dioxane and 8 ml of water containing 0.19 g (2.2 mmol) of sodium hydrogen carbonate was added under ice-cooling 0.52 g (1.0 mmol) of ethyl 5-(L-4-nitrophenylalanyl)-4,5,6,7-tetrahydropyrazolo[4,3-c]pyridin-2-acetate.CF$_3$CO$_2$H, and after stirring at the same temperature for 5 minutes, 0.23 g (1.1 mmol) of 4-amidinobenzoyl chloride.HCl was added to the mixture, and the resulting mixture was further stirred at room temperature for one hour.

The resulting reaction mixture was concentrated under reduced pressure, and after adjusting the pH to 6 with a saturated aqueous sodium bicarbonate solution, it was extracted with n-butanol. The organic layer was washed with a saturated saline solution, and then concentrated under reduced pressure. The residue was purified by the silica gel column chromatography method (eluent: chloroform/methanol/acetic acid=10/1/0.1–5/1/0.1) to obtain 0.30 g (0.52 mmol) of the title compound as white powder.

$^1$H-NMR (400 MHz, DMSO-d$_6$) δ; 9.53 (s, 2H), 9.23, 9.09 (each d, J=8.8 Hz, total 1H), 9.10 (s, 2H), 8.09–7.56 (m, 8H), 7.52, 7.45 (each s, total 1H), 5.35–5.25 (m, 1H), 4.95–4.30 (m, 4H), 4.12 (q, J=7.3 Hz, 2H), 3.95–3.10 (m, 2H), 3.70–3.60 (m, 2H), 3.28–3.10 (m, 2H), 2.58–2.52 (m, 1H), 1.19 (t, J=7.3 Hz, 3H).
FAB-MS (m/z); 548

Example I-99
Benzyl 5-[N-[4-(N,N,N'-tri-t-butoxycarbonylamidino)benozyl]-L-4-nitrophenylalanyl]-4,5,6,7-tetrahydropyrrolo[3,2-c]pyridin-2-acetate (Benzyl ester of Exemplary compound No. 5-116)

(99-A) In the same manner as in Example I-(1-A) except for using 0.15 g (0.31 mmol) of benzyl 4,5,6,7-tetrahydropyrrolo[3,2-c]pyridin-2-acetate.CF$_3$CO$_2$H in place of ethyl 4,5,6,7-tetrahydropyrazolo[3,2-c]pyridin-2-acetate.HCl and using 0.37 g (0.71 mmol) of PyBOP in place of BOP, the reaction was carried out to obtain 0.11 g (0.19 mmol) of benzyl 5-(N-t-butoxycarbonyl-L-4-nitrophenylalanyl)-4,5,6,7-tetrahydropyrrolo[3,2-c]pyridin-2-acetate as yellowish foamy product.

$^1$H-NMR (CDCl$_3$) δ; 8.27 (brs, 1H), 8.09–7.25 (m, 10H), 5.79–4.00 (m, 8H), 3.59 (s, 2H), 3.40–2.25 (m, 4H), 1.42, 1.39 (each s, total 9H).
CI-MS (m/z); 463

(99-B) In the same manner as in Example I-(1-B) except for using 0.11 g (0.19 mmol) of benzyl 5-(N-t-butoxycarbonyl-L-4-nitrophenylalanyl)-4,5,6,7- tetrahydropyrrolo[3,2-c]pyridin-2-acetate in place of ethyl 5-(N-t-butoxycarbonyl-L-4-nitrophenylalanyl)-4,5,6,7-tetrahydrothieno[3,2-c]pyridin-2-acetate and using 0.15g (0.28 mmol) of PyBOP in place of BOP, the reaction was carried out to obtain 0.13 g (0.14 mmol) of the title compound as yellowish foamy product.

$^1$H-NMR (CDCl$_3$) δ; 8.30–7.26 (m, 14H), 5.80, 5.52 (each s, total 1H), 5.50–5.40 (m, 1H), 5.16, 5.15 (each s, total 2H), 4.63–3.66 (m, 4H), 3.60 (s, 2H), 3.40–2.32 (m, 4H), 1.54 (s, 9H), 1.37 (s, 18H).

Example I-100

Benzyl 5-[N-(4-amidinobenzoyl)-L-4-nitrophenylalanyl]-4,5,6,7-tetrahydropyrrolo[3,2-c]pyridin-2-acetate.trifluoroacetate (Benzyl ester of Exemplary compound No. 5-3)

In the same manner as in Example I-2 except for using 0.13 g (0.14 mmol) of benzyl 5-[N-[4-(N,N,N'-tri-t-butoxycarbonylamidino)benozyl]-L-4-nitrophenylalanyl]-4,5,6,7-tetrahydropyrrolo[3,2-c]pyridin-2-acetate in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 0.075 g (0.10 nmmol) of the title compound as white powder.

Melting point; 132–138° C.

$^1$H-NMR (400 MHz, DMSO-d$_6$) δ; 10.41, 10.40 (each s, total 1H), 9.37–9.06 (m, 5H), 8.10–7.30 (m, 14H), 5.66, 5.61 (each s, total 1H), 5.33–4.98 (m, 2H), 5.08 (s, 2H), 4.56–3.10 (m, 8H).

FAB-MS (m/z); 609

Example I-101

Ethyl 1-benzyloxycarbonyl-5-[N-[4-(N,N,N'-tri-t-butoxycarbonylamidino)benzoyl]-L-4-nitrophenylalanyl]-4,5,6,7-tetrahydropyrrolo[3,2-c]pyridin-2-acetate (Ethyl ester of Exemplary compound No. 8-23)

(101-A) To 0.78 g (1.7 mmol) of ethyl 1-benzyloxycarbonyl-4,5,6,7-tetrahydropyrrolo[3,2-c]pyridin-2-acetate.CF$_3$CO$_2$H salt were added 10 ml of DMF and 1.1 ml (6.4 mmol) of diisopropylethylamine to dissolve the salt, and then, 0.52 g (1.7 mmol) of N-t-butoxycarbonyl-L-4-nitrophenylalanine and 0.65 g (1.7 mmol) of HBTU were added to the solution and the mixture was stirred at room temperature for 3 hours.

The resulting reaction.mixture was concentrated under reduced pressure, a 5% aqueous potassium hydrogen sulfate solution was added to the residue, and the mixture was extracted with ethyl acetate. The organic layer was successively washed with a saturated aqueous sodium bicarbonate solution and a saturated aqueous saline solution, and dried over anhydrous sodium sulfate. The organic layer was concentrated under reduced pressure and the residue was purified by the silica gel column chromatography method (eluent: chloroform/ethyl acetate=4/1) to obtain 0.65 g (1.0 mmol) of ethyl 1-benzyloxycarbonyl-5-(N-t-butoxycarbonyl-L-4-nitrophenylalanyl)-4,5,6,7-tetrahydropyrrolo[3,2-c]pyridin-2-acetate as pale yellowish foamy product.

$^1$H-NMR (CDCl$_3$) δ; 8.05–7.25 (m, 9H), 5.92, 5.66 (each s, total 1H), 5.50–5.25 (m, 3H), 4.92–4.85 (m, 1H), 4.53–2.25 (m, 11H), 1.42, 1.40 (each s, total 9H), 1.23–1.16 (m, 3H).

CI-MS (m/z); 535

(101-B) In 10 ml of methylene chloride was dissolved 0.65 g (1.0 mmol) of ethyl1-benzyloxycarbonyl-5-(N-t-butoxycarbonyl-L-4-nitrophenylalanyl)-4,5,6,7-tetrahydropyrrolo[3,2-c]pyridin-2-acetate, and under ice-cooling, 3.5 ml of CF$_3$CO$_2$H was added to the solution, and then, the mixture was stirred at room temperature for 1.5 hours.

The resulting reaction mixture was concentrated under reduced pressure to obtain the residue. To the resulting residue were added 10 ml of DMF and 0.68 ml (4.0 mmol) of diisopropylethylamine and the mixture was dissolved. Then, 0.48 g (1.0 mmol) of 4-(N,N,N'-tri-t-butoxycarbonylamidino)benzoic acid and 0.40 g (1.1 mmol) of HBTU were added to the solution, and the mixture was stirred at room temperature for 4 hours.

The resulting reaction mixture was concentrated under reduced pressure, a 5% aqueous potassium hydrogen sulfate solution was added to the residue and the mixture was extracted with ethyl acetate. The organic layer was washed successively with a saturated aqueous sodium bicarbonate solution and a saturated aqueous saline solution, and dried over anhydrous sodium sulfate. The organic layer was concentrated under reduced pressure and the residue was purified by the silica gel column chromatography method (eluent: chloroform/ethyl acetate=9/1) to otain 0.88 g (0.90 mmol) of the title compound as orange foamy product.

FAB-MS (m/z); 981

Example I-102

Ethyl 1-benzyloxycarbonyl-5-[N-(4-amidinobenzoyl)-L-4-nitrophenylalanyl]-4,5,6,7-tetrahydropyrrolo[3,2-c]pyridin-2-acetate.trifluoroacetate (Ethyl ester of Exemplary compound No. 8-24)

In the same manner as in Example I-2 except for using 0.13 g (0.14 mmol) of ethyl 1-benzyloxycarbonyl-5-[N-[4-(N,N,N'-tri-t-butoxycarbonylamidino)benozyl]-L-4-nitrophenylalanyl]-4,5,6,7-tetrahydropyrrolo[3,2-c]pyridin-2-acetate in place of ethyl 5-[N-[4-(N,N,N'-tri-t-butoxycarbonylamidino)benozyl]-L-4-nitrophenylalanyl]-4,5,6,7-tetrahydrothieno[3,2-c]pyridin-2-acetate, the reaction was carried out to obtain 0.19 g (0.24 mmol) of the title compound as white powder.

Melting point; 123–126° C.

$^1$H-NMR (400 MHz, DMSO-d$_6$) δ; 9.38 (brs, 2H), 9.15 (brs, 2H), 9.21–9.11 (m, 1H), 8.06–7.37 (m, 13H), 6.04, 5.93 (each s, total 1H), 5.35–5.22 (m, 3H), 4.48–4.25 (m, 2H), 3.95–3.70 (m, 5H), 3.30–3.15 (m, 2H), 2.80–2.60 (m, 2H), 1.10–1.05 (m, 3H).

FAB-MS (m/z); 681

Example I-103

Ethyl 5-[N-[4-(N-acetoxymethylcarbonylamidino)benzoyl]-L-4-nitrophenylalanyl]-4,5,6,7-tetrahydropyrazolo[4,3-c]pyridin-2-acetate (Ethyl ester of Exemplary compound No. 2-245)

In 5 ml of dehydrated THF was dissolved under argon gas stream 1.4 g (2.0 mmol) of ethyl 5-[N-(4-amidinobenzoyl)-L-4-nitrophenylalanyl]-4,5,6,7-tetrahydropyrazolo[4,3-c]pyridin-2-acetate.3/2CF$_3$CO$_2$H, and then, 6 ml of THF solution containing 1.0 M of lithium bis(trimethylsilyl)amide was added to the solution and the mixture was stirred at the same temperature for 2 hours. Then, 1 ml of a dehydrated THF solution containing 0.56 g (2.2 mmol) of acetoxymethyl(4-nitrophenyl)carbonate was added to the mixture and the resulting mixture was stirred for 2 hours.

To the resulting reaction mixture was added a saturated aqueous ammonium chloride solution, the mixture was extracted with ethyl acetate and the organic layer was washed with a saturated saline solution and dried over anhydrous magnesium sulfate. The organic layer was concentrated under reduced pressure and the residue was purified by the silica gel column chromatography method (eluent: chloroform/methanol=19/1) to obtain 0.99 g (1.5 mmol) of the title compound as white foamy product.

$^1$H-NMR (400 MHz, DMSO-d$_6$) δ; 9.32 (brs, 2H), 9.13, 9.01 (each d, J=8.8 Hz, total 1H), 8.10–8.00 (m, 4H), 7.88, 7.84 (each d, J=8.3 Hz, total 2H), 7.60, 7.56 (each d, J=8.8 Hz, total 2H), 7.51, 7.44 (each s, total 1H), 5.71 (s, 2H), 5.31–5.27 (m, 1H), 4.93–4.35 (m, 4H), 4.12 (q, J=7.3 Hz, 2H), 3.95–3.55 (m, 2H), 3.30–3.14 (m, 2H), 2.58–2.52 (m, 2H), 2.06 (s, 3H), 1.19 (t, J=7.3 Hz, 3H).

FAB-MS (m/z); 664

Example I-104
Ethyl 5-[N-[4-(N-pivaloyloxymethoxycarbonylamidino) benzoyl]-L-4-nitrophenylalanyl]-4,5,6,7-tetrahydropyrazolo[4,3-c]pyridin-2-acetate (Ethyl ester of Exemplary No. 2-246)

In the same manner as in Example I-103 except for using 0.65 g (2.2 mmol) of pivaloyloxymethyl(4-nitrophenyl) carbonate in place of acetoxymethyl(4-nitrophenyl) carbonate, the reaction was carried out to obtain 1.1 g (1.5 mmol) of the title compound as pale yellowish foamy product.

$^1$H-NMR (400 MHz, DMSO-d$_6$) δ; 9.31 (brs, 2H), 9.13, 9.02 (each d, J=8.8 Hz, total 1H), 8.10–8.00 (m, 4H), 7.88, 7.84 (each d, J=8.3 Hz, total 2H), 7.60, 7.56 (each d, J=8.8 Hz, total 2H), 7.51, 7.44 (each s, total 1H), 5.74 (s, 2H), 5.31–5.27 (m, 1H), 4.93–4.35 (m, 4H), 4.12 (q, J=7.3 Hz, 2H), 3.95–3.55 (m, 2H), 3.30–3.14 (m, 2H), 2.58–2.52 (m, 2H), 1.19 (t, J=7.3 Hz, 3H), 1.14 (s, 9H).

FAB-MS (m/z); 706

Example I-105
Ethyl 5-[N-[4-(N-benzoyloxymethoxycarbonylamidino) benzoyl]-L-4-nitrophenylalanyl]-4,5,6,7-tetrahydropyrazolo[4,3-c]pyridin-2-acetate (Ethyl ester of Exemplary compound No. 2-247)

In the same manner as in Example I-103 except for using 0.70 g (2.2 mmol) of benzoyloxymethyl(4-nitrophenyl) carbonate in place of acetoxymethyl(4-nitrophenyl) carbonate, the reaction was carried out to obtain 0.98 g (1.4 mmol) of the title compound as white foamy product.

$^1$H-NMR (400 MHz, DMSO-d$_6$) δ; 9.32 (brs, 2H), 9.12, 9.00 (each d, J=8.8 Hz, total 1H), 8.09–7.43 (m, 14H), 5.99 (s, 2H), 5.30–5.26 (m, 1H), 4.92–4.34 (m, 4H), 4.12 (q, J=7.3 Hz, 2H), 3.95–3.55 (m, 2H), 3.30–3.14 (m, 2H), 2.58–2.52 (m, 2H), 1.19 (t, J=7.3 Hz, 3H).

FAB-MS (m/z); 726

Example I-106
Ethyl 5-[N-[4-(N-nicotinoyloxymethoxycarbonylamidino) benzoyl]-L-4-nitrophenylalanyl]-4,5,6,7-tetrahydropyrazolo[4,3-c]pyridin-2-acetate (Ethyl ester of Exemplary compound No. 2-249)

In the same manner as in Example I-103 except for using 0.49 g (1.5 mmol) of nicotinoyloxymethyl(4-nitrophenyl) carbonate in place of acetoxymethyl(4-nitrophenyl) carbonate, the reaction was carried out to obtain 0.63 g (0.90 mmol) of the title compound as pale yellowish foamy product.

1H-NMR (400 MHz, DMSO-d$_6$) δ; 9.37 (brs, 2H), 9.14–9.00 (m, 2H), 8.84 (d, J=4.9 Hz, 1H), 8.32–8.30 (m, 1H), 8.09–8.00 (m, 4H), 7.87, 7.83 (each d, J=8.8 Hz, total 2H), 7.61–7.55 (m, 3H), 7.51, 7.43 (each s, total 1H), 6.02 (s, 2H), 5.30–5.26 (m, 1H), 4.93–4.35 (m, 4H), 4.12 (q, J=7.3 Hz, 2H), 3.95–3.55 (m, 2H), 3.30–3.14 (m, 2H), 2.58–2.52 (m, 2H), 1.19 (t, J=7.3 Hz, 3H).

FAB-MS (m/z); 727

Example I-107
Ethyl 5-[N-[4-(N-t-butoxyethoxycarbonylamidino) benzoyl]-L-4-nitrophenylalanyl]-4,5,6,7-tetrahydropyrazolo[4,3-c]pyridin-2-acetate (Ethyl ester of Exemplary compound No. 2-251)

In the same manner as in Example I-103 except for using 1.3 g (4.4 mmol) of 2-t-butoxyethyl(4-nitrophenyl) carbonate in place of acetoxymethyl(4-nitrophenyl) carbonate, the reaction was carried out to obtain 1.1 g (1.6 mmol) of the title compound as pale yellowish foamy product.

$^1$H-NMR (400 MHz, DMSO-d$_6$) δ; 9.12, 9.00 (each d, J=8.8 Hz, total 1H), 9.06 (brs, 2H), 8.10–7.98 (m, 4H), 7.88, 7.84 (each d, J=8.8 Hz, total 2H), 7.60, 7.56 (each d, J=8.8 Hz, total 2H), 7.51, 7.44 (each s, total 1H), 5.31–5.27 (m, 1H), 4.93–4.35 (m, 4H), 4.12 (q, J=7.3 Hz, 2H), 4.07 (t, J=5.1 Hz, 2H), 3.95–3.55 (m, 2H), 3.52 (t, J=5.1 Hz, 2H), 3.30–3.14 (m, 2H), 2.58–2.52 (m, 2H), 1.19 (t, J=7.3 Hz, 3H), 1.14 (s, 9H).

FAB-MS (m/z); 692

Example I-108
Ethyl 5-[N-(4-amidino-2-methoxybenzoyl)-L-4-nitrophenylalanyl]-4,5,6,7-tetrahydropyrazolo[4,3-c] pyridin-2-acetate.trifluoroacetate (Ethyl ester of Exemplary compound No. 2-67)

(108-A) In 12 ml of acetonitrile were dissolved 5.2 g (5.0 mmol) of 5-(L-4-nitrophenylalanyl)-4,5,6,7-tetrahydropyrazolo[4,3-c]pyridin-2-acetate.2CF$_3$CO$_2$H and 0.89 g (5.0 mmol) of 4-cyano-2-methoxybenzoic acid, and under ice-cooling, 2.0 g (20 mmol) of triethylamine and 2.1 g (5.5 mmol) of HBTU were added to the solution, and the mixture was stirred overnight.

The resulting reaction mixture was concentrated under reduced pressure, a 5% aqueous potassium hydrogen sulfate solution was added to the residue, and the mixture was extracted with ethyl acetate. The organic layer was successively washed with a saturated aqueous sodium bicarbonate solution and a saturated aqueous saline solution, and dried over anhydrous sodium sulfate. The organic layer was concentrated under reduced pressure and ether was added to the residue to precipitate a solid and the solid was collected by filtration. The resulting solid was washed with ether, and dried under reduced pressure at 50° C. to obtain 2.4 g (4.3 mmol) of ethyl 5-[N-(4-cyano-2-methoxybenzoyl)-L-4-nitrophenylalanyl]-4,5,6,7-tetrahydropyrazolo[4,3-c] pyridin-2-acetate as pale yellowish foamy product.

$^1$H-NMR (DMSO-d$_6$) δ; 8.76, 8.74 (each d, J=8.3 Hz, total 1H), 8.12, 8.06 (each d, J=8.3 Hz, total 2H), 7.63–7.46 (m, 6H), 5.33–5.27 (m, 1H), 4.98–4.36 (m, 4H), 4.12 (q, J=7.3 Hz, 2H), 3.95–3.55 (m, 2H), 3.84 (s, 3H), 3.30–3.09 (m, 2H), 2.62–2.52 (m, 2H), 1.19 (t, J=7.3 Hz, 3H).

CI-MS (m/z); 561

(108-B) In 10 ml of DMF was dissolved 1.2 g (2.2 mmol) of ethyl 5-[N-(4-cyano-2-methoxybenzoyl)-L-4-nitrophenylalanyl]-4,5,6,7-tetrahydropyrazolo[4,3-c] pyridin-2-acetate, and 0.21 g (2.2 mmol) of anhydrous magnesium chloride and 0.36 g (4.6 mmol) of sodium hydrosulfide hydrate were added to the solution and the mixture was stirred at room temperature for 2 hours.

To the resulting reaction mixture was added 25 ml of water and the precipitated solid was collected by filtration, washed with water and dried under reduced pressure at 60° C. to obtain concentrated under reduced pressure to obtain 0.46 g (0.80 mmol) of ethyl 5-[N-(2-methoxy-4-thiocarbamoylbenzoyl)-L-4-nitrophenylalanyl]-4,5,6,7-tetrahydropyrazolo[4,3-c]pyridin-2-acetate as yellowish powder.

FAB-MS (m/z); 595

(108-C) In 25 ml of acetone was dissolved 0.46 g (0.80 mmol) of ethyl 5-[N-(2-methoxy-4-thiocarbamoylbenzoyl)-

L-4-nitrophenylalanyl]-4,5,6,7-tetrahydropyrazolo[4,3-c]pyridin-2-acetate, and 1.1 g (7.7 mmol) of methyl iodide was added to the solution and the mixture was heated under reflux for 2 hours.

The resulting reaction mixture was concentrated under reduced pressure to obtain 0.63 g (0.80 mmol) of ethyl 5-[N-[2-methoxy-4-(methylthioimidoyl)benzoyl]-L-4-nitrophenylalanyl]-4,5,6,7-tetrahydropyrazolo[4,3-c]pyridin-2-acetate.HI as yellowish powder.

FAB-MS (m/z); 609

(108-D) In 10 ml of ethanol was dissolved 0.63 g (0.80 mmol) of ethyl 5-[N-[2-methoxy-4-(methylthioimidoyl)benzoyl]-L-4-nitrophenylalanyl]-4,5,6,7-tetrahydropyrazolo[4,3-c]pyridin-2-acetate.HI, and 0.13 g (1.7 mmol) of ammonium acetate was added to the solution and the mixture was reacted at 60° C. for 3 hours.

The resulting reaction mixture was concentrated under reduced pressure, acetone was added to the residue, the precipitated insoluble material was removed by filtration and the filtrate was concentrated under reduced pressure. The resulting concentrate was purified by the reverse phase column chromatography method (eluent: acetonitrile/0.05% aqueous TFA solution=0/5 to 1/5) to obtain 0.12 g (0.20 mmol) of the title compound as pale yellowish foamy product.

$^1$H-NMR (400 MHz, DMSO-$d_6$) δ; 9.36 (s, 2H), 9.03 (s, 2H), 8.74, 8.72 (each d, J=8.3 Hz, total 1H), 8.11, 8.05 (each d, J=8.8 Hz, total 2H), 7.71–7.39 (m, 6H), 5.33–5.27 (m, 1H), 4.95–4.32 (m, 4H), 4.12 (q, J=7.3 Hz, 2H), 3.95–3.55 (m, 2H), 3.88, 3.87 (each s, total 3H), 3.30–3.09 (m, 2H), 2.66–2.52 (m, 2H), 1.19 (t, J=7.3 Hz, 3H).

FAB-MS (m/z); 578

Example I-109

Ethyl 5-[N-(4-amidino-2-methylbenzoyl)-L-4-nitrophenylalanyl]-4,5,6,7-tetrahydropyrazolo[4,3-c]pyridin-2-acetate.trifluoroacetate (Ethyl ester of Exemplary compound No. 2-68)

(109-A) In the same manner as in Example I-(108-A) except for using 2.1 g (13 mmol) of 4-cyano-2-methylbenzoic acid in place of 4-cyano-2-methoxybenzoic acid, the reaction was carried out to obtain 2.8 g (5.1 mmol) of ethyl 5-[N-(4-cyano-2-methylbenzoyl)-L-4-nitrophenylalanyl]-4,5,6,7-tetrahydropyrazolo[4,3-c]pyridin-2-acetate as pale yellowish solid.

$^1$H-NMR (DMSO-$d_6$) δ; 9.08, 9.00 (each d, J=8.3 Hz, total 1H), 8.15, 8.10 (each d, J=8.8 Hz, total 2H), 7.70–7.46 (m, 6H), 5.33–5.27 (m, 1H), 4.98–4.36 (m, 4H), 4.12 (q, J=7.3 Hz, 2H), 3.95–3.55 (m, 2H), 3.30–3.09 (m, 2H), 2.62–2.52 (m, 2H), 2.06, 2.01 (each s, total 3H), 1.19 (t, J=7.3 Hz, 3H).

FAB-MS (m/z); 545

(109-B) In the same manner as in Example I-(108-B) except for using 2.8 g (5.1 mmol) of ethyl 5-[N-(4-cyano-2-methylbenzoyl)-L-4-nitrophenylalanyl]-4,5,6,7-tetrahydropyrazolo[4,3-c]pyridin-2-acetate in place of ethyl 5-[N-(4-cyano-2-methoxybenzoyl)-L-4-nitrophenylalanyl]-4,5,6,7-tetrahydropyrazolo[4,3-c]pyridin-2-acetate, the reaction was carried out to obtain 1.9 g (3.3 mmol) of ethyl 5-[N-(2-methyl-4-thiocarbamoylbenzoyl)-L-4-nitrophenylalanyl]-4,5,6,7-tetrahydropyrazolo[4,3-c]pyridin-2-acetate as yellowish solid.

FAB-MS (m/z); 579

(109-C) In the same manner as in Example I-(108-C) except for using 1.9 g (3.3 mmol) of ethyl 5-[N-(2-methyl-4-thiocarbamoylbenzoyl)-L-4-nitrophenylalanyl]-4,5,6,7-tetrahydropyrazolo[4,3-c]pyridin-2-acetate in place of ethyl 5-[N-(2-methoxy-4-thiocarbamoylbenzoyl)-L-4-nitrophenylalanyl]-4,5,6,7-tetrahydropyrazolo[4,3-c]pyridin-2-acetate, the reaction was carried out to obtain 2.7 g (3.3 mmol) of ethyl 5-[N-[2-methyl-4-(methylthioimidoyl)benzoyl]-L-4-nitrophenylalanyl]-4,5,6,7-tetrahydropyrazolo[4,3-c]pyridin-2-acetate.HI as yellowish brown powder.

FAB-MS (m/z); 593

(109-D) In the same manner as in Example I-(108-D) except for using 2.7 g (3.3 mmol) of ethyl 5-[N-[2-methyl-4-(methylthioimidoyl)benzoyl]-L-4-nitrophenylalanyl]-4,5,6,7-tetrahydropyrazolo[4,3-c]pyridin-2-acetate.HI in place of ethyl 5-[N-[2-methoxy-4-(methylthioimidoyl)benzoyl]-L-4-nitrophenylalanyl]-4,5,6,7-tetrahydropyrazolo[4,3-c]pyridin-2-acetate.HI, the reaction was carried out to obtain 0.24 g (0.40 mmol) of the title compound as pale yellowish foamy product.

$^1$H-NMR (400 MHz, DMSO-$d_6$) δ; 9.29 (s, 2H), 9.05, 9.00 (each d, J=8.8 Hz, total 1H), 8.93 (s, 2H), 8.13, 8.09 (each d, J=8.8 Hz, total 2H), 7.64–7.47 (m, 6H), 5.33–5.27 (m, 1H), 4.95–4.40 (m, 4H), 4.12 (q, J=7.3 Hz, 2H), 3.95–3.55 (m, 2H), 3.30–3.09 (m, 2H), 2.66–2.52 (m, 2H), 2.10, 2.05 (each s, total 3H), 1.19 (t, J=7.3 Hz, 3H).

FAB-MS (m/z); 562

Example I-110

Ethyl 5-[N-(4-amidino-2-chlorobenzoyl)-L-4-nitrophenylalanyl]-4,5,6,7-tetrahydropyrazolo[4,3-c]pyridin-2-acetate.trifluoroacetate (Ethyl ester of Exemplary compound No. 2-66)

(110-A) In the same manner as in Example I-(108-A) except for using 0.91 g (5.0 mmol) of 2-chloro-4-cyanobenzoic acid in place of 4-cyano-2-methoxybenzoic acid, the reaction was carried out to obtain 1.1 g (1.9 mmol) of ethyl 5-[N-(2-chloro-4-cyanobenzoyl)-L-4-nitrophenylalanyl]-4,5,6,7-tetrahydropyrazolo[4,3-c]pyridin-2-acetate as white solid.

$^1$H-NMR (DMSO-$d_6$) δ; 9.26, 9.18 (each d, J=8.3 Hz, total 1H), 8.16–7.48 (m, 8H), 5.33–5.27 (m, 1H), 4.95–4.36 (m, 4H), 4.12 (q, J=7.3 Hz, 2H), 3.90–3.70 (m, 2H), 3.30–3.00 (m, 2H), 2.62–2.52 (m, 2H), 1.19 (t, J=7.3 Hz, 3H).

FAB-MS (m/z); 565

(110-B) In the same manner as in Example I-(108-B) except for using 1.1 g (1.9 mmol) of ethyl 5-[N-(2-chloro-4-cyanobenzoyl)-L-4-nitrophenylalanyl]-4,5,6,7-tetrahydropyrazolo[4,3-c]pyridin-2-acetate in place of ethyl 5-[N-(4-cyano-2-methoxybenzoyl)-L-4-nitrophenylalanyl]-4,5,6,7-tetrahydropyrazolo[4,3-c]pyridin-2-acetate, the reaction was carried out to obtain 0.80 g (1.3 mmol) of ethyl 5-[N-(2-chloro-4-thiocarbamoylbenzoyl)-L-4-nitrophenylalanyl]-4,5,6,7-tetrahydropyrazolo[4,3-c]pyridin-2-acetate as yellowish solid.

FAB-MS (m/z); 599

(110-C) In the same manner as in Example I-(108-C) except for using 0.80 g (1.3 mmol) of ethyl 5-[N-(2-chloro-4-thiocarbamoylbenzoyl)-L-4-nitrophenylalanyl]-4,5,6,7-tetrahydropyrazolo[4,3-c]pyridin-2-acetate in place of ethyl 5-[N-(2-methoxy-4-thiocarbamoylbenzoyl)-L-4-nitrophenylalanyl]-4,5,6,7-tetrahydropyrazolo[4,3-c]pyridin-2-acetate, the reaction was carried out to obtain 1.2 g (1.3 mmol) of ethyl 5-[N-[2-chloro-4-(methylthioimidoyl)benzoyl]-L-4-nitrophenylalanyl]-4,5,6,7-tetrahydropyrazolo[4,3-c]pyridin-2-acetate.HI as yellowish brown powder.

FAB-MS (m/z); 613

(110-D) In the same manner as in Example I-(108-D) except for using 1.2 g (1.3 mmol) of ethyl 5-[N-[2-chloro-4-(methylthioimidoyl)benzoyl]-L-4-nitrophenylalanyl)-4,5, 6,7-tetrahydropyrazolo[4,3-c]pyridin-2-acetate.HI in place of ethyl 5-[N-[2-methoxy-4-(methylthioimidoyl)benzoyl]-L-4-nitrophenylalanyl]-4,5,6,7-tetrahydropyrazolo[4,3-c]pyridin-2-acetate.HI, the reaction was carried out to obtain 0.12 g (0.20 mmol) of the title compound as pale yellowish foamy product.

$^1$H-NMR (400 MHz, DMSO-$d_6$) δ; 9.40 (s, 2H), 9.27, 9.17 (each d, J=8.8 Hz, total 1H), 9.12 (s, 2H), 8.13, 8.08 (each d, J=8.8 Hz, total 2H), 7.87–7.41 (m, 6H), 5.33–5.27 (m, 1H), 4.94–4.40 (m, 4H), 4.12 (q, J=7.3 Hz, 2H), 3.95–3.55 (m, 2H), 3.30–3.09 (m, 2H), 2.66–2.52 (m, 2H), 1.19 (t, J=7.3 Hz, 3H).

ESI-MS (m/z); 582

Example I-111

Ethyl 5-[N-(4-amidino-2-fluorobenzoyl)-L-4-nitrophenylalanyl]-4,5,6,7-tetrahydropyrazolo[4,3-c]pyridin-2-acetate.trifluoroacetate (Ethyl ester of Exemplary compound No. 2-65)

(111-A) In the same manner as in Example I-(108-A) except for using 0.50 g (3.0 mmol) of 4-cyano-2-fluorobenzoic acid in place of 4-cyano-2-methoxybenzoic acid, the reaction was carried out to obtain 0.88 g (1.6 mmol) of ethyl 5-[N-(4-cyano-2-fluorobenzoyl)-L-4-nitrophenylalanyl]-4,5,6,7-tetrahydropyrazolo[4,3-c]pyridin-2-acetate as white solid.

$^1$H-NMR (DMSO-$d_6$) δ; 9.18, 9.08 (each d, J=8.3 Hz, total 1H), 8.14–7.47 (m, 8H), 5.33–5.27 (m, 1H), 4.95–4.37 (m, 4H), 4.14 (q, J=7.3 Hz, 2H), 3.95–3.65 (m, 2H), 3.30–3.05 (m, 2H), 2.62–2.52 (m, 2H), 1.21 (t, J=7.3 Hz, 3H).

FAB-MS (m/z); 549

(111-B) In the same manner as in Example I-(108-B) except for using 0.88 g (1.6 mmol) of ethyl 5-[N-(4-cyano-2-fluorobenzoyl)-L-4-nitrophenylalanyl]-4,5,6,7-tetrahydropyrazolo[4,3-c]pyridin-2-acetate in place of ethyl 5-[N-(4-cyano-2-methoxybenzoyl)-L-4-nitrophenylalanyl]-4,5,6,7-tetrahydropyrazolo[4,3-c]pyridin-2-acetate, the reaction was carried out to obtain 0.59 g (1.0 mmol) of ethyl 5-[N-(2-fluoro-4-thiocarbamoylbenzoyl)-L-4-nitrophenylalanyl]-4,5,6,7-tetrahydropyrazolo[4,3-c]pyridin-2-acetate as yellowish solid.

ESI-MS (m/z); 583

(111-C) In the same manner as in Example I-(108-C) except for using 0.59 g (1.0 mmol) of ethyl 5-[N-(2-fluoro-4-thiocarbamoylbenzoyl)-L-4-nitrophenylalanyl]-4,5,6,7-tetrahydropyrazolo[4,3-c]pyridin-2-acetate in place of ethyl 5-[N-(2-methoxy-4-thiocarbamoylbenzoyl)-L-4-nitrophenylalanyl]-4,5,6,7-tetrahydropyrazolo[4,3-c]pyridin-2-acetate, the reaction was carried out to obtain 0.81 g (1.0 mmol) of ethyl 5-[N-[2-fluoro-4-(methylthioimidoyl)benzoyl]-L-4-nitrophenylalanyl]-4,5,6,7-tetrahydropyrazolo[4,3-c]pyridin-2-acetate.HI as yellowish brown powder.

ESI-MS (m/z); 597

(111-D) In the same manner as in Example I-(108-D) except for using 0.81 g (1.0 mmol) of ethyl 5-[N-[2-fluoro-4-(methylthioimidoyl)benzoyl]-L-4-nitrophenylalanyl]-4,5,6,7-tetrahydropyrazolo[4,3-c]pyridin-2-acetate.HI in place of ethyl 5-[N-[2-methoxy-4-(methylthioimidoyl)benzoyl]-L-4-nitrophenylalanyl]-4,5,6,7-tetrahydropyrazolo[4,3-c]pyridin-2-acetate.HI, the reaction was carried out to obtain 0.06 g (0.10 mmol) of the title compound as pale yellowish foamy product.

$^1$H-NMR (400 MHz, DMSO-$d_6$) δ; 9.41 (s, 2H), 9.14 (s, 2H), 9.03, 8.96 (each d, J=8.8 Hz, total 1H), 8.12, 8.05 (each d, J=8.8 Hz, total 2H), 7.94–7.47 (m, 6H), 5.33–5.27 (m, 1H), 4.96–4.40 (m, 4H), 4.12 (q, J=7.3 Hz, 2H), 3.95–3.55 (m, 2H), 3.30–3.09 (m, 2H), 2.66–2.52 (m, 2H), 1.19 (t, J=7.3 Hz, 3H).

ESI-MS (m/z); 566

Example I-112

Ethyl 5-[N-(5-amidino-2-pyridylcarbonyl)-L-4-nitrophenylalanyl]-4,5,6,7-tetrahydropyrazolo[4,3-c]pyridin-2-acetate.trifluoroacetate (Ethyl ester of Exemplary compound No. 2-220)

(112-A) In the same manner as in Example I-(108-A) except for using 0.74 g (5.0 mmol) of 5-cyano-2-pyridincarboxylic acid in place of 4-cyano-2-methoxybenzoic acid, the reaction was carried out to obtain 1.7 g (3.2 mmol) of ethyl 5-[N-(5-cyano-2-pyridylcarbonyl)-L-4-nitrophenylalanyl]-4,5,6,7-tetrahydropyrazolo[4,3-c]pyridin-2-acetate as pale yellowish foamy product.

$^1$H-NMR (CDCl$_3$) δ; 8.87, 8.84 (each s, total 1H), 8.80, 8.68 (each d, J=8.3 Hz, total 1H), 8.27, 8.26 (each d, J=8.1 Hz, total 1H), 8.14 (d, J=8.1 Hz, 1H), 8.07, 7.98 (each d, J=8.8 Hz, total 2H), 7.37, 7.34 (each d, J=8.8 Hz, total 2H), 7.26, 7.03 (each s, total 1H), 5.54–5.32 (m, 1H), 4.85–4.37 (m, 4H), 4.26–4.18 (m, 3H), 3.75–3.68 (m, 1H), 3.55–3.15 (m, 2H), 2.75–2.40 (m, 2H), 1.29 (t, J=7.3 Hz, 3H).

FAB-MS (m/z); 532

(112-B) In the same manner as in Example I-(108-B) except for using 1.7 g (3.2 mmol) of ethyl 5-[N-(5-cyano-2-pyridylcarbonyl)-L-4-nitrophenylalanyl]-4,5,6,7-tetrahydropyrazolo[4,3-c]pyridin-2-acetate in place of ethyl 5-[N-(4-cyano-2-methoxybenzoyl)-L-4-nitrophenylalanyl]-4,5,6,7-tetrahydropyrazolo[4,3-c]pyridin-2-acetate, the reaction was carried out to obtain 1.0 g (1.8 mmol) of ethyl 5-[N-(5-thiocarbamoyl-2-pyridylcarbonyl)-L-4-nitrophenylalanyl]-4,5,6,7-tetrahydropyrazolo[4,3-c]pyridin-2-acetate as yellowish solid.

ESI-MS (m/z); 564

(112-C) In the same manner as in Example I-(108-C) except for using 1.0 g (1.8 mmol) of ethyl 5-[N-(5-thiocarbamoyl-2-pyridylcarbonyl)-L-4-nitrophenylalanyl]-4,5,6,7-tetrahydropyrazolo[4,3-c]pyridin-2-acetate in place of ethyl 5-[N-(2-methoxy-4-thiocarbamoylbenzoyl)-L-4-nitrophenylalanyl]-4,5,6,7-tetrahydropyrazolo[4,3-c]pyridin-2-acetate, the reaction was carried out to obtain 1.5 g (1.8 mmol) of ethyl 5-[N-[5-(methylthioimidoyl)-2-pyridylcarbonyl]-L-4-nitrophenylalanyl]-4,5,6,7-tetrahydropyrazolo[4,3-c]pyridin-2-acetate.HI as yellowish brown powder.

ESI-MS (m/z); 580

(112-D) In the same manner as in Example I-(108-D) except for using 1.5 g (1.8 mmol) of ethyl 5-[N-[5-(methylthioimidoyl)-2-pyridylcarbonyl]-L-4-nitrophenylalanyl]-4,5,6,7-tetrahydropyrazolo[4,3-c]pyridin-2-acetate.HI in place of ethyl 5-[N-[2-methoxy-4-(methylthioimidoyl)benzoyl]-L-4-nitrophenylalanyl]-4,5,6,7-tetrahydropyrazolo[4,3-c]pyridin-2-acetate.HI, the reaction was carried out to obtain 0.12 g (0.20 mmol) of the title compound as pale yellowish foamy product.

$^1$H-NMR (400 MHz, DMSO-$d_6$) δ; 9.54 (s, 2H), 9.28 (s, 2H), 9.18 (d, J=8.8 Hz, 1H), 9.11 (s, 1H), 8.50–7.44 (m, 7H), 5.33–5.27 (m, 1H), 4.95–4.30 (m, 4H), 4.12 (q, J=7.3 Hz, 2H), 3.95–3.55 (m, 2H), 3.30–3.09 (m, 2H), 2.66–2.52 (m, 2H), 1.19 (t, J=7.3 Hz, 3H).

ESI-MS (m/z); 549

Example I-113

Ethyl 5-[N-[4-(N-t-butoxycarbonylmorpholinoimidoyl)benzoyl]-L-4-nitrophenylalanyl]-4,5,6,7-tetrahydropyrazolo[4,3-c]pyridin-2-acetate (Ethyl ester of Exemplary compound No. 2-244)

In 10 ml of acetonitrile were dissolved 0.33 g (1.0 mmol) of 4-(N-t-butoxycarbonylmorpholinoimidoyl)benzoic acid and 0.41 g (1.0 mmol) of 5-(L-4-nitrophenylalanyl)-4,5,6,7-tetrahydropyrazolo[4,3-c]pyridin-2-acetate.2CF$_3$CO$_2$H, and after adding 1.5 ml of triethylamine and 0.40 g (1.1 mmol) of HBTU to the solution, the mixture was stirred at room temperature for one hour.

The resulting reaction mixture was concentrated under reduced pressure, water was added to the residue, and the mixture was extracted with ethyl acetate. The organic layer was washed successively with a saturated aqueous sodium bicarbonate solution and a saturated aqueous saline solution, and dried over anhydrous sodium sulfate. The organic layer was concentrated under reduced pressure and the residue was purified by the silica gel column chromatography method (chloroform/methanol=100/1 to 50/1) to obtain 0.75 g (1.0 mmol) of the title compound as pale yellowish powder.

$^1$H-NMR (400 MHz, CDCl$_3$) δ; 8.10–7.96 (m, 4H), 7.43–7.05 (m, 5H), 5.53–5.37 (m, 1H), 4.84–4.39 (m, 4H), 4.32–4.20 (m, 3H), 3.80–3.55 (brs, 7H), 3.54–3.35 (m, 2H), 3.28–3.16 (m, 2H), 2.88–2.54 (m, 2H), 1.62, 1.54, 1.23, 1.22 (each s, total 9H), 1.32–1.28 (m, 3H).

FAB-MS (m/z); 718

Example I-114

Ethyl 5-[N-[4-(morpholinoimidoyl)benzoyl]-L-4-nitrophenylalanyl]-4,5,6,7-tetrahydropyrazolo[4,3-c]pyridin-2-acetate.trifluoroacetate (Ethyl ester of Exemplary compound No. 2-226)

In 4 ml of methylene chloride was dissolved 0.75 g (1.0 mmol) of ethyl 5-[N-[4-(N-t-butoxycarbonylmorpholinoimidoyl)benzoyl]-L-4-nitrophenylalanyl]-4,5,6,7-tetrahydropyrazolo[4,3-c]pyridin-2-acetate, and after adding 4 ml of CF$_3$CO$_2$H, the mixture was stirred at room temperature for one hour.

The resulting reaction mixture was concentrated under reduced pressure, and the residue was purified by the silica gel column chromatography method (eluent: chloroform/methanol/acetic acid=150/10/5 to 150/25/15) to obtain 0.43 g (0.54 mmol) of the title compound as white powder.

Melting point; 116–117° C.

$^1$H-NMR (400 MHz, DMSO-d$_6$) δ; 9.07, 8.94 (each d, J=8.8 Hz, total 1H), 8.09, 8.04 (each d, J=8.8 Hz, total 2H), 7.88, 7.83 (each d, J=8.3 Hz, total 2H), 7.61, 7.56 (each d, J=8.8 Hz, total 2H), 7.48, 7.45 (each d, J=8.3 Hz, total 2H), 7.52, 7.44 (each s, total 1H), 5.25–5.35 (m, 1H), 4.93, 4.58 (each s, total 2H), 4.94–4.33 (m, 2H), 4.15–4.09 (m, 2H), 3.90–3.55 (m, 2H), 3.65–3.60 (m, 2H), 3.55–3.20 (m, 6H), 3.20–3.16 (m, 2H), 2.65–2.40 (m, 2H), 1.72–1.22 (m, 3H).

FAB-MS (m/z); 618

Example I-115

Ethyl 5-[N-[4-(N-phenoxycarbonylamidino)benzoyl]-L-4-nitrophenylalanyl]-4,5,6,7-tetrahydropyrazolo[4,3-c]pyridin-2-acetate (Ethyl ester of Exemplary compound No. 2-252)

In 20 ml of dehydrated THF was dissolved 2.0 g (3.0 mmol) of ethyl 5-(N-(4-amidinobenzoyl)-L-4-nitrophenylalanyl)-4,5,6,7-tetrahydropyrazolo[4,3-c]pyridin-2-acetate.2CF$_3$CO$_2$H, and under a cooling bath at −78° C., 7.5 ml (7.5 mmol) of a THF solution containing 1M lithium bis(trimethylsilyl)amide was added to the solutionand the mixture was stirred for one hour. To the solution was added 1.4 g (9.0 mmol) of phenylchloroformate and the mixture was further stirred for one hour.

To the resulting reaction mixture were added ethyl acetate and a saturated aqueous ammonium chloride solution, and the organic layer was separated. The organic layer was washed with a saturated aqueous saline solution, dried over anhydrous sodium sulfate and concentrated under reduced pressure. The residue was purified by the silica gel column chromatography method (eluent: chloroform/methanol= 100/1 to 20/1) to obtain 0.80 g (1.2 mmol) of the title compound as white solid.

Melting point; 119–122° C.

$^1$H-NMR (400 MHz, DMSO-d$_6$) δ; 9.28 (brs, 2H), 9.14–9.00 (m, 1H), 8.10–8.01 (m, 3H), 7.91–7.84 (m, 2H), 7.62–7.37 (m, 5H), 7.23–7.12 (m, 3H), 5.30–5.28 (m, 1H), 4.93–4.34 (m, 4H), 4.15–4.10 (m, 4H), 3.84–3.82 (m, 1H), 3.75–3.59 (m, 1H), 3.29–3.13 (m, 2H), 2.65–2.52 (m, 1H), 1.29–1.09 (m, 3H).

FAB-MS (m/z); 668

Example I-116

Ethyl 5-[N-[4-(N-4-octyloxyphenoxycarbonylamidino)benzoyl]-L-4-nitrophenylalanyl]-4,5,6,7-tetrahydropyrazolo[4,3-c]pyridin-2-acetate (Ethyl ester of Exemplary compound No. 2-256)

In 20 ml of dehydrated THF was dissolved 0.50 g (0.58 mmol) of ethyl 5-[N-(4-amidinobenzoyl)-L-4-nitrophenylalanyl)-4,5,6,7-tetrahydropyrazolo[4,3-c]pyridin-2-acetate.2CF$_3$CO$_2$H, and under a cooling bath at −78° C., 2.5 ml (2.5 mmol) of a THF solution containing 1M lithium bis(trimethylsilyl)amide was added to the solution and the mixture was stirred for one hour. To the solution was added 0.60 g (1.5 mmol) of 4-octyloxyphenyl(4-nitrophenyl)carbonate and the mixture was further stirred for one hour.

To the resulting reaction mixture was added a small amount of acetone and the mixture was filtered through Celite. The filtrate was concentratedunder reduced pressure and the residue was purified by the silica gel column chromatography method (eluent: chloroform/methanol= 100/1 to 20/1) to obtain 0.090 g (0.13 mmol) of the title compound as white powder.

Melting point; 93–96° C.

$^1$H-NMR (400 MHz, DMSO-d$_6$) δ; 9.24 (brs, 2H), 9.15–9.01 (m, 1H), 8.10–8.02 (m, 4H), 7.91–7.84 (m, 2H), 7.63–7.56 (m, 2H), 7.56, 7.44 (each s, total 1H), 7.06–7.04 (m, 2H), 6.92–6.90 (m, 2H), 5.31–5.28 (m, 1H), 4.93–4.34 (m, 4H), 4.15–4.09 (m, 2H), 4.00–3.84 (m, 2H), 3.87–3.84 (m, 2H), 3.69–3.61 (m, 2H), 3.30–3.14 (m, 2H), 2.57–2.48 (m, 1H), 1.71–1.66 (m, 2H), 1.41–1.17 (m, 13H), 0.87–0.84 (m, 3H).

FAB-MS (m/z); 786

Example I-117

Ethyl 5-[N-[4-(N-isopropenoxycarbonylamidino)benzoyl]-L-4-nitrophenylalanyl]-4,5,6,7-tetrahydropyrazolo[4,3-c]pyridin-2-acetate (Ethyl ester of Exemplary compound No. 2-253)

In 10 ml of dehydrated THF was dissolved 1.5 g (2.2 mmol) of ethyl 5-[N-(4-amidinobenzoyl)-L-4-nitrophenylalanyl]-4,5,6,7-tetrahydropyrazolo[4,3-c]pyridin-2-acetate.2CF$_3$CO$_2$H, and under a cooling bath at −78° C., 6.0 ml (6.0 mmol) of a THF solution containing 1M lithium bis(trimethylsilyl)amide to the solution and the mixture was stirred for one hour. To the solution was added 0.50 g (4.1 mmol) of isopropenylchloroformate and the mixture was further stirred for one hour.

To the resulting reaction mixture were added ethyl acetate and a saturated aqueous ammonium chloride solution, and the organic layer was separated. The organic layer was washed successively with a saturated aqueous sodium bicarbonate solution and a saturated aqueous saline solution, dried over anhydrous sodium sulfate and concentrated under reduced pressure. The residue was purified by the silica gel column chromatography method (eluent: chloroform/methanol=100/1 to 20/1) to obtain 0.10 g (0.14 mmol) of the title compound as white powder.

Melting point; 115–119° C.

$^1$H-NMR (400 MHz, DMSO-$d_6$) δ; 9.22 (s, 1H), 9.13–8.99 (m, 1H), 8.09–8.07 (m, 1H), 8.04–7.99 (m, 2H), 7.89–7.83 (m, 2H), 7.62–7.55 (m, 2H), 7.50–7.43 (m, 1H), 5.35–5.25 (m, 1H), 4.92–4.80 (m, 2H), 4.70–4.34 (m, 4H), 4.14–4.09 (m, 2H), 3.95–3.61 (m, 2H), 3.87–3.68 (m, 2H), 3.40–3.17 (m, 2H), 3.08–2.56 (m, 2H), 1.90 (s, 3H), 1.20–1.17 (m, 3H).

FAB-MS (m/z); 632

Example I-118

Ethyl 5-[N-[4-(N-benzyloxycarbonylamidino)benzoyl]-L-4-nitrophenylalanyl]-4,5,6,7-tetrahydropyrazolo[4,3-c]pyridin-2-acetate (Ethyl ester of Exemplary compound No. 2-255)

In 40 ml of dichloroethane was dissolved 0.50 g (0.72 mmol) of ethyl 5-[N-(4-amidinobenzoyl)-L-4-nitrophenylalanyl]-4,5,6,7-tetrahydropyrazolo[4,3-c]pyridin-2-acetate.2CF$_3$CO$_2$H, and then, 0.26 g (2.2 mmol) of 4-dimethylaminopyridine and 1 ml of N,O-bis(trimethylsilyl)acetamide were added to the solution. To the mixture was added under a cooling bath at −78° C., 1.5 ml (14 mmol) of trimethylsilyl chloride, and after 30 minutes stirring, 1.5 g (5.5 mmol) of benzyl chloroformate was added to the mixture and the mixture was further stirred for one hour.

The resulting reaction mixture was concentrated under reduced pressure, and the residue was purified by the silica gel column chromatography method (eluent: chloroform/methanol=100/1 to 20/1) to obtain 0.22 g (0.32 mmol) of the title compound as white powder.

Melting point; 105–107° C.

1H-NMR (400 MHz, DMSO-$d_6$) δ; 9.12–8.99 (m, 3H), 8.09–7.82 (m, 4H), 7.61–7.43 (m, 4H), 7.38–7.31 (m, 6H), 5.30–5.27 (m, 1H), 5.01–4.35 (m, 4H), 4.14–4.09 (m, 2H), 3.87–3.83 (m, 1H), 3.69–3.62 (m, 1H), 3.43–3.13 (m, 2H), 2.65–2.52 (m, 1H), 1.20–1.16 (m, 3H).

FAB-MS (m/z); 682

Example I-119

Ethyl 5-[N-[4-(N-isopropoxycarbonylamidino)benzoyl]-L-4-nitrophenylalanyl]-4,5,6,7-tetrahydropyrazolo[4,3-c]pyridin-2-acetate (Ethyl ester of Exemplary compound No. 2-148)

In 40 ml of dichloroethane was dissolved 0.37 g (0.54 mmol) of ethyl 5-[N-(4-amidinobenzoyl)-L-4-nitrophenylalanyl]-4,5,6,7-tetrahydropyrazolo[4,3-c]pyridin-2-acetate.2CF$_3$CO$_2$H, and then, 0.20 g (1.7 mmol) of 4-dimethylaminopyridine and 1 ml of N,O-bis(trimethylsilyl)acetamide were added to the solution, and the resulting solution was stirred under ice-bath for 30 minutes. To the solution was added 0.16 g (1.1 mmol) of isopropyl chloroformate and the mixture was further stirred for one hour.

The resulting reaction mixture was concentrated under reduced pressure, and the residue was purified by the silica gel column chromatography method (eluent: chloroform/methanol=100/1 to 20/1) to obtain 0.22 g (0.14 mmol) of the title compound as white powder.

Melting point; 110–114° C.

$^1$H-NMR (400 MHz, DMSO-$d_6$) δ; 9.14–9.00 (m, 3H), 8.10–7.98 (m, 2H), 7.89–7.83 (m, 2H), 7.63–7.56 (m, 4H), 7.52, 7.45 (each s, total 1H), 5.32–5.28 (m, 1H), 4.94–4.36 (m, 5H), 4.16–4.10 (m, 2H), 3.88–3.85 (m, 1H), 3.75–3.60 (m, 1H), 3.47–3.15 (m, 2H)., 2.58–2.50 (m, 1H), 1.22–1.18 (m, 3H).

FAB-MS (m/z); 636

Example I-120

Ethyl 5-[N-[4-(N-t-butoxycarbonylamidino)benzoyl]-L-4-nitrophenylalanyl]-4,5,6,7-tetrahydropyrazolo[4,3-c]pyridin-2-acetate (Ethyl ester of Exemplary compound No. 2-175)

In 20 ml of acetonitrile was dissolved 0.30 g (0.43 mmol) of ethyl 5-[N-(4-amidinobenzoyl)-L-4-nitrophenylalanyl]-4,5,6,7-tetrahydropyrazolo[4,3-c]pyridin-2-acetate.2CF$_3$CO$_2$H, and then, 0.050 g (0.41 mmol) of 4-dimethylaminopyridine and 0.30 g (2.7 mmol) of DABCO were added to the solution, and the resulting solution was stirred at room temperature for 30 minutes. To the solution was added 0.10 g (0.51 mmol) of di-t-butyl dicarbonate and the mixture was stirred under ice-cooling for one hour.

The resulting reaction mixture was concentrated under reduced pressure, ethyl acetate and a saturated aqueous sodium bicarbonate solution were added to the residue, and the organic layer was separated. The organic layer was washed with a saturated aqueous saline solution, dried over anhydrous magnesium sulfate and concentrated under reduced pressure. The residue was purified by the silica gel column chromatography method (eluent: chloroform/methanol=100/1 to 20/1) to obtain 0.12 g (0.31 mmol) of the title compound as white powder.

Melting point; 123–125° C.

$^1$H-NMR (400 MHz, DMSO-$d_6$) δ; 9.12–8.99 (m, 3H), 8.10–7.81 (m, 6H), 7.61–7.55 (m, 2H), 7.51, 7.44 (each s, total 1H), 5.31–5.27 (m, 1H), 4.93–4.35 (m, 4H), 4.15–4.09 (m, 2H), 3.87–3.84 (m, 1H), 3.69–3.61 (m, 2H), 3.30–3.14 (m, 2H), 2.57–2.49 (m, 1H), 1.43 (s, 9H), 1.20–1.17 (m, 3H).

FAB-MS (m/z); 636

Example I-121

Ethyl 5-[N-[4-(N-allyloxycarbonylamidino)benzoyl]-L-4-nitrophenylalanyl]-4,5,6,7-tetrahydropyrazolo[4,3-c]pyridin-2-acetate (Ethyl ester of Exemplary compound No. 2-254)

In 10 ml of acetonitrile was dissolved 1.0 g (1.5 mmol) of ethyl 5-[N-(4-amidinobenzoyl)-L-4-nitrophenylalanyl]-4,5,6,7-tetrahydropyrazolo[4,3-c]pyridin-2-acetate.2CF$_3$CO$_2$H, and then, 0.18 g (1.5 mmol) of 4-dimethylaminopyridine and 1.0 g (7.2 mmol) of DABCO were added to the solution, and the resulting solution was stirred at room temperature for 30 minutes. To the solution was added, under ice-cooling, 2.0 g (0.51 mmol) of diallyl dicarbonate over one hour and the mixture was stirred for further one hour.

The resulting reaction mixture was concentrated under reduced pressure, ethyl acetate and a saturated aqueous sodium bicarbonate solution were added to the residue, and the organic layer was separated. The organic layer was washed with a saturated aqueous saline solution, dried overanhydrous magnesium sulfate and concentrated under reduced pressure. The residue was purified by the silica gel column chromatography method (eluent: chloroform/methanol=100/1 to 20/1) to obtain 0.35 g (0.31 mmol) of title compound as white powder.

Melting point; 102–105° C.

$^1$H-NMR (400 MHz, DMSO-$d_6$) δ; 9.20 (brs, 2H), 9.13–9.00 (m, 1H), 8.10–7.83 (m, 6H), 7.61–7.55 (m, 2H), 7.51, 7.44 (each s, total 1H), 6.01–5.92 (m, 1H), 5.34–5.19 (m, 3H), 4.93–4.34 (m, 9H), 4.15–4.09 (m, 2H), 3.88–3.85 (m, 1H), 3.75–3.60 (m, 1H), 3.47–3.15 (m, 2H), 2.58–2.50 (m, 1H), 1.20–1.17 (m, 3H).

FAB-MS (m/z); 632

Example I-122
Ethyl 5-[N-[4-(N-n-hexyloxycarbonylamidino)benzoyl]-L-4-nitrophenylalanyl]-4,5,6,7-tetrahydropyrazolo[4,3-c]pyridin-2-acetate (Ethyl ester of Exemplary compound No. 2-180)

In 20 ml of dehydrated THF was dissolved 0.40 g (0.57 mmol) of ethyl 5-[N-(4-amidinobenzoyl)-L-4-nitrophenylalanyl]-4,5,6,7-tetrahydropyrazolo[4,3-c]pyridin-2-acetate.2CF$_3$CO$_2$H, and under a cooling bath at −78° C., 2.5 ml (2.5 mmol) of a THF solution containing 1M lithium bis(trimethylsilyl)amide was added to the solution and the mixture was stirred for one hour. To the solution was added 1.0 g (6.1 mmol) of n-hexylchloroformate and the mixture was further stirred for one hour.

To the resulting reaction mixture was added a small amount of acetone and the mixture was filtered through Celite. The filtrate was concentrated under reduced pressure and the residue was purified by the silica gel column chromatography method (eluent: chloroform/methanol= 1.00/1 to 20/1) to obtain 0.015 g (0.020 mmol) of the titlecompound as white powder.

Melting point; 83–86° C.
$^1$H-NMR (400 MHz, DMSO-d$_6$) δ; 9.14–9.00 (m, 3H), 8.10–7.82 (m, 6H), 7.62–7.55 (m, 2H), 7.51, 7.43 (each s, total 1H), 5.30–5.27 (m, 1H), 4.94–4.34 (m, 4H), 4.15–4.09 (m, 2H), 3.87–3.84 (m, 1H), 3.69–3.61 (m, 1H), 3.30–3.14 (m, 2H), 2.57–2.48 (m, 1H), 1.63–1.57 (m, 2H), 1.29 (s, 6H), 1.21–1.17 (m, 3H).
FAB-MS (m/z); 676

Example I-123
Ethyl 5-[N-[4-(N-cyclohexyloxycarbonylamidino)benzoyl]-L-4-nitrophenylalanyl]-4,5,6,7-tetrahydropyrazolo[4,3-c]pyridin-2-acetate (Ethyl ester of Exemplary compound No. 2-181)

In 20 ml of THF was dissolved 0.40 g (0.58 mmol) of ethyl 5-[N-(4-amidinobenzoyl)-L-4-nitrophenylalanyl]-4,5,6,7-tetrahydropyrazolo[4,3-c]pyridin-2-acetate.2CF$_3$CO$_2$H, and under a cooling bath at −78° C., 2.5 ml (2.5 mmol) of a THF solution containing 1M lithium bis(trimethylsilyl)amide was added to the solution and the mixture was stirred for one hour. To the solution was added 0.60 g (1.9 mmol) of cyclohexyl(4-nitrophenyl)carbonate and the mixture was further stirred for one hour.

To the resulting reaction mixture was added a small amount of acetone and the mixture was filtered through Celite. The filtrate was concentrated under reduced pressure and the residue was purified by the silica gel column chromatography method (eluent: chloroform/methanol= 100/1 to 20/1) to obtain 0.090 g (0.13 mmol) of the title compound as white powder.

Melting point; 115–117° C.
$^1$H-NMR (400 MHz, DMSO-d$_6$) δ; 9.13–8.99 (m, 3H), 8.10–7.82 (m, 6H), 7.61–7.55 (m, 2H), 7.51, 7.44 (each s, total 1H), 5.31–5.27 (m, 1H), 4.93–4.35 (m, 5H), 4.15–4.09 (m, 2H), 3.87–3.84 (m, 1H), 3.69–3.61 (m, 1H), 3.30–3.14 (m, 2H), 2.57–2.49 (m, 1H), 1.84–1.50 (m, 5H), 1.38–1.30 (m, 5H), 1.20–1.17 (m, 3H).
FAB-MS (m/z); 674

Example I-124
Ethyl 5-[N-[4-(N-pivaloylamidino)benzoyl]-L-4-nitrophenylalanyl]-4,5,6,7-tetrahydropyrazolo[4,3-c]pyridin-2-acetate (Ethyl ester of Exemplary compound No. 2-109)

In 20 ml of dehydrated THF was dissolved 0.50 g (0.71 mmol) of ethyl 5-[N-(4-amidinobenzoyl)-L-4-nitrophenylalanyl]-4,5,6,7-tetrahydropyrazolo[4,3-c]pyridin-2-acetate.2CF$_3$CO$_2$H, and under a cooling bath at −78° C., 2.5 ml (2.50 mmol) of a THF solution containing IM lithium bis(trimethylsilyl)amide was added to the solution and the mixture was stirred for one hour. To the solution was added 1.50 g (10.0 mmol) of chloromethyl pivalate and the mixture was further stirred for one hour.

To the resulting reactionmixture was added a small amount of acetone and the mixture was filtered through Celite. The filtrate was concentrated under reduced pressure and the residue was purified by the silica gel column chromatography method (eluent: chloroform/methanol= 100/1 to 20/1) to obtain 0.14 g (0.22 mmol) of the title compound as white powder.

Melting point; 103–106° C.
$^1$H-NMR (400 MHz, DMSO-d$_6$) δ; 10.45 (brs. 1H), 9.15–9.00 (m, 1H), 8.10–7.44 (m, 9H), 5.30–5.28 (m, 1H), 4.93–4.33 (m, 4H), 4.15–4.10 (m, 2H), 3.84–3.82 (m, 1H), 3.75–3.59 (m, 1H), 3.29–3.13 (m, 2H), 2.65–2.52 (m, 1H), 1.21–1.06 (m, 12H).
FAB-MS (m/z); 633

Example I-125
Ethyl 5-[N-7(4-N,N,N'-tri-t-butoxycarbonylamidinobenzoyl)-L-alanyl]-4,5,6,7-tetrahydropyrazolo[4,3-c]pyridin-2-acetate (Ethyl ester of Exemplary compound No. 2-293)

In the same manner as in Example I-(1-A) except for using 0.30 g (0.79 mmol) of ethyl 4,5,6,7-tetrahydropyrazolo[4,3-c]pyridin-2-acetate.TsOH in place of ethyl 4,5,6,7-tetrahydrothieno[3,2-c]pyridin-2-acetate.HCl, 0.15 g (0.79 mmol) of N-t-butoxycarbonyl-L-alanine in place of N-t-butoxycarbonyl-L-4-nirophenylalanine and 0.33 g (0.87 mmol) of HBTU in place of BOP, the reaction was carried out to obtain ethyl 5-(N-t-butoxycarbonyl-L-alanyl)-4,5,6,7-tetrahydropyrazolo[4,3-c]pyridin-2-acetate as pale brownish solid without purification.

EI-MS (m/z); 379
In the same manner as in Example I-(1-B) except for using the resulting ethyl 5-(N-t-butoxycarbonyl-L-alanyl)-4,5,6,7-tetrahydropyrazolo [4,3-c]pyridin-2-acetate andusing 0.33 g (0.87 mmol) of HBTU in place of BOP, the reaction was carried out to obtain 0.78 g (0.65 mmol) of the title compound as white foamy product.
$^1$H-NMR (CDCl$_3$) δ; 7.88–7.78 (m, 3H), 7.50–7.29 (m, 2H), 5.20–5.15 (m, 1H), 4.85–4.59 (m, 4H), 4.24 (q, J=7.3 Hz, 2H), 4.13–3.83 (m, 4H), 2.93–2.84 (m, 2H), 1.54 (s, 9H), 1.36 (s, 18H), 1.31–1.24 (m, 3H).

Example I-126
5-[N-(4-amidinobenzoyl)-L-alanyl]-4,5,6,7-tetrahydropyrazolo[4,3-c]pyridin-2-acetic acid.trifluoroacetate (Exemplary compound No. 2-394)

In the same manner as in Example I-4 except for using 0.78 g (1.1 mmol) of ethyl 5-[N-[4-(N,N,N'-tri-t-butoxycarbonylamidino)benzoyl]-L-alanyl]- 4,5,6,7-tetrahydropyrazolo[4,3-c]pyridin-2-acetate in place of ethyl 5-[N-[4-(N,N,N'-tri-t-butoxycarbonylamidino)benzoyl]-L-alanyl]-4,5,6,7-tetrahydrothieno[3,2-c]pyridin-2-acetate, the reaction was carried out to obtain 0.69 g (1.0 mmol) of 5-[N-[4-(N,N,N'-tri-t-butoxycarbonylamidino)benzoyl]-L-alanyl]-4,5,6,7-tetrahydropyrazolo[4,3-c]pyridin-2-acetic acid as white foamy product.

In the same manner as in Example I-2 except for using 0.30 g (0.043 mmol) of the resulting 5-[N-[4-(N,N,N'-tri-t-butoxycarbonylamidino)benzoyl]-L-alanyl]-4,5,6,7-tetrahydropyrazolo[4,3-c]pyridin-2-acetic acid in place of ethyl 5-[N-[4-(N,N,N'-tri-t-butoxycarbonylamidino) benzoyl]-L-alanyl]-4,5,6,7-tetrahydrothieno[3,2-c]pyridin-2-acetate, the reaction was carried out to obtain 0.22 g (0.043 mmol) of the title compound as white powder.

Melting point; 174–177 ° C.

$^1$H-NMR (400 MHz, DMSO-$d_6$) δ; 12.99 (brs, 1H), 9.42 (s, 2H), 9.26 (s, 2H), 9.03–8.87 (m, 1H), 8.18–7.88 (m, 4H), 7.51 (s, 1H), 5.10–5.00 (m, 1H), 4.92–4.03 (m, 4H), 3.90–3.67 (m, 2H), 2.68–2.60 (m, 2H), 1.53–1.29 (m, 3H).

FAB-MS (m/z); 399

Example I-127

Ethyl 5-[N-[4-(N,N,N'-tri-t-butoxycarbonylamidino) benzoyl]-L-phenylalanyl]-4,5,6,7-tetrahydropyrazolo[4,3-c]pyridin-2-acetate (Ethyl ester of Exemplary compound No. 2-297)

In the same manner as in Example I-(1-A) except for using 0.30 g (0.79 mmol) of ethyl 4,5,6,7-tetrahydropyrazolo[4,3-c]pyridin-2-acetate.TsOH in place of ethyl 4,5,6,7-tetrahydrothieno[3,2-c]pyridin-2-acetate.HCl, 0.20 g (0.79 mmol) of N-t-butoxycarbonyl-L-phenylalanine in place of N-t-butoxycarbonyl-L-4-nirophenylalanine and 0.33 g (0.87 mmol) of HBTU in place of BOP, the reaction was carried out to obtain ethyl 5-(N-t-butoxycarbonyl-L-phenylalanyl)-4,5,6,7-tetrahydropyrazolo[4,3-c]pyridin-2-acetate as pale brownish solid without purification.

CI-MS (m/z); 457

In the same manner as in Example I-(1-B) except for using the resulting ethyl 5-(N-t-butoxycarbonyl-L-phenylalanyl)-4,5,6,7-tetrahydropyrazolo[4,3-c]pyridin-2-acetate and using 0.33 g (0.87 mmol) of HBTU in place of BOP, the reaction was carried out to obtain 0.58 g (0.72 mmol) of the title compound as white foamy product.

$^1$H-NMR (CDCl$_3$) δ; 7.90–7.81 (m, 4H), 7.30–7.07 (m, 5H), 5.43–5.34 (m, 1H), 4.88–3.16 (m, 8H), 2.85–2.73 (m, 1H), 1.54 (s, 9H), 1.36 (s, 18H), 1.14–1.12 (m, 3H).

Example I-128

5-[N-(4-amidinobenzoyl)-L-phenylalanyl]-4,5,6,7-tetrahydropyrazolo[4,3-c]pyridin-2-acetic acid.trifluoroacetate (Exemplary compound No. 2-1)

In the same manner as in Example I-4 except for using 0.58 g (0.72 mmol) of ethyl 5-[N-[4-(N,N,N'-tri-t-butoxycarbonylamidino)benzoyl)-L-phenylalanyl]-4,5,6,7-tetrahydropyrazolo[4,3-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.30 g (0.39 mmol) of 5-[N-[4-(N,N,N'-tri-t-butoxycarbonylamidino)benzoyl]-L-phenylalanyl]-4,5,6,7-tetrahydropyrazolo[4,3-c]pyridin-2-acetic acid as white foamy product.

In the same manner as in Example I-2 except for using 0.30 g (0.39 mmol) of the resulting 5-[N-[4-(N,N,N'-tri-t-butoxycarbonylamidino)benzoyl]-L-phenylalanyl]-4,5,6,7-tetrahydropyrazolo[4,3-c]pyridin-2-acetic acid in place of ethyl 5-[N-[4-(N,N,N'-tri-t-butoxycarbonylamidino) benzoyl]-L-4-nitrophenylalanyl]-4,5,6,7-tetrahydrothieno [3,2-c]pyridin-2-acetate, the reaction was carried out to obtain 0.21 g (0.36 mmol) of the title compound as white powder.

Melting point; 146–150° C.

$^1$H-NMR (400 MHz, DMSO-$d_6$) δ; 13.00 (brs, 1H), 9.38 (s, 2H), 9.28 (s, 2H), 9.17–9.02 (m, 1H), 8.01–7.84 (m, 4H), 7.50 (s, 1H), 7.35–7.12 (m, 5H), 5.26–5.16 (m, 1H), 4.84–4.28 (m, 4H), 3.91–3.60 (m, 2H), 3.15–3.18 (m, 2H), 2.66–2.50 (m, 2H).

FAB-MS (m/z); 475

Example I-129

Ethyl 5-[N-(4-(N,N,N'-tri-t-butoxycarbonylamidino) benzoyl]-L-4-iodophenylalanyl]-4,5,6,7-tetrahydropyrazolo [4,3-c]pyridin-2-acetate (Ethyl ester of Exemplary compound No. 2-299)

In the same manner as in Example I-(1-A) except for using 0.30 g (0.79 mmol) of ethyl 4,5,6,7-tetrahydropyrazolo[4,3-c]pyridin-2-acetate.TsOH in place of ethyl 4,5,6,7-tetrahydrothieno[3,2-c]pyridin-2-acetate.HCl, 0.31 g (0.93 mmol) of N-t-butoxycarbonyl-L-4-iodophenylalanine in place of N-t-butoxycarbonyl-L-4-nirophenylalanine and 0.30 g (0.93 mmol) of TBTU in place of BOP, the reaction was carried out to obtain ethyl 5-(N-t-butoxycarbonyl-L-4-iodophenylalanyl)-4,5,6,7-tetrahydropyrazolo[4,3-c]pyridin-2-acetate as pale brownish solid without purification.

CI-MS (m/z); 583

In the same manner as in Example I-(1-B) except for using the resulting ethyl 5-(N-t-butoxycarbonyl-L-4-iodophenylalanyl)-4,5,6,7-tetrahydropyrazolo[4,3-c]pyridin-2-acetate and using 0.30 g (0.93 mmol) of TBTU in place of BOP, the reaction was carried out to obtain 0.78 g (0.65 mmol) of the title compound as white foamy product.

$^1$H-NMR (CDCl$_3$) δ; 7.89–7.70 (m, 4H), 7.23–6.90 (m, 5H), 5.43–5.35 (m, 1H), 4.92–4.35 (m, 3H), 4.21 (q, J=7.3 Hz, 2H), 4.17–4.08 (m, 1H), 3.66–2.57 (m, 6H), 1.48 (s, 9H), 1.36 (s, 18H), 1.31–1.24 (m, 3H).

Example I-130

5-[N-(4-amidinobenzoyl)-L-4-iodophenylalanyl]-4,5,6,7-tetrahydropyrazolo[4,3-c]pyridin-2-acetic acid.trifluoroacetate (Exemplary compound No. 2-62)

In the same manner as in Example I-4 except for using 0.78 g (1.1 mmol) of ethyl 5-[N-[4-(N,N,N'-tri-t-butoxycarbonylamidino)benzoyl]-L-4-iodophenylalanyl]-4,5,6,7-tetrahydropyrazolo[4,3-c]pyridin-2-acetate in place of ethyl 5-[N-[4-(N,N,N'-tri-t-butoxycarbonylamidino) benzoyl]-L-4-nitrophenylalanyl]-4,5,6,7-tetrahydrothieno [3,2-c]pyridin-2-acetate, the reaction was carried out to obtain 0.40 g (0.44 mmol) of 5-[N-[4-(N,N,N'-tri-t-butoxycarbonylamidino)benzoyl]-L-4-iodophenylalanyl]-4,5,6,7-tetrahydropyrazolo[4,3-c]pyridin-2-acetic acid as white foamy product.

In the same manner as in Example I-2 except for using 0.40 g (0.44 mmol) of the resulting 5-[N-[4-(N,N,N'-tri-t-butoxycarbonylamidino)benzoyl]-L-4-iodophenylalanyl]-4,5,6,7-tetrahydropyrazolo[4,3-c]pyridin-2-acetic acid in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.25 g (0.35 mmol) of the title compound as white powder.

Melting point; 178–182° C.

$^1$H-NMR (400 MHz, DMSO-$d_6$) δ; 13.00 (brs, 1H), 9.37 (s, 2H), 9.23 (s, 2H), 9.15–9.01 (m, 1H), 8.00–7.93 (m, 2H), 7.85–7.83 (m, 2H), 7.58–7.47 (m, 3H), 7.16–7.11 (m, 2H), 5.21–5.18 (m, 1H), 4.83–4.26 (m, 4H), 3.92–3.63 (m, 2H), 3.08–2.97 (m, 2H), 2.58–2.50 (m, 2H).

ESI-MS (m/z); 601

Example I-131

Ethyl 5-[N-[4-(N,N,N'-tri-t-butoxycarbonylamidino) benzoyl]-L-4-fluorophenylalanyl]-4,5,6,7-tetrahydropyrazolo[4,3-c]pyridin-2-acetate (Ethyl ester of Exemplary compound No. 2-298)

In the same manner as in Example I-(1-A) except for using 0.30 g (0.79 mmol) of ethyl 4,5,6,7- tetrahydropyrazolo[4,3-c]pyridin-2-acetate.TsOH in place of ethyl 4,5,6,7-tetrahydrothieno[3,2-c]pyridin-2-acetate.HCl, 0.22 g (0.79 mmol) of N-t-butoxycarbonyl-L-4-fluorophenylalanine in place of N-t-butoxycarbonyl-L-4-nirophenylalanine and 0.30 g (0.93 mmol) of TBTU in place of BOP, the reaction was carried out to obtain ethyl 5-(N-t-butoxycarbonyl-L-4-fluorophenylalanyl)- 4,5,6,7-tetrahydropyrazolo[4,3-c]pyridin-2-acetate as pale brownish solid without purification.

CI-MS (m/z); 475

In the same manner as in Example I-(1-B) except for using the resulting ethyl 5-(N-t-butoxycarbonyl-L-4-fluorophenylalanyl)-4,5,6,7-tetrahydropyrazolo[4,3-c]pyridin-2-acetate and using 0.30 g (0.93 mmol) of TBTU in place of BOP, the reaction was carried out to obtain 0.53 g (0.64 mmol) of the title compound as white foamy product.

$^1$H-NMR (CDCl$_3$) δ; 7.90–7.70 (m, 4H), 7.58–6.90 (m, 5H), 5.43–5.34 (m, 1H), 4.97–4.38 (m, 3H), 4.24 (q, J=7.3 Hz, 2H), 4.13–4.06 (m, 1H), 3.66–2.76 (m, 6H), 1.54 (s, 9H), 1.37 (s, 18H), 1.36–1.24 (m, 3H).

Example I-132

5-[N-(4-amidinobenzoyl)-L-4-fluorophenylalanyl)-4,5,6,7-tetrahydropyrazolo[4,3-c]pyridin-2-acetic acid.trifluoroacetate (Exemplary compound No. 2-63)

In the same manner as in Example I-4 except for using 0.78 g (1.1 mmol) of ethyl 5-[N-[4-(N,N,N'-tri-t-butoxycarbonylamidino)benzoyl]-L-4-fluorophenylalanyl]-4,5,6,7-tetrahydropyrazolo[4,3-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.26 g (0.32 mmol) of 5-[N-[4-(N,N,N'-tri-t-butoxycarbonylamidino)benzoyl]-L-4-fluorophenylalanyl]-4,5,6,7-tetrahydropyrazolo[4,3-c]pyridin-2-acetic acid as white foamy product.

In the same manner as in Example I-2 except for using 0.26 g (0.32 mmol) of the resulting 5-[N-[4-(N,N,N'-tri-t-butoxycarbonylamidino)benzoyl]-L-4-fluorophenylalanyl]-4,5,6,7-tetrahydropyrazolo[4,3-c]pyridin-2-acetic acid in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reactionwas carried out to obtain 0.15 g (0.25 mmol) of the title compound as white powder.

Melting point; 146–149° C.

$^1$H-NMR (400 MHz, DMSO-d$_6$) δ; 13.00 (brs, 1H), 9.37 (s, 2H), 9.23 (s, 2H), 9.14–9.00 (m, 1H), 8.00–7.93 (m, 2H), 7.88–7.83 (m, 2H), 7.49–7.47 (m, 1H), 7.37–7.31 (m, 2H), 7.16–7.11 (m, 2H), 5.21–5.20 (m, 1H), 4.83–4.27 (m, 4H), 3.92–3.73 (m, 2H), 3.10–3.01 (m, 2H), 2.56–2.48 (m, 2H).

ESI-MS (m/z); 493

Example I-133

Ethyl 5-[N-[4-(N,N,N'-tri-t-butoxycarbonylamidino)benzoyl]-L-4-cyanophenylalanyl]-4,5,6,7-tetrahydropyrazolo[4,3-c]pyridin-2-acetate (Ethyl ester of Exemplary compound No. 2-302)

In the same manner as in Example I-(1-A) except for using 0.90 g (2.3 mmol) of ethyl 4,5,6,7-tetrahydropyrazolo[4,3-c]pyridin-2-acetate.TsOH in place of ethyl 4,5,6,7-tetrahydrothieno[3,2-c]pyridin-2-acetate.HCl, 0.70 g (2.8 mmol) of N-t-butoxycarbonyl-L-4-cyanophenylalanine in place of N-t-butoxycarbonyl-L-4-nirophenylalanine and 0.90 g (2.8 mmol) of TBTU in place of BOP, the reaction was carried out to obtain ethyl 5-(N-t-butoxycarbonyl-L-4-cyanophenylalanyl)-4,5,6,7-tetrahydropyrazolo[4,3-c]pyridin-2-acetate as pale brownish solid without purification.

CI-MS (m/z); 482

In the same manner as in Example I-(1-B) except for using the resulting ethyl 5-(N-t-butoxycarbonyl-L-4-cyanophenylalanyl)-4,5,6,7-tetrahydropyrazolo[4,3-c]pyridin-2-acetate and using 0.90 g (2.8 mmol) of TBTU in place of BOP, the reaction was carried out to obtain 1.8 g (2.2 mmol) of the title compound as white foamy product.

$^1$H-NMR (CDCl$_3$) δ; 7.89–7.70 (m, 4H), 7.23–6.83 (m, 5H), 5.43–5.37 (m, 1H), 4.88–4.38 (m, 3H), 4.24 (q, J=7.3, 2H), 4.13–4.06 (m, 1H), 3.66–2.76 (m, 6H), 1.54 (s, 9H), 1.37 (s, 18H), 1.36–1.24 (m, 3H).

Example I-134

5-[N-(4-amidinobenzoyl)-L-4-cyanophenylalanyl]-4,5,6,7-tetrahydropyrazolo[4,3-c]pyridin-2-acetic acid.trifluoroacetate (Exemplary compound No. 2-4)

In the same manner as in Example I-4 except for using 1.8 g (2.2 mmol) of ethyl 5-[N-[4-(N,N,N'-tri-t-butoxycarbonylamidino)benzoyl]-L-4-cyanophenylalanyl]-4,5,6,7-tetrahydropyrazolo[4,3-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 1.3 g (1.6 mmol) of 5-[N-[4-(N,N,N'-tri-t-butoxycarbonylamidino)benzoyl]-L-4-cyanophenylalanyl]-4,5,6,7-tetrahydropyrazolo[4,3-c]pyridin-2-acetic acid as white foamy product.

In the same manner as in Example I-2 except for using 0.30 g (0.04 mmol) of the resulting 5-[N-[4-(N,N,N'-tri-t-butoxycarbonylamidino)benzoyl]-L-4-cyanophenylalanyl]-4,5,6,7-tetrahydropyrazolo[4,3-c]pyridin-2-acetic acid in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.22 g (0.36 mmol) of the title compound as white powder.

Melting point; 197° C.-changed to brown color $^1$H-NMR (400 MHz, DMSO-d$_6$) δ; 13.00 (brs, 1H), 9.32 (s, 4H), 9.20–9.18 (m, 1H), 7.97–7.91 (m, 2H), 7.84–7.82 (m, 2H), 7.70–7.63 (m, 2H), 7.54–7.42 (m, 3H), 5.26–5.16 (m, 1H), 4.78–4.27 (m, 4H), 3.91–3.60 (m, 2H), 3.15–3.08 (m, 2H), 2.54–2.48 (m, 2H).

ESI-MS (m/z); 500

Example I-135

Ethyl 5-[N-[4-(N,N,N'-tri-t-butoxycarbonylamidino)benzoyl]-N-methyl-L-4-nitrophenylalanyl]-4,5,6,7-tetrahydropyrazolo[4,3-c]pyridin-2-acetate (Ethyl ester of Exemplary compound No. 2-303)

In the same manner as in Example I-(1-A) except for using 0.50 g (1.3 mmol) of ethyl 4,5,6,7-tetrahydropyrazolo[4,3-c]pyridin-2-acetate.TsOH in place of ethyl 4,5,6,7-tetrahydrothieno[3,2-c]pyridin-2-acetate.HCl, 0.55 g (1.3 mmol) of N-t-butoxycarbonyl-N-methyl-L-4-nitrophenylalanine.DCHA in place of N-t-butoxycarbonyl-L-4-nirophenylalanine and 0.48 g (1.5 mmol) of TBTU in place of BOP, the reaction was carried out to obtain ethyl 5-(N-t-butoxycarbonyl-N-methyl-L-4-nitrophenylalanyl)-4,5,6,7-tetrahydropyrazolo[4,3-c]pyridin-2-acetate as pale brownish solid without purification.

CI-MS (m/z); 516

In the same manner as in Example I-(1-B) except for using the resulting ethyl 5-(N-t-butoxycarbonyl-N-methyl-L-4-nitrophenylalanyl)-4,5,6,7-tetrahydropyrazolo[4,3-c]pyridin-2-acetate and using 0.48 g (1.5 mmol) of TBTU in place of BOP, the reactionwas carried out to obtain 0.27 g (0.31 mmol) of the title compound as white foamy product.

$^1$H-NMR (CDCl$_3$) δ; 8.17–8.15 (d, J=7.4 Hz, 2H), 7.86–7.83 (d, J=6.0 Hz, 2H), 7.54–7.51 (d, J=7.4 Hz, 2H), 7.26–7.24 (d, J=6.0 Hz, 2H), 7.14–7.11 (m, 1H), 6.03–5.91 (m, 1H), 4.83–4.52 (m, 4H), 4.28–4.08 (m, 4H), 3.76–3.13 (m, 4H), 2.81 (s, 3H), 1.58 (s, 9H), 1.37 (s, 18H), 1.33–1.23 (m, 3H).

Example I-136

5-[N-(4-amidinobenzoyl)-N-methyl-L-4-nitrophenylalanyl]-4,5,6,7-tetrahydropyrazolo[4,3-c]pyridin-2-acetic acid.trifluoroacetate (Exemplary compound No. 2-43)

In the same manner as in Example I-4 except for using 0.27 g (0.31 mmol) of ethyl 5-[N-[4-(N,N,N'-tri-t-butoxycarbonylamidino)benzoyl]-N-methyl-L-4-nitrophenylalanyl]-4,5,6,7-tetrahydropyrazolo[4,3-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.16 g (0.19 mmol) of 5-[N-[4-(N,N,N'-tri-t-butoxycarbonylamidino)benzoyl]-N-methyl-L-4-nitrophenylalanyl]-4,5,6,7-tetrahydropyrazolo[4,3-c]pyridin-2-acetic acid as white foamy product.

In the same manner as in Example I-2 except for using 0.16 g (0.19 mmol) of the resulting 5-[N-[4-(N,N,N'-tri-t-butoxycarbonylamidino)benzoyl]-N-methyl-L-4-nitrophenylalanyl]- 4,5,6,7-tetrahydropyrazolo[4,3-c]pyridin-2-acetic acid in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.06 g (0.095 mmol) of the title compound as white powder.

Melting point; 158–162° C.

$^1$H-NMR (400 MHz, DMSO-d$_6$) δ; 13.00 (brs, 1H), 9.33 (s, 2H), 9.06 (s, 2H), 8.88–7.59 (m, 7H), 7.30 (s, 1H), 7.09 (s, 1H), 6.53–5.84 (m, 1H), 4.92–4.40 (m, 4H), 3.97–3.89 (m, 2H), 3.72–3.64 (m, 2H), 3.48–3.23 (m, 3H), 2.95–2.50 (m, 4H).

FAB-MS (m/z); 534

Example I-137

Ethyl 5-[N-[4-(N,N,N'-tri-t-butoxycarbonylamidino)benzoyl]-L-O-benzyltyrosyl]-4,5,6,7-tetrahydropyrazolo[4,3-c]pyridin-2-acetate (Ethyl ester of Exemplary compound No. 2-301)

In the same manner as in Example I-(1-A) except for using 0.50 g (1.3 mmol) of ethyl 4,5,6,7-tetrahydropyrazolo[4,3-c]pyridin-2-acetate.TsOH in place of ethyl 4,5,6,7-tetrahydrothieno[3,2-c]pyridin-2-acetate.HCl, 0.49 g (1.3 mmol) of N-t-butoxycarbonyl-L-O-benzyltyrosine in place of N-t-butoxycarbonyl-L-4-nirophenylalanine and 0.55 g (1.5 mmol) of HBTU in place of BOP, the reaction was carried out to obtain ethyl 5-(N-t-butoxycarbonyl-L-O-benzyltyrosyl)-4,5,6,7-tetrahydropyrazolo[4,3-c]pyridin-2-acetate as pale brownish solid without purification.

CI-MS (m/z); 563

In the same manner as in Example I-(1-B) except for using the resulting ethyl 5-(N-t-butoxycarbonyl-L-O-benzyltyrosyl)-4,5,6,7-tetrahydropyrazolo[4,3-c]pyridin-2-acetate and using 0.55 g (1.5 mmol) of HBTU in place of BOP, the reaction was carried out to obtain 0.86 g (0.95 mmol) of the title compound as white foamy product.

$^1$H-NMR (CDCl$_3$) δ; 7.89–7.81 (m, 4H), 7.23–6.80 (m, 6H), 5.40–5.39 (m, 1H), 5.00–4.99 (m, 2H), 4.84–4.77 (m, 2H), 4.43–4.39 (m, 1H), 4.21 (q, J=7.3 Hz, 2H), 4.15–4.11 (m, 1H), 3.97–2.40 (m, 6H), 1.54 (s, 9H), 1.38 (s, 18H), 1.29–1.20 (m, 3H).

Example I-138

5-[N-(4-amidinobenzoyl)-L-O-benzyltyrosyl]-4,5,6,7-tetrahydropyrazolo[4,3-c]pyridin-2-acetic acid.trifluoroacetate (Exemplary compound No. 2-7)

In the same manner as in Example I-4 except for using 0.12 g (0.13 mmol) of ethyl 5-[N-[4-(N,N,N'-tri-t-butoxycarbonylamidino)benzoyl]-L-O-benzyLtyrosyl]-4,5,6,7-tetrahydropyrazolo[4,3-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.10 g (0.11 mmol) of 5-[N-[4-(N,N,N'-tri-t-butoxycarbonylamidino)benzoyl]-L-O-benzyltyrosyl]-4,5,6,7-tetrahydropyrazolo[4,3-c]pyridin-2-acetic acid as white foamy product.

In the same manner as in Example I-2 except for using 0.10 g (0.11 mmol) of the resulting 5-[N-[4-(N,N,N'-tri-t-butoxycarbonylamidino)benzoyl]-L-O-benzyltyrosyl]-4,5,6,7-tetrahydropyrazolo[4,3-c]pyridin-2-acetic acid in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.020 g (0.028 mmol) of the title compound as white powder.

Melting point; 179–183° C.

$^1$H-NMR (400 MHz, DMSO-d$_6$) δ; 11.93 (brs, 1H), 9.17–9.00 (m, 3H), 8.01–7.78 (m, 4H), 7.42–7.15 (m, 8H), 6.88–6.85 (m, 2H), 5.23–5.02 (m, 1H), 4.99–4.35 (m, 4H), 4.10–4.01 (m, 4H), 3.32–3.07 (m, 2H), 2.97–2.91 (m, 2H), 2.51–2.34 (m, 2H).

FAB-MS (m/z); 581

Example I-139

Ethyl 5-[N-[4-(N,N,N'-tri-t-butoxycarbonylamidino)benzoyl]-L-leucyl]-4,5,6,7-tetrahydropyrazolo[4,3-c]pyridin-2-acetate (Ethyl ester of Exemplary compound No. 2-294)

In the same manner as in Example I-(1-A) except for using 0.30 g (0.79 mmol) of ethyl 4,5,6,7-tetrahydropyrazolo[4,3-c]pyridin-2-acetate.TsOH in place of ethyl 4,5,6,7-tetrahydrothieno[3,2-c]pyridin-2-acetate.HCl, 0.18 g (0.79 mmol) of N-t-butoxycarbonyl-L-leucine in place of N-t-butoxycarbonyl-L-4-nirophenylalanine and 0.30 g (0.79 mmol) of TBTU in place of BOP, the reaction was carried out to obtain ethyl 5-(N-t-butoxycarbonyl-L-leucyl)-4,5,6,7-tetrahydropyrazolo[4,3-c]pyridin-2-acetate as pale brownish solid without purification.

CI-MS (m/z); 379

In the same manner as in Example I-(1-B) except for using the resulting ethyl 5-(N-t-butoxycarbonyl-L-leucyl)-4,5,6,7-tetrahydropyrazolo[4,3-c]pyridin-2-acetate and using 0.30 g (0.79 mmol) of TBTU in place of BOP, the reaction was carried out to obtain 0.54 g (0.73 mmol) of the title compound as white foamy product.

$^1$H-NMR (CDCl$_3$) δ; 7.89–7.81 (m, 2H), 7.31–7.07 (m, 3H), 5.35–5.25 (m, 1H), 4.86–4.84 (m, 2H), 4.26–4.23 (m, 2H), 4.84–4.77 (m, 2H), 3.95–3.85 (m, 1H), 2.82–2.80 (m, 4H), 1.54 (s, 9H), 1.38 (s, 18H), 1.29–1.20 (m, 3H), 1.10–1.07 (m, 3H), 0.97–0.92 (m, 3H).

Example I-140

5-[N-(4-amidinobenzoyl)-L-leucyl]-4,5,6,7-tetrahydropyrazolo[4,3-c]pyridin-2-acetic acid.trifluoroacetate (Exemplary compound No. 2-409)

In the same manner as in Example I-4 except for using 0.54 g (0.73 mmol) of ethyl 5-[N-[4-(N,N,N'-tri-t-butoxycarbonylamidino)benzoyl]-L-leucyl]-4,5,6,7-tetrahydropyrazolo[4,3-c]pyridin-2-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.35 g (0.48 mmol) of 5-(N-[4-(N,N,N'-tri-t-butoxycarbonylamidino)benzoyl]-L-leucyl]-4,5,6,7-tetrahydropyrazolo[4,3-c]pyridin-2-acetic acid as white foamy product.

In the same manner as in Example I-2 except for using 0.30 g (0.41 mmol) of the resulting 5-[N-[4-(N,N,N'-tri-t-butoxycarbonylamidino)benzoyl]-L-leucyl]-4,5,6,7-tetrahydropyrazolo[4,3-c]pyridin-2-acetic acid in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 0.14 g (0.31 mmol) of the title compound as white powder.

Melting point; 165–169° C.
$^1$H-NMR (400 MHz, DMSO-$d_6$) δ; 12.99 (brs, 1H), 9.38 (s, 2H), 9.32 (s, 2H), 8.97–8.83 (m, 1H), 8.10–8.03 (m, 2H), 7.88–7.86 (m, 2H), 7.53–7.50 (m, 2H), 5.07–5.00 (m, 1H), 4.89–4.23 (m, 4H), 3.89–3.76 (m, 3H), 2.68–2.50 (m, 2H), 1.77–1.41 (m, 3H), 0.94–0.87 (m, 3H).
ESI-MS (m/z); 441

Example I-141
Ethyl 5-[N-[4-(N,N,N'-tri-t-butoxycarbonylamidino)benzoyl]-L-4-nitrophenylalanyl]-4,5,6,7-tetrahydropyrazolo[4,5-c]pyridin-1-acetate (Ethyl ester of Exemplary compound No. 3-115)

(141-A) In the same manner as in Example I-(1-A) except for using 0.90 g (3.00 mmol) of ethyl 4,5,6,7-tetrahydropyrazolo[4,5-c]pyridin-1-acetate.HCl in place of ethyl 4,5,6,7-tetrahydrothieno[3,2-c]pyridin-2-acetate.HCl, the reaction was carried out to obtain 1.50 g (3.00 mmol) of ethyl 5-(N-t-butoxycarbonyl-L-4-nitrophenylalanyl)-4,5,6,7-tetrahydropyrazolo[4,5-c]pyridin-1-acetate as white solid.

$^1$H-NMR (CDCl$_3$) δ; 8.11, 8.04 (each d, J=8.8 Hz, total 2H), 7.35, 7.28 (each d, J=8.8 Hz, total 2H), 7.27, 7.19 (each s, total 1H), 5.45, 5.39 (each d, J=8.8 Hz, total 1H), 4.97–4.92 (m, 1H), 4.76–4.13 (m, 6H), 3.80–3.52 (m, 2H), 3.22–3.00 (m, 2H), 2.70–2.25 (m, 2H), 1.42, 1.39 (each s, total 9H), 1.32–1.25 (m, 3H).
CI-MS (m/z); 502

(141-B) In the same manner as in Example I-(1-B) except for using 1.50 g (3.00 mmol) of ethyl 5-(N-t-butoxycarbonyl-L- 4-nitrophenylalanyl)-4,5,6,7-tetrahydropyrazolo[4,5-c]pyridin-1-acetate in place of ethyl 5-(N-t-butoxycarbonyl-L-4-nitrophenylalanyl)-4,5,6,7-tetrahydrothieno[3,2-c]-pyridin-2-acetate, the reaction was carried out to obtain 1.87 g (2.21 mmol) of the title compound as white foamy product.

$^1$H-NMR (CDCl$_3$) δ; 8.16–7.81 (m, 6H), 7.40–7.29 (m, 2H), 7.24–7.17 (m, 1H), 5.48–5.44 (m, 1H), 4.82–4.18 (m, 7H), 3.76–3.19 (m, 4H), 2.70–2.25 (m, 2H), 1.54 (s, 9H), 1.37, 1.36 (each s, total 18H), 1.33–1.24 (m, 3H).
FAB-MS (m/z); 848

Example I-142
Ethyl 5-[N-(4-amidinobenzoyl)-L-4-nitrophenylalanyl]-4,5,6,7-tetrahydropyrazolo[4,5-c]pyridin-1-acetate.trifluoroacetate (Ethyl ester of Exemplary compound No. 3-3)

In the same manner as in Example I-2 except for using 1.87 g (2.21 mmol) of ethyl 5-[N-[4-(N,N,N'-tri-t-butoxycarbonylamidino)benzoyl]-L-4-nitrophenylalanyl]-4,5,6,7-tetrahydropyrazolo[4,5-c]pyridin-1-acetate in place of ethyl 5-[N-[4-(N,N,N'-tri-t-butoxycarbonylamidino)benzoyl]-L-4-nitrophenylalanyl]-4,5,6,7-tetrahydrothieno[3,2-c]pyridin-2-acetate, the reaction was carried out to obtain 1.42 g (2.15 mmol) of the title compound as white solid.

Melting point; 128–134° C.
$^1$H-NMR (400 MHz, DMSO-$d_6$) δ; 9.37 (s, 2H), 9.20, 9.10 (each d, J=8.3 Hz, 1H), 9.12 (s, 2H), 8.09, 8.04 (each d, J=8.8 Hz, total 2H), 7.97–7.93 (m, 2H), 7.85–7.82 (m, 2H), 7.62, 7.56 (each d, J=8.8 Hz, total 2H), 7.30, 7.19 (each s, total 1H), 5.35–5.25 (m, 1H), 4.96–4.32 (m, 4H), 4.16–4.06 (m, 2H), 3.95–3.80 (m, 1H), 3.70–3.60 (m, 2H), 3.28–3.10 (m, 2H), 2.64–2.52 (m, 1H), 1.21–1.14 (m, 3H).
FAB-MS (m/z); 548

Example II-1
4-(N,N,N'-tri-t-butoxycarbonylamidino)benzoic acid
(1-1) To 3.18 g (13.9 mmol) of ethyl 4-amidinobenzoate.HCl were added 70 ml of methylene chloride, 1.90 g (17.0 mmol) of DABCO, 0.20 g (1.6 mmol) of 4-dimethylaminopyridine and 30 ml of di-t-butyl dicarbonate, and the mixture was stirred at room temperature for 5 hours.

The resulting reaction mixture was concentrated under reduced pressure, a 5% aqueous potassium hydrogen sulfate solution was added to the residue and the mixture was extracted with ethyl acetate. The organic layer was washed successively with a saturated aqueous sodium bicarbonate solution and a saturated aqueous saline solution, and dried over anhydrous sodium sulfate. The organic layer was concentrated under reduced pressure and the residue was purified by the silica gel column chromatography method (eluent; n-hexane/ethyl acetate=6/1) to obtain 5.85 g (11.9 mmol) of ethyl 4-(N,N,N'-tri-t-butoxycarbonylamidino)benzoate as white solid.

$^1$H-NMR (CDCl$_3$) δ; 8.10 (d, J=8.8 Hz, 2H), 7.89 (d, J=8.8 Hz, 2H), 4.43 (q, J=7.3 Hz, 2H), 1.57 (s, 9H), 1.48–1.40 (m, 3H), 1.39 (s, 18H).
CI-MS (m/z); 493

(1-2) To 5.76 g (11.7 mmol) of ethyl 4-(N,N,N'-tri-t-butoxycarbonylamidino)benzoate were added 40 ml of ethanol and 20 ml of water to dissolve the compound, and 0.68 g (16 mmol) of lithium hydroxide.H$_2$O was added to the solution, and the mixture was stirred at room temperature for one hour.

To the resulting reaction mixture was added a 5% aqueous potassium hydrogen sulfate solution to make a pH of the liquid to 7, and the mixture was concentrated under reduced pressure. The residue was extracted with ethyl acetate, the resulting organic layer was washed successively with a 5% aqueous potassium hydrogen sulfate solution and a saturated aqueous saline solution and dried over anhydrous sodium sulfate. The organic layer was concentrated under reduced pressure and the residue was purified by the silica gel column chromatography method (eluent: chloroform/methanol=20/1) to obtain 3.61 g (7.78 mmol) of the title compound as white solid.

$^1$H-NMR (CDCl$_3$) δ; 8.17 (d, J=8.1 Hz, 2H), 7.93 (d, J=8.8 Hz, 2H), 1.58–1.37 (m, 27H).

Example II-2
4-[N'-t-butoxycarbonyl-N-benzylamidino]benzoic acid
(2-1) In 20 ml of ethanol was dissolved 1.0 g (3.9 mmol) of ethyl 4-(ethoxyimidoyl)benzoate.HCl, and 0.95 ml (8.7 mmol) of benzylamine was added to the solution, and the mixture was stirred at room temperature for 4 hours to conduct the reaction.

The resulting reaction mixture was concentrated under reduced pressure, chloroform was added to the residue and the formed insoluble material was removed by filtration. The filtrate was concentrated under reduced pressure, diethyl ether was added to the residue and the resulting precipitates were collected by filtration. Theiprecipitates were washed with diethyl ether and dried to obtain 0.84 g (2.6 mmol) of ethyl 4-(N-benzylamidino)benzoate.HCl as white powder.

CI-MS (m/z); 283

(2-2) To 0.84 g (2.6 mmol) of ethyl 4-(N-benzylamidino)benzoate.HCl were added 20 ml of methylene chloride, 0.30 g (2.7 mmol) of DABCO, 30 mg (0.27 mmol) of 4-dimethylaminopyridine and 1.0 ml of di-t-butyl dicarbonate and the mixture was stirred at room temperature for 5 hours.

The resulting reaction mixture was concentrated under reduced pressure, a 5% aqueous potassium hydrogen sulfate solution was added to the residue and the mixture was extracted with ethyl acetate. The organic layer was washed successively with a saturated aqueous sodium bicarbonate solution and a saturated aqueous saline solution, and dried over anhydrous sodium sulfate. The organic layer was concentrated under reduced pressure and the residue was purified by the silica gel column chromatography method (eluent: n-hexane/ethyl acetate=4/1) to obtain 0.67 g (1.8 mmol) of ethyl 4-(N'-t-butoxycarbonyl-N-benzylamidino)benzoate as pale yellowish foamy product.

$^1$H-NMR (CDCl$_3$) δ; 8.19–7.18 (m, 9H), 4.70–4.31 (m, 4H), 1.64–1.31 (m, 12H).

CI-MS (m/z); 383

(2–3) To 0.66 g (1.7 mmol) of ethyl 4-(N'-t-butoxycarbonyl-N-benzylamidino)benzoate were added 5 ml of ethanol and 2 ml of water to dissolve the compound, and 0.11 g (2.6 mmol) of lithium hydroxide.H$_2$O was added to the solution, and the mixture was stirred at room temperature for 2 hours.

To the resulting reaction mixture was added a 5% aqueous potassium hydrogen sulfate solution to make a pH of the liquid to 7, and the mixture was concentrated under reduced pressure. The residue was extracted with ethyl acetate, the resulting organic layer was washed with a saturated aqueous saline solution and dried over anhydrous sodium sulfate. The organic layer was concentrated under reduced pressure to obtain 0.47 g (1.3 mmol) of the title compound.

1H-NMR (CDCl$_3$) δ; 8.15–7.29 (m, 9H), 4.69–4.31 (m, 2H), 1.59–1.35 (m, 9H).

CI-MS (m/z); 255

Example II-3

4-[N'-t-butoxycarbonyl-N-methylamidino]benzoic acid (3-1) In 15 ml of ethanol was dissolved 1.0 g (3.9 mmol) of ethyl 4-(ethoxyiminomethyl)benzoate.HCl, and 0.80 g (7.8 mmol) of a 30% methylamine-ethanol solution was added to the solution, and the mixture was stirred at room temperature for 2 hours.

The resulting reaction mixture was concentrated under reduced pressure to obtain 1.03 g (4.24 mmol) of ethyl 4-(N-methylamidino)benzoate.HCl as white foamy product.

$^1$H-NMR (CDCl$_3$) δ; 8.12 (d, J=8.8 Hz, 2H), 7.93 (d, J=8.8 Hz, 2H), 4.44–4.31 (m, 2H), 3.03 (s, 3H), 1.40–1.35 (m, 3H).

CI-MS (m/z); 207

(3–2) To 1.03 g (4.24 mmol) of ethyl 4-(N-methylamidino)benzoate.HCl were added 20 ml of methylene chloride, 0.48 g (4.2 mmol) of DABCO, 50 mg (0.41 mmol) of 4-dimethylaminopyridine and 1.5 ml of di-t-butyl dicarbonate and the mixture was stirred at room temperature for 4.5 hours.

The resulting reaction mixture was concentrated under reduced pressure, a 5% aqueous potassium hydrogen sulfate solution was added to the residue and the mixture was extracted with ethyl acetate. The organic layer was washed successively with a saturated aqueous sodium bicarbonate solution and a saturated aqueous saline solution, and dried over anhydrous sodium sulfate. The organic layer was concentrated under reduced pressure and the residue was purified by the silica gel column chromatography method (eluent: chloroform/ethyl acetate=9/1) to obtain 0.61 g (2.0 mmol) of ethyl 4-(N'-t-butoxycarbonyl-N-methylamidino)benzoate as white solid.

$^1$H-NMR (CDCl$_3$) δ; 8.12–7.50 (m, 4H), 4.43–4.36 (m, 2H), 2.95 (brs, 3H), 1.59–1.35 (m, 9H), 1.43–1.38 (m, 3H).

CI-MS (m/z); 307

(3-3) To 0.58 g (1.9 mmol) of ethyl 4-(N'-t-butoxycarbonyl-N-methylamidino)benzoate were added 5 ml of ethanol and 2 ml of water to dissolve the compound, and 0.10 g (2.4 mmol) of lithium hydroxide.H$_2$O was added to the solution, and the mixture was stirred at room temperature for 2 hours.

To the resulting reaction mixture was added a 5% aqueous potassium hydrogen sulfate solution to make a pH of the liquid to 7, and the mixture was concentrated under reduced pressure. The residue was extracted with ethyl acetate, the resulting organic layer was washed with a saturated aqueous saline solution and dried over anhydrous sodium sulfate. The organic layer was concentrated under reduced pressure to obtain 0.17 g (0.61 mmol) of the title compound as pale yellowish foamy product.

$^1$H-NMR (CDCl$_3$) δ; 8.15–7.77 (m, 4H), 3.10–2.89 (m, 3H), 1.59–1.40 (m, 9H).

CI-MS (m/z); 279

Example II-4

N-methyl-DL-4-nitrophenylalanine ethyl ester.hydrochloride (4-1) To 2.30 g (8.38 mmol) of DL-4-nitrophenylalanine ethyl ester.HCl was added 50 ml of methylene chloride, and under ice-cooling, 1.86 g (18.4 mmol) of triethylamine and 1.94 g (9.23 mmol) of anhydrous trifluoroacetic acid were added successively, and the mixture was stirred at room temperature for 6 hours.

Water was added to the resulting reaction mixture and the mixture was extracted with methylene chloride. The organic layer was dried over anhydrous sodium sulfate and then concentrated under reduced pressure. The residue was purified by the silica gel column chromatography method (eluent: n-hexane/ethyl acetate=4/1) to obtain 1.25 g (3.74 mmol) of N-trifluoroacetyl-DL-4-nitrophenylalanine ethyl ester as yellowish solid.

$^1$H-NMR (CDCl$_3$) δ; 8.18 (d, J=8.8 Hz, 2H), 7.29 (d, J=8.8 Hz, 2H), 6.95–6.75 (m, 1H), 4.88 (dd, J=5.9 Hz, 7.3 Hz, 1H), 4.26 (q, J=7.3 Hz, 2H), 3.39 (dd, J=14 Hz, 5.9 Hz, 1H), 3.26 (dd, J=14 Hz, 5.9 Hz, 1H), 1.30 (t, J=7.3 Hz, 3H).

CI-MS (m/z); 335

(4-2) In 5 ml of DMF was suspended 63 mg (1.7 mmol) of sodium hydride (oil coat, 63%), and 0.50 g (1.5 mmol) of N-trifluoroacetyl-DL-4-nitrophenylalanine ethyl ester was added thereto under room temperature and the mixture was stirred for 30 minutes. Then, 0.23 g (1.6 mmol) of methyl iodide was added thereto and the mixture was stirred for 3 hours.

Water was added to the resulting reaction mixture and the mixture was extracted with toluene. The organic layer was dried over anhydrous sodium sulfate and then concentrated under reduced pressure, and the residue was purified by the silica gel column chromatography method (eluent: n-hexane/ethyl acetate=4/1) to obtain 0.43 g (1.2 mmol) of N-trifluoroacetyl-N-methyl-DL-4-nitrophenylalanine ethyl ester as yellowish oily product.

$^1$H-NMR (CDCl$_3$) δ; 8.18 (d, J=8.8 Hz, 2H), 7.38 (d, J=8.8 Hz, 2H), 5.08 (dd, J=10.3 Hz, 5.9 Hz, 1H), 4.25 (q, J=7.3 Hz, 2H), 3.54 (dd, J=14.7 Hz, 5.9 Hz, 1H), 3.23 (dd, J=14.7 Hz, 10.3 Hz, 1H), 2.99 (s, 3H), 1.29 (t, J=7.3 Hz, 3H).

CI-MS (m/z); 349

(4-3) In 1 ml of ethanol was dissolved 0.43 g (1.2 mmol) of N-trifluoroacetyl-N-methyl-DL-4-nitrophenylalanine ethyl ester, and 4 ml of ethanol saturated by hydrogen chloride was added thereto, and the mixture was refluxed under heating for 24 hours.

The solvent was removed from the resulting reaction mixture, ether was added to the residue, and the resulting solid was collected by filtration and dried under reduced pressure to obtain 0.31 g (1.1 mmol) of the title compound as pale yellowish solid.

$^1$H-NMR (CDCl$_3$) δ; 8.25 (d, J=8.8 Hz, 2H), 7.55 (d, J=8.8 Hz, 2H), 4.42 (dd, J=8.4 Hz, 5.5 Hz, 1H), 4.22 (q, J=7.3 Hz, 2H), 3.51 (dd, J=14.3 Hz, 5.5 Hz, 1H), 3.30 (dd, J=14.3 Hz, 8.4 Hz, 1H), 2.79 (s, 3H), 1.17 (t, J=7.3 Hz, 3H).

CI-MS (m/z); 253

Example II-5
N-t-butoxycarbonyl-DL-4-cyanophenylalanine (5-1) In dried THF was dissolved 2.17 g (10.0 mmol) of diethyl acetamidomalonate, and under ice-cooling, 0.44 g (11 mmol) of sodium hydride (oil coat, 60%) was added thereto, and the mixture was stirred at room temperature for 30 minutes. Then, 1.97 g (10.1 mmol) of 4-cyanobenzyl bromide was added thereto and the mixture was refluxed for 7 hours.

The resulting reaction mixture was cooled to room temperature and then concentrated under reduced pressure. Ethyl acetate was added to the residue and the mixture was washed successively with water and a saturated aqueous saline solution and dried over anhydrous sodium sulfate. The organic layer was concentrated under reduced pressure and the residue was purified by the silica gel column chromatography method (eluent: n-hexane/ethyl acetate/chloroform=1/1/2) to obtain 3.08 g (9.28 mmol) of diethyl (4-cyanobenzyl)acetamidomalonate as white solid.

$^1$H-NMR (CDCl$_3$) δ; 7.57 (d, J=8.0 Hz, 2H), 7.13 (d, J=8.0 Hz, 2H), 6.53 (s, 1H), 4.34–4.22 (m, 4H), 3.73 (s, 2H), 2.04 (s, 3H), 1.30 (t, J=7 Hz, 6H).

CI-MS (m/z); 333

(5-2) A mixture of 2.06 g (6.20 mmol) of diethyl (4-cyanobenzyl)acetamidomalonate, 10 ml of water, 10 ml of acetic acid and 2 ml of conc. hydrochloric acid was refluxed for 24 hours.

The resulting reaction mixture was concentrated under reduced pressure, 14 ml of a 1N aqueous sodium hydroxide solution and 14 ml of 1,4-dioxane were added to the residue and the mixture was ice-cooled. Then, 2.00 g (9.20 mmol) of di-t-butyl dicarbonate was added to the mixture and the resulting mixture was stirred at room temperature for 2 hours and allowed to stand at room temperature overnight.

The resulting reaction mixture was concentrated under reduced pressure, and the pH of the mixture was adjusted to 2 by a 5% aqueous potassium hydrogen sulfate solution and the mixture was extracted with ethyl acetate. The organic layer was washed with a saturated aqueous saline solution and dried over anhydrous sodium sulfate. The organic layer was concentrated under reduced pressure to obtain 1.89 g (6.52 mmol) of the title compound as pale yellowish solid.

$^1$H-NMR (CDCl$_3$) δ; 7.60 (d, J=8.0 Hz, 2H), 7.32 (d, J=8.0 Hz, 2H), 5.10–4.25 (m, 2H), 3.38–2.95 (m, 2H), 1.35 (s, 9H).

CI-MS (m/z); 291

Example II-6
N-t-butoxycarbonyl-DL-4-trifluoromethylphenylalanine

In the same manner as in Example II-5 except for using 4-trifluoromethylbenzyl bromide in place of 4-cyanobenzyl bromide, the reaction was carried out to obtain the title compound (overall yield 60%) as white solid.

$^1$H-NMR (CDCl$_3$) δ; 8.04 (brs, 1H), 7.56 (d, J=8.0 Hz, 2H), 7.32 (d, J=8.0 Hz, 2H), 5.08–4.98 (m, 1H), 4.71–4.62 (m, 1H), 3.25–3.07 (m, 2H), 1.41 (s, 9H).

CI-MS (m/z); 278

Example II-7
N-t-butoxycarbonyl-DL-3-nitrophenylalanine

In the same manner as in Example II-5 except for using 3-nitrobenzyl bromide in place of 4-cyanobenzyl bromide, the reaction was carried out to obtain the title compound (overall yield 53%).

$^1$H-NMR (CDCl$_3$) δ; 8.60 (brs, 1H), 8.14–8.07 (m, 2H), 7.56–7.45 (m, 2H), 5.07–4.65 (m, 1H), 3.33–3.11 (m, 2H), 1.36 (s, 9H).

CI-MS (m/z); 255

Example II-8
N-t-butoxycarbonyl-DL-2-chloro-4-nitrophenylalanine

In the same manner as in Example II-5 except for using 2-chloro-4-nitrobenzyl bromide in place of 4-cyanobenzyl bromide, the reaction was carried out to obtain the title compound (overall yield 29%).

$^1$H-NMR (CDCl$_3$) δ; 8.23 (s, 1H), 8.04 (dd, J=8 Hz, 3 Hz, 1H), 7.48 (d, J=8 Hz, 1H), 5.40–4.61 (m, 1H), 3.55–3.48 (m, 1H), 3.18–3.09 (m, 1H), 1.35 (s, 9H).

CI-MS (m/z); 289

Example II-9
N-t-butoxycarbonyl-DL-4-(N-benzoylamino)phenylalanine (9-1) In 120 ml of ethanol was dissolved 4.95 g (14.6 mmol) of N-t-butoxycarbonyl-DL-4-nitrophenylalanine ethyl ester, and 500 mg of 10% palladium carbon was added to the solution and the mixture was stirred under hydrogen atmosphere at 50–60° C. for 6 hours.

The resulting reaction mixture was filtered and the filtrate was concentrated under reduced pressure. The residue was purified by the silica gel column chromatography ethod (eluent: chloroform/ethyl acetate=50/1) to obtain 3.97 g (12.8 mmol) of N-t-butoxycarbonyl-DL-4-aminophenylalanine ethyl ester as white solid.

$^1$H-NMR (CDCl$_3$) δ; 6.92 (d, J=8 Hz, 2H), 6.63 (d, J=8 Hz, 2H), 5.03–4.85 (m, 1H), 4.56–4.38 (m, 1H), 4.16 (q, J=7.3 Hz, 2H), 3.15–2.82 (m, 2H), 1.42 (s, 9H), 1.25 (t, J=7.3 Hz, 3H).

CI-MS (m/z); 253

(9-2) A mixture of 0.30 g (1.0 mmol) of N-t-butoxycarbonyl-DL-4-aminophenylalanine ethyl ester, 0.13 g (1.0 mmol) of benoic acid, 0.45 g (1.0 mmol) of BOP, 10 mg (0.1 mmol) of 4-dimethylaminopyridine and 5 ml of methylene chloride was stirred at room temperature for 24 hours.

The resulting reaction mixture was concentrated under reduced pressure. The residue was dissolved in ethyl acetate, and the solution was washed successively with a 5% aqueous potassium hydrogen sulfate solution, a saturated aqueous sodium bicarbonate solution and a saturated aqueous saline solution, and driedover anhydroussodium sulfate. The organic layerwas concentrated under reduced pressure, and the residue was purified by the silica gel column chromatography method (eluent: chloroform/ethyl acetate=50/1) toobtain0.15 g (0.36 mmol) of N-t-butoxycarbonyl-DL-4-(N-benzoylamino)phenylalanine ethyl ester as yellowish solid.

CI-MS (m/z); 357

(9-3) To 0.12 g (0.29 mmol) of N-t-butoxycarbonyl-DL-4-(N-benzoylamino)phenylalanine ethyl ester were added 5 ml of ethanol and 2 ml of a 1N aqueous sodium hydroxide solution, and the mixture was stirred at room temperature for one hour.

The resulting reaction mixture was concentrated under reduced pressure, a 5% aqueous potassium hydrogen sulfate solution was added to the residue and the resulting mixture was extracted with ethyl acetate. The organic layer was washed with a saturated aqueous saline solution and dried over anhydrous sodium sulfate, and then, the organic layer was evaporated to dryness under reduced pressure to obtain 0.10 g (0.26 mmol) of the title compound.

CI-MS (m/z); 385

Example II-10
N-t-butoxycarbonyl-DL-3-(4-pyridyl)alanine (10-1) To a mixed solution of 9.00 g (50.0 mmol) of N-benzoylglycine, 2.00 g of potassium hydrogen carbonate and 20 ml of acetic anhydride was added under water-cooling 5.60 g (52.3mmol) of isonicotinaldehyde, and the mixture was stirred at the same temperature for one hour.

To the resulting reaction mixture was added 200 ml of water, precipitated solid was collected by filtration, then washed successively with water and ethyl acetate, and dried to obtain 6.70 g (26.8 mmol) of 2-phenyl-4-(4-pyridylmethylene)-2-oxazolin-5-one as yellowish solid.

CI-MS (m/z); 251

(10-2) In 25 ml of methanol was suspended 1.92 g (7.68 mmol) of 2-phenyl-4-(4-pyridylmethylene)-2-oxazolin-5-one, and after adding 2.0 ml of oxalyl chloride to the suspension, the mixture was heated at 100° C. for 2 hours.

The resulting reaction mixture was concentrated under reduced pressure, ether was added to the residue and precipitated solid was collected by filtration and dried to obtain 2.20 g (6.91 mmol) of methyl 2-benzamido-3-(4-pyridyl) acrylate.HCl as white powder.

CI-MS (m/z); 283

(10-3) To 2.20 g (6.91 mmol) of methyl 2-benzamido-3-(4-pyridyl)acrylate.HCl were added 50 ml of methanol and 0.33 g of 10% palladium carbon, and the mixture was stirred under hydrogen atmosphere at 50° C. for 3 hours.

The resulting reaction mixture was filtered through Celite and the filtrate was concentrated under reduced pressure to obtain 2.21 g (6.90 mmol) of N-benzoyl-DL-3-(4-pyridyl) alanine methyl ester-HCl as yellowish oily product.

CI-MS (m/z); 285

(10-4) To 2.21 g (6.90 mmol) of N-benzoyl-DL-3-(4-pyridyl)alanine methyl ester.HCl were added 10 ml of water and 30 ml of conc. Hydrochloric acid, and the mixture was stirred at 120° C. for 9 hours.

The resulting reaction mixture was returned to room temperature, precipitated solid was filtered off and the filtrate was concentrated under reduced pressure. To the residue was added 50 ml of acetone, and the precipitated solid was collected by filtration. The solid was washed with acetone and dried to obtain 1.61 g (6.73 mmol) of DL-3-(4-pyridyl)alanine.2HCl as yellowish solid.

FAB-MS (m/z); 167

(10-5) To 0.24 g (1.0 mmol) of DL-3-(4-pyridyl) alanine.2HCl were added 5 ml of a 1N aqueous sodium hydroxide solution and 5 ml of THF, and while stirring the mixture, 0.5 ml of di-t-butyl dicarbonate was added dropwise and the mixture was stirred for 2 hours.

To the resulting reaction mixture was added 20 ml of water and the resulting mixture was washed with ethyl acetate. To the aqueous layer was added a 5% aqueous potassium hydrogen sulfate solution to adjust the pH of the mixture to about 4, and then, the mixture was extracted with n-butanol. The organic layer was concentrated under reduced pressure, precipitated solid was collected by filtration and dried to obtain 0.20 g (0.75 mmol) of the title compound as white solid.

$^1$H-NMR (CDCl$_3$) δ; 8.76 (d, J=6.6 Hz, 2H), 7.97 (d, J=6.6 Hz, 2H), 4.60–4.53 (m, 1H), 3.54 (dd, J=13.9 Hz, 5.1 Hz, 1H), 3.23 (dd, J=13.9 Hz, 9.5 Hz, 1H), 1.37 (s, 9H).

CI-MS (m/z); 267

Example II-11
N-t-butoxycarbonyl-L-4-(phenylsulfonylamino) phenylalanine (11-1) In 25 ml of ethanol was dissolved 1.00 g (2.96 mmol) of N-t-butoxycarbonyl-L-4-nitrophenylalanine ethyl ester, and 90 mg of 10% palladium carbon was added to the solution, and the mixture was stirred under hydrogen atmosphere at 50–60° C. for 6 hours.

The resulting reaction mixture was filtered by using Celite, and the filtrate was concentrated under reduced pressure. The residue was purified by the silica gel column chromatography method (eluent: chloroform/ethyl acetate= 50/1) to obtain 0.67 g (2.2 mmol) of N-t-butoxycarbonyl-L-4-aminophenylalanine ethyl ester as pale pink oily product.

$^1$H-NMR (CDCl$_3$) δ; 6.92 (d, J=8 Hz, 2H), 6.63 (d, J=8 Hz, 2H), 5.03–4.85 (m, 1H), 4.56–4.38 (m, 1H), 4.16 (q, J=7.3 Hz, 2H), 3.15–2.82 (m, 2H), 1.42 (s, 9H), 1.25 (t, J=7.3 Hz, 3H).

CI-MS (m/z); 253

(11-2) To 20 ml of a methylene chloride solution containing 0.65 g (2.1 mmol) of N-t-butoxycarbonyl-L-4-aminophenylalanine ethyl ester were added 1 ml of pyridine and 0.75 g (4.2 mmol) of benzenesulfonyl chloride, and the mixture was stirred at room temperature for 6 hours.

The resulting reaction mixture was concentrated under reduced pressure, ethyl acetate was added to the residue and the mixture was washed successively with a 5% aqueous potassium hydrogen sulfate solution, a saturated aqueous sodium bicarbonate solution and a saturated aqueous saline solution, and then, dried over anhydrous sodium sulfate. The organic layer was concentrated under reduced pressure and the residue was purified by the silica gel column chromatography method (eluent: chlorofor/ethyl acetate=100/1–50/ 1) to obtain 0.75 g (1.7 mmol) of N-t-butoxycarbonyl-L-4-(phenylsulfonylamino)phenylalanine ethyl ester as pink foamy product.

$^1$H-NMR (CDCl$_3$) δ; 7.74 (d, J=8 Hz, 2H), 7.58–7.42 (m, 3H), 7.05–6.95 (m, 4H), 6.58 (s, 2H), 5.02–4.87 (m, 1H), 4.55–4.44 (m, 1H), 4.13 (q, J=7.3 Hz, 2H), 3.09–2.92 (m, 2H), 1.42 (s, 9H), 1.20 (t, J=7.3 Hz, 3H).

CI-MS (m/z); 349

(11-3) To 0.75 g (1.7 mmol) of N-t-butoxycarbonyl-L-4-(phenylsulfonylamino)phenylalanine ethyl ester were added 10 ml of ethanol and 3 ml of a 1N aqueous sodium hydroxide solution, and the mixture was stirred at room temperature for 3 hours.

The resulting reaction mixture was concentrated under reduced pressure, ethyl acetate was added to the residue, and after washing the mixture with a 5% aqueous potassium hydrogen sulfate solution and a saturated aqueous saline solution, it was dried over anhydrous sodium sulfate. The organic layer was concentrated under reduced pressure, ethyl acetate and n-hexane were added to the residue and the precipitated solid was collected by filtration. The solid was dried under reduced pressure to obtain 0.58 g (1.4 mmol) of the title compound as pale pink solid.

$^1$H-NMR (CDCl$_3$+DMSO-d$_6$) δ; 9.45–9.20 (m, 1H), 7.87 (d, J=8 Hz, 2H), 7.52–7.38 (m, 3H), 7.08–7.00 (m, 4H), 6.58 (s, 2H), 5.12–4.99 (m, 1H), 4.52–4.37 (m, 1H), 3.11–2.91 (m, 2H), 1.40 (s, 9H).

CI-MS (m/z); 321

Example II-12
N-t-butoxycarbonyl-DL-4-(methylsulfonylamino)phenylalanine

In the same manner as in Example II-(11-2) and Example II-(11-3) except for using N-t-butoxycarbonyl-DL-4-aminophenylalanine ethyl ester in place of N-t-butoxycarbonyl-L-4-aminophenylalanine ethyl ester and using methanesulfonyl chloride in place of benzenesulfonyl chloride, the reactions were carried out to obtain the title compound (overall yeield 84%) as white solid.

$^1$H-NMR (CDCl$_3$+DMSO-d$_6$) δ; 9.13 (brs, 1H), 7.21 (d, J=8.5 Hz, 2H), 7.13 (d, J=8.5 Hz, 2H), 5.18–4.48 (m, 1H), 3.30–3.08 (m, 2H), 2.92 (s, 3H), 1.42 (s, 9H).

CI-MS (m/z); 259

Example II-13
N-t-butoxycarbonyl-DL-4-(benzylsulfonylamino)phenylalanine

In the same manner as in Example II-(11-2) and Example II-(11-3) except for using N-t-butoxycarbonyl-DL-4-aminophenylalanine ethyl ester in place of N-t-butoxycarbonyl-L-4-aminophenylalanine ethyl ester and using benzylsulfonyl chloride in place of benzenesulfonyl chloride, the reactions were carried out to obtain the title compound (overall yeield 92%) as palye yellowish foay product.

$^1$H-NMR (CDCl$_3$) δ; 7.33–7.25 (m, 5H), 7.12–6.99 (m, 4H), 6.90 (s, 1H), 5.06–4.88 (m, 1H), 4.63–4.57 (m, 1H), 4.32 (s, 2H), 3.18–3.02 (m, 2H), 1.43 (s, 9H).

CI-MS (m/z); 291

Example II-14
N-t-butoxycarbonyl-DL-4-[(4-fluorophenyl)sulfonylamino]-phenylalanine In the same manner as in Example II-(11-2) and Example II-(11-3) except for using N-t-butoxycarbonyl-DL-4-aminophenylalanine ethyl ester in place of N-t-butoxycarbonyl-L-4-aminophenylalanine ethyl ester and using 4-fluorobenzenesulfonyl chloride in place of benzenesulfonyl chloride, the reactions were carried out to obtain the title compound (overall yeield-quantitative) as white solid.

$^1$H-NMR (CDCl$_3$) δ; 7.78–7.71 (m, 2H), 7.21 (s, 1H), 7.13–6.91 (m, 6H), 5.03–4.88 (m, 1H), 4.67–4.49 (m, 1H), 3.19–2.89 (m, 2H), 1.42 (s, 9H).

CI-MS (m/z); 383

Example II-15
N-t-butoxycarbonyl-DL-4-(phenylsulfonylamino)phenylalanine

In the same manner as in Example II-(11-2) and Example II-(11-3) except for using N-t-butoxycarbonyl-DL-4-aminophenylalanine ethyl ester in place of N-t-butoxycarbonyl-L-4-aminophenylalanine ethyl ester and using triethylamine in place of pyridine, the reactions were carried out to obtain the title compound (overall yeield 57%) as white foamy product.

$^1$H-NMR (400 MHz, CDCl$_3$) δ; 7.74 (d, J=7.3 Hz, 2H), 7.53 (d, J=7.3 Hz, 1H), 7.43 (t, J=7.3 Hz, 2H), 7.04 (d, J=7.3 Hz, 2H), 6.93 (d, J=7.3 Hz, 2H), 6.91 (brs, 1H), 4.97–4.88 (m, 1H), 4.60–4.52 (m, 1H), 3.14–3.00 (m, 2H), 1.40 (s, 9H).

CI-MS (m/z); 365

Example II-16
4,5,6,7-Tetrahydrothieno[3,2-c]pyridin-2-acetic acid.hydrochloride (16-1) To 109.4 g (0.503 mol) of 4-chloro-1-ethoxycarbonyl-3-formyl-1,2,5,6-tetrahydropyridine (see Japanese Provisional Patent Publication No. 2992/1988) were added 98.5 g (0.657 mol) of mercaptosuccinic acid and 280 ml of pyridine, and after ice-cooling the mixture, 199.1 g (1.972 mol) of triethylamine was added dropwise to the mixture over 40 minutes. Then, the mixture was stirred at room temperature for 2.5 hours, 20 ml of piperidine was added to the mixture and the resulting mixture was stirred at 100–110° C. for 2.5 hours.

The resulting reaction mixture was cooled to room temperature and concentrated under reduced pressure. To the residue was added water and ethyl acetate, and the pH of the aqueous layer was adjusted to 2 by a 6M aqueous hydrochloric acid solution. The organic layer was washed three times with each 300 ml of a 1M aqueous hydrochloric acid solution, and after washing with a saturated aqueous saline solution, it was dried over anhydrous sodium sulfate. The organic layer was concentrated under reduced pressure and the residue was purified by the silica gel column chromatography method (eluent: chloroform/ethyl acetate/acetic acid=8/1.5/0.5) to obtain 91.5 g (0.340 mol) of 5-ethoxycarbonyl-4,5,6,7-tetrahydrothieno[3,2-c]pyridin-2-acetic acid as reddish brown oily product.

$^1$H-NMR (CDCl$_3$) δ; 6.64 (s, 1H), 4.48 (s, 2H), 4.21–4.14 (m, 2H), 3.79 (s, 2H), 3.78–3.7 (m, 2H), 2.75–2.85 (m, 2H), 1.32–1.25 (m, 3H).

CI-MS (m/z); 270

(16-2) To 32.1 g (0.119 mol) of 5-ethoxycarbonyl-4,5,6,7-tetrahydrothieno[3,2-c]pyridin-2-acetic acid were added 240 ml of water and 48.0 g (0.729 mol) of potassium hydroxide (85%) and the mixture was stirred at 100° C. for 4 hours.

The resulting reaction mixture was cooled to room temperature, and the pH of the mixture was adjusted to 2 by adding conc. hydrochloric acid. The pH-adjusted reaction mixture was evaporated under reduced pressure to remove water until the volume becomes 300 ml, then an equal amount of ethanol was added thereto and the formed precipitate was filtered off. The filtrate was concentrated under reduced pressure and ethanol was again added to the residue, and the formed precipitate was collected by filtration. The filtrate was concentrated under reduced pressure, diethyl ether was added to the residue and the formedsolidwas collectedbyfiltration. These solidswere combined and dried under reduced pressure to obtain 27.3 g (0.117 mol) of the title compound as brownish solid.

$^1$H-NMR (D$_2$O) δ; 6.77 (s, 1H), 4.27 (s, 2H), 3.88 (s, 2H), 3.57 (t, J=7 Hz, 2H), 3.12 (t, J=7 Hz, 2H).

Example II-17
Methyl 4,5,6,7-tetrahydrothieno[3,2-c]pyridin-2-acetate.hydrochloride In 100 ml of methanol was suspended 11.5 g (49.3 mmol) of 4,5,6,7-tetrahydrothieno[3,2-c]pyridin-2-acetic acid.HCl, and under ice-cooling, 6.0 ml of thionyl chloride was added dropwise to the suspension. The mixture was stirred at the same temperature for one hour, and after becoming uniform, it was refluxed for 2 hours.

The resulting reaction mixture was concentrated under reduced pressure, and diethyl ether was added to the residue and the precipitated solid was collected by filtration. The solid was dried under reduced pressure to obtain 10.6 g (42.8 mol) of the title compound as brownish solid.

$^1$H-NMR (DMSO-d$_6$) δ; 6.76 (s, 1H), 4.10 (s, 2H), 3.81 (s, 2H), 3.88 (s, 2H), 3.63 (s, 3H), 3.34 (t, J=7 Hz, 2H), 2.98 (t, J=7 Hz, 2H).

CI-MS (m/z); 212

Example II-18
Ethyl 4,5,6,7-tetrahydrothieno[3,2-c]pyridin-2-acetate.hydrochloride (18-1) To 50.5 g (0.188 mol) of 5-ethoxycarbonyl-4,5,6,7-tetrahydrothieno[3,2-c]pyridin-2-acetic acid were added 380 ml of water and 75.7 g (1.15 mol) of potassium hydroxide (85%), and the mixture was stirred at at 100° C. for 4 hours.

The resulting reaction mixture was cooled to room temperature and 200 ml of 1,4-dioxane was added thereto. Under ice-cooling, 56.0 g (0.257 mol) of di-t-butyl dicarbonate was added dropwise to the mixture. After stirring the mixture at this temperature for 30 minutes, returned to room temperature and the mixture was allowed to stand at room temperature overnight.

To the resulting reaction mixture was adjusted to pH 8 by adding a 4.8 M aqueous hydrochloric acid solution, and after concentrating under reduced pressure, it was washed with diethyl ether. Ethyl acetate was added to the aqueous layer, and the pH of the mixture was firstly adjusted to 4 by a 4.8 M aqueous hydrogen chloride solution, and then, the pH to 2 by a 10% aqueous potassium hydrogen sulfate solution. The organic layer was separated and washed successively with water and a saturated aqueous saline solution and dried over anhydrous sodium sulfate. The organic layer was concentrated under reduced pressure, n-hexane was added to the residue and the precipitated solid was collected by filtration. The solid was dried under reduced pressure to 43.3 g (0.146 mol) of 5-t-butoxycarbonyl-4,5,6,7-tetrahydrothieno[3,2-c]pyridin-2-acetic acid as yellowish brown powder.

$^1$H-NMR (CDCl$_3$) δ; 6.64 (s, 1H), 4.43 (s, 2H), 3.79 (s, 2H), 3.75–3.65 (m, 2H), 2.75–2.85 (m, 2H), 1.48 (s, 9H).

CI-MS (m/z); 242

(18-2) In 500 ml of ethanol was suspended 38.3 g (0.129 mol) of 5-t-butoxycarbonyl-4,5,6,7-tetrahydrothieno[3,2-c]pyridin-2-acetic acid, and under ice-cooling, 17.0 ml (0.198 mole) of oxalyl chloride was added dropwise. The mixture was stirred at the temperature for one hour, and after becoming uniform, it was refluxed for 3 hours and allowed to stand at room temperature overnight.

The resulting reaction mixture was concentrated under reduced pressure, ethyl acetate was added to the residue and the precipitated solid was collected by filtration. The solid was dried under reduced pressure to obtain 32.7 g (0.125 mol) of the title compound as yellowish brown powder.

$^1$H-NMR (CDCl$_3$) δ; 6.74 (s, 1H), 4.15 (q, J=7 Hz, 2H), 3.81 (s, 2H), 3.53 (t, J=5.9 Hz, 2H), 3.11 (t, J=6 Hz, 2H), 1.25 (t, J=7 Hz, 3H).

CI-MS (m/z); 226

Example II-19
Ethyl 3-methyl-4,5,6,7-tetrahydrothieno[3,2-c]pyridin-2-acetate.hydrochloride (19-1) A mixture of 5.00 g (29.2 mmol) of 1-ethoxycarbonyl-4-piperidone, 100 ml of benzene and 2.10 g (29.6 mmol) of pyrrolidine was heated and forming water was removed by using the Dehn-Stark dehydrating tube. After distillation of water was stopped, benzene was removed by evaporation under reduced pressure. To the residue was added 30 ml of pyridine, and under ice-cooling, 20 ml of 1,2-dichloroethane containing 3.10 g (30.4 mmol) of acetic anhydride was added dropwise over 30 minutes, and after stirring the mixture at room temperature for 5 hours, it was allowed to stand at room temperature overnight.

The resulting reaction mixture was concentrated under reduced pressure, ethyl acetate was added to the residue and the mixture was washed successively with a 5% aqueous potassium hydrogen sulfate solution, water and a saturated aqueous saline solution, and dried over anhydrous sodium sulfate. The organic layer was concentrated under reduced pressure and the residue was purified by the silica gel column chromatography method (eluent: n-hexane/ethyl acetate=3/2) to obtain 2.44 g (11.5 mmol) of 3-acetyl-1-ethoxycarbonyl-4-hydroxy-1,2,5,6-tetrahydropyridine as pale yellowish oily product.

$^1$H-NMR (CDCl$_3$) δ; 15.67 (s, 1H), 4.23–4.15 (m, 4H), 3.66–3.62 (m, 2H), 2.46 (t, J=5.9 Hz, 2H), 2.29 (s, 3H), 1.32–1.26 (m, 3H).

CI-MS (m/z); 214

(19-2) To a mixture of 2.44 g (11.5 mmol) of 3-acetyl-1-ethoxycarbonyl-4-hydroxy-1,2,5,6-tetrahydropyridine and 2.5 ml of methylenechloride solution containing 2.60 g (35.6 mmol) of DMF was added dropwise, under ice-cooling, 5 ml of a methylene chloride solution containing 1.86 g (11.9 mmol) of phosphorus oxychloride over 10 minutes. Then, at room temperature, the mixture was stirred for 7 hours and allowed to stand at room temperature overnight.

To the resulting reaction mixture were added 20 g of ice and 5 g of sodium acetate.3H$_2$O, and after stirring for 30 minutes, the mixture was extracted with benzene. The organic layer was washed successively with water and a saturated aqueous sodium bicarbonate solution and dried over anhydrous sodium sulfate. The organic layer was concentrated under reduced pressure to obtain 2.52 g (10.9 mmol) of 3-acetyl-4-chloro-1-ethoxycarbonyl-1,2,5,6-tetrahydropyridine as reddish brown oily product.

$^1$H-NMR (CDCl$_3$) δ; 4.23–4.13 (m, 4H), 3.62 (t, J=5.9 Hz, 2H), 2.64–2.55 (m, 2H), 2.53 (s, 3H), 1.29–1.25 (m, 3H).

CI-MS (m/z); 232

(19-3) A mixture of 2.52 g (10.9 mmol) of 3-acetyl-4-chloro-1-ethoxycarbonyl-1,2,5,6-tetrahydropyridine, 2.13 g (14.2 mmol) of mercaptosuccinic acid and 10 ml of pyridine was ice-cooled, and 4.30 g (42.6 mmol) of triethylamine was added dropwise to the mixture over 5 minutes. After stirring the mixture at room temperature for 5 hours, 0.5 ml of piperidine was added to the mixture and the resulting mixture was stirred at 100–110° C. for 3 hours.

The resulting reaction mixture was concentrated under reduced pressure, ethyl acetate was added to the residue and a 5% aqueous potassium hydrogen sulfate solution was added to the mixture to adjust the pH of the aqueous layer to 2. The organic layer was was washed successively with a 5% aqueous potassium hydrogen sulfate solution, water and a saturated aqueous saline solution, and dried over anhydrous sodium sulfate. The organic layer was concentrated under reduced pressure and the residue was purified by the silica gel column chromatography method (eluent: chloroform/ethyl acetate/acetic acid=8.8/1/0.2) to obtain 1.17 g (4.13 mmol) of 5-ethoxycarbonyl-3-methyl-4,5,6,7-tetrahydrothieno[3,2-c]pyridin-2-acetic acid as yellowish oily product.

$^1$H-NMR (CDCl$_3$) δ; 4.37 (brs, 2H), 4.23–4.15 (m, 2H), 3.78–3.70 (m, 2H), 3.72 (s, 2H), 2.85–2.75 (m, 2H), 2.03 (s, 3H), 1.31–1.26 (m, 3H).

CI-MS (m/z); 284

(19-4) To 1.15 g (4.06 mmol) of 5-ethoxycarbonyl-3-methyl-4,5,6,7-tetrahydrothieno[3,2-c]pyridin-2-acetic acid was added 25 ml of a 1N aqueous sodium hydroxide solution, and the mixture was stirred at 100–110° C. for 6 hours.

To the resulting reaction mixture was added 50 ml of 1,4-dioxane, and then, under ice-cooling, 1.80 g (8.26 mmol) of di-t-butyl dicarbonate was added dropwise. The mixture was stirred at the same temperature for 30 minutes, and further stirred at room temperature for 4 hours. To the reaction mixture was added a 20% aqueous potassium hydrogen sulfate solution, and after adjusting the pH to 8, the organic solvent was removed by evaporation under reduced pressure. Ethyl acetate was added to the residue, after adjusting the pH to 2 by a 5% aqueous potassium hydrogen sulfate solution, and the organic layer was washed successively with water and a saturated aqueous saline solution and dried over anhydrous sodium sulfate. The organic layer was concentrated under reduced pressure and the resdue was purified by the silica gel column chromatography method (eluent: chloroform/ethyl acetate/acetic acid=8.8/1/0.2) to obtain 0.95 g (3.1 mmol) of 5-t-butoxycarbonyl-3-methyl-4,5,6,7-tetrahydrothieno[3,2-c] pyridin-2-acetic acid as orange oily product.

$^1$H-NMR (CDCl$_3$) δ; 4.33 (brs, 2H), 3.72–3.65 (m, 2H), 3.72 (s, 2H), 2.82–2.72 (m, 2H), 2.01 (s, 3H), 1.48 (s, 9H).

CI-MS (m/z); 256

(19-5) To 15 ml of ethanol solution containing 0.94 g (3.0 mmol) of 5-t-butoxycarbonyl-3-methyl-4,5,6,7-tetrahydrothieno[3,2-c]pyridin-2-acetic acid was added dropwise, under ice-cooling, 0.42 ml (5.0 mmol) of oxalyl chloride. The mixture was stirred at the same temperature for one hour, and then, refluxed for 2.5 hours.

The resulting reaction mixture was concentrated under reduced pressure, ethyl acetate was added to the residue and the precipitated solid was collected by filtration to obtain 0.657 g (2.65 mmol) of the title compound as pale brownish powder.

$^1$H-NMR (CD$_3$OD) δ; 4.17–4.10 (m, 4H), 3.75 (s, 2H), 3.54–3.49 (m, 2H), 3.10–3.06 (m, 2H), 2.04 (s, 3H), 1.26–1.21 (m, 3H).

CI-MS (m/z); 240

Example II-20

Ethyl 3-propyl-4,5,6,7-tetrahydrothieno[3,2-c]pyridin-2-acetate.hydrochloride (20-1) In the same manner as in Example II-(19-1) except for using 5.05 g (32.0 mmol) of butyric anhydride in place of acetic anhydride, the reaction was carried out to obtain 1.51 g (6.30 mmol) of 3-butyryl-1-ethoxycarbonyl-4-hydroxy-1,2,5,6-tetrahydropyridine as pale yellowish oily product.

$^1$H-NMR (CDCl$_3$) δ; 15.79 (s, 1H), 4.24–4.14 (m, 4H), 3.66–3.61 (m, 2H), 2.48–2.31 (m, 4H), 1.72–1.63 (m, 2H), 1.32–1.26 (m, 3H), 1.01–0.92 (m, 3H).

CI-MS (m/z); 242

(20-2) In the same manner as in Example II-(19-2) except for using 1.51 g (6.30 mmol) of 3-butyryl-1-ethoxycarbonyl-4-hydroxy-1,2,5,6-tetrahydropyridine in place of 3-acetyl-1-ethoxycarbonyl-74-hydroxy-1,2,5,6-tetrahydropyridine, the reaction was carried out to obtain 1.31 g (5.20 mmol) of 3-butyryl-4-chloro-1-ethoxycarbonyl-1,2,5,6-tetrahydropyridine as yellowish oily product.

(20-3) In the same manner as in Example II-(19-3) except for using 1.31 g (5.20 mmol) of 3-butyryl-4-chloro-1-ethoxycarbonyl-1,2,5,6-tetrahydropyridine in place of 3-acetyl-4-chloro-1-ethoxycarbonyl-1,2,5,6-tetrahydropyridine, the reaction was carried out to obtain 0.70 g (2.3 mmol) of 5-ethoxycarbonyl-3-propyl-4,5,6,7-tetrahydrothieno[3,2-c]pyridin-2-acetic acid as yellowish oily product.

(20-4) In the same manner as in Example II-(19-4) except for using 0.70 g (2.3 mmol) of 5-ethoxycarbonyl-3-propyl-4,5,6,7-tetrahydrothieno[3,2-c]pyridin-2-acetic acid in place of 5-ethoxycarbonyl-3-methyl-4,5,6,7-tetrahydrothieno[3,2-c]pyridin-2-acetic acid, the reaction was carried out to obtain 0.48 g (1.4 mmol) of 5-t-butoxycarbonyl-3-propyl-4,5,6,7-tetrahydrothieno[3,2-c]pyridin-2-acetic acid as orange oily product.

$^1$H-NMR (CDCl$_3$) δ; 4.52–4.38 (m, 2H), 3.84–3.56 (m, 4H), 2.85–2.30 (m, 4H), 2.10 (s, 2H), 1.48 (s, 9H), 0.97–0.92 (m, 3H).

CI-MS (m/z); 284

(20-5) In the same manner as in Example II-(19-5) except for using 0.48 g (1.4 mmol) of 5-t-butoxycarbonyl-3-propyl-4,5,6,7-tetrahydrothieno[3,2-c]pyridin-2-acetic acid in place of 5-t-butoxycarbonyl-3-methyl-4,5,6,7-tetrahydrothieno[3,2-c]pyridin-2-acetic acid, the reaction was carried out to obtain 0.28 g (0.92 mmol) of the title compound as pale brownish powder.

CI-MS (m/z); 268

Example II-21

Ethyl 3-trifluoromethyl-4,5,6,7-tetrahydrothieno[3,2-c]-pyridin-2-acetate.hydrochloride (21-1) In the same manner as in Example II-(19-1) except for using 4.5 ml (32 mmol) of trifluoroacetic anhydride in place of acetic anhydride, the reaction was carried out to obtain 1.72 g (6.40 mmol) of 3-trifluoroacetyl-1-ethoxycarbonyl-4-hydroxy-1,2,5,6-tetrahydropyridine as pale yellowish oily product.

$^1$H-NMR (CDCl$_3$) δ; 14.78 (s, 1H), 4.22–4.14 (m, 2H), 3.71–3.55 (m, 2H), 2.64–2.59 (m, 2H), 2.04–1.90 (m, 2H), 1.33–1.26 (m, 3H).

CI-MS (m/z); 268

(21-2) In the same manner as in Example II-(19-2) except for using 1.72 g (6.40 mmol) of 3-trifluoroacetyl-1-ethoxycarbonyl-4-hydroxy-1,2,5,6-tetrahydropyridine in place of 3-acetyl-1-ethoxycarbonyl-4-hydroxy-1,2,5,6-tetrahydropyridine, the reaction was carried out to obtain 1.80 g (6.27 mmol) of 3-trifluoroacetyl-4-chloro-1-ethoxycarbonyl-1,2,5,6-tetrahydropyridine as yellowish oily product.

(21-3) In the same manner as in Example II-(19-3) except for using 1.80 g (6.27 mmol) of 3-trifluoroacetyl-4-chloro-1-ethoxycarbonyl-1,2,5,6-tetrahydropyridine in place of 3-acetyl-4-chloro-1-ethoxycarbonyl-1,2,5,6-tetrahydropyridine, the reaction was carried out to obtain 0.68 g (2.0 mmol) of 5-ethoxycarbonyl-3-trifluoromethyl-4,5,6,7-tetrahydrothieno[3,2-c]pyridin-2-acetic acid as yellowish oily product.

CI-MS (m/z); 338

(21-4) In the same manner as in Example II-(19-4) except for using 0.70 g (2.3 mmol) of 5-ethoxycarbonyl-3-trifluoromethyl-4,5,6,7-tetrahydrothieno[3,2-c]pyridin-2-acetic acid in place of 5-ethoxycarbonyl-3-methyl-4,5,6,7-tetrahydrothieno[3,2-c]pyridin-2-acetic acid, the reaction was carried out to obtain 0.24 g (0.66 mmol) of 5-t-butoxycarbonyl-3-trifluoromethyl-4,5,6,7-tetrahydrothieno[3,2-c]pyridin- 2-acetic acid as orange oily product.

(21-5) In the same manner as in Example II-(19-5) except for using 0.24 g (0.66 mmol) of 5-t-butoxycarbonyl-3-trifluoromethyl-4,5,6,7-tetrahydrothieno[3,2-c]pyridin-2-acetic acid in place of 5-t-butoxycarbonyl-3-methyl-4,5,6,7-tetrahydrothieno[3,2-c]pyridin-2-acetic acid, the reaction was carried out to obtain 0.20 g (0.61 mmol) of the title compound as pale brownish powder.

CI-MS (m/z); 294

Example II-22

Ethyl 4,6-ethano-4,5,6,7-tetrahydrothienof3,2-c]pyridin-2-acetate.hydrochloride (22-1) To 28.0 g (0.384 mol) of DMF was added dropwise, under ice-cooling, 38.8 g (0.253 mol) of phosphorus oxychloride over 15 minutes, and then, the mixture was stirred at room temperature for 1.5 hours. Then, under ice-cooling, 20 ml of a methylene chloride solution containing 25.0 g (0.127 mol) of N-ethoxycarbonyl-4-tropinone was added dropwise over 10 minutes to the mixture. After stirring the resulting mixture at room temperature for 2.5 hours, it was allowed to stand at room temperature overnight.

Then, under ice-cooling, 80 g of ice was added to the mixture, it was stirred for 30 minutes. Thereafter, 108 g of sodium acetate.3H$_2$O was added thereto and the mixture was stirred at 5–10° C. for 2 hours. The mixture was extracted with benzene, the organic layer was washed successively with water and a saturated aqueous sodium bicarbonate solution, and dried over anhydrous sodium sulfate. The organic layer was concentrated under reduced pressure to obtain 26.81 g (0.110 mol) of 3-chloro-8-ethoxycarbonyl-2-formyl-8-azabicyclo[3.2.1]octo-2-ene as dark brownish oily product.

$^1$H-NMR (CDCl$_3$) δ; 10.08 (s, 1H), 5.08–5.02 (m, 1H), 4.60–4.42 (m, 1H), 4.18–4.09 (m, 2H), 3.30–3.12 (m, 1H), 2.40–2.30 (m, 1H), 2.29–2.18 (m, 1H), 2.14–2.02 (m, 1H), 1.90–1.80 (m, 1H), 1.75–1.62 (m, 1H), 1.30–1.22 (m, 3H).

CI-MS (m/z); 244

(22-2) To a mixture of 26.8 g (0.110 mol) of 3-chloro-8-ethoxycarbonyl-2-formyl-8-azabicyclo[3.2.1]octo-2-ene, 21.6 g (0.144 mol) of mercaptosuccinic acid and 60 ml of pyridine was added dropwise, under ice-cooling, 43.6 g (0.432 mol) of triethylamine over 30 minutes, and the resulting mixture was stirred at room temperature for 3 hours. Then, 4.5 ml of piperidine was added to the mixture, and the mixture was stirred at 100–110° C. for 3 hours.

The resulting reaction mixture was concentrated under reduced pressure, water and ethyl acetate were added to the residue, and a 6M aqueous hydrochloric acid solution was added to the mixture to adjust the pH to 2. The organic layer was washed twice with each 100 ml of a 1M aqueous hydrochloric acid solution, and further washed with a saturated aqueous saline solution, it was dried over anhydrous sodium sulfate. The organic layer was concentrated under reduced pressure, and the residue was purified by the silica gel column chromatography method (eluent: chloroform/ethyl acetate/acetic acid=8/1.5/0.5) to obtain 25.1 g (85.0 mrol) of 5-ethoxycarbonyl-4,6-ethano-4,5,6,7-tetrahydrothieno[3,2-c]pyridin-2-acetic acid as yellowish brown oily product.

$^1$H-NMR (CDCl$_3$) δ; 6.65 (s, 1H), 5.07–4.90 (m, 1H), 4.72–4.50 (m, 1H), 4.15–4.08 (m, 2H), 3.76 (s, 2H), 3.42–3.23 (m, 1H), 2.52 (d, J=16.1 Hz, 1H), 2.32–2.18 (m, 1H), 2.15–2.02 (m, 1H), 1.94–1.86 (m, 1H), 1.73–1.62 (m, 1H), 1.25–1.20 (m, 3H).

CI-MS (m/z); 296

(22-3) To 25.0 g (84.8 mmol) of 5-ethoxycarbonyl-4,6-ethano-4,5,6,7-tetrahydrothieno[3,2-c]pyridin-2-acetic acid were added 170 ml of water and 33.7 g (0.517 mol) of potassium hydroxide (85%), and the mixture was stirred at 100–110° C. for 10 hours.

To the resulting reaction mixture was added 100 ml of 1,4-dioxane, and under ice-cooling, 31.0 g (0.142 mol) of di-t-butyl dicarbonate was added dropwise to the mixture. The mixture was stirred at the same temperature for 30 minutes and then further stirred at room temperature for 5 hours. After completion of the reaction, a 4.8M aqueous hydrochloric acid solution was added to the mixture to adjust the pH to 8, and the organic solvent was removed by evaporation under reduced pressure. After washing with diethyl ether, ethyl acetate was added to the residue, and then, the pH of the mixture was firstly adjusted to 6 by a 4.8M aqueous hydrochloric acid solution, and then, the pH to 2 by a 20% aqueous potassium hydrogen sulfate solution. The organic layer was separated and washed successively with water and a saturated aqueous saline solution and dried over anhydrous sodium sulfate. The organic layer was concentrated under reduced pressure, and the residue was purified by the silica gel column chromatography method (eluent: chloroform/ethyl acetate/acetic acid=8/1.5/0.5) to obtain 20.9 g (64.7 mmol) of 5-t-butoxycarbonyl-4,6-ethano-4,5,6,7-tetrahydrothieno[3,2-c]pyridin-2-acetic acid as yellowish brown oily product.

$^1$H-NMR (CDCl$_3$) δ; 6.64 (s, 1H), 5.02–4.81 (m, 1H), 4.68–4.40 (m, 1H), 3.76 (s, 2H), 3.43–3.21 (m, 1H), 2.50 (d, J=16.1 Hz, 1H), 2.30–2.18 (m, 1H), 2.12–2.00 (m, 1H), 1.90–1.84 (m, 1H), 1.74–1.59 (m, 1H), 1.41 (s, 9H).

CI-MS (m/z); 268

(22-4) To 50 ml of an ethanol solution containing 3.26 g (10.1 mmol) of 5-t-butoxycarbonyl-4,6-ethano-4,5,6,7-tetrahydrothieno[3,2-c]pyridin-2-acetic acid was added dropwise, under ice-cooling, 1.40 ml (16.3 mmol) of oxalyl chloride, and the mixture was stirred at the same temperature for one hour, and then, refluxed for 3 hours. The mixture was concentrated under reduced pressure to obtain 3.53 g of a mixture containing the title compound and diethyl oxalate as yellowish brown oily product.

1H-NMR (CDCl$_3$) δ; 10.31–10.10 (m, 1H), 9.60–9.39 (m, 1H), 6.65 (s, 1H), 4.81 (brs, 1H), 4.22–4.14 (m, 2H), 4.44–4.33 (m, 1H), 3.80–3.67 (m, 1H), 3.72 (s, 2H), 2.74 (d, J=16.9 Hz, 1H), 2.53–2.40 (m, 2H), 2.15–2.08 (m, 1H), 1.87–1.75 (m, 1H), 1.31–1.26 (m, 1H).

CI-MS (m/z); 252

Example II-23

Ethyl 5-t-butoxycarbonyl-4,6-ethano-4,5,6,7-tetrahydrothieno[3,2-c]pyridin-2-acetate A mixture of 17.7 g (54.6 mmol) of 5-t-butoxycarbonyl-4,6-ethano-4,5,6,7-tetrahydrothieno[3,2-c]pyridin-2-acetic acid, 5.00 g (110 mmol) of ethanol, 20.5 g (107 mmol) of EDC, 7.0 g (57 mmol) of 4-dimethylaminopyridine and 150 ml of methylene chloride was stirred at room temperature for 2 hours, and the mixture was allowed to stand at room temperature overnight.

The resulting reaction mixture was concentrated under reduced pressure, and ethyl acetate were added to the residue. The organic layer was washed successively with a 5% aqueous potassium hydrogen sulfate solution, a saturated aqueous sodium bicarbonate solution and a saturated aqueous saline solution, and dried over anhydrous sodium sulfate. The organic layer was concentrated under reduced pressure, and the residue was purified by the silica gel column chromatography method (eluent: chloroform/ethyl acetate/acetonitrile=7/2/1) to obtain 9.22 g (26.3 mmol) of the title compound as pale yellowish oily product.

$^1$H-NMR (CDCl$_3$) δ; 6.62 (s, 1H), 5.00–4.80 (m, 1H), 4.68–4.41 (m, 1H), 4.22–4.14 (m, 2H), 3.72 (s, 2H), 3.47–3.20 (m, 1H), 2.49 (d, J=16.1 Hz, 1H), 2.32–2.14 (m, 1H), 2.13–2.00 (m, 1H), 1.91–1.83 (m, 1H), 1.73–1.58 (m, 1H), 1.41 (s, 9H), 1.30–1.25 (m, 3H).

CI-MS (m/z); 296

Example II-24

(+)-Ethyl 4,6-ethano-4,5,6,7-tetrahydrothieno[3,2-c]pyridin-2-acetate.hydrochloride and (−)-ethyl 4,6-ethano-4,5,6,7-tetrahydrothieno[3,2-c]pyridin-2-acetate.hydrochloride (24-1) To 40 ml of a methylene chloride solution containing 6.81 g (19.5 mmol) of ethyl 5-t-butoxycarbonyl-4, 6-ethano-4,5,6,7-tetrahydrothieno[3,2-c]pyridin-2-acetate 270 was added under ice-cooling 17 ml of trifluoroacetic acid, and then, the mixture was stirred at room temperature for one hour.

The resulting reaction mixture was concentrated under reduced pressure, and 50 ml of methylene chloride and 2.90 g (28.7 mmol) of triethylamine were added to the residue. Moreover, 3.23 g (19.4 mmol) of (s)-(+)-α-methoxyphenylacetic acid, 0.366 g (3.00 mmol) of 4-dimethylaminopyridine and 11.0 g (21.1 mol) of PyBOP were added to the mixture and the resulting mixture was stirred at room temperature for 3.5 hours.

The resulting reaction mixture was concentrated under reduced pressure, and a 5% aqueous potassium hydrogen sulfate A solution was added to the residue and the mixture was extracted with ethyl acetate. The organic layer was washed successively with a saturated aqueous sodium bicarbonate solution and a saturated aqueous saline solution, and dried over sodium sulfate. The organic layer was concentrated under reduced pressure and the residue was separated and purified by the silica gel column chromatography method (eluent: n-hexanel ethyl acetate=6/1) to obtain 2.60 g (6.51 mmol) of ethyl 5-[(2S)-α-methoxyphenylacetyl]-(−)-4,6-ethano-4,5,6,7-tetrahydrothieno[3,2-c]pyridin-2-acetate as pale yellowish oily product and 1.93 g (4.83 mmol) of ethyl 5-[(2S)-α-methoxyphenylacetyl]-(+)-4,6-ethano-4,5,6,7-tetrahydrothieno[3,2-c]pyridin-2-acetate as yellowish oily product.

Ethyl 5-[(2S)-α-methoxyphenylacetyl]-(−)-4,6-ethano-4,5,6,7-tetrahydrothieno[3,2-c]pyridin-2-acetate $^1$H-NMR (CDCl$_3$) δ; 7.46–7.14 (m, 5H), 6.63, 6.11 (each s, total 1H), 5.53–4.61 (m, 3H), 4.21–4.14 (m, 2H), 3.71, 3.60 (each s, total 2H), 3.49, 3.46 (each s, total 3H), 2.99–2.89 (m, 1H), 2.56–2.41 (m, 1H), 2.19–1.43 (m, 4H), 1.33–1.26 (m, 3H).

CI-MS (m/z); 400

Ethyl 5-[(2S)-α-methoxyphenylacetyl]-(+)-4,6-ethano-4,5,6,7-tetrahydrothieno[3,2-c]pyridin-2-acetate $^1$H-NMR (CDCl$_3$) δ; 7.48–7.19 (m, 5H), 6.63, 6.34 (each s, total 1H), 5.46–4.40 (m, 3H), 4.21–4.15 (m, 2H), 3.70, 3.65 (each s, total 2H), 3.49–3.20 (m, 3H), 2.97–1.41 (m, 6H), 1.32–1.26 (m, 3H).

CI-MS (m/z); 400

(24-2) To 0.82 (2.1 mmol) of ethyl 5-[(2S)-α-methoxyphenylacetyl]-(−)-4,6-ethano-4,5,6,7-tetrahydrothieno[3,2-c]pyridine were added 4 ml of water, 4 ml of acetic acid and 0.7 ml of conc. Hydrochloric acid, and the mixture was refluxed for 25 hours.

The resulting reaction mixture was concentrated under reduced pressure, an aqueous sodium hydroxide solution was added to the residue to adjust the pH to 9 to 10, and then, 8 ml of 1,4-dioxane and 0.5 ml (2.2 mmol) of di-t-butyl dicarbonate were added to the mixture and the resulting mixture was stirred at room temperature for 5 hours.

The resulting reaction mixture was concentrated under reduced pressure, a 5% aqueous potassium hydrogen sulfate solution was added to the residue and the resulting mixture was extracted with ethyl acetate. The separated organic layer was washed with a saturated aqueous saline solution and dried over anhydrous sodium sulfate. The organic layer was concentrated under reduced pressure, and the residue was purified by the silica gel column chromatography method (eluent: chloroform/ethyl acetate=9/1) to obtain 0.68 g (2.1 mmol) of (−)-5-t-butoxycarbonyl-4,6-ethano-4,5,6,7-tetrahydrothieno[3,2-c]pyridin-2-acetic acid as yellowish oily product.

$^1$H-NMR (CDCl$_3$) δ; 6.63 (s, 1H), 4.99–4.44 (m, 2H), 3.76 (s, 2H), 3.51–3.24 (m, 1H), 2.49 (d, J=16.1 Hz, 1H), 2.29–1.99 (m, 2H), 1.91–1.81 (m, 1H), 1.72–1.59 (m, 1H) 1.40 (brs, 9H).

CI-MS (m/z); 268

(24-3) To 0.68 g (2.1 mmol) of (−)-5-t-butoxycarbonyl-4,6-ethano-4,5,6,7-tetrahydrothieno[3,2-c]pyridin-2-acetic acid was added 7 ml of ethanol, and under ice-cooling, 0.23 ml (3.2 mmol) of acetyl chloride was added to the mixture and the resulting mixture was refluxed for 1.5 hours.

The resulting reaction mixture was concentrated under reduced pressure, and after adding chloroform to the residue, diethyl ether was added to the resulting mixture and formed solid was collected by filtration. The resulting solid was dried under reduced pressure to obtain 0.20 g (0.70 mmol) of ethyl (−)-4,6-ethano-4,5,6,7-tetrahydrothieno[3,2-c]pyridin-2-acetate.HCl as pale brownish powder.

$^1$H-NMR (DMSO-d$_6$) δ; 6.80 (s, 1H), 4.83–4.79 (m, 1H), 4.39–4.28 (m, 1H), 4.09 (q, J=7.3 Hz, 2H), 3.95–3.78 (m, 2H), 3.30–3.24 (m, 1H), 2.85 (d, J=17.6 Hz, 1H), 2.29–1.71 (m, 4H), 1.27–1.18 (m, 3H).

CI-MS (m/z); 252

$[α]_D^{22}$; −36.0° (CHCl$_3$, c=0.200)

(24-4) In the same manner as in Example II-(24-2) except for using 1.93 g (4.83 mmol) of ethyl 5-[(2S)-α-methoxyphenylacetyl]-(+)-4,6-ethano-4,5,6,7-tetrahydrothieno[3,2-c]pyridin-2-acetate in place of ethyl 5-[(2S)-α-methoxyphenylacetyl]-(−)-4,6-ethano-4,5,6,7-tetrahydrothieno[3,2-c]pyridin-2-acetate, the similar reaction was carried out to obtain 1.10 g (3.40 mmol) of (+)-5-t-butoxycarbonyl-4,6-ethano-4,5,6,7-tetrahydrothieno[3,2-c]pyridin-2-acetic acid as yellowish oily product.

$^1$H-NMR (CDCl$_3$) δ; 6.64 (s, 1H), 4.99–4.45 (m, 2H), 3.77 (s, 2H), 3.50–3.22 (m, 1H), 2.49 (d, J=16.1 Hz, 1H), 2.31–1.99 (m, 2H), 1.94–1.81 (m, 1H), 1.73–1.59 (m, 1H), 1.40 (brs, 9H).

CI-MS (m/z); 268

(24-5) In the same manner as in Example II-(24-3) except for using 1.10 g (3.40 mmol) of (+)-5-t-butoxycarbonyl-4,6-ethano-4,5,6,7-tetrahydrothieno[3,2-c]pyridin-2-acetic acid in place of (−)-5-t-butoxycarbonyl-4,6-ethano-4,5,6,7-tetrahydrothieno[3,2-c]pyridin-2-acetic acid, the similar reaction was carried out to obtain 0.46 g (1.6 mmol) of ethyl (+)-4,6-ethano-4,5,6,7-tetrahydrothieno[3,2-c]pyridin-2-acetate.HCl as yellowish powder.

$^1$H-NMR (DMSO-d$_6$) δ; 6.80 (s, 1H), 4.83–4.79 (m, 1H), 4.41–4.29 (m, 1H), 4.15–4.04 (m, 1H), 3.86 (s, 2H), 3.29–3.21 (m, 1H), 2.85 (d, J=16.9 Hz, 1H), 2.29–1.71 (m, 4H), 1.24–1.19 (m, 3H).

CI-MS (m/z); 252

$[α]_D^{21}$; +35.0° (CHCl$_3$, c=0.200)

Example II-25

Ethyl 5-triphenylmethyl-4,5,6,7-tetrahydropyrazolo[4,3-c]pyridin-2-acetate and ethyl 5-triphenylmethyl-4,5,6,7-tetrahydropyrazolo[4,5-c]pyridin-1-acetate In 2 ml of ethanol was dissolved 1.55 g (22.8 mmol) of sodium ethoxide and 40 ml of diethyl ether was added to the solution. To the solution was added dropwise a mixed solution of 30 ml of a toluene solution containing 7.40 g (21.7 mmol) of 1-triphenylmethyl-4-pyeridone and 1.61 g (21.7 mmol) of ethyl formate at room temperature and the resulting mixture was stirred for 4 hours.

The resulting reaction mixture was concentrated under reduced pressure. The residue was dissolved in 150 ml of ethanol, 3.52 g (22.8 mmol) of ethyl hydrazinoacetate.HCl was added to the solution and the mixture was stirred at room temperature for 10 hours.

The resulting reaction mixture was concentrated under reduced pressure, 50 ml of a saturated sodium bicarbonate solution was added to the residue and the mixture was extracted with ethyl acetate. The organic layer was washed with a saturated aqueous saline solution and dried over anhydrous sodium sulfate. The organic layer was concentrated under reduced pressure and the residue was purified by the silica gel column chromatography method (eluent: hexane/ethyl acetate=7/3) to obtain 6.86 g (15.2 mmol) of a mixture of ethyl 5-triphenylmethyl-4,5,6,7-tetrahydropyrazolo[4,3-c]pyridin-2-acetate and ethyl 5-triphenylmethyl-4,5,6,7-tetrahydropyrazolo[4,5-c]pyridin-1-acetate as pale yellowish foamy product.

$^1$H-NMR (CDCl$_3$) δ; 7.55–7.07 (m, 16H), 4.80, 4.79 (each s, total 2H), 4.26–4.18 (m, 2H), 3.33 (brs, 2H), 2.95–2.85, 2.80–2.70 (each m, total 2H), 2.65–2.45 (m, 2H), 1.32–1.23 (m, 3H).

FAB-MS (m/z); 452

Example II-26
Ethyl 4,5,6,7-tetrahydropyrazolo[4,3-c]pyridin-2-acetate.p-toluenesulfonate (26-1) To 5.00 g (11.1 mmol) of ethyl 5-triphenylmethyl-4,5,6,7-tetrahydropyrazolo[4,3-c]pyridin-2-acetate (including ethyl 5-triphenylmethyl-4,5,6,7-tetrahydropyrazolo[4,5-c]pyridin-1-acetate as an isomer) were added 50 ml of tetrahydrofuran and 2.12 g (11.1 mmol) of TsOH.H$_2$O and the resulting mixture was stirred at 60° C. for 5 hours.

After cooling the resulting mixture by allowing to stand, the precipitated crystals were filtered, washed with tetrahydrofuran, and dried to obtain 3.74g (9.82 mmol) of ethyl 4,5,6,7-tetrahydropyrazolo[4,3-c]pyridin-2-acetate.TsOH (including ethyl 4,5,6,7-tetrahydropyrazolo[4,5-c]pyridin-1-acetate.TsOH as an isomer) as white crystals.

$^1$H-NMR (CD$_3$OD) δ; 7.69 (d, J=8.06 Hz, 2H), 7.62, 7.45 (each s, total 1H), 7.23 (d, J=8.06 Hz, 2H), 4.97, 4.96 (each s, total 2H), 4.28–4.17 (m, 4H), 3.53 (t, J=6.2 Hz, 2H), 3.01 (t, J=6.2 Hz, 2H), 2.36 (s, 3H), 1.29–1.24 (m, 3H)

CI-MS (m/z); 210

(26-2) In 30 ml of isopropanol was dissolved under heating 1.96 g of ethyl 4,5,6,7-tetrahydropyrazolo[4,3-c]pyridin-2-acetate.TsOH containing ethyl 4,5,6,7-tetrahydropyrazolo[4,5-c]pyridin-2-acetate.TsOH (20%).

The resulting reaction mixture was cooled by allowing to stand, precipitated solid was filtered, washed with isopropanol and dried. Thus, 1.35 g of ethyl 4,5,6,7-tetrahydropyrazolo[4,5-c]pyridin-2-acetate.TsOH was obtained as colorless needle crystals. The filtrate was concentrated and recrystallized from acetone to obtain 0.44 g of white solid with a mixing ratio of ethyl 4,5,6,7-tetrahydropyrazolo[4,5-c]pyridin-2-acetate.TsOH and ethyl 4,5,6,7-tetrahydropyrazolo[4,3-c]pyridin-2-acetate.TsOH being (1:1).
Ethyl 4,5,6,7-tetrahydropyrazolo[4,3-c]pyridin-2-acetate.TsOH Melting point; 163–164° C.

$^1$H-NMR (CD$_3$OD) δ; 7.69 (d, J=8.06 Hz, 2H), 7.62 (s, 1H), 7.23 (d, J=8.06 Hz, 2H), 4.97 (s, 2H), 4.28 (s, 2H), 4.21 (d, J=7.3 Hz, 2H), 3.53 (d, J=6.2 Hz, 2H), 3.00 (d, J=6.2 Hz, 2H), 2.36 (s, 3H), 1.27 (t, J=7.3 Hz, 3H).

Solid of ethyl 4,5,6,7-tetrahydropyrazolo[4,5-c]pyridin-1-acetate.TsOH/ethyl 4,5,6,7-tetrahydropyrazolo[4,3-c]pyridin-2-acetate,TsOH=1/1

$^1$H-NMR (CD$_3$OD) δ; 7.69 (d, J=8.06 Hz, 2H), 7.62, 7.45 (each s, total 1H), 7.23 (d, J=8.06 Hz, 2H), 4.97, 4.96 (each s, total 2H), 4.28–4.17 (m, 4H), 3.53 (t, J=6.2 Hz, 2H), 3.01 (t, J=6.2 Hz, 2H), 2.36 (s, 3H), 1.29–1.24 (m, 3H).

Example II-27
Ethyl 5-t-butoxycarbonyl-4,5,6,7-tetrahydropyrazolo[4,3-c]pyridin-2-acetate To 70 ml of ethanol solution containing 14.3 g (0.210 mol) of sodium ethoxide was added dropwise under ice-cooling 100 ml of an ethanol solution containing 20.1 g (0.101 mol) of N-t-butoxycarbonyl-4-piperidone and 9.82 g (0.130 mol) of ethyl formate over 20 minutes. After completion of dropwise addition, the mixture was stirred at room temperature for 10 hours, and allowed to stand at room temperature overnight. This mixture was cooled to −70° C., and 19.9 g (0.125 mol) of ethyl hydrazinoacetate.HCl was added to the mixture and the resulting mixture was stirred for 40 minutes. Cooling was stopped and and the temperature of the mixture was returned to room temperature over 2.5 hours while stirring.

To the resulting reaction mixture was added ethyl acetate, and insolubles were removed by filtration. The organic layer was washed successively with a 5% aqueous potassium hydrogen sulfate solution, a saturated aqueous sodium bicarbonate solution and a saturated aqueous saline solution, and dried over anhydrous sodium sulfate. The organic layer was concentrated under reduced pressure and the residue was treated by the silica gel column chromatography method (eluent: n-hexane/ethyl acetate=3/2) to obtain 18.7 g of a mixture of ethyl 5-t-butoxycarbonyl-4,5,6,7-tetrahydropyrazolo[4,3-c]pyridin-2-acetate and ethyl 5-t-butoxycarbonyl-4,5,6,7-tetrahydropyrazolo[4,5-c]pyridin-1-acetate as yellowish liquid.

To the above-mentioned mixture was added isopropyl ether, the precipitated solid was collected by filtration, washed with isopropyl ether and dried to obtain 15.5 g (50.2 mmol) of ethyl 5-t-butoxycarbonyl-4,5,6,7-tetrahydropyrazolo[4,3-c]pyridin-2-acetate as white solid.

Melting point; 90–91° C.

$^1$H-NMR (CDCl$_3$) δ; 7.22 (s, 1H), 4.83 (s, 2H), 4.49 (s, 2H), 4.23 (q, J=7.3 Hz, 2H), 3.70 (t, J=5.4 Hz, 2H), 2.76 (t, J=5.4 Hz, 2H), 1.48 (s, 9H), 1.27 (t, J=7.3 Hz, 3H).

CI-MS (m/z); 310

Example II-28
Ethyl 4,5,6,7-tetrahydropyrazolo[4,5-c]pyridin-1-acetate.dihydrochloride (28-1) In 500 ml of ethanol was dissolved 141.2 g (0.457 mol) of a mixture of ethyl 5-t-butoxycarbonyl-4,5,6,7-tetrahydropyrazolo[4,3-c]pyridin-2-acetate and ethyl 5-t-butoxycarbonyl-4,5,6,7-tetrahydropyrazolo[4,5-c]pyridin-1-acetate, and 20.1 g (0.503 mol) of sodium hydroxide and 500 ml of water were added to the solution, and the mixture was stirred at room temperature for 2 hours.

To the resulting reaction mixture was added a 5% aqueous potassium hydrogen sulfate solution, the pH of the mixture was adjusted to 3 and the mixture was extracted with ethyl acetate, and the extract was dried over anhydrous sodium sulfate. The organic layer was concentrated under reduced pressure, isopropanol was added to the residue and the precipitated solid was collected by filtration. After washing the solid with isopropyl ether, it was dried to obtain 73.48 g (0.261 mol) of a mixture of 5-t-butoxycarbonyl-4,5,6,7-tetrahydropyrazolo[4,3-c]pyridin-2-acetic acid and 5-t-butoxycarbonyl-4,5,6,7-tetrahydropyrazolo[4,5-c]pyridin-1-acetic acid as white powder.

$^1$H-NMR (CDCl$_3$) δ; 8.35 (brs, 1H), 7.38, 7.21 (each s, total 1H), 4.91, 4.88 (each s, total 2H), 4.47, 4.43 (each s, total 2H), 3.80–3.60 (m, 2H), 2.77, 2.65 (each t, J=5.4 Hz, total 2H), 1.47 (s, 9H).

CI-MS (m/z); 282

(28-2) In 50 ml of methylene chloride was dissolved 5.00 g (17.8 mmol) of a mixture of 5-t-butoxycarbonyl-4,5,6,7-tetrahydropyrazolo[4,3-c]pyridin-2-acetic acid and 5-t-butoxycarbonyl-4,5,6,7-tetrahydropyrazolo[4,5-c]pyridin- 1-acetic acid, 1.98 g (26.7 mmol) of t-butanol and 1.09 g (8.93 mmol) of 4-dimethylaminopyridine were added to the solution, and under ice-cooling, 5.12 g (26.7 mmol) of EDC was added to the mixture and the resulting mixture was stirred at the same temperature for 2 hours and allowed to stand at room temperature overnight.

The resulting reaction mixture was concentrated under reduced pressure, ethyl acetate was added to the residue and the mixture was washed successively with a 5% citric acid solution, a saturated aqueous sodium bicarbonate solution and a saturated aqueous saline solution, and dried over anhydrous sodium sulfate. The organic layer was concentrated under reduced pressure, and the residue was purified by the silica gel column chromatography method (eluent: n-hexane/ethyl acetate=3/1) and recrystallized from a mixed solution of ethyl acetate and isopropyl ether to obtain 2.06 g (6.1 mmol) of (t-butyl) 5-t-butoxycarbonyl-4,5,6,7-tetrahydropyrazolo[4,5-c]pyridin-1-acetate as white crystal.

Melting point; 126–127° C.

$^1$H-NMR (CD$_3$OD) δ; 7.34 (s, 1H), 4.70 (s, 2H), 3.72 (t, J=5.4 Hz, 2H), 2.62 (t, J=5.4 Hz, 2H), 1.48 (s, 9H), 1.46 (s, 9H).

(28-3) In 20 ml of ethanol was dissolved 1.01 g (3.00 mmol) of (t-butyl) 5-t-butoxycarbonyl-4,5,6,7-tetrahydropyrazolo[4,5-c]pyridin-1-acetate, and under ice-cooling, 0.39 g (3.30 mmol) of thionyl chloride was added to the solution and the resulting mixture was stirred at 80° C. for 3 hours. The reaction mixture was concentrated under reduced pressure, the residue was washed with ethyl acetate and dried to obtain 0.90 g (3.00 mmol) of the title compound as pale yellowish powder.

$^1$H-NMR (CD$_3$OD) δ; 7.57 (s, 1H), 5.03 (s, 2H), 4.28 (s, 2H), 4.24 (q, J=7.3 Hz, 2H), 3.57 (t, J=6.6 Hz), 3.06 (t, J=6.6 Hz), 1.29 (t, J=7.3 Hz, 3H).

Example II-29

Ethyl 3-hydroxy-4,5,6,7-tetrahydropyrazolo[4,3-c]pyridin-2-acetate.trifluoroacetate (29-1) To 20 ml of an ethanol solution containing 0.71 g (11 mmol) of sodium ethoxide were added under ice-cooling 1.86 g (12.0 mmol) of ethyl hydrazinoacetate.HCl and 2.57 g (10.0 mmol) of 1-t-butoxycarbonyl-4-hydroxy-3-methoxycarbonyl-1,2,5,6-tetrahydropyridine, and the mixture was stirred at room temperature for 8 hours.

The resulting reaction mixture was concentrated under reduced pressure, 20 ml of a saturated aqueous sodium bicarbonate solution was added to the residue and the mixture was extracted with ethyl acetate. The organic layer was washed with a saturated aqueous saline solution, and dried over anhydrous magnesium sulfate. The organic layer was concentrated under reduced pressure and the residue was purified by the silica gel column chromatography method (eluent: ethyl acetate/ethanol=19/1) to obtain 2.73 g (8.40 mmol) of ethyl 5-t-butoxycarbonyl-3-hydroxy-4,5,6,7-tetrahydropyrazolo[4,3-c]pyridin-2-acetate as white foamy product.

$^1$H-NMR (DMSO-d$_6$) δ; 10.80 (brs, 1H), 4.57 (brs, 2H), 4.16 (brs, 2H), 4.12 (q, J=7.3 Hz, 2H), 3.53 (t, J=5.9 Hz, 2H), 2.45 (t, J=5.9 Hz, 2H), 1.42 (s, 9H), 1.20 (t, J=7.3 Hz, 3H).

CI-MS (m/z); 326

(29-2) In 50 ml of methylene chloride was dissolved 2.73 g (8.40 mmol) of ethyl 5-t-butoxycarbonyl-3-hydroxy-4,5,6,7-tetrahydropyrazolo[4,3-c]pyridin-2-acetate, and under ice-cooling, 10 ml of CF$_3$CO$_2$H was added to the solution and the mixture was stirred at room temperature for 2 hours.

The reaction mixture was concentrated under reduced pressure to obtain the title compound as brownish oily product.

Example II-30

Ethyl 3-methoxy-4,5,6,7-tetrahydropyrazolo[4,3-c]pyridin-2-acetate.trifluoroacetate (30-1) To 10 ml of DMF was dissolved 1.00 g (3.10 mmol) of ethyl 5-t-butoxycarbonyl-3-hydroxy-4,5,6,7-tetrahydropyrazolo[4,3-c]pyridin-2-acetate and 0.25 g (3.7 mmol) of sodium ethoxide was to the solution. At room temperature, 0.47 g (3.7 mmol) of dimethyl sulfate was added to the mixture, and the mixture was stirred for 2 hours.

The resulting reaction mixture was concentrated under reduced pressure, 10 ml of a saturated aqueous ammonium chloride solution was added to the residue and the mixture was extracted with ethyl acetate. The organic layer was washed with a saturated aqueous saline solution, and dried over anhydrous magnesium sulfate. The organic layer was concentrated under reduced pressure and the residue was purified by the silica gel column chromatography method (eluent: hexane/ethyl acetate=1/1) to obtain 0.22 g (0.65 mmol) of ethyl 5-t-butoxycarbonyl-3-methoxy-4,5,6,7-tetrahydropyrazolo[4,3-c]pyridin-2-acetate as pale yellowish oily product.

$^1$H-NMR (CDCl$_3$) δ; 4.68 (s, 2H), 4.58 (s, 2H), 4.22 (q, J=1.3 Hz, 2H), 3.97 (s, 3H), 3.66 (t, J=5.9 Hz, 2H), 2.69 (t, J=5.9 Hz, 2H), 1.48 (s, 9H), 1.28 (t, J=7.3 Hz, 3H).

CI-MS (m/z); 340

(30-2) In 50 ml of methylene chloride was dissolved 2.73 g (8.40 mmol) of ethyl 5-t-butoxycarbonyl-3-methoxy-4,5,6,7-tetrahydropyrazolo[4,3-c]pyridin-2-acetate, and under ice-cooling, 10 ml of CF$_3$CO$_2$H was added to the solution and the mixture was stirred at room temperature for 2 hours.

The reaction mixture was concentrated under reduced pressure to obtain the title compound as brownish oily product.

Example II-31

Ethyl 4,6-ethano-4,5,6,7-tetrahydropyrazolo[4,3-c]pyridin-2-acetate.HCl and ethyl 4,6-ethano-4,5,6,7-tetrahydropyrazolo[4,5-c]pyridin-1-acetate.hydrochloride (31-1) In the same manner as in Example II-25 except for using 4.37 g (22.2 mmol) of N-ethoxycarbonyl-4-tropinone in place of 1-triphenylmethyl-4-piperidone, the reaction was similarly carried out to obtain 6.01 g (19.6 mmol) of a mixture of ethyl 5-ethoxycarbonyl-4,6-ethano-4,5,6,7-tetrahydropyrazolo[4,3-c]pyridin-2-acetate and ethyl 5-ethoxycarbonyl-4,6-ethano-4,5,6,7-tetrahydropyrazolo[4,5-c]pyridin-1-acetate as yellowish oily product.

$^1$H-NMR (CDCl$_3$) δ; 7.34, 7.20 (each s, total 1H), 5.15–4.51 (m, 4H), 4.30–4.00 (m, 4H), 2.60–1.55 (m, 6H), 1.21–1.23 (m, 6H).

CI-MS (m/z); 308

(31-2) To 6.01 g (19.6 mmol) of a mixture of ethyl 5-ethoxycarbonyl-4,6-ethano-4,5,6,7-tetrahydropyrazolo[4,3-c]pyridin-2-acetate and ethyl 5-ethoxycarbonyl-4,6-ethano-4,5,6,7-tetrahydropyrazolo[4,5-c]pyridin-1-acetate were added 40 ml of water and 3.87 g (59.4 mmol) of potassium hydroxide (85%) and the mixture was heated at 100–110° C. for 10 hours.

To the resulting reaction mixture was added 40 ml of 1,4-dioxane, and under ice-cooling, 6.40 g (29.4 mmol) of di-t-butyl dicarbonate was added dropwise to the mixture. The resulting mixture was stirred at the same temperature for 30 minutes, and further stirred at room temperature for 5 hours, and then, allowed to stand at room temperature overnight.

To the resulting reaction mixture was added a 20% aqueous potassium hydrogen sulfate solution and the pH of the mixture was adjusted to 7, and under reduced pressure, the organic solvent was removed by evaporation and the aqueous layer was washed with diethyl ether. To the separated aqueous layer was added ethyl acetate, and the pH of the mixture was adjusted to 2 with a 20% aqueous potassium hydrogen sulfate solution. The organic layer was washed successively with water and a saturated aqueous saline solution, and dried over anhydrous sodium sulfate. The organic layer was concentrated under reduced pressure to obtain 6.32 g (20.6 mmol) of a mixture of 5-t-butoxycarbonyl-4,6-ethano-4,5,6,7-tetrahydropyrazolo[4,3-c]pyridin-2-acetic acid and 5-t-butoxycarbonyl-4,6-ethano-4,5,6,7-tetrahydropyrazolo[4,5-c]pyridin-1-acetic acid as orange foamy product.

$^1$H-NMR (CDCl$_3$) δ; 8.40 (brs, 1H), 7.36, 7.19 (each s, total 1H), 5.15–4.45 (m, 4H), 2.60–1.55 (m, 6H), 1.42, 1.40 (each s, 9H).

CI-MS (m/z); 308

(31-3) In the same manner as in Example II-23 except for using 6.32 g (20.6 mmol) of a mixture of 5-t-butoxycarbonyl-4,6-ethano-4,5,6,7-tetrahydropyrazolo[4,3-c]pyridin-2-acetic acid and 5-t-butoxycarbonyl-4,6-ethano-4,5,6,7-tetrahydropyrazolo[4,5-c]pyridin-1-acetic acid in place of 5-t-butoxycarbonyl-4,6-ethano-4,5,6,7-tetrahydrothieno[3,2-c]pyridin-2-acetic acid, the reaction was carried out similarly to obtain 0.98 g (2.9 mmol) of a mixture of ethyl 5-t-butoxycarbonyl-4,6-ethano-4,5,6,7-tetrahydropyrazolo[4,3-c]pyridin-2-acetate and ethyl 5-t-butoxycarbonyl-4,6-ethano-4,5,6,7-tetrahydropyrazolo[4,5-c]pyridin-1-acetate as pale yellowish oily product.

$^1$H-NMR (CDCl$_3$) δ; 7.34, 7.19 (each s, total 1H), 5.12–4.45 (m, 4H), 4.26–4.05 (m, 2H), 2.60–1.53 (m, 6H), 1.47–1.24 (m, 12H).

CI-MS (m/z); 336

(31-4) In 15 ml of methylene chloride was dissolved 0.98 g (2.9 mmol) of a mixture of ethyl 5-t-butoxycarbonyl-4,6-ethano-4,5,6,7-tetrahydropyrazolo[4,3-c]pyridin-2-acetate and ethyl 5-t-butoxycarbonyl-4,6-ethano-4,5,6,7-tetrahydropyrazolo[4,5-c]pyridin-1-acetate, and under ice-cooling, 7.5 ml of CF$_3$CO$_2$H was added to the solution and the resulting mixture was stirred at room temperature for 4 hours.

The resulting reaction mixture was concentrated under reduced pressure, 25 ml of methylene chloride and 0.61 g (6.0 mmol) of triethylamine were added to the residue, and then, 0.52 g (3.1 mmol) of α-methoxyphenylacetic acid, 0.12 g (1.0 mmol) of 4-dimethylaminopyridine and 2.22 g (4.27 mmol) of PyBOP were added to the solution, and the resulting mixture was stirred at room temperature for 3 hours.

The resulting reaction mixture was concentrated under reduced pressure, a 5% aqueous potassium hydrogen sulfate solution was added to the residue and the mixture was extracted with ethyl acetate. The organic layer was washed successively with a saturated aqueous bicarbonate solution and a satutrated aqueous saline solution, and dried over anhydrous sodium sulfate. The organic layer was concentrated under reduced pressure and the residue was purified by the silica gel column chromatography method (elunent: n-hexane/acetone=4/1–7/3) to obtain 0.40 g (1.0 mmol) of ethyl 5-(α-methoxyphenylacetyl)-4,6-ethano-4,5,6,7-tetrahydropyrazolo[4,3-c]pyridin-2-acetate and 0.30 g (0.78 mmol) of ethyl 5-(α-methoxyphenylacetyl)-4,6-ethano-4,5,6,7-tetrahydropyrazolo[4,5-c]pyridin-1-acetate as pale yellowish oily product, respectively.

Ethyl 5-(α-methoxyphenylacetyl)-4,6-ethano-4,5,6,7-tetrahydropyrazolo[4,3-c]pyridin-2-acetate $^1$H-NMR (CDCl$_3$) δ; 7.42–7.23 (m, 5H), 7.12, 6.93 (each s, total 1H), 5.19–4.45 (m, 5H), 4.24–4.15 (m, 2H), 3.43, 3.25 (each s, total 3H), 2.43–1.43 (m, 6H), 1.29–1.23 (m, 3H).

CI-MS (m/z); 384

Ethyl 5-(α-methoxyphenylacetyl)-4,6-ethano-4,5,6,7-tetrahydropyrazolo[4,5-c]pyridin-1-acetate $^1$H-NMR (CDCl$_3$) δ; 7.45–7.20 (m, 6H), 5.19–4.60 (m, 5H), 4.24–4.15 (m, 2H), 3.46, 3.26 (each s, total 3H), 2.60–1.43 (m, 6H), 1.30–1.25 (m, 3H).

CI-MS (m/z); 384

(31-5) To 0.40 g (1.0 mmol) of ethyl 5-(α-methoxyphenylacetyl)-4,6-ethano-4,5,6,7-tetrahydropyrazolo[4,3-c]pyridin-2-acetate were added 2 ml of water, 2 ml of acetic anhydride and 0.4 ml of conc.hydrochloric acid, and the mixture was reluxed for 30 hours.

The resulting reaction mixture was concentrated under reduced pressure, an aqueous sodium hydroxide solution was added to the residue and the pH of the mixture was adjusted to pH 9–10. To the mixture were added 5 ml of 1,4-dioxane and 0.48 ml (2.2 mmol) of di-t-butyl dicarbonate, and the mixture was stirred at room temperature for 5 hours.

To the resulting reaction mixture was added a 5% aqueous potassium hydrogen sulfate solution, the pH of the mixture was adjusted to 2 and the mixture was extracted with ethyl ether. The organic layer was washed with a saturated aqueous saline solution, and dried over anhydrous sodium sulfate. The organic layer was concentrated under reduced pressure to obtain a crude product of 5-t-butoxycarbonyl-4,6-ethano-4,5,6,7-tetrahydropyrazolo[4,3-c]pyridin-2-acetic acid as yellowish oily product.

(31-6) To 5-t-butoxycarbonyl-4,6-ethano-4,5,6,7-tetrahydropyrazolo[4,3-c]pyridin-2-acetic acid was added 7 ml of ethanol, and under ice-cooling, 0.3 ml of acetyl chloride was added to the mixture and the resulting mixture was refluxed for 3 hours.

The resulting reaction mixture was concentrated under reduced pressure, ethyl acetate was added to the residue and the precipitated solid was collected by filtration to obtain 0.14 g (0.52 mmol) of ethyl 4,6-ethano-4,5,6,7-tetrahydropyrazolo[4,3-c]pyridin-2-acetate.HCl as brownish powder.

$^1$H-NMR (CD$_3$OD) δ; 7.50 (s, 1H), 4.95–4.47 (m, 4H), 4.30–4.18 (m, 2H), 3.37–1.80 (m, 6H), 1.31–1.24 (m, 3H).

CI-MS (m/z); 236

(31-7) In the same manner as in Example II-(31-5) except for using 0.40 g (1.0 mmol) of ethyl 5-(α-methoxyphenylacetyl)-4,6-ethano-4,5,6,7-tetrahydropyrazolo[4,5-c]pyridin-1-acetate in place of ethyl 5-(α-methoxyphenylacetyl)-4,6-ethano-4,5,6,7-tetrahydropyrazolo[4,3-c]pyridin-2-acetate, the reaction was carried our similarly to obtain a crude product of 5-t-butoxycarbonyl-4,6-ethano-4,5,6,7-tetrahydropyrazolo[4,5-c]pyridin-1-acetic acid as yellowish oily product.

(31-8) In the same manner as in Example II-(31-6) except for using 5-t-butoxycarbonyl-4,6-ethano-4,5,6,7-tetrahydropyrazolo[4,5-c]pyridin-1-acetic acid in place of using 5-t-butoxycarbonyl-4,6-rethano-4,5,6,7-tetrahydropyrazolo[4,3-c]pyridin-2-acetic acid, the reaction was carried out similarly to obtain 0.095 g (0.35 mmol) of the title compound as brownish powder.

$^1$H-NMR (CD$_3$OD) δ; 7.61 (s, 1H), 4.90–4.47 (m, 4H), 4.30–4.18 (m, 2H), 3.37–1.80 (m, 6H), 1.31–1.24 (m, 3H).

Example II-32

Ethyl 4,5,6,7-tetrahydrothiazolo[5,4-c]pyridin-2-acetate.trifluoroacetate (32-1) In 250 ml of chloroform and 250 ml of ethyl acetate was dissolved 34.2 g (0.200 mol) of 1-ethoxycarbonyl-4-piperidone, and 89.3 g (0.400 mol) of copper (II) bromide was added to the solution at room temperature and the resulting mixture was stirred at 60° C. for 3 hours.

The resulting reaction mixture was cooled to room temperature, and then, insolubles were removed by filtration and the filtrate was washed successively with water, a saturated aqueous sodium bicarbonate solution and a saturated aqueous saline solution, and dried over anhydrous sodium sulfate. The organic layer was concentrated under reduced pressure and the residue was purified by the silica gel column chromatography method (eluent: hexane/ethyl acetate=7/3) to obtain 43.1 g (0.170 mol) of 3-bromo-1-ethoxycarbonyl-4-piperidone as colorless oily product.

CI-MS (m/z); 250

(32-2) In 100 ml of DMF were dissolved 43.1 g (0.17 mol) of 3-bromo-1-ethoxycarbonyl-4-piperidone and 20.0 g (0.26 mol) of thioacetamide, and the mixture was stirred at 100° C. for 1.5 hours.

The resulting reaction mixture was concentrated under reduced pressure, a saturated aqueous sodium bicarbonate solution was added to the residue and the mixture was extracted with toluene. The organic layer was washed with a saturated aqueous saline solution, and dried over anhydrous sodium sulfate. The organic layer was concentrated under reduced pressure and the residue was purified by the silica gel column chromatography method (eluent: hexane/ethyl acetate=7/3) to obtain 27.0 g (0.12 mol) of 6-ethoxycarbonyl-2-methyl- 4,5,6,7-tetrahydrothiazolo[5,4-c]pyridine as yellowish oily product.

$^1$H-NMR (CDCl$_3$) δ; 4.63 (s, 2H), 4.19 (q, J=7.3 Hz, 2H), 3.78 (t, J=5.1 Hz, 2H), 2.86 (t, J=5.1 Hz, 2H), 2.67 (s, 3H), 1.29 (t, J=7.3 Hz, 3H).

CI-MS (m/z); 227

(32-3) To 27.0 g (0.12 mol) of 6-ethoxycarbonyl-2-methyl-4,5,6,7-tetrahydrothiazolo[5,4-c]pyridine were added 400 ml of a 1N aqueous potassium hydroxide solution and 200 ml of 1,4-dioxane and the mixture was refluxed for 7 hours. After cooling to room temperature, 28.6 g (0.130 mol) of di-t-butyl dicarbonate was added dropwise to the mixture and the resulting mixture was stirred at room temperature for one hour.

The resulting reaction mixture was extracted with ethyl acetate, and the organic layer was washed with a saturated aqueous saline solution and dried over anhydrous sodium sulfate. The organic layer was concentrated under reduced pressure and the residue was purified by the silica gel column chromatography method (eluent: hexane/ethyl acetate=4/1) to obtain 26.7 g (0.110 mol) of 6-t-butoxycarbonyl-2-methyl-4,5,6,7-tetrahydrothiazolo[5,4-c]pyridine as white solid.

$^1$H-NMR (CDCl$_3$) δ; 4.58 (s, 2H), 3.73 (t, J=5.1 Hz, 2H), 2.84 (t, J=5.1 Hz, 2H), 2.68 (s, 3H), 1.48 (s, 9H).

CI-MS (m/z); 255

(32-4) In 20 ml of dried THF was dissolved 3.81 g (15.0 mmol) of 6-t-butoxycarbonyl-2-methyl-4,5,6,7-tetrahydrothiazolo[5,4-c]pyridine under argon gas atmosphere. At −50° C., 35 ml (35 mmol) of a THF solution containing 1.0 M lithium bis(trimethylsilyl)amide was gradually added dropwise to the solution, and then, the mixture was stirred for 2 hours. Then, 2.13 ml (17.6 mmol) of diethyl carbonate was added to the mixture and the resulting mixture was stirred for 2 hours.

To the resulting reaction mixture was added a saturated aqueous ammonium chloride solution, and the mixture was extracted with ethyl acetate. The organic layer was washed with a saturated aqueous saline solution, dried over anhydrous magnesium sulfate and the organic layer was concentrated under reduced pressure, and the residue was purified by the silica gel column chromatography method (hexane/ethyl acetate=4/1) to obtain 4.10 g (12.6 mmol) of ethyl 6-t-butoxycarbonyl-4,5,6,7-tetrahydrothiazolo[5,4-c]pyridin-2-acetate as yellowish oily product.

$^1$H-NMR (CDCl$_3$) δ; 4.62 (s, 2H), 4.23 (q, J=7.3 Hz, 2H), 4.01 (s, 2H), 3.74 (t, J=5.9 Hz, 2H), 2.87 (t, J=5.9 Hz, 2H), 1.49 (s, 9H), 1.30 (t, J=7.3 Hz, 3H).

CI-MS (m/z); 327

(32-5) In 50 ml of methylene chloride was dissolved 4.10 g (12.6 mmol) of ethyl 6-t-butoxycarbonyl-4,5,6,7-tetrahydrothiazolo[5,4-c]pyridin-2-acetate, and under ice-cooling, 10 ml of CF$_3$CO$_2$H was added to the residue and the mixture was stirred at room temperature for 2 hours.

The resulting reaction mixture was concentrated under reduced pressure to obtain the title compound as brownish oily product.

Example II-33

Ethyl 4,5,6,7-tetrahydropyrrolo[3,4-c]pyridin-2-acetate.trifluoroacetate (33-1) In 50 ml of diethyl ether were suspended 1.28 g (31.9 mmol) of sodium hydride (60%, oily) and 2 ml of ethanol was added dropwise while stirring. Then, a 10 ml of diethyl ether solution containing 5.8 g (29 mmol) of 1-t-butoxycarbonyl-4-piperidone and 2.26 g (30.5 mmol) of ethyl formate was added dropwise to the above mixture over 30 minutes. After completion of the dropwise addition, the mixture was stirred at the same temperature for 2 hours. Then, 4.00 g (31.9 mmol) of glycine methyl ester.HCl was added to the mixture and the resulting mixture was further stirred for 2 hours.

The resulting reaction mixture was concentrated under reduced pressure, 50 ml of ethyl acetate was added to the residue and the resulting mixture was washed successively with a saturated aqueous sodium bicarbonate solution and a saturated aqueous saline solution, and dried over anhydrous sodium sulfate. The organic layer was concentrated under reduced pressure and the residue was purified by the silica gel column chromatography method (eluent: hexane/ethyl acetate=1/1) to obtain 5.68 g (19.1 mmol) of 1-t-butoxycarbonyl-3-(methoxycarbonylmethylaminomethyliden)-4-piperidone as yellowish oily product.

$^1$H-NMR (CDCl$_3$) δ; 9.80 (brs, 1H), 6.60, 6.55 (each s, total 1H), 4.13 (s, 2H), 3.97, 3.94 (each s, total 2H), 3.77 (s, 3H), 3.58 (t, J=5.4 Hz, 2H), 2.46 (t, J=5.4 Hz, 2H), 1.47 (s, 9H).

CI-MS (m/z); 299

(33-2) In 20 ml of methanol was dissolved 4.67 g (15.7 mmol) of 1-t-butoxycarbonyl-3-(methoxycarbonylmethylaminomethyliden)-4-piperidone, 1.02 g (15.7 mmol) of potassium hydroxide was added to the solution, and the mixture was stirred at 40° C. for 30 minutes to effect the reaction.

The resulting reaction mixture was concentrated under reduced pressure, 7.0 ml (74 mmol) of acetic anhydride was added to the residue and the mixture was stirred at 80° C. for 30 minutes.

To the resulting reaction mixture was added 20 ml of water, and the mixture was extracted with ethyl acetate, the organic layer was washed with a saturated aqueous saline solution and dried over anhydrous sodium sulfate. The organic layer was concentrated under reduced pressure and the residue was purified by the silica gel column chromatography method (eluent: hexane/ethyl acetate=4/1) to obtain 1.05 g (3.98 mmol) of 2-acetyl-5-t-butoxycarbonyl-4,5,6,7-tetrahydropyrrolo[3,4-c]pyridine as pale yellowish oily product.

$^1$H-NMR (CDCl$_3$) δ; 7.04 (brs, 2H), 4.48 (s, 2H), 3.60 (t, J=5.4 Hz, 2H), 2.64 (t, J=5.4 Hz, 2H), 2.48 (s, 3H), 1.48 (s, 9H).

CI-MS (m/z); 265

(33-3) In 8 ml of methanol was dissolved 1.38 g (5.23 mmol) of 2-acetyl-5-t-butoxycarbonyl-4,5,6,7-tetrahydropyrrolo[3,4-c]pyridine, and 7.5 ml (73 mmol) of a 40% methylamine methanol solution was added at room temperature and the mixture was stirred at room temperature for 1.5 hours.

The resulting reaction mixture was concentrated under reduced pressure and the residue was purified by the silica gel column chromatography method (eluent: hexane/ethyl acetate=4/1) to obtain 0.96 g (4.32 mmol) of 5-t-butoxycarbonyl-4,5,6,7-tetrahydropyrrolo[3,4-c]pyridine as white solid.

$^1$H-NMR (CDCl$_3$) δ; 8.08 (brs, 1H), 6.53 (s, 2H), 4.53 (s, 2H), 3.64 (t, J=5.4 Hz, 2H), 2.67 (t, J=5.4 Hz, 2H), 1.48 (s, 9H).

CI-MS (m/z); 223

(33-4) In 2 ml of dried THF was dissolved 0.10 g (0.45 mmol) of 5-t-butoxycarbonyl-4,5,6,7-tetrahydropyrrolo[3,4-c]pyridine under argon gas atmosphere and the mixture was cooled to −50° C. At the same temperature, 1.35 ml (0.68 mmol) of a toluene solution containing 0.5 M potassium bis(trimethylsilyl)amide was added dropwise to the solution. After dropwise addition, the temperature of the mixture was raised up to −10° C. over 2 hours. Then, 0.11 g (0.68 mmol) of ethyl bromoacetate was added to the mixture and the resulting mixture was stirred at the same temperature for 5 hours.

To the resulting reaction mixture was added 5 ml of a saturated aqueous ammonium chloride solution, and the mixture was extracted with ethyl acetate. The organic layer was washed with a saturated aqueous saline solution, and dried over anhydrous magnesium sulfate. The organic layer was concentrated under reduced pressure, and the residue was purified by the silica gel column chromatography method (eluent: hexane/ethyl acetate=4/1) to obtain 0.11 g (0.36 mmol) of ethyl 5-t-butoxycarbonyl-4,5,6,7-tetrahydropyrrolo[3,4-c]pyridin-2-acetate as pale yellowish oily product.

$^1$H-NMR (CDCl$_3$) δ; 6.39 (s, 2H), 4.53 (s, 2H), 4.49 (s, 2H), 4.23 (q, J=8.1 Hz, 2H), 3.62 (t, J=5.4 Hz, 2H), 2.65 (t, J=5.4 Hz, 2H), 1.47 (s, 9H), 1.29 (t, J=8.1 Hz, 3H).

CI-MS (m/z); 309

(33-5) In 2 ml of methylene chloride was dissolved 0.11 g (0.36 mmol) of ethyl 5-t-butoxycarbonyl-4,5,6,7-tetrahydropyrrolo[3,4-c]pyridin-2-acetate, and under ice-cooling, 0.4 ml of CF$_3$CO$_2$H was added to the residue and the mixture was stirred at room temperature for 2 hours.

The resulting reaction mixture was concentrated under reduced pressure to obtain the title compound as brownish oily product.

Example II-34
Benzyl 4,5,6,7-tetrahydropyrrolo[3,2-c]pyridin-2-acetate.trifluoroacetate (34-1) A mixture of 2.00 g (10.0 mmol) of 1-t-butoxycarbonyl-4-piperidone, 35 ml of benzene and 1.05 g (12.1 mmol) of morpholine was refluxed and the formed water was removed by using a Dehn-Stark dehydrating tube. After completion of distillation of water, the reaction mixture was concentrated under reduced pressure to obtain 2.69 g (10.0 mmol) of 1-t-butoxycarbonyl-4-morpholino-1,2,5,6-tetrahydropyridine as yellowish solid.

CI-MS (m/z); 269

(34-2) To 10 ml of a methylene chloride solution containing 3.23 g (10.0 mmol) of 2-t-butoxycarbonylamino-3-benzyloxycarbonylpropionic acid was added 1.02 g (10.0 mmol) of triethylamine, and then, 1.16 g (10.6 mmol) of ethyl chloroformate was added dropwise to the mixture and the resulting mixture was stirred at the same temperature for one hour. Then, under ice-cooling, 30 ml of a THF solution in which 0.40 g (20 mmol) of lithium boron hydride was suspended was added to the mixture and the resulting mixture was stirred at the same temperature for 5 hours. The mixture was allowed to stand at the same temperature overnight.

To the resulting reaction mixture was added a saturated aqueous sodium bicarbonate solution and the mixture was extracted with ethyl acetate. The organic layer was washed with a saturated aqueous saline solution and dried over anhydrous sodium sulfate. The organic layer was concentrated under reduced pressure, and the residue was purified by the silica gel column chromatography method (eluent; chloroform/ethyl acetate=3/1) to obtain 1.59 g (5.15 mmol) of benzyl 3-t-butoxycarbonylamino-4-hydroxybutanoate as colorless oily product (crystallized by allowing to stand).

$^1$H-NMR (CDCl$_3$) δ; 7.35 (s, 5H), 5.22 (brs, 1H), 5.13 (s, 2H), 4.06–3.98 (m, 1H), 3.68 (d, J=5.1 Hz, 2H), 2.67 (d, J=5.9 Hz, 2H), 2.56 (brs, 1H), 1.39 (s, 9H).

CI-MS (m/z); 254

(34-3) 8 ml of a methylene chloride solution containing 0.81 g (6.4 mmol) of oxalyl chloride was cooled to −70° C., and 2 ml of a methylene chloride solution containing 0.65 g of DMSO was added dropwise over 10 minutes. The mixture was stirred at −60° C. for 10 minutes, and then, 5 ml of a methylene chloride solution containing 1.01 g (3.27 mmol) of benzyl 3-t-butoxycarbonylamino-4-hydroxybutanoate was added dropwise over 10 minutes. The mixture was stirred at −50° C. for one hour, and then, 3.3 ml of triethylamine was added dropwise. After completion of the dropwise addition, the temperature of the mixture was gradually raised and when the temperature reached to 0° C., a saturated aqueous ammonium chloride solution was added to the mixture and the resulting mixture was extracted with ethyl acetate. The organic layer was washed with a saturated aqueous saline solution and dried over anhydrous sodium sulfate. The organic layer was concentrated under reduced pressure, and the residue was purified by the silica gel column chromatography method (n-hexane/ethyl acetate=7/3) to obtain 0.80 g (2.6 mmol) of benzyl 3-t-butoxycarbonylamino-3-formylpropionate as pale yellowish oily product.

$^1$H-NMR (CDCl$_3$) δ; 9.65 (s, 1H), 7.40–7.28 (m, 5H), 5.58 (d, J=7.0 Hz, 1H), 5.13 (s, 2H), 4.41–4.35 (m, 1H), 3.10–2.83 (m, 2H), 1.46 (s, 9H).

CI-MS (m/z); 252

(34-4) 15 ml of a methylene chloride solution containing 0.48 g (1.6 mmol) of benzyl 3-t-butoxycarbonylamino-3-formylpropionate was cooled to −60 ° C., and 0.20 ml of boron etherate trifluoride was added to the mixture. The resulting mixture was stirred at the same temperature for 5 minutes, and 5 ml of a methylene chloride solution containing 0.52 g (2.0 mmol) of 1-t-butoxycarbonyl-4-morpholino-1,2,5,6-tetrahydropyridine was added dropwise at −50° C. After completion of the dropwise addition, the temperature of the mixture was gradually raised and the mixture was stirred at room temperature for 2 hours.

To the resulting reaction mixture was added under ice-cooling 10 ml of a 6M hydrochloric acid aqueous solution and after stirring the mixture at room temperature for 3 hours, the mixture was extracted with methylene chloride. The organic layer was washed with a saturated aqueous saline solution and dried over anhydrous sodium sulfate. The organic layer was concentrated under reduced pressure, and the residue was purified by the silica gel column chromatography method (eluent: n-hexane/ethyl acetate=9/1) to obtain 0.14 g (0.30 mmol) of benzyl 1-t-butoxycarbonyl-5-t-butoxycarbonyl-4,5,6,7-tetrahydropyrrolo[3,2-c]pyridin-2-acetate as colorless oily product.

$^1$H-NMR (CDCl$_3$) δ; 7.36–7.31 (m, 5H), 5.89 (s, 1H), 5.15 (s, 2H), 4.30 (s, 2H), 3.88 (s, 2H), 3.64 (t, J=5.4 Hz, 2H), 2.88 (t, J=5.4 Hz, 2H), 1.50 (s, 9H), 1.47 (s, 9H).

CI-MS (m/z); 415

(34-5) In 5 ml of methylene chloride was dissolved 0.11 g (0.20 mmol) of benzyl 1-t-butoxycarbonyl-5-t-butoxycarbonyl-4,5,6,7-tetrahydropyrrolo [3,2-c]pyridin-2-acetate, and under ice-cooling, 1 ml of CF$_3$CO$_2$H was added to the solution and the resulting mixture was stirred at room temperature for one hour.

The resulting reaction mixture was concentrated under reduced pressure to obtain the title compound as reddish brown foamy product.

Example II-35
Ethyl 1-benzyloxycarbonyl-4,5,6,7-tetrahydropyrrolo[3,2-c]pyridin-2-acetate.trifluoroacetate (35-1) To 150 ml of a methylene chloride solution containing 28.7 g (97.4 mmol) of 2-benzyloxycarbonylamino-3-ethoxycarbonylpropionic acid was added under ice-cooling 9.84 g (97.4 mmol) of triethylamine, and then, 11.9 g (97.4 mmol) of isopropyl chloroformate was added dropwise at the same temperature and the resulting mixture was stirred for 2 hours. Then, 25 ml of a THF solution containing 2M lithium boron hydride was added dropwise to the mixture, and the resulting mixture was stirred at the same temperature for 2 hours and further allowed to stand at room temperature overnight.

To the resulting reaction mixture was added a saturated aqueous ammonium chloride solution and the mixture was extracted with ethyl acetate. The organic layer was washed with a saturated aqueous saline solution and dried over anhydrous sodium sulfate. The organic layer was concentrated under reduced pressure. The residue was purified by the silica gel column chromatography method (eluent; chloroform/ethyl acetate=1/1) to obtain 8.41 g (29.9 mmol) of ethyl 3-benzyloxycarbonylamino-4-hydroxybutanoate as colorless oily product (crystallized by allowing to stand).

$^1$H-NMR (CDCl$_3$) δ; 7.36–7.31 (m, 5H), 5.52 (brs, 1H), 5.10 (s, 2H), 4.16–4.05 (m, 3H), 3.72 (d, J=4.9 Hz, 2H), 2.64 (d, J=5.9 Hz, 2H), 1.24 (t, J=7.1 Hz, 3H).

CI-MS (m/z); 282

(35-2) In the same manner as in Example II-(34-3) except for using ethyl 3-benzyloxycarbonylamino-4-hydroxybutanoate in place of benzyl 3-t-butoxycarbonylamino-4-hydroxybutanoate and purification was carried out by changing the eluent composition of the silica gel column chromatography to n-hexane/ethyl acetate=3/2, the procedure was carried out similarly to obtain ethyl 3-benzyloxycarbonylamino-3-formylpropionate as pale yellowish liquid (obtained yield 70%).

$^1$H-NMR (CDCl$_3$) δ; 9.66 (s, 1H), 7.37–7.32 (m, 5H), 5.99 (d, J=7.8H, 1H), 5.14 (s, 2H), 4.57–4.41 (m, 1H), 4.13 (q, J=7.3 Hz, 2H), 3.06–2.81 (m, 2H), 1.25 (t, J=7.3 Hz, 3H).

CI-MS (m/z); 280

(35-3) In the same manner as in Example II-(34-4) except for using ethyl 3-benzyloxycarbonylamino-3-formylpropionate in place of benzyl 3-t-butoxycarbonylamino-3-formylpropionate, the reaction was carried out similarly to obtain ethyl 1-benzyloxycarbonyl-5-t-butoxycarbonyl-4,5,6,7-tetrahydropyrrolo[3,2-c]pyridin-2-acetate as colorless liquid (obtained yield 8%).

$^1$H-NMR (CDCl$_3$) δ; 7.38–7.30 (m, 5H), 5.92 (s, 1H), 5.29 (s, 2H), 4.29 (s, 2H), 4.13–4.05 (m, 2H), 3.80 (s, 2H), 3.61 (t, J=5.9 Hz, 2H), 2.86 (t, J=5.9 Hz, 2H), 1.46 (s, 9H), 1.21 (t, J=7.3 Hz, 3H).

CI-MS (m/z); 387

(35-4) In the same manner as in Example II-(34-5) except for using ethyl 1-benzyloxycarbonyl-5-t-butoxycarbonyl-4,5,6,7-tetrahydropyrrolo[3,2-c]pyridin-2-acetate in place of benzyl 1-t-butoxycarbonyl-5-t-butoxycarbonyl-4,5,6,7-tetrahydropyrrolo[3,2-c]pyridin-2-acetate, the reaction was carried out similarly to obtain the title compound as orange foamy product (obtained yield 100%).

FAB-MS (m/z); 535

Example II-36
Acetoxymethyl(4-nitrophenyl)carbonate (36-1) In 200 ml of methylene chloride was dissolved 5.56 g (40.0 mmol) of 4-nitrophenol, 3.16 g (40.0 mmol) of pyridine was added to the solution, and under ice-cooling, 5.67 g (44.0 mmol) of chloromethyl chloroformate was added dropwise to the mixture and the resulting mixture was stirred at room temperature for one hour.

The resulting reaction mixture was washed successively with water, 0.5% aqueous sodium hydroxide solution and water. The organic layer was dried over anhydrous sodium sulfate and concentrated under reduced pressure to obtain 8.91 g (38.6 mmol) of chloromethyl(4-nitrophenyl)carbonate as pale yellowish crystal.

$^1$H-NMR (CDCl$_3$) δ; 8.31 (d, J=8.8 Hz, 2H), 7.45 (d, J=8.8 Hz, 2H), 5.85 (s, 2H).

CI-MS (m/z); 232

(36-2) In 24 ml of acetone was dissolved 4.34 g (18.8 mmol) of chloromethyl(4-nitrophenyl)carbonate, 5.63 g (37.6 mmol) of sodium iodide was added to the solution and the mixture was stirred under argon gas atmosphere at 45° C. for 7 hours.

The resulting reaction mixture was filtered and concentrated, and then, ether was added to the residue, precipitated material was filtered off and the organic layer was concentrated under reduced pressure to obtain 5.90 g (18.3 mmol) of iodomethyl(4-nitrophenyl)carbonate as yellowish brown crystal.

$^1$H-NMR (CDCl$_3$) δ; 8.30 (d, J=8.8 Hz, 2H), 7.42 (d, J=8.8 Hz, 2H), 6.07 (s, 2H).

CI-MS (m/z); 324

(36-3) In 16 ml of toluene was dissolved 2.58 g (8.00 mmol) of iodomethyl(4-nitrophenyl)carbonate, 1.60 g (9.60 mmol) of silver acetate was added to the solution and the mixture was stirred at 80° C. for 40 minutes.

The resulting reaction mixture was filtered and concentrated, and the residue was purified by the silica gel column chromatography method (eluent: hexane/ethyl acetate=4/1) to obtain 1.90 g (7.42 mmol) of the title compound as white crystal.

$^1$H-NMR (CDCl$_3$) δ; 8.30 (d, J=8.8 Hz, 2H), 7.42 (d, J=8.8 Hz, 2H), 5.88 (s, 2H), 2.19 (s, 3H).

CI-MS (m/z); 256

Example II-37
Pivaloyloxymethyl(4-nitrophenyl)carbonate

In 10 ml of toluene was dissolved 0.51 g (5.0 mmol) of pivalic acid, and under argon gas atmosphere, 0.83 g (3.0 mmol) of silver carbonate and 1.6 g (5.0 mmol) of iodomethyl(4-nitrophenyl)carbonate were added to the solution, and the mixture was stirred at 80° C. for 20 minutes.

The resulting reaction mixture was filtered and concentrated. The residue was purified by the silica gel column chromatography method (eluent: hexane/ethyl acetate=4/1) to obtain 0.95 g (3.2 mmol) of the title compound as pale yellowish oily product.

¹H-NMR (CDCl₃) δ; 8.30 (d, J=8.8 Hz, 2H), 7.41 (d, J=8.8 Hz, 2H), 5.89 (s, 2H), 1.26 (s, 9H).
CI-MS (m/z); 298

Example II-38
Benzoyloxymethyl(4-nitrophenyl)carbonate
In the same manner as in Example II-37 except for using 0.61 g (5.0 mmol) of benzoic acid in place of pivalic acid, the reaction was carried out similarly to obtain 1.4 g (4.4 mmol) of the title compound as white crystal.
¹H-NMR (CDCl₃) δ; 8.29 (d, J=8.8 Hz, 2H), 8.14–8.10 (m, 2H), 7.67–7.61 (m, 1H), 7.52–7.45 (m, 2H), 7.42 (d, J=8.8 Hz, 2H), 6.14 (s, 2H).
CI-MS (m/z); 318

Example II-39
Nicotinoyloxymethyl(4-nitrophenyl)carbonate
In the same manner as in Example II-37 except for using 0.62 g (5.0 mmol) of nicotinic acid in place of pivalic acid, the reaction was carried out similarly to obtain 0.94 g (3.0 mmol) of the title compound as white crystal.
¹H-NMR (CDCl₃) δ; 9.31–9.30 (m, 1H), 8.87–8.85 (m, 1H), 8.41–8.34 (m, 1H), 8.29 (d, J=8.8 Hz, 2H), 7.50–7.47 (m, 1H), 7.42 (d, J=8.8 Hz, 2H), 6.17 (s, 2H).
CI-MS (m/z); 319

Example II-40
2-t-Butoxyethyl(4-nitrophenyl)carbonate
In 16 ml of methylene chloride was dissolved 1.77 g (15.0 mmol) of 2-t-butoxyethanol, 1.31 g (16.5 mmol) of pyridine was added to the solution, and under ice-cooling, 15 ml of a methylene chloride solution containing 3.12 g (15.0 mmol) of 4-nitrophenylchloroformate was added dropwise to the mixture, and the resulting mixture was stirred at room temperature for 7 hours.
The resulting reaction mixture was washed successively with water, a saturated aqueous sodium hydrogen carbonate solution and a saturated aqueous saline solution. The organic layer was dried over anhydrous sodium sulfate and concentrated under reduced pressure. The residue was purified by the silica gel column chromatography method (eluent: chloroform) to obtain 4.19 g (14.8 mmol) of the title compound as pale yellowish oily product.
¹H-NMR (CDCl₃) δ; 8.28 (d, J=8.8 Hz, 2H), 7.38 (d, J=8.8 Hz, 2H), 4.39 (t, J=5.1 Hz, 2H), 3.67 (t, J=5.1 Hz, 2H), 1.24 (s, 9H).
CI-MS (m/z); 284

Example II-41
2-Chloro-4-cyanobenzoic acid
(41-1) To a mixture of 1.2 g (1.6 mmol) of dibromobis(triphenylphosphine)nickel, 0.35 g (4.8 mmol) of zinc powder, 0.85 g (3.2 mmol) of triphenylphosphine and 3.5 g (53 mmol) of potassium cyanide was added under argon gas atmosphere at room temperature 20 ml of acetonitrile containing 11.0 g (48.0 mmol) of ethyl 2,4-dichlorobenzoate dissolved therein, and the mixture was stirred at 50° C. for 6 hours.
The resulting reaction mixture was concentrated under reduced pressure, and 100 ml of ethyl acetate was added to the residue. The organic layer was washed with a saturated aqueous saline solution, dried over anhydrous sodium sulfate and concentrated under reduced pressure. The residue was purified by the silica gel column chromatography method (eluent: hexane/ethyl acetate=19/1) to obtain 1.1 g (5. 0 mmol) of ethyl 2-chloro-4-cyanobenzoate as white crystal.
¹H-NMR (CDCl₃) δ; 7.88 (d, J=8.1 Hz, 1H), 7.75 (s, 1H), 7.61 (d, J=8.1 Hz, 1H), 4.43 (q, J=7.3 Hz, 2H), 1.42 (t, J=7.3 Hz, 3H).
CI-MS (m/z); 210

(41-2) In 15 ml of ethanol was dissolved 1.1 g (5.0 mmol) of ethyl 2-chloro-4-cyanobenzoate, and 10 ml of a 1N aqueous sodium hydroxide solution was added to the solution and the resulting mixture was stirred overnight.
To the resulting reaction mixture was added 11 ml of 1N hydrochloric acid and the mixture was extracted with 50 ml of ethyl acetate. The organic layer was dried over anhydrous sodium sulfate and concentrated under reduced pressure to obtain 0.91 g (5.0 mmol) of the title compound as white crystal.
¹H-NMR (CDCl₃) δ; 8.05 (d, J=8.1 Hz, 1H), 7.79 (s, 1H), 7.64 (d, J=8.1 Hz, 1H).
CI-MS (m/z); 182

Example II-42
2-Fluoro-4-cyanobenzoic acid
(42-1) In the same manner as in Example II-(41-2) except for using 1.0 g (5.0 mmol) of ethyl 4-chloro-2-fluorobenzoate in place of ethyl 2,4-dichlorobenzoate, the reaction was carried out similarly to obtain 0.58 g (3.0 mmol) of ethyl 4-cyano-2-fluorobenzoate as white crystal.
1H-NMR (CDCl₃) δ; 8.06, 8.03 (dd, J=8.1 Hz, 6.6 Hz, 1H), 7.51 (d, J=8.1 Hz, 1H), 7.47, 7.43 (dd, J=8.1 Hz, 1.5 Hz, 1H), 4.43 (q, J=7.3 Hz, 2H), 1.41 (t, J=7.3 Hz, 3H).
CI-MS (m/z); 194

(42-2) In the same manner as in Example II-(41-2) except for using 0.58 g (3.0 mmol) of ethyl 4-cyano-2-fluorobenzoate tit in place of ethyl 2-chloro-4-cyanobenzoate, the reaction was carried out similarly to obtain 0.50 g (3.0 mmol) of the title compound as white crystal.
¹H-NMR (CDCl₃) δ; 8.16, 8.13 (dd, J=8.1 Hz, 6.6 Hz, 1H), 7.90 (d, J=8.1 Hz, 1H), 7.58, 7.54 (dd, J=8.1 Hz, 1.5 Hz, 1H).
CI-MS (m/z); 166

Example II-43
4-Cyano-2-methoxybenzoic acid
(43-1) In the same manner as in Example II-(41-1) except for using 8.53 g (39.8 mmol) of ethyl 4-chloro-2-methoxybenzoate in place of ethyl 2,4-dichlorobenzoate, the reaction was carried out similarly to obtain 4.30 g (21.0 mmol) of ethyl 4-cyano-2-methoxybenzoate as white crystal.
1H-NMR (CDCl₃) δ; 7.81 (d, J=7.8 Hz, 1H), 7.29, 7.27 (dd, J=7.8 Hz, 1.5 Hz, 1H), 7.21 (d, J=1.5 Hz, 1H), 4.38 (q, J=7.3 Hz, 2H), 3.93 (s, 3H), 1.39 (t, J=7.3 Hz, 3H).
CI-MS (m/z); 206

(43-2) In the same manner as in Example II-(41-2) except for using 1.0 g (5.0 mmol) of ethyl 4-cyano-2-methoxybenzoate in place of ethyl 2-chloro-4-cyanobenzoate, the reaction was carried out similarly to obtain 0.89 g (5.0 mmol) of the title compound as white crystal.
¹H-NMR (CDCl₃) δ; 8.27 (d, J=8.1 Hz, 1H), 7.45, 7.42 (dd, J=8.1 Hz, 1.5 Hz, 1H), 7.33 (d, J=1.5 Hz, 1H), 4.13 (s, 3H).
CI-MS (m/z); 178

Example II-44
4-Cyano-2-methylbenzoic acid
(44-1) In the same manner as in Example II-(41-1) except for using 5.96 g (24.5 mmol) of ethyl 4-bromo-2-methylbenzoate in place of ethyl 2,4-dichlorobenzoate, the reaction was carried out similarly to obtain 3.24 g (17.1 mmol) of ethyl 4-cyano-2-methylbenzoate as white crystal.
¹H-NMR (CDCl₃) δ; 7.97 (d, J=8.8 Hz, 1H), 7.55 (s, 1H), 7.48 (d, J=8.8 Hz, 1H), 4.38 (q, J=7.3 Hz, 2H), 2.62 (s, 3H), 1.39 (t, J=7.3 Hz, 3H).

CI-MS (m/z); 190

(44-2) In the same manner as in Example II-(41-2) except for using 3.24 g (17.1 mmol) of ethyl 4-cyano-2-methylbenzoate in place of ethyl 2-chloro-4-cyanobenzoate, the reaction was carried out similarly to obtain 2.06 g (12.8 mmol) of the title compound as white crystal.

$^1$H-NMR (CDCl$_3$) δ; 8.07 (d, J=8.3 Hz, 1H), 7.58 (s, 1H), 7.56 (d, J=8.3 Hz, 1H), 2.67 (s, 3H).

CI-MS (m/z); 162

Example II-45
5-Cyano-2-pyridincarboxylic acid (45-1) In 40 ml of conc. sulfuric acid was dissolved 5.53 g (46.8 mmol) of 6-methylnicotinonitrile, and 16.7 g (56.2 mmol) of sodium dichromate.2H$_2$O was added little by little so that the reaction temperature did not exceed 45° C. This mixture was further stirred for 5 hours.

The resulting reaction mixture was poured into ice-water, neutralized by sodium hydroxide and the precipitated solid was collected by filtration. The resulting solid was washed with water, dried under reduced pressure at 90° C. to obtain 3.06 g (18.4 mmol) of 5-carbamoyl-2-pyridincarboxylic acid as white solid.

CI-MS (m/z); 167

(45-2) To 3.06 g (18.4 mmol) of 5-carbamoyl-2-pyridincarboxylic acid was added 12 ml of phosphorus oxychloride and the mixture was refluxed for one hour.

The resulting reaction mixture was poured into ice-water, adjusted pH to 1 to 2 with sodium hydroxide, and the precipitated solid was collected by filtration The resulting solid was washed with water, dried under reduced pressure at 90° C. to obtain 2.10 g (14.2 mmol) of the title compound as pale yellowish solid.

$^1$H-NMR (DMSO-d$_6$) δ; 13.82 (br.s, 1H), 9.14 (d, J=2.2 Hz, 1H), 8.52, 8.48 (dd, J=8.1 Hz, 2,2 Hz, 1H), 8.17 (d, J=8.1 Hz, 1H).

CI-MS (m/z); 149

Example II-46
4-(N-t-butoxycarbonylmorpholinoimidoyl)benzoic acid (46-1) In 50 ml of DMF was dissolved 2.50 g (13.3 mmol) of allyl 4-cyanobenzoate, then, 2.8 g of magnesium chloride.6H$_2$O and 2.20 g (27.5 mmol) of 70% sodium hydrosulfide were added to the solution at room temperature, and after stirring at the same temperature for one hour, 150 ml of water was added to the mixture. After adjusting the pH to 3 with a 20% aqueous potassium hydrogen sulfate, the precipitated solid was collected by filtration to obtain 2.92 g (13.2 mmol) of allyl 4-thiocarbamoylbenzoate as yellowish solid.

CI-MS (m/z); 222

(46-2) In 150 ml of acetone was suspended 2.92 g (13.2 mmol) of allyl 4-thiocarbamoylbenzoate, 9.0 ml of methyl iodide was added to the suspension and the mixture was refluxed for 2 hours.

The resulting reaction mixture was concentrated under reduced pressure, a mixed solvent of methylene chloride/hexane (1/1) was added to the residue and the precipitated solid was collected by filtration to obtain 4.53 g (12.5 mmol) of allyl 4-(methylthioimidoyl)benzoate.HI as yellowish solid.

CI-MS (m/z); 236

(46-3) A mixed solution of 1.61 g (4.50 mmol) of allyl 4-(methylthioimidoyl)benzoate.HI, 20 ml of methanol, 0.2 ml of acetic acid and 0.590 g (6.75 mmol) of morpholine was stirred at 90° C. for 2 hours.

The resulting reaction mixture was concentrated under reduced pressure, the reside was suspended in 20 ml of acetonitrile, 0.750 g (6.70 mmol) of DABCO, catalytic amount of 4-dimethylaminopyridine and 4.5 ml of di-t-butyl dicarbonate were added to the suspension and the mixture was stirred at room temperature for 30 minutes.

The resulting reaction mixture was concentrated under reduced pressure, a 5% aqueous potassium hydrogen sulfate solution was added to the reside and the mixture was extracted with ethyl acetate. The organic layer was washed with a saturated aqueous sodium bicarbonate solution and a saturated aqueous saline solution, dried over anhydrous sodium sulfate and concentrated under reduced pressure. The residue was purified by the silica gel column chromatography method (eluent: hexane/ethyl acetate=2/1 to 1/3) to obtain 0.870 g (2.32 mmol) of allyl 4-(N-t-butoxycarbonylmorpholinoimidoyl)benzoate as pale brownish oily product.

$^1$H-NMR (CDCl$_3$) δ; 8.13 (d, J=6.6 Hz, 2H), 7.42 (d, J=6.6 Hz, 2H) 6.11–5.97 (m, 1H), 5.45–5.30 (m, 2H), 4.86–4.83 (m, 2H), 3.69 (brs, 4H), 3.30 (brs, 4H), 1.20 (s, 9H).

CI-MS (m/z); 279

(46-4) In 20 ml of dehydrated THF were dissolved 0.87 g (2.32 mmol) of allyl 4-(N-t-butoxycarbonylmorpholinoimidoyl)benzoate and 0.26 g (0.23 mmol) of tetrakis(triphenylphosphin)palladium under argon gas atmosphere, under ice-cooling, 2.00 ml of morpholine was added to the mixture, and after the resulting mixture was returned to room temperature, it was stirred for one hour.

The resulting reaction mixture was concentrated under reduced pressure, a 5% aqueous potassium hydrogen carbonate solution was added to the residue to adjust the pH thereof to 3, and then, the mixture was extracted with ethyl acetate. The organic layer was washed with a saturated aqueous saline solution, dried over anhydrous sodium sulfate and concentrated under reduced pressure. The residue was purified by the silica gel column chromatography method (eluent: chloroform/methanol=30/1) to obtain 0.62 g (1.9 mmol) of the title compound as pale yellowish powder.

$^1$H-NMR (400 MHz, CDCl$_3$) δ; 8.19, 8.16 (each d, J=8.3 Hz, 2H), 7.90, 7.44 (each d, J=8.3 Hz, 2H), 3.70, 3.20 (each brs, 8H), 1.55, 1.21 (each s, 9H).

CI-MS (m/z); 279

Example II-47
Cyclohexyl(4-nitrophenyl)carbonate

In 100 ml of THF was dissolved 7.44 g (74.4 mmol) of cyclohexanol, and 12.5 g (123 mmol) of triethylamine was added to the solution. To the mixture was added 10.0 g (49.6 mmol) of 4-nitrophenylchloroformate under ice-cooling and the mixture was stirred for one hour.

The resulting reaction mixture was concentrated under reduced pressure, ethyl acetate and a 5% aqueous potassium hydrogen sulfate solution were added to the residue and the organic layer was separated. The organic layer was washed with a saturated aqueous saline solution, dried over anhydrous magnesium sulfate and concentrated under reduced pressure. The residue was purified by the silica gel column chromatography method (eluent: ethyl acetate/n-hexane=20/80) to obtain 10.5 g (39.6 mmol) of the title compound.

$^1$H-NMR (400 MHz, CDCl$_3$) δ; 8.29–8.24 (m, 2H), 7.41–7.30 (m, 2H), 4.81–4.71 (m, 1H), 2.04–1.10 (m, 10H).

CI-MS (m/z); 266

Example II-48
4-Octyloxyphenyl(4-nitrophenyl)carbonate

In 100 ml of methylene chloride was dissolved 3.00 g (13.5 mmol) of 4-octyloxyphenol, and 10.0 g (99.0 mmol) of triethylamine was added to the solution. To the mixture was added 2.72 g (13.5 mmol) of 4-nitrophenylchloroformate under ice-cooling and the mixture was stirred for one hour.

The resulting reaction mixture was concentrated under reduced pressure, ethyl acetate and a 5% aqueous potassium hydrogen sulfate solution were added to the residue and the organic layer was separated. The organic layer was washed with a saturated aqueous saline solution, dried over anhydrous magnesium sulfate and concentrated under reduced pressure. The residue was purified by the silica gel column chromatography method (eluent: ethyl acetate/n-hexane=20/80) to obtain 3.92 g (10.1 mmol) of the title compound.

$^1$H-NMR (400 MHz, CDCl$_3$) δ; 8.32–8.28 (m, 2H), 7.50–7.44 (m, 2H), 7.20–7.14 (m, 2H), 7.09–6.87 (m, 2H), 3.97–3.91 (m, 2H), 1.83–1.73 (m, 2H), 1.45–1.29 (m, 10H), 0.91–0.86 (m, 3H).

What is claimed is:

1. An N-acylamino acid amide compound represented by the following formula (I):

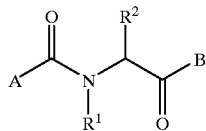

(I)

wherein $R^1$ represents a hydrogen atom or a $C_1$ to $C_4$ alkyl group;

$R^2$ represents a hydrogen atom, a $C_1$ to $C_4$ alkyl group, a benzyl group which may be substituted or a pyridylmethyl group which may be substituted (said substituent is a hydroxyl group, a nitro group, a cyano group, a trifluoromethyl group, a carboxyl group, an amino group, a benzoylamino group, a halogen atom, a $C_1$ to $C_4$ alkyl group, a $C_1$ to $C_4$ alkoxy group, a $C_7$ to $C_{10}$ aralkyloxy group, a ($C_1$ to $C_4$ alkoxy)carbonyl group, a $C_1$ to $C_6$ alkanoylamino group, a $C_1$ to C4 alkylsulfonylamino group, a phenylsulfonylamino group which may be substituted (said substituent is a halogen atom, a methyl group or a methoxy group) or a $C_7$ to $C_{10}$ aralkylsulfonylamino group);

A represents the formula (a-1):

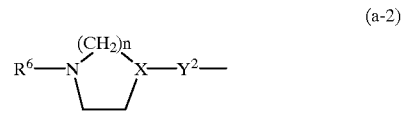

(a-1)

wherein $R^3$, $R^4$ and $R^5$ each independently represents a hydrogen atom, a hydroxyl group, a $C_1$ to $C_4$ alkyl group, a $C_7$ to $C_{10}$ aralkyl group, a $C_1$ to $C_6$ alkanoyl group, a ($C_2$ to $C_6$ alkanoyl)oxymethyl group, a ($C_1$ to $C_{10}$ alkoxy)carbonyl group, a ($C_3$ to $C_7$ cycloalkoxy) carbonyl group, a ($C_2$ to $C_6$ alkenyl)oxycarbonyl group, a ($C_7$ to $C_{10}$ aralkyl)oxycarbonyl group, a phenoxycarbonyl group which may be substituted (said substituent is a $C_1$ to $C_{10}$ alkyl group or a $C_1$ to $C_{10}$ alkoxy group), a ($C_1$ to $C_2$ alkoxy)carbonyl group substituted by a $C_1$ to $C_4$ alkoxy group, a ($C_2$ to $C_6$ alkanoyl) oxymethoxycarbonyl group, an aromatic acyloxymethoxycarbonyl group (the aromatic ring portion is a phenyl group or a pyridyl group) or an alkylene group formed by $R^4$ and $R^5$ in combination and may contain one hetero atom selected from the group consisting of O, N and S, $Y^1$ represents a phenylene group which may be substituted (said substituent is a halogen atom, a $C_1$ to $C_4$ alkyl group or a $C_1$ to $C_4$ alkoxy group) or a 5- or 6-membered divalent heteroaromatic ring group containing 1 or 2 hetero atoms selected from the group consisting of O, N and S, aor represents the formula (a-2):

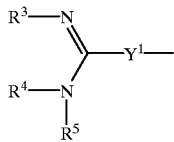

(a-2)

wherein $R^6$ represents a hydrogen atom, a $C_1$ to $C_4$ alkyl group, a $C_7$ to $C_{10}$ aralkyl group, a $C_1$ to $C_6$ alkanoyl group, a ($C_2$ to $C_6$ alkanoyl)oxymethyl group or a ($C_1$ to $C_4$ alkoxy)carbonyl group; X represents a nitrogen atom or >CH— group; $Y^2$ represents a —(CH$_2$)$_m$— group (where m=1, 2 or 3), a —CH=CH— group (cis or trans), a —C≡C— group, a —CH$_2$—CH=CH— group (cis or trans), a —CH=CH—CH$_2$— group (cis or trans), a —CH$_2$—C≡C— group, a —C≡C—CH$_2$— group, a —OCH$_2$— group, a —SCH$_2$— group, a —OCH$_2$CH$_2$— group, a —CH$_2$OCH$_2$— group, a —SCH$_2$CH$_2$— group or a —CH$_2$SCH$_2$— group; and n is 1, 2 or 3;

B represents the formula (b):

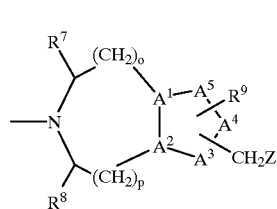

(b)

wherein $A^1$, $A^2$, $A^3$, $A^4$ and $A^5$ represent atoms selected from the group consisting of C, N, O and S, and the 5-membered ring formed by $A^1$ to $A^5$ represents a heteroaromatic ring containing 1 or 2 hetero atoms selected from the group consisting of N, O and S, said heteroaromatic ring has, as an essential component, a —CH$_2$Z group, and as a desired component, it may be substituted by $R^9$ ($R^9$ represents a hydroxyl group, a trifluoromethyl group, a $C_1$ to $C_4$ alkyl group, a $C_1$ to $C_4$ alkoxy group or a ($C_7$ to $C_{10}$ aralkyl)oxycarbonyl group), $R^7$ and $R^8$ each represents a hydrogen atom, or a $C_2$ to $C_3$ alkylene group formed by $R^7$ and $R^8$ in combination thereof, Z represents a carboxyl group which may be protected, and o and p each represents 0 or 1, or a pharmaceutically acceptable salt thereof.

2. The N-acylamino acid amide compound or a pharmaceutically acceptable salt thereof according to claim 1, wherein $R^1$ is a hydrogen atom or a methyl group.

3. The N-acylamino acid amide compound or a pharmaceutically acceptable salt thereof according to claim 1, wherein $R^2$ is a hydrogen atom, a $C_1$ to $C_4$ alkyl group, a benzyl group which may be substituted or a pyridylmethyl group which may be substituted (said substituent is a hydroxyl group, a nitro group, a cyano group, a trifluoromethyl group, an amino group, a benzoylamino group, a halogen atom, a benzyloxy group, a $C_1$ to $C_4$ alkylsulfonylamino group, a phenylsulfonylamino group which may be substituted by a halogen atom, or a benzylsulfonylamino group).

4. The N-acylamino acid amide compound or a pharmaceutically acceptable salt thereof according to claim 1, wherein $R^2$ is a methyl group, an isopropyl group, an isobutyl group, a s-butyl group or a benzyl group which may be substituted (said substituent is a nitro group, a cyano group, a fluorine atom, a chlorine atom, a benzyloxy group, a methylsulfonylamino group, an ethylsulfonylamino group, a propylsulfonylamino group, a butylsulfonylamino group, an isobutylsulfonylamino group, a phenylsulfonylamino group which may be substituted by a fluorine atom or a chlorine atom, or a benzylsulfonylamino group).

5. The N-acylamino acid amide compound or a pharmaceutically acceptable salt thereof according to claim 1, wherein $R^2$ is a methyl group or a benzyl group which may be substituted (said substituent is a nitro group, a benzyloxy group, a methylsulfonylamino group, an ethylsulfonylamino group, a propylsulfonylamino group, a butylsulfonylamino group, an isobutylsulfonylamino group, a phenylsulfonylamino group or a benzylsulfonylamino group).

6. The N-acylamino acid amide compound or a pharmaceutically acceptable salt thereof according to claim 1, wherein A is the group of the formula (a-1), $R^3$, $R^4$ and $R^5$ in the group of the formula (a-1) each independently represents a hydrogen atom, a hydroxyl group, a $C_1$ to $C_3$ alkyl group, a $C_2$ to $C_5$ alkanoyl group, an acetoxymethyl group, a pivaloyloxymethylgroup, a ($C_1$ to $C_6$ alkoxy)carbonyl group, a ($C_5$ to $C_6$ cycloalkoxy)carbonyl group, a ($C_2$ to $C_4$ alkenyl)oxycarbonyl group, a benzyloxycarbonyl group, a phenoxycarbonyl group which may be substituted by a $C_1$ to $C_4$ alkyl group or a $C_1$ to $C_{10}$ alkoxy group, an ethoxycarbonyl group the 2-position of which is substituted by a $C_1$ to $C_4$ alkoxy group, a ($C_2$ to $C_6$ alkanoyl)oxymethoxycarbonyl group, an aromatic acyloxymethoxycarbonyl group or a group formed by $R^4$ and $R^5$ in combination which is selected from the group consisting of a tetramethylene group, a pentamethylene group, a —$CH_2CH_2OCH_2CH_2$— group, a —$CH_2CH_2S$—$CH_2CH_2$— group and a —$CH_2CH_2NHCH_2CH_2$— group, $Y^1$ is a 1,4-phenylene group which may be substituted (said substituent is a halogen atom, a $C_1$ to $C_4$ alkyl group or a $C_1$ to $C_4$ alkoxy group), a 2,5-pyridinediyl group, a 3,6-pyridazinediyl group, a 2,5-pyrimidinediyl group or a 2,5-pyrazinediyl group.

7. The N-acylamino acid amide compound or a pharmaceutically acceptable salt thereof according to claim 1, wherein A is the group of the formula (a-1), $R^3$, $R^4$ and $R^5$ in the group of the formula (a-1) each independently represents a hydrogen atom, a hydroxyl group, a methyl group, a ($C_1$ to $C_4$ alkoxy)carbonyl group, a ($C_2$ to $C_4$ alkenyl) oxycarbonyl group, a phenoxycarbonyl group which may be substituted by a $C_1$ to $C_2$ alkyl group or a $C_1$ to $C_4$ alkoxy group, an ethoxycarbonyl group the 2-position of which is substituted by a $C_2$ to $C_4$ alkoxy group, a ($C_2$ to $C_5$ alkanoyl)oxymethoxycarbonyl group, a benzoyloxymethoxycarbonyl group, a nicotinoyloxymethoxycarbonyl group, a group formed by $R^4$ and $R^5$ in combination which is selected from the group consisting of a pentamethylene group, a —$CH_2CH_2OCH_2CH_2$— group and a —$CH_2CH_2NHCH_2CH_2$— group, $Y^1$ is a 1,4-phenylene group which may be substituted (said substituent is a halogen atom, a methyl group, an ethyl group, a methoxy group or an ethoxy group) or a 2,5-pyridinediyl group.

8. The N-acylamino acid amide compound or a pharmaceutically acceptable salt thereof according to claim 1, wherein A is the group of the formula (a-1), $R^3$, $R^4$ and $R^5$ in the group of the formula (a-1) each independently represents a hydrogen atom, a hydroxyl group, a methoxycarbonyl group, an ethoxycarbonyl group, a propoxycarbonyl group, an isopropoxycarbonyl group, a butoxycarbonyl group, an isobutoxycarbonyl group, a t-butoxycarbonyl group, an isopropenyloxycarbonyl group, an acetoxymethoxycarbonyl group, a pivaloyloxymethoxycarbonyl group, a phenoxycarbonyl group, a 2-t-butoxyethoxycarbonyl group, a benzoyloxymethoxycarbonyl group, and a group formed by $R^4$ and $R^5$ in combination which is selected from the group consisting of a —$CH_2CH_2OCH_2CH_2$— group, $Y^1$ is a 1,4-phenylene group which may be substituted (said substituent is a fluorine atom, a chlorine atom, a methyl group or a methoxy group) or a 2,5-pyridinediyl group.

9. The N-acylamino acid amide compound or a pharmaceutically acceptable salt thereof according to claim 1, wherein A is the group of the formula (a-2), $R^6$ in the group of the formula (a-2) is a hydrogen atom, a methyl group, an ethyl group, an acetyl group, a propanoyl group, a butanoyl group, an acetoxymethyl group, a propanoyloxymethyl group, a pivaloyloxymethyl group or a ($C_1$ to $C_4$ alkoxy) carbonyl group, X is a >CH— group, $Y^2$ is a —$CH_2CH_2$— group, a —$CH_2CH_2CH_2$— group, a —CH=CH— group, a —$OCH_2$— group or a —$CH_2OCH_2$— group, and n is 1 or 2.

10. The N-acylamino acid amide compound or a pharmaceutically acceptable salt thereof according to claim 1, wherein A is the group of the formula (a-2), $R^6$ in the group of the formula (a-2) is a hydrogen atom, an acetoxymethyl group, a pivaloyloxymethyl group, a methoxycarbonyl group, an ethoxycarbonyl group, a propoxycarbonyl group, an isopropoxycarbonyl group, a butoxycarbonyl group or a t-butoxycarbonyl group, X is a >CH— group, $Y^2$ is a —$CH_2CH_2$— group or a —$OCH_2$— group, and n is 2.

11. The N-acylamino acid amide compound or a pharmaceutically acceptable salt thereof according to claim 1, wherein A is the group of the formula (a-2), $R^6$ in the group of the formula (a-2) is a hydrogen atom, an acetoxymethyl group or a pivaloyloxymethyl group, X is a >CH— group, $Y^2$ is a —$OCH_2$— group, and n is 2.

12. The N-acylamino acid amide compound or a pharmaceutically acceptable salt thereof according to claim 1, wherein the heteroaromatic ring in the group of the formula (b) is a furan ring where $A^1$=$A^2$=$A^4$=$A^5$=C and $A^3$=O; a thiophene ring where $A^1$=$A^2$=$A^4$=$A^5$=C and $A^3$=S; a pyrrole ring where $A^1$=$A^2$=$A^4$=$A^5$=C and $A^3$=N; a pyrrole ring where $A^1$=$A^2$=$A^3$=$A^5$=C and $A^4$=N; an oxazole ring where $A^1$=$A^2$=$A^4$=C, $A^3$=O and $A^5$=N; a thiazole ring where $A^1$=$A^2$=$A^4$=C, $A^3$=S and $A^5$=N; a pyrazole ring where $A^1$=$A^2$=$A^5$=C and $A^3$=$A^4$=N; or an imidazole ring where $A^1$=$A^2$=$A^4$=C and $A^3$=$A^5$=N, o=0 and p=1 or o=1 and p=0.

13. The N-acylamino acid amide compound or a pharmaceutically acceptable salt thereof according to claim 1, wherein the heteroaromatic ring in the group of the formula (b) is a thiophene ring where $A^1$=$A^2$=$A^4$=$A^5$=C and $A^3$=S; a pyrrole ring where $A^1$=$A^2$=$A^4$=$A^5$=C and $A^3$=N; a pyrrole ring where $A^1$=$A^2$=$A^3$=$A^5$=C and $A^4$=N; a thiazole ring where $A^1$=$A^2$=$A^4$=C, $A^3$=S and $A^5$=N; or a pyrazole ring where $A^1$=$A^2$=C and $A^3$=$A^4$=N, o=0 and p=1 or o=1 and p=0, $R^7$ and $R^8$ each represents a hydrogen atom or an ethylene group formed in combination thereof, and $R^9$ is a methyl group, an ethyl group, a methoxy group, an ethoxy group, a benzyloxycarbonyl group, a hydroxyl group or a trifluoromethyl group.

14. The N-acylamino acid amide compound or a pharmaceutically acceptable salt thereof according to claim 1, wherein the heteroaromatic ring in the group of the formula (b) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, the position of the —$CH_2Z$ group is the $A^3$ or $A^4$ position, o=0 and p=1 or o=1 and p=0, $R^7$ and $R^8$ each represents a hydrogen atom or an ethylene group formed in combination thereof, $R^9$ is a methyl group, an ethyl group, a methoxy group or a trifluoromethyl group, and the protective group for the protected-carboxyl group of Z is a $C_1$ to $C_4$ alkyl group, a benzyl group, a $C_1$ to $C_2$ alkyl group substituted by a $C_2$ to $C_5$ alkanoyloxy group, a $C_1$ to $C_2$ alkyl group substituted by a ($C_1$ to $C_4$ alkoxy)carbonyloxy group, a (5-methyl-2-oxo-1,3-dioxolen-1-yl)methyl group or a (5-phenyl-2-oxo-1,3-dioxolen-1-yl)methyl group.

15. The N-acylamino acid amide compound or a pharmaceutically acceptable salt thereof according to claim 1, wherein the heteroaromatic ring in the group of the formula (b) is a thiophene ring where $A^1=A^2=A^4=A^5=C$ and $A^3=S$; a thiazole ring where $A^1=A^2=A^4=C$, $A^3=S$ and $A^5=N$; or a pyrazole ring where $A^1=A^2=A^5=C$ and $A^3=A^4=N$, the position of the —$CH_2Z$ group is the $A^4$ position, o0 and p=1, $R^7$ and $R^8$ each represents a hydrogen atom or an ethylene group formed in combination thereof, $R^9$ is a methyl group, and the protective group for the protected-carboxyl group of Z is a methyl group, an ethyl group, a propyl group, an isopropyl group, a butyl group, an isobutyl group, a benzyl group, an acetoxymethyl group, a 1-acetoxyethyl group, a pivaloyloxymethyl group, a 1-pivaloyloxyethyl group, an ethoxycarbonyloxymethyl group, a 1-ethoxycarbonyloxyethyl group, or a (5-methyl-2-oxo-1,3-dioxolen-1-yl)methyl group.

16. The N-acylamino acid amide compound or a pharmaceutically acceptable salt thereof according to claim 1, wherein $R^1$ is a hydrogen atom or a methyl group, $R^2$ is a hydrogen atom, a $C_1$ to $C_4$ alkyl group, a benzyl group which may be substituted or a pyridylmethyl group which may be substituted (said substituent is a hydroxyl group, a nitro group, a cyano group, a trifluoromethyl group, an amino group, a benzoylamino group, a halogen atom, a benzyloxy group, a $C_1$ to $C_4$ alkylsulfonylamino group, a phenylsulfonylamino group which may be substituted by a halogen atom, or a benzylsulfonylamino group), A is the group of the formula (a-1), $R^3$ in the group of the formula (a-1) is a group selected from the group consisting of a hydrogen atom, a hydroxyl group, a $C_1$ to $C_3$ alkyl group, a $C_2$ to $C_5$ alkanoyl group, an acetoxymethyl group, a pivaloyloxymethyl group, a ($C_1$ to $C_6$ alkoxy)carbonyl group, a ($C_5$ to $C_6$ cycloalkoxy)carbonyl group, a ($C_2$ to $C_4$ alkenyl) oxycarbonyl group, a benzyloxycarbonyl group, a phenoxycarbonyl group which may be substituted by a $C_1$ to $C_4$ alkyl group or a $C_1$ to $C_{10}$ alkoxy group, an ethoxycarbonyl group the 2-position of which is substituted by a $C_1$ to $C_4$ alkoxy group, a ($C_2$ to $C_6$ alkanoyl)oxymethoxycarbonyl group and an aromatic acyloxymethoxycarbonyl group, $R^4$ and $R^5$ each independently represents a hydrogen atom or a ($C_1$ to $C_4$ alkoxy)carbonyl group, or a group formed by $R^4$ and $R^5$ in combination which is selected from the group consisting of a tetramethylene group, a pentamethylene group, a —$CH_2CH_2OCH_2CH_2$— group, a —$CH_2CH_2S$—$CH_2CH_2$— group and a —$CH_2CH_2NHCH_2CH_2$— group, $Y^1$ is a 1,4-phenylene group which may be substituted (said substituent is a halogen atom, a $C_1$ to $C_4$ alkyl group or a $C_1$ to $C_4$ alkoxy group), a 2,5-pyridinediyl group, a 3,6-pyridazinediyl group, a 2,5-pyrimidinediyl group or a 2,5-pyrazinediyl group, the heteroaromatic ring in the group of the formula (b) is a furan ring where $A^1=A^2=A^4=A^5=C$ and $A^3=O$; a thiophene ring where $A^1=A^2=A^4=A^5=C$ and $A^3=S$; a pyrrole ring where $A^1=A^2=A^4=A^5C$ and $A^3=N$; a pyrrole ring where $A^1=A^2=A^3=A^5=C$ and $A^4=N$; an oxazole ring where $A^1=A^2=A^4=C$, $A^3=O$ and $A^5=N$; a thiazole ring where $A^1=A^2=A^4=C$, $A^3=S$ and $A^5=N$; a pyrazole ring where $A^1=A^2=A^5=C$ and $A^3=A^4=N$; or an imidazole ring where $A^1=A^2=A^4=C$ and $A^3=A^5=N$, o=0 and p=1 or o=1 and p=0.

17. The N-acylamino acid amide compound or a pharmaceutically acceptable salt thereof according to claim 1, wherein $R^1$ is a hydrogen atom or a methyl group, $R^2$ is a methyl group, an isopropyl group, an isobutyl group, a s-butyl group or a benzyl group which may be substituted (said substituent is a nitro group, a cyano group, a fluorine atom, a chlorine atom, a benzyloxy group, a $C_1$ to $C_4$ alkylsulfonylamino group, a phenylsulfonylamino group which may be substituted by a fluorine atom or a chlorine atom, or a benzylsulfonylamino group), A is the group of the formula (a-1), $R^3$ in the group of the formula (a-1) is a group selected from the group consisting of a hydrogen atom, a hydroxyl group, a methyl group, a ($C_1$ to $C_4$ alkoxy)carbonyl group, a ($C_2$ to $C_4$ alkenyl) oxycarbonyl group, a phenoxycarbonyl group which may be substituted by a $C_1$ to $C_2$ alkyl group or a $C_1$ to $C_4$ alkoxy group, an ethoxycarbonyl group the 2-position of which is substituted by a $C_2$ to $C_4$ alkoxy group, a ($C_2$ to $C_5$ alkanoyl) oxymethoxycarbonyl group, a benzoyloxymethoxycarbonyl group and a nicotinoyloxymethoxycarbonyl group, $R^4$ and $R^5$ each independently represents a hydrogen atom or a ($C_1$ to $C_4$ alkoxy)carbonyl group, or a group formed by $R^4$ and $R^5$ in combination which is selected from the group consisting of a pentamethylene group, a —$CH_2CH_2OCH_2CH_2$— group and a —$CH_2CH_2NHCH_2CH_2$— group, $Y^1$ is a 1,4-phenylene group which may be substituted (said substituent is a halogen atom, a methyl group, an ethyl group, a methoxy group or an ethoxy group) or a 2,5-pyridinediyl group, the heteroaromatic ring in the group of the formula (b) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, o=0 and p=1 or o=1 and p=0, $R^7$ and $R^8$ each represents a hydrogen atom or an ethylene group formed in combination thereof, and $R^9$ is a methyl group, an ethyl group, a methoxy group, an ethoxy group, a benzyloxycarbonyl group, a hydroxyl group or a trifluoromethyl group.

18. The N-acylamino acid amide compound or a pharmaceutically acceptable salt thereof according to claim 1, wherein $R^1$ is a hydrogen atom or a methyl group, $R^2$ is a methyl group or a benzyl group which may be substituted (said substituent is a nitro group, a benzyloxy group, a methylsulfonylamino group, an ethylsulfonylamino group, a propylsulfonylamino group, a butylsulfonylamino group, an isobutylsulfonylamino group, a phenylsulfonylamino group, or a benzylsulfonylamino group), A is the group of the formula (a-1), $R^3$ in the group of the formula (a-1) is a group selected from the group consisting of a hydrogen atom, a hydroxyl group, a methoxycarbonyl group, an ethoxycarbonyl group, a propoxycarbonyl group, an isopropoxycarbonyl group, a butoxycarbonyl group, an isobutoxycarbonyl group, a t-butoxycarbonyl group, an isopropenyloxycarbonyl group, an acetoxymethoxycarbonyl group, a pivaloyloxymethoxycarbonyl group, a phenoxycarbonyl group, a 2-t-butoxyethoxycarbonyl group and a benzoyloxymethoxycarbonyl group, $R^4$ and $R^5$ each independently represents a hydrogen atom or a ($C_1$ to $C_4$ alkoxy)carbonyl group, or a $-CH_2CH_2OCH_2CH_2-$ group formed by $R^4$ and $R^5$ in combination, $Y^1$ is a 1,4-phenylene group which maybe substituted (said substituent is a fluorine atom, a chlorine atom, a methyl group or a methoxy group) or a 2,5-pyridinediyl group, the heteroaromatic ring in the group of the formula (b) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C, A^3=S$ and $A^5=N$; or a pyrazole ring where $A^1=A^2=A^5=C$ and $A^3=A^4=N$, the position of the $-CH_2Z$ group is the $A^3$ or $A^4$ position, o=0 and p=1 or o=1 and p=0, $R^7$ and $R^8$ each represents a hydrogen atom or an ethylene group formed in combination thereof, $R^9$ is a methyl group, an ethyl group, a methoxy group or a trifluoromethyl group, and the protective group for the protected-carboxyl group of Z is a $C_1$ to $C_4$ alkyl group, a benzyl group, a $C_1$ to $C_2$ alkyl group substituted by a $C_2$ to $C_5$ alkanoyloxy group, a $C_1$ to $C_2$ alkyl group substituted by a ($C_1$ to $C_4$ alkoxy)carbonyloxy group, a (5-methyl-2-oxo-1,3-dioxolen-1-yl)methyl group or a (5-phenyl-2-oxo-1,3-dioxolen-1-yl)methyl group.

19. The N-acylamino acid amide compound or a pharmaceutically acceptable salt thereof according to claim 1, wherein $R^1$ is a hydrogen atom or a methyl group, $R^2$ is a methyl group or a benzyl group which may be substituted (said substituent is a nitro group, a benzyloxy group, a methylsulfonylamino group, an ethylsulfonylamino group, a propylsulfonylamino group, a butylsulfonylamino group, an isobutylsulfonylamino group, a phenylsulfonylamino group, or a benzylsulfonylamino group), A is the group of the formula (a-1), $R^3$ in the group of the formula (a-1) is a group selected from the group consisting of a hydrogen atom, a hydroxyl group, a methoxycarbonyl group, an ethoxycarbonyl group, a propoxycarbonyl group, an isopropoxycarbonyl group, a butoxycarbonyl group, an isobutoxycarbonyl group, a t-butoxycarbonyl group, an isopropenyloxycarbonyl group, an acetoxymethoxycarbonyl group, a pivaloyloxymethoxycarbonyl group, a phenoxycarbonyl group, a 2-t-butoxyethoxycarbonyl group and a benzoyloxymethoxycarbonyl group, $R^4$ and $R^5$ each represents a hydrogen atom, $Y^1$ is a 1,4-phenylene group which maybe substituted (said substituent is a fluorine atom, a chlorine atom, a methyl group or a methoxy group) or a 2,5-pyridinediyl group, the heteroaromatic ring in the group of the formula (b) is a thiophene ring where $A^1=A^2=A^4=A^5=C$ and $A^3=S$; a thiazole ring where $A^1=A^2=A^4=C, A^3=S$ and $A^5=N$; or a pyrazole ring where $A^1=A^2=A^5=C$ and $A^3=A^4=N$, the position of the $-CH_2Z$ group is the $A^4$ position, o=0 and p=1, $R^7$ and $R^8$ each represents a hydrogen atom or an ethylene group formed in combination thereof, $R^9$ is a methyl group, and the protective group for the protected-carboxyl group of Z is a methyl group, an ethyl group, a propyl group, an isopropyl group, a butyl group, an isobutyl group, a benzyl group, an acetoxymethyl group, a 1-acetoxyethyl group, a pivaloyloxymethyl group, a 1-pivaloyloxyethyl group, an ethoxycarbonyloxymethyl group, a 1-ethoxycarbonyloxyethyl group, or a (5-methyl-2-oxo-1,3-dioxolen-1-yl)methyl group.

20. The N-acylamino acid amide compound or a pharmaceutically acceptable salt thereof according to claim 1, wherein $R^1$ is a hydrogen atom or a methyl group, $R^2$ is a hydrogen atom, a $C_1$ to $C_4$ alkyl group, a benzyl group which may be substituted or a pyridylmethyl group which may be substituted (said substituent is a hydroxyl group, a nitro group, a cyano group, a trifluoromethyl group, an amino group, a benzoylamino group, a halogen atom, a benzyloxy group, a $C_1$ to $C_4$ alkylsulfonylamino group, a phenylsulfonylamino group which may be substituted by a halogen atom, or a benzylsulfonylamino group), A is the group of the formula (a-2), $R^6$ in the group of the formula (a-2) is a hydrogen atom, a methyl group, an ethyl group, an acetyl group, a propanoyl group, a butanoyl group, an acetoxymethyl group, a propanoyloxymethyl group, a pivaloyloxymethyl group or a ($C_1$ to $C_4$ alkoxy)carbonyl group, X is a >CH— group, $Y^2$ is a $-CH_2CH_2-$ group, a $-CH_2CH_2CH_2-$ group, a $-CH=CH-$ group, a $-OCH_2-$ group or a $-CH_2OCH_2-$ group, and n is 1 or 2, the heteroaromatic ring in the group of the formula (b) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C, A^3=S$ and $A^5=N$; or a pyrazole ring where $A^1=A^2=A^5=C$ and $A^3=A^4=N$, o=0 and p=1 or o=1 and p=0, $R^7$ and $R^8$ each represents a hydrogen atom or an ethylene group formed in combination thereof, and $R^9$ is a methyl group, an ethyl group, a methoxy group, an ethoxy group, a benzyloxycarbonyl group, a hydroxyl group or a trifluoromethyl group.

21. The N-acylamino acid amide compound or a pharmaceutically acceptable salt thereof according to claim 1, wherein $R^1$ is a hydrogen atom or a methyl group, $R^2$ is a methyl group, an isopropyl group, an isobutyl group, a s-butyl group or a benzyl group which may be substituted (said substituent is a nitro group, a cyano group, a fluorine atom, a chlorine atom, a benzyloxy group, a $C_1$ to $C_4$ alkylsulfonylamino group, a phenylsulfonylamino group which may be substituted by a fluorine atom or a chlorine atom, or a benzylsulfonylamino group), A is the group of the formula (a-2), $R^6$ in the group of the formula (a-2) is a hydrogen atom, an acetoxymethyl group, a pivaloyloxymethyl group, a methoxycarbonyl group, an ethoxycarbonyl group, a propoxycarbonyl group, an isopropoxycarbonyl group, a butoxycarbonyl group or a t-butoxycarbonyl group, X is a >CH— group, $Y^2$ is a —$CH_2CH_2$— group or a —$OCH_2$— group, n is 2, the heteroaromatic ring in the group of the formula (b) is a thiophene ring where $A^1=A^2=A^4=A^5=C$ and $A^3=S$; a pyrrole ring 35 where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, the position of the —$CH_2Z$ group is the $A^3$ or $A^4$ position, o=0 and p=1 or o=1 and p=0, $R^7$ and $R^8$ each represents a hydrogen atom or an ethylene group formed in combination thereof, $R^9$ is a methyl group, an ethyl group, a methoxy group or a trifluoromethyl group, and the protective group for the protected-carboxyl group of Z is a $C_1$ to $C_4$ alkyl group, a benzyl group, a $C_1$ to $C_2$ alkyl group substituted by a $C_2$ to $C_5$ alkanoyloxy group, a $C_1$ to $C_2$ alkyl group substituted by a ($C_1$ to $C_4$ alkoxy)carbonyloxy group, a (5-methyl-2-oxo-1,3-dioxolen-1-yl)methyl group or a (5-phenyl-2-oxo-1,3-dioxolen-1-yl)methyl group.

22. The N-acylamino acid amide compound or a pharmaceutically acceptable salt thereof according to claim 1, wherein $R^1$ is a hydrogen atom or a methyl group, p1 $R^2$ is a methyl group or a benzyl group which may be substituted (said substituent is a nitro group, a benzyloxy group, a methylsulfonylamino group, an ethylsulfonylamino group, a propylsulfonylamino group, a butylsulfonylamino group, an isobutylsulfonylamino group, a phenylsulfonylamino group, or a benzylsulfonylamino group), A is the group of the formula (a-2), $R^6$ in the group of the formula (a-2) is a hydrogen atom, an acetoxymethyl group or a pivaloyloxymethyl group, X is a >CH— group, $Y^2$ is a —$OCH_2$— group, and n is 2, the heteroaromatic ring in the group of the formula (b) is a thiophene ring where $A^1=A^2=A^4=A^5=C$ and $A^3=S$; a thiazole ring where $A^1=A^2=A^4=C, A^3=S$ and $A^5=N$; or a pyrazole ring where $A^1=A^2=A^5=C$ and $A^3=A^4=N$, the position of the —$CH_2Z$ group is the $A^4$ position, o=0 and p=1, $R^7$ and $R^8$ each represents a hydrogen atom or an ethylene group formed in combination thereof, $R^9$ is a methyl group, and the protective group for the protectedcarboxyl group of Z is a methyl group, an ethyl group, a propyl group, an isopropyl group, a butyl group, an isobutyl group, an acetoxymethyl group, a 1-acetoxyethyl group, a pivaloyloxymethyl group, a 1-pivaloyloxyethyl group, an ethoxycarbonyloxymethyl group, a 1-ethoxycarbonyloxyethyl group, or a (5-methyl-2-oxo-1,3-dioxolen-1-yl)methyl group.

23. The N-acylamino acid amide compound or a pharmaceutically acceptable salt thereof according to claim 1, wherein the compound is 5-[N-(4-amidinobenzoyl)-L-4-nitrophenylalanyl]-4,5,6,7-tetrahydrothieno[3,2-c]pyridin-2-acetic acid, ethyl 5-[N-(4-amidinobenzoyl)-L-4-nitrophenylalanyl]-4,5,6,7-tetrahydrothieno[3,2-c]pyridin-2-acetate, ethyl 5-[N-(4-amidinobenzoyl)-L-4-(butylsulfonylamino)phenylalanyl]-4,5,6,7-tetrahydrothieno[3,2-c]pyridin-2-acetate, ethyl 5-[N-(4-amidinobenzoyl)-L-4-(phenylsulfonylamino)phenylalanyl]-4,5,6,7-tetrahydrothieno[3,2-c]pyridin-2-acetate, ethyl 5-[N-(4-amidinobenzoyl)-L-4-nitrophenylalanyl]-3-methyl-4,5,6,7-tetrahydrothieno[3,2-c]pyridin-2-acetate, ethyl 5-[N-(4-amidinobenzoyl)-L-4-nitrophenylalanyl]-4,6-ethano-4,5,6,7-tetrahydrothieno[3,2-c]pyridin-2-acetate, ethyl 5-(N-(4-(N-hydroxyamidino)benzoyl]-L-4-nitrophenylalanyl]-4,5,6,7-tetrahydrothieno[3,2-c]pyridin-2-acetate, ethyl 5-[N-[4-(N-ethoxycarbonylamidino)benzoyl]-L-4-nitrophenylalanyl]-4,5,6,7-tetrahydrothieno[3,2-c]pyridin-2-acetate, 5-[N-(4-amidinobenzoyl)-L-phenylalanyl]-4,5,6,7-tetrahydropyrazolo[4,3-c]pyridin-2-acetic acid, 5-[N-(4-amidinobenzoyl)-L-4-nitrophenylalanyl]-4,5,6,7-tetrahydropyrazolo[4,3-c]pyridin-2-acetic acid, ethyl 5-[N-(4-amidinobenzoyl)-L-4-nitrophenylalanyl]-4,5,6,7-tetrahydropyrazolo[4,3-c]pyridin-2-acetate, isopropyl 5-[N-(4-amidinobenzoyl)-L-4-nitrophenylalanyl]-4,5,6,7-tetrahydropyrazolo[4,3-c]pyridin-2-acetate, pivaloyloxymethyl 5-[N-(4-amidinobenzoyl)-L-4-nitrophenylalanyl]-4,5,6,7-tetrahydropyrazolo[4,3-c]pyridin-2-acetate, 5-[N-(4-amidinobenzoyl)-L-O-benzyltyrosyl]-4,5,6,7-tetrahydropyrazolo[4,3-c]pyridin-2-acetic acid, 5-[N-(4-amidinobenzoyl)-L-4-nitrophenylalanyl]-4,6-ethano-4,5,6,7-tetrahydropyrazolo[4,3-c]pyridin-2-acetic acid, ethyl 5-[N-(4-amidinobenzoyl)-L-4-nitrophenylalanyl]-4,6-ethano-4,5,6,7-tetrahydropyrazolo[4,3-c]pyridin-2-acetate, 5-[N-(4-amidinobenzoyl)-N-methyl-L-4-nitrophenylalanyl]-4,5,6,7-tetrahydropyrazolo[4,3-c]pyridin-2-acetic acid, ethyl 5-[N-(4-amidino-2-fluorobenzoyl)-L-4-nitrophenylalanyl]-4,5,6,7-tetrahydropyrazolo[4,3-c]pyridin-2-acetate, ethyl 5-[N-(4-amidino-2-chlorobenzoyl)-L-4-nitrophenylalanyl]-4,5,6,7-tetrahydropyrazolo[4,3-c]pyridin-2-acetate, ethyl 5-[N-(4-amidino-2-methoxybenzoyl)-L-4-nitrophenylalanyl]-4,5,6,7-tetrahydropyrazolo[4,3-c]pyridin-2-acetate, ethyl 5-[N-(4-amidino-2-methylbenzoyl)-L-4-nitrophenylalanyl]-4,5,6,7-tetrahydropyrazolo[4,3-c]pyridin-2-acetate, 5-[N-[4-(N-hydroxyamidino)benzoyl]-L-4-nitrophenylalanyl]-4,5,6,7-tetrahydropyrazolo[4,3-c]pyridin-2-acetic acid, ethyl 5-[N-[4-(N-hydroxyamidino)benzoyl]-L-4-nitrophenylalanyl]-4,5,6,7-tetrahydropyrazolo[4,3-c]pyridin-2-acetate, ethyl 5-[N-[4-(N-hydroxyamidino)benzoyl]-L-4-nitrophenylalanyl]-4,6-ethano-4,5,6,7-tetrahydropyrazolo[4,3-c]pyridin-2-acetate, ethyl 5-[N-[4-(N-ethoxycarbonylamidino)benzoyl]-L-4-nitrophenylalanyl]-4,5,6,7-tetrahydropyrazolo[4,3-c]pyridin-2-acetate, pivaloyloxymethyl 5-[N-[4-(N-ethoxycarbonylamidino)benzoyl]-L-4-nitrophenylalanyl]-4,5,6,7-tetrahydropyrazolo[4,3-c]pyridin-2-acetate, ethyl 5-[N-[4-(N-ethoxycarbonylamidino)benzoyl]-L-4-nitrophenylalanyl]-4,6-ethano-4,5,6,7-tetrahydropyrazolo[4,3-c]pyridin-2-acetate, ethyl 5-[N-(5-amidino-2-pyridylcarbonyl)-L-4-nitrophenylalanyl]-4,5,6,7-tetrahydropyrazolo[4,3-c]pyridin-2-acetate, ethyl 5-[N-[4-(morpholinoimidoyl)benzoyl]-L-4-nitrophenylalanyl]-4,5,6,7-tetrahydropyrazolo[4,3-c]pyridin-2-acetate, ethyl 5-[N-(piperidin-4-yloxyacetyl)-L-4-nitrophenylalanyl]-4,5,6,7-tetrahydropyrazolo[4,3-c]pyridin-2-acetate, ethyl 5-[N-[4-(N-benzoyloxymethoxycarbonylamidino)benzoyl]-L-4-nitrophenylalanyl]-4,5,6,7-tetrahydropyrazolo[4,3-c]pyridin-2-acetate, ethyl 5-[N-[4-[N-(2-t-butoxyethoxy)carbonylamidino]benzoyl]-L-4-nitrophenylalanyl]-4,5,6,7-tetrahydropyrazolo[4,3-c]pyridin-2-acetate, ethyl 5-[N-[4-(N-phenoxycarbonylamidino)benzoyl]-L-4-nitrophenylalanyl]-4,5,6,7-tetrahydropyrazolo[4,3-c]pyridin-2-acetate, ethyl 5-[N-[4-(N-isopropenyloxycarbonylamidino)benzoyl]-L-4-nitrophenylalanyl]-4,5,6,7-tetrahydropyrazolo[4,3-c]pyridin-2-acetate, 5-[N-(4-amidinobenzoyl)-L-alanyl]-4,5,6,7-tetrahydropyrazolo[4,3-c]pyridin-2-acetate, ethyl 5-[N-(4-amidinobenzoyl)-L-4-nitrophenylalanyl]-4,5,6,7-tetrahydropyrazolo[4,5-c]pyridin-1-acetate, 5-[N-(4-amidinobenzoyl)-L-4-nitrophenylalanyl]-4,5,6,7-tetrahydrothiazolo[5,4-c]pyridin-2-acetic acid, ethyl 5-[N-(4-amidinobenzoyl)-L-4-nitrophenylalanyl]-4,5,6,7-tetrahydrothiazolo[5,4-c]pyridin-2-acetate, ethyl 5-[N-[4-(N-hydroxyamidino)benzoyl]-L-4-nitrophenylalanyl]-4,5,6,7-tetrahydrothiazolo[5,4-c]pyridin-2-acetate, benzyl 5-[N-(4-amidinobenzoyl)-L-4-nitrophenylalanyl]-4,5,6,7-tetrahydropyrrolo[3,2-c]pyridin-2-acetate, or ethyl 5-[N-(4-amidinobenzoyl)-L-4-nitrophenylalanyl]-4,5,6,7-tetrahydropyrrolo[3,4-c]pyridin-2-acetate.

24. A prophylactic or therapeutic agent of a disease to which fibrinogen receptor pertains, which comprises the N-acylamino acid amide compound or a pharmaceutically acceptable salt thereof according to claim 1 as an active ingredient.

25. A prophylactic or therapeutic agent of thrombosis which comprises the N-acylamino acid amide compound or a pharmaceutically acceptable salt thereof according to claim 1 as an active ingredient.

26. A compound represented by the formula (II):

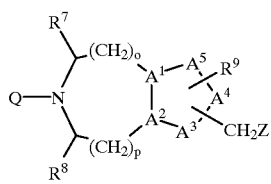

(II)

wherein $A^1$, $A^2$, $A^3$, $A^4$ and $A^5$ represent atoms selected from the group consisting of C, N, O and S, and the 5-membered ring formed by $A^1$ to $A^5$ represents a heteroaromatic ring containing 1 or 2 hetero atoms selected from the group consisting of N, O and S, said heteroaromatic ring has, as an essential component, a —$CH_2Z$ group, and as a desired component, it may be substituted by $R^9$ ($R^9$ represents a hydroxyl group, a trifluoromethyl group, a $C_1$ to $C_4$ alkyl group, a $C_1$ to $C_4$ alkoxy group or a ($C_7$ to $C_{10}$ aralkyl)oxycarbonyl group), $R^7$ and $R^8$ each represents a hydrogen atom, or a $C_2$ to $C_3$ alkylene group formed by $R^7$ and R8 in combination thereof, Z represents a carboxyl group which may be protected, Q represents a hydrogen atom, a ($C_1$–$C_4$ alkoxy)carbonyl group, a benzyloxycarbonyl group or a trityl group, and o and p each represent 0 or 1.

27. The compound according to claim 26, wherein the heteroaromatic ring in the formula (II) is a furan ring where $A^1=A^2=A^4=A^5=C$ and $A^3=O$; a thiophene ring where $A^1=A^2=A^4=A^5C$ and $A^3=S$; a pyrrole ring where $A^1=A^2=A^4=A^5=C$ and $A^3=N$; a pyrrole ring where $A^1=A^2=A^3=A^5=C$ and $A^4=N$; an oxazole ring where $A^1=A^2=A^4=C$, $A^3=O$ and $A^5=N$; a thiazole ring where $A^1=A^2=A^4=C$, $A^3=S$ and $A^5=N$; a pyrazole ring where $A^1=A^2=A^5=C$ and $A^3=A^4=N$; or an imidazole ring where $A^1=A^2=A^4=C$ and $A^3=A^5=N$, o=0 and p=1 or o=1 and p=0.

28. The compound according to claim 26, wherein the heteroaromatic ring in the formula (II) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and$A^4=N$; a thiazole ring where $A^1=A^2=A^4=C$, $A^3=S$ and $A^5=N$; or a pyrazole ring where $A^1=A^2=A^5=C$ and $A^3=A^4=N$, $R^7$ and $R^8$ each represents a hydrogen atom or an ethylene group formed in combination thereof, $R^9$ is a methyl group, an ethyl group, a methoxy group, an ethoxy group, a trifluoromethyl group or a benzyloxycarbonyl group, Z is a methyl group, an ethyl group, a propyl group, an isopropyl group, a butyl group, a t-butyl group or a benzyl group, Q is, a hydrogen atom, an ethoxycarbonyl group, a t-butoxycarbonyl group, a benzyloxycarbonyl group or a trityl group, and o=0 and p=1 or o=1 and p=0.

29. The compound according to claim 26, wherein the 35 heteroaromatic ring in the formula (II) is a thiophene ring where $A^1=A^2=A^4=A^5=C$ and $A^3=S$; a pyrrole ring where $A^1=A^2=A^4=A^5=C$ and $A^3=N$; a pyrrole ring where $A^1=A^2=A^3=A^5=C$ and $A^4=N$; a thiazole ring where $A^1=A^2=A^4=C$, $A^3=S$ and $A^5=N$; or a pyrazole ring where $A^1=A^2=A^5=C$ and $A^3=A^4=N$, $R^7$ and $R^8$ each represents a hydrogen atom or an ethylene group formed in combination thereof, $R^9$ is a methyl group, an ethyl group, a methoxy group, an ethoxy group, a trifluoromethyl group or a benzyloxycarbonyl group, Z is a methyl group, an ethyl group, a propyl group, a t-butyl group or a benzyl group, Q is a hydrogen atom, an ethoxycarbonyl group, a t-butoxycarbonyl group, a benzyloxycarbonyl group or a trityl group, and o=0 and p=1.

* * * * *